US012005116B2

(12) United States Patent
Houghton et al.

(10) Patent No.: US 12,005,116 B2
(45) Date of Patent: Jun. 11, 2024

(54) HEPATITIS C VIRUS IMMUNOGENIC COMPOSITIONS AND METHODS OF USE THEREOF

(71) Applicant: The Governors of the University of Alberta, Edmonton (CA)

(72) Inventors: Michael Houghton, Danville, CA (US); John L. Law, Edmonton (CA); Michael Logan, Edmonton (CA); Darren Hockman, Edmonton (CA); Abdolamir Landi, Edmonton (CA)

(73) Assignee: The Governors of the University of Alberta, Edmonton (CA)

( * ) Notice: Subject to any disclaimer, the term of this patent is extended or adjusted under 35 U.S.C. 154(b) by 0 days.

(21) Appl. No.: 18/099,044

(22) Filed: Jan. 19, 2023

(65) Prior Publication Data

US 2023/0310590 A1 Oct. 5, 2023

Related U.S. Application Data

(63) Continuation of application No. 17/122,578, filed on Dec. 15, 2020, now Pat. No. 11,576,967, which is a continuation of application No. 16/374,403, filed on Apr. 3, 2019, now Pat. No. 10,881,727, which is a continuation of application No. 15/574,427, filed as application No. PCT/IB2016/001051 on Jul. 6, 2016, now Pat. No. 10,300,131.

(60) Provisional application No. 62/189,657, filed on Jul. 7, 2015.

(51) Int. Cl.

| | |
|---|---|
| ***A61K 39/29*** | (2006.01) |
| ***A61K 39/00*** | (2006.01) |
| ***A61K 39/12*** | (2006.01) |
| ***A61K 39/295*** | (2006.01) |
| ***A61P 31/04*** | (2006.01) |
| ***A61P 31/14*** | (2006.01) |
| ***A61P 37/04*** | (2006.01) |
| ***C12N 15/861*** | (2006.01) |

(52) U.S. Cl.

CPC .............. *A61K 39/29* (2013.01); *A61K 39/12* (2013.01); *A61K 39/295* (2013.01); *A61P 31/04* (2018.01); *A61P 31/14* (2018.01); *A61P 37/04* (2018.01); *C12N 15/861* (2013.01); *A61K 2039/55544* (2013.01); *C07K 2319/00* (2013.01); *C12N 2770/24234* (2013.01)

(58) Field of Classification Search

CPC ...... A61K 39/12; A61K 39/29; A61K 39/295; A61K 2039/70; A61P 31/14

See application file for complete search history.

(56) References Cited

FOREIGN PATENT DOCUMENTS

| | | |
|---|---|---|
| EP | 2915544 A1 | 9/2015 |
| WO | WO 2007/081848 | 7/2007 |
| WO | WO 2008/024518 | 2/2008 |
| WO | WO 2014/060851 | 4/2014 |

OTHER PUBLICATIONS

Botti, et al.; "The Hepatitis C Virus E1 Glycoprotein Undergoes Productive Folding but Accelerated Degradation When Expressed as an Individual Subunit in CHO Cells"; PLoS One; vol. 6, No. 8, 10 pages (Aug. 2011).
Fournillier, et al.; "Expression of Noncovalent Hepatitis C Virus Envelope E1-E2 Complexes Is Not Required for the Induction of Antibodies with Neutralizing Properties following DNA Immunization"; Journal of Virology; vol. 73, No. 9, pp. 7497-7504 (Sep. 1999).
Gededzha, et al.; "Prediction of T-cell epitopes of hepatitis C virus genotype 5a"; Virology Journal; vol. 11, No. 187, 13 pages (2014).
Law, et al.; "Progress towards a hepatitis C virus vaccine"; Emerging Microbes and Infections; vol. 2, No. 11, 6 pages (2013).
Logan, et al.; "Native Folding of a Recombinant gpE1/gpE2 Heterodimer Vaccine Antigen from a Precursor Protein Fused with Fc IgG"; Journal of Virology; vol. 91, No. 1, 14 pages (Jan. 2017).
Prabdial-Sing, et al.; "Sequence-based in silico analysis of well studied Hepatitis C Virus epitopes and their variants in other genotypes (particularly genotype 5a) against South African human leukocyte antigen backgrounds"; BMC Immunology; vol. 13, No. 67, 15 pages (2012).

(Continued)

*Primary Examiner* — Barry A Chestnut

(74) *Attorney, Agent, or Firm* — Bozicevic, Field & Francis LLP; Shweta Chandra

(57) ABSTRACT

The present disclosure provides heterodimeric polypeptides comprising: 1) a variant hepatitis C virus (HCV) E2 polypeptide and an HCV E1 polypeptide; 2) a variant HCV E1 polypeptide and an HCV E2 polypeptide; or 3) a variant HCV E1 polypeptide and a variant HCV E2 polypeptide, where the variant HCV E2 polypeptide and/or the HCV E1 polypeptide comprises one or more T cell epitopes, present in an HCV polypeptide other than an HCV E1 polypeptide or an HCV E2 polypeptide. The present disclosure provides nucleic acids encoding a polyprotein that includes E1 and variant E2, E2 and variant E1, or variant E2 and variant E1. The present disclosure provides a method of producing an E1/E2 heterodimer of the present disclosure. The present disclosure provides a method of inducing an immune response in an individual. The present disclosure provides variant E2 polypeptides and variant E1 polypeptides; and nucleic acids encoding same.

24 Claims, 55 Drawing Sheets

Specification includes a Sequence Listing.

(56) References Cited

OTHER PUBLICATIONS

Seong, et al.; "Immunogenicity of the E1E2 proteins of hepatitis C virus expressed by recombinant adenoviruses"; Vaccine; vol. 19, pp. 2955-2964 (2001).
Shehzadi, et al; "Promiscuous prediction and conservancy analysis of CTL binding epitopes of HCV 3a viral proteome from Punjab Pakistan: an In *Silico* Approach"; Virology Journal; vol. 8, No. 55, 13 pages (2011).
Terpe, et al.; "Overview of tag protein fusions: from molecular and biochemical fundamentals to commercial systems"; Appl. Microbiol. Biotechnol; vol. 60, No. 5, pp. 523-533 (Jan. 2003).
Verstrepen, et al.; "Immune mechanisms of vaccine induced protection against chronic hepatitis C virus infection in chimpanzees"; World Journal of Hepatology; vol. 7, No. 1, pp. 53-69 (Jan. 27, 2015).
Whidby, et al.; "Blocking hepatitis C virus infection with recombinant form of envelope protein 2 ectodomain"; J. Virol.; vol. 83, No. 21, pp. 11078-11089 (Nov. 2009).
Yusim, et al.; "Hepatitis C Genotype 1 Mosaic Vaccines Are Immunogenic in Mice and Induce Stronger T-Cell Responses than Natural Strains"; Clinical and Vaccine Immunology; vol. 20, No. 2, pp. 302-305 (Feb. 2013).
Zeng, et al.; "A novel combined vaccine candidate containing epitopes of HCV NS3, core and E1 proteins induces multi-specific immune responses in BALB/c mice"; Antiviral Research; vol. 84, pp. 23-30 (2009).

Position markers: 640 650 660 670 680 690 700 710 720 730 740 750

| Group | Sequence ID | Sequence |
|---|---|---|
| | Consensus | YVGGVEHRLXAACNWTRGERCDLDDRDRSELSPLLLSTTQWQVLPCSFTTLPALSTGLIHLHQNIVDVQYLYGVGSSXVSWAIKWEYVILLFLLLADARICXCLWMMLLISQAEA |
| | | E2 protein peptide |
| 1A | AVI1a129 | YLGGVEHRLEAACNWTRGERCDLEDRDRSELSPLLLSTTQWQVLPCSFTTLPALSTGLIHLHQNIVDVQYLYGVGSSVASWAIKWDYVVLLFLLLADARICSCLWMMLLISQAEA |
| 1A | NP_671491(H77) | YVGGVEHRLEAACNWTRGERCDLEDRDRSELSPLLLSTTQWQVLPCSFTTLPALSTGLIHLHQNIVDVQYLYGVGSSIASWAIKWEYVVLLFLLLADARVCSCLWMMLLISQAEA |
| 1A | EU155269 | YVGGVEHRLEVACNWTRGERCDLDDRDRSELSPLLLSTTQWQVLPCSFTTLPALTTGLIHLHQNIVDVQYLYGVGSSIVSWAIKWEYVILLFLLLADARICSCLWMMLLISQAEA |
| 1A | EU781810 | YVGGVEHRLEVACNWTRGERCDLDDRDRSELSPLLLSTTQWQVLPCSFTTLPALTTGLIHLHQNIVDVQYLYGVGSSLVSWAIKWEYVILLFLLLADARICSCLWMMLLISQAEA |
| 1A | EU781771 | YVGGVEHRLQAACNWTRGERCDLDDRDRSELSPLLLSTTQWQVLPCSFTTLPALTTGLIHLHQNIVDVQYLYGVGSSIVSWAIKWEYVILLFLLLADARICSCLWMMLLISQAEA |
| 1A | AB520610 | YVGGVEHRLEVACNWTRGERCDLDDRDRSELSPLLLSTTQWQVLPCSFTTLPALTTGLIHLHQNIVDVQYLYGVGSSIVSWAIKWEYVILLFLLLADARICSCLWMMLLISQAEA |
| 1A | EU781752 | YVGGVEHRLVAACNWTYGERCNLDDRDRSELSPLLLSTTQWQVLPCSFTTLPALTTGLIHLHQNIVDVQYLYGVGSSIVSWAIKWEYVILLFLLLADARICSCLWMMLLISQAEA |
| 1A | EU781759 | YVGGVEHRLEAACNWTRGERCDLDDRDRSELSPLLLSTTQWQVLPCSFTTLPALTTGLIHLHQNIVDVQYLYGVGSSIVSWAIKWEYVILLFLLLADARICSCLWMMLLISQAEA |
| 1A | EF407439 | YVGGVEHRLEAACNWTRGERCNLDDRDRSELSPLLLSTTQWQVLPCSFTTLPALTTGLIHLHQNIVDVQYLYGVGSSIVSWAIKWEYVILLFLLLADARVCSCLWMMLLISQVEA |
| 1A | EF407427 | YVGGVEHRLDVACNWTRGERCNLDDRDRSELSPLLLSTTQWQVLPCSFTTLPALSTGLIHLHQNIVDVQYLYGVGSSIVSWAIKWEYVILLFLLLADARICSCLWMMLLISQAEA |
| 1A | EU362905 | YVGGVEHRLDVACNWTRGERCNLDDRDRSELSPLLLSTTQWQVLPCSFTTLPALSTGLIHLHQNIVDVQYLYGVGSSIVSWAIKWEYVILLFLLLADARICSCLWMMLLISQAEA |
| 1A | EF407413 | YVGGVEHRLDVACNWTRGERCNLDDRDRSELSPLLLSTTQWQVLPCSFTTLPALSTGLIHLHQNIVDVQYLYGVGSSIVSWAIKWEYVILLFLLLADARICSCLWMMLLISQAEA |
| 1A | EU781808 | YVGGIEHRLEVACNWTRGERCNLDDRDRSELSPLLLTTTQWQVLPCSFTTLPALTTGLIHLHQNVVDVQYLYGVGSSIVSWAIKWEYVILLFLLLADARICSCLWMMLLISQAEA |
| 1A | EU781790 | YVGGVEHRLEVACNWTRGERCNLDDRDRSELSPLLLSTTQWQVLPCSFTTLPALTTGLIHLHQNIVDVQYLYGVGSSIVSWAVKWEYVILLFLLLADARICSCLWMMLLISQAEA |
| 1B | AJ238799(Con1) | YVGGVEHRLEAACNWTRGERCNLEDRDRSELSPLLLSTTEWQVLPCSFTTLPALSTGLIHLHQNVVDVQYLYGIGSAVVSFAIKWEYVLLLFLLLADARVCACLWMMLLIAQAEA |
| 1B | AAK97744 | YVGGVEHRLDAACNWTRGERCNLEDRDRLELSPLLLSTTEWQVLPCSFTTLPALSTGLIHLHQNIVDVQYLYGIGSAVVSFAIKWDYIVILFLLLADARVCACLWMMLLIAQAEA |
| 1B | AF139594 | YVGGVEHRLNAACNWTRGERCNLDDRDRSELSPLLLSTTEWQVLPCSFTTLPALSTGLIHLHQNIVDVQYLYGIGSAVVSFAIKWEYVVLLFLLLADARVCACLWMMLLIAQAEA |
| 1B | AF176573 | YVGGVEHRLNAACNWTRGERCDLEDRDRSELSPLLLSTTEWQVLPCSFTTLPALSTGLIHLHQNIVDVQYLYGIGSAVIPFAIKWEYVLLLFLLLADARVCACLWMMLLIAQAEA |
| 1B | BAA19625 | YVGGIEHRLDAACNWTRGERCDLEDRDRSELSPLLLSTTEWQILPCSFTTLPALSTGLIHLHRNIVDVQYLYGIGSAVVSFAIKWEYVLLLFLLLADARVCACLWMMLLIAQAEA |
| 1B | BAA25076 | YVGGVEHRLDAACNWTRGERCDLEDRDRAELSPLLLSTTEWQILPCSYTTLPALSTGLIHLHQNIVDIQYLYGIGSAVVSIAIKWEYVVLLFLLLADARVCACLWMMLLIAQAEA |
| 1B | BAC54896 | YVGGIEHRLDAACNWTRGERCDLEDRDRSELSPLLLSTTEWQILPCSFTTLPALSTGLIHLHRNIVDVQYLYGIGSAVVSFAIKWEYILLLFLLLADARVCACLWMMLLIAQAEA |
| 1B | BAD91386 | YVGGVEHRLDAACNWTRGERCNVEDRDRSELSPLLLSTTEWQILPCSFTTLPALSTGLIHLHQNIVDVQYLYGVGSVVVSVVIRWEYVVLLFLLLADARVCACLWMMLLIAQAEA |
| 1B | BAF46764 | YVGGVEHRLTAACNWTRGERCDLEDRDRSELSPLLLSTTEWQIMPCSFTTLPALSTGLIHLHQNIVDIQYLYGIGSAAVSFAIRWEYVLLLFLLLADARVCACLWMMLLIAQAEA |
| 1B | BAG30950 | YVGGVEHRLTAACNWTRGERCDLEDRDRSELSPLLLSTTEWQIMPCSFTTLPALSTGLIHLHQNIVDIQYLYGIGSAAVSFAIRWEYVLLLFLLLADARVCACLWMMLLIAQAEA |
| 1B | CAB41951 | YVGGIEHRLSAACNWTRGERCDLEDRDRSELSPLLLSTTEWQILPCSFTTLPALSTGLIHLHQNTVDVQYLYGVGSVLVSFAIKWEYILLFFLLLADARVCACLWMMLLIAQAEA |
| 1C | AAK95832 | FVGGIEHRLTAACNWTRGERCDLDDRDRAELSPLLLSTTQWQVLPCSFTTLPALSTGLIHLHQNIVDVQYLYGLSSVVTSWAIRWEYVVLLFLLLADARICACLWMMLLISQVEA |
| 1C | AAT69968 | FVGGVEHRLDAACNWTRGERCDLDDRDRAELSPLLLSTTQWQVLPCSFTTLPALSTGLIHLHQNIVDVQYLYGLSSAVTSWVIKWEYVVLLFLLLADARICACLWMMLLISQVEA |
| 1C | BAA03581 | FVGGVEHRLDAACNWTRGERCDLDDRDRAELSPLLLSTTQWQVLPCSFTTLPALSTGLIHLHQNIVDVQYLYGLSSAVTSWVIKWEYVVLLFLLLADARICACLWMMLLISQVEA |

FIG. 1C

```
             1        10        20        30        40        50        60        70        80
Consensus           MSTLPKPQRKTKRNTIRRPQDVKFPGGGQIVGGVYVLPRRGPRLGVRATRKTSERSQPRGRRQPIPKARRSEGRSWAQPGYPWPLYGN
                    Core
3A  AVI3a177        MSTLPKPQRKTKRNTIRRPQDVKFPGGGQIVGGVYVLPRRGPRLGVRATRKTSERSQPRERRQPIPKARRSDGRSWAQPGYPWPLYGN
    ADF97232(S52)   MSTLPKPQRKTKRNTIRRPQDVKFPGGGQIVGGVYVLPRRGPRLGVRATRKTSERSQPRGRRQPIPKARRSEGRSWAQPGYPWPLYGN
    YP_001469631    MSTLPKPQRKTKRNTIRRPQDVKFPGGGQIVGGVYVLPRRGPRLGVRATRKTSERSQPRGRRQPIPKARRSEGRSWAQPGYPWPLYGN
    CAA54244        MSTLPKPQRKTKRNTIRRPQDVKFPGGGQIVGGVYVLPRRGPRLGVRATRKTSERSQPRGRRQPIPKARRSEGRSWAQPGYPWPLYGN
    AAC03058        MSTLPKPQRKTKRNTIRRPQDVKFPGGGQIVGGVYVLPRRGPRLGVCATRKTSERSQPRRRRQPIPKARQSGGRSWAQPGYPWPLYGN
    AAY29642        MSTLPKPQRKTKRNTVCRPQDVKFPGGGQIVGGVYVLPRRGPRLGVRATRKTSERSQPRGRRQPIPKARRSEGRSWAQPGYPWPLYGN
    ABD85062        MSTLPKPQRKTKRNTIRRPQDVKFPGGGQIVGGVYVLPRRGPRLGVRATRKTSERSQPRGRRQPIPKARRSEGRSWAQPGYPWPLYGN
    ABD85063        MSTLPKPQRKTKRNTIRRPQDVKFPGGGQIVGGVYVLPRRGPRLGVRATRKTSERSQPRGRRQPIPKARRSEGRSWAQPGYPWPLYGN
    ABD97104        MSTLPKPQRKTKRNTIRRPQDVKFPGGGQIVGGVYVLPRRGPRLGVCATRKTSERSQPRGRRQPIPKARRSEGRSWAQPGYPWPLYGN
    BAA06044        MSTLPKPQRKTKRNTIRRPQDVKFPGGGVIYVGVYVLPRRGPRLGVRATRKTSERSQPRGRRKPIPKARRSEGRSWAQPGYPWPLYGN
3B  BAA08372        MSTLPKPKRQTKRNTLRRPKNVKFPAGGQIVGEVYVLPRRGPQLGVREVRKTSERSQPRGRRQPTPKARPREGRSWAQPGYPWPLYGN
3K  BAA09890        MSTLPKPQRITKRNINRRPQDVKFPGGGQIVGGVYVLPRRGPKLGVRAVRKTSERSQPRSRRQPIPRARRTEGRSWAQPGYPWPLYGN

              90       100       110       120       130       140       150       160       170
Consensus           EGCGWAGWLLSPRGSRPSWGPNDPRRRSRNLGKVIDTLTCGFADLMGYIPLVGAPVGGVARALAHGVRALEDGINFATGNLPGCSFSI
                    Core
3A  AVI3a177        EGCGWAGWLLSPRGSRPSWGPNDPRRRSRNLGKVIDTLTCGFADLMGYIPIVGAPVGGVARALAHGVRALEDGINFATGNLPGCSFSI
    ADF97232(S52)   EGCGWAGWLLSPRGSRPSWGPNDPRRRSRNLGKVIDTLTCGFADLMGYIPLVGAPVGGVARALAHGVRALEDGINFATGNLPGCSFSI
    YP_001469631    EGCGWAGWLLSPRGSRPSWGPNDPRRRSRNLGKVIDTLTCGFADLMGYIPLVGAPVGGVARALAHGVRALEDGINFATGNLPGCSFSI
    CAA54244        EGCGWAGWLLSPRGSRPSWGQNDPRRRSRNLGKVIDTLTCGFADLMGYIPLVGAPVGGVARALAHGVRALEDGINFATGNLPGCSFSI
    AAC03058        EGCGWAGWLLSPRGSRPSWGPNDPRRRSRNLGKVIDTLTCGFADLMGYIPLVGAPVGGVARALAHGVRALEDGINFATGNLPGCSFSI
    AAY29642        EGCGWAGWLLSPRGSRPSWGPNDPRRRSRNLGKVIDTLTCGFADLMGYIPLVGAPVGGVARALAHGVRALEDGINFATGNLPGCSFSI
    ABD85062        EGCGWAGWLLSPRGSRPSWGPNDPRRRSRNLGKVIDTLTCGFADLMGYIPLVGAPVGGVARALAHGVRALEDGINFATGNLPGCSFSI
    ABD85063        EGCGWAGWLLSPRGSRPSWGPNDPRRRSRNLGKVIDTLTCGFADLMGYIPLVGAPVGGVARALAHGVRALEDGINFATGNLPGCSFSI
    ABD97104        EGCGWAGWLLSPRGSRPSWGPNDPRRRSRNLGKVIDTLTCGFADLMGYIPLVGAPVGGVARALAHGVRALEDGINFATGNLPGCSFSI
    BAA06044        EGCGWAGWLLSPRGSRPNWAPNDPRRRSRNLGKVIDTLTCGFADLMGYIPLVGAPLGGAARALAHGVRALEDGINFATGNLPGCSFSI
3B  BAA08372        EGCGWAGWLLPPRGSRPSWGQNDPRRRSRNLGKVIDTLTCGFADLMGYIPLIGAPVGGVARALAHGVRALEDGVNYATGNLPGCSFSI
3K  BAA09890        EGCGWAGWLLSPRGSRPSWGPNDPRRRSRNLGKVIDTLTCGFADLMGYIPLVGAPVGGVARALAHGVRALEDGINFATGNLPGCSFSI

             180       190       200       210       220       230       240       250       260
Consensus           FLLALFSCLIHPAASLEWRNTSGLYVLTNDCSNSSIVYEADDVILHTPGCVPCVQ-DGNTSTCWTPVTPTVAVRYVGATTASIRSHVD
                    Core         E1
3A  AVI3a177        FLLALLSCLIHPAASLEWRNTSGLYILTNDCPNSSIVYEADDVILHTPGCIPCVQ-DGNTSTCWTSVSPTVAVRYVGATTASIRSHVD
    ADF97232(S52)   FLLALFSCLVHPAASLEWRNTSGLYVLTNDCSNSSIVYEADDVILHTPGCVPCVQ-DDNTSTCWTPVTPTVAVRYVGATTASIRSHVD
    YP_001469631    FLLALFSCLIHPAASLEWRNTSGLYVLTNDCSNSSIVYEADDVILHTPGCVPCVQ-DGNTSTCWTPVTPTVAVRYVGATTASIRSHVD
    CAA54244        FLLALFSCLIHPAASLEWRNTSGLYVLTNDCSNSSIVYEADDVILHTPGCVPCVQ-DGNTSTCWTPVTPTVAVRYVGATTASIRSHVD
    AAC03058        FLLALFSCLIHPAASLEWRNTSGLYVLTNDCSNSSIVYEADDVILHTPGCVPCVQ-NDNISTCWTPVTPTVAVRYVGATTASIRSHVD
    AAY29642        FLLALFSCLIHPAASLEWRNVSGLYILTNDCPNSSIVYEADDVILHTPGCIPCVQ-DGNTSTCWTALTPTVAVRYVGATTASIRSHVD
    ABD85062        FLLALFSCLIHPAASLQWRNTSGLYVLTNDCSNSSIVYEADDVILHTPGCVPCVQ-DGNTSTCWTPVTPTVAVRYVGATTASIRSHVD
    ABD85063        FLLALFSCLIHPAASLQWRNTSGLYVLTNDCSNSSIVYEADDVILHTPGCVPCVQ-DGNTSTCWTPVTPTVAVRYVGATTASIRSHVD
    ABD97104        FLLALFSCLVHPAASLEWRNTSGLYVLTNDCPNSSIVYEADDVILHTPGCIPCVQ-DGNKSTCWTSVTPTVAVKYVGATTASIRSHVD
    BAA06044        FLLALFSCLIHPAASLEWRNTSGLYVLTNDCSNSSIVYEADDVILHTPGCIPCVQ-DGNTSTCWTPVTPTVAVRYVGATTASIRSHVD
3B  BAA08372        FLLALFSCLTCPASSLEYRNASGLYLLTNDCSNRSIVYEADDVILHLPGCVPCVETDNNNTSCWTPISPTVAVKHPGVTTASIRNHVN
3K  BAA09890        FLLALLSCLLTPTAGLEYRNASGLYTVTNDCSNGSIVYEAGDVILHLPGCIPCVR-LNNASKCWTPVSPTVAVSRPGAATASLRTHVD
```

FIG. 3A

Positions 530–616 (E2)

| Group | Sequence | 530–616 |
|---|---|---|
| | Consensus | YTWGENETDVFLLESLRPPSGRWFGCTWMNSTGFVKTCGAPPCNIYGGGGNPH-NESDLFCPTDCFRKHPEATYSRCGAGPWLTPRCM |
| 3A | AVI3a177 | YTWGENETDVFLLRSLRPPSGQWFGCTWMNSTGFVKTCGAPPCDIYGGGGNRC-NESDLFCPTDCFRKHPEATYSRCGAGPWLTPRCL |
| 3A | ADF97232(S52) | YNWGENETDVFLLESLRPPSGRWFGCAWMNSTGFLKTCGAPPCNIYGGEGDPE-NETDLFCPTDCFRKHPEATYSRCGAGPWLTPRCM |
| 3A | YP_001469631 | YTWGENEKDVFLLKSQRPPSGRWFGCSWMNSTGFLKTCGAPPCNIYGGEGNPH-NESDLFCPTDCFRKHPETTYSRCGAGPWLTPRCM |
| 3A | CAA54244 | YNWGENESDVFLLESLRPPSGRWFGCAWMNSTGFLKTCGAPPCNIYGGGGNPN-NESHLFCPTDCFRKHPDATYSRCGAGPWLTPRCM |
| 3A | AAC03058 | YTWGANDTDVFLLESLRPPGGRWFGCTWMNSTGFVKTCGASPCDIYGGGGNSG-NESDLFCPTDCFRKHPEATYSRCGAGPWLTPRCM |
| 3A | AAY29642 | YTWGENETDVFLLKSLRPPGGRWFGCTWMNSTGFVQTCGAPPCNIYGGGGDLK-NESDLFCPTDCFRKHPEATYSRCGAGPWLTPRCM |
| 3A | ABD85062 | YTWGANETDVFLLESLRPPSGRWFGCAWMNSTGFLKTCGAPPCNIYGGGGNPH-NESDLFCPTDCFRKHPEATYSRCGAGPWLTPRCM |
| 3A | ABD85063 | YTWGANETDVFLLESLRPPSGRWFGCAWMNSTGFLKTCGAPPCNIYGGGGNPH-NESDLFCPTDCFRKHPEATYSRCGAGPWLTPRCM |
| 3A | ABD97104 | YNWGANETDMFLLQSLRPPSGRWFGCTWMNSTGFTKTCGAPPCNIYGGGGNLN-NESDLFCPTDCFRKHPEATYSRCGAGPWLTPRCL |
| 3A | BAA06044 | YTWGANKTDVFLLESLRPPSGRWFGCTWMNSTGFVKTCGAPPCNIYGDGRDAQ-NESDLFCPTDCFRKHPEATYSRCGAGPWLTPRCL |
| 3B | BAA08372 | YRFGVNESDVFLLTSLRPPQGRWFGCVWMNSTGFVKTCGAPPCNIYGGMKDIEANQTHLKCPTDCFRKHHDATFTRCGSGPWLTPRCL |
| 3K | BAA09890 | YTWGENESDVFLLESARPPTEPWFGCTWMNGSGYVKTCGAPPCHIYGGREGK--SNNSLVCPTDCFRKHPDATYNRCGAGPWLTPRCL |

Positions 620–704 (E2)

| Group | Sequence | 620–704 |
|---|---|---|
| | Consensus | VDYPYRLWHYPCTVNFTLFKVRMFVGGFEHRFTAACNWTRGERCDIEDRDRSEQHPLLHSTTELAILPCSFTPMPALSTGLIHLHQNI |
| 3A | AVI3a177 | VDYPYRLWHYPCTVNFTLFKVRMFVGGFEHRFTAACNWTRGERCNIEDRDRSEQHPLLHSTTELAILPCSFTPMPALSTGLIHLHQNI |
| 3A | ADF97232(S52) | VDYPYRLWHYPCTVNFTLFKVRMFVGGFEHRFTAACNWTRGERCNIEDRDRSEQHPLLHSTTELAILPCSFTPMPALSTGLIHLHQNI |
| 3A | YP_001469631 | VDYPYRLWHYPCTVDFRLFKVRMFVGGFEHRFTAACNWTRGERCDIEDRDRSEQHPLLHSTTELAILPCSFTPMPALSTGLIHLHQNI |
| 3A | CAA54244 | VDYPYRLWHYPCTVNFTLFKVRMFVGGFEHRFTAACNWTRGERCNIEDRDRSEQHPLLHSTTELAILPCSFTPMPALSTGLIHLHQNI |
| 3A | AAC03058 | VDYPYRLWHYPCTVNFTLFKVRMFVGGFEHRFTAACNWTRGERCDIEDRDRSEQHPLLHSTTELAILPCSFTPMPALSTGLIHLHQNI |
| 3A | AAY29642 | VDYPYRLWHYPCTVNFTLFKVRMFVGGFEHRFTAACNWTRGERCDIEDRDRSELHPLLHSTTELAILPCSFTPMPALSTGLIHLHQNI |
| 3A | ABD85062 | VDYPYRLWHYPCTVNFTLFKMRTFVGGFEHRFTAACNWTRGERCDIEDRDRSEQHPLLHSTTELAILPCSFTPMPALSTGLIHLHQNI |
| 3A | ABD85063 | VDYPYRLWHYPCTVNFTLFKMRTFVGGFEHRFTAACNWTRGERCDIEDRDRSEQHPLLHSTTELAILPCSFTPMPALSTGLIHLHQNI |
| 3A | ABD97104 | VDYPYRLWHYPCTVNFTLFRMRTFVGGFEHRFTAACNWTRGERCNIEDRDRSEQHPLLHSTTELAILPCSFTPMPALSTGLIHLHQNI |
| 3A | BAA06044 | VDYPYRLWHYPCTVNFTLFKVRMFVGGFEHRFTAACNWTRGERCDIEDRDRSEQHPLLHSTTELAILPCSFTPMPALSTGLIHLHQNI |
| 3B | BAA08372 | VDYPYRLWHYPCTVNFSIFKVRMFVGGHEHRFSAACNWTRGERCDLEDRDRSEQQPLLHSTTDSLILPCSFTPMRRLSTGLIHLHQNI |
| 3K | BAA09890 | VDYPYRLWHYPCTVNYTIFKVRMFVGGLEHRFNAACNWTRGERCNLEDRDRSEMYPLLHSTTEQAILPCSFVPIPALSTGLIHLHQNI |

Positions 710–754 (E2)

| Group | Sequence | 710–754 |
|---|---|---|
| | Consensus | VDVQYLYGVGSGMVGWALKWEFVILVFLLLADARVCVALWLMLMISQAEA |
| 3A | AVI3a177 | VDVQYLYGVGSGVVGWALRWEFVVLVFLLLADARVCVALWLMLMISQAEA |
| 3A | ADF97232(S52) | VDVQYLYGVGSDMVGWALKWEFVILVFLLLADARVCVALWLMLMVSQAEA |
| 3A | YP_001469631 | VDVQYLYGVGSGMVGWALKWEFVILVFLLLADARVCVALWLMLMISQTEA |
| 3A | CAA54244 | VDVQYLYGVGSGMVGWALKWEFVILIFLLLADARVCVALWLMLMISQAEA |
| 3A | AAC03058 | VDVQYLYGVGSGMVGWALKWEFVILIFLLLADRRVCVALWLMLMITQAEA |
| 3A | AAY29642 | VDVQYLYGVGSGMVGWAVKWEFVILVFLLLADARVCVALWLMLMISQAEA |
| 3A | ABD85062 | VDVQYLYGVGSGMVGWALKWEFVILVFLLLADARVCVALWLMLMISQAEA |
| 3A | ABD85063 | VDVQYLYGVGSGMVGWALKWEFVILVFLLLADARVCVALWLMLMISQAEA |
| 3A | ABD97104 | VDVQYLYGIGSGVVGWALKWEFVILVFLLLADARVCVALWLMLMISQAEA |
| 3A | BAA06044 | VDVQYLYGIGSGMVGWALKWEFVILIFLLLADARVCVALWLILTISQAEA |
| 3B | BAA08372 | VDVQYLYGVGSAVVGWALKWEFVVLVFLLLADARVCVALWMMLLISQAEA |
| 3K | BAA09890 | VDVQYLYGISSGLVGWAIKWEFVILIFLLLADARVCVVLWMMMLISQAEA |

FIG. 3C

```
                    1         10         20         30         40         50         60         70         80
AVI1a129         MDAMKRGLCCVLLLCGAVFVSPSYQVRNSTGLYHVTNDCPNSSIVYEAADAILHTPGCVPCVREGNTSRCWVAMTPTVATRDGK
AVI1a129 TP29    MDAMKRGLCCVLLLCGAVFVSPSYQVRNSTGLYHVTNDCPNSSIVYEAADAILHTPGCVPCVREGNTSRCWVAMTPTVATRDGK
AVI1a129 TP52    MDAMKRGLCCVLLLCGAVFVSPSYQVRNSTGLYHVTNDCPNSSIVYEAADAILHTPGCVPCVREGNTSRCWVAMTPTVATRDGK
AVI1a129 TP100   MDAMKRGLCCVLLLCGAVFVSPSYQVRNSTGLYHVTNDCPNSSIVYEAADAILHTPGCVPCVREGNTSRCWVAMTPTVATRDGK
H77              MDAMKRGLCCVLLLCGAVFVSPSYQVRNSSGLYHVTNDCPNSSIVYEAADAILHTPGCVPCVREGNASRCWVAVTPTVATRDGK
H77 TP29         MDAMKRGLCCVLLLCGAVFVSPSYQVRNSSGLYHVTNDCPNSSIVYEAADAILHTPGCVPCVREGNASRCWVAVTPTVATRDGK
H77 TP52         MDAMKRGLCCVLLLCGAVFVSPSYQVRNSSGLYHVTNDCPNSSIVYEAADAILHTPGCVPCVREGNASRCWVAVTPTVATRDGK
H77 TP100        MDAMKRGLCCVLLLCGAVFVSPSYQVRNSSGLYHVTNDCPNSSIVYEAADAILHTPGCVPCVREGNASRCWVAVTPTVATRDGK
                 tPA Signal Sequence                                    E1

                    90        100        110        120        130        140        150        160
AVI1a129         LPTTQLRRHIDLLVGSATLCSALYVGDLCGSIFLVGQMFTFSPRRHWTTQDCNCSLYPGHITGHRMAWDMMMNWSPTAALITAQ
AVI1a129 TP29    LPTTQLRRHIDLLVGSATLCSALYVGDLCGSIFLVGQMFTFSPRRHWTTQDCNCSLYPGHITGHRMAWDMMMNWSPTAALITAQ
AVI1a129 TP52    LPTTQLRRHIDLLVGSATLCSALYVGDLCGSIFLVGQMFTFSPRRHWTTQDCNCSLYPGHITGHRMAWDMMMNWSPTAALITAQ
AVI1a129 TP100   LPTTQLRRHIDLLVGSATLCSALYVGDLCGSIFLVGQMFTFSPRRHWTTQDCNCSLYPGHITGHRMAWDMMMNWSPTAALITAQ
H77              LPTTQLRRHIDLLVGSATLCSALYVGDLCGSVFLVGQLFTFSPRRHWTTQDCNCSIYPGHITGHRMAWDMMMNWSPTAALVVAQ
H77 TP29         LPTTQLRRHIDLLVGSATLCSALYVGDLCGSVFLVGQLFTFSPRRHWTTQDCNCSIYPGHITGHRMAWDMMMNWSPTAALVVAQ
H77 TP52         LPTTQLRRHIDLLVGSATLCSALYVGDLCGSVFLVGQLFTFSPRRHWTTQDCNCSIYPGHITGHRMAWDMMMNWSPTAALVVAQ
H77 TP100        LPTTQLRRHIDLLVGSATLCSALYVGDLCGSVFLVGQLFTFSPRRHWTTQDCNCSIYPGHITGHRMAWDMMMNWSPTAALVVAQ
                                                          E1

                    170       180        190        200        210        220        230        240        250
AVI1a129         LLRIPQAILDMIAGAHWGVLAGIAYFSMVGNWAKVLVVLLLFAGVDAQTDKTHTCPPCPAPEAEGAPSVFLFPPKPKDTLMISR
AVI1a129 TP29    LLRIPQAILDMIAGAHWGVLAGIAYFSMVGNWAKVLVVLLLFAGVDAQTDKTHTCPPCPAPEAEGAPSVFLFPPKPKDTLMISR
AVI1a129 TP52    LLRIPQAILDMIAGAHWGVLAGIAYFSMVGNWAKVLVVLLLFAGVDAQTDKTHTCPPCPAPEAEGAPSVFLFPPKPKDTLMISR
AVI1a129 TP100   LLRIPQAILDMIAGAHWGVLAGIAYFSMVGNWAKVLVVLLLFAGVDAQTDKTHTCPPCPAPEAEGAPSVFLFPPKPKDTLMISR
H77              LLRIPQAIMDMIAGAHWGVLAGIAYFSMVGNWAKVLVVLLLFAGVDAETDKTHTCPPCPAPEAEGAPSVFLFPPKPKDTLMISR
H77 TP29         LLRIPQAIMDMIAGAHWGVLAGIAYFSMVGNWAKVLVVLLLFAGVDAETDKTHTCPPCPAPEAEGAPSVFLFPPKPKDTLMISR
H77 TP52         LLRIPQAIMDMIAGAHWGVLAGIAYFSMVGNWAKVLVVLLLFAGVDAETDKTHTCPPCPAPEAEGAPSVFLFPPKPKDTLMISR
H77 TP100        LLRIPQAIMDMIAGAHWGVLAGIAYFSMVGNWAKVLVVLLLFAGVDAETDKTHTCPPCPAPEAEGAPSVFLFPPKPKDTLMISR
                                         E1                          ↑*            FC Tag

                    260       270        280        290        300        310        320        330
AVI1a129         TPEVTCVVVDVSHEDPEVKFNWYVDGVEVHNAKTKPREEQYNSTYRVVSVLTVLHQDWLNGKEYKCKVSNKALPAPIEKTISKA
AVI1a129 TP29    TPEVTCVVVDVSHEDPEVKFNWYVDGVEVHNAKTKPREEQYNSTYRVVSVLTVLHQDWLNGKEYKCKVSNKALPAPIEKTISKA
AVI1a129 TP52    TPEVTCVVVDVSHEDPEVKFNWYVDGVEVHNAKTKPREEQYNSTYRVVSVLTVLHQDWLNGKEYKCKVSNKALPAPIEKTISKA
AVI1a129 TP100   TPEVTCVVVDVSHEDPEVKFNWYVDGVEVHNAKTKPREEQYNSTYRVVSVLTVLHQDWLNGKEYKCKVSNKALPAPIEKTISKA
H77              TPEVTCVVVDVSHEDPEVKFNWYVDGVEVHNAKTKPREEQYNSTYRVVSVLTVLHQDWLNGKEYKCKVSNKALPAPIEKTISKA
H77 TP29         TPEVTCVVVDVSHEDPEVKFNWYVDGVEVHNAKTKPREEQYNSTYRVVSVLTVLHQDWLNGKEYKCKVSNKALPAPIEKTISKA
H77 TP52         TPEVTCVVVDVSHEDPEVKFNWYVDGVEVHNAKTKPREEQYNSTYRVVSVLTVLHQDWLNGKEYKCKVSNKALPAPIEKTISKA
H77 TP100        TPEVTCVVVDVSHEDPEVKFNWYVDGVEVHNAKTKPREEQYNSTYRVVSVLTVLHQDWLNGKEYKCKVSNKALPAPIEKTISKA
                                                          FC Tag

                    340       350        360        370        380        390        400        410        420
AVI1a129         KGQPREPQVYTLPPSREEMTKNQVSLTCLVKGFYPSDIAVEWESNGQPENNYKTTPPVLDSDGSFFLYSKLTVDKSRWQQGNVF
AVI1a129 TP29    KGQPREPQVYTLPPSREEMTKNQVSLTCLVKGFYPSDIAVEWESNGQPENNYKTTPPVLDSDGSFFLYSKLTVDKSRWQQGNVF
AVI1a129 TP52    KGQPREPQVYTLPPSREEMTKNQVSLTCLVKGFYPSDIAVEWESNGQPENNYKTTPPVLDSDGSFFLYSKLTVDKSRWQQGNVF
AVI1a129 TP100   KGQPREPQVYTLPPSREEMTKNQVSLTCLVKGFYPSDIAVEWESNGQPENNYKTTPPVLDSDGSFFLYSKLTVDKSRWQQGNVF
H77              KGQPREPQVYTLPPSREEMTKNQVSLTCLVKGFYPSDIAVEWESNGQPENNYKTTPPVLDSDGSFFLYSKLTVDKSRWQQGNVF
H77 TP29         KGQPREPQVYTLPPSREEMTKNQVSLTCLVKGFYPSDIAVEWESNGQPENNYKTTPPVLDSDGSFFLYSKLTVDKSRWQQGNVF
H77 TP52         KGQPREPQVYTLPPSREEMTKNQVSLTCLVKGFYPSDIAVEWESNGQPENNYKTTPPVLDSDGSFFLYSKLTVDKSRWQQGNVF
H77 TP100        KGQPREPQVYTLPPSREEMTKNQVSLTCLVKGFYPSDIAVEWESNGQPENNYKTTPPVLDSDGSFFLYSKLTVDKSRWQQGNVF
                                                          FC Tag

                    430       440        450        460        470        480        490        500
AVI1a129         SCSVMHEALHNHYTQKSLSLSPGKLEVLFQGP--------------------------------
AVI1a129 TP29    SCSVMHEALHNHYTQKSLSLSPGKLEVLFQGP--------------AIPLEVIKGGRHLIFCHSKKKCDELAAKL---------
AVI1a129 TP52    SCSVMHEALHNHYTQKSLSLSPGKLEVLFQGP--------------AIPLEVIKGGRHLIFCHSKKKCDELAAKLVALGINAVA
AVI1a129 TP100   SCSVMHEALHNHYTQKSLSLSPGKLEVLFQGPVALSTTGEIPFYGKAIPLEVIKGGRHLIFCHSKKKCDELAAKLVALGINAVA
H77              SCSVMHEALHNHYTQKSLSLSPGKLEVLFQGP--------------------------------
H77 TP29         SCSVMHEALHNHYTQKSLSLSPGKLEVLFQGP--------------AIPLEVIKGGRHLIFCHSKKKCDELAAKL---------
H77 TP52         SCSVMHEALHNHYTQKSLSLSPGKLEVLFQGP--------------AIPLEVIKGGRHLIFCHSKKKCDELAAKLVALGINAVA
H77 TP100        SCSVMHEALHNHYTQKSLSLSPGKLEVLFQGPVALSTTGEIPFYGKAIPLEVIKGGRHLIFCHSKKKCDELAAKLVALGINAVA
                           FC Tag               PP Site                TPx
```

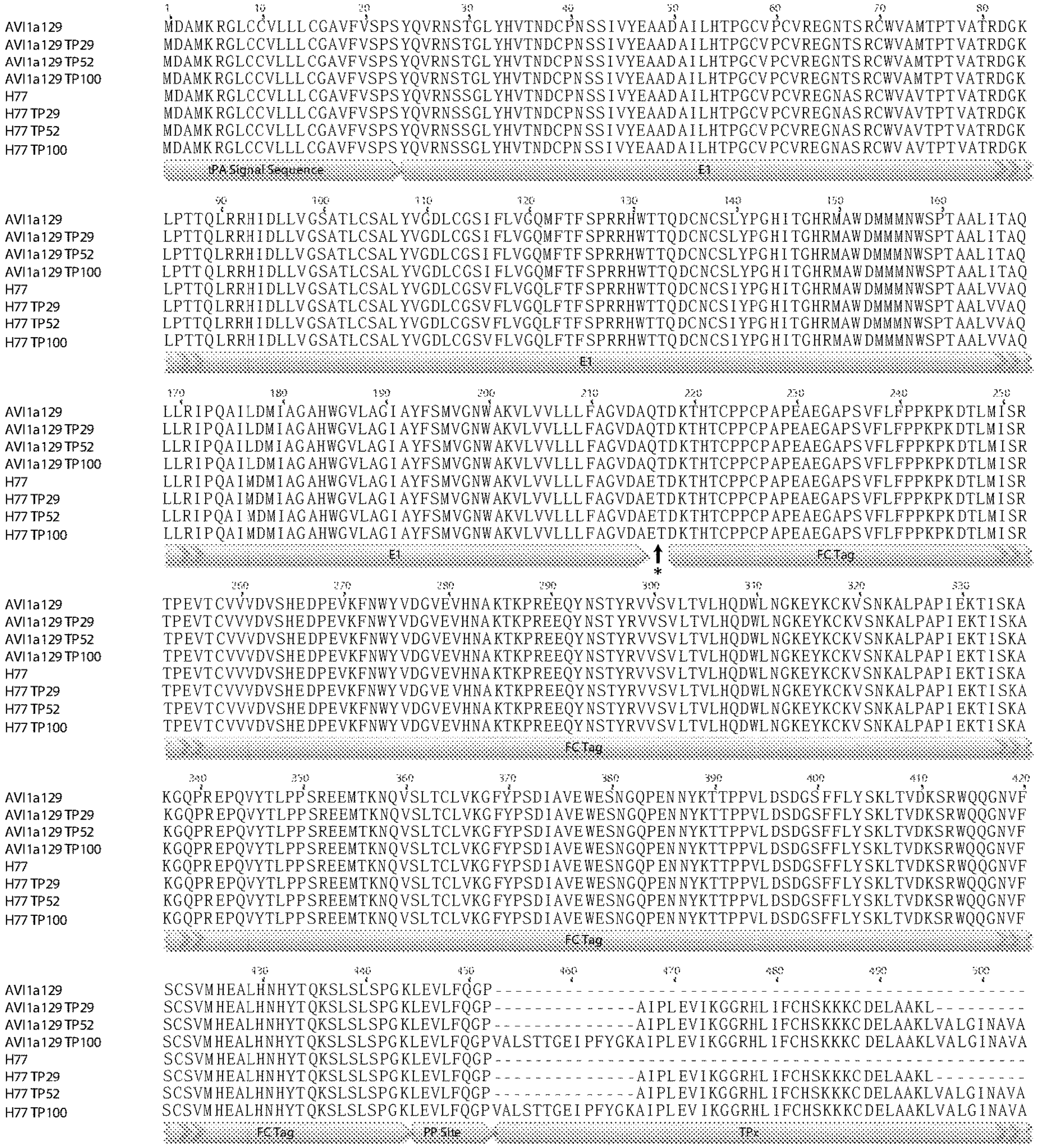

FIG. 6A

```
                510       520       530       540       550       560       570       580
AVI1a129        ------------------------------------------------QTHVTGGRAAHITAGLTSLFSPGPSQKLQLVNTNGS
AVI1a129 TP29   ------------------------------------------------QTHVTGGRAAHITAGLTSLFSPGPSQKLQLVNTNGS
AVI1a129 TP52   YYRGLDVSVIPTS-----------------------------------QTHVTGGRAAHITAGLTSLFSPGPSQKLQLVNTNGS
AVI1a129 TP100  YYRGLDVSVIPTSGDVVVVATDALMTGFTGDFDSVIDCNTCVTQTVDFQTHVTGGRAAHITAGLTSLFSPGPSQKLQLVNTNGS
H77             ------------------------------------------------ETHVTGGSAGRTTAGLVGLLTPGAKQNIQLINTNGS
H77 TP29        ------------------------------------------------ETHVTGGSAGRTTAGLVGLLTPGAKQNIQLINTNGS
H77 TP52        YYRGLDVSVIPTS-----------------------------------ETHVTGGSAGRTTAGLVGLLTPGAKQNIQLINTNGS
H77 TP100       YYRGLDVSVIPTSGDVVVVATDALMTGFTGDFDSVIDCNTCVTQTVDFETHVTGGSAGRTTAGLVGLLTPGAKQNIQLINTNGS
                TPx                                             E2 Protein

                590       600       610       620       630       640       650       660       670
AVI1a129        WHINSTALNCNDSLKTGWIAGLLYSYKFNSSGCPERLASCRRLTDFAQGWGPISHANGSGPDERPYCWHYPPRPCGIVPAKSVC
AVI1a129 TP29   WHINSTALNCNDSLKTGWIAGLLYSYKFNSSGCPERLASCRRLTDFAQGWGPISHANGSGPDERPYCWHYPPRPCGIVPAKSVC
AVI1a129 TP52   WHINSTALNCNDSLKTGWIAGLLYSYKFNSSGCPERLASCRRLTDFAQGWGPISHANGSGPDERPYCWHYPPRPCGIVPAKSVC
AVI1a129 TP100  WHINSTALNCNDSLKTGWIAGLLYSYKFNSSGCPERLASCRRLTDFAQGWGPISHANGSGPDERPYCWHYPPRPCGIVPAKSVC
H77             WHINSTALNCNESLNTGWLAGLFYQHKFNSSGCPERLASCRRLTDFAQGWGPISYANGSGLDERPYCWHYPPRPCGIVPAKSVC
H77 TP29        WHINSTALNCNESLNTGWLAGLFYQHKFNSSGCPERLASCRRLTDFAQGWGPISYANGSGLDERPYCWHYPPRPCGIVPAKSVC
H77 TP52        WHINSTALNCNESLNTGWLAGLFYQHKFNSSGCPERLASCRRLTDFAQGWGPISYANGSGLDERPYCWHYPPRPCGIVPAKSVC
H77 TP100       WHINSTALNCNESLNTGWLAGLFYQHKFNSSGCPERLASCRRLTDFAQGWGPISYANGSGLDERPYCWHYPPRPCGIVPAKSVC
                E2 Protein

                680       690       700       710       720       730       740       750
AVI1a129        GPVYCFTPSPVVVGTTDKSGAPTYNWGENDWDVFVLNNTRPPLGNWFGCTWMNSTGFTKVCGAPPCVIGGAGNNTLRCPTDCFR
AVI1a129 TP29   GPVYCFTPSPVVVGTTDKSGAPTYNWGENDWDVFVLNNTRPPLGNWFGCTWMNSTGFTKVCGAPPCVIGGAGNNTLRCPTDCFR
AVI1a129 TP52   GPVYCFTPSPVVVGTTDKSGAPTYNWGENDWDVFVLNNTRPPLGNWFGCTWMNSTGFTKVCGAPPCVIGGAGNNTLRCPTDCFR
AVI1a129 TP100  GPVYCFTPSPVVVGTTDKSGAPTYNWGENDWDVFVLNNTRPPLGNWFGCTWMNSTGFTKVCGAPPCVIGGAGNNTLRCPTDCFR
H77             GPVYCFTPSPVVVGTTDRSGAPTYSWGANDTDVFVLNNTRPPLGNWFGCTWMNSTGFTKVCGAPPCVIGGVGNNTLLCPTDCFR
H77 TP29        GPVYCFTPSPVVVGTTDRSGAPTYSWGANDTDVFVLNNTRPPLGNWFGCTWMNSTGFTKVCGAPPCVIGGVGNNTLLCPTDCFR
H77 TP52        GPVYCFTPSPVVVGTTDRSGAPTYSWGANDTDVFVLNNTRPPLGNWFGCTWMNSTGFTKVCGAPPCVIGGVGNNTLLCPTDCFR
H77 TP100       GPVYCFTPSPVVVGTTDRSGAPTYSWGANDTDVFVLNNTRPPLGNWFGCTWMNSTGFTKVCGAPPCVIGGVGNNTLLCPTDCFR
                E2 Protein

                760       770       780       790       800       810       820       830       840
AVI1a129        KHPDATYSRCGSGPWITPRCLVDYPYRLWHYPCTVNYSIFKIRMYLGGVEHRLEAACNWTRGERCDLEDRDRSELSPLLLSTTQ
AVI1a129 TP29   KHPDATYSRCGSGPWITPRCLVDYPYRLWHYPCTVNYSIFKIRMYLGGVEHRLEAACNWTRGERCDLEDRDRSELSPLLLSTTQ
AVI1a129 TP52   KHPDATYSRCGSGPWITPRCLVDYPYRLWHYPCTVNYSIFKIRMYLGGVEHRLEAACNWTRGERCDLEDRDRSELSPLLLSTTQ
AVI1a129 TP100  KHPDATYSRCGSGPWITPRCLVDYPYRLWHYPCTVNYSIFKIRMYLGGVEHRLEAACNWTRGERCDLEDRDRSELSPLLLSTTQ
H77             KHPEATYSRCGSGPWITPRCMVDYPYRLWHYPCTINYTIFKVRMYVGGVEHRLEAACNWTRGERCDLEDRDRSELSPLLLSTTQ
H77 TP29        KHPEATYSRCGSGPWITPRCMVDYPYRLWHYPCTINYTIFKVRMYVGGVEHRLEAACNWTRGERCDLEDRDRSELSPLLLSTTQ
H77 TP52        KHPEATYSRCGSGPWITPRCMVDYPYRLWHYPCTINYTIFKVRMYVGGVEHRLEAACNWTRGERCDLEDRDRSELSPLLLSTTQ
H77 TP100       KHPEATYSRCGSGPWITPRCMVDYPYRLWHYPCTINYTIFKVRMYVGGVEHRLEAACNWTRGERCDLEDRDRSELSPLLLSTTQ
                E2 Protein

                850       860       870       880       890       900       910  915
AVI1a129        WQVLPCSFTTLPALSTGLIHLHQNIVDVQYLYGVGSSVASWAIKWDYVVLLFLLLADARICSCLWMMLLISQAEA
AVI1a129 TP29   WQVLPCSFTTLPALSTGLIHLHQNIVDVQYLYGVGSSVASWAIKWDYVVLLFLLLADARICSCLWMMLLISQAEA
AVI1a129 TP52   WQVLPCSFTTLPALSTGLIHLHQNIVDVQYLYGVGSSVASWAIKWDYVVLLFLLLADARICSCLWMMLLISQAEA
AVI1a129 TP100  WQVLPCSFTTLPALSTGLIHLHQNIVDVQYLYGVGSSVASWAIKWDYVVLLFLLLADARICSCLWMMLLISQAEA
H77             WQVLPCSFTTLPALSTGLIHLHQNIVDVQYLYGVGSSIASWAIKWEYVVLLFLLLADARVCSCLWMMLLISQAEA
H77 TP29        WQVLPCSFTTLPALSTGLIHLHQNIVDVQYLYGVGSSIASWAIKWEYVVLLFLLLADARVCSCLWMMLLISQAEA
H77 TP52        WQVLPCSFTTLPALSTGLIHLHQNIVDVQYLYGVGSSIASWAIKWEYVVLLFLLLADARVCSCLWMMLLISQAEA
H77 TP100       WQVLPCSFTTLPALSTGLIHLHQNIVDVQYLYGVGSSIASWAIKWEYVVLLFLLLADARVCSCLWMMLLISQAEA
                E2 Protein
```

FIG. 6B

|  | 1 10 20 30 40 50 60 70 80 |
|---|---|
| S52 | MDAMKRGLCCVLLLCGAVFVSPSLEWRNTSGLYVLTNDCSNSSIVYEADDVILHTPGCVPCVQDDNTSTCWTPVTPTVAVRYV |
| S52 TP29 | MDAMKRGLCCVLLLCGAVFVSPSLEWRNTSGLYVLTNDCSNSSIVYEADDVILHTPGCVPCVQDDNTSTCWTPVTPTVAVRYV |
| S52 TP52 | MDAMKRGLCCVLLLCGAVFVSPSLEWRNTSGLYVLTNDCSNSSIVYEADDVILHTPGCVPCVQDDNTSTCWTPVTPTVAVRYV |
| S52 TP100 | MDAMKRGLCCVLLLCGAVFVSPSLEWRNTSGLYVLTNDCSNSSIVYEADDVILHTPGCVPCVQDDNTSTCWTPVTPTVAVRYV |
| AVI3a177 | MDAMKRGLCCVLLLCGAVFVSPSLEWRNTSGLYILTNDCPNSSIVYEADDVILHTPGCIPCVQDGNTSTCWTSVSPTVAVRYV |
| AVI3a177 TP29 | MDAMKRGLCCVLLLCGAVFVSPSLEWRNTSGLYILTNDCPNSSIVYEADDVILHTPGCIPCVQDGNTSTCWTSVSPTVAVRYV |
| AVI3a177 TP52 | MDAMKRGLCCVLLLCGAVFVSPSLEWRNTSGLYILTNDCPNSSIVYEADDVILHTPGCIPCVQDGNTSTCWTSVSPTVAVRYV |
| AVI3a177 TP100 | MDAMKRGLCCVLLLCGAVFVSPSLEWRNTSGLYILTNDCPNSSIVYEADDVILHTPGCIPCVQDGNTSTCWTSVSPTVAVRYV |
|  | tPA Signal Sequence / E1 |

|  | 90 100 110 120 130 140 150 160 |
|---|---|
| S52 | GATTASIRSHVDLLVGAATLCSALYVGDMCGAVFLVGQAFTFRPRRHQTVQTCNCSLYPGHVSGHRMAWDMMMNWSPAVGMVV |
| S52 TP29 | GATTASIRSHVDLLVGAATLCSALYVGDMCGAVFLVGQAFTFRPRRHQTVQTCNCSLYPGHVSGHRMAWDMMMNWSPAVGMVV |
| S52 TP52 | GATTASIRSHVDLLVGAATLCSALYVGDMCGAVFLVGQAFTFRPRRHQTVQTCNCSLYPGHVSGHRMAWDMMMNWSPAVGMVV |
| S52 TP100 | GATTASIRSHVDLLVGAATLCSALYVGDMCGAVFLVGQAFTFRPRRHQTVQTCNCSLYPGHVSGHRMAWDMMMNWSPAVGMVV |
| AVI3a177 | GATTASIRSHVDLLVGAATLCSALYVGDMCGAVFLVGQAFTFRPRRHQTVQTCNCSLYPGHLTGHRMAWDMMMNWSPAVGMVV |
| AVI3a177 TP29 | GATTASIRSHVDLLVGAATLCSALYVGDMCGAVFLVGQAFTFRPRRHQTVQTCNCSLYPGHLTGHRMAWDMMMNWSPAVGMVV |
| AVI3a177 TP52 | GATTASIRSHVDLLVGAATLCSALYVGDMCGAVFLVGQAFTFRPRRHQTVQTCNCSLYPGHLTGHRMAWDMMMNWSPAVGMVV |
| AVI3a177 TP100 | GATTASIRSHVDLLVGAATLCSALYVGDMCGAVFLVGQAFTFRPRRHQTVQTCNCSLYPGHLTGHRMAWDMMMNWSPAVGMVV |
|  | E1 |

|  | 170 180 190 200 210 220 230 240 |
|---|---|
| S52 | AHILRLPQTLFDILAGAHWGILAGLAYYSMQGNWAKVAIVMIMFSGVDAETDKTHTCPPCPAPEAEGAPSVFLFPPKPKDTLM |
| S52 TP29 | AHILRLPQTLFDILAGAHWGILAGLAYYSMQGNWAKVAIVMIMFSGVDAETDKTHTCPPCPAPEAEGAPSVFLFPPKPKDTLM |
| S52 TP52 | AHILRLPQTLFDILAGAHWGILAGLAYYSMQGNWAKVAIVMIMFSGVDAETDKTHTCPPCPAPEAEGAPSVFLFPPKPKDTLM |
| S52 TP100 | AHILRLPQTLFDILAGAHWGILAGLAYYSMQGNWAKVAIVMIMFSGVDAETDKTHTCPPCPAPEAEGAPSVFLFPPKPKDTLM |
| AVI3a177 | AHVLRMPQTVFDIIAGAHWGILAGLAYYSMQGNWAKVAIIMVMFSGVDAETDKTHTCPPCPAPEAEGAPSVFLFPPKPKDTLM |
| AVI3a177 TP29 | AHVLRMPQTVFDIIAGAHWGILAGLAYYSMQGNWAKVAIIMVMFSGVDAETDKTHTCPPCPAPEAEGAPSVFLFPPKPKDTLM |
| AVI3a177 TP52 | AHVLRMPQTVFDIIAGAHWGILAGLAYYSMQGNWAKVAIIMVMFSGVDAETDKTHTCPPCPAPEAEGAPSVFLFPPKPKDTLM |
| AVI3a177 TP100 | AHVLRMPQTVFDIIAGAHWGILAGLAYYSMQGNWAKVAIIMVMFSGVDAETDKTHTCPPCPAPEAEGAPSVFLFPPKPKDTLM |
|  | E1 ↑* FC Tag |

|  | 250 260 270 280 290 300 310 320 330 |
|---|---|
| S52 | ISRTPEVTCVVVDVSHEDPEVKFNWYVDGVEVHNAKTKPREEQYNSTYRVVSVLTVLHQDWLNGKEYKCKVSNKALPAPIEKT |
| S52 TP29 | ISRTPEVTCVVVDVSHEDPEVKFNWYVDGVEVHNAKTKPREEQYNSTYRVVSVLTVLHQDWLNGKEYKCKVSNKALPAPIEKT |
| S52 TP52 | ISRTPEVTCVVVDVSHEDPEVKFNWYVDGVEVHNAKTKPREEQYNSTYRVVSVLTVLHQDWLNGKEYKCKVSNKALPAPIEKT |
| S52 TP100 | ISRTPEVTCVVVDVSHEDPEVKFNWYVDGVEVHNAKTKPREEQYNSTYRVVSVLTVLHQDWLNGKEYKCKVSNKALPAPIEKT |
| AVI3a177 | ISRTPEVTCVVVDVSHEDPEVKFNWYVDGVEVHNAKTKPREEQYNSTYRVVSVLTVLHQDWLNGKEYKCKVSNKALPAPIEKT |
| AVI3a177 TP29 | ISRTPEVTCVVVDVSHEDPEVKFNWYVDGVEVHNAKTKPREEQYNSTYRVVSVLTVLHQDWLNGKEYKCKVSNKALPAPIEKT |
| AVI3a177 TP52 | ISRTPEVTCVVVDVSHEDPEVKFNWYVDGVEVHNAKTKPREEQYNSTYRVVSVLTVLHQDWLNGKEYKCKVSNKALPAPIEKT |
| AVI3a177 TP100 | ISRTPEVTCVVVDVSHEDPEVKFNWYVDGVEVHNAKTKPREEQYNSTYRVVSVLTVLHQDWLNGKEYKCKVSNKALPAPIEKT |
|  | FC Tag |

|  | 340 350 360 370 380 390 400 410 |
|---|---|
| S52 | ISKAKGQPREPQVYTLPPSREEMTKNQVSLTCLVKGFYPSDIAVEWESNGQPENNYKTTPPVLDSDGSFFLYSKLTVDKSRWQ |
| S52 TP29 | ISKAKGQPREPQVYTLPPSREEMTKNQVSLTCLVKGFYPSDIAVEWESNGQPENNYKTTPPVLDSDGSFFLYSKLTVDKSRWQ |
| S52 TP52 | ISKAKGQPREPQVYTLPPSREEMTKNQVSLTCLVKGFYPSDIAVEWESNGQPENNYKTTPPVLDSDGSFFLYSKLTVDKSRWQ |
| S52 TP100 | ISKAKGQPREPQVYTLPPSREEMTKNQVSLTCLVKGFYPSDIAVEWESNGQPENNYKTTPPVLDSDGSFFLYSKLTVDKSRWQ |
| AVI3a177 | ISKAKGQPREPQVYTLPPSREEMTKNQVSLTCLVKGFYPSDIAVEWESNGQPENNYKTTPPVLDSDGSFFLYSKLTVDKSRWQ |
| AVI3a177 TP29 | ISKAKGQPREPQVYTLPPSREEMTKNQVSLTCLVKGFYPSDIAVEWESNGQPENNYKTTPPVLDSDGSFFLYSKLTVDKSRWQ |
| AVI3a177 TP52 | ISKAKGQPREPQVYTLPPSREEMTKNQVSLTCLVKGFYPSDIAVEWESNGQPENNYKTTPPVLDSDGSFFLYSKLTVDKSRWQ |
| AVI3a177 TP100 | ISKAKGQPREPQVYTLPPSREEMTKNQVSLTCLVKGFYPSDIAVEWESNGQPENNYKTTPPVLDSDGSFFLYSKLTVDKSRWQ |
|  | FC Tag |

|  | 420 430 440 450 460 470 480 490 |
|---|---|
| S52 | QGNVFSCSVMHEALHNHYTQKSLSLSPGKLEVLFQGP-------------------------------- |
| S52 TP29 | QGNVFSCSVMHEALHNHYTQKSLSLSPGKLEVLFQGP--------------AIPLEVIKGGRHLIFCHSKKKCDELAAKL--- |
| S52 TP52 | QGNVFSCSVMHEALHNHYTQKSLSLSPGKLEVLFQGP--------------AIPLEVIKGGRHLIFCHSKKKCDELAAKLVAL |
| S52 TP100 | QGNVFSCSVMHEALHNHYTQKSLSLSPGKLEVLFQGPVALSTTGEIPFYGKAIPLEVIKGGRHLIFCHSKKKCDELAAKLVAL |
| AVI3a177 | QGNVFSCSVMHEALHNHYTQKSLSLSPGKLEVLFQGP-------------------------------- |
| AVI3a177 TP29 | QGNVFSCSVMHEALHNHYTQKSLSLSPGKLEVLFQGP--------------AIPLEVIKGGRHLIFCHSKKKCDELAAKL--- |
| AVI3a177 TP52 | QGNVFSCSVMHEALHNHYTQKSLSLSPGKLEVLFQGP--------------AIPLEVIKGGRHLIFCHSKKKCDELAAKLVAL |
| AVI3a177 TP100 | QGNVFSCSVMHEALHNHYTQKSLSLSPGKLEVLFQGPVALSTTGEIPFYGKAIPLEVIKGGRHLIFCHSKKKCDELAAKLVAL |
|  | FC Tag / PP Site / TPx |

FIG. 7A

```
          500        510        520        530        540        550        560        570        580
S52             ------------------------------------------------------ETYVTGGSVAHSARGLTSLFSMGAKQKLQ
S52TP29         ------------------------------------------------------ETYVTGGSVAHSARGLTSLFSMGAKQKLQ
S52TP52         GINAVAYYRGLDVSVIPTS-----------------------------------ETYVTGGSVAHSARGLTSLFSMGAKQKLQ
S52TP100        GINAVAYYRGLDVSVIPTSGDVVVVATDALMTGFTGDFDSVIDCNTCVTQTVDFETYVTGGSVAHSARGLTSLFSMGAKQKLQ
AVI3a177        ------------------------------------------------------ETHTTGGTAARNAFTLTGLFTQGARQKLE
AVI3a177TP29    ------------------------------------------------------ETHTTGGTAARNAFTLTGLFTQGARQKLE
AVI3a177TP52    GINAVAYYRGLDVSVIPTSG----------------------------------ETHTTGGTAARNAFTLTGLFTQGARQKLE
AVI3a177TP100   GINAVAYYRGLDVSVIPTSGDVVVVATDALMTGFTGDFDSVIDCNTCVTQTVDFETHTTGGTAARNAFTLTGLFTQGARQKLE
                TPx                                                   E2 Protein

          590        600        610        620        630        640        650        660
S52             LVNTNGSWHINSTALNCNESINTGFIAGLFYYHKFNSTGCPQRLSSCKPIISFRQGWGPLTDANITGPSDDRPYCWHYAPRPC
S52TP29         LVNTNGSWHINSTALNCNESINTGFIAGLFYYHKFNSTGCPQRLSSCKPIISFRQGWGPLTDANITGPSDDRPYCWHYAPRPC
S52TP52         LVNTNGSWHINSTALNCNESINTGFIAGLFYYHKFNSTGCPQRLSSCKPIISFRQGWGPLTDANITGPSDDRPYCWHYAPRPC
S52TP100        LVNTNGSWHINSTALNCNESINTGFIAGLFYYHKFNSTGCPQRLSSCKPIISFRQGWGPLTDANITGPSDDRPYCWHYAPRPC
AVI3a177        LINTNGSWHINRTALNCNESLNTGFIAGLFYLHKFNSTGCPERLSSCKPITFFRQGWGSLTDANITGPSDDKPYCWHYAPRPC
AVI3a177TP29    LINTNGSWHINRTALNCNESLNTGFIAGLFYLHKFNSTGCPERLSSCKPITFFRQGWGSLTDANITGPSDDKPYCWHYAPRPC
AVI3a177TP52    LINTNGSWHINRTALNCNESLNTGFIAGLFYLHKFNSTGCPERLSSCKPITFFRQGWGSLTDANITGPSDDKPYCWHYAPRPC
AVI3a177TP100   LINTNGSWHINRTALNCNESLNTGFIAGLFYLHKFNSTGCPERLSSCKPITFFRQGWGSLTDANITGPSDDKPYCWHYAPRPC
                E2 Protein

          670        680        690        700        710        720        730        740
S52             SVVPASSVCGPVYCFTPSPVVVGTTDIKGKPTYNWGENETDVFLLESLRPPSGRWFGCAWMNSTGFLKTCGAPPCNIYGGEGD
S52TP29         SVVPASSVCGPVYCFTPSPVVVGTTDIKGKPTYNWGENETDVFLLESLRPPSGRWFGCAWMNSTGFLKTCGAPPCNIYGGEGD
S52TP52         SVVPASSVCGPVYCFTPSPVVVGTTDIKGKPTYNWGENETDVFLLESLRPPSGRWFGCAWMNSTGFLKTCGAPPCNIYGGEGD
S52TP100        SVVPASSVCGPVYCFTPSPVVVGTTDIKGKPTYNWGENETDVFLLESLRPPSGRWFGCAWMNSTGFLKTCGAPPCNIYGGEGD
AVI3a177        EVVPALNVCGPVYCFTPSPVVVGTTDRQGVPTYTWGENETDVFLLRSLRPPSGQWFGCTWMNSTGFVKTCGAPPCDIYGGGGN
AVI3a177TP29    EVVPALNVCGPVYCFTPSPVVVGTTDRQGVPTYTWGENETDVFLLRSLRPPSGQWFGCTWMNSTGFVKTCGAPPCDIYGGGGN
AVI3a177TP52    EVVPALNVCGPVYCFTPSPVVVGTTDRQGVPTYTWGENETDVFLLRSLRPPSGQWFGCTWMNSTGFVKTCGAPPCDIYGGGGN
AVI3a177TP100   EVVPALNVCGPVYCFTPSPVVVGTTDRQGVPTYTWGENETDVFLLRSLRPPSGQWFGCTWMNSTGFVKTCGAPPCDIYGGGGN
                E2 Protein

          750        760        770        780        790        800        810        820        830
S52             PENETDLFCPTDCFRKHPEATYSRCGAGPWLTPRCMVDYPYRLWHYPCTVNFTLFKVRMFVGGFEHRFTAACNWTRGERCNIE
S52TP29         PENETDLFCPTDCFRKHPEATYSRCGAGPWLTPRCMVDYPYRLWHYPCTVNFTLFKVRMFVGGFEHRFTAACNWTRGERCNIE
S52TP52         PENETDLFCPTDCFRKHPEATYSRCGAGPWLTPRCMVDYPYRLWHYPCTVNFTLFKVRMFVGGFEHRFTAACNWTRGERCNIE
S52TP100        PENETDLFCPTDCFRKHPEATYSRCGAGPWLTPRCMVDYPYRLWHYPCTVNFTLFKVRMFVGGFEHRFTAACNWTRGERCNIE
AVI3a177        RCNESDLFCPTDCFRKHPEATYSRCGAGPWLTPRCLVDYPYRLWHYPCTVNFTLFKVRMFVGGFEHRFTAACNWTRGERCNIE
AVI3a177TP29    RCNESDLFCPTDCFRKHPEATYSRCGAGPWLTPRCLVDYPYRLWHYPCTVNFTLFKVRMFVGGFEHRFTAACNWTRGERCNIE
AVI3a177TP52    RCNESDLFCPTDCFRKHPEATYSRCGAGPWLTPRCLVDYPYRLWHYPCTVNFTLFKVRMFVGGFEHRFTAACNWTRGERCNIE
AVI3a177TP100   RCNESDLFCPTDCFRKHPEATYSRCGAGPWLTPRCLVDYPYRLWHYPCTVNFTLFKVRMFVGGFEHRFTAACNWTRGERCNIE
                E2 Protein

          840        850        860        870        880        890        900        910
S52             DRDRSEQHPLLHSTTELAILPCSFTPMPALSTGLIHLHQNIVDVQYLYGVGSDMVGWALKWEFVILVFLLLADARVCVALWLM
S52TP29         DRDRSEQHPLLHSTTELAILPCSFTPMPALSTGLIHLHQNIVDVQYLYGVGSDMVGWALKWEFVILVFLLLADARVCVALWLM
S52TP52         DRDRSEQHPLLHSTTELAILPCSFTPMPALSTGLIHLHQNIVDVQYLYGVGSDMVGWALKWEFVILVFLLLADARVCVALWLM
S52TP100        DRDRSEQHPLLHSTTELAILPCSFTPMPALSTGLIHLHQNIVDVQYLYGVGSDMVGWALKWEFVILVFLLLADARVCVALWLM
AVI3a177        DRDRSEQHPLLHSTTELAILPCSFTPMPALSTGLIHLHQNIVDVQYLYGVGSGVVGWALRWEFVVLVFLLLADARVCVALWLM
AVI3a177TP29    DRDRSEQHPLLHSTTELAILPCSFTPMPALSTGLIHLHQNIVDVQYLYGVGSGVVGWALRWEFVVLVFLLLADARVCVALWLM
AVI3a177TP52    DRDRSEQHPLLHSTTELAILPCSFTPMPALSTGLIHLHQNIVDVQYLYGVGSGVVGWALRWEFVVLVFLLLADARVCVALWLM
AVI3a177TP100   DRDRSEQHPLLHSTTELAILPCSFTPMPALSTGLIHLHQNIVDVQYLYGVGSGVVGWALRWEFVVLVFLLLADARVCVALWLM
                E2 Protein

                921
S52             LMVSQAEA
S52TP29         LMVSQAEA
S52TP52         LMVSQAEA
S52TP100        LMVSQAEA
AVI3a177        LMISQAEA
AVI3a177TP29    LMISQAEA
AVI3a177TP52    LMISQAEA
AVI3a177TP100   LMISQAEA
                E...
```

FIG. 7B

FIG. 9A
GenBank 3S7G_A
*Homo sapiens* IgG1 Fc
227 aa

```
  1 dkthtcppcp apellggpsv flfppkpkdt lmisrtpevt cvvvdvshed pevkfnwyvd
 61 gvevhnaktk preeqynsty rvvsvltvlh qdwlngkeyk ckvsnkalpa piektiskak
121 gqprepqvyt lppsrdeltk nqvsltclvk gfypsdiave wesngqpenn ykttppvlds
181 dgsfflyskl tvdksrwqqg nvfscsvmhe alhnhytqks lslspgk
```

GenBank AAN76044
*Homo sapiens* IgG2 Fc (amino acids 99-325)
227 aa

```
  1 stkgpsvfpl apcsrstses taalgclvkd yfpepvtvsw nsgaltsgvh tfpavlqssg
 61 lyslssvvtv pssnfgtqty tcnvdhkpsn tkvdktverk ccvecppcpa ppvagpsvfl
121 fppkpkdtlm isrtpevtcv vvdvshedpe vqfnwyvdgv evhnaktkpr eeqfnstfrv
181 vsvltvvhqd wlngkeykck vsnkglpapi ektisktkgq prepqvytlp psreemtknq
241 vsltclvkgf ypsdiavewe sngqpennyk ttppmldsdg sfflyskltv dksrwqqgnv
301 fscsvmheal hnhytqksls lspgk
```

GenBank AAW65947
*Homo sapiens* IgG3 Fc (amino acids 19-246)
238 aa

```
  1 hkpsntkvdk rvelktplgd tthtcppcpa pellggpsvf lfppkpkdtl misrtpevtc
 61 vvvdvshedp evkfnwyvdg vevhnaktkp reeqynstyr vvsvltvlhq dwlngkeykc
121 kvsnkalpap iektiskakg qprepqvytl ppsrdeltkn qvsltclvkg fypsdiavew
181 esngqpenny kttppvldsd gsfflysklt vdksrwqqgn vfscsvmhea lhnhytqksl
241 slspgk
```

FIG. 9B

GenBank AAA52770
*Homo sapiens* IgD Fc (amino acids 162-383)
222 aa 1 ptkapdvfpi isgcrhpkdn spvvlaclit gyhptsvtvt wymgtqsqpq rtfpeiqrrd
61 syymtssqls tplqqwrqge ykcvvqhtas kskkeifrwp espkaqassv ptaqpqaegs
121 lakattapat trntgrggee kkkekekeeq eeretktpec p<u>sht</u>qplgvy lltpavqdlw
181 lrdkatftcf vvgsdlkdah ltwevagkvp tggveeglle rhsngsqsqh srltlprslw
241 nagtsvtctl nhpslppqrl malrepaaqa pvklslnlla ssdppeaasw llcevsgfsp
301 pnillmwled qrevntsgfa parpppqprs ttfwawsvlr vpappspqpa tytcvvshed
361 srtllnasrs levsyvtdhg pmk GenBank 0308221A
*Homo sapiens* IgM Fc
276 aa 1 vtstltikzs dwlgesmftc rvdhrgltfq qnassmcvpd qdtairvfai ppsfasiflt
61 kstkltclvt dlttybsvti swtreengav kthtnisesh pnatfsavge asicedbdws
121 gerftctvth tdlpsplkqt isrpkgvalh rpbvyllppa rzzlnlresa titclvtgfs
181 padvfvewmq rgeplspqky vtsapmpepq apgryfahsi ltvseeewnt ggtytcvvah
241 ealpnrvter tvdkstgkpt lynvslvmsd tagtcy

FIG. 9C

GenBank P01876
*Homo sapiens* IgA Fc (amino acids 120-353)
234 aa

```
  1 asptspkvfp lslcstqpdg nvviaclvqg ffpqeplsvt wsesgqgvta rnfppsqdas
 61 gdlyttssql tlpatqclag ksvtchvkhy tnpsqdvtvp cpvpstpptp spstpptpsp
121 scchprlslh rpaledlllg seanltctlt glrdasgvtf twtpssgksa vqgpperdlc
181 gcysvssvlp gcaepwnhgk tftctaaype sktpltatls ksgntfrpev hllpppseel
241 alnelvtltc largfspkdv lvrwlqgsqe lprekyltwa srqepsqgtt tfavtsilrv
301 aaedwkkgdt fscmvgheal plaftqktid rlagkpthvn vsvvmaevdg tcy
```

GenBank 1F6A_B
*Homo sapiens* IgE Fc (amino acids 6-222)
212 aa

```
  1 adpcdsnprg vsaylsrpsp fdlfirkspt itclvvdlap skgtvnltws rasgkpvnhs
 61 trkeekqrng tltvtstlpv gtrdwieget yqcrvthphl pralmrsttk tsgpraapev
121 yafatpewpg srdkrtlacl iqnfmpedis vqwlhnevql pdarhsttqp rktkgsgffv
181 fsrlevtrae weqkdeficr avheaaspsq tvqravsvnp gk
```

GenBank P01861
*Homo sapiens* IgG4 Fc (amino acids 100-327)
228 aa

```
  1 astkgpsvfp lapcsrstse staalgclvk dyfpepvtvs wnsgaltsgv htfpavlqss
 61 glyslssvvt vpssslgtkt ytcnvdhkps ntkvdkrves kygppcpscp apeflggpsv
121 flfppkpkdt lmisrtpevt cvvvdvsqed pevqfnwyvd gvevhnaktk preeqfnsty
181 rvvsvltvlh qdwlngkeyk ckvsnkglps siektiskak gqprepqvyt lppsqeemtk
241 nqvsltclvk gfypsdiave wesngqpenn ykttppvlds dgsfflysrl tvdksrwqeg
301 nvfscsvmhe alhnhytqks lslslgk
```

FIG. 10

Table 1. Conserved Regions based on the conserved CD4 epitopes

| No. | Residues* | Length | Sequence | Genotype Conservancy | # of included Epitopes |
|---|---|---|---|---|---|
| **CD4-R1** | 1251-1265 | 15 | VLVLNPSVAATLGFG | HCV1a, 1b, 2a, 2b, 3, 4, 5, 6, 7 | 2 |
| **CD4-R2** | 1295-1309 | 15 | TYGKFLADGGCSGGA | HCV1a, 1b, 3, 4, 5, 6, 7 | 2 |
| **CD4-R3** | 1387-1401 | 15 | GGRHLIFCHSKKKCD | HCV1a, 1b, 2a, 2b, 3, 4, 5, 6, 7 | 4 |
| **CD4-R4** | 1415-1425 | 11 | VAYYRGLDVSV | HCV1a, 1b, 2b, 3, 4, 7 | 4 |
| **CD4-R5** | 1436-1453 | 18 | ATDALMTGFTGDFDSVID | HCV1a, 1b, 3, 4, 7 | 2 |
| **CD4-R6** | 1563-1577 | 15 | TGLTHIDAHFLSQTK | HCV1a, 1b, 2a, 2b, 3, 7 | 1 |
| **CD4-R7** | 1773-1785 | 13 | QYLAGLSTLPGNP | HCV1a, 1b, 2a, 2b, 3, 4, 5, 6, 7 | 4 |
| **CD4-R8** | 1881-1888 | 8 | NLLPAILS | HCV1a, 1b, 2b, 3, 4, 7 | 1 |
| **CD4-R9** | 1904-1930 | 27 | RHVGPGEGAVQWMNRLIAFASRGNHVS | HCV1a, 1b, 3, 4 | 3 |
| **CD4-R10** | 2201-2215 | 15 | SSASQLSAPSLKATC | HCV1a, 1b, 2b, 3, 4, 5, 6 | 1 |
| **CD4-R11** | 2788-2792 | 5 | SNVSV | HCV1a, 1b, 2a, 2b, 3, 4, 5, 6, 7 | 1 |

* Numbers are based on HCV1a genotype sequence. R = region

FIG. 11

Table 2. Number of located HCV CD8 T cell epitopes and anchor positions for common each MHC-I Alleles in USA

| MHC-I Allele | Total Epitopes (#) | Located Epitopes (#) | Allele-specific Anchor Positions | | | |
|---|---|---|---|---|---|---|
| | | | 2 | | 9 | Others |
| A*02:01 | 48 | 29 | **M#**, **L**, Q, V, I | | **V**, **L**, **I**, A, M | F (1, 3, 7) |
| A*24:02 | 33 | 20 | **Y**, **W**, F | | **F**, **I**, **W**, L, M | F, W (7) |
| A*03:01 | 10 | 6 | **M**,**L**, **I**, **V**, **T**, S, Q, A | | **K**, Y, R | F & Y (3), K & R (1) |
| A*01:01 | 4 | 3 | **T**, **S**, A, V, M, I, L | | **Y**, F | **D** (3) |
| B*35:01 | 1 | 1 | **P**, G, A | | **Y**, **M**, **F**, H | M (1), A (8), W (1), F (1), Y (1), P (8) |
| | | | 5 | | 9 | Others |
| B*08:01 | 2 | 1 | **R**, **K**, **H**, F | | **L**, **M**, **I**, **F**, **V**, A, W | K (3), R (3), L (2), F (6), M (1, 2, 3), P (2), S (8) |
| | | | 1 | 2 | 9 | Others |
| B*40:02 | 2 | 2 | **Y**, **K**, **R**, **A**, **H**, **W**, **G**, **F**, Q, L, S, C, I, T, M, V | E, D | **I**, **L**, **A**, **V**, **F**, **M**, **T**, W, S, C | F (3), P (8), A (8) |
| C*03:03 | 2 | 2 | NA## | | NA | NA |
| A*33:03 | 1 | 0 | - | | - | - |
| A*02:06 | 1 | 0 | - | | - | - |
| A*26:01 | 1 | 0 | - | | - | - |
| A*31:01 | 1 | 0 | - | | - | - |
| Total | 106 | 64 | | | | |

Bold Anchor positions describe the optimal amino acid for that location. ## Not Available

FIG. 12

Table 3. Conserved Regions based on the conserved CD8 Epitopes

| No. | Residues* | Length | Sequence | Conserved HCV1a, 1b, & 3 | Conserved 9** Genotypes | # of epitopes |
|---|---|---|---|---|---|---|
| CD8-R1 | 1292-1300 | 9 | TYSTYGKFL | Yes | Yes | 2 |
| CD8-R2 | 1391-1399 | 9 | LIFCHSKKK | Yes | Yes | 2 |
| CD8-R3 | 1436-1451 | 16 | ATDALMTGFTGDFDSV | Yes | No | 2 |
| CD8-R4 | 1666-1675 | 10 | VLAALAAYCL | Yes | No | 1 |
| CD8-R5 | 1851-1859 | 9 | ILAGYGAGV | Yes | No | 1 |
| CD8-R6 | 1373-1380 | 8 | IPFYGKAI | Yes | No | 1 |
| CD8-R7 | 1596-1604 | 9 | RAQAPPPSW | Yes | No | 1 |
| CD8-R8 | 1910-1945 | 36 | EGAVQWMNRLIAFASRGN HVSPTHYVPESDAAARVT | Yes | No | 3 |
| CD8-R9 | 2290-2298 | 9 | RPDYNPPLL | Yes | No | 1 |
| CD8-R10 | 2557-2565 | 9 | TIMAKNEVF | Yes | Yes | 1 |

* Numbers are based on HCV1a genotype sequence.

** Nine genotypes include HCV1a, 1b, 2a, 2b, 3, 4, 5, 6, and 7

FIG. 13A. CD4 and CD8 epitopes for Core, P7, and NS2 regions

| Name | Type of epitope | Start* | End* |
|---|---|---|---|
| **Core-1** | CD4 | 1 | 20 |
| **Core-2** | CD4 | 11 | 30 |
| **Core-3** | CD4 | 21 | 40 |
| **Core-4** | CD4 | 39 | 63 |
| **Core-5** | CD4 | 47 | 70 |
| **Core-6** | CD4 | 61 | 80 |
| **Core-7** | CD4 | 71 | 90 |
| **Core-8** | CD4 | 81 | 100 |
| **Core-9** | CD4 | 91 | 110 |
| **Core-10** | CD4 | 101 | 115 |
| **Core-11** | CD4 | 111 | 130 |
| **Core-12** | CD4 | 125 | 139 |
| **Core-13** | CD4 | 131 | 150 |
| **Core-14** | CD4 | 151 | 170 |
| **Core-15** | CD4 | 161 | 180 |
| **Core-16** | CD8 | 35 | 44 |
| **Core-17** | CD8 | 43 | 51 |
| **Core-18** | CD8 | 51 | 59 |
| **Core-19** | CD8 | 129 | 137 |
| **Core-20** | CD8 | 131 | 140 |
| **Core-21** | CD8 | 150 | 158 |
| **Core-22** | CD8 | 154 | 162 |
| **Core-23** | CD8 | 168 | 176 |
| **Core-24** | CD8 | 177 | 187 |
| **Core-25** | CD8 | 178 | 187 |
| **P7-1** | CD8 | 803 | 811 |
| **NS2-1** | CD4 | 955 | 974 |
| **NS2-2** | CD4 | 975 | 994 |
| **NS2-3** | CD4 | 985 | 1,004 |
| **NS2-4** | CD4 | 1,015 | 1,034 |
| **NS2-5** | CD4 | 1,035 | 1,054 |
| **NS2-6** | CD8 | 924 | 933 |
| **NS2-7** | CD8 | 961 | 970 |
| **NS2-8** | CD8 | 989 | 997 |

* Start and End numbers are based on sequence designated “Consensus” in Fig. 16A-16L.

FIG. 13B. CD4 and CD8 epitopes that are conserved among genotypes 1a, 1b, 2a, 2b, and 3

| Name | Type of epitope | Start* | End* |
|---|---|---|---|
| NS3-1 | CD4 | 1,265 | 1,279 |
| NS3-2 | CD4 | 1,309 | 1,323 |
| NS3-3 | CD4 | 1,401 | 1,415 |
| NS3-4 | CD4 | 1,402 | 1,412 |
| NS3-5 | CD4 | 1,429 | 1,439 |
| NS3-6 | CD4 | 1,450 | 1,464 |
| NS3-7 | CD4 | 1,453 | 1,467 |
| NS3-8 | CD4 | 1,577 | 1,591 |
| NS3-9 | CD8 | 1,306 | 1,314 |
| NS3-10 | CD8 | 1,387 | 1,394 |
| NS3-11 | CD8 | 1,405 | 1,413 |
| NS3-12 | CD8 | 1,450 | 1,458 |
| NS3-13 | CD8 | 1,457 | 1,465 |
| NS3-14 | CD8 | 1,610 | 1,618 |
| NS4a-1 | CD8 | 1,683 | 1,692 |
| NS4b-1 | CD4 | 1,790 | 1,801 |
| NS4b-2 | CD4 | 1,792 | 1,802 |
| NS4b-3 | CD4 | 1,898 | 1,905 |
| NS4b-4 | CD4 | 1,921 | 1,935 |
| NS4b-5 | CD4 | 1,922 | 1,941 |
| NS4b-6 | CD4 | 1,928 | 1,947 |
| NS4b-7 | CD8 | 1,868 | 1,876 |
| NS4b-8 | CD8 | 1,927 | 1,942 |
| NS4b-9 | CD8 | 1,932 | 1,940 |
| NS4b-10 | CD8 | 1,948 | 1,962 |
| NS5a-1 | CD4 | 2,218 | 2,232 |
| NS5a-2 | CD8 | 2,309 | 2,317 |
| NS5b-1 | CD4 | 2,847 | 2,851 |
| NS5b-2 | CD8 | 2,602 | 2,610 |

* Start and End numbers are based on sequence designated “Consensus” in Fig. 16A-16L.

FIG. 14A

| Name | Sequence* | Start** | End** | Contained Epitopes |
|---|---|---|---|---|
| **TP29** | AIPLEVIKGGRHLIFCHSKKKCDELAAKL | 1,393 | 1,421 | NS3-3, NS3-4, NS3-11 |
| **TP50** | LGALTGTYVYNHLTPLRDWAHNGLRDLA VAVEPVVFSQMETKLITWGADT | 955 | 1,004 | NS2-1, NS2-2, NS2-3, NS2-7, NS2-8 |
| **TP52** | AIPLEVIKGGRHLIFCHSKKKCDELAAKLV ALGINAVAYYRGLDVSVIPTSG | 1,393 | 1,444 | NS3-3, NS3-4, NS3-5, NS3-11 |
| **TP70** | KGGRHLIFCHSKKKCDELAAKLVALGINA VAYYRGLDVSVIPTSGDVVVVATDALMTG FTGDFDSVIDCN | 1,400 | 1,469 | NS3-3, NS3-4, NS3-5, NS3-6, NS3-7, NS3-11, NS3-12, NS3-13 |
| **TP100** | VALSTTGEIPFYGKAIPLEVIKGGRHLIFCHS KKKCDELAAKLVALGINAVAYYRGLDVS VIPTSGDVVVVATDALMTGFTGDFDSVIDC NTCVTQTVDF | 1,379 | 1,478 | NS3-3, NS3-4, NS3-5, NS3-6, NS3-7, NS3-10, NS3-11, NS3-12, NS3-13 |
| **TP171** | MSTNPKPQRKTKRNTNRRPQDVKFPGGGQIVG GVYLLPRRGPRLGVRATRKTSERSQPRGRRQPI PKARRPEGRTWAQPGYPWPLYGNEGCGWAG WLLSPRGSRPSWGPTDPRRRSRNLGKVIDTLT CGFADLMGYIPLVGAPLGGAARALAHGVRVLED GVNYATGNLPG | 1 | 171 | Core-1, Core-2, Core-3, Core-4, Core-5, Core-6, Core-7, Core-8, Core-9, Core-10, Core-11, Core-12, Core-13, Core-14, Core-16, Core-17, Core-18, Core-19, Core-20, Core-21, Core-22 |
| **TP228** | LHAPTGSGKSTKVPAAYAAQGYKVLVLNP SVAATLGFGAYMSKAHGIDPNIRTGVRTIT TGSPITYSTYGKFLADGGCSGGAYDIIICDE CHSTDATSILGIGTVLDQAETAGARLVVLA TATPPGSVTVPHPNIEEVALSTTGEIPFYGK AIPLEVIKGGRHLIFCHSKKKCDELAAKLV ALGINAVAYYRGLDVSVIPTSGDVVVVAT DALMTGFTGDFDSVIDCN | 1,242 | 1,469 | NS3-1, NS3-2, NS3-3, NS3-4, NS3-5, NS3-6, NS3-7, NS3-9, NS3-10, NS3-11, NS3-12, NS3-13 |
| **TP553** | QASLLKVPYFVRVQGLLRICALARKMAGG HYVQMAIIKLGALTGTYVYN<u>A</u>LTPLRDWA HNGLRDLAVAVEPVVFSQMETKLITWGAD TAACGDIINGLPVSARRGREILLGPADGMV SKGWRLLAPITAYAQQTRGLLGCIITSLTG RDKNQVEGEVQIVSTAAQTFLATCINGVC WTVYHGAGTRTIASPKGPVIQMYTNVDQD LVGWPAPQGARSLTPCTCGSSDLYLVTRH ADVIPVRRRGDSRGSLLSPRPISYLKGS<u>A</u>GG PLLCPAGHAVGIFRAAVCTRGVAKAVDFIP VENLETTMRSPVFTDNSSPPAVPQSFQVAH LHAPTGSGKSTKVPAAYAAQGYKVLVLNP SVAATLGFGAYMSKAHGIDPNIRTGVRTIT TGSPITYSTYGKFLADGGCSGGAYDIIICDE CHSTDATSILGIGTVLDQAETAGARLVVLA TATPPGSVTVPHPNIEEVALSTTGEIPFYGK | 917 | 1,469 | NS2-1, NS2-2, NS2-3, NS2-4, NS2-5, NS2-6, NS2-7, NS2-8, NS3-1, NS3-2, NS3-3, NS3-4, NS3-5, NS3-6, NS3-7, NS3-9, NS3-10, NS3-11, NS3-12, NS3-13 |

FIG. 14B

| | | | | |
|---|---|---|---|---|
| | AIPLEVIKGGRHLIFCHSKKKCDELAAKLV ALGINAVAYYRGLDVSVIPTSGDVVVVAT DALMTGFTGDFDSVIDCN | | | |
| **TP778** | LHAPTGSGKSTKVPAAYAAQGYKVLVLNP SVAATLGFGAYMSKAHGIDPNIRTGVRTIT TGSPITYSTYGKFLADGGCSGGAYDIIICDE CHSTDATSILGIGTVLDQAETAGARLVVLA TATPPGSVTVPHPNIEEVALSTTGEIPFYGK AIPLEVIKGGRHLIFCHSKKKCDELAAKLV ALGINAVAYYRGLDVSVIPTSGDVVVVAT DALMTGFTGDFDSVIDCNTCVTQTVDFSL DPTFTIETTTLPQDAVSRTQRRGRTGRGKP GIYRFVAPGERPSGMFDSSVLCECYDAGCA WYELTPAETTVRLRAYMNTPGLPVCQDHL EFWEGVFTGLTHIDAHFLSQTKQSGENLPY LVAYQATVCARAQAPPPSWDQMWKCLIR LKPTLHGPTPLLYRLGAVQNEVTLTHPITK YIMTCMSADLEVVTSTWVLVGGVLAALA AYCLSTGCVVIVGRIVLSGKPAIIPDREVLY REFDEMEECSQHLPYIEQGMMLAEQFKQK ALGLLQTASRQAEVIAPAVQTNWQKLEAF WAKHMWNFISGIQYLAGLSTLPGNPAIASL MAFTAAVTSPLTTSQTLLFNILGGWVAAQ LAAPGAATAFVGAGLAGAAIGSVGLGKVL VDILAGYGAGVAGALVAFKIMSGEVPSTE DLVNLLPAILSPGALVVGVVCAAILRRHVG PGEGAVQWMNRLIAFASRGNHVSPTHYVP ESDAAARVTAILSSLTVTQLLRRLHQWISS ECTTPCSGSWLRDIWDWICEVLSDFKTWL KAKLMPQLPG | 1,242 | 2,022 | NS3-1, NS3-2, NS3-3, NS3-4, NS3-5, NS3-6, NS3-7, NS3-8, NS3-9, NS3-10, NS3-11, NS3-12, NS3-13, NS3-14, NS4a-1, NS4b-1, NS4b-2, NS4b-3, NS4b-4, NS4b-5, NS4b-6, NS4b-7, NS4b-8, NS4b-9, NS4b-10 |

FIG. 14C

| | | | | |
|---|---|---|---|---|
| **TP1985** | APITAYAQQTRGLLGCIITSLTGRDKNQVE<br>GEVQIVSTAAQTFLATCINGVCWTVYHGA<br>GTRTIASPKGPVIQMYTNVDQDLVGWPAP<br>QGARSLTPCTCGSSDLYLVTRHADVIPVRR<br>RGDSRGSLLSPRPISYLKGS<u>**A**</u>GGPLLCPAG<br>HAVGIFRAAVCTRGVAKAVDFIPVENLETT<br>MRSPVFTDNSSPPAVPQSFQVAHLHAPTGS<br>GKSTKVPAAYAAQGYKVLVLNPSVAATL<br>GFGAYMSKAHGIDPNIRTGVRTITTGSPITY<br>STYGKFLADGGCSGGAYDIIICDECHSTDA<br>TSILGIGTVLDQAETAGARLVVLATATPPG<br>SVTVPHPNIEEVALSTTGEIPFYGKAIPLEVI<br>KGGRHLIFCHSKKKCDELAAKLVALGINA<br>VAYYRGLDVSVIPTSGDVVVVATDALMTG<br>FTGDFDSVIDCNTCVTQTVDFSLDPTFTIET<br>TTLPQDAVSRTQRRGRTGRGKPGIYRFVAP<br>GERPSGMFDSSVLCECYDAGCAWYELTPA<br>ETTVRLRAYMNTPGLPVCQDHLEFWEGVF<br>TGLTHIDAHFLSQTKQSGENLPYLVAYQAT<br>VCARAQAPPPSWDQMWKCLIRLKPTLHGP<br>TPLLYRLGAVQNEVTLTHPITKYIMTCMSA<br>DLEVVTSTWVLVGGVLAALAAYCLSTGC<br>VVIVGRIVLSGKPAIIPDREVLYREFDEMEE<br>CSQHLPYIEQGMMLAEQFKQKALGLLQTA<br>SRQAEVIAPAVQTNWQKLEAFWAKHMWN<br>FISGIQYLAGLSTLPGNPAIASLMAFTAAVT<br>SPLTTSQTLLFNILGGWVAAQLAAPGAATA<br>FVGAGLAGAAIGSVGLGKVLVDILAGYGA<br>GVAGALVAFKIMSGEVPSTEDLVNLLPAIL<br>SPGALVVGVVCAAILRRHVGPGEGAVQW<br>MNRLIAFASRGNHVSPTHYVPESDAAARV<br>TAILSSLTVTQLLRRLHQWISSECTTPCSGS<br>WLRDIWDWICEVLSDFKTWLKAKLMPQLP<br>GIPFVSCQRGYRGVWRGDGIMHTRCHCGA<br>EITGHVKNGTMRIVGPRTCRNMWSGTFPIN<br>AYTTGPCTPLPAPNYTFALWRVSAEEYVEI<br>RQVGDFHYVTGMTTDNLKCPCQVPSPEFF<br>TELDGVRLHRFAPPCKPLLREEVSFRVGLH<br>EYPVGSQLPCEPEPDVAVLTSMLTDPSHIT<br>AEAAGRRLARGSPPSVASSSASQLSAPSLK<br>ATCTANHDSPDAELIEANLLWRQEMGGNI<br>TRVESENKVVILDSFDPLVAEEDEREISVPA<br>EILRKSRRFAPALPIWARPDYNPPLLETWK<br>KPDYEPPVVHGCPLPPPQSPPVPPPRKKRT<br>VVLTESTVSTALAELATKSFGSSSTSGITGD<br>NTTTSSEPAPSGCPPDSDAESYSSMPPLEGE | 1041 | 3073 | NS3-1, NS3-2, NS3-3, NS3-4, NS3-5, NS3-6, NS3-7, NS3-8, NS3-9, NS3-10, NS3-11, NS3-12, NS3-13, NS3-14, NS4a-1, NS4b-1, NS4b-2, NS4b-3, NS4b-4, NS4b-5, NS4b-6, NS4b-7, NS4b-8, NS4b-9, NS4b-10, NS5a-1, NS5a-2, NS5b-1, NS5b-2 |

FIG. 14D

| | | | | |
|---|---|---|---|---|
| | PGDPDLSDGSWSTVSSEADTEDVVCCSMS YSWTGALVTPCAAEEQKLPINALSNSLLRH HNLVYSTTSRSACQRQKKVTFDRLQVLDS HYQDVLKEVKAAASKVKANLLSVEEACSL TPPHSAKSKFGYGAKDVRCHARKAVNHIN SVWKDLLEDSVTPIDTTIMAKNEVFCVQPE KGGRKPARLIVFPDLGVRVCEKMALYDVV SKLPLAVMGSSYGFQYSPGQRVEFLVQAW KSKKTPMGFSYDTRCFDSTVTESDIRTEEAI YQCCDLDPQARVAIKSLTERLYVGGPLTNS RGENCGYRRCRASGVLTTSCGNTLTCYIK ARAACRAAGLQDCTMLVCGNNLVVICESA GVQEDAASLRAFTEAMTRYSAPPGDPPQP EYDLELITSCSSNVSVAHDGAGKRVYYLTR DPTTPLARAAWETARHTPVNSWLGNIIMF APTLWARMILMTHFFSVLIARDQLEQALD CEIYGACYSIEPLDLPPIIQRLHGLSAFSLHS YSPGEINRVAACLRKLGVPPLRAWRHRAR SVRARLLSRGGRAAICGKYLFNWAVRTKL KLTPIAAAGQLDLSGWFTAGYSGGDIYHS VSHARPRWFWFCLLLLAAGVGIYLLPNR | | | |

* TP sequences are based on HCV1a consensus sequence and gaps were removed

** Start and End numbers are based on sequence designated "Consensus" in Fig. 16A-16L.

```
                 230       240       250       260       270       280       290
                                                 E1
HCV1a consensus  TPGCVPCVR-EGNASRCWVAVTPTVATRDGKLPTTQLRRHIDLLVGSATLCSALYVGDLCGSVFLVGQLFTFSP

             300       310       320       330       340       350       360       370
                                           E1
HCV1a consensus  RRHWTTQDCNCSIYPGHITGHRMAWDMMMNWSPTTALVVAQLLRIPQAILDMIAGAHWGVLAGIAYFSMVGNWA

                       380       390       400       410       420       430       440
                     E1                                E2
HCV1a consensus  KVLVVLLLFAGVDAETHVTGGSAARTTSGLASLFTPGAKQNIQLINTNGSWHINRTALNCNDSLNTGWLAGLFY
```

FIG. 15B

```
                  450       460       470       480       490       500       510
                                                E2
HCV1a consensus  YHKFNSSGCPERLASCRPLTDFDQGWGPISYANG-SGP-DQRPYCWHYPPKPCGIVPAKSVCGPVYCFTP--SP

                 520       530       540       550       560       570       580       590
                                                E2
HCV1a consensus  VVVGTTDRSGAPTYNWGENDTDVFVLNNTRPPLGNWFGCTWMNST-GFTKVCGAPPCVI-GGVGN-----NTLH

                       600       610       620       630       640       650       660
                                                E2
HCV1a consensus  CPTDCFRKHPEATYSRCGSGPWITPRCLVDYPYRLWHYPCTINYTIFKVRMYVGGVEHRLEAACNWTRGERCDL
```

HCV1a consensus EDRDRSELSPLLLSTTQWQVLPCSFTTLPALSTGLIHLHQNIVDVQYLYGVGSSIASWAIKWEYVVLLFLLAD 750 760 770 780 790 800 810

E2 P7

HCV1a consensus ARVCSCLWMMLLISQAEAALENLVVLNAASLAGTHGLVSFLVFFCFAWYLK--GRWVPGAAYALYGMWPLLLLL 820 830 840 850 860 870 880

P7 NS2

HCV1a consensus LALPQRAYALDTEVAASCGGVVLVGLMALTLSPYYKRYISWCLWWLQYFLTRVEAQLHVWVPPLNVRGGRDAVI

FIG. 15D

HCV1a consensus  VNSWLGNIIMFAPTLWARMILMTHFFSVLIARDQLEQALDCEIYGACYSIEPLDLPPIIQRLHGLSAFSLHSYS
                 2,890    2,900    2,910    2,920    2,930    2,940    2,950    2,960

HCV1a consensus  PGEINRVAACLRKLGVPPLRAWRHRARSVRARLLSRGGRAAICGKYLFNWAVRTKLKLTPIAAAGQLDLSGWFT
                 2,970    2,980    2,990    3,000    3,010    3,020    3,030

HCV1a consensus  AGYSGGDIYHSVSSHARPRWFWFCLLLLAAGVGIYLLPNRX
                 3,040    3,050    3,060    3,070 3,074

```
                       1        10        20        30        40        50        60        70        80
Consensus              MSTNPKPQRKTKRNTNRRPQDVKFPGGGQIVGGVYLLPRRGPRLGVRATRKTSERSQPRGRRQPIPKARRSEGRSWAQPGYPWPLY
                                                          Core

1. HCV1a consensus     MSTNPKPQRKTKRNTNRRPQDVKFPGGGQIVGGVYLLPRRGPRLGVRATRKTSERSQPRGRRQPIPKARRPEGRTWAQPGYPWPLY
2. HCV1b consensus     MSTNPKPQRKTKRNTNRRPQDVKFPGGGQIVGGVYLLPRRGPRLGVRATRKTSERSQPRGRRQPIPKARRPEGRAWAQPGYPWPLY
3. HCV2a Consensus     MSTNPKPQRKTKRNTNRRPQDVKFPGGGQIVGGVYLLPRRGPRLGVRATRKTSERSQPRGRRQPIPKDRRSTGKSWGKPGYPWPLY
4. HCV2b Consensus     MSTNPKPQRKTKRNTNRRPQDVKFPGGGQIVGGVYLLPRRGPRLGVRATRKTSERSQPRGRRQPIPKDRRSTGKSWGKPGYPWPLY
5. HCV 3 Consensus     MSTLPKPQRKTKRNTIRRPQDVKFPGGGQIVGGVYVLPRRGPRLGVRATRKTSERSQPRGRRQPIPKARRSEGRSWAQPGYPWPLY
6. HCV 4 Consensus     MSTNPKPQRKTKRNTNRRPMDVKFPGGGQIVGGVYLLPRRGPRLGVRATRKTSERSQPRGRRQPIPKARRSEGRSWAQPGYPWPLY
7. HCV5 consensus      MSTNPKPQRKTKRNTNRRPQDVKFPGGGQIVGGVYLLPRRGPRLGVRATRKTSERSQPRGRRQPIPKARRPTGRSWGQPGYPWPLY
8. HCV6 consensus      MSTLPKPQRKTKRNTNRRPMDVKFPGGGQIVGGVYLLPRRGPRLGVRATRKTSERSQPRGRRQPIPKARQPTGRHWAQPGYPWPLY
9. HCV7: ABN05226      MSTNPKPQRLTKRNTVRRPQNVKFPGGGQIVGGVYLLPRRGPRLGVRGTRKSSERSQPRGRRQRIPKAASSQGKAWGKPGYPWPLY
14. AVI1a-129           MSTNPKPQRKTKRNTNRRPQDVKFPGGGQIVGGVYLLPRRGPRLGVRATRKTSERSQPRGRRQPIPKARRPEGRTWAQPGYPWPLY
15. AVI3a-177           MSTLPKPQRKTKRNTIRRPQDVKFPGGGQIVGGVYVLPRRGPRLGVRATRKTSERSQPRERRQPIPKARRSDGRSWAQPGYPWPLY

                         90       100       110       120       130       140       150       160       170
Consensus              GNEGCGWAGWLLSPRGSRPSWGPTDPRRRSRNLGKVIDTLTCGFADLMGYIPLVGAPLGGVARALAHGVRVLEDGINYATGNLPGC
                                                          Core

1. HCV1a consensus     GNEGCGWAGWLLSPRGSRPSWGPTDPRRRSRNLGKVIDTLTCGFADLMGYIPLVGAPLGGAARALAHGVRVLEDGVNYATGNLPGC
2. HCV1b consensus     GNEGMGWAGWLLSPRGSRPSWGPTDPRRRSRNLGKVIDTLTCGFADLMGYIPLVGAPLGGAARALAHGVRVLEDGVNYATGNLPGC
3. HCV2a Consensus     GNEGLGWAGWLLSPRGSRPSWGPTDPRHRSRNVGKVIDTLTCGFADLMGYIPVVGAPLGGVARALAHGVRVLEDGVNYATGNLPGC
4. HCV2b Consensus     GNEGCGWAGWLLSPRGSRPTWGPTDPRHRSRNLGKVIDTITCGFADLMGYIPVVGAPVGGVARALAHGVRVLEDGINYATGNLPGC
5. HCV 3 Consensus     GNEGCGWAGWLLSPRGSRPSWGPNDPRRRSRNLGKVIDTLTCGFADLMGYIPLVGAPVGGVARALAHGVRALEDGINFATGNLPGC
6. HCV 4 Consensus     GNEGCGWAGWLLSPRGSRPSWGPNDPRRRSRNLGKVIDTLTCGFADLMGYIPLVGAPVGGVARALAHGVRAVEDGINYATGNLPGC
7. HCV5 consensus      ANEGLGWAGWLLSPRGSRPNWGPNDPRRKSRNLGKVIDTLTCGFADLMGYIPLVGGPVGGVARALAHGVRVLEDGINYATGNLPGC
8. HCV6 consensus      GNEGCGWAGWLLSPRGSRPHWGPNDPRRRSRNLGKVIDTLTCGFADLMGYIPVVGAPLGGVAAALAHGVRAIEDGINYATGNLPGC
9. HCV7: ABN05226      GNEGCGWAGWLLSPRGSRPTWGPTDPRHRSRNLGKVIDTMTCGFADLMGYIPVLGAPLGGVARALAHGVRVLEDGVNYATGNLPGC
14. AVI1a-129           GNEGCGWAGWLLSPRGSRPSWGPTDPRRRSRNLGKVIDTLTCGFADLMGYIPLVGAPLGGAARALAHGVRVLEDGVNYATGNLPGC
15. AVI3a-177           GNEGCGWAGWLLSPRGSRPSWGPNDPRRRSRNLGKVIDTLTCGFADLMGYIPIVGAPVGGVARALAHGVRALEDGINFATGNLPGC

                             180       190       200       210       220       230       240       250
Consensus              SFSIFLLALLSCLTVPASAYEVRNXSGLYHVTNDCPNSSIVYEADAILHTPGCVPCVR-EGNTSRCWVXVTPTVAVRYXGAPTTS
                               Core                                  E1

1. HCV1a consensus     SFSIFLLALLSCLTVPASAYQVRNSTGLYHVTNDCPNSSIVYEAADAILHTPGCVPCVR-EGNASRCWVAVTPTVATRDGKLPTTQ
2. HCV1b consensus     SFSIFLLALLSCLTIPASAYEVRNVSGVYHVTNDCSNSSIVYEAADMIMHTPGCVPCVR-ENNSSRCWVALTPTLAARNASVPTTT
3. HCV2a Consensus     SFSIFLLALLSCITVPVSAAQVKNTSSSYMVTNDCSNDSITWQLQAAVLHVPGCVPCEKVGNNTSRCWIPVSPNVAVXQPGALTQG
4. HCV2b Consensus     SFSIFLLALLSCVTVPVSAVEVRNISSSYYATNDCSNNSITWQLTNAVLHLPGCVPCEN-DNGTLRCWIQVTPNVAVKHRGALTHN
5. HCV 3 Consensus     SFSIFLLALFSCLIHPAASLEWRNTSGLYVLTNDCSNSSIVYEADDVILHTPGCIPCVQTDGNTSTCWTPVTPTVAVKYVGATTAS
6. HCV 4 Consensus     SFSIFLLALLSCLTVPASAINYRNTSGIYHVTNDCPNSSIVYEADHHILHLPGCVPCVR-XGNQSRCWVALTPTVAAPYIGAPLES
7. HCV5 consensus      SFSIFXLALLSCLTVPXSAVPYRNASGVYHVTNDCPNSSIVYEAENLILHAPGCVPCVR-XGNVSRCWVQITPTLSAPSXGAVTAX
8. HCV6 consensus      SFSIFLLALLSCLTTPASAVHYXNSSGIYHLTNDCPNSSIVYEADAMILHLPGCVPCVR-VGNQSXCWVPVSPTLAVPNASTPATG
9. HCV7: ABN05226      SFSIFLLALLSCLTVPASAYEVRNSSGVYHLTNDCPNASIVYETDNAILHEPGCVPCVR-EGNTSRCWEPVAPTLAVRYRGALTDD
14. AVI1a-129           SFSIFLLALLSCLTVPASAYQVRNSTGLYHVTNDCPNSSIVYEAADAILHTPGCVPCVR-EGNTSRCWVAMTPTVATRDGKLPTTQ
15. AVI3a-177           SFSIFLLALLSCLIHPAASLEWRNTSGLYILTNDCPNSSIVYEADDVILHTPGCIPCVQ-DGNTSTCWTSVSPTVAVRYVGATTAS
```

FIG. 16A

```
                        260           270           280           290           300           310           320           330           340
Consensus               LRRHVDLLVGAATLCSALYVGDLCGAVFLVGQXFTFSPRRHWTVQDCNCSIYPGHITGHRMAWDMMMNWSPTTXLVXAQLLRIPQX
                                                      E1

1. HCV1a consensus      LRRHIDLLVGSATLCSALYVGDLCGSVFLVGQLFTFSPRRHWTTQDCNCSIYPGHITGHRMAWDMMMNWSPTTALVVAQLLRIPQA
2. HCV1b consensus      IRRHVDLLVGAAAFCSAMYVGDLCGSVFLVSQLFTFSPRRHETVQDCNCSIYPGHVSGHRMAWDMMMNWSPTTALVVSQLLRIPQA
3. HCV2a Consensus      LRTHIDMVVMSATLCSALYVGDLCGGVMLAAQMFIVSPQHHWFVQECNCSIYPGTITGHRMAWDMMMNWSPTATMILAYAMRVPEV
4. HCV2b Consensus      LRTHVDMIVMAATVCSALYVGDVCGAVMIVSQALIVSPERHNFTQECNCSIYQGHITGHRMAWDMMLNWSPTLTMILAYAARVPEL
5. HCV 3 Consensus      IRSHVDLLVGAATMCSALYVGDMCGAVFLVGQAFTFRPRRHQTVQTCNCSLYPGHLSGHRMAWDMMMNWSPAVGMVVAHVLRLPQT
6. HCV 4 Consensus      LRSHVDLMVGAATVCSALYIGDLCGGLFLVGQMFSFRPRRHWTTQDCNCSIYTGHITGHRMAWDMMMNWSPTTTLVLAQVMRIPST
7. HCV5 consensus       LRRAVDYLAGGAALCSALYVGDACGAVXLVGQMFTYSPRXHTXVQDCNCSIYSGHITGHRMAWDMMMNWSPTTALXMAQLLRIPQV
8. HCV6 consensus       FRRHVDLLVGAAAFCSALYIGDLCGGVFLVGQLFTFRPRRHQTVQDCNCSIYTGHVTGHRMAWDMMMNWSPTATLVLSSILRVPQL
9. HCV7: ABN05226       LRTHIDLVVASATLCSALYVGDICGAIFIASQAVLWKPGGGRIVQDCNCSIYPGHVTGHRMAWDMMQNWAPALSMVAAYAVRVPGV
14. AVI1a-129           LRRHIDLLVGSATLCSALYVGDLCGSVFLVGQMFTFSPRRHWTTQDCNCSLYPGHITGHRMAWDMMMNWSPTAALITAQLLRIPQA
15. AVI3a-177           IRSHVDLLVGAATLCSALYVGDMCGAVFLVGQAFTFRPRRHQTVQTCNCSLYPGHLTGHRMAWDMMMNWSPAVGMVVAHVLRMPQT

                          350           360           370           380           390           400           410           420           430
Consensus               XLDIIAGAHWGVLAGLAYFSMQGNWAKVJXVLLLFAGVDAETHTTGGXAARTTSGLTSLFSPGPXQNLQLINTNGSWHINRTALNC
                                        E1                                            E2

1. HCV1a consensus      ILDMIAGAHWGVLAGIAYFSMVGNWAKVLVVLLLFAGVDAETHVTGGSAARTTSGLASLFTPGAKQNIQLINTNGSWHINRTALNC
2. HCV1b consensus      VVDMVAGAHWGVLAGLAYYSMVGNWAKVLIVMLLFAGVDG-THVTGGAAARTTSGFTSLFSPGPSQKIQLINTNGSWHINRTALNC
3. HCV2a Consensus      IIDIISGAHWGVMFGLAYFSMQGAWAKVVVILLLAAGVDAGTHTVGGSAAHTTSGLAGLFSXGXXQNIQLINTNGSWHINRTALNC
4. HCV2b Consensus      VLEVVFGGHWGVVFGLAYFSMQGAWAKVIAILLLVAGVDATTYSSGAQAGRTTSGFAGLFSPGPKQNIQLINTNGSWHINRTALNC
5. HCV 3 Consensus      LFDIIAGAHWGILAGLAYYSMQGNWAKVAIIMVMFSGVDAXTHTTGGSAARGARGLTSLFSVGPXQNLQLVNTNGSWHINRTALNC
6. HCV 4 Consensus      LVDLLAGGHWGVLVGVAYFSMQANWAKVILVLFLFAGVDAETHVSGGAAGRTTXGLTSLFSPGXQQNLQLINSNGSWHINRTALNC
7. HCV5 consensus       VIDIIAGAHWGVLFAAAYFASXANWAKVILVLFLFAGVDAXTXTVGGXAGQGXXXLTSFFXPGPQQNLQLINTNGSWHINRTALNC
8. HCV6 consensus       LLDIFLGGHWGVLGAVLYYSMVANWAKVLAVLLLFAGVDATT-TTGXAAGRTTSGLTXLFXPGAKQNLQLINTNGSWHINRTALNC
9. HCV7: ABN05226       IITTVAGGHWGVLFGLAYFGMAGNWAKVILIMLLMSGVDAETMAVGARAAHTTGALVSLLNPGPSQRLQLINTNGSWHINRTALNC
14. AVI1a-129           ILDMIAGAHWGVLAGIAYFSMVGNWAKVLVVLLLFAGVDAQTHVTGGRAAHITAGLTSLFSPGPSQKLQLVNTNGSWHINSTALNC
15. AVI3a-177           VFDIIAGAHWGILAGLAYYSMQGNWAKVAIIMVMFSGVDAETHTTGGTAARNAFTLTGLFTQGARQKLQLINTNGSWHINRTALNC

                              440           450           460           470           480           490           500           510
Consensus               NDSLXTGFIAGLFYTHKFNSSGCPERLASCRPLTDFDQGWGPLTYANXISGPSDDRPYCWHYPPRPCGIVPARSVCGPVYCFTP--
                                                      E2

1. HCV1a consensus      NDSLNTGWLAGLFYYHKFNSSGCPERLASCRPLTDFDQGWGPISYANG-SGP-DQRPYCWHYPPKPCGIVPAKSVCGPVYCFTP--
2. HCV1b consensus      NDSLQTGFLAALFYTHKFNSSGCPERMASCRPIDKFAQGWGPITYA---EPSSDQRPYCWHYAPRPCGIVPASQVCGPVYCFTP--
3. HCV2a Consensus      NDSLNTGFLASLFYTHRFNSSGCPERLSACRNIEAFRIGWGTLQYEDNVTNPEDMRPYCWHYPPKQCGIVPARSVCGPVYCFTP--
4. HCV2b Consensus      NDSLQTGFIASLFYTNNFNSSGCPERLSSCRGLDDFRIGWGTLEYETNVTNDEDMRPYCWHYPPKPCGIVSARTVCGPVYCFTP--
5. HCV 3 Consensus      NDSINTGFIAGLFYYHKFNSTGCPQRLSSCKPITFFRQGWGPLTDANNITGPSDDKPYCWHYAPRPCDVVPASSVCGPVYCFTPHH
6. HCV 4 Consensus      NDSLNTGFLASLFYTHKFNSSGCPERLASCKSLDSFDQGWGPLGVANNISGPSDDRPYCWHYPPRPCGIVPASSVCGPVYCFTP--
7. HCV5 consensus       NDSLQTGFIAGLXYXHKFNSSGCPQRMASCRPLAAFDQGWGTISYAX-VSGPSDDKPYCWHYPPRPCGVVPARXVCGPVYCFTP--
8. HCV6 consensus       NDSLQTGFIAGLFYTHKFNSSGCPERMSSCKPLTDFDQGWGPITYAN-ISGPSEDRPYCWHYAPRPCDVVPARTVCGPVYCFTP--
9. HCV7: ABN05226       NDSLQTGFIAALFYTHRFNSSGCPERMASCKPLSDFDQGWGPLWY-NSTERPSDQRPYCWHYAPSPCGIVPAKDVCGPVYCFTP--
14. AVI1a-129           NDSLKTGWIAGLLYSYKFNSSGCPERLASCRRLTDFAQGWGPISHANG-SGP-DERPYCWHYPPRPCGIVPAKSVCGPVYCFTP--
15. AVI3a-177           NESLNTGFIAGLFYLHKFNSTGCPERLSSCKPITFFRQGWGSLTDAN-ITGPSDDKPYCWHYAPRPCEVVPALNVCGPVYCFTP--
```

FIG. 16B

```
                    520       530       540       550       560       570       580       590       600
Consensus           SPVVVGTTDRXGVPTYTWGENETDVFLLNSTRPPQGNWFGCTWMNST-GFTKTCGAPPCNI-GGGGN-----NDLLCPTDCFRKHP
                    E2

1. HCV1a consensus  SPVVVGTTDRSGAPTYNWGENDTDVFVLNNTRPPLGNWFGCTWMNST-GFTKVCGAPPCVI-GGVGN-----NTLHCPTDCFRKHP
2. HCV1b consensus  SPVVVGTTDRFGVPTYSWGENETDVLLLNNTRPPQGNWFGCTWMNST-GFTKTCGGPPCNI-GGVGN-----NTLTCPTDCFRKHP
3. HCV2a Consensus  SPVVVGTTDRLGVPTYTWGENETDVFLLNSTRPPQGSWFGCTWMNST-GFTKTCGAPPCRI-RADFNAS---TDLLCPTDCFRKHP
4. HCV2b Consensus  SPVVVGTTDRQGVPTYSWGENETDVFLLNSTRPPQGAWFGCTWMNGT-GFTKTCGAPPCRI-RRDYNST---LDLLCPTDCFRKHP
5. HCV 3 Consensus  SPVVVGTTDAKGVPTYTWGENETDVFLLESLRPPSGRWFGCTWMNSTRGFVKTCGAPPCNIYGGGGNPXNNESDLFCPTDCFRKHP
6. HCV 4 Consensus  SPVVVGTTDRLGVPTYTWGENESDVFLLNSTRPPQGAWFGCVWMNST-GFTKACGAPPCEVRTNNGTS----TDWPCPTDCFRKHP
7. HCV5 consensus   SPVVVGTTDRXGXPTYXWGXNETDIFLLNNTRPPXGNWFGCTWMNST-GFVKTCGAPPCNL-GPTGN-----NSLKCPTDCFRKHP
8. HCV6 consensus   SPVVVGTTDRRGLPTYTWGENETDVFLLESLRPPTGGWFGCTWMNST-GFVKTCGAPPCNIXPNSSN-----NSLLCPTDCFRKHP
9. HCV7: ABN05226   SPVVVGTTDRRGVPTYTWGENESDVFLLNSTRPPQGSWFGCSWMNTT-GFTKTCGGPPCKIRPQGAQSN---TSLTCPTDCFRKHP
14. AVI1a-129       SPVVVGTTDKSGAPTYNWGENDWDVFVLNNTRPPLGNWFGCTWMNST-GFTKVCGAPPCVI-GGAGN-----NTLRCPTDCFRKHP
15. AVI3a-177       SPVVVGTTDRQGVPTYTWGENETDVFLLRSLRPPSGQWFGCTWMNST-GFVKTCGAPPCDIYGGGGNRCN-ESDLFCPTDCFRKHP

                         610       620       630       640       650       660       670       680
Consensus           EATYSXCGSGPWLTPRCLVDYPYRLWHYPCTVNFTIFKVRMYVGGVEHRLEAACNWTRGERCDLEDRDRSELSPLLHSTTEWAILP
                    E2

1. HCV1a consensus  EATYSRCGSGPWITPRCLVDYPYRLWHYPCTINYTIFKVRMYVGGVEHRLEAACNWTRGERCDLEDRDRSELSPLLLSTTQWQVLP
2. HCV1b consensus  EATYTKCGSGPWLTPRCLVDYPYRLWHYPCTVNFTIFKVRMYVGGVEHRLNAACNWTRGERCDLEDRDRSELSPLLLSTTEWQILP
3. HCV2a Consensus  EATYIKCGSGPWLTPRCLVDYPYRLWHYPCTVNYTIFKIRMYVGGVEHRLTAACNFTRGDRCNLEDRDRSQLSPLLHSTTEWAILP
4. HCV2b Consensus  DATYLKCGAGPWLTPRCLVDYPYRLWHYPCTVNFTIFKVRMYVGGVEHRLSAACNFTRGDRCRLEDRDRGQQSPLLHSTTEWAVLP
5. HCV 3 Consensus  EATYSRCGAGPWLTPRCMVDYPYRLWHYPCTVNFTLFKVRMFVGGFEHRFTAACNWTRGERCDIEDRDRSEQHPLLHSTTELAILP
6. HCV 4 Consensus  ETTYAKCGSGPWITPRCLIHYPYRLWHYPCTVNFTVFKIRTFIGGIEHRMEAACNWTRGEVCGLEHRDRAELSPLLLSTTTWQXLP
7. HCV5 consensus   DATYTKCGSGPWLTPRCLVHYPYRLWHYPCTVNYTIFKVRMFIGGLEHRLEAACNWTRGERCDLEDRDRAELSPLLHTTTQWAILP
8. HCV6 consensus   EATYARCGSGPWLTPRCLVDYPYRLWHYPCTVNFTIHKVRMFVGGVEHRFDAACNWTRGERCELDDRDRIEMSPLLFSTTELAILP
9. HCV7: ABN05226   RATYSACGSGPWLTPRCMVHYPYRLWHYPCTVNFTIHKVRLYIGGVEHRLDAACNWTRGERCDLEDRDRVDMSPLLHSTTELAILP
14. AVI1a-129       DATYSRCGSGPWITPRCLVDYPYRLWHYPCTVNYSIFKIRMYLGGVEHRLEAACNWTRGERCDLEDRDRSELSPLLLSTTQWQVLP
15. AVI3a-177       EATYSRCGAGPWLTPRCLVDYPYRLWHYPCTVNFTLFKVRMFVGGFEHRFTAACNWTRGERCNIEDRDRSEQHPLLHSTTELAILP

                    690       700       710       720       730       740       750       760       770
Consensus           CSFTTLPALSTGLIHLHQNIVDVQYLYGVGSAVVSWAXKWEYVVLLFLLLADARVCACLWMMLLISQAEAALENLVVLNAASAAGT
                    E2                                                                                 P7

1. HCV1a consensus  CSFTTLPALSTGLIHLHQNIVDVQYLYGVGSSIASWAIKWEYVVLLFLLLADARVCSCLWMMLLISQAEAALENLVVLNAASLAGT
2. HCV1b consensus  CSFTTLPALSTGLIHLHQNIVDVQYLYGIGSAVVSFAIKWEYVLLLFLLLADARVCACLWMMLLIAQAEAALENLVVLNAASVAGA
3. HCV2a Consensus  CSYSDLPALSTGLLHLHQNIVDVQYMYGLSPALTKYVVRWEWVVLLFLLLADARVCACLWMLILLGQAEAALEKLVVLHAASAASC
4. HCV2b Consensus  CSFSDLPALSTGLLHLHQNIVDVQYLYGLSPAITRYIVKWEWVVLLFLLLADARVCACLWMLIILGQAEAALEKLIILHSASAASA
5. HCV 3 Consensus  CSFTPMPALSTGLIHLHQNIVDVQYLYGVGSGMVGWALKWEFVILVFLLLADARVCVALWLMLMISQAEAALENLVTLNAVAAAGT
6. HCV 4 Consensus  CSFTTLPALSTGLIHLHQNIVDVQYLYGVGSAVVSWALKWEYVVLAFLLLADARVSACLWMMFMVSQVEAALSNLININAASAAGT
7. HCV5 consensus   CSFTPTPALSTGLIHLHQNIVDTQYLYGLSSSIVSWAVKWEYIVLXFLLLADARICTCLWILLLXCQAEAALENVIVLNAAAAAGX
8. HCV6 consensus   CSFTTMPALSTGLIHLHQNIVDVQYLYGVSSSVVSWAVKWEYVVLAFLVLADARICACLWLMLLIGQAEAALENLIVLNAASAAST
9. HCV7: ABN05226   CSFVPLPALSTGLIHLHQNIVDAQYLYGLSPAIISWAIRWEWVVLVFLLLADARICACLWMMMLMAQAEAALENLIHLNAASLAGT
14. AVI1a-129       CSFTTLPALSTGLIHLHQNIVDVQYLYGVGSSVASWAIKWDYVVLLFLLLADARICSCLWMMLLISQAEAALENLVVLNAASLAGT
15. AVI3a-177       CSFTPMPALSTGLIHLHQNIVDVQYLYGVGSGVVGWALRWEFVVLVFLLLADARVCVALWLMLMISQAEAALENLVTLNAVAAAGT
```

FIG. 16C

```
                    780       790       800       810       820       830       840       850       860
Consensus           HGIXWFLVFFCAAWYLK--GRLVPXATYALXGLWPLLLLLLALPQRAYALDREVAASLGXAVLVXLTIFTLSPHYKHLLSRXLWWL
                                      P7                                     NS2

1. HCV1a consensus  HGLVSFLVFFCFAWYLK--GRWVPGAAYALYGMWPLLLLLLALPQRAYALDTEVAASCGGVVLVGLMALTLSPYYKRYISWCLWWL
2. HCV1b consensus  HGILSFLVFFCAAWYIK--GRLVPGAAYAFYGVWPLLLLLLALPPRAYAMDREMAASCGGAVFVGLALLTLSPHYKVFLARLIWWL
3. HCV2a Consensus  NGFLYFVIFFVAAWYIK--GRAVPLAAYSLTGLWPFCLLLLALPQQAYAYDASVHGQIGAALLILITLFTLTPGYKTLLSRCLWWL
4. HCV2b Consensus  NGPLWFFIFFTAAWYLK--GRVVPVATYSVLGLWSFLLLVLALPQQAYALDAAEQGELGLVILVIISIFTLTPAYKILLSRSVWWL
5. HCV 3 Consensus  HGIGWYLVAFCAAWHVRRAGKLVPLVTYSLTGLWSLALLVLLLPQRAYAWSGEDSATLGAGILVLFGFFTLSPWYKHWIGRLMWWN
6. HCV 4 Consensus  HGFWYAIFFICIAWHVK--GRLPAAATYAACGMWPLLLLLLMLPERAYAYDREVAGSLGGAVVVALTILTLSPHYKSWLARGLWWI
7. HCV5 consensus   HGFFWGLLVXCXAWHXK--GRLVPGATYLCLGXWPLLLLLLLLPQRALALDSSDGGTVGCLVLXILTIFTLTPGYKKXVVLVXWWL
8. HCV6 consensus   QGWWWGLLFLCCAWYVK--GRLVPACTYALLQLWPLLLLVLALPRRAYAYDNEQAASLGALVLLVITIFTLTPAYKQLLVSFLWWN
9. HCV7: ABN05226  HGIWWLLLVFCASWHLR--GRVVPLVTYGICGMWPFFLMLLSLPPRAYALDREVSAALGTGMLAIILLVTLGPHYKRLLALILWWV
14. AVI1a-129       HGLAPFLVFFCLAWYLK--GKWAPGAVYAVYGMWPLLLLLLALPQRAYALDTEVAASCGGAVLVGLMVLTLSPHYKHYISWCLWWL
15. AVI3a-177       HGIGWYLVAFCAAWHLR--GKLVPLVTYSLTGLWSLAVLVLLLPQRAYAWSGEDSATLGAGILVLFGFFTLSPWYKHWIGRLMWWN

                           870       880       890       900       910       920       930       940
Consensus           QYFITRAEAXLQVWVPPLNVRGGRDXXILLTCLLHPXLVFDITKLLLAVLGPLYLLQASLLRVPYFVRAHALLRXCMLVRXLAGGK
                                                        NS2

1. HCV1a consensus  QYFLTRVEAQLHVWVPPLNVRGGRDAVILLMCVVHPTLVFDITKLLLAVFGPLWILQASLLKVPYFVRVQGLLRICALARKMAGGH
2. HCV1b consensus  QYFITRAEAHLQVWIPPLNVRGGRDAIILLTCAVHPELIFDITKLLLAILGPLMVLQAGITRVPYFVRAQGLIRACMLVRKVAGGH
3. HCV2a Consensus  CYLLTLGEAMVQEWAPPMQARGGRDGIIWAATIFCPGVVFDITKWLLAVLGPAYLLRDALTRVPYFVRAHALLRMCTMVRHLAGGR
4. HCV2b Consensus  SYMLVLAEAQIQQWVPPLEARGGRDGIIWVAVILHPRLVFEVTKWLLAILGPAYLLKASLLRVPYFVRAHALLRVCTLVRHLAGAR
5. HCV 3 Consensus  QYTICRCEAALQVWVPPLLARGSRDGVILLTSLLYPSLIFDITKLLIAVLGPLYLIQAAITTTPYFVRAHVLVRLCMLVRSVMGGK
6. HCV 4 Consensus  QYFIARAEALLHVYVPSFDVRGPRDSLIILAVLACPHLVFDITKYLLAILGPLYILQASLLRVPYFVRAHALVKICSLLRGVVYGK
7. HCV5 consensus   QYFIARVEAXIHVWVPPLQVRGGRDAIIMLTCLFHPALGFEVTKILLGILGPLYLLQXSLXKVPYFXRARALLRACLLAKHLVXGK
8. HCV6 consensus   QYFIARAEAMLHVWVPSLRVRGGRDAVILLTCLLHPQLGFEVTKILLALLGPLYLLQYSLLKVPYFVRAHILLRACLLVRRLAGGK
9. HCV7: ABN05226  TYFLTRCEAALQTWVPPLNPRGGRDGFILCVLLCYPGLVFDITKWLLVMMCPLYLLQLCLVRTPYFVRAQALIRVCSLFKTLAGGR
14. AVI1a-129       QYFLTRAEAQLHVWVPPLNVRGGRDAVILLMCVVHPTLVFDITKLLLAV?GPLWILQTSLLKVPYFVRVQGLLRICALARKIAGGH
15. AVI3a-177       QYTICRCEAALQVWVPPLLARGSRDGAILLTSLLYPSLIFDITKLLIAVLGPLYLIQAAITTTPYFVRAHVLVRLCMLVRSVMGGK

                    950       960       970       980       990       1,000     1,010     1,020     1,030
Consensus           YVQMALLKLGRWTGTYIYDHLXPLSDWAAAGLRDLAVAVEPVIFSPMEKKVITWGADTAACGDILCGLPVSARLGREILLGPADDY
                                                        NS2

1. HCV1a consensus  YVQMAIIKLGALTGTYVYNHLTPLRDWAHNGLRDLAVAVEPVVFSQMETKLITWGADTAACGDIINGLPVSARRGREILLGPADGM
2. HCV1b consensus  YVQMAFMKLAALTGTYVYDHLTPLRDWAHAGLRDLAVAVEPVVFSDMETKIITWGADTAACGDIILGLPVSARRGREILLGPADSL
3. HCV2a Consensus  YVQMALLALGRWTGTYIYDHLTPMSDWAASGLRDLAVAVEPIIFSPMEKKVIVWGAETAACGDILHGLPVSARLGREILLGPADGY
4. HCV2b Consensus  YIQMLLITIGRWTGTYIYDHLSPLSTWAAQGLRDLAVAVEPVVFSPMEKKVIVWGAETVACGDILHGLPVSARLGREVLLGPADSY
5. HCV 3 Consensus  YFQMIILSIGRWFNTYLYDHLAPMQHWAAAGLKDLAVATEPVIFSPMEIKVITWGADTAACGDILCGLPVSARLGREVLLGPADDY
6. HCV 4 Consensus  YCQMAVLKVGALTGTYIYDHLTPLSDWAAEGLRDLAVALEPVVFTPMEKKVIVWGADTAACGDIIXGLPVSARLGNEILLGPADSE
7. HCV5 consensus   YVQAALLHLGRLTGTYIYDHLAPMKDWAASGLRDLAVATEPIIFSPMETKVITWGADTAACGDILAGLPVSARRGREIFLGPADDI
8. HCV6 consensus   YVQACLLRLGAWTGTYIYDHLAPLSDWASDGLRDLAVAVEPVIFSPMEKKVITWGADTAACGDILAGLPVSARRGNLVLLGPADDM
9. HCV7: ABN05226  YVQAALLTIGRWTGTYIYNHLAPLETWAAGGLRDLAVAVEPVIFSPMEKKIIVWGAETTACGDILCGLPVSARLGREVLLGPADDY
14. AVI1a-129       YVQMAIIKLGALTGTYIYDHLTPLRDWAHNGLRDLAVAVEPVVFSRMETKLITWGADTAACGDIINGLPVSARRGQEILLGPADGM
15. AVI3a-177       YFQMIILSIGRWFNTYLYDHLAPMQHWAAAGLKDLAVATEPVIFSPMEIKVITWGADTAACGDILCGLPVSARLGHEVLLGPADDY
```

FIG. 16D

```
                      1,040     1,050     1,060     1,070     1,080     1,090     1,100     1,110
Consensus             XSKGWRLLAPITAYAQQTRGLLGTIVTSLTGRDKNEVEGEVQVLSTATQTFLGTCINGVMWTVYHGAGSKTLAGPKGPVXQMYTNV
                      NS2 NS3

1. HCV1a consensus    VSKGWRLLAPITAYAQQTRGLLGCIITSLTGRDKNQVEGEVQIVSTAAQTFLATCINGVCWTVYHGAGTRTIASPKGPVIQMYTNV
2. HCV1b consensus    EGQGWRLLAPITAYSQQTRGLLGCIITSLTGRDKNQVEGEVQVVSTATQSFLATCVNGVCWTVYHGAGSKTLAGPKGPITQMYTNV
3. HCV2a Consensus    TSKGWRLLAPITAYAQQTRGLLGAIVVSMTGRDKTEQAGEIQVLSTVTQSFLGTSISGVLWTVYHGAGNKTLAGSRGPVTQMYSSA
4. HCV2b Consensus    TSKGWKLLAPITAYTQQTRGLLGAIVVSLTGRDKNEQAGQVQVLSSVTQSFLGTSISGVLWTVYHGAGNKTLAGPKGPVTQMYTSA
5. HCV 3 Consensus    REMGWRLLAPITAYAQQTRGLLGTIVTSLTGRDKNVVTGEVQVLSTATQTFLGTTVGGVMWTVYHGAGSRTLAGAKHPALQMYTNV
6. HCV 4 Consensus    TSKGWRLLAPITAYAQQTRGLFSTIITSLTGRDTNENCGEVQVLSTATQSFLGTAVNGVMWTVYHGAGSKTISGPKGPVNQMYTNV
7. HCV5 consensus     XXAGWRLLAPITAYAQQTRGVLGAIVVSLTGRDKNEAEGEVQVLSTATQTFLGTCINGVMWTVFHGAGXKTLAGPKGPVVQMYTNV
8. HCV6 consensus     KRGGWRLLAPITAYAQQTRGLLGTIVTSLTGRDKNEVEGEVQVVSTATQSFLATSINGVLWTVYHGAGSKTLAGPKGPVCQMYTNV
9. HCV7: ABN05226     RSMGWQLLAPISAYAQQTRGLISTLVVSLTGRDKNETAGEVQVLSTSTQTFLGTNVGGVMWGPYHGAGTRTVAGRGGPVLQMYTSV
14. AVI1a-129         VSKGWRLLAPITAYAQQTRGLLGCIITSLTGRDKNQVEGEVQIVSTAAQTFLATCINGVCWTVYHGAGTRTIASPKGPVIQMYTNV
15. AVI3a-177         REMGWRLLAPITAYAQQTRGLLGTIVTSLTGRDKNVVTGEVQVLSTATQTFLGTTIGGVMWTVYHGAGSRTLAGVKHPALQMYTNV

                    1,120     1,130     1,140     1,150     1,160     1,170     1,180     1,190     1,200
Consensus             DQDLVGWPAPPGAKSLTPCTCGSSDLYLVTRHADVIPXRRRGDSRGSLLSPRPISXLKGSSGGPVLCPSGHAVGIFRAAVCTRGVA
                      NS3

1. HCV1a consensus    DQDLVGWPAPQGARSLTPCTCGSSDLYLVTRHADVIPVRRRGDSRGSLLSPRPISYLKGSSGGPLLCPAGHAVGIFRAAVCTRGVA
2. HCV1b consensus    DQDLVGWQAPPGARSLTPCTCGSSDLYLVTRHADVIPVRRRGDSRGSLLSPRPVSYLKGSSGGPLLCPSGHAVGIFRAAVCTRGVA
3. HCV2a Consensus    EGDLVGWPSPPGTKSLEPCTCGAVDLYLVTRNADVIPARRRGDKRGALLSPRPLSTLKGSSGGPVLCPRGHAVGIFRAAVCSRGVA
4. HCV2b Consensus    EGDLVGWPSPPGTKSLDPCTCGAVDLYLVTRNADVIPVRRKDDRRGALLSPRPLSTLKGSSGGPVLCPRGHAVGLFRAAVCARGVA
5. HCV 3 Consensus    DQDLVGWPAPPGAKSLEPCACGSADLYLVTRDADVIPARRRGDSTASLLSPRPLACLKGSSGGPVMCPSGHVAGIFRAAVCTRGVA
6. HCV 4 Consensus    DQDLVGWPAPPGVKSLAPCTCGASDLYLVTRHADVVPVRRRGDTRGALLSPRPISTLKGSSGGPLLCPMGHAAGIFRAAVCTRGVA
7. HCV5 consensus     DKDLVGWPXPPGXRSLTPCTCGSADLYLVTRHADVIPARRRGDTRASLLSPRPISYLKGSSGGPIMCPSGHVVGVFRAAVCTRGVA
8. HCV6 consensus     DQDLVGWPAPPGARSLTPCTCGSSDLYLVTRNADVIPARRRGDTRAALLSPRPISTLKGSSGGPILCPSGHVVGLFRAAVCTRGVA
9. HCV7: ABN05226     SDDLVGWPAPPGSKSLEPCSCGSADLYLVTRNADVLPLRRKGDGTASLLSPRPVSSLKGSSGGPVLCPQSHCVGIFRAAVCTRGVA
14. AVI1a-129         DKDLVGWPAPPGSRSLTPCTCGSSDLYLVTRHADVIPVRRRGDSRGSLLSPRPISYLKGSSGGPLLCPAGHAVGIFRAAVCTRGVA
15. AVI3a-177         DQDLVGWPAPPGAKSLEPCSCGSTDLYLVTREADVIPARRRGDSTASLLSPRPLACLKGSSGGPVMCPSGHVAGIFRAAVCTRGVA

                      1,210     1,220     1,230     1,240     1,250     1,260     1,270     1,280     1,290
Consensus             KAVDFIPVESLETTMRSPXFTDNSTPPAVPQXYQVGYLHAPTGSGKSTKVPAAYAAQGYKVLVLNPSVAATLGFGAYMSKAHGIDP
                      NS3

1. HCV1a consensus    KAVDFIPVENLETTMRSPVFTDNSSPPAVPQSFQVAHLHAPTGSGKSTKVPAAYAAQGYKVLVLNPSVAATLGFGAYMSKAHGIDP
2. HCV1b consensus    KAVDFVPVESMETTMRSPVFTDNSSPPAVPQTFQVAHLHAPTGSGKSTKVPAAYAAQGYKVLVLNPSVAATLGFGAYMSKAHGVDP
3. HCV2a Consensus    KSIDFIPVETLDIVTRSPTFSDNSTPPAVPQTYQVGYLHAPTGSGKSTKVPVAYAAQGYKVLVLNPSVAATLGFGAYLSKAHGINP
4. HCV2b Consensus    KSIDFIPVESLDIATRTPSFSDNSTPPAVPQSYQVGYLHAPTGSGKSTKVPAAYASQGYKVLVLNPSVAATLGFGAYMSKAHGINP
5. HCV 3 Consensus    KALQFIPVETLSTQARSPSFSDNSTPPAVPQSYQVGYLHAPTGSGKSTKVPAAYVAQGYNVLVLNPSVAATLGFGSFMSRAYGIDP
6. HCV 4 Consensus    KAVDFVPVESLETTMRSPVFTDNSTPPAVPQTYQVAHLHAPTGSGKSTKVPAAYAAQGYKVLVLNPSVAATLGFGAYMSKAYGIDP
7. HCV5 consensus     KALDFIPVENLETTMRSPVFTDNSTPPAVPHEFQVGHLHAPTGSGKSTKVPAAYAAQGYKVLVLNPSVAATLGFGAYMSRAYGVDP
8. HCV6 consensus     KSLDFVPVENMETTMRSPSFTDNSTPPAVPQTYQVGYLHAPTGSGKSTKVPAAYASQGYKVLVLNPSVAATLGFGSYMSKAHGIDP
9. HCV7: ABN05226     KAVQFVPIEKMQVAQRSPSFSDNSTPPAVPSTYQVGYLHAPTGSGKSTKVPAAYASQGYKVLVLNPSVAATLGFGAYMSKAYGIDP
14. AVI1a-129         KAVDFIPVESLETTMRSPVFTDNSSPPVVPQSFQVAHLHAPTGSGKSTKVPAAYAAQGYKVLVLNPSVAATL?FGAYMSKAHGVDP
15. AVI3a-177         KALQFIPVETLSAQARSPSFSDNSTPPIVPQSYQVGYLHAPTGSGKSTKVPAAYVAQGYNVLVLNPSVAATLGFGSFMSRAYGIDP
```

FIG. 16E 1,300 1,310 1,320 1,330 1,340 1,350 1,360 1,370

Consensus NIRTGVRTVTTGAPITYSTYGKFLADGGCSGGAYDIIICDECHSTDATTILGIGTVLDQAETAGVRLVVLATATPPGSVTVPHPNI

NS3

1. HCV1a consensus NIRTGVRTITTGSPITYSTYGKFLADGGCSGGAYDIIICDECHSTDATSILGIGTVLDQAETAGARLVVLATATPPGSVTVPHPNI
2. HCV1b consensus NIRTGVRTITTGAPITYSTYGKFLADGGCSGGAYDIIICDECHSTDSTTILGIGTVLDQAETAGARLVVLATATPPGSVTVPHPNI
3. HCV2a Consensus NIRTGVRTVTTGEAITYSTYGKFLADGGCAGGAYDIIICDECHAVDATTILGIGTVLDQAETAGVRLTVLATATPPGSVTTPHPNI
4. HCV2b Consensus NIRTGVRTVTTGDPITYSTYGKFLADGGCSAGAYDVIICDECHSVDATTILGIGTVLDQAETAGARLVVLATATPPGTVTTPHSNI
5. HCV 3 Consensus NIRTGNRTVTTGAKLTYSTYGKFLADGGCSGGAYDVIICDECHAQDATSILGIGTVLDQAETAGVRLTVLATATPPGSITVPHSNI
6. HCV 4 Consensus NIRSGVRTITTGAPITYSTYGKFLADGGCSGGAYDIIICDECHSTDSTTILGIGTVLDQAETAGVRLVVLATATPPGSVTTPHSNI
7. HCV5 consensus NIRTGVRTVTTGAAITYSTYGKFLADGGCSGGAYDVIICDECHSQDATTILGIGTVLDQAETAGARLVVLATATPPGSVTTPHPNI
8. HCV6 consensus NIRTGVRTITTGGAITYSTYGKFLADGGCSGGAYDIIICDECHSTDPTTVLGIGTVLDQAETAGVRLTVLATATPPGSVTVPHPNI
9. HCV7: ABN05226 SVRTGARTVTTGAPITYSTYGKFLADGGCSGGAYDIIICDECHAIDATTVVGIGTVLDQAETSGVRLVVLATATPPGSVTVPHPNI
14. AVI1a-129 NIRTGVRTITTGSPITYSTYGKFLADGGCSGGAYDIIICDECHSTDATSILGIGTVLDQAETAGARLVVLATATPPGSVTVPHPNI
15. AVI3a-177 NIRTGNRTVTTGAKLTYSTYGKFLADGGCSGGAYDVIICDECHAQDATSILGIGTVLDQAETAGVRLTVLATATPPGSITVPHSNI 1,380 1,390 1,400 1,410 1,420 1,430 1,440 1,450 1,460

Consensus EEVALGTXGEIPFYGKAIPLEXIKGGRHLIFCHSKKKCDELAAKLXGLGLNAVAYYRGLDVSVIPTSGDVVVVATDALMTGFTGDF

NS3

1. HCV1a consensus EEVALSTTGEIPFYGKAIPLEVIKGGRHLIFCHSKKKCDELAAKLVALGINAVAYYRGLDVSVIPTSGDVVVVATDALMTGFTGDF
2. HCV1b consensus EEVALSNTGEIPFYGKAIPIETIKGGRHLIFCHSKKKCDELAAKLSGLGLNAVAYYRGLDVSVIPTSGDVVVVATDALMTGFTGDF
3. HCV2a Consensus EEVALGQEGEIPFYGRAIPLSYIKGGRHLIFCHSKKKCDELAAALRGMGLNAVAYYRGLDVSIIPTQGDVVVVATDALMTGYTGDF
4. HCV2b Consensus EEVALGHEGEIPFYGKAIPLAFIKGGRHLIFCHSKKKCDELAAALRGMGVNAVAYYRGLDVSVIPTQGDVVVVATDALMTGYTGDF
5. HCV 3 Consensus EEVALGSEGEIPFYGKAIPIAQLKGGRHLIFCHSKKKCDEIASKLRGMGLNAVAYYRGLDVSVIPTTGDVVVCATDALMTGFTGDF
6. HCV 4 Consensus EEVALPTTGEIPFYGKAIPLELIKGGRHLIFCHSKKKCDELAKQLTSLGLNAVAYYRGLDVSVIPTSGDVVVCATDALMTGFTGDF
7. HCV5 consensus EEVALPSEGEIPFYGRAIPLXLIKGGRHLIFCHSKKKCDELAKQLTSLGVNAVAYYRGLDVAVIPATGDVVVCSTDALMTGFTGDF
8. HCV6 consensus TETALPTTGEIPFYGKAIPLEYIKGGRHLIFCHSKKKCDELAKQLTSLGLNAVAFYRGVDVSVIPTSGDVVVCATDALMTGYTGDF
9. HCV7: ABN05226 EEVALGNDGEIPFYGKAIPLQHIKGGRHLIFCHSKKKCDELAGKLTSLGLTAVAYYRGLDVSVIPTSGDVVVVATDALMTGFTGDF
14. AVI1a-129 EEVALSTTGEIPFYGKAIPLEVIKGGRHLIFCHSKKKCDELAAKLVALGINAVAYYRGLDVSVIPTSGDVVVVATDALMTGYTGDF
15. AVI3a-177 EEVALGSEGEIPFYGKAIPLAQLKGGRHLIFCHSKKKCDEMASKLRGMGLNAVAYYRGLDVSVIPTAGDVVVCATDALMTGFTGDF 1,470 1,480 1,490 1,500 1,510 1,520 1,530 1,540

Consensus DSVIDCNVAVTQTVDFSLDPTFTIETTTVPQDAVSRSQRRGRTGRGRLGIYRYVSPGERPSGMFDSVVLCECYDAGCAWYELTPAE

NS3

1. HCV1a consensus DSVIDCNTCVTQTVDFSLDPTFTIETTTLPQDAVSRTQRRGRTGRGKPGIYRFVAPGERPSGMFDSSVLCECYDAGCAWYELTPAE
2. HCV1b consensus DSVIDCNTCVTQTVDFSLDPTFTIETTTVPQDAVSRSQRRGRTGRGRRGIYRFVTPGERPSGMFDSSVLCECYDAGCAWYELTPAE
3. HCV2a Consensus DSVIDCNVAVTQVVDFSLDPTFTITTQTVPQDAVSRSQRRGRTGRGRLGIYRYVSTGERASGMFDSVVLCECYDAGAAWYELTPAE
4. HCV2b Consensus DSVIDCNVAVTQIVDFSLDPTFTITTQTVPQDAVSRSQRRGRTGRGRLGIYRYVSSGERPSGMFDSVVLCECYDAGAAWYELTPAE
5. HCV 3 Consensus DSVIDCNVAVEQYVDFSLDPTFSIETRTAPQDAVSRSQRRGRTGRGRLGTYRYVTPGERPSGMFDSVVLCECYDAGCSWYDLQPAE
6. HCV 4 Consensus DSVIDCNTSVIQTVDFSLDPTFSIETTTVPQDAVSRSQRRGRTGRGRLGIYRYVTPGERPSGIFDTSVLCECYDAGCAWYELTPAE
7. HCV5 consensus DSVIDCNTAVTQTVDFSLDPTFTIETTTVPQDAVSRSQRRGRTGRGRHGIYRYVSSGERPSGIFDSVVLCECYDAGCAWYDLTPAE
8. HCV6 consensus DSVIDCNVAVTQVVDFSLDPTFSIETTTVPQDAVSRSQRRGRTGRGKPGVYRYVSQGERPSGMFDTVVLCEAYDTGCAWYELTPSE
9. HCV7: ABN05226 DSVIDCNVAVTQTVDFSLDPTFTIETTTVPQDSVSRSQRRGRTGRGRLGIYRYVSSGERPSGMFDTSVLCECYDLGCSWYELTPSE
14. AVI1a-129 DSVIDCNTCVTQTVDFSLDPTFTIETTTLPQDAVSRTQRRGRTGRGKPGIYRFVAPGERPSGMFDSSVLCECYDAGCAWYELTPAE
15. AVI3a-177 DSVIDCNVTVEQYVDFSLDPTFSIETRTAPQDAVSRSQRRGRTGRGRLGTYRYVAPGERPSGMFDSVVLCECYDAGCSWYDLQPAE

FIG. 16F

```
                     1,550     1,560     1,570     1,580     1,590     1,600     1,610     1,620     1,630
Consensus            TTVRLRAYLNTPGLPVCQDHLEFWEGVFTGLTHIDAHFLSQTKQSGENFPYLVAYQATVCARAXAPPPSWDXMWKCLIRLKPTLHG
                     NS3

1. HCV1a consensus   TTVRLRAYMNTPGLPVCQDHLEFWEGVFTGLTHIDAHFLSQTKQSGENLPYLVAYQATVCARAQAPPPSWDQMWKCLIRLKPTLHG
2. HCV1b consensus   TSVRLRAYLNTPGLPVCQDHLEFWESVFTGLTHIDAHFLSQTKQAGDNFPYLVAYQATVCARAQAPPPSWDQMWKCLIRLKPTLHG
3. HCV2a Consensus   TTVRLRAYFNTPGLPVCQDHLEFWEAVFTGLTHIDAHFLSQTKQSGENFAYLVAYQATVCARAKAPPPSWDVMWKCLTRLKPTLVG
4. HCV2b Consensus   TTVRLRAYFNTPGLPVCQDHLEFWEAVFTGLTHIDAHFLSQTKQGGDNFAYLTAYQATVCARAKAPPPSWDVMWKCLTRLKPTLTG
5. HCV 3 Consensus   TTVRLRAYLSTPGLPVCQDHLDFWESVFTGLTHIDAHFLSQTKQQGLNFSYLTAYQATVCARAQAPPPSWDETWKCLVRLKPTLHG
6. HCV 4 Consensus   TTTRLRAYFNTPGLPVCQDHLEFWESVFTGLTQIDGHFLSQTKQSGENFPYLVAYQATVCARALAPPPSWDTMWKCLIRLKPTLHG
7. HCV5 consensus    TTVRLRAYLNTPGLPVCQDHLEFWEGVFTGLTNIDAHMLSQTKQGGENFPYLVAYQATVCVRAKAPPPSWDTMWKCMXRLKPTLTG
8. HCV6 consensus    TTVRLRAYLNTPGLPVCQDHLEFWEGVFTGLTHIDAHFLSQTKQGGENFAYLVAYQATVCARAKAPPPSWDTMWKCLIRLKPMLTG
9. HCV7: ABN05226   TTTRLRAYLNCPGLPVCQDHLEFWEGVFTGLTHIDAHFLSQTKQEGQNYAYLTAYQATVCARAKAPPPSWDVQWKCLQRLKPLLVG
14. AVI1a-129        TTVRLRAYMNTPGLPVCQDHLEFWEGVFTGLTHIDAHFLSQTKQSGENFPYLVAYQATVCARAQAPPPSWDQMWKCLIRLKPTLHG
15. AVI3a-177        TTVRLRAYLSTPGLPVCQDHLDFWESVFTGLTHIDAHFLSQTKQQGLNFSYLTAYQATVCARAQAPPPSWDEMWKCLLRLKPTLHG

                     1,640     1,650     1,660     1,670     1,680     1,690     1,700     1,710     1,720
Consensus            PTPLLYRLGAVQNEVTLTHPITKYIMTCMSADLEVVT---STWVLVGGVLAALAAYCLSTGCVVIVGRIVLSGKPAXIPDREVLYQ
                     NS3                                     NS4a

1. HCV1a consensus   PTPLLYRLGAVQNEVTLTHPITKYIMTCMSADLEVVT---STWVLVGGVLAALAAYCLSTGCVVIVGRIVLSGKPAIIPDREVLYR
2. HCV1b consensus   PTPLLYRLGAVQNEVTLTHPITKYIMACMSADLEVVT---STWVLVGGVLAALAAYCLTTGSVVIVGRIILSGKPAIIPDREVLYQ
3. HCV2a Consensus   PTPLLYRLGSVTNEVTLTHPVTKYIATCMQADLEVMT---STWVLAGGVLAAVAAYCLATGCVSIIGRLHINQRAVVAPDKEVLYE
4. HCV2b Consensus   PTPLLYRLGAVTNEVTLTHPVTKYIATCMQADLEIMT---STWVLAGGVLAAVAAYCLATGCISIIGRLHLNDQVVVAPDKEILYE
5. HCV 3 Consensus   PTPLLYRLGPVQNEICLTHPITKYIMACMSADLEVTTSTWSTWVLLGGVLAALAAYCLSVGCVVIVGHIELGGKPALVPDKEVLYQ
6. HCV 4 Consensus   PTPLLYRLGSVQNEVTLTHPITKYIMACMSADLEVVT---STWVLVGGVLAALAAYCLSVGSVVIVGRVVLSGQPAVIPDREVLYQ
7. HCV5 consensus    PTPLLYRLGAVQNEITLTHPITKYIMACMSADLEVIT---STWVLVGGVVAALAAYCLTVGSVAIVGRIILSGRPAIIPDREVLYQ
8. HCV6 consensus    PTPLLYRLGAVQNEITTTHPITKYIMTCMSADLEVIT---STWVLVGGVLAALAAYCLSVGCVVICGRITTTGKPAVIPDREVLYQ
9. HCV7: ABN05226   PTPLLYRLGSVTNEVTFTHPITKYIATCMAADLEVTT---STWVIVGGVLAAVAAYCMSTGSVVVVGRVVLGSNVVTAPDREVLYQ
14. AVI1a-129        PTPLLYRLGAVQNEVVLTHPITKYIMTCMSADLEVVT---STWVLVGGVLAALAAYCLSTGCVVIVGRVVLSGKPAIIPDREVLYQ
15. AVI3a-177        PTPLLYRLGPVQNETCLTHPVTKYIMACMSADLEVTT---STWVLLGGVLAALAAYCLSVGCVVIVGHIELGGKPALIPDKEVLYQ

                     1,730     1,740     1,750     1,760     1,770     1,780     1,790     1,800
Consensus            QFDEMEECSQHLPYIEQGQQIAEQFKQKALGLLQTATKQAEVIAPAVQXNWQKLEQFWAKHMWNFISGIQYLAGLSTLPGNPAVAS
                     NS4a        NS4b

1. HCV1a consensus   EFDEMEECSQHLPYIEQGMMLAEQFKQKALGLLQTASRQAEVIAPAVQTNWQKLEAFWAKHMWNFISGIQYLAGLSTLPGNPAIAS
2. HCV1b consensus   EFDEMEECASHLPYIEQGMQLAEQFKQKALGLLQTATKQAEAAAPVVESKWRALE-FWAKHMWNFISGIQYLAGLSTLPGNPAIAS
3. HCV2a Consensus   AFDEMEECASRAALIEEGQRIAEMLKSKIQGLLQQASKQAQDIQPAVQASWPKVEQFWAKHMWNFISGIQYLAGLSTLPGNPAVAS
4. HCV2b Consensus   AFDEMEECASKAALIEEGQRMAEMLKSKIQGLLQQATRQAQDIQPAIQSSWPKLEQFWAKHMWNFISGIQYLAGLSTLPGNPAVAS
5. HCV 3 Consensus   QYDEMEECSQAAPYIEQAQVIAHQFKEKVLGLLQRATQQQAVIEPIVATNWQKLEAFWHKHMWNFVSGIQYLAGLSTLPGNPAVAS
6. HCV 4 Consensus   QFDEMEECSKHLPLVEHGLQLAEQFKQKAVGLLNFAGKQAQEATPVIQSNFAKLEQFWAKHMWNFISGIQYLAGLSTLPGNPAIAS
7. HCV5 consensus    QFDEMEECSASLPYMDEARAIAEQFKEKVLGLIGTAGQKAETLKPAATSMWXKAEQFWAKHMWNFVSGIQYLAGLSTLPGNPAVAT
8. HCV6 consensus    QFDEMEECSRHIPYLAEGQQIAEQFKQKVLGLLQTTAKQAEELKPAVHSAWPKLEQFWQKHLWNFVSGIQYLAGLSTLPGNPAVAS
9. HCV7: ABN05226   HFDEMEECSKAPELLKHAQTIGGMFKDKALAVLDTLKPAAQAAVPIVETNFQKVEKLWNQHMWNFISGIQYLAGLSTLPGNPTVAS
14. AVI1a-129        EFDEMEECSQHLPYIEQGMMLAEQFKQKALGLLQTASRQAEVIAPAVQTNWQKLEAFWAKHMWNFISGIQYLAGLSTLPGTPAIAS
15. AVI3a-177        QYDEMEECSQAAPYVEQAQAIAHQFKEKLLGLLQRATQQQAVIEPIVATNWQKLEAFWHKHMWNFVSGIQYLAGLSTLPGNPAVAS
```

FIG. 16G

```
                     1,810     1,820     1,830     1,840     1,850     1,860     1,870     1,880     1,890
Consensus            LMAFTAAVTSPLTTSQTLLFNILGGWVASQLAPPTAATAFVVSGLAGAAVGSIGLGKVLVDILAGYGAGVAGALVAFKIMSGEXPS
                     NS4b

1. HCV1a consensus   LMAFTAAVTSPLTTSQTLLFNILGGWVAAQLAAPGAATAFVGAGLAGAAIGSVGLGKVLVDILAGYGAGVAGALVAFKIMSGEVPS
2. HCV1b consensus   LMAFTASITSPLTTQHTLLFNILGGWVAAQLAPPSAASAFVGAGIAGAAVGSIGLGKVLVDILAGYGAGVAGALVAFKVMSGEMPS
3. HCV2a Consensus   MMAFSAALTSPLSTSTTILLNILGGWLASQIAPPAGATGFVVSGLVGAAVGSIGLGKVLVDILAGYGAGISGALVAFKIMSGEKPS
4. HCV2b Consensus   MMAFSAALTSPLPTSTTILLNIMGGWLASQIAPPAGATGFVVSGLVGAAVGSIGLGKILVDVLAGYGAGISGALVAFKIMSGEKPS
5. HCV 3 Consensus   LMAFTASVTSPLTTNQTMFFNILGGWVATHLAGPQSSSAFVVSGLAGAAIGGIGLGRVLLDILAGYGAGVSGALVAFKIMGGELPT
6. HCV 4 Consensus   LMSFTAAVTSPLTTQQTLLFNILGGWVASQIATPTASTAFVVSGLAGAAVGSVGLGKILVDILAGYGAGVAGAVVTFKIMSGEMPS
7. HCV5 consensus    LMSFTAAVTSPLTTQQTLLFNILGGWVASQIAPPTAATAFVVSGMAGAAVGSIGLGRVLIDILAGYGAGVAGALVAFKIMCGERPT
8. HCV6 consensus    LMSFSASLTSPLSTSTTLLLNILGGWVASQLAPPTASTAFVVSGLAGAAVGSIGLGRVLVDILAGYGAGVSGALVAFKIMSGETPA
9. HCV7: ABN05226   LMAFTASVTSPLATSTTLLVNILGGWFASQLAPPSAATTFVVSGLAGAAVGSVGLGKVLVDVLAGYGAGIAGALVAFKIMSGEVPS
14. AVI1a-129        LMAFTAAVTSPLTTSQTLLFNILGGWVAAQLAAPGAATAFVGAGLAGAAIGSVGLGKVLVDILAGYGAGVAGALVAFKIMSGE?PS
15. AVI3a-177        LMAFTASVTSPLTTNQTMFFNILGGWVATHLAGPQSSSAFVVSGLAGAAIGGIGLGRVLLDILAGYGAGVSGALVAFKIMGGEIPT

                         1,900     1,910     1,920     1,930     1,940     1,950     1,960     1,970
Consensus            TEDLVNLLPAILSPGALVVGVVCAAILRRHVGPGEGAVQWMNRLIAFASRGNHVSPTHYVPESDAAARVTQILSSLTVTSLLRRLH
                     NS4b

1. HCV1a consensus   TEDLVNLLPAILSPGALVVGVVCAAILRRHVGPGEGAVQWMNRLIAFASRGNHVSPTHYVPESDAAARVTAILSSLTVTQLLRRLH
2. HCV1b consensus   TEDLVNLLPAILSPGALVVGVVCAAILRRHVGPGEGAVQWMNRLIAFASRGNHVSPTHYVPESDAAARVTQILSSLTITQLLKRLH
3. HCV2a Consensus   MEDVVNLLPGILSPGALVVGVICAAILRRHVGPGEGAVQWMNRLIAFASRGNHVAPTHYVTESDASQRVTQLLGSLTITSLLRRLH
4. HCV2b Consensus   VEDVVNLLPAILSPGALVVGVICAAILRRHVGQGEGAVQWMNRLIAFASRGNHVAPTHYVAESDASQRVTQVLSSLTITSLLRRLH
5. HCV 3 Consensus   AEDMVNLLPAILSPGALVVGVICAAILRRHVGPGEGAVQWMNRLIAFASRGNHVSPTHYVPESDAAARVTALLSSLTVTSLLRRLH
6. HCV 4 Consensus   TEDLVNLLPAILSPGALVVGVVCAAILRRHVGPGEGAVQWMNRLIAFASRGNHVSPTHYVPESDAAARVTQILSSLTVTSLLRRLH
7. HCV5 consensus    AEDLVNLLPSILCPGALVVGVICAAVLRRHIGPGEGAVQWMNRLIAFASRGNHVSPTHYVPETDASAKVTQLLSSLTVTSLLKRLH
8. HCV6 consensus    XEDMVNLLPALLSPGALVVGVVCAAILRRHVGPAEGATQWMNRLIAFASRGNHVSPTHYVPETDASRXVTTILSSLTITSLLRRLH
9. HCV7: ABN05226   TEDLANLLPAILSPGALVVGVVCAAIIKRHTGTSEGVTQWMNRLIAFASRGNHVSPTHYIQDDDASKRVMGILSSLTITSLIKRVL
14. AVI1a-129        TEDLVNLLPAILSPGALVVGVVCAAILRRHVGPGEGAVQWMNRLIAFASRGNHVSPTHYVPESDAAARVTAILSSLTVTQLLRRLH
15. AVI3a-177        AEDMVNLLPAILSPGALVVGVICAAILRRHVGPGEGAVQWMNRLIAFASRGNHVSPTHYVPESDAAARVTALLSSLTVTSLLRRLH

                     1,980     1,990     2,000     2,010     2,020     2,030     2,040     2,050     2,060
Consensus            QWINEDCSTPCSGSWLRDIWDWVCTVLSDFKTWLKAKLLPQLPGIPFLSCQRGYKGVWRGDGVMHTRCPCGAEITGHVKNGSMRIV
                     NS4b  NS5a

1. HCV1a consensus   QWISSECTTPCSGSWLRDIWDWICEVLSDFKTWLKAKLMPQLPGIPFVSCQRGYRGVWRGDGIMHTRCHCGAEITGHVKNGTMRIV
2. HCV1b consensus   QWINEDCSTPCSGSWLRDVWDWICTVLTDFKTWLQSKLLPRLPGVPFLSCQRGYKGVWRGDGIMQTTCPCGAQITGHVKNGSMRIV
3. HCV2a Consensus   NWITEDCPIPCAGSWLRDVWDWVCTILTDFKNWLTSKLFPKMPGLPFISCQKGYKGVWAGTGIMTTRCPCGANISGNVRLGSMRIT
4. HCV2b Consensus   AWITEDCPVPCSGSWLRDIWDWVCSILTDFKNWLSSKLLPKMPGLPFISCQKGYRGVWAGTGVMTTRCPCGANISGHVRMGTMKIT
5. HCV 3 Consensus   QWINEDYPSPCSGDWLRTIWDWVCTVLSDFKTWLSAKIMPALPGLPFISCQKGYKGVWRGDGVMSTRCPCGASITGHVKNGSMRLA
6. HCV 4 Consensus   KWINEDCSTPCAESWLWEVWDWVCTVLSDFKTWLKAKLLPLMPGIPFLSCQRGYKGEWRGDGVMHTTCPCGAELAGHIKNGSMRIT
7. HCV5 consensus    TWIGEDYSTPCDGTWLRAIWDWVCTALTDFKAWLQAKLLPQLPGVPFLSCQRGYKGVWRGDGVNSTKCPCGATISGHVKNGTMRIV
8. HCV6 consensus    EWINXDWSTPCATSWLRDIWDWVCTVLSDFKTWLKAKLVPSLPGIPFLSCQRGFRGVWRGDGVCHTTCTCGAVIAGHVKNGTMKIS
9. HCV7: ABN05226   AWAQTDYSAPCAGSWLREVWDWVCMVLSDFASWLKAKVLPSLPGIPFLSCQKGYKGEWRNDGIMNTKCPCGALIAGHVKNGSMRIV
14. AVI1a-129        QWISSECTTPCSGSWLRDIWDWICEVLSDFKTWLKAKLMPQLPGIPFVSCQRGYRGVWRGDGIMHTRCHCGAEITGHVKNGTMRIV
15. AVI3a-177        HWINEDYPSPCSGDWLRTIWDWVCMVLSDFRTWLSAKIMPALPGLPFLSCQKGYKGVWRGDGVVSTRCPCGASITGHVKNGSMRLA
```

FIG. 16H 2,070 2,080 2,090 2,100 2,110 2,120 2,130 2,140 2,150
Consensus GPKTCSNTWHGTFPINAYTTGPXXPXPAPNYKRALWRVXAEEYVEVRRVGDFHYVTGXTTDNLKCPCQVPAPEFFTEVDGVRLHRX
NS5a 1. HCV1a consensus GPRTCRNMWSGTFPINAYTTGPCTPLPAPNYTFALWRVSAEEYVEIRQVGDFHYVTGMTTDNLKCPCQVPSPEFFTELDGVRLHRF
2. HCV1b consensus GPKTCSNTWHGTFPINAYTTGPCTPSPAPNYSRALWRVAAEEYVEVTRVGDFHYVTGMTTDNVKCPCQVPAPEFFTEVDGVRLHRY
3. HCV2a Consensus GPKTCMNTWQGTFPINCYTEGQCVPKPAPNFKTAIWRVAASEYAEVTQHGSYSYITGLTTDNLKVPCQLPSPEFFSWVDGVQIHRF
4. HCV2b Consensus GPKTCLNLWQGTFPINCYTEGPCVPKPPPNYKTAIWRVAASEYVEVTQHGSFSYVTGLTSDNLKVPCQVPAPEFFSWVDGVQIHRF
5. HCV 3 Consensus GPRTCANMWHGTFPINEYTTGPSTPCPSPNYTRALWRVAANSYVEVRRVGDFHYITGATEDELKCPCQVPAAEFFTEVDGVRLHRY
6. HCV 4 Consensus GPKTCSNTWHGTFPINAYTTGPGVPIPAPNYKFALWRVSAEEYVEVRRVGDFHYVTGVTQDNIKCPCQVPAPEFFTEVDGIRLHRH
7. HCV5 consensus GPKLCSNTWHGTFPINATTTGPSVPAPAPNYKFALWRVGAADYAEVRRVGDYHYITGVTQDNLKCPCQVPSPEFFTELDGVRIHRY
8. HCV6 consensus GPRTCSNTWHGTFPINATTTGPSVPIPEPNYKRALWRVSAEDYVEVVRVGDCHYVVGATADNLKCPCQVPAPEFFTEVDGVRLHRY
9. HCV7: ABN05226 GPKTCRNTWWGTFPINSHTTGPSSPVPSHCYQRALWRVSATEYVEILRHNDQHYVVGVTAEDLKCPCQVPSPEFFSFVDGVRIHRF
14. AVI1a-129 GPRTCRNMWSGTFPINAYTTGPCTPLPAPNYKFALWRVSAEEYVEIRQVGDFHYVTGMTTDDLKCPCQVPSPEFFTELDGVRLHRF
15. AVI3a-177 GPRTCANMWHGTFPINEYTTGPSTPCPSPNYTRALWRVAANSYVEVRQVGDFHYITGATEDGLKCPCQVPAAEFFTEVDGVRLHRY 2,160 2,170 2,180 2,190 2,200 2,210 2,220 2,230
Consensus APPCKPLLRDEVTFSVGLNSYVVGSQLPCEPEPDVAVLTSMLTDPSHITAETAARRLARGSPPSLASSSASQLSAPSLKATCTTHH
NS5a 1. HCV1a consensus APPCKPLLREEVSFRVGLHEYPVGSQLPCEPEPDVAVLTSMLTDPSHITAEAAGRRLARGSPPSVASSSASQLSAPSLKATCTANH
2. HCV1b consensus APACKPLLREEVTFQVGLNQYLVGSQLPCEPEPDVAVLTSMLTDPSHITAETAKRRLARGSPPSLASSSASQLSAPSLKATCTTRH
3. HCV2a Consensus APTPKPFFRDEVSFCVGLNSFVVGSQLPCDPEPDTDVLMSMLTDPSHITAEAAARRLARGSPPSEASSSASQLSAPSLRATCTTHG
4. HCV2b Consensus APTPGPFFRDEVTFTVGLNSFVVGSQLPCDPEPDTEVLASMLTDPSHITAEAAARRLARGSPPSQASSSASQLSAPSLKATCTTHK
5. HCV 3 Consensus APPCKPLLRDEITFMVGLNSYAIGSQLPCEPEPDVSVLTSMLRDPSHITAETAARRLARGSPPSEASSSASQLSAPSLKATCQTHR
6. HCV 4 Consensus APKCKPLLRDEVSFSVGLNSFVVGSQLPCEPEPDVAVLTSMLTDPSHITAETASRRLARGSPPSLASSSASQLSAPSLKATCTARH
7. HCV5 consensus APPCNPLLREEVCFSVGLHSYVVGSQLPCEPEPDVTVLTSMLSDPAHITAETAKRRLDRGSPPSLASSSASQLSAPSLKATCTTQG
8. HCV6 consensus APPCKPLLRDEVTFSVGLSSYAIGSQLPCEPEPDVTVVTSMLTDPSHITAETAARRLARGSPPSLASSSASQLSAPSLKATCTTHG
9. HCV7: ABN05226 APEPKPMIREEAAFVVGLHSYVVGSQLPCEPEPDVQTVSQLLTDPSHITAETAARRLRRGSPPSNASSSASQLSAPSLKATHTTLP
14. AVI1a-129 APPCKPLLREEVSFRVGLHAYPVGSQLPCEPEPDVAVLTSMLTDPSHITAETA?RRLARGSPPSVASSSASQLSAPSLKATCTANH
15. AVI3a-177 APPCKPLLRDEITFMVGLNSYAIGSQLPCEPEPDVSVLTSMLRDPSHITAETAARRLARGSPPSEASSSASQLSAPSLKATCQTHR 2,240 2,250 2,260 2,270 2,280 2,290 2,300 2,310 2,320
Consensus DHPDAELIEANLLWRQEMGGNITRVESENKVVILDSFDPLVAE-EDDREISVPAECLRKXR-KFPPALPIWARPDYNPPLLETWKR
NS5a 1. HCV1a consensus DSPDAELIEANLLWRQEMGGNITRVESENKVVILDSFDPLVAE-EDEREISVPAEILRKSR-RFAPALPIWARPDYNPPLLETWKK
2. HCV1b consensus DSPDADLIEANLLWRQEMGGNITRVESENKVVILDSFDPLRAE-EDEREVSVPAEILRKSR-KFPPAMPIWARPDYNPPLLESWKD
3. HCV2a Consensus KTYDVDMVDANLF----MGGDVTRIESESKVVVLDSLDPM-AEERSDLEPSIPSEYMLPRN-RFPPALPAWARPDYNPPLVESWKR
4. HCV2b Consensus MAYDCDMVDANLF----MGGDVTRIESDSKVIVLDSLDSM-TEVEDDREPSVPSEYLIRRR-KFPPALPPWARPDYNPPVIETWKR
5. HCV 3 Consensus PHPDAELVDANLLWRQEMGSNITRVESETKVVILDSFEPLRAE-TDDAELSVAAECFKKPP-KYPPALPIWARPDYNPPLLDRWKA
6. HCV 4 Consensus DSPGTDLLEANLLW----GSTATRVETDEKVIILDSFEPCVAEPDDDREVSVAAEILRPTK-KFPPALPIWARPDYNPPLTETWKQ
7. HCV5 consensus HHPDADLIEANLLWRQCMGGNITRVEAENKVVILDSFEPLKXE-EDDREISVSADCFRRGP-AFPPALPIWARPGYDPPLLETWKR
8. HCV6 consensus DHPDAELIEANLLWRQEMGGNITRVESENKVIVLDSFDPLVAE-YDDREISVSAECHRPPRPKFPPALPIWARPDYNPPLLETWKA
9. HCV7: ABN05226 QHPDAELIEANLMWEHKVGA-IRRMETDTKVIILDSFDSA-SSVEDDMEPSTAAECLRTRK-VFPPAMPIWARPDYNPPVVENWKD
14. AVI1a-129 DSPDAELIEANLLWRQEMGGNITRVESENKVVILDSFDPLVAE-EDEREISVPAEILRKSR-RFTQALPVWARPDYNPPLVEAWKK
15. AVI3a-177 PHPDAELVDANLLWRQEMGSNITRVESETKVVILDSFEPLRAE-ADDAELSVAAECFKKPP-KYPPALPIWARPDYNPPLLDRWKT

FIG. 16I

```
                     2,330     2,340     2,350     2,360     2,370     2,380     2,390     2,400
Consensus            PDYEPPTVHGCALPPPXAPPVPPPRRK-RTVXLTESTVSTALAELAEKSFGSSEXSGXX-SXSGXDTTSSXXSXPP-DCDAXSDAE
                     NS5a

1. HCV1a consensus   PDYEPPVVHGCPLPPPQSPPVPPPRKK-RTVVLTESTVSTALAELATKSFGSSSTSGI----TGDNTTTSSEPAPS-GCPPDSDAE
2. HCV1b consensus   PDYVPPVVHGCPLPPTKAPPIPPPRRK-RTVVLTESTVSSALAELATKTFGSSESSA-----VDSGTATAPPDQPSDDGDAGSDVE
3. HCV2a Consensus   PDYQPPTVAGCALPPPKKTPTPPPRRR-RTVGLSESTIGDALQQLAIKTFGQPPPSGDSGLSTGADAADSGGRTPP-DELALSETG
4. HCV2b Consensus   PGYEPPTVLGCALPPTPQAPVPPPRRR-RAKVLTQDNVEGVLREMADKVLSPLQDHNDSGHSTGADTGGDSVQQPS-DETAASEAG
5. HCV 3 Consensus   PDYVPPTVHGCALPPRGAPPVPPPRRK-RTIQLDGSNVSAALAALAEKSFPSSKPQEENSSSSGVDTQSSTTSKVPPSPGGESDSE
6. HCV 4 Consensus   QDYKPPTVHGCALPPSKQPPVPPPRRK-RTVQLTESVVSTALAELAAKTFGQSELGSDSGADLTTGPTETTDSGPILVDDA-SDDG
7. HCV5 consensus    PDYDPPQVSGCPLPPAGLPPVPPPRRKRKPVELSDSTVSQVLADLADARF-KXDTPSIEGQDSAVGTSSQXDSGPEEKRDDXSDAA
8. HCV6 consensus    PDYEPPVVSGCALPPPGPPPIPPPRRK-KVVHLDESTVSHALAQLAEKSFPESSSDSTS-SDSGLSITSSGSPEPTTDDDACSEAG
9. HCV7: ABN05226    PEYAPPQVSGCALPPAQTPPVPPPRRKRAVIQLTESAVSTALAELAERSFPKEEAPP---SDSAISLDSPAANDPPSDCDQGSEI-
14. AVI1a-129        PDYEPPVVHGCPLPPPKSPPVPPPRKK-RTVVLTESTLSTALAELATKSFGSSSTSGI----TGDNTTTSSEPAPP-GCSPDSDAE
15. AVI3a-177        PDYVPPTVHGCALPPRGAPPVPPPRRK-RTVQLDGSNVSAALAALAEKSFPSLEPQGENSSSSGIDIQSSTASEVPPSPEGESDSE
                   2,410     2,420     2,430     2,440     2,450     2,460     2,470     2,480     2,490
Consensus            SYSSMPPLEGEPGDPDLSD--------------------GSWSTVSDEE--DSVVCCSMSYSWTGALITPCAAEEEKLPINPLSNS
                     NS5a                                                   NS5b

1. HCV1a consensus   SYSSMPPLEGEPGDPDLSD--------------------GSWSTVSSEADTEDVVCCSMSYSWTGALVTPCAAEEQKLPINALSNS
2. HCV1b consensus   SYSSMPPLEGEPGDPDLSD--------------------GSWSTVSEEAS-EDVVCCSMSYTWTGALITPCAAEESKLPINALSNS
3. HCV2a Consensus   SISSMPPLEGEPGDPDLEPEQVELQPPPQGGEVAPGSDSGSWSTCSEED--DSVVCCSMSYSWTGALITPCSPEEEKLPINPLSNS
4. HCV2b Consensus   SLSSMPPLEGEPGDPDLEFEPAGSAPPSEGECEVIDSDSKSWSTVSDQE--DSVICCSMSYSWTGALITPCGPEEEKLPINPLSNS
5. HCV 3 Consensus   SCSSMPPLEGEPGDPDLSCDQVELQPPPQGGGVAPGSGSGSWSTVSDSEE-QSVVCCSMSYSWTGALITPCSAEEEKLPISPLSNS
6. HCV 4 Consensus   SYSSMPPLEGEPGDPDLTSDQVELQPPPQGGGVAPGSGSGSWSTVSGSE--DTVVCCSMSYSWTGALVTPCAAEESKLPISPLSNS
7. HCV5 consensus    SYSSMPPLEGEPGDPDLSS--------------------GSWSTVSDE---DSVVCCSMSYSWTGALITPCSAEEEKLPINPLSNT
8. HCV6 consensus    SYSSMPPLEGEPGDPDLSS--------------------GSWSTVSEE---DSVVCCSMSYSWTGALITPCAAEEEKLPINPLSNS
9. HCV7: ABN05226    SFSSMPPLEGEPGDPDLSD--------------------GSWSTVSTR---SDVICCSMSYSWTGALVTPSGPEEERLPINALSNT
14. AVI1a-129        SCSSMPPLEGEPGDPDLSD--------------------GSWSTVSSEADTEDVVCCSMSYTWTGALITPCAAEEQKLPINALSNS
15. AVI3a-177        SCTSMPPLEGEPGDPDLSC--------------------DSWSTVSDSEE-QSVVCCSMSYSWTGALITPCSAEEEKLPISPLSNS
                         2,500     2,510     2,520     2,530     2,540     2,550     2,560     2,570     2,580
Consensus            LLRHHNLVYSTTSRSASQRQKKVTFDRLQVLDDHYXDVLKEVKAXASKVKARLLSVEEACALTPPHSARSKFGYGAKDVRSLSRKA
                     NS5b

1. HCV1a consensus   LLRHHNLVYSTTSRSACQRQKKVTFDRLQVLDSHYQDVLKEVKAAASKVKANLLSVEEACSLTPPHSAKSKFGYGAKDVRCHARKA
2. HCV1b consensus   LLRHHNMVYATTSRSASQRQKKVTFDRLQVLDDHYRDVLKEMKAKASTVKAKLLSVEEACKLTPPHSARSKFGYGAKDVRNLSSKA
3. HCV2a Consensus   LLRYHNKVYCTTSKSASLRAKKVTFDRMQVLDAHYDSVLKDIKLAASKVSARLLTLEEACQLTPPHSARSKYGFGAKEVRSLSGRA
4. HCV2b Consensus   LMRFHNKVYSTTSRSASLRAKKVTFDRVQVLDAHYDSVLQDVKRAASKVSARLLSVEEACALTPPHSAKSRYGFGAKEVRSLSRRA
5. HCV 3 Consensus   LLRHHNLVYSTSSRSASQRQKKVTFDRLQVLDDHYKTALKEVKERASRVKARMLTIEEACALVPPHSARSKFGYSAKDVRSLSSKA
6. HCV 4 Consensus   LLRHHNMVYATTTRSAVTRQKKVTFDRLQVVDNHYNETLKEIKARASRVKARLLTTEEACDLTPPHSAKSKFGYGAKDVRSHSRKA
7. HCV5 consensus    LLRHHNLVYSTSSRSAGLRQKKVTFDRLQVLDDHYREVVDEMKRLASKVKARLLPLEEACGLTPPHSARSKYGYGAKEVRSLDKKA
8. HCV6 consensus    LIRHHNLVYSTTSRSASLRQKKVTFDRVQVLDQHYQDVLKEIKLRASQVQARLLSTEEACDLTPPHSARSKFGYGAKDVRSHASKA
9. HCV7: ABN05226    MLRHYNMVYSTTSRSASQRAKKVTFDRLQVLDDHYKRALADVKADASTVKAQLLSVEEAAALTPAHSARSKFGYGAKEVRSLAPKA
14. AVI1a-129        LLRHHNLVYSTTSRSACQRQKKVTFDRLQVLDNHYQDVLKEVKAAASKVKANLLSVEEACSLTPPHSAKSKFGYGAKDVRCHARKA
15. AVI3a-177        LLRHHNLVYSTSSRSASQRQKKVTFDRLQVLDDHYKAVLKEVKERASRVKARMLTIEEACALVPPHSARSKFGYSAKDVRSLSGRA
```

FIG. 16J

```
                    2,590     2,600     2,610     2,620     2,630     2,640     2,650     2,660
Consensus           VNHIXSVWXDLLEDSTTPIPTTIMAKNEVFCVDPXKGGRKPARLIVYPDL-GVRVCEKRALYDVXQKLPKAVMGSSYGFQYSPAQR
                    NS5b

1. HCV1a consensus  VNHINSVWKDLLEDSVTPIDTTIMAKNEVFCVQPEKGGRKPARLIVFPDL-GVRVCEKMALYDVVSKLPLAVMGSSYGFQYSPGQR
2. HCV1b consensus  VNHIRSVWKDLLEDTETPIDTTIMAKNEVFCVQPEKGGRKPARLIVFPDL-GVRVCEKMALYDVVSTLPQAVMGSSYGFQYSPGQR
3. HCV2a Consensus  VNHIKSVWKDLLEDSQTPIPTTIMAKNEVFCVDPTKGGKKAARLIVYPDL-GVRVCEKMALYDVTQKLPQAVMGASYGFQYSPAQR
4. HCV2b Consensus  VNHIRSVWEDLLEDQHTPIDTTIMAKNEVFCVDPTKGGKKPARLIVYPDL-GVRVCEKMALYDIAQKLPKAIMGPSYGFQYSPAER
5. HCV 3 Consensus  INQIRSVWEDLLEDTTTPIPTTIMAKNEVFCVDPAKGGRKPARLIVYPDL-GVRVCEKRALYDVIQKLSIETMGSAYGFQYSPQQR
6. HCV 4 Consensus  INHINSVWEDLLEDNNTPIPTTIMAKNEVFAVNPAKGGRKPARLIVYPDLGGVRVCEKRALHDVINQLPKAVMGAAYGFQYSPAQR
7. HCV5 consensus   LXHIEGVWQDLLDDSDTPLPTTIMAKNEVFAVEPSKGGKKPARLIVYPDL-GVRVCEKRALYDXAQKLPTALMGPSYGFQYSPAQR
8. HCV6 consensus   INHINSVWEDLLEDNQTPIPTTIMAKNEVFCVDPSKGGRKPARLIVYPDL-GVRVCEKRALYDITRKLPVAVMGDAYGFQYSPKQR
9. HCV7: ABN05226  MSHIKEVWKDLLQDMTTPIPTTIMAKNEVFCVNPAKGGKKPARLIVYPDL-GVRVCEKRALYDIAQKLPKAIMGQAYGFQYSPSQR
14. AVI1a-129       VNHINSVWKDLLEDSVTPIDTTIMAKNEVFCVQPEKGGRKPARLIVFPDL-GVRVCEKMALYDVVSKLPLAVMGDSYGFQYSPGQR
15. AVI3a-177       VNQIRSVWEDLLEDTTTPIPTTIMAKNEVFCVDPSKGGRKPARLIVYPDL-GVRVCEKRALYDVIQKLSIATMGSAYGFQYSPQQR

                    2,670     2,680     2,690     2,700     2,710     2,720     2,730     2,740     2,750
Consensus           VEFLLKAWKSKKTPMG--FSYDTRCFDSTVT-EXDIRTEEXIYQCCDLDPEARKAIXSLTERLYVGGPMXNSKGQXCGYRRCRASG
                    NS5b

1. HCV1a consensus  VEFLVQAWKSKKTPMG--FSYDTRCFDSTVT-ESDIRTEEAIYQCCDLDPQARVAIKSLTERLYVGGPLTNSRGENCGYRRCRASG
2. HCV1b consensus  VEFLVNAWKSKKCPMG--FAYDTRCFDSTVT-ESDIRVEESIYQCCDLAPEARQAIRSLTERLYIGGPLTNSKGQNCGYRRCRASG
3. HCV2a Consensus  VEFLLKAWAEKKDPMG--FSYDTRCFDSTVT-ERDIRTEESIYQACSLPEEARTAIHSLTERLYVGGPMFNSKGQTCGYRRCRASG
4. HCV2b Consensus  VDFLLKAWGSKKDPMG--FSYDTRCFDSTVT-ERDIRTEESIYQACSLPQEARTVIHSLTERLYVGGPMTNSKGQSCGYRRCRASG
5. HCV 3 Consensus  VERLLKMWTSKKTPLGVLFSYDTRCFDSTVTGEQDIRVEEEIYQCCNLEPEARKVISSLTERLYCGGPMFNSKGAQCGYRRCRASG
6. HCV 4 Consensus  VEFLLTSWKSKKTPMG--FSYDTRCFDSTVT-EKDIRTEEEVYQCCDLEPEARKVITALTERLYVGGPMHNSKGDLCGYRRCRASG
7. HCV5 consensus   VEFLLKTWKSKKXPMA--FSYDTRCFDSTVT-EHDIMTEESIYQSCDLQPEARXAIRSLTQRLYCGGPMYNSKGQQCGYRRCRASG
8. HCV6 consensus   VDYLLKMWRSKKTPMG--FSYDTRCFDSTVT-ERDIRTEHDIYQSCQLDPEARKAITSLTERLYVGGPMYNSKGQSCGYRRCRASG
9. HCV7: ABN05226  VEYLVKTWKSKRTPMG--FSYDTRCFDSTVT-EQDIRTESEIYQCCNLDPEARTIINALTERLYVGGPMFNSKGQRVGYRRCRASG
14. AVI1a-129       VEFLVQAWKSKKTPMG--FSYDTRCFDSTVT-ESDIRTEEAIYQCCDLDPQARVAIKSLTERLYVGGPLTNSRGENCGYRRCRASG
15. AVI3a-177       VERLLEMWTSKKTPMG--FSYDTRCFDSTVT-EQDIRVEEEIYQCCNLEPEARKVISSLTERLYCGGPMFNSKGAQCGYRRCRASG

                    2,760     2,770     2,780     2,790     2,800     2,810     2,820     2,830
Consensus           VLTTSMGNTLTCYIKAXAACRAAGLRDCTMLVCGDDLVVICESAGVZEDAAXLRAFTEAMTR-----YSAPPGDPP-----QPEYD
                    NS5b

1. HCV1a consensus  VLTTSCGNTLTCYIKARAACRAAGLQDCTMLVCGDDLVVICESAGVQEDAASLRAFTEAMTR-----YSAPPGDPP-----QPEYD
2. HCV1b consensus  VLTTSCGNTLTCYLKASAACRAAKLQDCTMLVCGDDLVVICESAGTQEDAASLRVFTEAMTR-----YSAPPGDPP-----QPEYD
3. HCV2a Consensus  VLTTSMGNTITCYVKALAACKAAGIVAPTMLVCGDDLVVISESQGTEEDERNLRAFTEAMTR-----YSAPPGDPP-----RPEYD
4. HCV2b Consensus  VFTTSMGNTMTCYIKALAACKAAGIVDPIMLVCGDDLVVISESQGNEEDERNLRAFTEAMTR-----YSAPPGDLP-----RPEYD
5. HCV 3 Consensus  VLPTSFGNTITCYIKATAAARAAGLRNPDFLVCGDDLVVVAESDGVDEDRAALRAFTEAMTRLWTRYYSAPPGDAPHRPTLQPTYD
6. HCV 4 Consensus  VYTTSFGNTLTCYLKATAAIKAAGLRDCTMLVCGDDLVVIAESDGVEEDNRALRAFTEAMTR-----YSAPPGDAP-----QPAYD
7. HCV5 consensus   VFTTSMGNTMTCYIKALASCRAAKLRDCTLLVCGDDLVAICESQGTHEDEASLRAFTEAMTR-----YSAPPGDPP-----VPAYD
8. HCV6 consensus   VLPTSLGNTLTCYLKAQAACRAAGLKDFDMLVCGDDLVVISESAGVQEDAAALRAFTEAMTR-----YSAPPGDEP-----QPTYD
9. HCV7: ABN05226  VFPTSMGNTMTCYIKAKAAAAAAGLESTDFLVCGDDLVVICESKGVERDRADLQAFAAAMTR-----YSAPPGDMP-----QPAYD
14. AVI1a-129       VLTTSCGNTLTCYIKAKAACRAAGLQNCTMLVCGDDLVVICESAGVQEDAASLRAFTEAMTR-----YSAPPGDPP-----QPEYD
15. AVI3a-177       VLPTSFGNTITCYIKATAAARAAGLRNPDFLVCGDDLVLVAESDGVDEDRAALRAFTEAMTR-----YSAPPGDAP-----QPTYD
```

FIG. 16K 2,840 2,850 2,860 2,870 2,880 2,890 2,900 2,910 2,920

Consensus LELITSCSSNVSVAHDXSGKRVYYLTRDPTTPLARAAWETARHTP---VNSWLGNIIMYAPTIWVRMVLMTHFFSILQXQEQLEXA NS5b 1. HCV1a consensus LELITSCSSNVSVAHDGAGKRVYYLTRDPTTPLARAAWETARHTP---VNSWLGNIIMFAPTLWARMILMTHFFSVLIARDQLEQA
2. HCV1b consensus LELITSCSSNVSVAHDASGKRVYYLTRDPTTPLARAAWETARHTP---VNSWLGNIIMYAPTLWARMILMTHFFSILLAQEQLEKA
3. HCV2a Consensus LELITSCSSNVSVALGPQGRRRYYLTRDPTTPIARAAWETVRHSP---VNSWLGNIIQYAPTIWVRMVLMTHFFSILMAQDTLDQN
4. HCV2b Consensus LELITSCSSNVSVALDSRGRRRYFLTRDPTTPITRAAWETVRHSP---VNSWLGNIIQYAPTIWVRMVIMTHFFSILLAQDTLNQN
5. HCV 3 Consensus LELITSCSSNVSVARDNKGKRYYYLTRDATTPLARAAWETARHTPGWGVNSWLGNIIMYAPTIWVRMVMMTHFFSILQSQEILDRP
6. HCV 4 Consensus LELITSCSSNVSVAHDATGKKVYYLTRDPETPLARAAWETVRHTP---VNSWLGNIIVYAPTIWVRMVLMTHFFSILQSQEALEKA
7. HCV5 consensus LELVTSCSSNVSVARDASGNRVYYLTRDPQVPLARAAWETAKHSP---VNSWLGNIIMYAPTLWARIVLMTHFFSVLQSQEQLEKA
8. HCV6 consensus LELITSCSSNVSVAHDGTGQRYYYLTRDPTTPLARAAWETARHTP---VNSWLGNIIMYAPTIWVRMVLMTHFFQILQSQEQLHKA
9. HCV7: ABN05226 LEHIDSCSSNVSVARDNSGKRVYYLTRDPTNPLSRAAWETARHSP---VNSWVGNIIMFAPTIWVRMVLMTHFFALLLNEERLNDP
14. AVI1a-129 LELITSCSSNVSVAHDGAGKRVYYLTRDPTTPLARAAWETARHTP---VNSWLGNIIMFAPTLWARMVLMTHFFSVLIARDQLEQA
15. AVI3a-177 LELITSCSSNVSVARDNKGKRYYYLTRDATTPLARAAWETARHTP---VNSWLGNIIMYAPTIWVRMVMMTHFFSILQSQEILDRP 2,930 2,940 2,950 2,960 2,970 2,980 2,990 3,000 3,010

Consensus LDFEMYGATYSVTPLDLPAIIQRLHGLSAFSLHSYSPGELNRVAACLRKLGVPPLRAWRHRARAVRAKLIAQGGRAAICGKYLFNW NS5b 1. HCV1a consensus LDCEIYGACYSIEPLDLPPIIQRLHGLSAFSLHSYSPGEINRVAACLRKLGVPPLRAWRHRARSVRARLLSRGGRAAICGKYLFNW
2. HCV1b consensus LDCQIYGACYSIEPLDLPQIIQRLHGLSAFSLHSYSPGEINRVASCLRKLGVPPLRVWRHRARSVRAKLLSQGGRAATCGKYLFNW
3. HCV2a Consensus LNFEMYGSVYSVSPLDLPAIIERLHGLDAFSLHTYTPHELTRVASALRKLGAPPLRAWKSRARAVRASLISRGGRAAVCGRYLFNW
4. HCV2b Consensus LNFEMYGAVYSVNPLDLPAIIERLHGLDAFSLHTYSPHELSRVAATLRKLGAPPLRAWKSRARAVRASLIAQGGRAAICGRYLFNW
5. HCV 3 Consensus LDFEMYGATYSVTPLDLPAIIERLHGLSAFTLHSYSPVELNRVAGTLRKLGCPPLRAWRHRARAVRAKLIAQGGKAKICGLYLFNW
6. HCV 4 Consensus LDFDMYGVTYSITPLDLPAIIQRLHGLSAFTLHGYSPHELNRVAGSLRKLGVPPLRAWRHRARAVRAKLIAQGGKAKICGIYLFNW
7. HCV5 consensus LAFEMYGSVYSVTPLDLPAIIQRLHGLSAFSLHSYSPSEINRVASCLRKLGVPPLRAWRHRARAVRAKLIAQGGKAAICGIYLFNW
8. HCV6 consensus LDFDIYGVTYSITPLDLPAIIQRLHGMAAFSLHGYSPGELNRVAACLRKLGAPPLRAWRHRARAVRAKLIAQGGKAAICGKYLFNW
9. HCV7: ABN05226 VSFEMYGATYTVCPTDLPDIIQRLHGLRAFELHTYSPAELTRVAATLRKLGVPPLRTWRQRARKVRAGLIGQGGRARICGLYLFNW
14. AVI1a-129 LDCEIYGACYSIEPLDLPPIIQRLHGLSAFSLHSYSPGEINRVAACLRKLGVPPLRTWRHRARSVRAKLLSRGGRAAICGKYLFNW
15. AVI3a-177 LDFEMYGATYSVTPLDLPAIIERLHGLSAFTLHSYSPVELNRVAGTLRKLGCPPLRAWRHRARAVRAKLIAQGGKAKICGLYLFNW 3,020 3,030 3,040 3,050 3,060 3,074

Consensus AVRTKLKLTPLPAAGXLDLSSWFTVGAGGGDIYHSVSRARPRWLLLCLLLLXVGVGIFLLPARX

NS5b

1. HCV1a consensus AVRTKLKLTPIAAAGQLDLSGWFTAGYSGGDIYHSVSHARPRWFWFCLLLLAAGVGIYLLPNRX
2. HCV1b consensus AVRTKLKLTPIPAASQLDLSGWFVAGYSGGDIYHSLSRARPRWFMWCLLLLSVGVGIYLLPNRX
3. HCV2a Consensus AVKTKLKLTPLPEARLLDLSSWFTVGAGGGDIYHSVSRARPRLLLLSLLLLXVGVGLFLLPAR
4. HCV2b Consensus AVKTKLKLTPLPEASRLDLSGWFTVGAGGGDIFHSVSHARPRLLLLCLLLLSVGVGIFLLPAR
5. HCV 3 Consensus AVRTKTKLTPLPAAGQLDLSSWFTVGVGGNDIYHSVSRARTRXLLLCLLLLTVGVGIFLLPAR
6. HCV 4 Consensus AVKTKLKLTPLPAAANLDLSSWFTVGAGGGDIYHSVSRARPRYLLLCLLLLSVGVGIFLLPAR
7. HCV5 consensus AVKTKRKLTPLADADRLDLSSWFTVGAGGGDIYHSMSRARPRXJLLCLLLLXVGVGIFLLPAR
8. HCV6 consensus AVKTKLKLTPLRGASKLDLSGWFVAGYSGGDIYHSVSRARPRMLLLCLLLLTVGVGIFLLPAR
9. HCV7: ABN05226 AVRTKIKLTPLAGAGRLDLSSWFSVCAGEADVDHSTPRAHPRPLLLCLLLLAVGVGIFLLPAR
14. AVI1a-129 AVRTKLKLTPIAAAGRLDLSGWFTAGYSGGDIYHSVSHARPRWFWFCLLLLAAGVGIYLLPNR
15. AVI3a-177 AVRTKTNLTPLPAAGQLDLSSWFTVGVGGNDIYHSVSRARTRHLLLCLLLLTVGVGIFLLPAR

FIG. 16L

HEPATITIS C VIRUS IMMUNOGENIC COMPOSITIONS AND METHODS OF USE THEREOF

CROSS-REFERENCE

This application is a continuation of U.S. patent application Ser. No. 17/122,578, now U.S. Pat. No. 11,576,967, filed Dec. 15, 2020, which is a continuation of U.S. patent application Ser. No. 16/374,403, now U.S. Pat. No. 10,881,727, filed Apr. 3, 2019, which is a continuation of U.S. patent application Ser. No. 15/574,427, now U.S. Pat. No. 10,300,131, filed Nov. 15, 2017, which is a U.S. National Phase application of PCT Application No. PCT/IB2016/001051, which claims the benefit of U.S. Provisional Patent Application No. 62/189,657, filed Jul. 7, 2015, which applications are incorporated herein by reference in their entirety.

INCORPORATION BY REFERENCE OF SEQUENCE LISTING PROVIDED AS A SEQUENCE LISTING XML FILE

A Sequence Listing is provided herewith as a Sequence Listing XML, "UALB-027CON3_SEQ_LIST" created on Jun. 2, 2023_and having a size of 390,166 bytes. The contents of the Sequence Listing XML are incorporated by reference herein in their entirety.

INTRODUCTION

Hepatitis C virus (HCV) is a blood-borne pathogen that is estimated to infect 150-200 million people worldwide. Infection by HCV may be non-symptomatic, and can be cleared by patients, sometimes without medical intervention. However, the majority of patients develop a chronic HCV infection, which may lead to liver inflammation, scarring, and even to liver failure or liver cancer. In the United States alone, over 3 million people have a chronic infection.

The HCV virion contains a positive-sense single stranded RNA genome of about 9.5 kb. The genome encodes a single polyprotein of 3,010 to 3,030 amino acids. The structural proteins comprise a core protein forming the viral nucleocapsid and two envelope glycoproteins, E1 and E2.

A vaccine based on the recombinant envelope glycoproteins (rE1E2) from a single genotype 1a strain (HCV-1) protected chimpanzees from chronic infection following homologous and heterologous genotype 1a (gt1a) viral challenge (reviewed in Houghton, M Immunol Rev 2011). Antisera from the immunized chimpanzees were shown to exhibit in vitro cross-neutralizing activity (Meunier et al. (2011) *J. Infect. Dis.* 204:1186). A phase I clinical trial was conducted in human volunteers with a similar antigen (Frey et al. (2010) *Vaccine* 28:6367). Antisera from selected vaccinated individuals were similarly capable of neutralizing chimeric cell culture-derived viruses (HCVcc) expressing the structural proteins of strains representing all 7 major HCV genotypes in vitro (Law et al. (2013) *PLoS One* 8:e59776) and to be able to compete with the binding of numerous discrete monoclonal antibodies with broad cross-neutralising activities (Wong et al. (2014) *J. Virol.* 88:14278).

There is a need in the art for compositions and methods for inducing immune responses to HCV.

SUMMARY

The present disclosure provides heterodimeric polypeptides comprising a variant hepatitis C virus (HCV) E2 polypeptide and an HCV E1 polypeptide, or comprising a variant HCV E1 polypeptide and an HCV E2 polypeptide, or comprising a variant HCV E1 polypeptide and a variant HCV E2 polypeptide, where the variant HCV E2 polypeptide and/or the variant HCV E1 polypeptide comprises one or more T cell epitopes, e.g., one or more T cell epitopes present in an HCV polypeptide other than an HCV E1 polypeptide or an HCV E2 polypeptide. The present disclosure provides nucleic acids encoding a polyprotein that includes E1 and variant E2, or that includes E2 and variant E1, or that includes variant E2 and variant E1. The present disclosure provides a method of producing an E1/E2 heterodimer of the present disclosure. The present disclosure provides a method of inducing an immune response in an individual. The present disclosure provides variant E2 polypeptides and variant E1 polypeptides; and nucleic acids encoding the variant polypeptides.

The present disclosure provides a heterodimeric polypeptide comprising: a) a variant HCV E2 polypeptide comprising: i) an HCV E2 polypeptide; and ii) a heterologous polypeptide comprising a T-cell epitope present in an HCV protein other than E1 and E2; and b) an HCV E1 polypeptide. In some cases, the heterologous polypeptide comprises one or more T cell epitopes present in one or more of: a) an HCV non-structural polypeptide-3 (NS3) polypeptide; b) an HCV non-structural polypeptide-2 (NS2) polypeptide; c) an HCV non-structural polypeptide-4A (NS4A) polypeptide; d) an HCV non-structural polypeptide-4B (NS4B) polypeptide; e) an HCV non-structural polypeptide-5A (NS5A) polypeptide; f) an HCV non-structural polypeptide-5B (NS5B) polypeptide; g) an HCV core polypeptide; and h) an HCV p7 polypeptide. In some cases, a) the HCV E2 polypeptide is derived from an HCV of genotype 1, 2, 3, or 7; and b) the HCV E1 polypeptide is derived from an HCV of genotype 1, 2, 3, or 7. In some cases, the HCV E2 polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to an E2 polypeptide depicted in one of FIGS. 1A-1C, FIGS. 2A-2C, FIGS. 3A-3C, and FIGS. 4A-4B. In some cases, the heterologous polypeptide has a length of from about 10 amino acids to about 3000 amino acids. In some cases the heterologous polypeptide has a length of from about 10 amino acids to about 100 amino acids. In some cases the heterologous polypeptide comprises one or more T cell epitopes present in an HCV NS3 polypeptide. In some cases, the heterologous polypeptide comprises an amino acid sequence having at least 20% amino acid sequence identity to the following amino acid sequence:

AIPLEVIKGGRHLIFCHSKKKCDELAAKL (SEQ ID NO:1). In some cases, the heterologous polypeptide comprises an amino acid sequence having at least 20% amino acid sequence identity to the following amino acid sequence:

AIPLEVIKGGRHLIFCHSKKKCDELAAKLVALGINAVAYYRGLDVSVIPTSG (SEQ ID NO:2). In some cases, the heterologous polypeptide comprises an amino acid sequence having at least 20% amino acid sequence identity to the following amino acid sequence:

KGGRHLIFCHSKKKCDELAAKLVALGINAVAYYRGLDVSVIPTSGDVVVVATD ALMTGFTGDFDS-

VIDCN (SEQ ID NO:3). In some cases, the heterologous polypeptide comprises an amino acid sequence having at least 20% amino acid sequence identity to the following amino acid sequence:

VALSTTGEIPFYGKAIPLEVIKGGRHLIFCHSKKK-CDELAAKLVALGINAVAYYR GLDVSVIPTS-GDVVVVATDALMTGFTGDFDSVIDCNTCVT-QTVDF (SEQ ID NO:4). In some cases, the variant HCV E2 polypeptide comprises, in order from N-terminus to C-terminus: i) the heterologous polypeptide; and ii) the HCV E2 polypeptide. In some cases, the variant HCV E2 polypeptide comprises, in order from N-terminus to C-terminus: i) the HCV E2 polypeptide; and ii) the heterologous polypeptide. In some cases, the heterologous polypeptide comprises one or more T cell epitopes present in: a) cholera toxin or toxoid; and/or b) tetanus toxin or toxoid; and/or c) diphtheria toxin or toxoid; and/or d) CRM197. In some cases, the E2 polypeptide and/or the E1 polypeptide lacks a C-terminal transmembrane domain. In some cases, the modified HCV E2 polypeptide and the HCV E1 polypeptide are derived from an HCV of the same genotype. In some cases, the modified HCV E2 polypeptide and the HCV E1 polypeptide are derived from an HCV of different genotypes. In some cases, the HCV E1 polypeptide comprises an amino acid sequence having at least 20% amino acid sequence identity to an E1 polypeptide depicted in FIGS. 1A-1C, FIGS. 2A-2C, FIGS. 3A-3C, and FIGS. 4A-4B.

The present disclosure provides a nucleic acid comprising nucleotide sequences encoding any one of the heterodimeric polypeptides as described above or elsewhere herein. In some cases, the nucleotide sequence encoding the variant HCV E2 polypeptide and the nucleotide sequence encoding the HCV E1 polypeptide are operably linked to a promoter. The present disclosure provides a recombinant expression vector comprising the nucleic acid.

The present disclosure provides a heterodimeric polypeptide comprising: a) a variant HCV E1 polypeptide comprising: i) an HCV E1 polypeptide; and ii) a heterologous polypeptide comprising a T-cell epitope present in an HCV protein other than E1 and E2; and b) an HCV E2 polypeptide. In some cases, the heterologous polypeptide comprises one or more T cell epitopes present in one or more of: a) an HCV NS3 polypeptide; b) an HCV NS2 polypeptide; c) an HCV NS-4A polypeptide; d) an HCV NS4B polypeptide; e) an HCV NS5A polypeptide; f) an HCV NS5B polypeptide; g) an HCV core polypeptide; and h) an HCV p7 polypeptide. In some cases, a) the HCV E2 polypeptide is derived from an HCV of genotype 1, 2, 3, or 7; and b) the HCV E1 polypeptide is derived from an HCV of genotype 1, 2, 3, or 7. In some cases, the HCV E1 polypeptide comprises an amino acid sequence having at least 20% amino acid sequence identity to an E1 polypeptide depicted in one of FIGS. 1A-1C, FIGS. 2A-2C, FIGS. 3A-3C, and FIGS. 4A-4B. In some cases, the heterologous polypeptide has a length of from about 10 amino acids to about 3000 amino acids. In some cases, the heterologous polypeptide has a length of from about 10 amino acids to about 100 amino acids. In some cases, the heterologous polypeptide comprises one or more T cell epitopes present in an HCV NS3 polypeptide. In some cases, the heterologous polypeptide comprises an amino acid sequence having at least 20% amino acid sequence identity to the following amino acid sequence:

AIPLEVIKGGRHLIFCHSKKKCDELAAKL (SEQ ID NO:1). In some cases, the heterologous polypeptide comprises an amino acid sequence having at least 20% amino acid sequence identity to the following amino acid sequence:

AIPLEVIKGGRHLIFCHSKKKCDELAAKLVALGI-NAVAYYRGLDVSVIPTSG (SEQ ID NO:2). In some cases, the heterologous polypeptide comprises an amino acid sequence having at least 20% amino acid sequence identity to the following amino acid sequence:

KGGRHLIFCHSKKKCDELAAKLVALGINAVAYYR-GLDVSVIPTSGDVVVVATD ALMTGFTGDFDS-VIDCN (SEQ ID NO:3). In some cases, the heterologous polypeptide comprises an amino acid sequence having at least 20% amino acid sequence identity to the following amino acid sequence:

VALSTTGEIPFYGKAIPLEVIKGGRHLIFCHSKKKC-DELAAKLVALGINAVAYYR GLDVSVIPTSG-DVVVVATDALMTGFTGDFDSVIDCNTCVTQT-VDF (SEQ ID NO:4). In some cases, the variant HCV E1 polypeptide comprises, in order from N-terminus to C-terminus: i) the heterologous polypeptide; and ii) the HCV E1 polypeptide. In some cases, the variant HCV E1 polypeptide comprises, in order from N-terminus to C-terminus: i) the HCV E1 polypeptide; and ii) the heterologous polypeptide. In some cases, the heterologous polypeptide comprises one or more T cell epitopes present in: a) cholera toxin or toxoid; and/or b) tetanus toxin or toxoid; and/or c) diphtheria toxin or toxoid; and/or d) CRM197. In some cases, the E2 polypeptide and/or the E1 polypeptide lacks a C-terminal transmembrane domain. In some cases, the modified HCV E2 polypeptide and the HCV E1 polypeptide are derived from an HCV of the same genotype. In some cases, the modified HCV E2 polypeptide and the HCV E1 polypeptide are derived from an HCV of different genotypes. In some cases, the HCV E2 polypeptide comprises an amino acid sequence having at least 20% amino acid sequence identity to an E2 polypeptide depicted in FIGS. 1A-1C, FIGS. 2A-2C, FIGS. 3A-3C, and FIGS. 4A-4B.

The present disclosure provides nucleic acid comprising nucleotide sequences encoding any one of the heterodimeric polypeptides described above or elsewhere herein. In some cases, the nucleotide sequence encoding the variant HCV E2 polypeptide and the nucleotide sequence encoding the HCV E1 polypeptide are operably linked to a promoter. The present disclosure provides a recombinant expression vector comprising the nucleic acid.

The present disclosure provides a heterodimeric polypeptide comprising: a) a variant HCV E1 polypeptide comprising: i) an HCV E1 polypeptide; and ii) a first heterologous polypeptide comprising a T-cell epitope present in an HCV protein other than E1 and E2; and b) a variant HCV E2 polypeptide comprising: i) an HCV E2 polypeptide; and ii) a second heterologous polypeptide comprising a T-cell epitope present in an HCV protein other than E1 and E2. In some cases, the first and the second heterologous polypeptides comprise one or more T cell epitopes present in one or more of: a) an HCV NS3 polypeptide; b) an HCV NS2 polypeptide; c) an HCV NS-4A polypeptide; d) an HCV NS4B polypeptide; e) an HCV NS5A polypeptide; f) an HCV NS5B polypeptide; g) an HCV core polypeptide; and h) an HCV p7 polypeptide. In some cases, a) the HCV E2 polypeptide is derived from an HCV of genotype 1, 2, 3, or 7; and b) the HCV E1 polypeptide is derived from an HCV of genotype 1, 2, 3, or 7. In some cases, the HCV E1 polypeptide comprises an amino acid sequence having at least 20% amino acid sequence identity to an E1 polypeptide depicted in one of FIGS. 1A-1C, FIGS. 2A-2C, FIGS. 3A-3C, and FIGS. 4A-4B. In some cases, each of the first and the second heterologous polypeptide independently has a length of from about 10 amino acids to about 3000 amino acids. In some cases, each of the first and the second heterologous polypeptide independently has a length of from about 10 amino acids to about 100 amino acids. In some cases, the first and/or the second heterologous polypeptide comprises one or more T cell epitopes present in an HCV NS3 polypeptide. In some cases, the first and/or the second heterologous polypeptide comprises an amino acid sequence having at least 20% amino acid sequence identity to the following amino acid sequence: AIPLEVIKGGRHLIFCHSKKKCDELAAKL (SEQ ID NO:1). In some cases, the first and/or the second heterologous polypeptide comprises an amino acid sequence having at least 20% amino acid sequence identity to the following amino acid sequence:

AIPLEVIKGGRHLIFCHSKKKCDELAAKLVALGINAVAYYRGLDVSVIPTSG (SEQ ID NO:2). In some cases, the first and/or the second heterologous polypeptide comprises an amino acid sequence having at least 20% amino acid sequence identity to the following amino acid sequence:

KGGRHLIFCHSKKKCDELAAKLVALGINAVAYYRGLDVSVIPTSGDVVVVATD ALMTGFTGDFDSVIDCN (SEQ ID NO:3). In some cases, the first and/or the second heterologous polypeptide comprises an amino acid sequence having at least 20% amino acid sequence identity to the following amino acid sequence:

VALSTTGEIPFYGKAIPLEVIKGGRHLIFCHSKKKCDELAAKLVALGINAVAYYR GLDVSVIPTSGDVVVVATDALMTGFTGDFDSVIDCNTCVTQTVDF (SEQ ID NO:4). In some cases, the variant HCV E1 polypeptide comprises, in order from N-terminus to C-terminus: i) the heterologous polypeptide; and ii) the HCV E1 polypeptide, and wherein the variant HCV E2 polypeptide comprises, in order from N-terminus to C-terminus: i) the heterologous polypeptide; and ii) the HCV E2 polypeptide. In some cases, the variant HCV E1 polypeptide comprises, in order from N-terminus to C-terminus: i) the HCV E1 polypeptide; and ii) the heterologous polypeptide, and wherein the variant HCV E2 polypeptide comprises, in order from N-terminus to C-terminus: i) the HCV E2 polypeptide; and ii) the heterologous polypeptide. In some cases, the first and/or the second heterologous polypeptide comprises one or more T cell epitopes present in: a) cholera toxin or toxoid; and/or b) tetanus toxin or toxoid; and/or c) diphtheria toxin or toxoid; and/or d) CRM197. In some cases, the E2 polypeptide and/or the E1 polypeptide lacks a C-terminal transmembrane domain. In some cases, the modified HCV E2 polypeptide and the HCV E1 polypeptide are derived from an HCV of the same genotype. In some cases, the modified HCV E2 polypeptide and the HCV E1 polypeptide are derived from an HCV of different genotypes. In some cases, the HCV E2 polypeptide comprises an amino acid sequence having at least 20% amino acid sequence identity to an E2 polypeptide depicted in FIGS. 1A-1C, FIGS. 2A-2C, FIGS. 3A-3C, and FIGS. 4A-4B.

The present disclosure provides a nucleic acid comprising nucleotide sequences encoding any one of the heterodimeric polypeptides described above or elsewhere herein. In some cases, the nucleotide sequence encoding the variant HCV E2 polypeptide and the nucleotide sequence encoding the HCV E1 polypeptide are operably linked to a promoter. The present disclosure provides a recombinant expression vector comprising the nucleic acid.

The present disclosure provides a composition comprising: a) a heterodimeric polypeptide as described above or elsewhere herein; and b) a pharmaceutically acceptable excipient. In some cases, the pharmaceutically acceptable excipient comprises an adjuvant. In some cases, the adjuvant is MF59, alum, poly(DL-lactide co-glycolide), a CpG oligonucleotide, or keyhole limpet hemocyanin.

The present disclosure provides a nucleic acid comprising a nucleotide sequence encoding an HCV E1-E2 polyprotein comprising: a) an HCV E1 polypeptide; b) an HCV E2 polypeptide; and c) a heterologous polypeptide that comprises one or more T cell epitopes present in an HCV polypeptide other than an HCV E1 polypeptide or an HCV E2 polypeptide. In some cases, the HCV E1 polypeptide comprises an amino acid sequence having at least 20% amino acid sequence identity to an E1 polypeptide depicted in FIGS. 1A-1C, FIGS. 2A-2C, FIGS. 3A-3C, and FIGS. 4A-4B. In some cases, the HCV E2 polypeptide is derived from an HCV of genotype 1, 2, 3, or 7. In some cases, the HCV E2 polypeptide comprises an amino acid sequence having at least 20% amino acid sequence identity to an E2 polypeptide depicted in FIGS. 1A-1C, FIGS. 2A-2C, FIGS. 3A-3C, and FIGS. 4A-4B. In some cases, the HCV E2 polypeptide is derived from an HCV of genotype 1, 2, 3, or 7. In some cases, the HCV E2 polypeptide and the HCV E1 polypeptide are of the same genotype. In some cases, the HCV E2 polypeptide and the HCV E1 polypeptide are of different genotypes. In some cases, the heterologous polypeptide has a length of from about 10 amino acids to about 3000 amino acids. In some cases, the heterologous polypeptide has a length of from about 10 amino acids to about 100 amino acids. In some cases, the E1-E2 polyprotein comprises, in order from N-terminus to C-terminus: i) the HCV E1 polypeptide; ii) the heterologous polypeptide; and iii) the HCV E2 polypeptide. In some cases, the E1-E2 polyprotein comprises, in order from N-terminus to C-terminus: i) the HCV E1 polypeptide; ii) the HCV E2 polypeptide; and iii) the heterologous polypeptide. In some cases, the E1-E2 polyprotein comprises, in order from N-terminus to C-terminus: i) the heterologous polypeptide; ii) the HCV E1 polypeptide; and iii) the HCV E2 polypeptide. In some cases, the E1-E2 polyprotein comprises, in order from N-terminus to C-terminus: i) the HCV E1 polypeptide; ii) the heterologous polypeptide; and iii) the HCV E2 polypeptide. In some cases, the nucleic acid comprises a nucleotide sequence encoding an immunoglobulin Fc polypeptide. In some cases, the polypeptide encoded by the nucleic acid comprises, in order from N-terminus to C-terminus: i) the E1 polypeptide; ii) the Fc polypeptide; iii) the heterologous polypeptide; and iv) the HCV E2 polypeptide. In some cases, the polypeptide encoded by the nucleic acid comprises a proteolytically cleavable linker interposed between the Fc polypeptide and the heterologous polypeptide. In some cases, the polypeptide encoded by the nucleic acid comprises, in order from N-terminus to C-terminus: i) the E1 polypeptide; ii) the Fc polypeptide; iii) the HCV E2 polypeptide; and iv) the heterologous polypeptide. In some cases, a proteolytically cleavable linker is interposed between the Fc polypeptide and the HCV E2 polypeptide. In some cases, a) the proteolytically cleavable linker comprises the sequence LEVLFQGP (SEQ ID NO:5), wherein cleavage occurs between the glutamine and the glycine; b) the proteolytically cleavable linker comprises the sequence ENLYTQS (SEQ ID NO:6), wherein cleavage occurs between the glutamine and the serine; c) the proteolytically cleavable linker comprises the sequence DDDDK (SEQ ID NO:7), wherein cleavage occurs immediately C-terminal to the lysine residue; or d) the proteolytically cleavable linker comprises the sequence LVPR (SEQ ID NO:8). In some cases, the heterologous polypeptide comprises one or more T cell epitopes present in one or more of: a) an HCV NS3 polypeptide; b) an HCV NS2 polypeptide; c) an HCV NS4A polypeptide; d) an HCV NS4B polypeptide; e) an HCV NS5A polypeptide; f) an HCV NS5B polypeptide; g) an HCV core polypeptide; and h) an HCV p7 polypeptide. In some cases, the heterologous polypeptide comprises one or more T cell epitopes present in: a) cholera toxin or toxoid; and/or b) tetanus toxin or toxoid; and/or c) diphtheria toxin or toxoid; and/or d) CRM197. In some cases, the heterologous polypeptide comprises one or more T cell epitopes present in an HCV NS3 polypeptide. In some cases, the heterologous polypeptide comprises an amino acid sequence having at least 20% amino acid sequence identity to the following amino acid sequence:

AIPLEVIKGGRHLIFCHSKKKCDELAAKL (SEQ ID NO:1). In some cases, the heterologous polypeptide comprises an amino acid sequence having at least 20% amino acid sequence identity to the following amino acid sequence:

AIPLEVIKGGRHLIFCHSKKKCDELAAKLVALGINAVAYYRGLDVSVIPTSG (SEQ ID NO:2). In some cases, the heterologous polypeptide comprises an amino acid sequence having at least 20% amino acid sequence identity to the following amino acid sequence:

KGGRHLIFCHSKKKCDELAAKLVALGINAVAYYRGLDVSVIPTSGDVVVVATD ALMTGFTGDFDSVIDCN (SEQ ID NO:3). In some cases, the heterologous polypeptide comprises an amino acid sequence having at least 20% amino acid sequence identity to the following amino acid sequence:

```
                                        (SEQ ID NO: 4)
VALSTTGEIPFYGKAIPLEVIKGGRHLIFCHSKKKCDELAAKLVALGINA

VAYYRGLDVSVIPTSGDVVVVATDALMTGFTGDFDSVIDCNTCVTQTVDF.
```

The present disclosure provides a recombinant expression vector comprising a nucleic acid as described above or elsewhere herein. In some cases, the nucleotide sequence is operably linked to a promoter. In some cases, the promoter is functional in a eukaryotic cell. The present disclosure provides a genetically modified in vitro host cell comprising a nucleic acid as described above or elsewhere herein, or the recombinant vector. In some cases, the host cell is a eukaryotic cell. In some cases, the host cell is a mammalian cell.

The present disclosure provides a method of making a variant HCV E1-E2 heterodimer, the method comprising: a) contacting a lysate of a genetically modified host cell described above, or elsewhere herein, with an Fc-binding polypeptide immobilized on an insoluble support, wherein the encoded HCV E1-E2 heterodimer comprises an Fc polypeptide, and wherein the HCV E1-E2 heterodimer present in the lysate binds to the immobilized Fc-binding polypeptide, generating an immobilized HCV E1-E2 heterodimer; and b) contacting the immobilized HCV E1-E2 heterodimer with an enzyme that cleaves the proteolytic cleavage site interposed between the Fc polypeptide and the heterologous polypeptide, thereby releasing the variant HCV E1-E2 heterodimer. In some cases, the released variant HCV E1-E2 heterodimer is at least 50% pure. In some cases, the Fc binding polypeptide is Protein A, Protein G, or a Protein A/G fusion. In some cases, a) the proteolytically cleavable linker comprises the sequence LEVLFQGP (SEQ ID NO:5), wherein cleavage occurs between the glutamine and the glycine; b) the proteolytically cleavable linker comprises the sequence ENLYTQS (SEQ ID NO:6), wherein cleavage occurs between the glutamine and the serine; c) the proteolytically cleavable linker comprises the sequence DDDDK (SEQ ID NO:7), wherein cleavage occurs immediately C-terminal to the lysine residue; or d) the proteolytically cleavable linker comprises the sequence LVPR (SEQ ID NO:8). In some cases, the enzyme is human rhinovirus 3C protease, a tobacco etch virus protease, an enterokinase, or thrombin. In some cases, the method further comprises subjecting a composition comprising the released HCV E1-E2 heterodimer to hydroxyapatite chromatography. Hydroxyapatite chromatography can be carried out as described in, e.g., Mazzocca et al. (2005) *J. Biol. Chem.* 280:11329.

The present disclosure provides a variant HCV E2 polypeptide comprising: a) an HCV E2 polypeptide; and b) a heterologous polypeptide that comprises one or more T cell epitopes present in an HCV protein other than E1 and E2. In some cases, the HCV E2 polypeptide is derived from an HCV of genotype 1, 2, 3, or 7. In some cases, the HCV E2 polypeptide comprises an amino acid sequence having at least 20% amino acid sequence identity to an E2 polypeptide depicted in one of FIGS. 1A-1C, FIGS. 2A-2C, FIGS. 3A-3C, and FIGS. 4A-4B. In some cases, the heterologous polypeptide has a length of from about 10 amino acids to about 3000 amino acids. In some cases, the heterologous polypeptide has a length of from about 10 amino acids to about 100 amino acids. In some cases, wherein the heterologous polypeptide comprises one or more T cell epitopes present in one or more of: a) an HCV NS3 polypeptide; b) an HCV NS2 polypeptide; c) an HCV NS-4A polypeptide; d) an HCV NS4B polypeptide; e) an HCV NS5A polypeptide; f) an HCV NS5B polypeptide; g) an HCV core polypeptide; and h) an HCV p7 polypeptide. In some cases, the HCV E2 polypeptide lacks a C-terminal transmembrane domain. In some cases, the heterologous polypeptide comprises one or more T cell epitopes present in: a) cholera toxin or toxoid; and/or b) tetanus toxin or toxoid; and/or c) diphtheria toxin or toxoid; and/or d) CRM197. In some cases, the heterologous polypeptide comprises one or more T cell epitopes present in an HCV NS3 polypeptide. In some cases, the heterologous polypeptide comprises an amino acid sequence having at least 20% amino acid sequence identity to the following amino acid sequence: AIPLEVIKGGRHLIFCHSKKKCDELAAKL (SEQ ID NO:1). In some cases, the heterologous polypeptide comprises an amino acid sequence having at least 20% amino acid sequence identity to the following amino acid sequence:

AIPLEVIKGGRHLIFCHSKKKCDELAAKLVALGINAVAYYRGLDVSVIPTSG (SEQ ID NO:2). In some cases, the heterologous polypeptide comprises an amino acid sequence having at least 20% amino acid sequence identity to the following amino acid sequence:

KGGRHLIFCHSKKKCDELAAKLVALGINAVAYYRGLDVSVIPTSGDVVVVATD ALMTGFTGDFDSVIDCN (SEQ ID NO:3). In some cases, the heterologous polypeptide comprises an amino acid sequence having at least 20% amino acid sequence identity to the following amino acid sequence:

VALSTTGEIPFYGKAIPLEVIKGGRHLIFCHSKKK-CDELAAKLVALGINAVAYYR GLDVSVIPTS-GDVVVVATDALMTGFTGDFDSVIDCNTCVTQ-TVDF (SEQ ID NO:4). In some cases, the variant HCV E2 polypeptide comprises, in order from N-terminus to C-terminus: i) the heterologous polypeptide; and ii) the HCV E2 polypeptide. In some cases, the varian HCV E2 polypeptide comprises, in order from N-terminus to C-terminus: i) the HCV E2 polypeptide; and ii) the heterologous polypeptide. In some cases, the variant HCV E2 polypeptide comprises an immunoglobulin Fc polypeptide. In some cases, the variant HCV E2 polypeptide comprises, in order from N-terminus to C-terminus: i) the Fc polypeptide; ii) the heterologous polypeptide; and iii) the HCV E2 polypeptide. In some cases, the variant HCV E2 polypeptide comprises a proteolytic cleavage site interposed between the Fc polypeptide and the heterologous polypeptide. In some cases, the proteolytic cleavage site comprises the sequence LEVLFQGP (SEQ ID NO:5), wherein cleavage occurs between the glutamine and the glycine.

The present disclosure provides a variant HCV E1 polypeptide comprising: a) an HCV E1 polypeptide; and b) a heterologous polypeptide that comprises one or more T cell epitopes. In some cases, the HCV E1 polypeptide is derived from an HCV of genotype 1, 2, 3, or 7. In some cases, the HCV E1 polypeptide comprises an amino acid sequence having at least 20% amino acid sequence identity to an E1 polypeptide depicted in one of FIGS. 1A-1C, FIGS. 2A-2C, FIGS. 3A-3C, and FIGS. 4A-4B. In some cases, the heterologous polypeptide has a length of from about 10 amino acids to about 3000 amino acids. In some cases, the heterologous polypeptide has a length of from about 10 amino acids to about 100 amino acids. In some cases, the HCV E1 polypeptide lacks a transmembrane domain. In some cases, the heterologous polypeptide comprises one or more T cell epitopes present in one or more of: a) an HCV NS3 polypeptide; b) an HCV NS2 polypeptide; c) an HCV NS-4A polypeptide; d) an HCV NS4B polypeptide; e) an HCV NS5A polypeptide; f) an HCV NS5B polypeptide; g) an HCV core polypeptide; and h) an HCV p7 polypeptide. In some cases, the heterologous polypeptide comprises one or more T cell epitopes present in: a) cholera toxin or toxoid; and/or b) tetanus toxin or toxoid; and/or c) diphtheria toxin or toxoid; and/or d) CRM197. In some cases, the heterologous polypeptide comprises one or more T cell epitopes present in an HCV NS3 polypeptide. In some cases, the heterologous polypeptide comprises an amino acid sequence having at least 20% amino acid sequence identity to the following amino acid sequence: AIPLEVIKGGRHLIFCHS-KKKCDELAAKL (SEQ ID NO:1). In some cases, the heterologous polypeptide comprises an amino acid sequence having at least 20% amino acid sequence identity to the following amino acid sequence:

AIPLEVIKGGRHLIFCHSKKKCDELAAKLVALGI-NAVAYYRGLDVSVIPTSG (SEQ ID NO:2). In some cases, the heterologous polypeptide comprises an amino acid sequence having at least 20% amino acid sequence identity to the following amino acid sequence:

KGGRHLIFCHSKKKCDELAAKLVALGINAVAYYR-GLDVSVIPTSGDVVVVATD ALMTGFTGDF-DSVIDCN (SEQ ID NO:3). In some cases, the heterologous polypeptide comprises an amino acid sequence having at least 20% amino acid sequence identity to the following amino acid sequence:

VALSTTGEIPFYGKAIPLEVIKGGRHLIFCHSKKKC-DELAAKLVALGINAVAYYR GLDVSVIPTSG-DVVVVATDALMTGFTGDFDSVIDCNTCVTQT-VDF (SEQ ID NO:4). In some cases, the variant HCV E1 polypeptide comprises, in order from N-terminus to C-terminus: i) the heterologous polypeptide; and ii) the HCV E1 polypeptide. In some cases, the variant HCV E1 polypeptide comprises, in order from N-terminus to C-terminus: i) the HCV E1 polypeptide; and ii) the heterologous polypeptide. In some cases, the variant HCV E1 polypeptide comprises an immunoglobulin Fc polypeptide. In some cases, the variant HCV E1 polypeptide comprises, in order from N-terminus to C-terminus: i) the Fc polypeptide; ii) the heterologous polypeptide; and iii) the HCV E1 polypeptide. In some cases, the variant HCV E1 polypeptide comprises a proteolytic cleavage site interposed between the Fc polypeptide and the heterologous polypeptide. In some cases, the proteolytic cleavage site comprises the sequence LEVLFQGP (SEQ ID NO:5), wherein cleavage occurs between the glutamine and the glycine.

The present disclosure nucleic acid comprising a nucleotide sequence encoding a variant HCV E2 polypeptide as described above or elsewhere herein, or a variant HCV E1 polypeptide as described above or elsewhere herein. The present disclosure provides a recombinant expression vector comprising the nucleic acid. In some cases, the nucleotide sequence is operably linked to a promoter. In some cases, the promoter is functional in a eukaryotic cell. The present disclosure provides a genetically modified in vitro host cell comprising a nucleic acid as described above or elsewhere herein, or a recombinant vector as described above or elsewhere herein. In some cases, the host cell is a eukaryotic cell. In some cases, the host cell is a mammalian cell.

The present disclosure provides a method of inducing an immune response in an individual, the method comprising administering to the individual an effective amount of a heterodimeric polypeptide as described above or elsewhere herein, or a composition as described above or elsewhere herein. The present disclosure provides a method of inducing an immune response in an individual, the method comprising administering to the individual an effective amount of a nucleic acid as described above or elsewhere herein.

The present disclosure provides a method of inducing an immune response in an individual, the method comprising administering to the individual an effective amount of a recombinant expression vector as described above or elsewhere herein. In some cases, the recombinant expression vector is a recombinant modified vaccinia Ankara vector. In some cases, the recombinant expression vector is a recombinant replication-defective adenovirus. In some cases, administration of the recombinant expression vector is by intramuscular administration. In some cases, administration of the recombinant expression vector is by subcutaneous administration.

BRIEF DESCRIPTION OF THE DRAWINGS

FIGS. 1A-1C provide an amino acid sequence alignment of examples of the core-E1-E2 coding regions of a HCV genotype 1 virus, specifically representative HCV 1A, 1B and 1C genotypes. Genbank database sequences for the coding region core-E1-E2 were aligned using Geneious software v5.6.4. Numbering of amino acids is according to strain NP_671941 (H77). Consensus: SEQ ID NO:74; AVI1a129: SEQ ID NO:75; NP_671491 (H77): SEQ ID NO:76; EU155269: SEQ ID NO:77; EU781810: SEQ ID NO:78; EU781771: SEQ ID NO:79; AB250610: SEQ ID NO:80; EU781752: SEQ ID NO:81; EU781759: SEQ ID NO:82; EF407439: SEQ ID NO:83; EF407427: SEQ ID NO:84; EU362905: SEQ ID NO:85; EF407413: SEQ ID NO:86; EU781808: SEQ ID NO:87; EU78170: SEQ ID NO:88; AJ238799 (Con1): SEQ ID NO:89; AAK97744: SEQ ID NO:90; AF139594: SEQ ID NO:91; AF176573: SEQ ID NO:92; BAA19625: SEQ ID NO:93; BAA25076: SEQ ID NO:94; BAC54896: SEQ ID NO:95; BAD91386: SEQ ID NO:96; BAF46764: SEQ ID NO:97; BAG30950: SEQ ID NO:98; CAB41951: SEQ ID NO:99; AAK95832: SEQ ID NO:100; AAT69968: SEQ ID NO:101; and BAA03581: SEQ ID NO:102.

FIGS. 3A-3C provide an amino acid sequence alignment of the core-E1-E2 coding region for representative HCV 3A, 3B and 3K genotypes. Genbank database sequences for the coding region core-E1-E2 were aligned using Geneious software v5.6.4. Consensus: SEQ ID NO:116; AVI3a177: SEQ ID NO: 117; ADF97232(S52): SEQ ID NO: 118; YP_0014696: SEQ ID NO: 119; CAA54244: SEQ ID NO:120; AAC03058: SEQ ID NO:121; AAY29642: SEQ ID NO:122; ABD85062: SEQ ID NO:123; ABD85063: SEQ ID NO:124; ABD97104: SEQ ID NO:125; BAA06044: SEQ ID NO:126; BAA08372: SEQ ID NO:127; and BAA09890: SEQ ID NO:128.

FIG. 5A depicts a schematic representation of an Fc-tagged E1E2 expression construct and polypeptide processing. SP denotes signal peptidase cleavage site. PP denotes cleavage site for precision protease. TPx denotes the addition of a polytope (a polypeptide comprising T-cell epitope(s)) to the E1E2 polypeptide at the N-terminus of E2. SEQ ID NO:5. FIG. 5B depicts a schematic representation of an un-tagged E1E2 expression construct and polypeptide processing.

FIGS. 6A-6B depict an alignment of Fc-tagged E1-E2 polypeptide, with and without a polytope (TPx) for H77 (GenBank NP_671941) and Alberta isolate Avi1a129 (genotype 1A). AVI1a129: SEQ ID NO:130; AVI1a129TP29: SEQ ID NO:131; AVI1a29TP52: SEQ ID NO:132; AVI1a129TP100: SEQ ID NO:133; H77: SEQ ID NO:134; H77 TP29: SEQ ID NO:135; H77 TP52: SEQ ID NO:136; H77 TP100: SEQ ID NO:137.

FIGS. 7A-7B depict an alignment of Fc-tagged E1-E2 polypeptide, with and without a polytope (TPx) for S52 (GenBank ADF97232.1) and Alberta isolate Avi3a177 (genotype 3A). S52: SEQ ID NO:138; S52 TP29: SEQ ID NO:139; S52 TP52: SEQ ID NO:140; S52 TP100: SEQ ID NO:141; AVI3a177: SEQ ID NO:142; AVI3a177 TP29: SEQ ID NO:143; AVI3a177 TP52: SEQ ID NO:144; AVI3a177 TP100: SEQ ID NO:145.

FIGS. 9A-9C provide amino acid sequences of immunoglobulin Fc regions (SEQ ID NOs:146-153).

FIG. 10 presents Table 1, which provides conserved regions based on conserved CD4 epitopes ($CD4^+$ T cell epitopes) (SEQ ID NOs:154-164).

FIG. 11 presents Table 2, which provides the number of located HCV $CD8^+$ T cell epitopes and anchor positions for common human leukocyte antigen (HLA)-I Alleles in the United States.

FIG. 12 presents Table 3, which provides conserved regions based on conserved CD8 epitopes ($CD8^+$ T cell epitopes) (SEQ ID NOs:165-174).

FIGS. 13A-13B provide a list of CD4 and CD8 epitopes that are conserved among HCV genotypes 1a, 1b, 2a, 2b, and 3.

FIGS. 14A-14D provide amino acid sequences of examples of T-cell polytopes ("TP"). The start and end amino acids are based on the sequence designated "Consensus" in FIGS. 16A-16L. The T-cell epitopes contained within each TP are provided; the T-cell epitope designations correspond to those presented in FIGS. 15A-15N (SEQ ID NOs:175-184).

FIGS. 16A-16L provide consensus amino acid sequences of HCV polypeptides (SEQ ID NOs:186-197).

DEFINITIONS

Figure 1A:
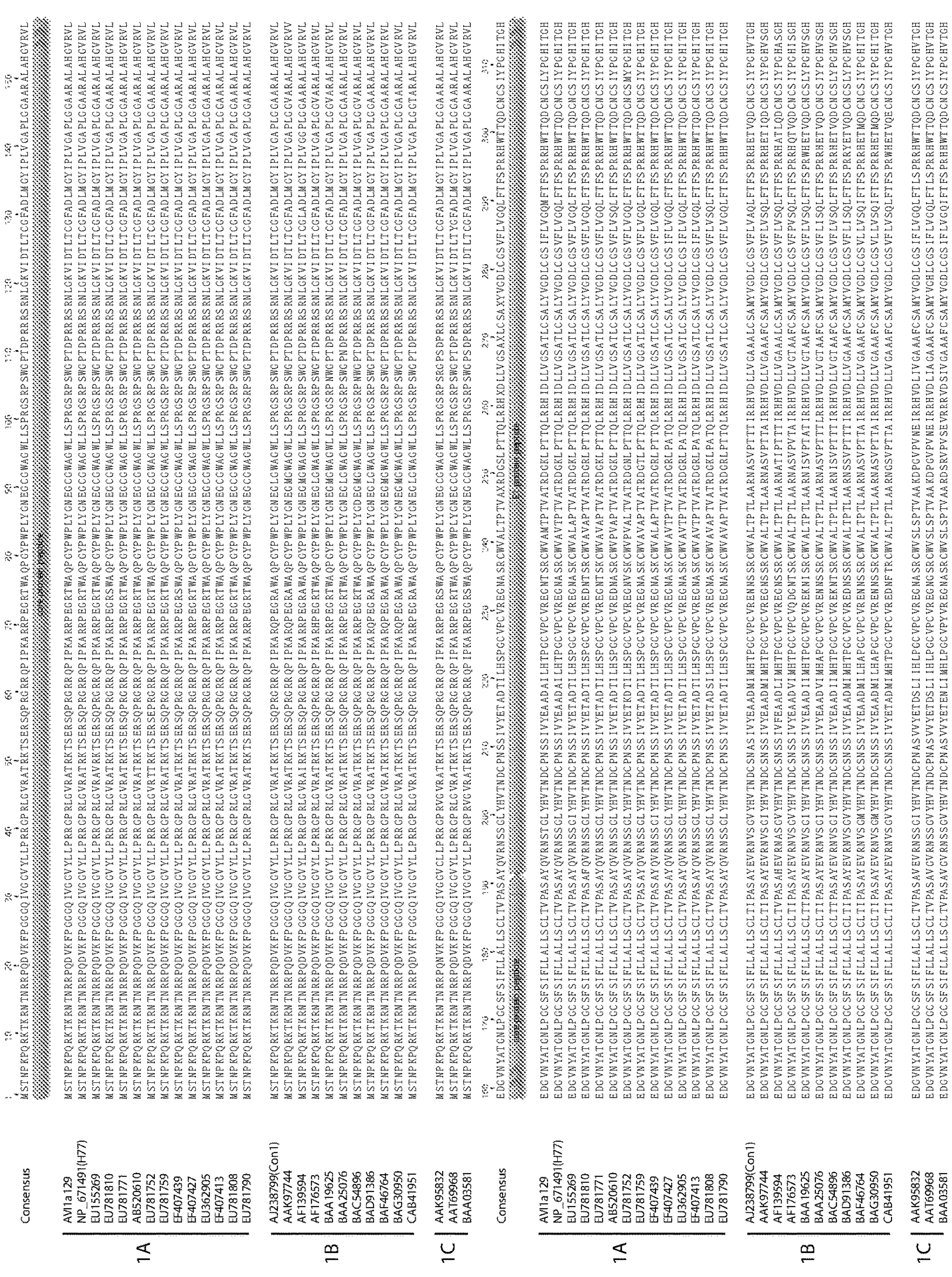

The term "hepatitis C virus" ("HCV"), as used herein, refers to any one of a number of different genotypes and isolates of hepatitis C virus. Thus, "HCV" encompasses any of a number of genotypes, subtypes, or quasispecies, of HCV, including, e.g., genotype 1, 2, 3, 4, 6, 7, etc. and subtypes (e.g., 1a, 1b, 2a, 2b, 3a, 4a, 4c, etc.), and quasispecies. Representative HCV genotypes and isolates include: the "Chiron" isolate HCV-1, H77, J6, Con1, isolate 1, BK, EC1, EC10, HC-J2, HC-J5; HC-J6, HC-J7, HC-J8, HC-JT, HCT18, HCT27, HCV-476, HCV-KF, "Hunan", "Japanese", "Taiwan", TH, type 1, type 1a, H77 type 1b, type 1c, type 1d, type 1e, type 1f, type 10, type 2, type 2a, type 2b, type 2c, type 2d, type 2f, type 3, type 3a, type 3b, type 3g, type 4, type 4a, type 4c, type 4d, type 4f, type 4h, type 4k, type 5, type 5a, type 6 and type 6a.

The terms "individual," "host," "subject," and "patient" are used interchangeably herein, and refer to a mammal, including, but not limited to, non-human primates (e.g., simians), equines (e.g., horses), and humans.

As used herein, the term "isolated," in reference to a polypeptide, refers to a polypeptide that is in an environment different from that in which the polypeptide naturally occurs. An isolated polypeptide can be purified. By "purified" is meant a compound of interest (e.g., a polypeptide) has been separated from components that accompany it in nature. "Purified" can also be used to refer to a polypeptide separated from components that can accompany it during production of the polypeptide (e.g., during synthesis in vitro, etc.). In some embodiments, a polypeptide (or a mixture of polypeptides) is substantially pure when the polypeptide (or mixture of polypeptides) is at least 60% or at least 75% by weight free from organic molecules with which it is naturally associated or with which it is associated during production. In some embodiments, the polypeptide is from 30% to 60% pure. In some embodiments, the polypeptide (or mixture of polypeptides) is at least 60%, at least 75%, at least 80%, at least 85%, at least 90%, at least 95%, or at least 99%, by weight, pure. For example, in some embodiments, an E1 or an E2 polypeptide (or a mixture of E1 and E2 polypeptides) is substantially pure when the E1 or E2 polypeptide (or mixture of E1 and E2 polypeptides) is at least 60% or at least 75% by weight free from organic molecules with which the polypeptide(s) is naturally associated or with which it is associated during production. In some embodiments, the E1 or E2 polypeptide (or mixture of E1 and E2 polypeptides) is at least 60%, at least 75%, at least 80%, at least 85%, at least 90%, at least 95%, or at least 99%, by weight, pure. In some embodiments, where a composition comprises an E2 polypeptide, the E2 polypeptide is at least 60%, at least 75%, at least 80%, at least 85%, at least 90%, at least 95%, or at least 99%, by weight, pure. In some embodiments, where a composition comprises an E1/E2 heterodimeric complex polypeptide, the E1/E2 heterodimeric complex polypeptide is at least 60%, at least 75%, at least 80%, at least 85%, at least 90%, at least 95%, or at least 99%, by weight, pure. In some embodiments, where a composition comprises an E1/variant E2 heterodimeric complex polypeptide, the E1/variant E2 heterodimeric complex polypeptides are at least 60%, at least 75%, at least 80%, at least 85%, at least 90%, at least 95%, or at least 99%, by weight, pure. In some embodiments, where a composition comprises a variant E1/E2 heterodimeric complex polypeptide, the variant E1/E2 heterodimeric complex polypeptides are at least 60%, at least 75%, at least 80%, at least 85%, at least 90%, at least 95%, or at least 99%, by weight, pure. In some embodiments, where a composition comprises a variant E1/variant E2 heterodimeric complex polypeptide, the variant E1/variant E2 heterodimeric complex polypeptides are at least 60%, at least 75%, at least 80%, at least 85%, at least 90%, at least 95%, or at least 99%, by weight, pure. In some embodiments, where a composition comprises a variant E1 polypeptide, the variant E1 polypeptide is at least 60%, at least 75%, at least 80%, at least 85%, at least 90%, at least 95%, or at least 99%, by weight, pure. In some embodiments, where a composition comprises a variant E2 polypeptide, the variant E2 polypeptide is at least 60%, at least 75%, at least 80%, at least 85%, at least 90%, at least 95%, or at least 99%, by weight, pure.

The terms "polynucleotide" and "nucleic acid," used interchangeably herein, refer to a polymeric form of nucleotides of any length, either ribonucleotides or deoxyribonucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases. In some cases, a polynucleotide is RNA. In some cases, a polynucleotide is DNA. A "polynucleotide" includes a nucleic acid that is incorporated into a viral vector or a bacterial vector.

The terms "peptide," "polypeptide," and "protein" are used interchangeably herein, and refer to a polymeric form of amino acids of any length, which can include coded and non-coded amino acids, chemically or biochemically modified or derivatized amino acids, and polypeptides having modified peptide backbones. The term "polypeptide" includes glycosylated polypeptides.

The term "heterologous" refers to two components that are defined by structures derived from different sources. For example, where "heterologous" is used in the context of a polypeptide, where the polypeptide includes operably linked amino acid sequences that can be derived from one or more different polypeptides, e.g., amino acid sequences that are not operably linked to the polypeptide in nature.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a variant HCV E2 polypeptide" includes a plurality of such polypeptides and reference to "the HCV E1 polypeptide" includes reference to one or more HCV E1 polypeptides and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

T cell responses and antibody responses to HCV can be protective against HCV infection. The present disclosure provides heterodimeric polypeptides comprising: 1) a variant hepatitis C virus (HCV) E2 polypeptide and an HCV E1 polypeptide; 2) a variant HCV E1 polypeptide and an HCV E2 polypeptide; and 3) a variant HCV E1 polypeptide and a variant HCV E2 polypeptide, where the variant HCV E2 polypeptide and/or or the HCV E1 polypeptide comprises a heterologous polypeptide comprising one or more T cell epitopes, e.g., one or more T cell epitopes present in an HCV polypeptide other than an HCV E1 polypeptide or an HCV E2 polypeptide, where the one or more T-cell epitopes are referred to as a "polytope." Inclusion of T cell epitopes provides for a more robust T-cell response to HCV, including cytotoxic $CD8^+$ T-cell responses to HCV-infected cells, and $CD4^+$ T helper responses. Enhanced $CD4^+$ responses may also result in a higher titer of neutralizing anti-E1/E2 antibodies to HCV. Such T-cell responses and antibody titers can provide a protective response against HCV infection. The T-cell epitopes that are included within the polytope can include conserved T-cell epitopes and/or immunodominant T-cell epitopes. It was found that inclusion, in an HCV E2 polypeptide, of a heterologous polypeptide comprising a polytope (one or more T-cell epitopes) allows formation of an E1/E2 heterodimer. A purification scheme was devised, which provides for ease of production of E1/E2 heterodimers (where one or both of the E1 and E2 polypeptides comprises a heterologous polypeptide comprising one or more T-cell epitopes), and which provides for highly purified E1/E2 heterodimers using a scaleable vaccine manufacturing level process.

E1/E2 heterodimers of the present disclosure provide improvements to previously-described vaccine candidates by 1) eliciting higher levels of HCV-specific $CD4^+$ T helper responses, which are known to contribute to protection against HCV infection; 2) eliciting higher levels of HCV-specific $CD8^+$ cytotoxic T cell responses, which are known to contribute to protection against HCV infection; and 3) via the inclusion of extra CD4+ T helper epitopes, leading to higher titers of HCV neutralizing antibodies which are also known to be associated with protection against HCV infection.

A variant E2 polypeptide, also referred to as an "E2 fusion polypeptide," comprises an HCV E2 polypeptide and a heterologous polypeptide, where the heterologous polypeptide is also referred to as a "fusion partner." The heterologous polypeptide is covalently linked to the HCV E2 polypeptide. A variant E1 polypeptide, also referred to as an "E1 fusion polypeptide," comprises an HCV E1 polypeptide and a heterologous polypeptide, where the heterologous polypeptide is also referred to as a "fusion partner." The heterologous polypeptide is covalently linked to the HCV E1 polypeptide. The heterologous polypeptide ("fusion partner") comprises one or more T-cell epitopes present in an HCV polypeptide other than an HCV E1 polypeptide or an HCV E2 polypeptide. The heterologous polypeptide can be fused to the N-terminus or the C-terminus of the HCV E1 or HCV E2 polypeptide.

The present disclosure provides heterodimeric polypeptides comprising a variant HCV E2 polypeptide and an HCV E1 polypeptide, or comprising a variant HCV E1 polypeptide and an HCV E2 polypeptide, or comprising a variant HCV E1 polypeptide and a variant HCV E2 polypeptide, where the variant HCV E2 polypeptide and/or the HCV E1 polypeptide comprises a heterologous polypeptide comprising one or more T cell epitopes, e.g., one or more T cell epitopes present in an HCV polypeptide other than an HCV E1 polypeptide or an HCV E2 polypeptide. The present disclosure provides nucleic acids encoding a polyprotein that includes E1 and variant E2, or that includes E2 and variant E1, or that includes variant E2 and variant E1. The present disclosure provides a method of producing an E1/E2 heterodimer of the present disclosure. The present disclosure also provides variant E2 polypeptides and variant E1 polypeptides; and nucleic acids encoding the variant polypeptides. The present disclosure provides a method of inducing an immune response in an individual. The present disclosure provides a method of inducing an immune response (e.g., a protective immune response) to HCV antigens in an individual. The present disclosure provides a method of inducing a protective immune response to one or more HCV genotypes in an individual. In some cases, the HCV E2 polypeptide is an HCV E2 ectodomain polypeptide. In some cases, the HCV E2 polypeptide is a full-length HCV E2 polypeptide. In some cases, the HCV E1 polypeptide is an HCV E1 ectodomain polypeptide. In some cases, the HCV E1 polypeptide is a full-length HCV E1 polypeptide.

The present disclosure provides heterodimeric polypeptides comprising: a) a variant HCV E2 polypeptide and an HCV E1 polypeptide; b) a variant HCV E1 polypeptide and an HCV E2 polypeptide; or c) a variant HCV E1 polypeptide and a variant HCV E2 polypeptide, where the variant HCV E2 polypeptide or the HCV E1 polypeptide comprises one or more T cell epitopes, e.g., one or more T cell epitopes present in an HCV polypeptide other than an HCV E1 polypeptide or an HCV E2 polypeptide. The one or more T-cell epitopes can include one or more T-cell epitopes present in: a) an HCV non-structural polypeptide-3 (NS3) polypeptide; b) an HCV non-structural polypeptide-2 (NS2) polypeptide; c) an HCV non-structural polypeptide-4A (NS4A) polypeptide; d) an HCV non-structural polypeptide-4B (NS4B) polypeptide; e) an HCV non-structural polypeptide-5A (NS5A) polypeptide; f) an HCV non-structural polypeptide-5B (NS5B) polypeptide; g) an HCV core polypeptide; or h) an HCV p7 polypeptide. In some cases, the one or more T-cell epitopes are T-cell epitopes present in an HCV NS3 polypeptide. In some cases, the heterologous polypeptide further comprises one or more T cell epitopes present in: a) cholera toxin or toxoid; and/or b) tetanus toxin or toxoid; and/or c) diphtheria toxin or toxoid; and/or d) a meningococcal outer membrane protein. Thus, in some cases, a variant HCV E1 polypeptide or variant HCV E2 polypeptide of an E1/E2 heterodimer of the present disclosure includes: a) an HCV E1 polypeptide or an HCV E2 polypeptide; and b) a heterologous polypeptide that comprises one or more T-cell epitopes, where the one or more T-cell epitopes are T-cell epitopes present in: i) one or more of an HCV NS3 polypeptide, an HCV NS2 polypeptide, an HCV NS4A polypeptide, an HCV NS4B polypeptide, an HCV NS5A polypeptide, an HCV NS5B polypeptide, an HCV core polypeptide, and an HCV p7 polypeptide; and ii) one or more of cholera toxin or toxoid, tetanus toxin or toxoid, diphtheria toxin or toxoid, and a meningococcal outer membrane protein.

In some cases, a heterodimeric polypeptide of the present disclosure includes: a) an HCV E1 polypeptide; and b) a variant HCV E2 polypeptide comprising: i) an HCV E2 polypeptide; and ii) a heterologous polypeptide that comprises one or more T-cell epitopes (e.g., one or more T cell epitopes present in an HCV polypeptide other than an HCV E1 polypeptide or an HCV E2 polypeptide). The one or more T-cell epitopes can include one or more T-cell epitopes present in: a) an HCV NS3 polypeptide; b) an HCV NS2 polypeptide; c) an HCV NS4A polypeptide; d) an HCV NS4B polypeptide; e) an HCV NS5A polypeptide; f) an HCV NS5B polypeptide; g) an HCV core polypeptide; or h) an HCV p7 polypeptide. In some cases, the one or more T-cell epitopes are T-cell epitopes present in an HCV NS3 polypeptide. In some cases, the heterologous polypeptide further comprises one or more T cell epitopes present in: a) cholera toxin or toxoid; and/or b) tetanus toxin or toxoid; and/or c) diphtheria toxin or toxoid; and/or d) a meningococcal outer membrane protein. In some cases, a variant HCV E2 polypeptide of an E1/E2 heterodimer of the present disclosure includes: a) an HCV E2 polypeptide; and b) a heterologous polypeptide that comprises one or more T-cell epitopes, where the one or more T-cell epitopes are T-cell epitopes present in: i) one or more of an HCV NS3 polypeptide, an HCV NS2 polypeptide, an HCV NS4A polypeptide, an HCV NS4B polypeptide, an HCV NS5A polypeptide, an HCV NS5B polypeptide, an HCV core polypeptide, and an HCV p7 polypeptide; and ii) one or more of cholera toxin or toxoid, tetanus toxin or toxoid, diphtheria toxin or toxoid, and a meningococcal outer membrane protein In some cases, a heterodimeric polypeptide of the present disclosure includes: a) a variant HCV E1 polypeptide comprising: i) an HCV E1 polypeptide; and ii) a heterologous polypeptide that comprises one or more T-cell epitopes (e.g., one or more T cell epitopes present in an HCV polypeptide other than an HCV E1 polypeptide or an HCV E2 polypeptide); and b) an HCV E2 polypeptide. The one or more T-cell epitopes can include one or more T-cell epitopes present in: a) an HCV NS3 polypeptide; b) an HCV NS2 polypeptide; c) an HCV NS4A polypeptide; d) an HCV NS4B polypeptide; e) an HCV NS5A polypeptide; f) an HCV NS5B polypeptide; g) an HCV core polypeptide; or h) an HCV p7 polypeptide. In some cases, the one or more T-cell epitopes are T-cell epitopes present in an HCV NS3 polypeptide. In some cases, the heterologous polypeptide further comprises one or more T cell epitopes present in: a) cholera toxin or toxoid; and/or b) tetanus toxin or toxoid; and/or c) diphtheria toxin or toxoid; and/or d) a meningococcal outer membrane protein. In some cases, a variant HCV E1 polypeptide of an E1/E2 heterodimer of the present disclosure includes: a) an HCV E1 polypeptide; and b) a heterologous polypeptide that comprises one or more T-cell epitopes, where the one or more T-cell epitopes are T-cell epitopes present in: i) one or more of an HCV NS3 polypeptide, an HCV NS2 polypeptide, an HCV NS4A polypeptide, an HCV NS4B polypeptide, an HCV NS5A polypeptide, an HCV NS5B polypeptide, an HCV core polypeptide, and an HCV p7 polypeptide; and ii) one or more of cholera toxin or toxoid, tetanus toxin or toxoid, diphtheria toxin or toxoid, and a meningococcal outer membrane protein.

In some cases, a heterodimeric polypeptide of the present disclosure includes: a) a variant HCV E1 polypeptide comprising: i) an HCV E1 polypeptide; and ii) a heterologous polypeptide that comprises one or more T-cell epitopes (e.g., one or more T cell epitopes present in an HCV polypeptide other than an HCV E1 polypeptide or an HCV E2 polypeptide); and b) a variant HCV E2 polypeptide comprising: i) an HCV E2 polypeptide; and ii) a heterologous polypeptide that comprises one or more T-cell epitopes (e.g., one or more T cell epitopes present in an HCV polypeptide other than an HCV E1 polypeptide or an HCV E2 polypeptide). The one or more T-cell epitopes can include one or more T-cell epitopes present in: a) an HCV NS3 polypeptide; b) an HCV NS2 polypeptide; c) an HCV NS4A polypeptide; d) an HCV NS4B polypeptide; e) an HCV NS5A polypeptide; f) an HCV NS5B polypeptide; g) an HCV core polypeptide; or h) an HCV p7 polypeptide. In some cases, the one or more T-cell epitopes are T-cell epitopes present in an HCV NS3 polypeptide. In some cases, the heterologous polypeptide further comprises one or more T cell epitopes present in: a) cholera toxin or toxoid; and/or b) tetanus toxin or toxoid; and/or c) diphtheria toxin or toxoid; and/or d) a meningococcal outer membrane protein. In some cases, a variant HCV E2 and a variant HCV E1 polypeptide of an E1/E2 heterodimer of the present disclosure includes: 1) a) an HCV E2 polypeptide; and b) a heterologous polypeptide that comprises one or more T-cell epitopes, where the one or more T-cell epitopes are T-cell epitopes present in: i) one or more of an HCV NS3 polypeptide, an HCV NS2 polypeptide, an HCV NS4A polypeptide, an HCV NS4B polypeptide, an HCV NS5A polypeptide, an HCV NS5B polypeptide, an HCV core polypeptide, and an HCV p7 polypeptide; and ii) one or more of cholera toxin or toxoid, tetanus toxin or toxoid, diphtheria toxin or toxoid, and a meningococcal outer membrane protein; and 2) a) an HCV E1 polypeptide; and b) a heterologous polypeptide that comprises one or more T-cell epitopes, where the one or more T-cell epitopes are T-cell epitopes present in: i) one or more of an HCV NS3 polypeptide, an HCV NS2 polypeptide, an HCV NS4A polypeptide, an HCV NS4B polypeptide, an HCV NS5A polypeptide, an HCV NS5B polypeptide, an HCV core polypeptide, and an HCV p7 polypeptide; and ii) one or more of cholera toxin or toxoid, tetanus toxin or toxoid, diphtheria toxin or toxoid, and a meningococcal outer membrane protein.

As noted above, the present disclosure provides heterodimeric polypeptides comprising: a) a variant HCV E2 polypeptide and an HCV E1 polypeptide; b) a variant HCV E1 polypeptide and an HCV E2 polypeptide; or c) a variant HCV E1 polypeptide and a variant HCV E2 polypeptide, where the variant HCV E2 polypeptide or the HCV E1 polypeptide comprises one or more T cell epitopes, e.g., one or more T cell epitopes present in an HCV polypeptide other than an HCV E1 polypeptide or an HCV E2 polypeptide. The presence of the one or more T-cell epitopes (e.g., one or more T-cell epitopes conserved among the hepacivirus genus; e.g., one or more immunodominant T-cell epitopes) provides for a more robust cellular immune response (e.g., a $CD4^+$ and/or a $CD8^+$ immune response) to HCV than a wild-type HCV E1/E2 heterodimer. For example, the addition of the one or more T-cell epitopes provides for a more robust $CD4^+$ helper and $CD8^+$ cytotoxic T cell response to HCV than a wild-type HCV E1/E2 heterodimer, and provides greater T helper activity to promote stronger antibody responses to the E1/E2 heterodimer. These features provide for superior HCV vaccine antigens.

The present disclosure provides variant HCV E2 polypeptides, and variant HCV E1 polypeptides. A variant E2 polypeptide of the present disclosure heterodimerizes with an HCV E1 polypeptide. A variant E1 polypeptide of the present disclosure heterodimerizes with an HCV E2 polypeptide. The heterodimer, or a polynucleotide(s) comprising a nucleotide sequence encoding the heterodimer, can be used to induce an immune response against HCV in an individual. For example, the heterodimer, or a polynucleotide(s) comprising a nucleotide sequence encoding the heterodimer, can be used to induce a protective immune response against HCV in an individual. In some cases, the heterodimer, or a polynucleotide(s) comprising a nucleotide sequence encoding the heterodimer, can be used to induce a protective immune response against HCV of more than one genotype.

Suitable T-cell epitopes (e.g., one or more conserved T-cell epitopes; e.g., one or more immunodominant T-cell epitopes) are described in detail below; and in the Figures. Suitable T-cell epitopes can be identified using the methods described in the Examples section, or using any other method that identifies conserved T-cell epitopes or immunodominant T-cell epitopes.

In some cases, a heterologous polypeptide present in a variant E1 polypeptide or a variant E2 polypeptide described herein, where the heterologous polypeptide comprises one or more T-cell epitopes present in an HCV polypeptide other than an HCV E1 polypeptide or an HCV E2 polypeptide, comprises: a) two or more (2, 3, 4, 5, 6, 7, 8, 9, or 10, or more than 10) T cell epitopes of an HCV NS3 polypeptide; b) two or more (2, 3, 4, 5, 6, 7, 8, 9, or 10, or more than 10) T cell epitopes of an HCV NS2 polypeptide; c) two or more (2, 3, 4, 5, 6, 7, 8, 9, or 10, or more than 10) T cell epitopes of an HCV NS4A polypeptide; d) two or more (2, 3, 4, 5, 6, 7, 8, 9, or 10, or more than 10) T cell epitopes of an HCV NS4B polypeptide; e) two or more (2, 3, 4, 5, 6, 7, 8, 9, or 10, or more than 10) T cell epitopes of an HCV NS5A polypeptide; f) two or more (2, 3, 4, 5, 6, 7, 8, 9, or 10, or more than 10) T cell epitopes of an HCV NS5B polypeptide; g) two or more (2, 3, 4, 5, 6, 7, 8, 9, or 10, or more than 10) T cell epitopes of an HCV core polypeptide; h) two or more (2, 3, 4, 5, 6, 7, 8, 9, or 10, or more than 10) T cell epitopes of an HCV p7 polypeptide; i) one or more T-cell epitopes of an HCV NS3 polypeptide and one or more T-cell epitopes of an HCV NS2 polypeptide; j) one or more T-cell epitopes of an HCV NS3 polypeptide and one or more T-cell epitopes of an HCV NS4B polypeptide; k) one or more T-cell epitopes of an HCV NS3 polypeptide and one or more T-cell epitopes of an HCV NS5A polypeptide; 1) one or more T-cell epitopes of an HCV NS3 polypeptide and one or more T-cell epitopes of an HCV NS5B polypeptide; m) one or more T-cell epitopes of an HCV NS3 polypeptide and one or more T-cell epitopes of an HCV core polypeptide; n) one or more T-cell epitopes of an HCV NS3 polypeptide, one or more T-cell epitopes of an HCV NS2 polypeptide, and one or more T-cell epitopes of an HCV core polypeptide; o) one or more T-cell epitopes of an HCV NS3 polypeptide, one or more T-cell epitopes of an HCV NS2 polypeptide, and one or more T-cell epitopes of an HCV NS4B polypeptide; or p) one or more T-cell epitopes of an HCV NS3 polypeptide, one or more T-cell epitopes of an HCV NS2 polypeptide, and one or more T-cell epitopes of an HCV NS5A polypeptide. Other combinations are possible and are contemplated by the present disclosure.

In some cases, a variant E2 polypeptide and/or a variant E1 polypeptide comprises a heterologous polypeptide comprising a polytope that comprises: 1) a contiguous NS3-NS4a polypeptide in which the NS3-encoded serine protease is rendered inactive by mutation of any one of the catalytic triad amino acids (H,D,S); 2) a contiguous NS3-NS4a-NS4a polypeptide in which the NS3-encoded serine protease is rendered inactive by mutation of any one of the catalytic triad amino acids (H,D,S); 3) a contiguous NS3-NS4a-NS4a-NS5a polypeptide in which the NS3-encoded serine protease is rendered inactive by mutation of any one of the catalytic triad amino acids (H,D,S); or 4) a contiguous NS3-NS4a-NS4a-NS5a-NS5a polypeptide in which the NS3-encoded serine protease is rendered inactive by mutation of any one of the catalytic triad amino acids (H,D,S) and the NS5b-encoded RNA polymerase is rendered inactive by mutation of any residues in the GDD motif that is required for polymerase activity.

In some cases, a linker can be interposed between the heterologous polypeptide ("polytope") and the HCV E1 or HCV E2 polypeptide. The linker peptide may have any of a variety of amino acid sequences. A linker can be a peptide of between about 6 and about 40 amino acids in length, or between about 6 and about 25 amino acids in length. These linkers can be produced by using synthetic, linker-encoding oligonucleotides to couple the proteins. Peptide linkers allowing a degree of flexibility can be used. The linking peptides may have virtually any amino acid sequence, bearing in mind that suitable linkers will have a sequence that results in a generally flexible peptide. The use of small amino acids, such as glycine and alanine, are of use in creating a flexible peptide. The creation of such sequences is routine to those of skill in the art.

Suitable linkers can be readily selected and can be of any of a suitable of different lengths, such as from 1 amino acid (e.g., Gly, Ala, or Ser) to 20 amino acids, from 2 amino acids to 15 amino acids, from 3 amino acids to 12 amino acids, including 4 amino acids to 10 amino acids, 5 amino acids to 9 amino acids, 6 amino acids to 8 amino acids, or 7 amino acids to 8 amino acids, and may be 1, 2, 3, 4, 5, 6, or 7 amino acids.

Exemplary flexible linkers include glycine polymers $(G)_n$, glycine-serine polymers (including, for example, $(GS)_n$, $(GSGGS)_n$ (SEQ ID NO:55) and $(GGGS)_n$ (SEQ ID NO:56), where n is an integer of at least one), glycine-alanine polymers, alanine-serine polymers, and other flexible linkers known in the art. Glycine and glycine-serine polymers are of interest since both of these amino acids are relatively unstructured, and therefore may serve as a neutral tether between components. Glycine polymers are of particular interest since glycine accesses significantly more phi-psi space than even alanine, and is much less restricted than residues with longer side chains (see Scheraga, Rev. Computational Chem. 11173-142 (1992)). Exemplary flexible linkers include, but are not limited to, GGSG (SEQ ID NO:57), GGSGG (SEQ ID NO:58), GSGSG (SEQ ID NO:59), GSGGG (SEQ ID NO:60), GGGSG (SEQ ID NO:61), GSSSG (SEQ ID NO:62), and the like. The ordinarily skilled artisan will recognize that design of a peptide conjugated to any elements described above can include linkers that are all or partially flexible, such that the linker can include a flexible linker as well as one or more portions that confer less flexible structure.

I. E1/E2 Heterodimers

The present disclosure provides heterodimeric polypeptides comprising: a) a variant HCV E2 polypeptide and an HCV E1 polypeptide; b) a variant HCV E1 polypeptide and an HCV E2 polypeptide; or c) a variant HCV E1 polypeptide and a variant HCV E2 polypeptide, where the variant HCV E2 polypeptide or the HCV E1 polypeptide comprises one or more T cell epitopes, e.g., one or more T cell epitopes present in an HCV polypeptide other than an HCV E1 polypeptide or an HCV E2 polypeptide.

An E1/E2 heterodimer of the present disclosure, or a nucleic acid(s) (e.g., one or more recombinant expression vectors; an mRNA molecule(s); a DNA molecule(s)) comprising a nucleotide sequence encoding the E1/E2 heterodimer, can be used to induce an immune response to HCV in an individual. The nucleic acid may be in the form of DNA or RNA, or may be complexed with a polymer such as poly-lactic-co-glycolide (PLG) or liposomal formulations or may be inserted into a viral vaccine vector or bacterial vaccine vectors. Nucleic acid vaccines are feasible using either viral or bacterial vectors to deliver the nucleic acids encoding vaccine antigens or by delivering the encoding DNA or RNA into an immunogenic vaccine formulation (Deering et al. (2014) *Expert Opin Drug Deliv.* 11(6):885-99).

IA. E1E2 Heterodimers Comprising HCV E1 and a Variant HCV E2

The present disclosure provides an E1/E2 heterodimer, where the E1/E2 heterodimer comprises: a) a variant HCV E2 polypeptide, where the variant HCV E2 polypeptide comprises: i) an HCV E2 polypeptide; and ii) a heterologous polypeptide that comprises one or more T-cell epitopes (e.g., one or more T-cell epitopes not present in an HCV E1 or an HCV E2 polypeptide; e.g., one or more T-cell epitopes present in an HCV polypeptide other than an HCV E1 or an HCV E2 polypeptide); and b) an HCV E1 polypeptide. Thus, in some cases, a heterodimeric polypeptide of the present disclosure includes: a) an HCV E1 polypeptide; and b) a variant HCV E2 polypeptide comprising: i) an HCV E2 polypeptide; and ii) a heterologous polypeptide that comprises one or more T-cell epitopes (e.g., one or more T cell epitopes present in an HCV polypeptide other than an HCV E1 polypeptide or an HCV E2 polypeptide). The one or more T-cell epitopes can include one or more T-cell epitopes present in: a) an HCV NS3 polypeptide; b) an HCV NS2 polypeptide; c) an HCV NS4A polypeptide; d) an HCV NS4B polypeptide; e) an HCV NS5A polypeptide; f) an HCV NS5B polypeptide; g) an HCV core polypeptide; or h) an HCV p7 polypeptide. In some cases, the one or more T-cell epitopes are T-cell epitopes present in an HCV NS3 polypeptide. In some cases, the heterologous polypeptide further comprises one or more T cell epitopes present in: a) cholera toxin or toxoid; and/or b) tetanus toxin or toxoid; and/or c) diphtheria toxin or toxoid; and/or d) a meningococcal outer membrane protein. The heterologous polypeptide is also referred to as a "polytope."

An E1/E2 heterodimer of the present disclosure (e.g., an E1/E2 heterodimer comprising: a) an HCV E1 polypeptide; and b) a variant HCV E2 polypeptide comprising: i) an HCV E2 polypeptide; and ii) a heterologous polypeptide comprising one or more T-cell epitopes), when administered to an individual in need thereof, induces an immune response in the individual to one or more HCV genotypes. An E1/E2 heterodimer of the present disclosure, when administered to an individual in need thereof, induces an immune response in the individual to one or more HCV genotypes, where the immune response is greater than the immune response induced by administration of an HCV E1/E2 heterodimer comprising a wild-type E1 and a wild-type E2 polypeptide or an E2 polypeptide lacking the polytope.

For example, in some cases, an E1/E2 heterodimer of the present disclosure (e.g., an E1/E2 heterodimer comprising: a) an HCV E1 polypeptide; and b) a variant HCV E2 polypeptide comprising: i) an HCV E2 polypeptide; and ii) a heterologous polypeptide comprising one or more T-cell epitopes), when administered to an individual in need thereof, induces cytotoxic T lymphocytes (CTLs) specific for HCV, where the number of HCV-specific CTLs induced is at least 10%, at least 15%, at least 20%, at least 25%, at least 30%, at least 40%, at least 50%, at least 75%, at least 100% (or 2-fold), at least 2.5-fold, at least 5-fold, at least 7.5-fold, at least 10-fold, at least 20-fold, at least 50-fold, or at least 100-fold, or more than 100-fold, higher than the number of HCV-specific CTLs induced by administration of an HCV E1/E2 heterodimer comprising a wild-type E1 and a wild-type E2 polypeptide or an E2 polypeptide lacking the polytope.

In some cases, an E1/E2 heterodimer of the present disclosure (e.g., an E1/E2 heterodimer comprising: a) an HCV E1 polypeptide; and b) a variant HCV E2 polypeptide comprising: i) an HCV E2 polypeptide; and ii) a heterologous polypeptide comprising one or more T-cell epitopes present in an HCV polypeptide other than an HCV E1 polypeptide or an HCV E2 polypeptide), when administered to an individual in need thereof, induces production of HCV-specific $CD4^+$ T cells and $CD8^+$ T cells in the individual, where the number of HCV-specific $CD4^+$ T cells and $CD8^+$ T cells is increased, such that the percent of the total peripheral blood T cells (i.e., the total number of $CD4^+$ T cells+$CD8^+$ T cells in the peripheral blood) that are HCV-specific $CD4^+$ T cells and $CD8^+$ T cells is from 0.05% to 10% (e.g., from 0.05% to 0.1%, from 0.1% to 0.5%, from 0.5% to 1%, from 1% to 2%, from 2% to 5%, or from 5% to 10%). The number of HCV-specific $CD4^+$ T cells and $CD8^+$ T cells in a control individual (e.g., an individual not infected with HCV) not treated with the E1/E2 heterodimer would be undetectable.

For example, in some cases, an E1/E2 heterodimer of the present disclosure (e.g., an E1/E2 heterodimer comprising: a) an HCV E1 polypeptide; and b) a variant HCV E2 polypeptide comprising: i) an HCV E2 polypeptide; and ii) a heterologous polypeptide comprising one or more HCV NS3 T-cell epitopes), when administered to an individual in need thereof, induces production of HCV NS3-specific $CD4^+$ T cells and $CD8^+$ T cells in the individual, where the number of HCV NS3-specific $CD4^+$ T cells and $CD8^+$ T cells is increased, such that the percent of the total peripheral blood T cells (i.e., the total number of $CD4^+$ T cells+$CD8^+$ T cells in the peripheral blood) that are HCV NS3-specific $CD4^+$ T cells and $CD8^+$ T cells is from 0.05% to 10% (e.g., from 0.05% to 0.1%, from 0.1% to 0.5%, from 0.5% to 1%, from 1% to 2%, from 2% to 5%, or from 5% to 10%). The number of HCV NS3-specific $CD4^+$ T cells and $CD8^+$ T cells in a control individual (e.g., an individual not infected with HCV) not treated with the E1/E2 heterodimer would be undetectable.

In some cases, an E1/E2 heterodimer of the present disclosure (e.g., an E1/E2 heterodimer comprising: a) an HCV E1 polypeptide; and b) a variant HCV E2 polypeptide comprising: i) an HCV E2 polypeptide; and ii) a heterologous polypeptide comprising one or more T-cell epitopes present in an HCV polypeptide other than an HCV E1 polypeptide or an HCV E2 polypeptide), when administered to an individual in need thereof, increases the number of HCV E1/E2-specific $CD4^+$ T cells and $CD8^+$ T cells in the individual by at least 10%, at least 15%, at least 20%, at least 25%, at least 30%, at least 40%, at least 50%, at least 75%, at least 100% (or 2-fold), at least 2.5-fold, at least 5-fold, at least 7.5-fold, at least 10-fold, at least 20-fold, at least 50-fold, or at least 100-fold, or more than 100-fold, compared to the number of HCV E1/E2-specific $CD4^+$ T cells and $CD8^+$ T cells in the individual induced by administration of an E1/E2 heterodimer comprising a wild-type E1 polypeptide and a wild-type E2 polypeptide, or an E2 polypeptide lacking the polytope, or compared to the number of HCV E1/E2-specific $CD4^+$ T cells and $CD8^+$ T cells in the individual before administration of the E1/E2 heterodimer of the present disclosure.

As another example, in some cases, an E1/E2 heterodimer of the present disclosure (e.g., an E1/E2 heterodimer comprising: a) an HCV E1 polypeptide; and b) a variant HCV E2 polypeptide comprising: i) an HCV E2 polypeptide; and ii) a heterologous polypeptide comprising one or more T-cell epitopes present in an HCV polypeptide other than an HCV E1 polypeptide or an HCV E2 polypeptide), when administered to an individual in need thereof, induces helper T lymphocytes (e.g., $CD4^+$ T cells) specific for HCV, where the number of HCV-specific helper T cells induced is at least 10%, at least 15%, at least 20%, at least 25%, at least 30%, at least 40%, at least 50%, at least 75%, at least 100% (or 2-fold), at least 2.5-fold, at least 5-fold, at least 7.5-fold, at least 10-fold, at least 20-fold, at least 50-fold, or at least 100-fold, or more than 100-fold, higher than the number of HCV-specific helper T cells induced by administration of an E1/E2 heterodimer comprising a wild-type E1 polypeptide and a wild-type E2 polypeptide, or an E2 polypeptide lacking the polytope, or compared to the number of HCV-specific helper T cells in the individual before administration of the E1/E2 heterodimer of the present disclosure.

In some cases, an E1/E2 heterodimer of the present disclosure (e.g., an E1/E2 heterodimer comprising: a) an HCV E1 polypeptide; and b) a variant HCV E2 polypeptide comprising: i) an HCV E2 polypeptide; and ii) a heterologous polypeptide comprising one or more T-cell epitopes present in an HCV polypeptide other than an HCV E1 polypeptide or an HCV E2 polypeptide), when administered to an individual in need thereof, induces antibody specific for HCV (e.g., anti-E1/E2 antibody), where the level of HCV-specific antibody induced is at least at high as the level of HCV-specific antibody induced by administration of an E1/E2 heterodimer comprising a wild-type E1 polypeptide and a wild-type E2 polypeptide, or an E2 polypeptide lacking the polytope.

In some cases, an E1/E2 heterodimer of the present disclosure (e.g., an E1/E2 heterodimer comprising: a) an HCV E1 polypeptide; and b) a variant HCV E2 polypeptide comprising: i) an HCV E2 polypeptide; and ii) a heterologous polypeptide comprising one or more T-cell epitopes present in an HCV polypeptide other than an HCV E1 polypeptide or an HCV E2 polypeptide), when administered to an individual in need thereof, induces antibody specific for HCV (e.g., anti-E1/E2 antibody), where the level of HCV-specific antibody induced is at least 10%, at least 15%, at least 20%, at least 25%, at least 30%, at least 40%, at least 50%, at least 75%, at least 100% (or 2-fold), at least 2.5-fold, at least 5-fold, at least 7.5-fold, at least 10-fold, at least 20-fold, at least 50-fold, or at least 100-fold, or more than 100-fold, higher than the level of HCV-specific antibody induced by administration of an E1/E2 heterodimer comprising a wild-type E1 polypeptide and a wild-type E2 polypeptide, or an E2 polypeptide lacking the polytope.

An E1/E2 heterodimer of the present disclosure (e.g., an E1/E2 heterodimer comprising: a) an HCV E1 polypeptide; and b) a variant HCV E2 polypeptide comprising: i) an HCV E2 polypeptide; and ii) a heterologous polypeptide comprising one or more T-cell epitopes present in an HCV polypeptide other than an HCV E1 polypeptide or an HCV E2 polypeptide), when administered to an individual in need thereof, induces an immune response (e.g., a cellular immune response) in the individual to one or more HCV genotypes. In some cases, an E1/E2 heterodimer of the present disclosure (e.g., an E1/E2 heterodimer comprising: a) an HCV E1 polypeptide; and b) a variant HCV E2 polypeptide comprising: i) an HCV E2 polypeptide; and ii) a heterologous polypeptide comprising one or more T-cell epitopes present in an HCV polypeptide other than an HCV E1 polypeptide or an HCV E2 polypeptide), when administered to an individual in need thereof, induces an immune response in the individual to HCV genotype 1. In some cases, an E1/E2 heterodimer of the present disclosure (e.g., an E1/E2 heterodimer comprising: a) an HCV E1 polypeptide; and b) a variant HCV E2 polypeptide comprising: i) an HCV E2 polypeptide; and ii) a heterologous polypeptide comprising one or more T-cell epitopes present in an HCV polypeptide other than an HCV E1 polypeptide or an HCV E2 polypeptide), when administered to an individual in need thereof, induces an immune response in the individual to HCV genotype 2. In some cases, an E1/E2 heterodimer of the present disclosure (e.g., an E1/E2 heterodimer comprising: a) an HCV E1 polypeptide; and b) a variant HCV E2 polypeptide comprising: i) an HCV E2 polypeptide; and ii) a heterologous polypeptide comprising one or more T-cell epitopes present in an HCV polypeptide other than an HCV E1 polypeptide or an HCV E2 polypeptide), when administered to an individual in need thereof, induces an immune response in the individual to HCV genotype 3. In some cases, an E1/E2 heterodimer of the present disclosure (e.g., an E1/E2 heterodimer comprising: a) an HCV E1 polypeptide; and b) a variant HCV E2 polypeptide comprising: i) an HCV E2 polypeptide; and ii) a heterologous polypeptide comprising one or more T-cell epitopes present in an HCV polypeptide other than an HCV E1 polypeptide or an HCV E2 polypeptide), when administered to an individual in need thereof, induces an immune response in the individual to HCV genotype 1 and HCV genotype 3. In some cases, an E1/E2 heterodimer of the present disclosure (e.g., an E1/E2 heterodimer comprising: a) an HCV E1 polypeptide; and b) a variant HCV E2 polypeptide comprising: i) an HCV E2 polypeptide; and ii) a heterologous polypeptide comprising one or more T-cell epitopes present in an HCV polypeptide other than an HCV E1 polypeptide or an HCV E2 polypeptide), when administered to an individual in need thereof, induces an immune response in the individual to HCV genotype 1, HCV genotype 2, and HCV genotype 3. In some cases, an E1/E2 heterodimer of the present disclosure (e.g., an E1/E2 heterodimer comprising: a) an HCV E1 polypeptide; and b) a variant HCV E2 polypeptide comprising: i) an HCV E2 polypeptide; and ii) a heterologous polypeptide comprising one or more T-cell epitopes present in an HCV polypeptide other than an HCV E1 polypeptide or an HCV E2 polypeptide), when administered to an individual in need thereof, induces an immune response in the individual to HCV genotype 1, HCV genotype 2, HCV genotype 3, and HCV genotype 7. In some cases, an E1/E2 heterodimer of the present disclosure (e.g., an E1/E2 heterodimer comprising: a) an HCV E1 polypeptide; and b) a variant HCV E2 polypeptide comprising: i) an HCV E2 polypeptide; and ii) a heterologous polypeptide comprising one or more T-cell epitopes present in an HCV polypeptide other than an HCV E1 polypeptide or an HCV E2 polypeptide), when administered to an individual in need thereof, induces an immune response in the individual to 1, 2, 3, 4, 5, 6, or all, of HCV genotype 1, HCV genotype 2, HCV genotype 3, HCV genotype 4, HCV genotype 5, HCV genotype 6, and HCV genotype 7. In some cases, an E1/E2 heterodimer of the present disclosure (e.g., an E1/E2 heterodimer comprising: a) an HCV E1 polypeptide; and b) a variant HCV E2 polypeptide comprising: i) an HCV E2 polypeptide; and ii)

a heterologous polypeptide comprising one or more T-cell epitopes present in an HCV polypeptide other than an HCV E1 polypeptide or an HCV E2 polypeptide), when administered to an individual in need thereof, induces an immune response in the individual to HCV genotype 1, HCV genotype 2, HCV genotype 3, HCV genotype 4, HCV genotype 5, HCV genotype 6, and HCV genotype 7.

Variant E2

As noted above, a variant E2 polypeptide of an HCV E1/E2 heterodimer of the present disclosure comprises: i) an HCV E2 polypeptide; and ii) a heterologous polypeptide comprising one or more T cell epitopes (e.g., one or more T-cell epitopes not present in an HCV E1 or an HCV E2 polypeptide; e.g., one or more T-cell epitopes present in an HCV polypeptide other than an HCV E1 or an HCV E2 polypeptide). In some cases, the variant HCV E2 polypeptide comprises, in order from amino terminus (N-terminus) to carboxyl terminus (C-terminus): i) an HCV E2 polypeptide; and ii) a heterologous polypeptide comprising one or more T cell epitopes. In some cases, the variant HCV E2 polypeptide comprises, in order from N-terminus to C-terminus: i) a heterologous polypeptide comprising one or more T cell epitopes; and ii) an HCV E2 polypeptide.

In some cases, a variant E2 polypeptide of an HCV E1/E2 heterodimer of the present disclosure comprises from 1 to 10 amino acids at the N-terminus of the variant E2 polypeptide, which 1 to 10 amino acids are part of a cleavable linker that remains following cleavage of a polyprotein precursor, as described below. For example, where the cleavable linker comprises the amino acid sequence LEVLFQGP (SEQ ID NO:5), the variant E2 polypeptide can comprise Gly-Pro residues at the N-terminus of the polypeptide, e.g., as depicted in FIG. 5A.

E2

An E2 polypeptide suitable for inclusion in a variant E2 polypeptide of an E1/E2 heterodimer of the present disclosure can have a length of from about 200 amino acids (aa) to about 250 aa, from about 250 aa to about 275 aa, from about 275 aa to about 300 aa, from about 300 aa to about 325 aa, from about 325 aa to about 350 aa, or from about 350 aa to about 365 aa. In some cases, an HCV E2 polypeptide suitable for inclusion in a variant E2 polypeptide of an E1/E2 heterodimer of the present disclosure is an HCV E2 ectodomain polypeptide. In some cases, an HCV E2 polypeptide suitable for inclusion in a variant E2 polypeptide of an E1/E2 heterodimer of the present disclosure is a full-length HCV E2 polypeptide.

Figure 2A:
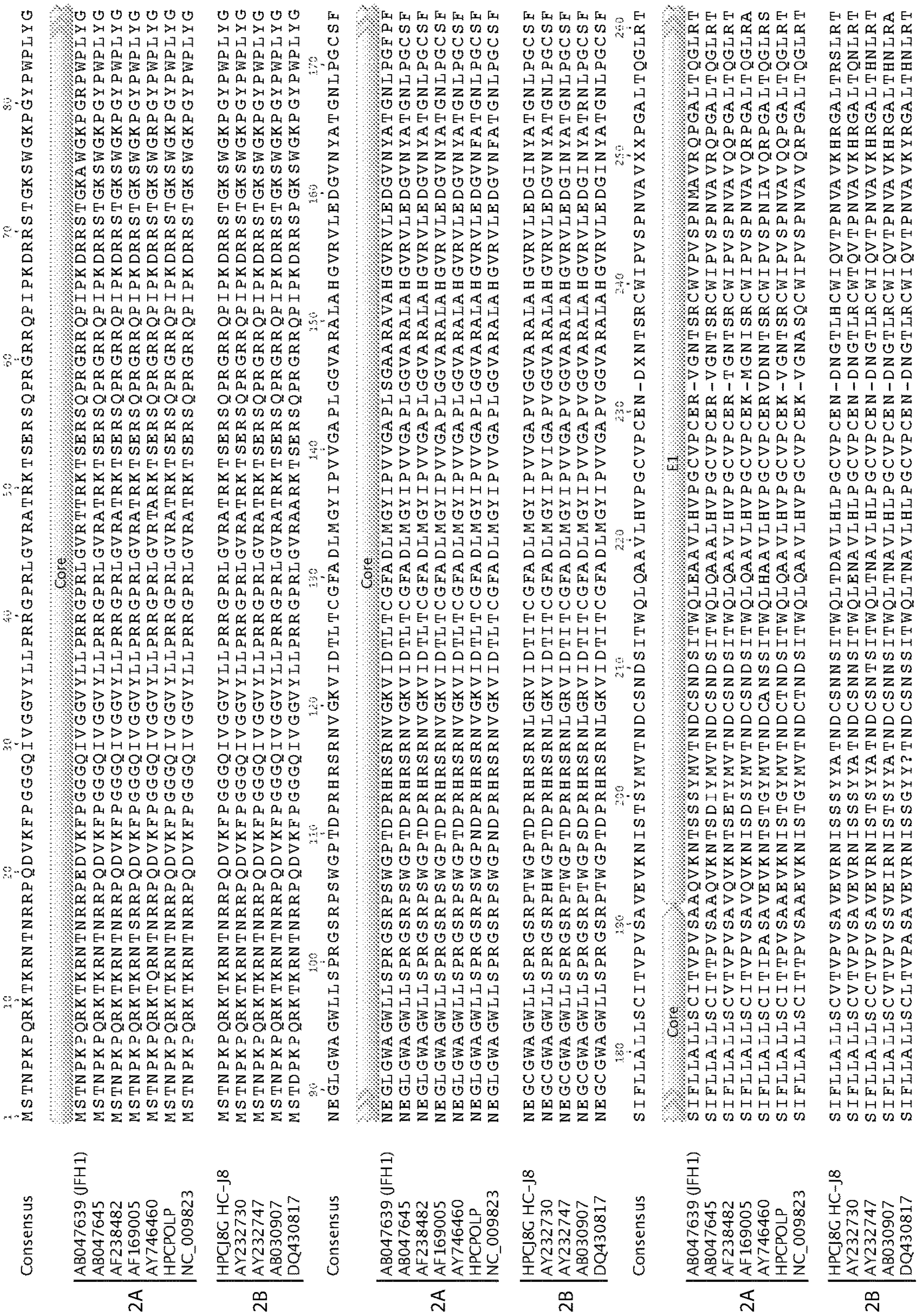
FIGS. 2A-2C provide an alignment of amino acid sequences of the core-E1-E2 coding region of representative HCV 2A and HCV2B subtypes. Genbank database sequences for the coding region core-E1-E2 were aligned using Geneious software v5.6.4. The amino acid numbering depicted is in accordance to the common HCV strains: ABO47639 (JFH1) and HPCJ8G-J8 (J8) for HCV2A and HCV2B, respectively. AB047639 (JFH1): SEQ ID NO:103; AB047645: SEQ ID NO:104; AF169003: SEQ ID NO:105; AF169005: SEQ ID NO:106; AF238482: SEQ ID NO:107; AY746460: SEQ ID NO:108; HPCPOLP: SEQ ID NO:109; NC_009823: SEQ ID NO: 110; HPCJ8G HC-J8: SEQ ID NO:111; AB030907: SEQ ID NO: 112; AY232730: SEQ ID NO: 113; AY232747: SEQ ID NO: 114; and DQ430817: SEQ ID NO: 115.
Figure 2B:
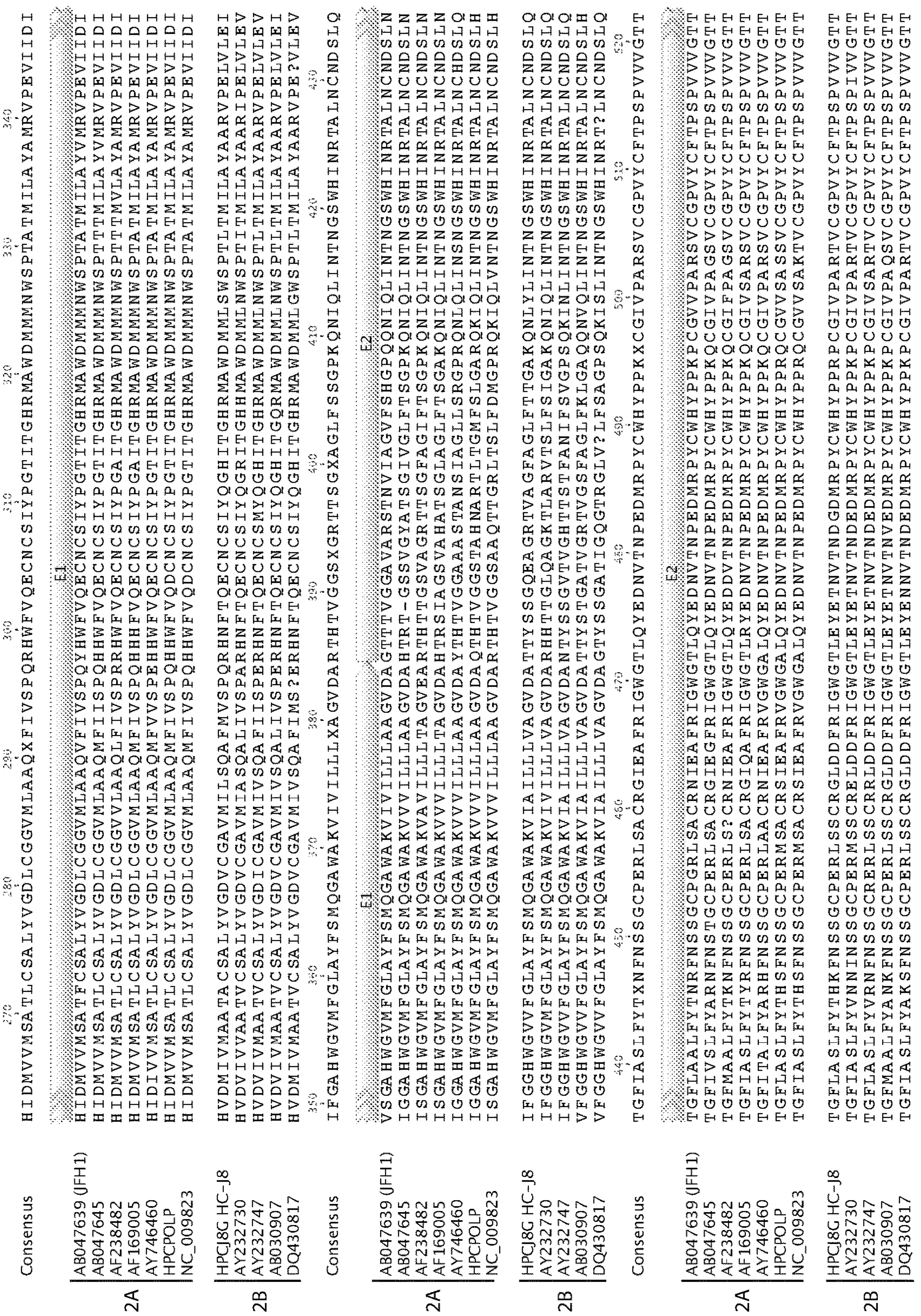
Figure 3B:
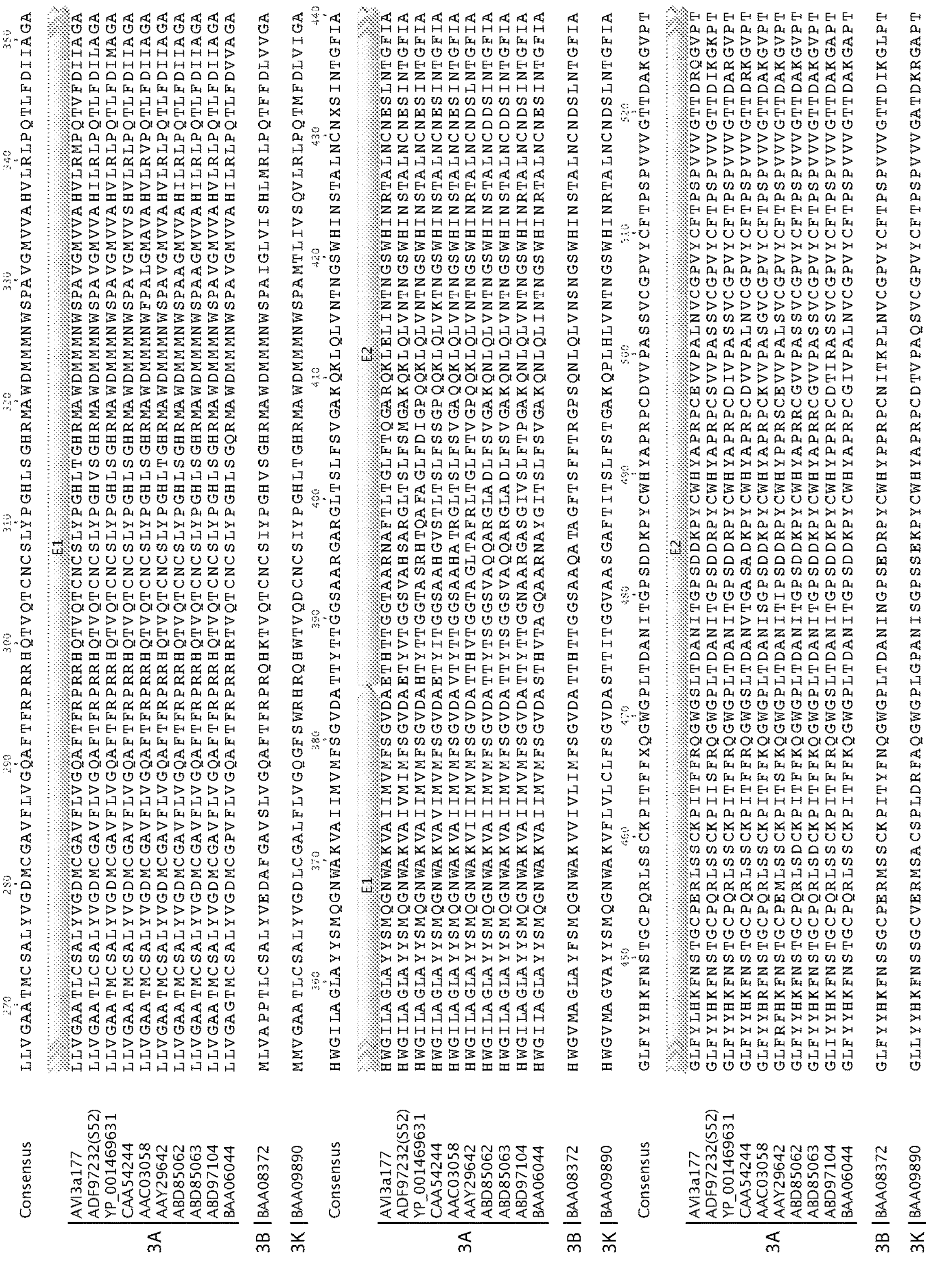
Figure 4A:
FIGS. 4A-4B provide an amino acid sequence of the core-E1-E2 coding region for HCV genotype 7a. Amino acid sequence for the coding region core-E1-E2 of genotype 7a (isolate QC69; Genbank: ABN05226.1; SEQ ID NO:129) is shown according to the numbering scheme of the reference strain, NP_671941 (H77).
Figure 4B:
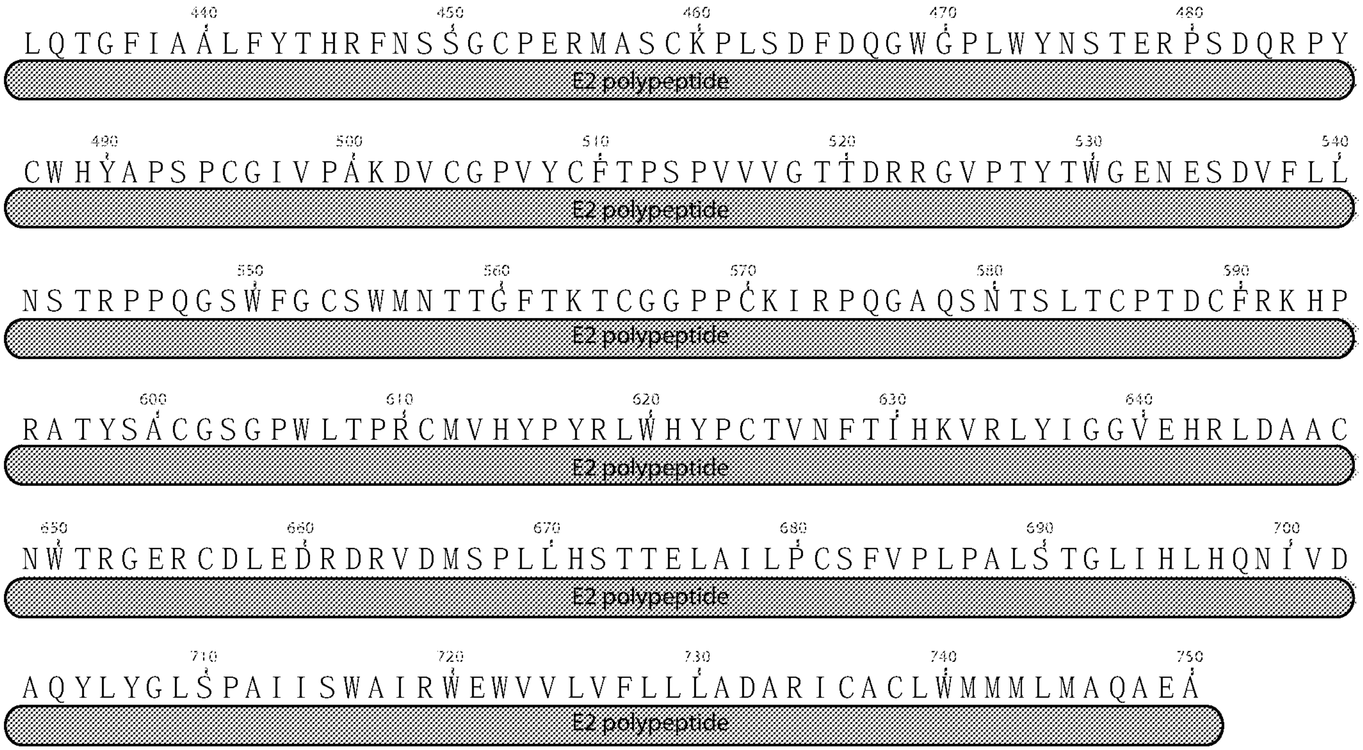

In FIGS. 1A-AC, the amino acid sequence of E2 is amino acid 384 to amino acid 746. In FIGS. 2A-2B, the amino acid sequence of E2 is amino acid 384 to amino acid 751. In FIGS. 3A-3C, the amino acid sequence of E2 is amino acid 385 to amino acid 754. In FIGS. 4A-4B, the amino acid sequence of E2 is amino acid 384 to amino acid 750. As used herein, an "E2 polypeptide" includes a precursor E2 protein, including the signal sequence; includes a mature E2 polypeptide which lacks this sequence; and includes an E2 polypeptide with a heterologous signal sequence. An E2 polypeptide can include a C-terminal membrane anchor sequence which occurs at approximately amino acid positions 715-730 and may extend as far as approximately amino acid residue 746 (see, Lin et al., J. Virol. (1994) 68:5063-5073).

Figure 1B:
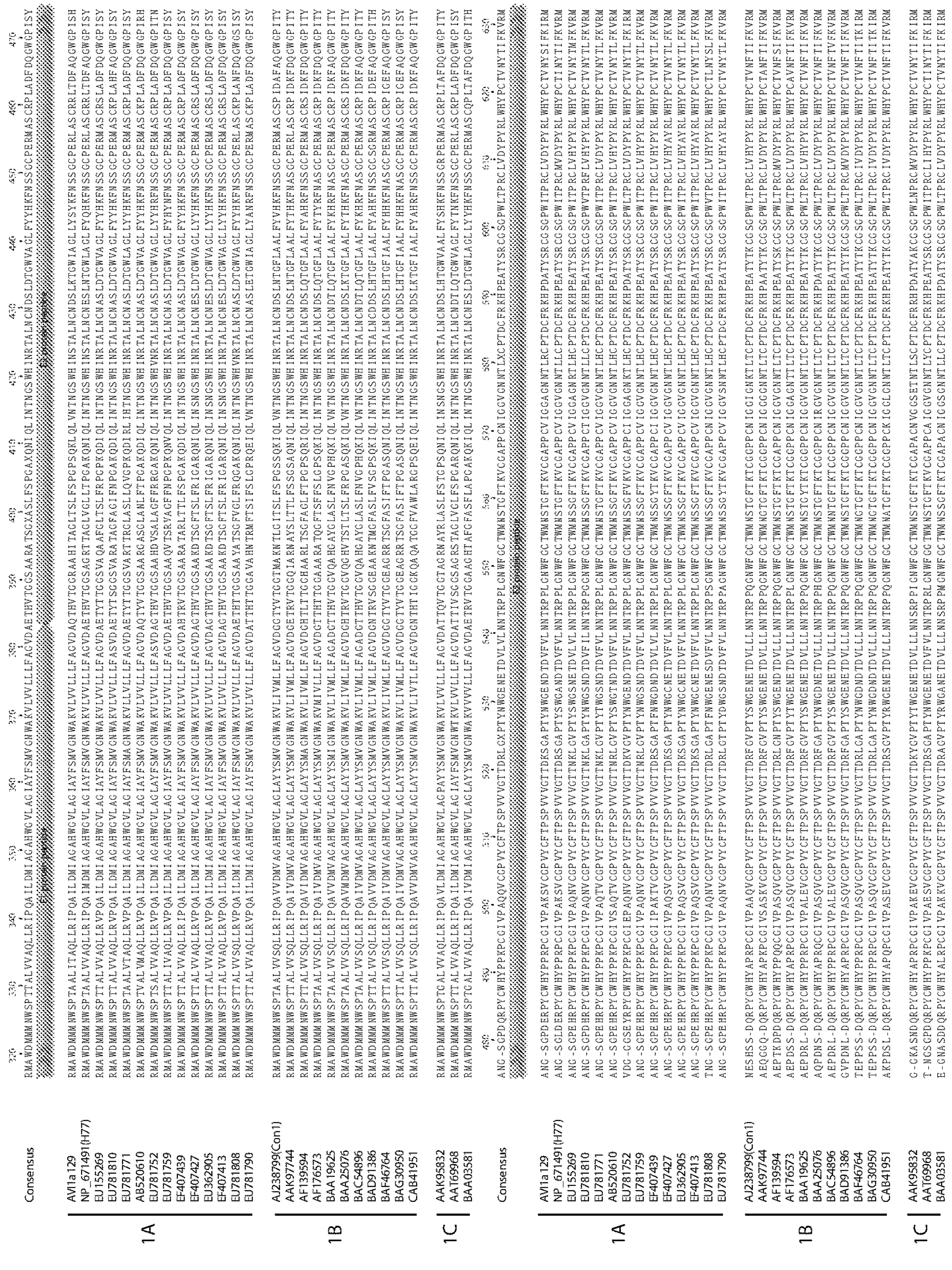

In some cases, a E2 polypeptide suitable for inclusion in a variant E2 polypeptide of an E1/E2 heterodimer of the present disclosure lacks a portion of its C-terminal region, e.g., from about amino acid 715 to the C-terminus; from about amino acid 625 to the C-terminus; from about amino acid 661 to the C-terminus; from about amino acid 655 to the C-terminus; from about amino acid 500 to the C-terminus, where the amino acid numbering is with reference to the numbering in FIGS. 1A-1C. See, e.g., U.S. Pat. No. 6,521,423.

An E2 polypeptide suitable for inclusion in a variant E2 polypeptide of an E1/E2 heterodimer of the present disclosure can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to an amino acid sequence of an E2 polypeptide depicted in FIGS. 1A-1C, FIGS. 2A-2C, FIGS. 3A-3C, or FIGS. 4A-4B. An E2 polypeptide suitable for inclusion in a variant E2 polypeptide of an E1/E2 heterodimer of the present disclosure can comprise an amino acid sequence having at least about 20%, at least about 25%, at least about 30%, at least about 35%, at least about 40%, at least about 45%, at least about 50%, at least about 60%, at least about 70%, or at least about 75%, amino acid sequence identity to an amino acid sequence of an E2 polypeptide depicted in FIGS. 1A-1C, FIGS. 2A-2C, FIGS. 3A-3C, or FIGS. 4A-4B.

An E2 polypeptide suitable for inclusion in a variant E2 polypeptide of an E1/E2 heterodimer of the present disclosure can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to an amino acid sequence of an E2 polypeptide depicted in FIGS. 1A-1C. For example, an E2 polypeptide of genotype 1 can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 384-746 of an amino acid sequence depicted in FIGS. 1A-1C. For example, an E2 polypeptide of genotype 1A can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 384-746 of an amino acid sequence identified as 1A and depicted in FIGS. 1A-1C. For example, an E2 polypeptide of genotype 1B can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 384-746 of an amino acid sequence identified as 1B and depicted in FIGS. 1A-1C. For example, an E2 polypeptide of genotype 1C can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 384-746 of an amino acid sequence identified as 1C and depicted in FIGS. 1A-1C.

Figure 2C:
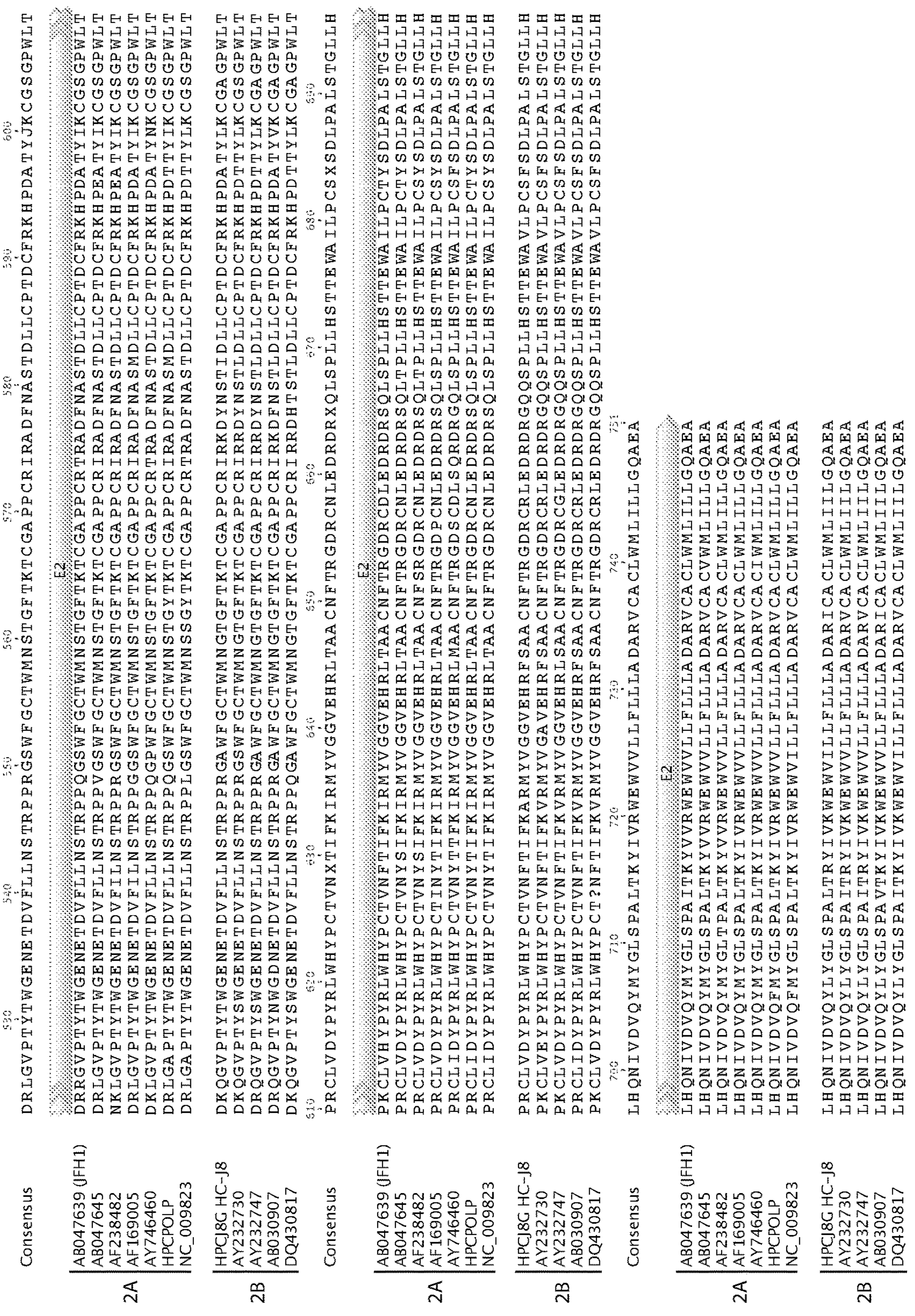

An E2 polypeptide suitable for inclusion in a variant E2 polypeptide of an E1/E2 heterodimer of the present disclosure can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to an amino acid sequence of an E2 polypeptide depicted in FIGS. 2A-2C. For example, an E2 polypeptide can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 384-751 of an amino acid sequence depicted in FIGS. 2A-2C. For example, an E2 polypeptide of genotype 2A can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 384-751 of the "consensus" amino acid sequence depicted in FIGS. 2A-2C. For example, an E2 polypeptide of genotype 2B can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 384-751 of the "consensus" amino acid sequence depicted in FIGS. 2A-2C.

An E2 polypeptide suitable for inclusion in a variant E2 polypeptide of an E1/E2 heterodimer of the present disclosure can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to an amino acid sequence of an E2 polypeptide depicted in FIGS. 3A-3C. For example, an E2 polypeptide of genotype 3 can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 385-754 of an amino acid sequence depicted in FIGS. 3A-3C. For example, an E2 polypeptide of genotype 3A can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 385-754 of an amino acid sequence identified as 3A and depicted in FIGS. 3A-3C. For example, an E2 polypeptide of genotype 3B can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 385-754 of the amino acid sequence identified as 3B and depicted in FIGS. 3A-3C. For example, an E2 polypeptide of genotype 3K can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 385-754 of the amino acid sequence identified as 3K and depicted in FIGS. 3A-3C.

An E2 polypeptide suitable for inclusion in a variant E2 polypeptide of an E1/E2 heterodimer of the present disclosure can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the amino acid sequence of the E2 polypeptide depicted in FIGS. 4A-4B. For example, an E2 polypeptide of genotype 7A can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 384-750 of the amino acid sequence depicted in FIGS. 4A-4B.

Heterologous Polypeptide

In some cases, the heterologous polypeptide comprises 1, 2, 3, 4, 5, 6, 7, 8, 9, or 10, or more than 10 (e.g., from 10 to 15, from 15 to 20, from 20 to 25, or from 25 to 30, or more than 30), T cell epitopes. T-cell epitopes are epitopes that, when presented with a major histocompatibility complex (MHC) (e.g., a human leukocyte antigen (HLA)) Class I or MHC Class II molecule, are recognized and bound by a T-cell receptor (TCR) present on a T cell surface. T-cell epitopes include epitopes recognized by cytotoxic T cells (e.g., $CD8^+$ T cells), and epitopes recognized by helper T cells (e.g., $CD4^+$ T cells).

The one or more T-cell epitopes can include one or more T-cell epitopes present in: a) an HCV NS3 polypeptide; b) an HCV NS2 polypeptide; c) an HCV NS4A polypeptide; d) an HCV NS4B polypeptide; e) an HCV NS5A polypeptide; f) an HCV NS5B polypeptide; g) an HCV core polypeptide; or h) an HCV p7 polypeptide. In some cases, the one or more T-cell epitopes are T-cell epitopes present in an HCV NS3 polypeptide. In some cases, the heterologous polypeptide further comprises one or more T cell epitopes present in: a) cholera toxin or toxoid; and/or b) tetanus toxin or toxoid; and/or c) diphtheria toxin or toxoid; and/or d) a meningococcal outer membrane protein. A suitable source of T-cell epitopes non-toxic mutants of toxins, where the mutants are referred to as "cross-reactive material (CRM)." Other examples of strong T helper epitopes are diphtheria toxoid, tetanus toxoid, meningococcal outer membrane protein, or mutant diphtheria protein CRM197 (see, e.g.: http://www (dot)medscape(dot)com/viewarticle/431127).

In some cases, the heterologous polypeptide comprises a single T-cell epitope. In some cases, the heterologous polypeptide comprises a single HCV-NS3 T-cell epitope. In some cases, the heterologous polypeptide comprises 2 or more T-cell epitopes. In some cases, the heterologous polypeptide comprises 2 or more HCV-NS3 T-cell epitopes. In some cases, the heterologous polypeptide comprises 3 or more HCV-NS3 T-cell epitopes. In some cases, the heterologous polypeptide comprises 4 or more HCV-NS3 T-cell epitopes. In some cases, the heterologous polypeptide comprises a single HCV-NS3 $CD4^+$ T-cell epitope. In some cases, the heterologous polypeptide comprises 2 or more HCV-NS3 $CD4^+$ T-cell epitopes. In some cases, the heterologous polypeptide comprises one or more HCV $CD8^+$ T cell epitopes. In some cases, the heterologous polypeptide comprises a single HCV-NS3 $CD8^+$ T-cell epitope. In some cases, the heterologous polypeptide comprises 2 or more HCV-NS3 $CD8^+$ T-cell epitopes. In some cases, the heterologous polypeptide comprises at least one HCV $CD4^+$ T cell epitope and at least one HCV $CD8^+$ T cell epitope. In some cases, the heterologous polypeptide comprises at least one HCV-NS3 $CD4^+$ T cell epitope and at least one HCV-NS3 $CD8^+$ T cell epitope. In some cases, heterologous polypeptide comprises 2 or more HCV-NS3 $CD4^+$ T-cell epitopes and 2 or more HCV-NS3 $CD8^+$ T-cell epitopes. In some cases, the heterologous polypeptide comprises 2, 3, 4, or 5 HCV-NS3 $CD4^+$ T-cell epitopes and 2, 3, 4, or 5 HCV-NS3 $CD8^+$ T-cell epitopes.

In some cases, the heterologous polypeptide comprises a single T-cell epitope. In some cases, the heterologous polypeptide comprises a single HCV-NS2 T-cell epitope. In some cases, the heterologous polypeptide comprises 2 or more T-cell epitopes. In some cases, the heterologous polypeptide comprises 2 or more HCV-NS2 T-cell epitopes. In some cases, the heterologous polypeptide comprises 3 or more HCV-NS2 T-cell epitopes. In some cases, the heterologous polypeptide comprises 4 or more HCV-NS2 T-cell epitopes. In some cases, the heterologous polypeptide comprises a single HCV-NS2 $CD4^+$ T-cell epitope. In some cases, the heterologous polypeptide comprises 2 or more HCV-NS2 $CD4^+$ T-cell epitopes. In some cases, the heterologous polypeptide comprises one or more HCV $CD8^+$ T cell epitopes. In some cases, the heterologous polypeptide comprises a single HCV-NS2 $CD8^+$ T-cell epitope. In some cases, the heterologous polypeptide comprises 2 or more HCV-NS2 $CD8^+$ T-cell epitopes. In some cases, the heterologous polypeptide comprises at least one HCV $CD4^+$ T cell epitope and at least one HCV $CD8^+$ T cell epitope. In some cases, the heterologous polypeptide comprises at least one HCV-NS2 $CD4^+$ T cell epitope and at least one HCV-NS2 $CD8^+$ T cell epitope. In some cases, heterologous polypeptide comprises 2 or more HCV-NS2 $CD4^+$ T-cell epitopes and 2 or more HCV-NS2 $CD8^+$ T-cell epitopes. In some cases, the heterologous polypeptide comprises 2, 3, 4, or 5 HCV-NS2 $CD4^+$ T-cell epitopes and 2, 3, 4, or 5 HCV-NS2 $CD8^+$ T-cell epitopes.

In some cases, the heterologous polypeptide comprises a single T-cell epitope. In some cases, the heterologous polypeptide comprises a single HCV-NS4A T-cell epitope. In some cases, the heterologous polypeptide comprises 2 or more T-cell epitopes. In some cases, the heterologous polypeptide comprises 2 or more HCV-NS4A T-cell epitopes. In some cases, the heterologous polypeptide comprises 3 or more HCV-NS4A T-cell epitopes. In some cases, the heterologous polypeptide comprises 4 or more HCV-NS4A T-cell epitopes. In some cases, the heterologous polypeptide comprises a single HCV-NS4A $CD4^+$ T-cell epitope. In some cases, the heterologous polypeptide comprises 2 or more HCV-NS4A $CD4^+$ T-cell epitopes. In some cases, the heterologous polypeptide comprises one or more HCV $CD8^+$ T cell epitopes. In some cases, the heterologous polypeptide comprises a single HCV-NS4A $CD8^+$ T-cell epitope. In some cases, the heterologous polypeptide comprises 2 or more HCV-NS4A $CD8^+$ T-cell epitopes. In some cases, the heterologous polypeptide comprises at least one HCV $CD4^+$ T cell epitope and at least one HCV $CD8^+$ T cell epitope. In some cases, the heterologous polypeptide comprises at least one HCV-NS4A $CD4^+$ T cell epitope and at least one HCV-NS4A $CD8^+$ T cell epitope. In some cases, heterologous polypeptide comprises 2 or more HCV-NS4A $CD4^+$ T-cell epitopes and 2 or more HCV-NS4A $CD8^+$ T-cell epitopes. In some cases, the heterologous polypeptide comprises 2, 3, 4, or 5 HCV-NS4A $CD4^+$ T-cell epitopes and 2, 3, 4, or 5 HCV-NS4A $CD8^+$ T-cell epitopes.

In some cases, the heterologous polypeptide comprises a single T-cell epitope. In some cases, the heterologous polypeptide comprises a single HCV-NS5A T-cell epitope. In some cases, the heterologous polypeptide comprises 2 or more T-cell epitopes. In some cases, the heterologous polypeptide comprises 2 or more HCV-NS5A T-cell epitopes. In some cases, the heterologous polypeptide comprises 3 or more HCV-NS5A T-cell epitopes. In some cases, the heterologous polypeptide comprises 4 or more HCV-NS5A T-cell epitopes. In some cases, the heterologous polypeptide comprises a single HCV-NS5A $CD4^+$ T-cell epitope. In some cases, the heterologous polypeptide comprises 2 or more HCV-NS5A $CD4^+$ T-cell epitopes. In some cases, the heterologous polypeptide comprises one or more HCV $CD8^+$ T cell epitopes. In some cases, the heterologous polypeptide comprises a single HCV-NS5A $CD8^+$ T-cell epitope. In some cases, the heterologous polypeptide comprises 2 or more HCV-NS5A $CD8^+$ T-cell epitopes. In some cases, the heterologous polypeptide comprises at least one HCV $CD4^+$ T cell epitope and at least one HCV $CD8^+$ T cell epitope. In some cases, the heterologous polypeptide comprises at least one HCV-NS5A $CD4^+$ T cell epitope and at least one HCV-NS5A $CD8^+$ T cell epitope. In some cases, heterologous polypeptide comprises 2 or more HCV-NS5A $CD4^+$ T-cell epitopes and 2 or more HCV-NS5A $CD8^+$ T-cell epitopes. In some cases, the heterologous polypeptide comprises 2, 3, 4, or 5 HCV-NS5A $CD4^+$ T-cell epitopes and 2, 3, 4, or 5 HCV-NS5A $CD8^+$ T-cell epitopes.

In some cases, the heterologous polypeptide comprises a single T-cell epitope. In some cases, the heterologous polypeptide comprises a single HCV-NS5B T-cell epitope. In some cases, the heterologous polypeptide comprises 2 or more T-cell epitopes. In some cases, the heterologous polypeptide comprises 2 or more HCV-NS5B T-cell epitopes. In some cases, the heterologous polypeptide comprises 3 or more HCV-NS5B T-cell epitopes. In some cases, the heterologous polypeptide comprises 4 or more HCV-NS5B T-cell epitopes. In some cases, the heterologous polypeptide comprises a single HCV-NS5B $CD4^+$ T-cell epitope. In some cases, the heterologous polypeptide comprises 2 or more HCV-NS5B $CD4^+$ T-cell epitopes. In some cases, the heterologous polypeptide comprises one or more HCV $CD8^+$ T cell epitopes. In some cases, the heterologous polypeptide comprises a single HCV-NS5B $CD8^+$ T-cell epitope. In some cases, the heterologous polypeptide comprises 2 or more HCV-NS5B $CD8^+$ T-cell epitopes. In some cases, the heterologous polypeptide comprises at least one HCV $CD4^+$ T cell epitope and at least one HCV $CD8^+$ T cell epitope. In some cases, the heterologous polypeptide comprises at least one HCV-NS5B $CD4^+$ T cell epitope and at least one HCV-NS5B $CD8^+$ T cell epitope. In some cases, heterologous polypeptide comprises 2 or more HCV-NS5B $CD4^+$ T-cell epitopes and 2 or more HCV-NS5B $CD8^+$ T-cell epitopes. In some cases, the heterologous polypeptide comprises 2, 3, 4, or 5 HCV-NS5B $CD4^+$ T-cell epitopes and 2, 3, 4, or 5 HCV-NS5B $CD8^+$ T-cell epitopes.

In some cases, the heterologous polypeptide comprises a single T-cell epitope. In some cases, the heterologous polypeptide comprises a single HCV-core T-cell epitope. In some cases, the heterologous polypeptide comprises 2 or more T-cell epitopes. In some cases, the heterologous polypeptide comprises 2 or more HCV-core T-cell epitopes. In some cases, the heterologous polypeptide comprises 3 or more HCV-core T-cell epitopes. In some cases, the heterologous polypeptide comprises 4 or more HCV-core T-cell epitopes. In some cases, the heterologous polypeptide comprises a single HCV-core $CD4^+$ T-cell epitope. In some cases, the heterologous polypeptide comprises 2 or more HCV-core $CD4^+$ T-cell epitopes. In some cases, the heterologous polypeptide comprises one or more HCV $CD8^+$ T cell epitopes. In some cases, the heterologous polypeptide comprises a single HCV-core $CD8^+$ T-cell epitope. In some cases, the heterologous polypeptide comprises 2 or more HCV-core $CD8^+$ T-cell epitopes. In some cases, the heterologous polypeptide comprises at least one HCV $CD4^+$ T cell epitope and at least one HCV $CD8^+$ T cell epitope. In some cases, the heterologous polypeptide comprises at least one HCV-core $CD4^+$ T cell epitope and at least one HCV-core $CD8^+$ T cell epitope. In some cases, heterologous polypeptide comprises 2 or more HCV-core $CD4^+$ T-cell epitopes and 2 or more HCV-core $CD8^+$ T-cell epitopes. In some cases, the heterologous polypeptide comprises 2, 3, 4, or 5 HCV-core $CD4^+$ T-cell epitopes and 2, 3, 4, or 5 HCV-core $CD8^+$ T-cell epitopes.

In some cases, the heterologous polypeptide comprises a single T-cell epitope. In some cases, the heterologous polypeptide comprises a single HCV-p7 T-cell epitope. In some cases, the heterologous polypeptide comprises 2 or more T-cell epitopes. In some cases, the heterologous polypeptide comprises 2 or more HCV-p7 T-cell epitopes. In some cases, the heterologous polypeptide comprises 3 or more HCV-p7 T-cell epitopes. In some cases, the heterologous polypeptide comprises 4 or more HCV-p7 T-cell epitopes. In some cases, the heterologous polypeptide comprises a single HCV-p7 $CD4^+$ T-cell epitope. In some cases, the heterologous polypeptide comprises 2 or more HCV-core $CD4^+$ T-cell epitopes. In some cases, the heterologous polypeptide comprises one or more HCV $CD8^+$ T cell epitopes. In some cases, the heterologous polypeptide comprises a single HCV-p7 $CD8^+$ T-cell epitope. In some cases, the heterologous polypeptide comprises 2 or more HCV-p7 $CD8^+$ T-cell epitopes. In some cases, the heterologous polypeptide comprises at least one HCV $CD4^+$ T cell epitope and at least one HCV $CD8^+$ T cell epitope. In some cases, the heterologous polypeptide comprises at least one HCV-p7 $CD4^+$ T cell epitope and at least one HCV-p7 $CD8^+$ T cell epitope. In some cases, heterologous polypeptide comprises 2 or more HCV-p7 $CD4^+$ T-cell epitopes and 2 or more HCV-p7 $CD8^+$ T-cell epitopes. In some cases, the heterologous polypeptide comprises 2, 3, 4, or 5 HCV-p7 $CD4^+$ T-cell epitopes and 2, 3, 4, or 5 HCV-p7 $CD8^+$ T-cell epitopes.

In some cases, the heterologous polypeptide comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, or 63, of the T-cell epitopes set out in FIGS. 13A-13B. In some cases, the heterologous polypeptide comprises from 1 to 3, from 3 to 5, from 5 to 10, from 10 to 15, from 15 to 20, from 20 to 25, or from 25 to 30 of the T-cell epitopes set out in FIGS. 13A-13B. For example, in some cases, the heterologous polypeptide comprises the T-cell epitopes designated NS3-3, NS3-4, and NS3-11 in FIGS. 13A-13B and FIGS. 15A-15N. As another example, in some cases, the heterologous polypeptide comprises the T-cell epitopes designated NS2-1, NS2-2, NS2-3, NS2-7, and NS2-8 in FIGS. 13A-13B and FIGS. 15A-15N. As another example, in some cases, the heterologous polypeptide comprises the T-cell epitopes designated NS3-3, NS3-4, NS3-5, and NS3-11 in FIGS. 13A-13B and FIGS. 15A-15N. As another example, in some cases, the heterologous polypeptide comprises the T-cell epitopes designated NS3-3, NS3-4, NS3-5, NS3-6, NS3-7, NS3-11, NS3-12, and NS3-13 in FIGS. 13A-13B and FIGS. 15A-15N. As another example, in some cases, the heterologous polypeptide comprises the T-cell epitopes designated NS3-3, NS3-4, NS3-5, NS3-6, NS3-7, NS3-10, NS3-11, NS3-12, and NS3-13 in FIGS. 13A-13B and FIGS. 15A-15N. As another example, in some cases, the heterologous polypeptide comprises the T-cell epitopes designated Core-1, Core-2, Core-3, Core-4, Core-5, Core-6, Core-7, Core-8, Core-9, Core-10, Core-11, Core-12, Core-13, Core-14, Core-16, Core-17, Core-18, Core-19, Core-20, Core-21, and Core-22 in FIGS. 13A-13B and FIGS. 15A-15N. As another example, in some cases, the heterologous polypeptide comprises the T-cell epitopes designated NS3-1, NS3-2, NS3-3, NS3-4, NS3-5, NS3-6, NS3-7, NS3-9, NS3-10, NS3-11, NS3-12, and NS3-13 in FIGS. 13A-13B and FIGS. 15A-15N. As another example, in some cases, the heterologous polypeptide comprises the T-cell epitopes designated NS2-1, NS2-2, NS2-3, NS2-4, NS2-5, NS2-6, NS2-7, NS2-8, NS3-1, NS3-2, NS3-3, NS3-4, NS3-5, NS3-6, NS3-7, NS3-9, NS3-10, NS3-11, NS3-12, and NS3-13 in FIGS. 13A-13B and FIGS. 15A-15N. As another example, in some cases, the heterologous polypeptide comprises the T-cell epitopes designated NS3-1, NS3-2, NS3-3, NS3-4, NS3-5, NS3-6, NS3-7, NS3-8, NS3-9, NS3-10, NS3-11, NS3-12, NS3-13, NS3-14, NS4a-1, NS4b-1, NS4b-2, NS4b-3, NS4b-4, NS4b-5, NS4b-6, NS4b-7, NS4b-8, NS4b-9, and NS4b-10 in FIGS. 13A-13B and FIGS. 15A-15N. As another example, in some cases, the heterologous polypeptide comprises the T-cell epitopes designated NS3-1, NS3-2, NS3-3, NS3-4, NS3-5, NS3-6, NS3-7, NS3-8, NS3-9, NS3-10, NS3-11, NS3-12, NS3-13, NS3-14, NS4a-1, NS4b-1, NS4b-2, NS4b-3, NS4b-4, NS4b-5, NS4b-6, NS4b-7, NS4b-8, NS4b-9, NS4b-10, NS5a-1, NS5a-2, NS5b-1, and NS5b-2 in FIGS. 13A-13B and FIGS. 15A-15N. In some cases, the T-cell epitopes are contiguous. In some cases, any two T-cell epitopes are separated by linkers (e.g., a linker having a length of from 1 amino acid to about 50 amino acids, e.g., from 1 amino acid to 5 amino acids (aa), from 5 aa to 10 aa, from 10 aa to 15 aa, from 15 aa to 20 aa, from 20 aa to 25 aa, from 25 aa to 30 aa, from 30 aa to 40 aa, or from 40 aa to 50 aa).

In some cases, the heterologous polypeptide comprises at least one HCV $CD4^+$ T cell epitope and at least one HCV $CD8^+$ T cell epitope, where epitopes are conserved among HCV genotypes 1 and 2. In some cases, the heterologous polypeptide comprises at least one HCV $CD4^+$ T cell epitope and at least one HCV $CD8^+$ T cell epitope, where epitopes are conserved among HCV genotypes 1 and 3. In some cases, the heterologous polypeptide comprises at least one HCV CD4$^+$ T cell epitope and at least one HCV CD8$^+$ T cell epitope, where epitopes are conserved among HCV genotypes 1, 2, and 3. In some cases, the heterologous polypeptide comprises at least one HCV CD4$^+$ T cell epitope and at least one HCV CD8$^+$ T cell epitope, where epitopes are conserved among HCV genotypes 1, 2, 3, and 7. In some cases, the heterologous polypeptide comprises at least one HCV CD4$^+$ T cell epitope and at least one HCV CD8$^+$ T cell epitope, where epitopes are conserved among HCV genotypes 1-7.

The heterologous polypeptide can have a length of from about 10 amino acids to about 2000 amino acids; e.g., the heterologous polypeptide can have a length of from 10 amino acids (aa) to 15 aa, from 15 aa to 20 aa, from 20 aa to 25 aa, from 25 aa to 50 aa, from 50 aa to 75 aa, from 75 an to 100 aa, from 100 an to 150 aa, from 150 aa to 200 aa, from 200 aa to 250 aa, from 250 aa to 300 aa, from 300 an to 350 aa, from 350 aa to 400 aa, from 450 an to 500 aa, from 500 an to 550 aa, from 550 an to 600 aa, from 600 an to 650 aa, from 650 aa to 700 aa, from 700 aa to 750 aa, or from 750 aa to 800 aa. The heterologous polypeptide can have a length of from about 25 amino acids to about 2000 amino acids, e.g., from about 25 amino acids (aa) to 50 aa, from 50 an to 75 aa, from 75 an to 100 aa, from 100 an to 150 aa, from 150 an to 200 aa, from 200 aa to 250 aa, from 250 an to 300 aa, from 300 aa to 350 aa, from 350 an to 400 aa, from 400 an to 500 aa, from 500 aa to 600 aa, from 600 an to 700 aa, from 700 an to 800 aa, from 800 aa to 900 aa, from 900 an to 1000 aa, from 1000 aa to 1100 aa, from 1100 aa to 1200 aa, from 1200 an to 1300 aa, from 1300 aa to 1400 aa, from 1400 aa to 1500 aa, from 1500 aa to 1600 aa, from 1600 aa to 1700 aa, from 1700 aa to 1800 aa, from 1800 aa to 1900 aa, or from 1900 aa to 2000 aa. The heterologous polypeptide can have a length of from about 25 amino acids to about 3000 amino acids, e.g., from about 25 amino acids (aa) to 50 aa, from 50 aa to 75 aa, from 75 aa to 100 aa, from 100 aa to 150 aa, from 150 aa to 200 aa, from 200 aa to 250 aa, from 250 aa to 300 aa, from 300 aa to 350 aa, from 350 an to 400 aa, from 400 an to 500 aa, from 500 an to 600 aa, from 600 an to 700 aa, from 700 an to 800 aa, from 800 an to 900 aa, from 900 aa to 1000 aa, from 1000 aa to 1100 aa, from 1100 an to 1200 aa, from 1200 aa to 1300 aa, from 1300 an to 1400 aa, from 1400 aa to 1500 aa, from 1500 an to 1600 aa, from 1600 aa to 1700 aa, from 1700 an to 1800 aa, from 1800 an to 1900 aa, from 1900 aa to 2000 aa, from 2000 an to 2250 aa, from 2250 an to 2500 aa, from 2500 an to 2750 aa, or from 2750 an to 3000 aa.

The heterologous polypeptide can have a length of from about 25 amino acids to about 800 amino acids, e.g., from about 25 amino acids (aa) to 50 aa, from 50 an to 75 aa, from 75 an to 100 aa, from 100 an to 150 aa, from 150 an to 200 aa, from 200 an to 250 aa, from 250 aa to 300 aa, from 300 an to 350 aa, from 350 aa to 400 aa, from 450 an to 500 aa, from 500 an to 550 aa, from 550 aa to 600 aa, from 600 an to 650 aa, from 650 an to 700 aa, from 700 aa to 750 aa, or from 750 an to 800 aa. The heterologous polypeptide can have a length of from about 25 amino acids to about 400 amino acids, e.g., from about 25 amino acids (aa) to 50 aa, from 50 an to 75 aa, from 75 an to 100 aa, from 100 an to 150 aa, from 150 an to 200 aa, from 200 aa to 250 aa, from 250 aa to 300 aa, from 300 an to 350 aa, or from 350 aa to 400 aa. The heterologous polypeptide can have a length of 25 amino acids (aa), 26 aa, 27 aa, 28 aa, 29 aa, 30 aa, 31 aa, 32 aa, 33 aa, 34 aa, 35 aa, 36 aa, 37 aa, 38 aa, 39 aa, 40 aa, 41 aa, 42 aa, 43 aa, 44 aa, 45 aa, 46 aa, 47 aa, 48 aa, 49 aa, or 50 aa. The heterologous polypeptide can have a length of from about 100 amino acids (aa) to 800 aa, e.g., from 100 aa to 150 aa, from 150 aa to 200 aa, from 200 aa to 250 aa, from 250 an to 300 aa, from 300 aa to 350 aa, from 350 an to 400 aa, from 450 an to 500 aa, from 500 aa to 550 aa, from 550 aa to 600 aa, from 600 aa to 650 aa, from 650 aa to 700 aa, from 700 an to 750 aa, or from 750 aa to 800 aa. The heterologous polypeptide can have a length of from 25 aa to 30 aa. The heterologous polypeptide can have a length of from 30 an to 40 aa. The heterologous polypeptide can have a length of from 40 an to 50 aa. The heterologous polypeptide can have a length of from 50 aa to 60 aa (e.g., 50 aa, 51 aa, 52, aa, 53 aa, 54 aa, 55 aa, 56 aa, 57 aa, 58 aa, 59 aa, or 60 aa). The heterologous polypeptide can have a length of from 60 aa to 70 aa. The heterologous polypeptide can have a length of from 65 an to 75 aa (e.g., 65, 66, 67, 68, 69, 70, 71, 72, 7, 74, or 75 aa). The heterologous polypeptide can have a length of 70 aa. The heterologous polypeptide can have a length of from 70 an to 80 aa. The heterologous polypeptide can have a length of from 80 aa to 90 aa. The heterologous polypeptide can have a length of from 90 an to 100 aa. The heterologous polypeptide can have a length of from 100 an to 105 aa (e.g., 100, 101, 102, 103, 104, 105, 106, 107, 108, 109, or 110 aa). The heterologous polypeptide can have a length of 100 aa. The heterologous polypeptide can have a length of from 10 amino acids (aa) to 50 aa; e.g., from 10 aa to 15 aa, from 15 an to 20 aa, from 20 an to 25 aa, from 25 an to 30 aa, from 30 an to 35 aa, from 35 aa to 40 aa, from 40 an to 45 aa, or from 45 an to 50 aa. The heterologous polypeptide can have a length of from 10 amino acids (aa) to 20 aa, e.g., 10, 11, 12, 13, 14, 15, 16, 17, 18, 19, or 20 aa.

HCV NS3 T-Cell Epitopes

In some cases, the heterologous polypeptide present in an E2 variant polypeptide of an E1/E2 heterodimer of the present disclosure includes one or more T-cell epitopes present in an HCV NS3 polypeptide. Examples of T-cell epitopes present in NS3 polypeptides are depicted in FIGS. 15A-15N, FIG. 13B, and FIGS. 14A-14B.

The heterologous polypeptide can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence:

AIPLEVIKGGRHLIFCHSKKKCDELAAKL (SEQ ID NO:1). In some cases, the heterologous polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence:

AIPLEVIKGGRHLIFCHSKKKCDELAAKL (SEQ ID NO:1); and has a length of from 25 an to 35 aa (e.g., 25 aa, 26 aa, 27 aa, 28 aa, 29 aa, 30 aa, 31 aa, 32 aa, 33 aa, 34 aa, or 35 aa). In some cases, the heterologous polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence:

AIPLEVIKGGRHLIFCHSKKKCDELAAKL (SEQ ID NO:1); and has a length of 29 amino acids. Such a polytope can include NS3 T-cell epitopes designated NS3-3, NS3-4, and NS3-11 in FIG. 13B and FIGS. 15A-15N.

The heterologous polypeptide can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence:

AIPLEVIKGGRHLIFCHSKKKCDELAAKLVALGINAVAYYRGLDVSVIPTSG (SEQ ID NO:2). In some cases, the heterologous polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence: AIPLEVIKGGRHLIFCHSKKKCDELAAKLVALGINAVAYYRGLDVSVIPTSG (SEQ ID NO:2); and has a length of from 45 amino acids to 60 amino acids (e.g., 45 aa, 46 aa, 47 aa, 48 aa, 49 aa, 50 aa, 51 aa, 52 aa, 53 aa, 54 aa, 55 aa, 56 aa, 57 aa, 58 aa, 59 aa, or 60 aa). In some cases, the heterologous polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence:

AIPLEVIKGGRHLIFCHSKKKCDELAAKLVALGINAVAYYRGLDVSVIPTSG (SEQ ID NO:2); and has a length of 52 amino acids. Such a polytope can include NS3 T-cell epitopes designated NS3-3, NS3-4, NS3-5, and NS3-11 in FIG. 13B and FIGS. 15A-15N.

The heterologous polypeptide can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence:

KGGRHLIFCHSKKKCDELAAKLVALGINAVAYYRGLDVSVIPTSGDVVVVATDALMTG FTGDFDSVIDCN (SEQ ID NO:3); and has a length of from 65 amino acids to 80 amino acids (e.g., 65 aa, 66 aa, 67 aa, 68 aa, 69 aa, 70 aa, 71 aa, 72 aa, 73 aa, 74 aa, 75 aa, 76 aa, 77 aa, 78 aa, 79 aa, or 80 aa). In some cases, the heterologous polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence:

KGGRHLIFCHSKKKCDELAAKLVALGINAVAYYRGLDVSVIPTSGDVVVVATDALMTG FTGDFDSVIDCN (SEQ ID NO:3); and has a length of 70 amino acids. Such a polytope can include NS3 T-cell epitopes designated NS3-3, NS3-4, NS3-5, NS3-6, NS3-7, NS3-11, NS3-12, and NS3-13 in FIG. 13B and FIGS. 15A-15N.

The heterologous polypeptide can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence:

VALSTTGEIPFYGKAIPLEVIKGGRHLIFCHSKKKCDELAAKLVALGINAVAYYRGLDVS VIPTSGDVVVVATDALMTGFTGDFDSVIDCNTCVTQTVDF (SEQ ID NO:4); and has a length of from 95 amino acids (aa) to 105 an (e.g., 95 aa, 96 aa, 97 aa, 98 aa, 99 aa, 100 aa, 101 aa, 102 aa, 103 aa, 104 aa, or 105 aa). In some cases, the heterologous polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence:

VALSTTGEIPFYGKAIPLEVIKGGRHLIFCHSKKKCDELAAKLVALGINAVAYYRGLDVS VIPTSGDVVVVATDALMTGFTGDFDSVIDCNTCVTQTVDF (SEQ ID NO:4); and has a length of 100 amino acids. Such a polytope can include NS3 T-cell epitopes designated NS3-3, NS3-4, NS3-5, NS3-6, NS3-7, NS3-10, NS3-11, NS3-12, and NS3-13 in FIG. 13B and FIGS. 15A-15N.

The heterologous polypeptide can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence:

MSTNPKPQRKTKRNTNRRPQDVKFPGGGQIVGGVYLLPRRGPRLGVRATRKTSERSQP RGRRQPIPKARRPEGRTWAQPGYPWPLYGNEGCGWAGWLLSPRGSRPSWGPTDPRRRS RNLGKVIDTLTCGFADLMGYIPLVGAPLGGAARALAHGVRVLEDGVNYATGNLPGCSF SIFLLALLSCLTVPASA (SEQ ID NO:9); and has a length of from 190 amino acids (aa) to 200 aa (e.g., 190 aa, 191 aa, 192 aa, 193 aa, 194 aa, 195 aa, 196 aa, 197 aa, 198 aa, 199 aa, or 200 aa. In some cases, the heterologous polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence:

MSTNPKPQRKTKRNTNRRPQDVKFPGGGQI-VGGVYLLPRRGPRLGVRATRKTSERSQP RGRRQPIPKARRPEGRTWAQPGYPWPLYG-NEGCGWAGWLLSPRGSRPSWGPTDPRRRS RNLGKVIDTLTCGFADLMGYIPLVGAPLG-GAARALAHGVRVLEDGVNYATGNLPGCSF SIFLLALLSCLTVPASA (SEQ ID NO:9); and has a length of 191 amino acids.

The heterologous polypeptide can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence:

LHAPTGSGKSTKVPAAYAAQGYKVLVLNP-SVAATLGFGAYMSKAHGIDPNIRTGVRTIT TGSPITYSTYGKFLADGGCSGGAYDIIICDECH-STDATSILGIGTVLDQAETAGARLVVLA TATPPGSVTVPHPNIEEVALSTTGEIPFYG-KAIPLEVIKGGRHLIFCHSKKKCDELAAKLV ALGINAVAYYRGLDVSVIPTSGDVVV-VATDALMTGFTGDFDSVIDCN (SEQ ID NO:10); and has a length of from 215 amino acids (aa) to 235 an (e.g., 215 aa, 216 aa, 217 11, 218 aa, 219 aa, 220 aa, 221 aa, 222 aa, 223 aa, 224 aa, 225 aa, 226 aa, 227 aa, 228 aa, 229 aa, 230 aa, 231 aa, 232 aa, 233 aa, 234 aa, or 235 aa). In some cases, the heterologous polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence:

```
                                        (SEQ ID NO: 10)
LHAPTGSGKSTKVPAAYAAQGYKVLVLNPSVAATLGFGAYMSKAHGIDPN

IRTGVRTITTGSPITYSTYGKFLADGGCSGGAYDIIICDECHSTDATSIL

GIGTVLDQAETAGARLVVLATATPPGSVTVPHPNIEEVALSTTGEIPFYG

KAIPLEVIKGGRHLIFCHSKKKCDELAAKLVALGINAVAYYRGLDVSVIP

TSGDVVVVATDALMTGFTGDFDSVIDCN;
```

and has a length of 228 amino acids. Such a polytope can include NS3 T-cell epitopes designated NS3-1, NS3-2, NS3-3, NS3-4, NS3-5, NS3-6, NS3-7, NS3-9, NS3-10, NS3-11, NS3-12, and NS3-13 in FIG. 13B and FIGS. 15A-15N.

As another example, the heterologous polypeptide can comprise an HCV NS3 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1265-1279 of the amino acid sequence designated "Consensus" in FIGS. 16A-16L, or a corresponding HCV NS3 amino acid sequence of any HCV genotype; and the HCV NS3 T-cell epitope can have a length of from 15 amino acids (aa) to 20 amino acids (e.g., 15 aa, 16 aa, 17 aa, 18 aa, 19 aa, or 20 aa).

As another example, the heterologous polypeptide can comprise an HCV NS3 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1309-1323 of the amino acid sequence designated "Consensus" in FIGS. 16A-16L, or a corresponding HCV NS3 amino acid sequence of any HCV genotype; and the HCV NS3 T-cell epitope can have a length of from 15 amino acids (aa) to 20 amino acids (e.g., 15 aa, 16 aa, 17 aa, 18 aa, 19 aa, or 20 aa).

As another example, the heterologous polypeptide can comprise an HCV NS3 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1401-1415 of the amino acid sequence designated "Consensus" in FIGS. 16A-16L, or a corresponding HCV NS3 amino acid sequence of any HCV genotype; and the HCV NS3 T-cell epitope can have a length of from 15 amino acids (aa) to 20 amino acids (e.g., 15 aa, 16 aa, 17 aa, 18 aa, 19 aa, or 20 aa).

As another example, the heterologous polypeptide can comprise an HCV NS3 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1402-1412 of the amino acid sequence designated "Consensus" in FIGS. 16A-16L, or a corresponding HCV NS3 amino acid sequence of any HCV genotype; and the HCV NS3 T-cell epitope can have a length of from 11 amino acids (aa) to 16 amino acids (e.g., 11 aa, 12 aa, 13 aa, 14 aa, 15 aa, or 16 aa).

As another example, the heterologous polypeptide can comprise an HCV NS3 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1429-1439 of the amino acid sequence designated "Consensus" in FIGS. 16A-16L, or a corresponding HCV NS3 amino acid sequence of any HCV genotype; and the HCV NS3 T-cell epitope can have a length of from 11 amino acids (aa) to 16 amino acids (e.g., 11 aa, 12 aa, 13 aa, 14 aa, 15 aa, or 16 aa).

As another example, the heterologous polypeptide can comprise an HCV NS3 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1450-1464 of the amino acid sequence designated "Consensus" in FIGS. 16A-16L, or a corresponding HCV NS3 amino acid sequence of any HCV genotype; and the HCV NS3 T-cell epitope can have a length of from 15 amino acids (aa) to 20 amino acids (e.g., 15 aa, 16 aa, 17 aa, 18 aa, 19 aa, or 20 aa).

As another example, the heterologous polypeptide can comprise an HCV NS3 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1453-1467 of the amino acid sequence designated "Consensus" in FIGS. 16A-16L, or a corresponding HCV NS3 amino acid sequence of any HCV genotype; and the HCV NS3 T-cell epitope can have a length of from 15 amino acids (aa) to 20 amino acids (e.g., 15 aa, 16 aa, 17 aa, 18 aa, 19 aa, or 20 aa).

As another example, the heterologous polypeptide can comprise an HCV NS3 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1577-1591 of the amino acid sequence designated "Consensus" in FIGS. 16A-16L, or a corresponding HCV NS3 amino acid sequence of any HCV genotype; and the HCV NS3 T-cell epitope can have a length of from 15 amino acids (aa) to 20 amino acids (e.g., 15 aa, 16 aa, 17 aa, 18 aa, 19 aa, or 20 aa).

As another example, the heterologous polypeptide can comprise an HCV NS3 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1306-1314 of the amino acid sequence designated "Consensus" in FIGS. 16A-16L, or a corresponding HCV NS3 amino acid sequence of any HCV genotype; and the HCV NS3 T-cell epitope can have a length of from 9 amino acids (aa) to 15 amino acids (e.g., 9 aa, 10 aa, 11 aa, 12 aa, 13 aa, 14 aa, or 15 aa).

As another example, the heterologous polypeptide can comprise an HCV NS3 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1387-1394 of the amino acid sequence designated "Consensus" in FIGS. 16A-16L, or a corresponding HCV NS3 amino acid sequence of any HCV genotype; and the HCV NS3 T-cell epitope can have a length of from 1 amino acids (aa) to 15 amino acids (e.g., 8 aa, 9 aa, 10 aa, 11 aa, 12 aa, 13 aa, 14 aa, or 15 aa).

As another example, the heterologous polypeptide can comprise an HCV NS3 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1405-1413 of the amino acid sequence designated "Consensus" in FIGS. 16A-16L, or a corresponding HCV NS3 amino acid sequence of any HCV genotype; and the HCV NS3 T-cell epitope can have a length of from 9 amino acids (aa) to 15 amino acids (e.g., 9 aa, 10 aa, 11 aa, 12 aa, 13 aa, 14 aa, or 15 aa).

As another example, the heterologous polypeptide can comprise an HCV NS3 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1450-1458 of the amino acid sequence designated "Consensus" in FIGS. 16A-16L, or a corresponding HCV NS3 amino acid sequence of any HCV genotype; and the HCV NS3 T-cell epitope can have a length of from 9 amino acids (aa) to 15 amino acids (e.g., 9 aa, 10 aa, 11 aa, 12 aa, 13 aa, 14 aa, or 15 aa).

As another example, the heterologous polypeptide can comprise an HCV NS3 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1457-1465 of the amino acid sequence designated "Consensus" in FIGS. 16A-16L, or a corresponding HCV NS3 amino acid sequence of any HCV genotype; and the HCV NS3 T-cell epitope can have a length of from 9 amino acids (aa) to 15 amino acids (e.g., 9 aa, 10 aa, 11 aa, 12 aa, 13 aa, 14 aa, or 15 aa).

As another example, the heterologous polypeptide can comprise an HCV NS3 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1610-1618 of the amino acid sequence designated "Consensus" in FIGS. 16A-16L, or a corresponding HCV NS3 amino acid sequence of any HCV genotype; and the HCV NS3 T-cell epitope can have a length of from 9 amino acids (aa) to 15 amino acids (e.g., 9 aa, 10 aa, 11 aa, 12 aa, 13 aa, 14 aa, or 15 aa).

HCV NS2 T-Cell Epitopes

Figure 15A:
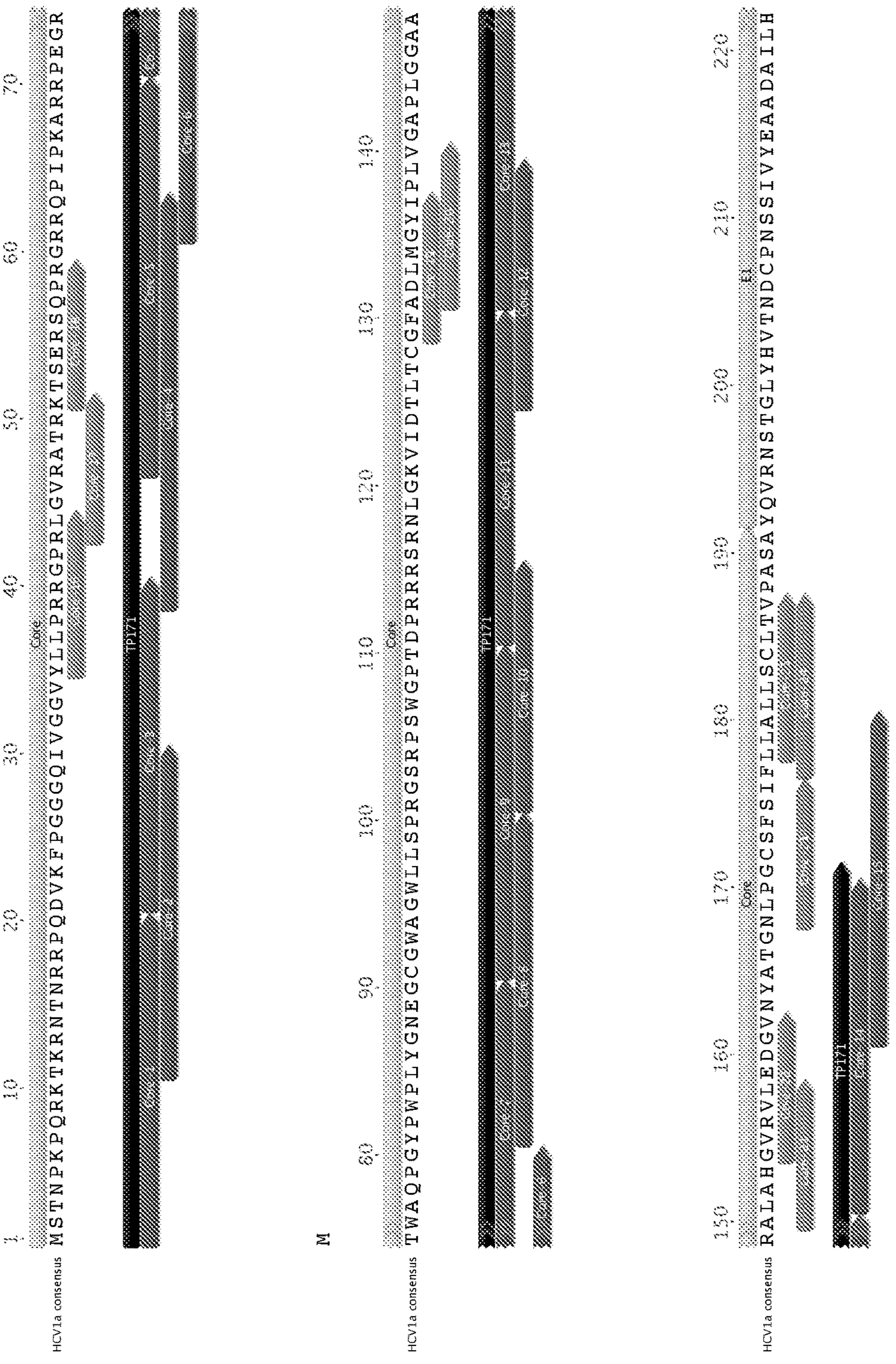
FIGS. 15A-15N provide consensus amino acid sequences of HCV polypeptides; and depict the locations of T-cell epitopes (SEQ ID NO:185).
Figure 15E:
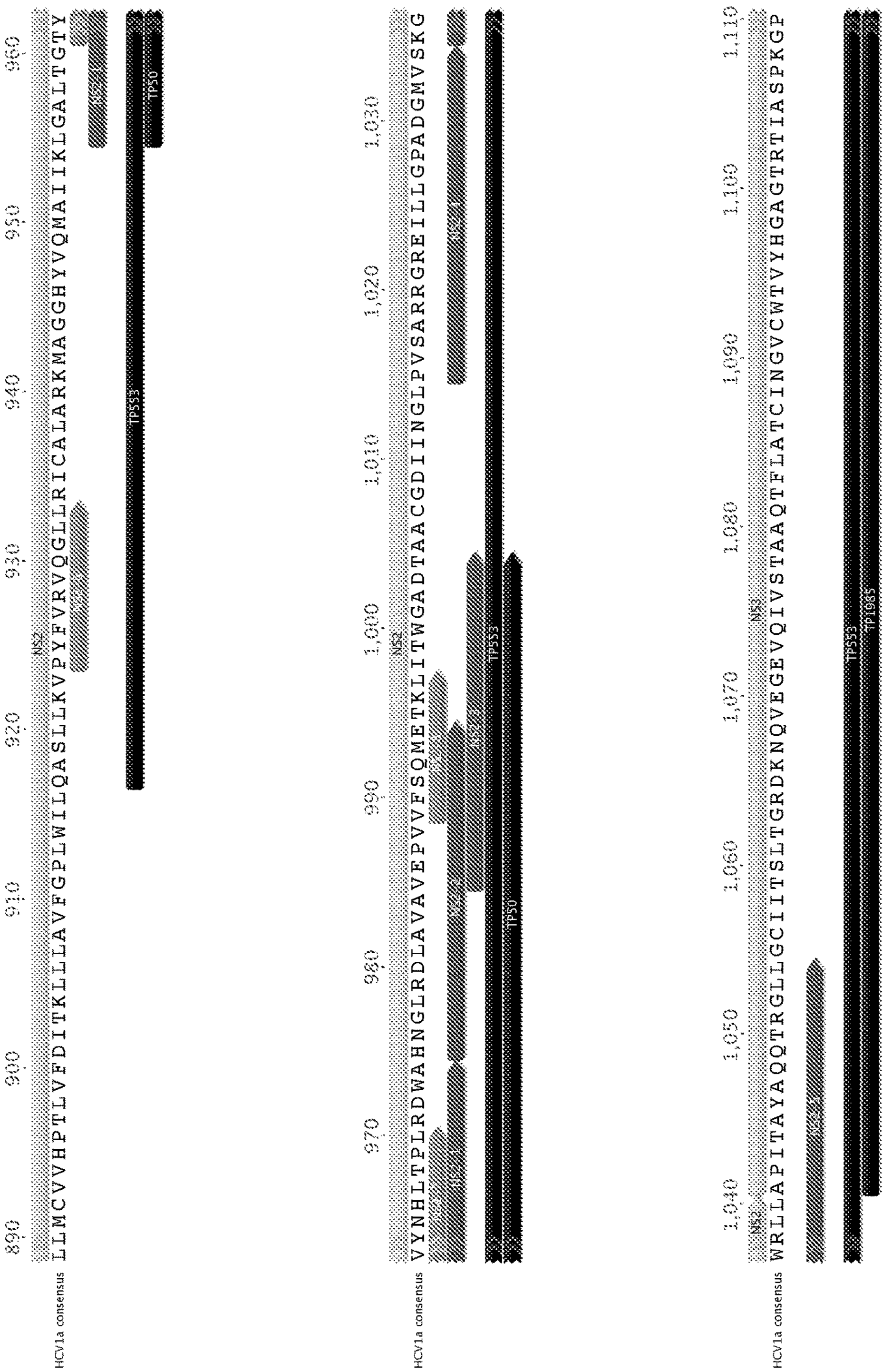
Figure 15F:
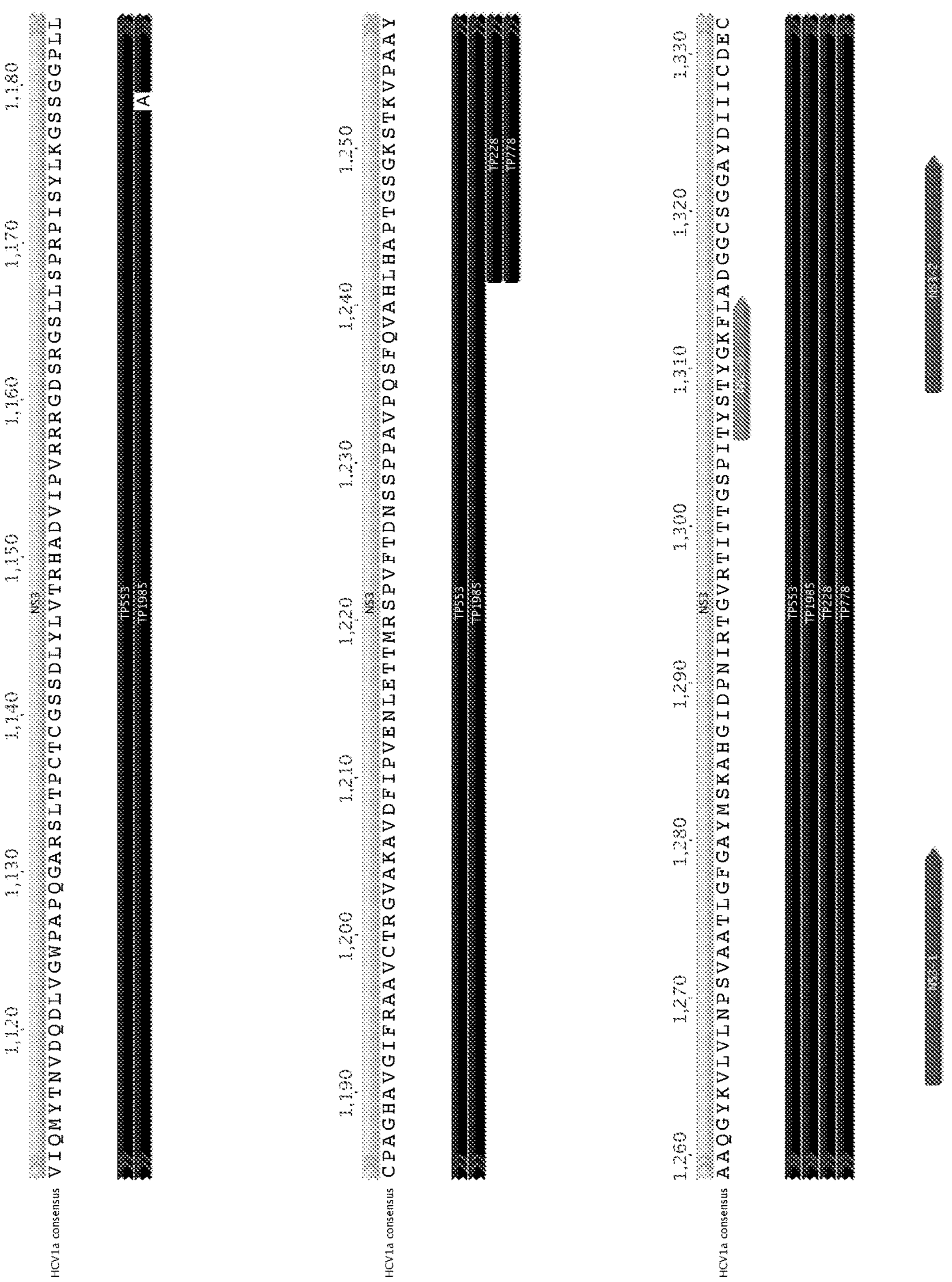
Figure 15G:
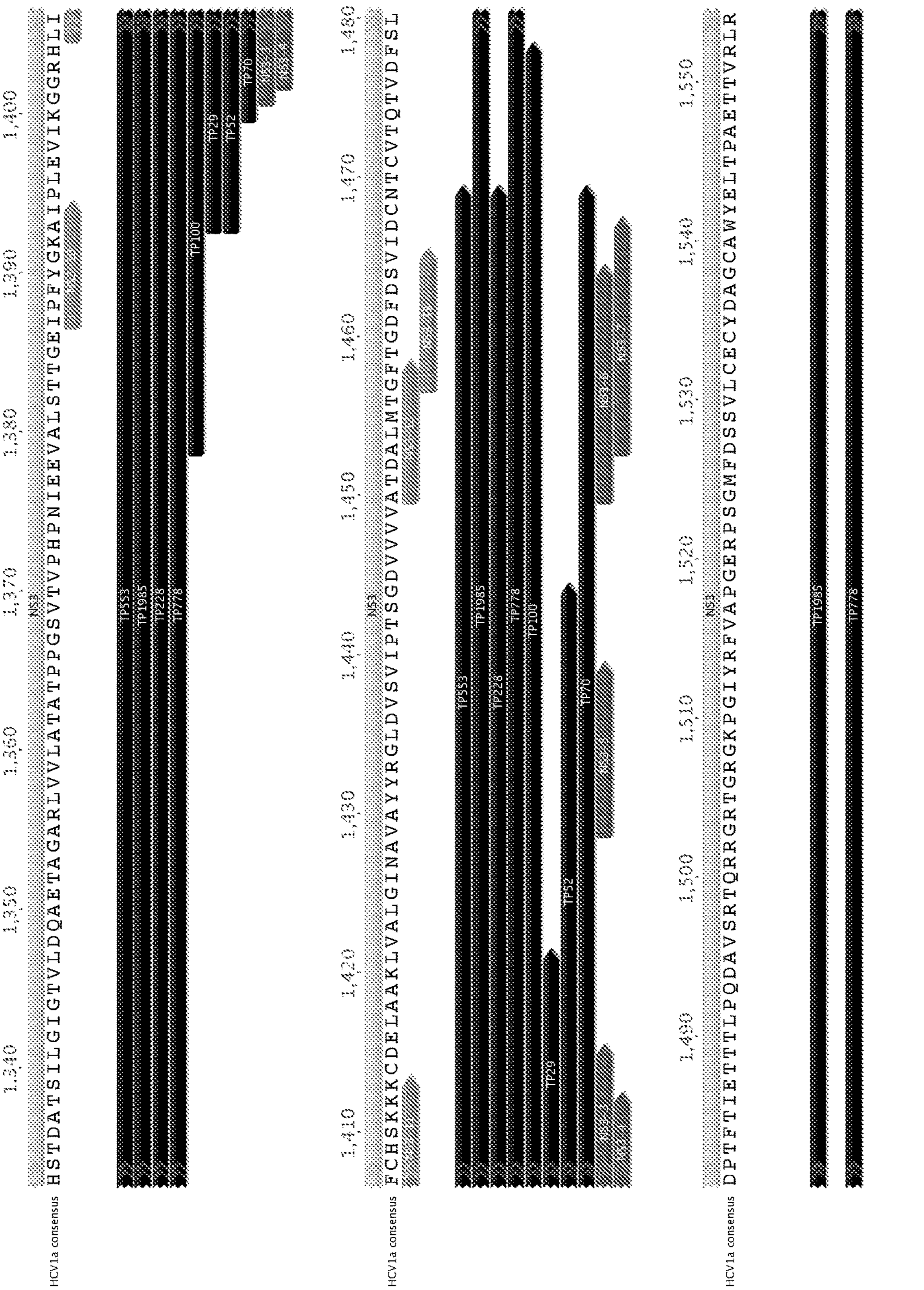
Figure 15H:
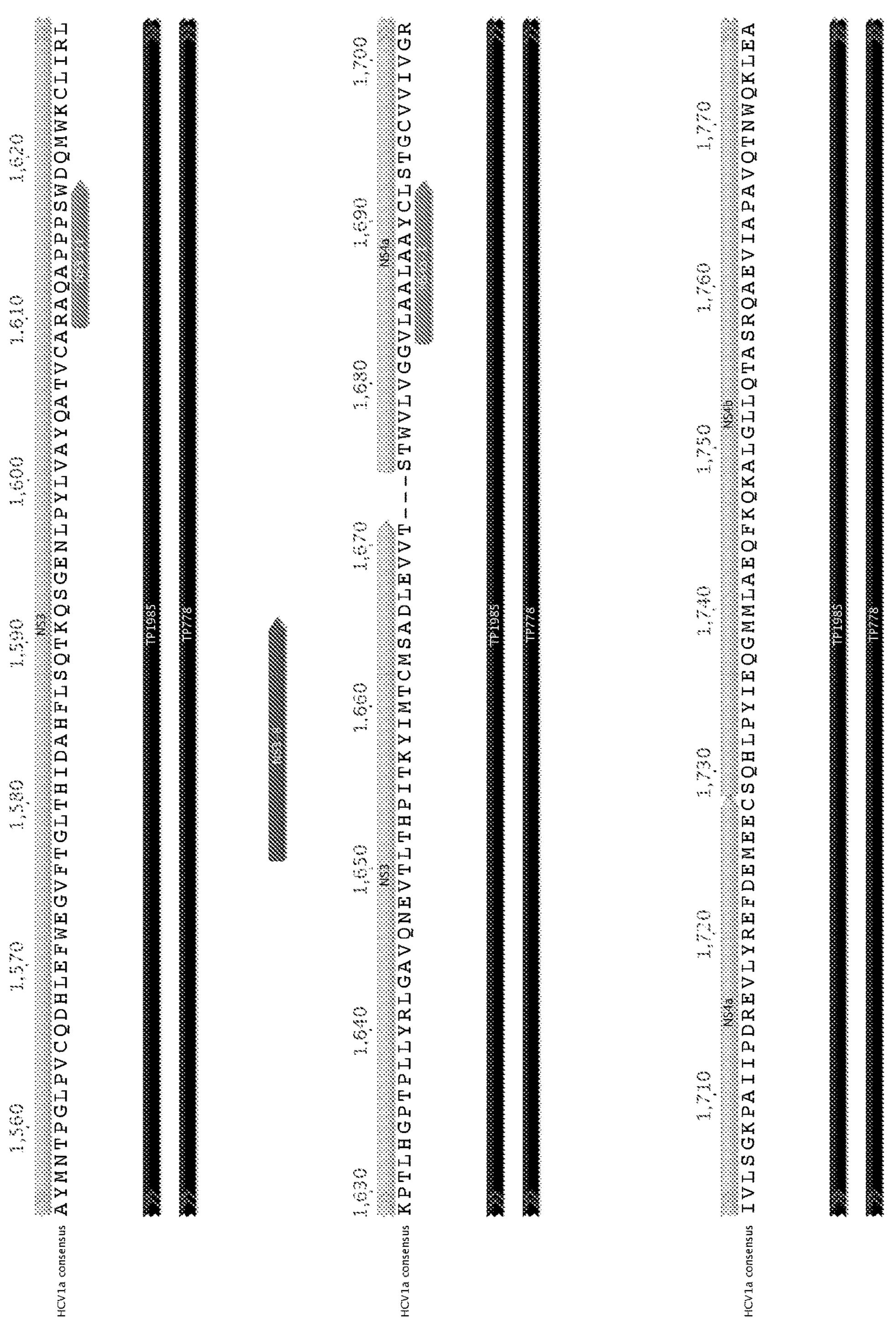
Figure 15I:
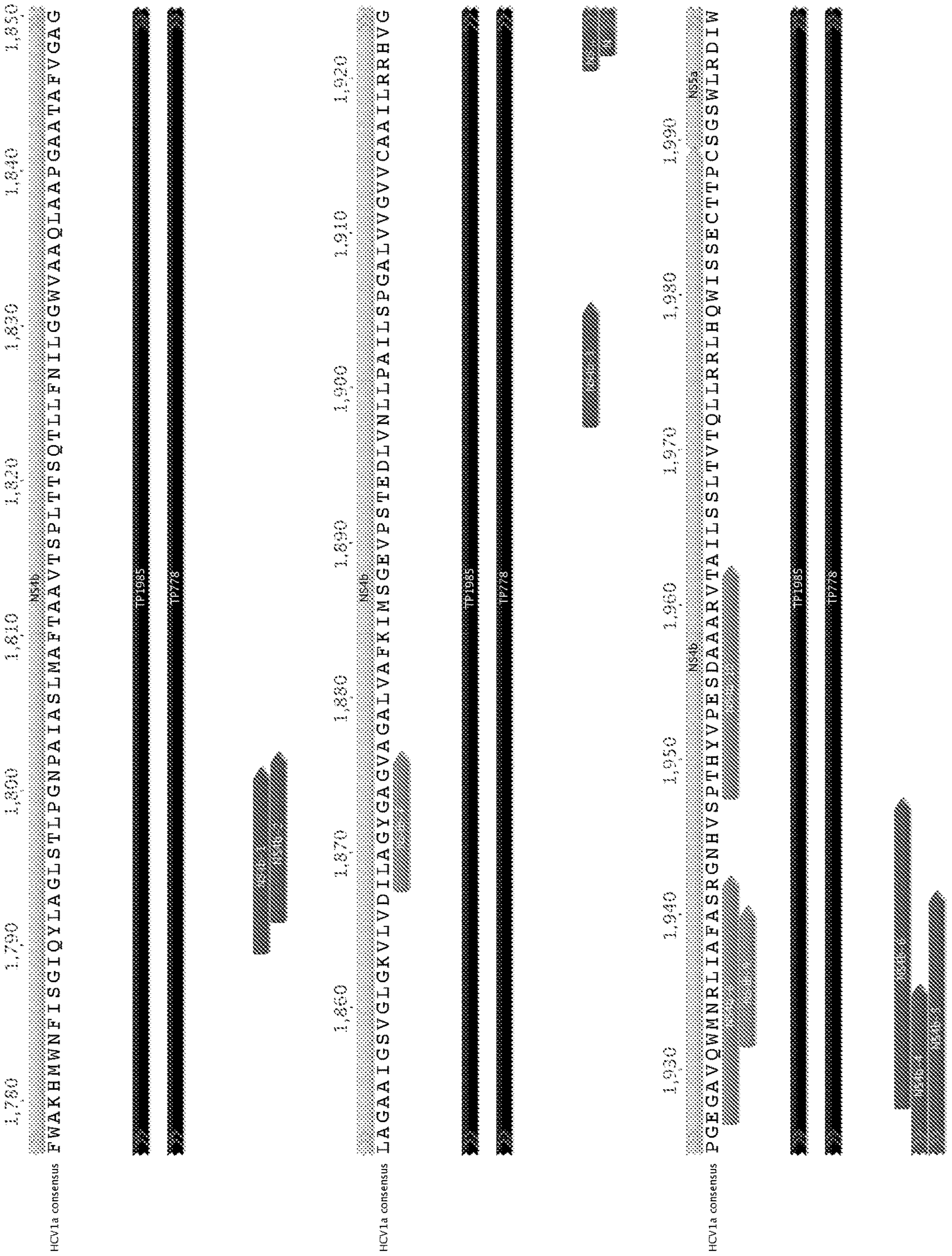
Figure 15J:
Figure 15K:
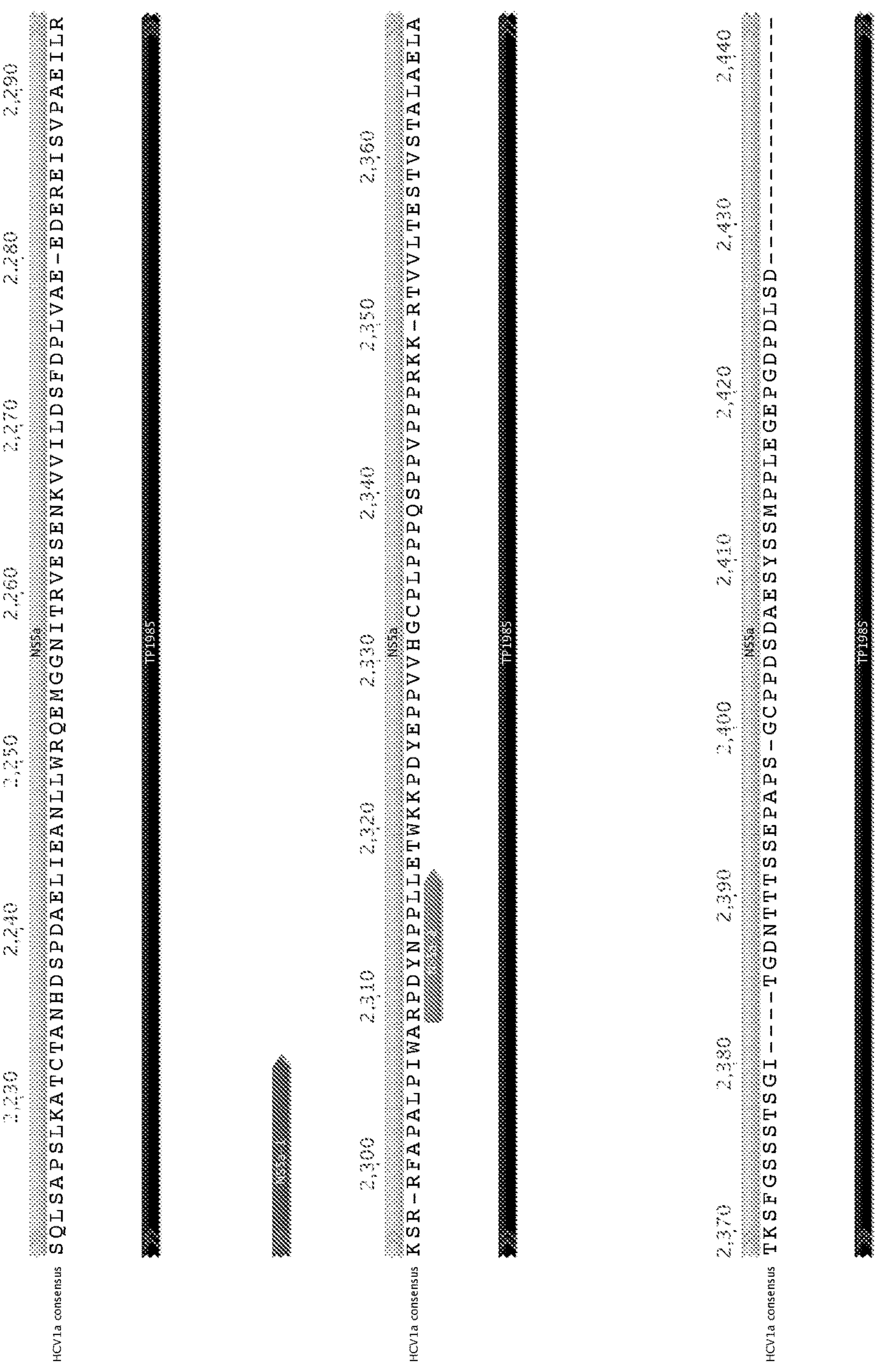
Figure 15L:
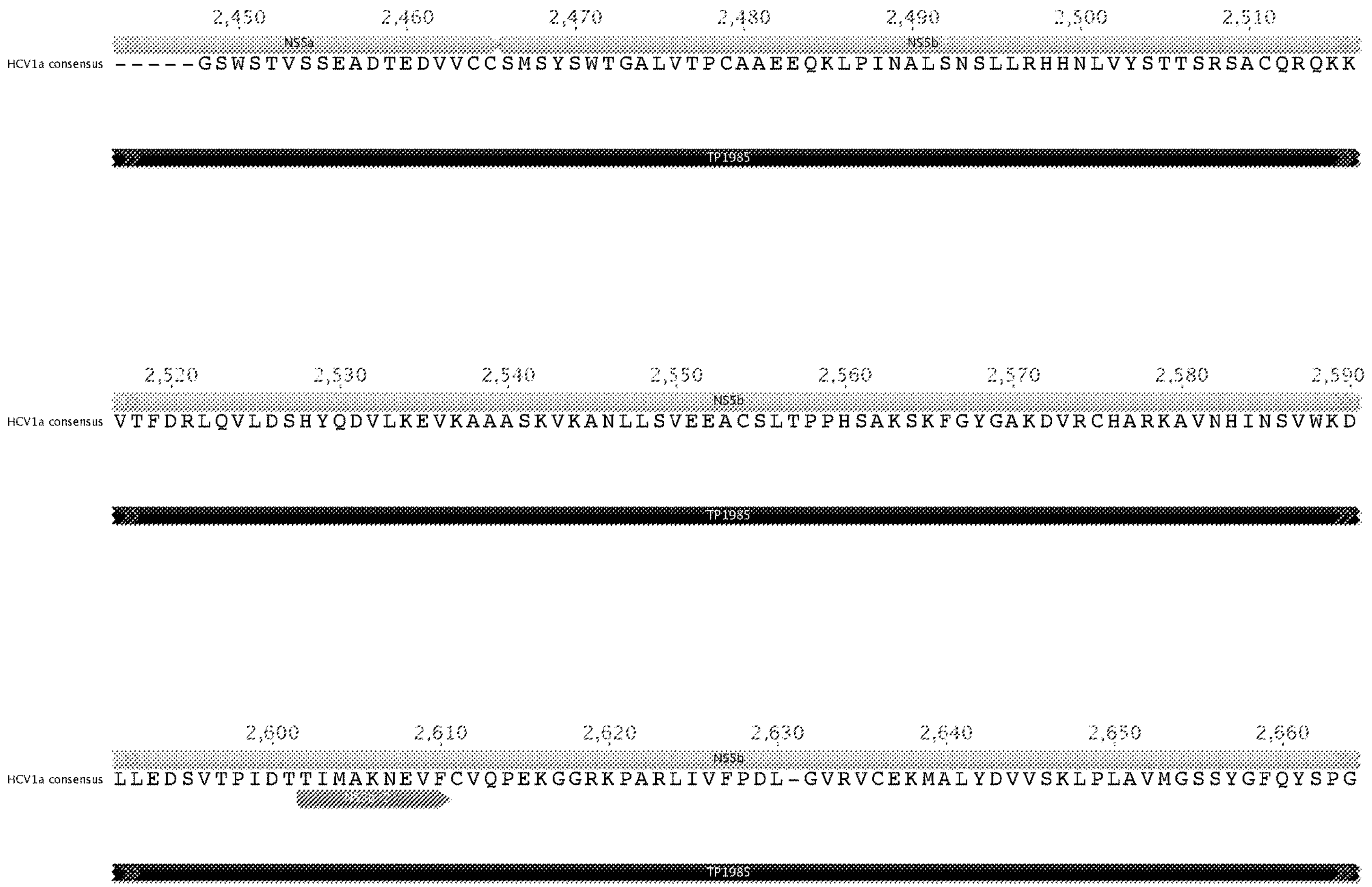
Figure 15M:
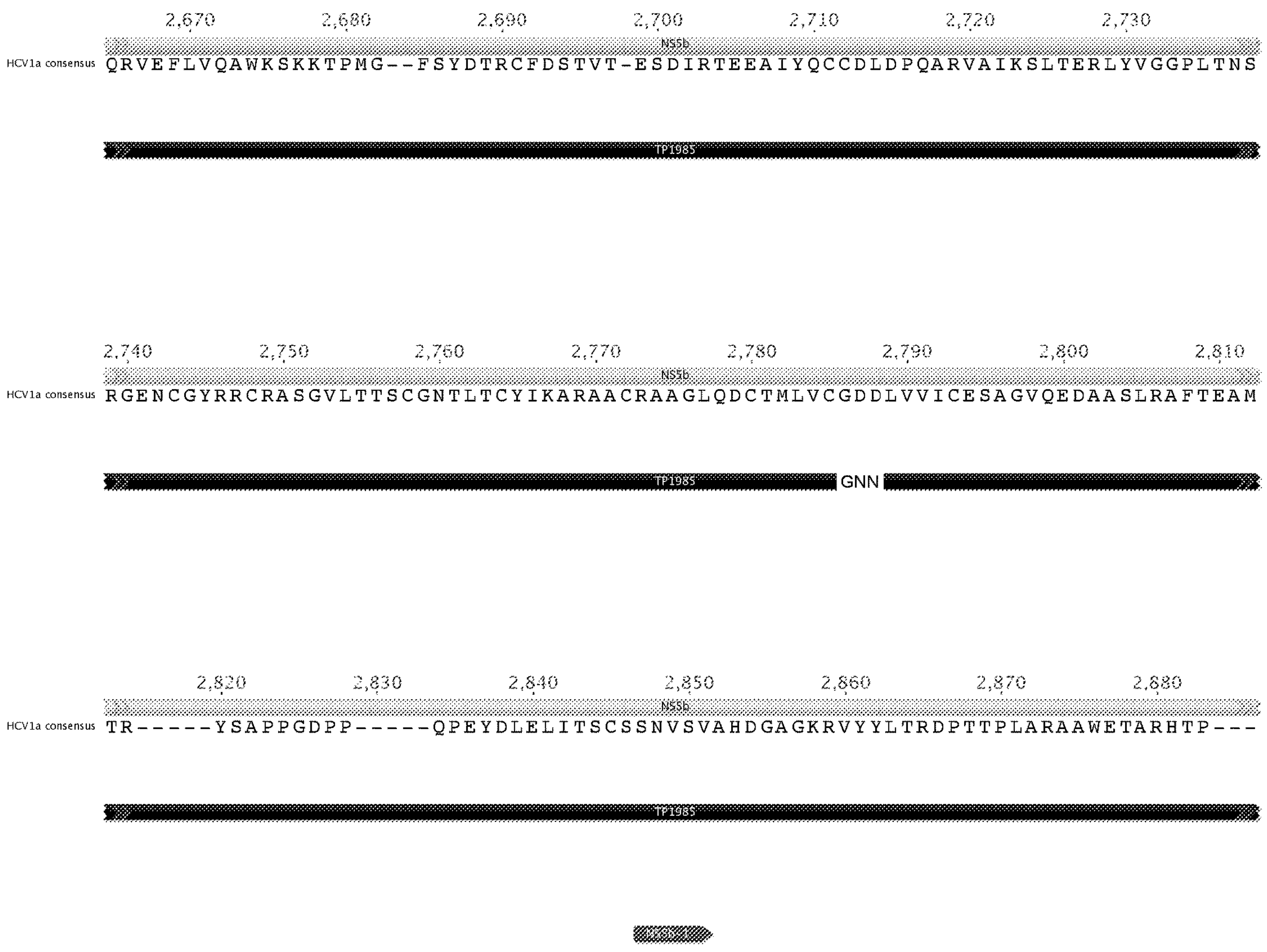
Figure 15N:
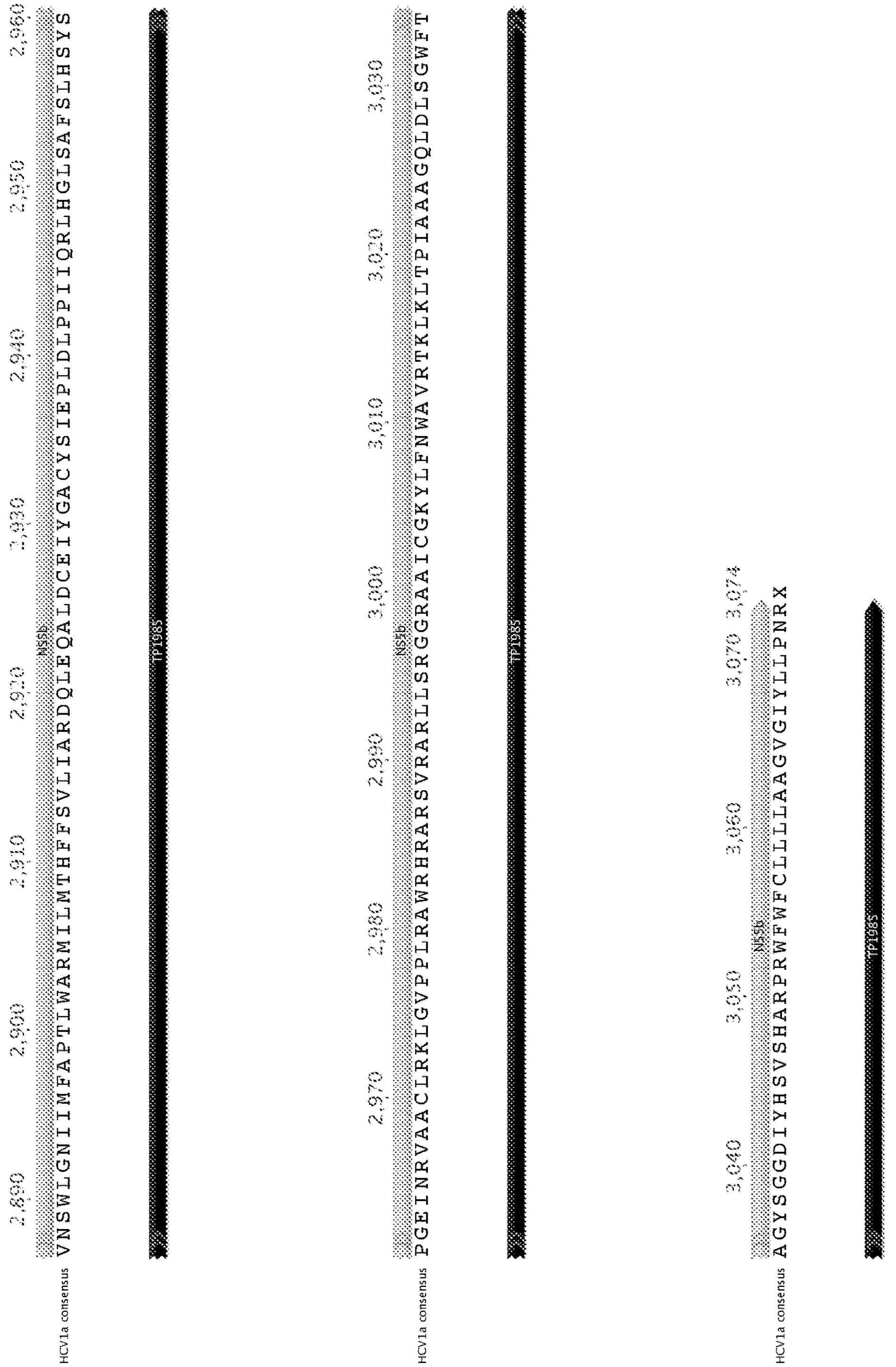

In some cases, the heterologous polypeptide present in an E2 variant polypeptide of an E1/E2 heterodimer of the present disclosure includes one or more T-cell epitopes present in an HCV NS2 polypeptide. Examples of T-cell epitopes present in NS2 polypeptides are depicted in FIGS. 15A-15N, and FIG. 13A.

For example, the heterologous polypeptide can comprise an NS2 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 955-974 of the amino acid sequence designated "Consensus" in FIGS. 16A-16L, or a corresponding HCV NS2 amino acid sequence of any HCV genotype; and the NS2 T cell epitope can have a length of from 20 amino acids (aa) to 25 amino acids (e.g., 20 aa, 21 aa, 22 aa, 23 aa, 24 aa, or 25 aa).

As another example, the heterologous polypeptide can comprise an NS2 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 975-994 of the amino acid sequence designated "Consensus" in FIGS. 16A-16L, or a corresponding HCV NS2 amino acid sequence of any HCV genotype; and the NS2 T cell epitope can have a length of from 20 amino acids (aa) to 25 amino acids (e.g., 20 aa, 21 aa, 22 aa, 23 aa, 24 aa, or 25 aa).

As another example, the heterologous polypeptide can comprise an NS2 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 985-1004 of the amino acid sequence designated "Consensus" in FIGS. 16A-16L, or a corresponding HCV NS2 amino acid sequence of any HCV genotype; and the NS2 T cell epitope can have a length of from 20 amino acids (aa) to 25 amino acids (e.g., 20 aa, 21 aa, 22 aa, 23 aa, 24 aa, or 25 aa).

As another example, the heterologous polypeptide can comprise an NS2 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1015-1034 of the amino acid sequence designated "Consensus" in FIGS. 16A-16L, or a corresponding HCV NS2 amino acid sequence of any HCV genotype; and the NS2 T cell epitope can have a length of from 20 amino acids (aa) to 25 amino acids (e.g., 20 aa, 21 aa, 22 aa, 23 aa, 24 aa, or 25 aa).

As another example, the heterologous polypeptide can comprise an NS2 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1035-1054 of the amino acid sequence designated "Consensus" in FIGS. 16A-16L, or a corresponding HCV NS2 amino acid sequence of any HCV genotype; and the NS2 T cell epitope can have a length of from 20 amino acids (aa) to 25 amino acids (e.g., 20 aa, 21 aa, 22 aa, 23 aa, 24 aa, or 25 aa).

As another example, the heterologous polypeptide can comprise an NS2 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 924-933 of the amino acid sequence designated "Consensus" in FIGS. 16A-16L, or a corresponding HCV NS2 amino acid sequence of any HCV genotype; and the NS2 T cell epitope can have a length of from 10 amino acids (aa) to 15 amino acids (e.g., 10 aa, 11 aa, 12 aa, 13 aa, 14 aa, or 15 aa).

As another example, the heterologous polypeptide can comprise an NS2 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 961-970 of the amino acid sequence designated "Consensus" in FIGS. 16A-16L, or a corresponding HCV NS2 amino acid sequence of any HCV genotype; and the NS2 T cell epitope can have a length of from 10 amino acids (aa) to 15 amino acids (e.g., 10 aa, 11 aa, 12 aa, 13 aa, 14 aa, or 15 aa).

As another example, the heterologous polypeptide can comprise an NS2 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 989-997 of the amino acid sequence designated "Consensus" in FIGS. 16A-16L, or a corresponding HCV NS2 amino acid sequence of any HCV genotype; and the NS2 T cell epitope can have a length of from 9 amino acids (aa) to 15 amino acids (e.g., 9 aa, 10 aa, 11 aa, 12 aa, 13 aa, 14 aa, or 15 aa).

In some cases, the heterologous polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to a contiguous stretch of from 10 amino acids (aa) to 50 an (e.g., from 10 aa to 25 aa, or from 25 an to 50 aa) of amino acids 955-1004 of the amino acid sequence designated "Consensus" in FIGS. 16A-16L, or a corresponding HCV NS2 amino acid sequence of any HCV genotype; and has a length of from 10 amino acids (aa) to 25 aa, or from 25 aa to 50 aa. In some cases, the heterologous polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 955-1004 of the amino acid sequence designated "Consensus" in FIGS. 16A-16L, or a corresponding HCV NS2 amino acid sequence of any HCV genotype; and has a length of about 50 amino acids.

In some cases, the heterologous polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to a contiguous stretch of from 10 amino acids (aa) to 553 an (e.g., from 10 aa to 25 aa, from 25 aa to 50 aa, from 50 aa to 100 aa, from 100 aa to 200 aa, from 200 aa to 300 aa, from 300 aa to 400 aa, from 400 aa to 500 aa, or from 500 an to 553 aa) of amino acids 917-1469 of the amino acid sequence designated “Consensus” in FIGS. 16A-16L, or a corresponding HCV NS2 and NS3 amino acid sequence of any HCV genotype; and has a length of from 10 amino acids (aa) to 25 aa, from 25 an to 50 aa, from 50 an to 100 aa, from 100 an to 200 aa, from 200 aa to 300 aa, from 300 aa to 400 aa, from 400 aa to 500 aa, or from 500 an to 553 aa. In some cases, the heterologous polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 917-1469 of the amino acid sequence designated “Consensus” in FIGS. 16A-16L, or a corresponding HCV NS2 and NS3 amino acid sequence of any HCV genotype; and has a length of about 553 amino acids.

The heterologous polypeptide can comprise an amino acid sequence having at least about 20%, at least about 25%, at least about 30%, at least about 35%, at least about 40%, at least about 45%, at least about 50%, at least about 60%, at least about 0%, at least about 75%, at least about 80%, at least about 85%, at least about 90%, at least about 95%, at least about 98%, at least about 99%, or 100%, amino acid sequence identity to the following amino acid sequence:

LGALTGTYVYNHLTPLRDWAHNGLRDLAVAVE-PVVFSQMETKLITWGADT (SEQ ID NO:11). In some cases, the heterologous polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence:

LGALTGTYVYNHLTPLRDWAHNGLRDLAVAVE-PVVFSQMETKLITWGADT (SEQ ID NO:11); and has a length of from 50 amino acids to 60 amino acids (e.g., 50 aa, 51 aa, 52 aa, 53 aa, 54 aa, 55 aa, 56 aa, 57 aa, 58 aa, 59 aa, or 60 aa). In some cases, the heterologous polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence:

LGALTGTYVYNHLTPLRDWAHNGLRDLAVAVE-PVVFSQMETKLITWGADT (SEQ ID NO:11); and has a length of 50 amino acids. Such a polytope can include NS2 T-cell epitopes designated NS2-1, NS2-2, NS2-3, NS2-7, and NS2-8 in FIG. 13A and FIGS. 15A-15N.

HCV NS4A T-Cell Epitopes

In some cases, the heterologous polypeptide present in an E2 variant polypeptide of an E1/E2 heterodimer of the present disclosure includes one or more T-cell epitopes present in an HCV NS4A polypeptide. Examples of T-cell epitopes present in NS4A polypeptides are depicted in FIGS. 15A-15N and FIG. 13B.

The heterologous polypeptide can comprise an NS4A T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1683-1692 of the amino acid sequence designated “Consensus” in FIGS. 16A-16L, or a corresponding HCV NS4A amino acid sequence of any HCV genotype; and the NS4A T-cell epitope can have a length of from 10 amino acids (aa) to 15 amino acids (e.g., 10 aa, 11 aa, 12 aa, 13 aa, 14 aa, or 15 aa).

HCV NS4B T-Cell Epitopes

In some cases, the heterologous polypeptide present in an E2 variant polypeptide of an E1/E2 heterodimer of the present disclosure includes one or more T-cell epitopes present in an HCV NS4B polypeptide. Examples of T-cell epitopes present in NS4B polypeptides are depicted in FIGS. 15A-15N and FIG. 13B.

As one example, the heterologous polypeptide can comprise an NS4B T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1790-1801 of the amino acid sequence designated “Consensus” in FIGS. 16A-16L, or a corresponding HCV NS4B amino acid sequence of any HCV genotype; and the NS4B T-cell epitope can have a length of from 12 amino acids (aa) to 20 amino acids (e.g., 12 aa, 13 aa, 14 aa, 15 aa, 16 aa, 17 aa, 18 aa, 19 aa, or 20 aa).

As another example, the heterologous polypeptide can comprise an NS4B T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1792-1802 of the amino acid sequence designated “Consensus” in FIGS. 16A-16L, or a corresponding HCV NS4B amino acid sequence of any HCV genotype; and the NS4B T-cell epitope can have a length of from 11 amino acids (aa) to 20 amino acids (e.g., 11 aa, 12 aa, 13 aa, 14 aa, 15 aa, 16 aa, 17 aa, 18 aa, 19 aa, or 20 aa).

As another example, the heterologous polypeptide can comprise an NS4B T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1898-1905 of the amino acid sequence designated “Consensus” in FIGS. 16A-16L, or a corresponding HCV NS4B amino acid sequence of any HCV genotype; and the NS4B T-cell epitope can have a length of from 8 amino acids (aa) to 15 amino acids (e.g., 8 aa, 9 aa, 10 aa, 11 aa, 12 aa, 13 aa, 14 aa, or 15 aa).

As another example, the heterologous polypeptide can comprise an NS4B T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1921-1935 of the amino acid sequence designated "Consensus" in FIGS. 16A-16L, or a corresponding HCV NS4B amino acid sequence of any HCV genotype; and the NS4B T-cell epitope can have a length of from 15 amino acids (aa) to 20 amino acids (e.g., 15 aa, 16 aa, 17 aa, 18 aa, 19 aa, or 20 aa).

As another example, the heterologous polypeptide can comprise an NS4B T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1922-1941 of the amino acid sequence designated "Consensus" in FIGS. 16A-16L, or a corresponding HCV NS4B amino acid sequence of any HCV genotype; and the NS4B T-cell epitope can have a length of from 20 amino acids (aa) to 25 amino acids (e.g., 20 aa, 21 aa, 22 aa, 23 aa, 24 aa, or 25 aa).

As another example, the heterologous polypeptide can comprise an NS4B T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1928-1947 of the amino acid sequence designated "Consensus" in FIGS. 16A-16L, or a corresponding HCV NS4B amino acid sequence of any HCV genotype; and the NS4B T-cell epitope can have a length of from 20 amino acids (aa) to 25 amino acids (e.g., 20 aa, 21 aa, 22 aa, 23 aa, 24 aa, or 25 aa).

As another example, the heterologous polypeptide can comprise an NS4B T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1868-1876 of the amino acid sequence designated "Consensus" in FIGS. 16A-16L, or a corresponding HCV NS4B amino acid sequence of any HCV genotype; and the NS4B T-cell epitope can have a length of from 9 amino acids (aa) to 15 amino acids (e.g., 9 aa, 10 aa, 11 aa, 12 aa, 13 aa, 14 aa, or 15 aa).

As another example, the heterologous polypeptide can comprise an NS4B T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1927-1942 of the amino acid sequence designated "Consensus" in FIGS. 16A-16L, or a corresponding HCV NS4B amino acid sequence of any HCV genotype; and the NS4B T-cell epitope can have a length of from 16 amino acids (aa) to 20 amino acids (e.g., 16 aa, 17 aa, 18 aa, 19 aa, or 20 aa).

As another example, the heterologous polypeptide can comprise an NS4B T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1932-1940 of the amino acid sequence designated "Consensus" in FIGS. 16A-16L, or a corresponding HCV NS4B amino acid sequence of any HCV genotype; and the NS4B T-cell epitope can have a length of from 9 amino acids (aa) to 15 amino acids (e.g., 9 aa, 10 aa, 11 aa, 12 aa, 13 aa, 14 aa, or 15 aa).

As another example, the heterologous polypeptide can comprise an NS4B T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1948-1962 of the amino acid sequence designated "Consensus" in FIGS. 16A-16L, or a corresponding HCV NS4B amino acid sequence of any HCV genotype; and the NS4B T-cell epitope can have a length of from 15 amino acids (aa) to 20 amino acids (e.g., 15 aa, 16 aa, 17 aa, 18 aa, 19 aa, or 20 aa).

HCV NS5A T-Cell Epitopes

In some cases, the heterologous polypeptide present in an E2 variant polypeptide of an E1/E2 heterodimer of the present disclosure includes one or more T-cell epitopes present in an HCV NS5A polypeptide. Examples of T-cell epitopes present in NS5A polypeptides are depicted in FIGS. 15A-15N and FIG. 13B.

As one example, the heterologous polypeptide can comprise an NSSA T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 2218-2232 of the amino acid sequence designated "Consensus" in FIGS. 16A-16L, or a corresponding HCV NS5A amino acid sequence of any HCV genotype; and the NSSA T-cell epitope can have a length of from 15 amino acids (aa) to 20 amino acids (e.g., 15 aa, 16 aa, 17 aa, 18 aa, 19 aa, or 20 aa).

As another example, the heterologous polypeptide can comprise an NSSA T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 2309-2317 of the amino acid sequence designated "Consensus" in FIGS. 16A-16L, or a corresponding HCV NSSA amino acid sequence of any HCV genotype; and the NSSA T-cell epitope can have a length of from 9 amino acids (aa) to 15 amino acids (e.g., 9 aa, 10 aa, 11 aa, 12 aa, 13 aa, 14 aa, or 15 aa).

HCV NS5B T-Cell Epitopes

In some cases, the heterologous polypeptide present in an E2 variant polypeptide of an E1/E2 heterodimer of the present disclosure includes one or more T-cell epitopes present in an HCV NS5B polypeptide. Examples of T-cell epitopes present in NS5B polypeptides are depicted in FIGS. 15A-15N and FIG. 13B.

As one example, the heterologous polypeptide can comprise an NS5B T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 2847-2851 of the amino acid sequence designated "Consensus" in FIGS. 16A-16L, or a corresponding HCV NS5B amino acid sequence of any HCV genotype; and the NS5B T-cell epitope can have a length of from 5 amino acids (aa) to 10 amino acids (e.g., 5 aa, 6 aa, 7 aa, 8 aa, 9 aa, or 10 aa).

As another example, the heterologous polypeptide can comprise an NS5B T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 2602-2610 of the amino acid sequence designated "Consensus" in FIGS. 16A-16L, or a corresponding HCV NS5B amino acid sequence of any HCV genotype; and the NS5B T-cell epitope can have a length of from 9 amino acids (aa) to 15 amino acids (e.g., 9 aa, 10 aa, 11 aa, 12 aa, 13 aa, 14 aa, or 15 aa).

HCV Core T-Cell Epitopes

In some cases, the heterologous polypeptide present in an E2 variant polypeptide of an E1/E2 heterodimer of the present disclosure includes one or more T-cell epitopes present in an HCV core polypeptide. Examples of T-cell epitopes present in HCV Core polypeptides are depicted in FIGS. 15A-15N and FIG. 13A.

As one example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1-20 of the amino acid sequence designated "Consensus" in FIGS. 16A-16L, or a corresponding HCV core amino acid sequence of any HCV genotype; and the HCV core T-cell epitope can have a length of from 20 amino acids (aa) to 25 amino acids (e.g., 20 aa, 21 aa, 22 aa, 23 aa, 24 aa, or 25 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 11-30 of the amino acid sequence designated "Consensus" in FIGS. 16A-16L, or a corresponding HCV core amino acid sequence of any HCV genotype; and the HCV core T-cell epitope can have a length of from 20 amino acids (aa) to 25 amino acids (e.g., 20 aa, 21 aa, 22 aa, 23 aa, 24 aa, or 25 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 21-40 of the amino acid sequence designated "Consensus" in FIGS. 16A-16L, or a corresponding HCV core amino acid sequence of any HCV genotype; and the HCV core T-cell epitope can have a length of from 20 amino acids (aa) to 25 amino acids (e.g., 20 aa, 21 aa, 22 aa, 23 aa, 24 aa, or 25 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 39-63 of the amino acid sequence designated "Consensus" in FIGS. 16A-16L, or a corresponding HCV core amino acid sequence of any HCV genotype; and the HCV core T-cell epitope can have a length of from 23 amino acids (aa) to 28 amino acids (e.g., 23 aa, 24 aa, 25 aa, 26 aa, 27 aa, or 28 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 47-70 of the amino acid sequence designated "Consensus" in FIGS. 16A-16L, or a corresponding HCV core amino acid sequence of any HCV genotype; and the HCV core T-cell epitope can have a length of from 24 amino acids (aa) to 29 amino acids (e.g., 24 aa, 25 aa, 26 aa, 27 aa, 28 aa, or 29 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 61-80 of the amino acid sequence designated "Consensus" in FIGS. 16A-16L, or a corresponding HCV core amino acid sequence of any HCV genotype; and the HCV core T-cell epitope can have a length of from 20 amino acids (aa) to 25 amino acids (e.g., 20 aa, 21 aa, 22 aa, 23 aa, 24 aa, or 25 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 71-90 of the amino acid sequence designated "Consensus" in FIGS. 16A-16L, or a corresponding HCV core amino acid sequence of any HCV genotype; and the HCV core T-cell epitope can have a length of from 20 amino acids (aa) to 25 amino acids (e.g., 20 aa, 21 aa, 22 aa, 23 aa, 24 aa, or 25 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 81-100 of the amino acid sequence designated "Consensus" in FIGS. 16A-16L, or a corresponding HCV core amino acid sequence of any HCV genotype; and the HCV core T-cell epitope can have a length of from 20 amino acids (aa) to 25 amino acids (e.g., 20 aa, 21 aa, 22 aa, 23 aa, 24 aa, or 25 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 91-110 of the amino acid sequence designated "Consensus" in FIGS. 16A-16L, or a corresponding HCV core amino acid sequence of any HCV genotype; and the HCV core T-cell epitope can have a length of from 20 amino acids (aa) to 25 amino acids (e.g., 20 aa, 21 aa, 22 aa, 23 aa, 24 aa, or 25 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 101-115 of the amino acid sequence designated "Consensus" in FIGS. 16A-16L, or a corresponding HCV core amino acid sequence of any HCV genotype; and the HCV core T-cell epitope can have a length of from 15 amino acids (aa) to 20 amino acids (e.g., 15 aa, 16 aa, 17 aa, 18 aa, 19 aa, or 20 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 111-130 of the amino acid sequence designated "Consensus" in FIGS. 16A-16L, or a corresponding HCV core amino acid sequence of any HCV genotype; and the HCV core T-cell epitope can have a length of from 20 amino acids (aa) to 25 amino acids (e.g., 20 aa, 21 aa, 22 aa, 23 aa, 24 aa, or 25 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 125-139 of the amino acid sequence designated "Consensus" in FIGS. 16A-16L, or a corresponding HCV core amino acid sequence of any HCV genotype; and the HCV core T-cell epitope can have a length of from 15 amino acids (aa) to 20 amino acids (e.g., 15 aa, 16 aa, 17 aa, 18 aa, 19 aa, or 20 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 131-150 of the amino acid sequence designated "Consensus" in FIGS. 16A-16L, or a corresponding HCV core amino acid sequence of any HCV genotype; and the HCV core T-cell epitope can have a length of from 20 amino acids (aa) to 25 amino acids (e.g., 20 aa, 21 aa, 22 aa, 23 aa, 24 aa, or 25 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 151-170 of the amino acid sequence designated "Consensus" in FIGS. 16A-16L, or a corresponding HCV core amino acid sequence of any HCV genotype; and the HCV core T-cell epitope can have a length of from 20 amino acids (aa) to 25 amino acids (e.g., 20 aa, 21 aa, 22 aa, 23 aa, 24 aa, or 25 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 161-180 of the amino acid sequence designated "Consensus" in FIGS. 16A-16L, or a corresponding HCV core amino acid sequence of any HCV genotype; and the HCV core T-cell epitope can have a length of from 20 amino acids (aa) to 25 amino acids (e.g., 20 aa, 21 aa, 22 aa, 23 aa, 24 aa, or 25 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 35-44 of the amino acid sequence designated "Consensus" in FIGS. 16A-16L, or a corresponding HCV core amino acid sequence of any HCV genotype; and the HCV core T-cell epitope can have a length of from 10 amino acids (aa) to 15 amino acids (e.g., 10 aa, 11 aa, 12 aa, 13 aa, 14 aa, or 15 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 43-51 of the amino acid sequence designated "Consensus" in FIGS. 16A-16L, or a corresponding HCV core amino acid sequence of any HCV genotype; and the HCV core T-cell epitope can have a length of from 9 amino acids (aa) to 15 amino acids (e.g., 9 aa, 10 aa, 11 aa, 12 aa, 13 aa, 14 aa, or 15 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 51-59 of the amino acid sequence designated "Consensus" in FIGS. 16A-16L, or a corresponding HCV core amino acid sequence of any HCV genotype; and the HCV core T-cell epitope can have a length of from 9 amino acids (aa) to 15 amino acids (e.g., 9 aa, 10 aa, 11 aa, 12 aa, 13 aa, 14 aa, or 15 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 129-137 of the amino acid sequence designated "Consensus" in FIGS. 16A-16L, or a corresponding HCV core amino acid sequence of any HCV genotype; and the HCV core T-cell epitope can have a length of from 9 amino acids (aa) to 15 amino acids (e.g., 9 aa, 10 aa, 11 aa, 12 aa, 13 aa, 14 aa, or 15 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 131-140 of the amino acid sequence designated "Consensus" in FIGS. 16A-16L, or a corresponding HCV core amino acid sequence of any HCV genotype; and the HCV core T-cell epitope can have a length of from 10 amino acids (aa) to 15 amino acids (e.g., 10 aa, 11 aa, 12 aa, 13 aa, 14 aa, or 15 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 150-158 of the amino acid sequence designated "Consensus" in FIGS. 16A-16L, or a corresponding HCV core amino acid sequence of any HCV genotype; and the HCV core T-cell epitope can have a length of from 9 amino acids (aa) to 15 amino acids (e.g., 9 aa, 10 aa, 11 aa, 12 aa, 13 aa, 14 aa, or 15 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 154-162 of the amino acid sequence designated "Consensus" in FIGS. 16A-16L, or a corresponding HCV core amino acid sequence of any HCV genotype; and the HCV core T-cell epitope can have a length of from 9 amino acids (aa) to 15 amino acids (e.g., 9 aa, 10 aa, 11 aa, 12 aa, 13 aa, 14 aa, or 15 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 168-176 of the amino acid sequence designated "Consensus" in FIGS. 16A-16L, or a corresponding HCV core amino acid sequence of any HCV genotype; and the HCV core T-cell epitope can have a length of from 9 amino acids (aa) to 15 amino acids (e.g., 9 aa, 10 aa, 11 aa, 12 aa, 13 aa, 14 aa, or 15 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 177-187 of the amino acid sequence designated "Consensus" in FIGS. 16A-16L, or a corresponding HCV core amino acid sequence of any HCV genotype; and the HCV core T-cell epitope can have a length of from 11 amino acids (aa) to 16 amino acids (e.g., 11 aa, 12 aa, 13 aa, 14 aa, 15 aa, or 16 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 178-187 of the amino acid sequence designated "Consensus" in FIGS. 16A-16L, or a corresponding HCV core amino acid sequence of any HCV genotype; and the HCV core T-cell epitope can have a length of from 10 amino acids (aa) to 15 amino acids (e.g., 10 aa, 11 aa, 12 aa, 13 aa, 14 aa, or 15 aa).

In some cases, the heterologous polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to a contiguous stretch of from 10 amino acids (aa) to 191 aa (e.g., from 10 aa to 25 aa, from 25 aa to 50 aa, from 50 aa to 75 aa, from 75 aa to 100 aa, from 100 aa to 150 aa, or from 150 aa to 191aa) of amino acids 1-191 of the amino acid sequence designated "Consensus" in FIGS. 16A-16L, or a corresponding HCV core amino acid sequence of any HCV genotype; and has a length of from 10 amino acids (aa) to 25 aa, from 25 an to 50 aa, from 50 an to 100 aa, or from 100 aa to 150 aa, or from 150 an to 191 aa. In some cases, the heterologous polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1-191 of the amino acid sequence designated "Consensus" in FIGS. 16A-16L, or a corresponding HCV core amino acid sequence of any HCV genotype; and has a length of about 191 amino acids.

The heterologous polypeptide can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence:

MSTNPKPQRKTKRNTNRRPQDVKFPGGGQIVGG-VYLLPRRGPRLGVRATRKTS ERSQPRGRRQPI-PKARRPEGRTWAQPGYPWPLYGNEGCG-WAGWLLSPRGSRPS WGPTDPRRRSRNLGKVID-TLTCGFADLMGYIPLVGAPLGGAARALAHGV-RVLE DGVNYATGNLPG (SEQ ID NO:63); and has a length of from 171 amino acids (aa) to 180 an (e.g., 171 aa, 172 aa, 173 aa, 174 aa, 175 aa, 176 aa, 177 aa, 178 aa, 179 aa, or 180 aa. In some cases, the heterologous polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence:

MSTNPKPQRKTKRNTNRRPQDVKFPGGGQIVGG-VYLLPRRGPRLGVRATRKTS ERSQPRGRRQPI-PKARRPEGRTWAQPGYPWPLYGNEGCGWAG-WLLSPRGSRPS WGPTDPRRRSRNLGKVIDTLTC-GFADLMGYIPLVGAPLGGAARALAHGVRVLE DGVNYATGNLPG (SEQ ID NO:63); and has a length of 171 amino acids. Such a polytope can include core T-cell epitopes designated Core-1, Core-2, Core-3, Core-4, Core-5, Core-6, Core-7, Core-8, Core-9, Core-10, Core-11, Core-12, Core-13, Core-14, Core-16, Core-17, Core-18, Core-19, Core-20, Core-21, Core-22 in FIG. 13A and FIGS. 15A-15N.

HCV p7 T-cell Epitopes

In some cases, the heterologous polypeptide present in an E2 variant polypeptide of an E1/E2 heterodimer of the present disclosure includes one or more T-cell epitopes present in an HCV p7 polypeptide. Examples of T-cell epitopes present in HCV p7 polypeptides are depicted in FIGS. 15A-15N or FIG. 13A.

As another example, the heterologous polypeptide can comprise an HCV p7 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 803-811 of the amino acid sequence designated "Consensus" in FIGS. 16A-16L, or a corresponding HCV p7 amino acid sequence of any HCV genotype; and the HCV p7 T-cell epitope can have a length of from 9 amino acids (aa) to 15 amino acids (e.g., 9 aa, 10 aa, 11 aa, 12 aa, 13 aa, 14 aa, or 15 aa).

Polytopes including HCV T-cell epitopes from more than one HCV polypeptide other than E1 and E2

As noted above, a heterologous polypeptide can include T-cell epitopes from more than one HCV polypeptide other than E1 and E2.

As one example, a heterologous polypeptide can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence:

QASLLKVPYFVRVQGLLRICALARKMAGGHYVQ-MAIIKLGALTGTYVYNALTP LRDWAHNGLRD-LAVAVEPVVFSQMETKLITWGADTAACGDI-INGLPVSARRGR EILLGPADGMVSKGWRLL-APITAYAQQTRGLLGCIITSLTGRDKNQVEG-EVQIVS TAAQTFLATCINGVCWTVYHGAGTR-TIASPKGPVIQMYTNVDQDLVGWPAPQG ARSLTPCTCGSSDLYLVTRHADVIPVRRRGDS-RGSLLSPRPISYLKGSAGGPLLCP AGHAVGI-FRAAVCTRGVAKAVDFIPVENLETTMRSPVFT-DNSSPPAVPQSFQVA HLHAPTGSGKSTKVPAAY-AAQGYKVLVLNPSVAATLGFGAYMSKAHGIDP-NIR TGVRTITTGSPITYSTYGKFLADGGCSGGAY-DIIICDECHSTDATSILGIGTVLDQA ETAGARLVV-LATATPPGSVTVPHPNIEEVALSTTGEIPFYGK-AIPLEVIKGGRHLIF CHSKKKCDELAAKLVALGI-NAVAYYRGLDVSVIPTSGDVVVVATDALMT-GFTG DFDSVIDCN (SEQ ID NO:12); and has a length of from 550 amino acids (aa) to 560 aa (e.g., 550 aa, 551 aa, 552 aa, 553 aa, 554 aa, 555 aa, 556 aa, 557 aa, 558 aa, 559 aa, or 560 aa). In some cases, the heterologous polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence:

QASLLKVPYFVRVQGLLRICALARKMAGGHYVQ-MAIIKLGALTGTYVYNALTP LRDWAHNGLRD-LAVAVEPVVFSQMETKLITWGADTAACGDI-INGLPVSARRGR EILLGPADGMVSKGWRLLA-PITAYAQQTRGLLGCIITSLTGRDKNQVEG-EVQIVS TAAQTFLATCINGVCWTVYHGAGTR-TIASPKGPVIQMYTNVDQDLVGWPAPQG ARSLTPCTCGSSDLYLVTRHADVIPVRRRGDS-RGSLLSPRPISYLKGSAGGPLLCP AGHAVGI-FRAAVCTRGVAKAVDFIPVENLETTMRSPVFT-DNSSPPAVPQSFQVA HLHAPTGSGKSTKVPA-

AYAAQGYKVLVLNPSVAATLGFGAYMSKAH-GIDPNIR TGVRTITTGSPITYSTYGKFLADGGCS-GGAYDIIICDECHSTDATSILGIGTVLDQA ETAGARLVVLATATPPGSVTVPHPNIEEVALSTT-GEIPFYGKAIPLEVIKGGRHLIF CHSKKKCDE-LAAKLVALGINAVAYYRGLDVSVIPTSGDVVV-VATDALMTGFTG DFDSVIDCN (SEQ ID NO:12); and has a length of 553 amino acids. Such a polytope can include T-cell epitopes designated NS2-1, NS2-2, NS2-3, NS2-4, NS2-5, NS2-6, NS2-7, NS2-8, NS3-1, NS3-2, NS3-3, NS3-4, NS3-5, NS3-6, NS3-7, NS3-9, NS3-10, NS3-11, NS3-12, and NS3-13 in FIGS. 13A-13B and FIGS. 15A-15N. This polytope is also referred to as "TP553" (FIGS. 14A-14D). In order to prevent self cleavage of the TP553 polytope (amino acids 917-1469) (FIGS. 15E-G) at the NS2-NS3 junction that is mediated by the catalytic domain of the NS2 protease (amino acids 917-1040), the histidine at position 966 (H966), a critical residue for NS2 protease activity, is mutated to alanine (H966A) (FIG. 15E). See, e.g., Grakoui, A. et al. A second hepatitis C virus-encoded proteinase. Proc. Natl Acad. Sci. USA 90, 10583-10587 (1993); Hijikata, M. et al. Two distinct proteinase activities required for the processing of a putative nonstructural precursor protein of hepatitis C virus. J. Virol. 67, 4665-4675 (1993); and Lorenz. I C. Structure of the catalytic domain of the hepatitis C virus NS2-3 protease. Nature. August 17; 442(7104):831-5 (2006).

As another example, the heterologous polypeptide can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to a contiguous stretch of from 25 amino acids (aa) to 778 aa (e.g., from 25 aa to 50 aa, from 50 aa to 75 aa, from 75 aa to 100 aa, from 100 an to 150 aa, from 150 an to 200 aa, from 200 aa to 250 aa, from 250 an to 300 aa, from 300 an to 350 aa, from 350 an to 400 aa, from 400 aa to 450 aa, from 450 aa to 500 aa, from 500 an to 550 aa, from 550 aa to 600 aa, from 600 an to 650 aa, from 650 an to 700 aa, from 700 aa to 750 aa, or from 750 an to 778 aa) the following amino acid sequence:

LHAPTGSGKSTKVPAAYAAQGYKVLVLNPSVAA-TLGFGAYMSKAHGIDPNIRTGVRTIT TGSPITYS-TYGKFLADGGCSGGAYDIIICDECHSTDATSIL-GIGTVLDQAETAGARLVVLA TATPPGSVTVP-HPNIEEVALSTTGEIPFYGKAIPLEVIKGGRHLIF-CHSKKKCDELAAKLV ALGINAVAYYRGLDVS-VIPTSGDVVVVATDALMTGFTGDFDSVIDCN-TCVTQTVDFSLD PTFTIETITLPQDAVSRTQRR-GRTGRGKPGIYRFVAPGERPSGMFDSSVL-CECYDAGCA WYELTPAETTVRLRAYMNTPG-LPVCQDHLEFWEGVFTGLTHIDAHFLSQTKQS-GENLP YLVAYQATVCARAQAPPPSWDQMWKC-LIRLKPTLHGPTPLLYRLGAVQNEVTLTHPIT KYIMTCMSADLEVVTSTWVLVGGVLAALAAY-CLSTGCVVIVGRIVLSGKPAIIPDREVL YREFDE-MEECSQHLPYIEQGMMLAEQFKQKALGLLQ-TASRQAEVIAPAVQTNWQKLEA FWAKHM-WNFISGIQYLAGLSTLPGNPAIASLMAFTAAVT-SPLTTSQTLLFNILGGWVAA QLAAPGAATAFV-GAGLAGAAIGSVGLGKVLVDILAGYGAGVA-GALVAFKIMSGEVPST EDLVNLLPAILSPGALV-VGVVCAAILRRHVGPGEGAVQWMNRLIAFAS-RGNHVSPTHY VPESDAAARVTAILSSLTVTQL-LRRLHQWISSECTTPCSGSWLRDIWDWICE-VLSDFKTW LKAKLMPQLPG (SEQ ID NO:64). In some cases, the heterologous polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to a contiguous stretch of from 25 amino acids (aa) to 778 an (e.g., from 25 an to 50 aa, from 50 aa to 75 aa, from 75 aa to 100 aa, from 100 aa to 150 aa, from 150 aa to 200 aa, from 200 aa to 250 aa, from 250 aa to 300 aa, from 300 aa to 350 aa, from 350 aa to 400 aa, from 400 an to 450 aa, from 450 an to 500 aa, from 500 an to 550 aa, from 550 aa to 600 aa, from 600 aa to 650 aa, from 650 an to 700 aa, from 700 aa to 750 aa, or from 750 an to 778 aa) of the following amino acid sequence:

LHAPTGSGKSTKVPAAYAAQGYKVLVLNPSVA-ATLGFGAYMSKAHGIDPNIRTGVRTIT TGSPI-TYSTYGKFLADGGCSGGAYDIIICDECHSTDAT-SILGIGTVLDQAETAGARLVVLA TATPPGSVT-VPHPNIEEVALSTTGEIPFYGKAIPLEVIKGGRH-LIFCHSKKKCDELAAKLV ALGINAVAYYRGLD-VSVIPTSGDVVVVATDALMTGFTGDFDSVI-DCNTCVTQTVDFSLD PTFTIETITLPQDAVSR-TQRRGRTGRGKPGIYRFVAPGERPSGMFDSSVL-CECYDAGCA WYELTPAETTVRLRAYMNTPG-LPVCQDHLEFWEGVFTGLTHIDAHFLSQTKQS-GENLP YLVAYQATVCARAQAPPPSWDQMWKC-LIRLKPTLHGPTPLLYRLGAVQNEVTLTHPIT KYIMTCMSADLEVVTSTWVLVGGVLAALAAY-CLSTGCVVIVGRIVLSGKPAIIPDREVL YREFDE-MEECSQHLPYIEQGMMLAEQFKQKALGLLQ-TASRQAEVIAPAVQTNWQKLEA FWAKHMW-NFISGIQYLAGLSTLPGNPAIASLMAFTAAVT-SPLTTSQTLLFNILGGWVAA QLAAPGAATAF-VGAGLAGAAIGSVGLGKVLVDILAGYGAGV-AGALVAFKIMSGEVPST EDLVNLLPAILSP-GALVVGVVCAAILRRHVGPGEGAVQWMNRLIA-FASRGNHVSPTHY VPESDAAARVTAILSSLTV-TQLLRRLHQWISSECTTPCSGSWLRDIWDWICE-VLSDFKTW LKAKLMPQLPG (SEQ ID NO:64); and has a length of from 25 amino acids (aa) to 50 aa, from 50 aa to 100 aa, from 100 aa to 200 aa, from 200 aa to 300 aa, from 300 aa to 400 aa, from 400 aa to 500 aa, from 500 aa to 600 aa, from 600 an to 700 aa, or from 700 an to 778 aa. In some cases, the heterologous polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence:

LHAPTGSGKSTKVPAAYAAQGYKVLVLNPSVAA-TLGFGAYMSKAHGIDPNIRTGVRTIT TGSPITYS-TYGKFLADGGCSGGAYDIIICDECHSTDATSIL-GIGTVLDQAETAGARLVVLA TATPPGSVTV-PHPNIEEVALSTTGEIPFYGKAIPLEVIKGGRHL-IFCHSKKKCDELAAKLV ALGINAVAYYRGLD-VSVIPTSGDVVVVATDALMTGFTGDFDSVID-CNTCVTQTVDFSLD PTFTIETITLPQDAVSRTQ-

RRGRTGRGKPGIYRFVAPGERPSGMFDSSVL-CECYDAGCA WYELTPAETTVRLRAYMNTPG-LPVCQDHLEFWEGVFTGLTHIDAHFLSQTKQS-GENLP YLVAYQATVCARAQAPPPSWDQMWKC-LIRLKPTLHGPTPLLYRLGAVQNEVTLTHPIT KYIMTCMSADLEVVTSTWVLVGGVLAALAAY-CLSTGCVVIVGRIVLSGKPAIIPDREVL YREFDE-MEECSQHLPYIEQGMMLAEQFKQKALGLLQ-TASRQAEVIAPAVQTNWQKLEA FWAKHMWN-FISGIQYLAGLSTLPGNPAIASLMAFTAAVTSPLT-TSQTLLFNILGGWVAA QLAAPGAATAFVGAGL-AGAAIGSVGLGKVLVDILAGYGAGVAGALVAF-KIMSGEVPST EDLVNLLPAILSPGALVVGVVCA-AILRRHVGPGEGAVQWMNRLIAFASRGNHVSP-THY VPESDAAARVTAILSSLTVTQLLRRLHQ-WISSECTTPCSGSWLRDIWDWICEVLSDFKTW LKAKLMPQLPG (SEQ ID NO:64); and has a length of 778 amino acids. Such a polytope can include T-cell epitopes designated NS3-1, NS3-2, NS3-3, NS3-4, NS3-5, NS3-6, NS3-7, NS3-8, NS3-9, NS3-10, NS3-11, NS3-12, NS3-13, NS2-14, NS4a-1, NS4b-1, NS4b-2, NS4b-3, NS4b-4, NS4b-5, NS4b-6, NS4b-7, NS4b-8, NS4b-9, and NS4b-10 in FIG. 13B and FIGS. 15A-15N.

As another example, the heterologous polypeptide can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to a contiguous stretch of from 25 amino acids (aa) to 1985 aa (e.g., from 25 an to 50 aa, from 50 an to 75 aa, from 75 an to 100 aa, from 100 an to 150 an, from 150 an to 200 aa, from 200 aa to 250 aa, from 250 aa to 500 aa, from 500 an to 750 an, from 750 an to 1000 aa, from 1000 aa to 1500 aa, or from 1500 an to 1985 aa) of the following amino acid sequence:

(SEQ ID NO: 13)

APITAYAQQTRGLLGCIITSLTGRDKNQVEGEVQIVSTAAQTFLATCING

VCWTVYHGAGTRTIASPKGPVIQMYTNVDQDLVGWPAPQGARSLTPCTCG

SSDLYLVTRHADVIPVRRRGDSRGSLLSPRPISYLKGSAGGPLLCPAGHA

VGIFRAAVCTRGVAKAVDFIPVENLETTMRSPVFTDNSSPPAVPQSFQVA

HLHAPTGSGKSTKVPAAYAAQGYKVLVLNPSVAATLGFGAYMSKAHGIDP

NIRTGVRTITTGSPITYSTYGKFLADGGCSGGAYDIIICDECHSTDATSI

LGIGTVLDQAETAGARLVVLATATPPGSVTVPHPNIEEVALSTTGEIPFY

GKAIPLEVIKGGRHLIFCHSKKKCDELAAKLVALGINAVAYYRGLDVSVI

PTSGDVVVVATDALMTGFTGDFDSVIDCNTCVTQTVDFSLDPTFTIETTT

LPQDAVSRTQRRGRTGRGKPGIYRFVAPGERPSGMFDSSVLCECYDAGCA

WYELTPAETTVRLRAYMNTPGLPVCQDHLEFWEGVFTGLTHIDAHFLSQT

KQSGENLPYLVAYQATVCARAQAPPPSWDQMWKCLIRLKPTLHGPTPLLY

RLGAVQNEVTLTHPITKYIMTCMSADLEVVTSTWVLVGGVLAALAAYCLS

TGCVVIVGRIVLSGKPAIIPDREVLYREFDEMEECSQHLPYIEQGMMLAE

QFKQKALGLLQTASRQAEVIAPAVQTNWQKLEAFWAKHMWNFISGIQYLA

GLSTLPGNPAIASLMAFTAAVTSPLTTSQTLLFNILGGWVAAQLAAPGAA

-continued

TAFVGAGLAGAAIGSVGLGKVLVDILAGYGAGVAGALVAFKIMSGEVPST

EDLVNLLPAILSPGALVVGVVCAAILRRHVGPGEGAVQWMNRLIAFASRG

NHVSPTHYVPESDAAARVTAILSSLTVTQLLRRLHQWISSECTTPCSGSW

LRDIWDWICEVLSDFKTWLKAKLMPQLPGIPFVSCQRGYRGVWRGDGIMH

TRCHCGAEITGHVKNGTMRIVGPRTCRNMWSGTFPINAYTTGPCTPLPAP

NYTFALWRVSAEEYVEIRQVGDFHYVTGMTTDNLKCPCQVPSPEFFTELD

GVRLHRFAPPCKPLLREEVSFRVGLHEYPVGSQLPCEPEPDVAVLTSMLT

DPSHITAEAAGRRLARGSPPSVASSSASQLSAPSLKATCTANHDSPDAEL

IEANLLWRQEMGGNITRVESENKVVILDSFDPLVAEEDEREISVPAEILR

KSRRFAPALPIWARPDYNPPLLETWKKPDYEPPVVHGCPLPPPQSPPVPP

PRKKRTVVLTESTVSTALAELATKSFGSSSTSGITGDNTTTSSEPAPSGC

PPDSDAESYSSMPPLEGEPGDPDLSDGSWSTVSSEADTEDVVCCSMSYSW

TGALVTPCAAEEQKLPINALSNSLLRHHNLVYSTTSRSACQRQKKVTFDR

LQVLDSHYQDVLKEVKAAASKVKANLLSVEEACSLTPPHSAKSKFGYGAK

DVRCHARKAVNHINSVWKDLLEDSVTPIDTTIMAKNEVFCVQPEKGGRKP

ARLIVFPDLGVRVCEKMALYDVVSKLPLAVMGSSYGFQYSPGQRVEFLVQ

AWKSKKTPMGFSYDTRCFDSTVTESDIRTEEAIYQCCDLDPQARVAIKSL

TERLYVGGPLTNSRGENCGYRRCRASGVLTTSCGNTLTCYIKARAACRAA

GLQDCTMLVCGNNLVVICESAGVQEDAASLRAFTEAMTRYSAPPGDPPQP

EYDLELITSCSSNVSVAHDGAGKRVYYLTRDPTTPLARAAWETARHTPVN

SWLGNIIMFAPTLWARMILMTHFFSVLIARDQLEQALDCEIYGACYSIEP

LDLPPIIQRLHGLSAFSLHSYSPGEINRVAACLRKLGVPPLRAWRHRARS

VRARLLSRGGRAAICGKYLFNWAVRTKLKLTPIAAAGQLDLSGWFTAGYS

GGDIYHSVSHARPRWFWFCLLLLAAGVGIYLLPNR.

In some cases, the heterologous polypeptide can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence:

(SEQ ID NO: 13)

APITAYAQQTRGLLGCIITSLTGRDKNQVEGEVQIVSTAAQTFLATCING

VCWTVYHGAGTRTIASPKGPVIQMYTNVDQDLVGWPAPQGARSLTPCTCG

SSDLYLVTRHADVIPVRRRGDSRGSLLSPRPISYLKGSAGGPLLCPAGHA

VGIFRAAVCTRGVAKAVDFIPVENLETTMRSPVFTDNSSPPAVPQSFQVA

HLHAPTGSGKSTKVPAAYAAQGYKVLVLNPSVAATLGFGAYMSKAHGIDP

NIRTGVRTITTGSPITYSTYGKFLADGGCSGGAYDIIICDECHSTDATSI

LGIGTVLDQAETAGARLVVLATATPPGSVTVPHPNIEEVALSTTGEIPFY

GKAIPLEVIKGGRHLIFCHSKKKCDELAAKLVALGINAVAYYRGLDVSVI

-continued

```
PTSGDVVVVATDALMTGFTGDFDSVIDCNTCVTQTVDFSLDPTFTIETTT

LPQDAVSRTQRRGRTGRGKPGIYRFVAPGERPSGMFDSSVLCECYDAGCA

WYELTPAETTVRLRAYMNTPGLPVCQDHLEFWEGVFTGLTHIDAHFLSQT

KQSGENLPYLVAYQATVCARAQAPPPSWDQMWKCLIRLKPTLHGPTPLLY

RLGAVQNEVTLTHPITKYIMTCMSADLEVVTSTWVLVGGVLAALAAYCLS

TGCVVIVGRIVLSGKPAIIPDREVLYREFDEMEECSQHLPYIEQGMMLAE

QFKQKALGLLQTASRQAEVIAPAVQTNWQKLEAFWAKHMWNFISGIQYLA

GLSTLPGNPAIASLMAFTAAVTSPLTTSQTLLFNILGGWVAAQLAAPGAA

TAFVGAGLAGAAIGSVGLGKVLVDILAGYGAGVAGALVAFKIMSGEVPST

EDLVNLLPAILSPGALVVGVVCAAILRRHVGPGEGAVQWMNRLIAFASRG

NHVSPTHYVPESDAAARVTAILSSLTVTQLLRRLHQWISSECTTPCSGSW

LRDIWDWICEVLSDFKTWLKAKLMPQLPGIPFVSCQRGYRGVWRGDGIMH

TRCHCGAEITGHVKNGTMRIVGPRTCRNMWSGTFPINAYTTGPCTPLPAP

NYTFALWRVSAEEYVEIRQVGDFHYVTGMTTDNLKCPCQVPSPEFFTELD

GVRLHRFAPPCKPLLREEVSFRVGLHEYPVGSQLPCEPEPDVAVLTSMLT

DPSHITAEAAGRRLARGSPPSVASSSASQLSAPSLKATCTANHDSPDAEL

IEANLLWRQEMGGNITRVESENKVVILDSFDPLVAEEDEREISVPAEILR

KSRRFAPALPIWARPDYNPPLLETWKKPDYEPPVVHGCPLPPPQSPPVPP

PRKKRTVVLTESTVSTALAELATKSFGSSSTSGITGDNTTTSSEPAPSGC

PPDSDAESYSSMPPLEGEPGDPDLSDGSWSTVSSEADTEDVVCCSMSYSW

TGALVTPCAAEEQKLPINALSNSLLRHHNLVYSTTSRSACQRQKKVTFDR

LQVLDSHYQDVLKEVKAAASKVKANLLSVEEACSLTPPHSAKSKFGYGAK

DVRCHARKAVNHINSVWKDLLEDSVTPIDTTIMAKNEVFCVQPEKGGRKP

ARLIVFPDLGVRVCEKMALYDVVSKLPLAVMGSSYGFQYSPGQRVEFLVQ

AWKSKKTPMGFSYDTRCFDSTVTESDIRTEEAIYQCCDLDPQARVAIKSL

TERLYVGGPLTNSRGENCGYRRCRASGVLTTSCGNTLTCYIKARAACRAA

GLQDCTMLVCGNNLVVICESAGVQEDAASLRAFTEAMTRYSAPPGDPPQP

EYDLELITSCSSNVSVAHDGAGKRVYYLTRDPTTPLARAAWETARHTPVN

SWLGNIIMFAPTLWARMILMTHFFSVLIARDQLEQALDCEIYGACYSIEP

LDLPPIIQRLHGLSAFSLHSYSPGEINRVAACLRKLGVPPLRAWRHRARS

VRARLLSRGGRAAICGKYLFNWAVRTKLKLTPIAAAGQLDLSGWFTAGYS

GGDIYHSVSHARPRWFWFCLLLLAAGVGIYLLPNR;
```

and has a length of 1985 amino acids. Such a polytope can include T-cell epitopes designated NS3-1, NS3-2, NS3-3, NS3-4, NS3-5, NS3-6, NS3-7, NS3-8, NS3-9, NS3-10, NS3-11, NS3-12, NS3-13, NS3-14, NS4a-1, NS4b-1, NS4b-2, NS4b-3, NS4b-4, NS4b-5, NS4b-6, NS4b-7, NS4b-8, NS4b-9, NS4b-10, NS5a-1, NS5a-2, NS5b-1, NS5b-2 in FIGS. 13A-13B and FIGS. 15A-15N.

Additional T-Cell Epitopes

As discussed above, an E1/E2 a heterodimeric polypeptide of the present disclosure includes: a) an HCV E1 polypeptide; and b) a variant HCV E2 polypeptide comprising: i) an HCV E2 polypeptide; and ii) a heterologous polypeptide that comprises one or more T-cell epitopes (e.g., one or more T cell epitopes present in an HCV polypeptide other than an HCV E1 polypeptide or an HCV E2 polypeptide). The one or more T-cell epitopes can include one or more T-cell epitopes present in: a) an HCV NS3 polypeptide; b) an HCV NS2 polypeptide; c) an HCV NS4A polypeptide; d) an HCV NS4B polypeptide; e) an HCV NS5A polypeptide; f) an HCV NS5B polypeptide; g) an HCV core polypeptide; or h) an HCV p7 polypeptide. In some cases, the one or more T-cell epitopes are T-cell epitopes present in an HCV NS3 polypeptide. In some cases, the heterologous polypeptide further comprises one or more T cell epitopes present in: a) cholera toxin or toxoid; and/or b) tetanus toxin or toxoid; and/or c) diphtheria toxin or toxoid; and/or d) a meningococcal outer membrane protein.

Thus, in some cases, a variant HCV E2 polypeptide of an E1/E2 heterodimer of the present disclosure includes: a) an HCV E2 polypeptide; and b) a heterologous polypeptide that comprises one or more T-cell epitopes, where the one or more T-cell epitopes are T-cell epitopes present in: i) one or more of an HCV NS3 polypeptide, an HCV NS2 polypeptide, an HCV NS4A polypeptide, an HCV NS4B polypeptide, an HCV NS5A polypeptide, an HCV NS5B polypeptide, an HCV core polypeptide, and an HCV p7 polypeptide; and ii) one or more of cholera toxin or toxoid, tetanus toxin or toxoid, diphtheria toxin or toxoid, and a meningococcal outer membrane protein.

A T helper tetanus toxin epitope or other bacterial T-cell epitope could be fused (e.g., by recombinant expression) or chemically conjugated to the HCV polytope/E2 fusion protein and/or to the HCV polytope E1 fusion protein of an E1/E2 heterodimer of the present disclosure to further enhance both T and B cell responses to both the HCV polytope and E1/E2 moieties. Alternatively, the whole or part of the detoxified toxin ("toxoid") could be fused (e.g., by recombinant expression) or chemically conjugated to the HCV polytope/E1E2 protein, wherein specific amino acids of the toxins are mutated to render the toxins inactive, thereby generating toxoids. Methods of generating toxoids are well known in the art. Examples of bacterial epitopes include the use of diphtheria toxoid, meningococcal outer membrane protein, or mutant diphtheria protein CRM197 (see, e.g.: http://www(dot)medscape(dot)com/viewarticle/431127)

In some cases, a suitable tetanus toxoid polypeptide comprises the amino acid sequence QYIKANSKFIGIFE (SEQ ID NO:14). In some cases, a suitable tetanus toxoid polypeptide comprises the amino acid sequence QYIKANSKFIGITE (SEQ ID NO:65).

In some cases, a heterologous polypeptide can comprise cholera toxin (or toxoid) epitope. In some cases, a suitable heterologous polypeptide comprising a cholera toxoid epitope comprises a fragment of cholera toxin-B subunit (CT-B), e.g., a fragment of from 5 amino acids to 25 amino acids, or from 25 amino acids to 50 amino acids, of the following amino acid sequence: MIKLKFGVFF TVLLSSAYAH GTPQNITDLC AEYHNTQIHT LNDKIFSYTE SLAGKREMAI ITFKNGATFQ VEVPGSQHID SQKKAIERMK DTLRIAYLTE AKVEKLCVWN NKTPHAIAAI SMAN (SEQ ID NO:15).

In some cases, a heterologous polypeptide can comprise a tetanus toxin (or toxoid) T-cell epitope. In some cases, a suitable heterologous polypeptide comprising a tetanus toxin T-cell epitope comprises the amino acid sequence: ILMQYIKANSKFIGI (SEQ ID NO:16); and has a length of from 15 amino acids to 20 amino acids. In some cases, a suitable heterologous polypeptide comprising a tetanus toxin T-cell epitope comprises the amino acid sequence:

VNNESSE (SEQ ID NO:17). In some cases, a suitable heterologous polypeptide comprising a tetanus toxin T-cell epitope comprises the amino acid sequence: PGINGKAIHLVNNESSE (SEQ ID NO:18). In some cases, a suitable heterologous polypeptide comprising a tetanus toxin T-cell epitope comprises the amino acid sequence: PNRDIL (SEQ ID NO:19). In some cases, a suitable heterologous polypeptide comprising a tetanus toxin T-cell epitope comprises the amino acid sequence: FIGITEL (SEQ ID NO:20). In some cases, a suitable tetanus toxin T-cell epitope comprises the amino acid sequence: SYFPSV (SEQ ID NO:21). In some cases, a suitable heterologous polypeptide comprising a tetanus toxin T-cell epitope comprises the amino acid sequence: NSVDDALINSTKIYSYFPSV (SEQ ID NO:22). In some cases, a suitable heterologous polypeptide comprising a tetanus toxin T-cell epitope comprises the amino acid sequence: IDKISDVSTIVPYIGPALNI (SEQ ID NO:23).

In some cases, a heterologous polypeptide can comprise a diphtheria toxin T-cell epitope In some cases, a suitable heterologous polypeptide comprising a diphtheria toxin T-cell epitope comprises the amino acid sequence: QSIALSSLMVAQAIP (SEQ ID NO:24); and has a length of from 15 amino acids to 20 amino acids. In some cases, a suitable heterologous polypeptide comprising a diphtheria toxin T-cell epitope comprises the amino acid sequence:

PVFAGANYAAWAVNVAQVI (SEQ ID NO:25). In some cases, a suitable heterologous polypeptide comprising a diphtheria toxin T-cell epitope comprises the amino acid sequence:

VHHNTEEIVAQSIALSSLMV (SEQ ID NO:26). In some cases, a suitable heterologous polypeptide comprising a diphtheria toxin T-cell epitope comprises the amino acid sequence:

QSIALSSLMVAQAIPLVGEL (SEQ ID NO:66). In some cases, a suitable heterologous polypeptide comprising a diphtheria toxin T-cell epitope comprises the amino acid sequence:

VDIGFAAYNFVESIINLFQV (SEQ ID NO:67). In some cases, a suitable heterologous polypeptide comprising a diphtheria toxin T-cell epitope comprises the amino acid sequence:

QGESGHDIKITAENTPLPIA (SEQ ID NO:68). In some cases, a suitable heterologous polypeptide comprising a diphtheria toxin T-cell epitope comprises the amino acid sequence:

GVLLPTIPGKLDVNKSKTHI (SEQ ID NO:69). In some cases, a suitable heterologous polypeptide comprising a diphtheria toxin T-cell epitope comprises the amino acid sequence of CRM197 (see, e.g., Giannini et al. (1984) Nucl. Acids. Res. 12:4063).

The amino acid sequence of CRM197 is as follows:

```
                                          (SEQ ID NO: 27)
laddvvdssksfvmenfssyhgtkpgyvdsiqkgiqkpksgtqgnydddw

kefystdnkydaagysvdnenplsgkaggyvkvtypgltkvlalkvdnae

tikkelglsltteplmeqvgteefikrfgdgasrvvlslpfaegsssveyi

nnweqakalsveleinfetrgkrgqdamyeymaqacagnrvrrsvgssls

cinldwdvirdktktkieslkehgpiknkmsespnktvseekakqyleef

hqtalehpelselktvtgtnpvfaganyaawavnvaqvidsetadnlekt

taalsilpgigsvmgiadgavhhnteeivaqsialsslmvqaiplvgelv

digfaaynfvesiinlfqvvhnsynrpayspghktqpflhdgyavswntv
```

-continued

```
edsiirtgfqgesghdikitaentplpiagvllptipgkldvnkskthis

vngrkirmrcraidgdvtfcrpkspvyvgngvhanlhvafhrsssekihs

neissdsigvlgyqktvdhtkvnsklslffeiks.
```

In some cases, a heterologous polypeptide can comprise a tetanus toxin T-cell epitope and a diphtheria toxin T-cell epitope. In some of these cases, the heterologous polypeptide can comprise the amino acid sequence: IMQYIKANSKFIGIQSIALSSLMVAQ (SEQ ID NO:28); and can have a length of from 26 amino acids to 30 amino acids.

E1

An HCV E1 polypeptide suitable for inclusion in an E1/E2 heterodimer of the present disclosure can have a length of from about 150 amino acids (aa) to about 175 aa, from about 175 aa to about 195 aa, from about 131 aa to about 175 aa, or from about 175 aa to about 193 aa. In some cases, an HCV E1 polypeptide suitable for inclusion in an E1/E2 heterodimer of the present disclosure is an HCV E1 ectodomain polypeptide. In some cases, an HCV E1 polypeptide suitable for inclusion in an E1/E2 heterodimer of the present disclosure is a full-length HCV E1 polypeptide.

In FIGS. 1A-1C, the amino acid sequence of E1 is amino acid 192 to amino acid 383. In FIGS. 2A-2C, the amino acid sequence of E1 is amino acid 192 to amino acid 383. In FIGS. 3A-3C, the amino acid sequence of E1 is amino acid 192 to amino acid 384. In FIGS. 4A-4B, the amino acid sequence of E1 is amino acid 192 to amino acid 383. Amino acids at around 170 through approximately 191 serve as a signal sequence for E1. As used herein, "E1 polypeptide" includes a precursor E1 protein, including the signal sequence; includes a mature E1 polypeptide which lacks this sequence; and includes an E1 polypeptide with a heterologous signal sequence. An E1 polypeptide can include a C-terminal membrane anchor sequence which occurs at approximately amino acid positions 360-383 (see, e.g., WO 96/04301). In some cases, a suitable E1 polypeptide lacks a C-terminal portion that includes a transmembrane region. For example, in some cases, a suitable E1 polypeptide lacks the C-terminal portion from amino acid 330 to amino acid 384, or from amino acid 360 to amino acid 384. E1 polypeptides can be an E1 polypeptide of any genotype, subtype or isolate of HCV. E1 polypeptides of genotype 1 and E1 polypeptides of genotype 3 are included in an E1/E2 heterodimer of the present disclosure.

An E1 polypeptide can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to an amino acid sequence of an E1 polypeptide depicted in FIGS. 1A-1C, FIGS. 2A-2C, FIGS. 3A-3C, or FIGS. 4A-4B.

An E1 polypeptide can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to an amino acid sequence of an E1 polypeptide depicted in FIGS. 1A-1C. For example, an E1 polypeptide of genotype 1A can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 192-383 of an amino acid sequence identified as 1A and depicted in FIGS. 1A-1C. For example, an E1 polypeptide of genotype 1B can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 192-383 of an amino acid sequence identified as 1B and depicted in FIGS. 1A-1C. For example, an E1 polypeptide of genotype 1C can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 192-383 of an amino acid sequence identified as 1C and depicted in FIGS. 1A-1C.

An E1 polypeptide can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to an amino acid sequence of an E1 polypeptide depicted in FIGS. 2A-2C. For example, an E1 polypeptide of genotype 2A can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 192-383 of an amino acid sequence identified as 2A and depicted in FIGS. 2A-2C. For example, an E1 polypeptide of genotype 2B can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 192-383 of an amino acid sequence identified as 2B and depicted in FIGS. 2A-2C.

An E1 polypeptide can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the consensus E1 polypeptide amino acid sequence depicted in FIGS. 3A-3C.

An E1 polypeptide can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to an amino acid sequence of an E1 polypeptide depicted in FIGS. 4A-4B. For example, an E1 polypeptide of genotype 7A can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 192-383 of the amino acid sequence depicted in FIGS. 4A-4B.

Additional Polypeptides

In any of the above-described embodiments, one or both of the polypeptide chains of the E1/E2 heterodimer can include one or more additional polypeptides. For example, in some cases, the E1 polypeptide or the variant E2 polypeptide can include an Ig Fc polypeptide at the C-terminus of the E1 polypeptide or the variant E2 polypeptide. As another example, in some cases, the E1 polypeptide or the variant E2 polypeptide can include an Ig Fc polypeptide at the N-terminus of the E1 polypeptide or the variant E2 polypeptide. Ig Fc polypeptides are known in the art, and are described elsewhere herein.

IB. E1E2 Heterodimers Comprising a Variant HCV E1 and HCV E2

The present disclosure provides an E1/E2 heterodimer, where the E1/E2 heterodimer comprises: a) a variant HCV E1 polypeptide, where the variant HCV E1 polypeptide comprises: i) an HCV E1 polypeptide; and ii) a heterologous polypeptide that comprises one or more T-cell epitopes (e.g., one or more T-cell epitopes not present in an HCV E1 or an HCV E2 polypeptide; e.g., one or more T-cell epitopes present in an HCV polypeptide other than an HCV E1 or an HCV E2 polypeptide); and b) an HCV E2 polypeptide. Thus, in some cases, a heterodimeric polypeptide of the present disclosure includes: a) an HCV E2 polypeptide; and b) a variant HCV E1 polypeptide comprising: i) an HCV E1 polypeptide; and ii) a heterologous polypeptide that comprises one or more T-cell epitopes (e.g., one or more T cell epitopes present in an HCV polypeptide other than an HCV E1 polypeptide or an HCV E2 polypeptide). The one or more T-cell epitopes can include one or more T-cell epitopes present in: a) an HCV NS3 polypeptide; b) an HCV NS2 polypeptide; c) an HCV NS4A polypeptide; d) an HCV NS4B polypeptide; e) an HCV NS5A polypeptide; f) an HCV NS5B polypeptide; g) an HCV core polypeptide; or h) an HCV p7 polypeptide. In some cases, the one or more T-cell epitopes are T-cell epitopes present in an HCV NS3 polypeptide. In some cases, the heterologous polypeptide further comprises one or more T cell epitopes present in: a) cholera toxin or toxoid; and/or b) tetanus toxin or toxoid; and/or c) diphtheria toxin or toxoid; and/or d) a meningococcal outer membrane protein. The heterologous polypeptide is also referred to as a "polytope."

An E1/E2 heterodimer of the present disclosure (e.g., an E1/E2 heterodimer comprising: a) an HCV E2 polypeptide; and b) a variant HCV E2 polypeptide comprising: i) an HCV E2 polypeptide; and ii) a heterologous polypeptide comprising one or more T-cell epitopes), when administered to an individual in need thereof, induces an immune response in the individual to one or more HCV genotypes. An E1/E2 heterodimer of the present disclosure, when administered to an individual in need thereof, induces an immune response in the individual to one or more HCV genotypes, where the immune response is greater than the immune response induced by administration of an HCV E1/E2 heterodimer comprising a wild-type E2 and a wild-type E1 polypeptide or an E1 polypeptide lacking the polytope.

For example, in some cases, an E1/E2 heterodimer of the present disclosure (e.g., an E1/E2 heterodimer comprising: a) an HCV E2 polypeptide; and b) a variant HCV E1 polypeptide comprising: i) an HCV E1 polypeptide; and ii) a heterologous polypeptide comprising one or more T-cell epitopes), when administered to an individual in need thereof, induces CTLs specific for HCV, where the number of HCV-specific CTLs induced is at least 10%, at least 15%, at least 20%, at least 25%, at least 30%, at least 40%, at least 50%, at least 75%, at least 100% (or 2-fold), at least 2.5-fold, at least 5-fold, at least 7.5-fold, at least 10-fold, at least 20-fold, at least 50-fold, or at least 100-fold, or more than 100-fold, higher than the number of HCV-specific CTLs induced by administration of an HCV E1/E2 heterodimer comprising a wild-type E2 and a wild-type E1 polypeptide or an E1 polypeptide lacking the polytope.

In some cases, an E1/E2 heterodimer of the present disclosure (e.g., an E1/E2 heterodimer comprising: a) an HCV E2 polypeptide; and b) a variant HCV E1 polypeptide comprising: i) an HCV E1 polypeptide; and ii) a heterologous polypeptide comprising one or more T-cell epitopes present in an HCV polypeptide other than an HCV E1 polypeptide or an HCV E2 polypeptide), when administered to an individual in need thereof, induces production of HCV-specific $CD4^+$ T cells and $CD8^+$ T cells in the individual, where the number of HCV-specific $CD4^+$ T cells and $CD8^+$ T cells is increased, such that the percent of the total peripheral blood T cells (i.e., the total number of $CD4^+$ T cells+$CD8^+$ T cells in the peripheral blood) that are HCV-specific $CD4^+$ T cells and $CD8^+$ T cells is from 0.5% to 10% (e.g., from 0.5% to 1%, from 1% to 2%, from 2% to 5%, or from 5% to 10%). The number of HCV-specific $CD4^+$ T cells and $CD8^+$ T cells in a control individual (e.g., an individual not infected with HCV) not treated with the E1/E2 heterodimer would be undetectable.

For example, in some cases, an E1/E2 heterodimer of the present disclosure (e.g., an E1/E2 heterodimer comprising: a) an HCV E2 polypeptide; and b) a variant HCV E1 polypeptide comprising: i) an HCV E1 polypeptide; and ii) a heterologous polypeptide comprising one or more HCV NS3 T-cell epitopes), when administered to an individual in need thereof, induces production of HCV NS3-specific $CD4^+$ T cells and $CD8^+$ T cells in the individual, where the number of HCV NS3-specific $CD4^+$ T cells and $CD8^+$ T cells is increased, such that the percent of the total peripheral blood T cells (i.e., the total number of $CD4^+$ T cells+$CD8^+$ T cells in the peripheral blood) that are HCV NS3-specific $CD4^+$ T cells and $CD8^+$ T cells is from 0.1% to 10% (e.g., from 0.1% to 0.5%, from 0.5% to 1%, from 1% to 2%, from 2% to 5%, or from 5% to 10%). The number of HCV NS3-specific $CD4^+$ T cells and $CD8^+$ T cells in a control individual (e.g., an individual not infected with HCV) not treated with the E1/E2 heterodimer would be undetectable.

In some cases, an E1/E2 heterodimer of the present disclosure (e.g., an E1/E2 heterodimer comprising: a) an HCV E2 polypeptide; and b) a variant HCV E1 polypeptide comprising: i) an HCV E1 polypeptide; and ii) a heterologous polypeptide comprising one or more T-cell epitopes present in an HCV polypeptide other than an HCV E1 polypeptide or an HCV E2 polypeptide), when administered to an individual in need thereof, increases the number of HCV E1/E2-specific $CD4^+$ T cells and $CD8^+$ T cells in the individual by at least 10%, at least 15%, at least 20%, at least 25%, at least 30%, at least 40%, at least 50%, at least 75%, at least 100% (or 2-fold), at least 2.5-fold, at least 5-fold, at least 7.5-fold, at least 10-fold, at least 20-fold, at least 50-fold, or at least 100-fold, or more than 100-fold, compared to the number of HCV E1/E2-specific $CD4^+$ T cells and $CD8^+$ T cells in the individual induced by administration of an E1/E2 heterodimer comprising a wild-type E2 polypeptide and a wild-type E1 polypeptide, or an E1 polypeptide lacking the polytope, or compared to the number of HCV E1/E2-specific $CD4^+$ T cells and $CD8^+$ T cells in the individual before administration of the E1/E2 heterodimer of the present disclosure.

As another example, in some cases, an E1/E2 heterodimer of the present disclosure (e.g., an E1/E2 heterodimer comprising: a) an HCV E2 polypeptide; and b) a variant HCV E1 polypeptide comprising: i) an HCV E1 polypeptide; and ii) a heterologous polypeptide comprising one or more T-cell epitopes present in an HCV polypeptide other than an HCV E1 polypeptide or an HCV E2 polypeptide), when administered to an individual in need thereof, induces helper T lymphocytes (e.g., $CD4^+$ T cells) specific for HCV, where the number of HCV-specific helper T lymphocytes induced is at least 10%, at least 15%, at least 20%, at least 25%, at least 30%, at least 40%, at least 50%, at least 75%, at least 100% (or 2-fold), at least 2.5-fold, at least 5-fold, at least 7.5-fold, at least 10-fold, at least 20-fold, at least 50-fold, or at least 100-fold, or more than 100-fold, higher than the number of HCV-specific helper T cells induced by administration of an E1/E2 heterodimer comprising a wild-type E2 polypeptide and a wild-type E1 polypeptide, or an E1 polypeptide lacking the polytope, or compared to the number of HCV-specific helper T cells in the individual before administration of the E1/E2 heterodimer of the present disclosure.

In some cases, an E1/E2 heterodimer of the present disclosure (e.g., an E1/E2 heterodimer comprising: a) an HCV E2 polypeptide; and b) a variant HCV E1 polypeptide comprising: i) an HCV E1 polypeptide; and ii) a heterologous polypeptide comprising one or more T-cell epitopes present in an HCV polypeptide other than an HCV E1 polypeptide or an HCV E2 polypeptide), when administered to an individual in need thereof, induces antibody specific for HCV, where the level of HCV-specific antibody induced is at least at high as the level of HCV-specific antibody induced by administration of an E1/E2 heterodimer comprising a wild-type E2 polypeptide and a wild-type E1 polypeptide, or an E1 polypeptide lacking the polytope.

In some cases, an E1/E2 heterodimer of the present disclosure (e.g., an E1/E2 heterodimer comprising: a) an HCV E2 polypeptide; and b) a variant HCV E1 polypeptide comprising: i) an HCV E1 polypeptide; and ii) a heterologous polypeptide comprising one or more T-cell epitopes present in an HCV polypeptide other than an HCV E1 polypeptide or an HCV E2 polypeptide), when administered to an individual in need thereof, induces antibody specific for HCV, where the level of HCV-specific antibody induced is at least 10%, at least 15%, at least 20%, at least 25%, at least 30%, at least 40%, at least 50%, at least 75%, at least 100% (or 2-fold), at least 2.5-fold, at least 5-fold, at least 7.5-fold, at least 10-fold, at least 20-fold, at least 50-fold, or at least 100-fold, or more than 100-fold, higher than the level of HCV-specific antibody induced by administration of an E1/E2 heterodimer comprising a wild-type E2 polypeptide and a wild-type E1 polypeptide, or an E1 polypeptide lacking the polytope.

An E1/E2 heterodimer of the present disclosure (e.g., an E1/E2 heterodimer comprising: a) an HCV E2 polypeptide;

and b) a variant HCV E1 polypeptide comprising: i) an HCV E1 polypeptide; and ii) a heterologous polypeptide comprising one or more T-cell epitopes present in an HCV polypeptide other than an HCV E1 polypeptide or an HCV E2 polypeptide), when administered to an individual in need thereof, induces an immune response (e.g., a cellular immune response) in the individual to one or more HCV genotypes. In some cases, an E1/E2 heterodimer of the present disclosure (e.g., an E1/E2 heterodimer comprising: a) an HCV E2 polypeptide; and b) a variant HCV E1 polypeptide comprising: i) an HCV E1 polypeptide; and ii) a heterologous polypeptide comprising one or more T-cell epitopes present in an HCV polypeptide other than an HCV E1 polypeptide or an HCV E2 polypeptide), when administered to an individual in need thereof, induces an immune response in the individual to HCV genotype 1. In some cases, an E1/E2 heterodimer of the present disclosure (e.g., an E1/E2 heterodimer comprising: a) an HCV E2 polypeptide; and b) a variant HCV E1 polypeptide comprising: i) an HCV E1 polypeptide; and ii) a heterologous polypeptide comprising one or more T-cell epitopes present in an HCV polypeptide other than an HCV E1 polypeptide or an HCV E2 polypeptide), when administered to an individual in need thereof, induces an immune response in the individual to HCV genotype 2. In some cases, an E1/E2 heterodimer of the present disclosure (e.g., an E1/E2 heterodimer comprising: a) an HCV E2 polypeptide; and b) a variant HCV E1 polypeptide comprising: i) an HCV E1 polypeptide; and ii) a heterologous polypeptide comprising one or more T-cell epitopes present in an HCV polypeptide other than an HCV E1 polypeptide or an HCV E2 polypeptide), when administered to an individual in need thereof, induces an immune response in the individual to HCV genotype 3. In some cases, an E1/E2 heterodimer of the present disclosure (e.g., an E1/E2 heterodimer comprising: a) an HCV E2 polypeptide; and b) a variant HCV E1 polypeptide comprising: i) an HCV E1 polypeptide; and ii) a heterologous polypeptide comprising one or more T-cell epitopes present in an HCV polypeptide other than an HCV E1 polypeptide or an HCV E2 polypeptide), when administered to an individual in need thereof, induces an immune response in the individual to HCV genotype 1 and HCV genotype 3. In some cases, an E1/E2 heterodimer of the present disclosure (e.g., an E1/E2 heterodimer comprising: a) an HCV E2 polypeptide; and b) a variant HCV E1 polypeptide comprising: i) an HCV E1 polypeptide; and ii) a heterologous polypeptide comprising one or more T-cell epitopes present in an HCV polypeptide other than an HCV E1 polypeptide or an HCV E2 polypeptide), when administered to an individual in need thereof, induces an immune response in the individual to HCV genotype 1, HCV genotype 2, and HCV genotype 3. In some cases, an E1/E2 heterodimer of the present disclosure (e.g., an E1/E2 heterodimer comprising: a) an HCV E2 polypeptide; and b) a variant HCV E1 polypeptide comprising: i) an HCV E1 polypeptide; and ii) a heterologous polypeptide comprising one or more T-cell epitopes present in an HCV polypeptide other than an HCV E1 polypeptide or an HCV E2 polypeptide), when administered to an individual in need thereof, induces an immune response in the individual to HCV genotype 1, HCV genotype 2, HCV genotype 3, and HCV genotype 7. In some cases, an E1/E2 heterodimer of the present disclosure (e.g., an E1/E2 heterodimer comprising: a) an HCV E2 polypeptide; and b) a variant HCV E1 polypeptide comprising: i) an HCV E1 polypeptide; and ii) a heterologous polypeptide comprising one or more T-cell epitopes present in an HCV polypeptide other than an HCV E1 polypeptide or an HCV E2 polypeptide), when administered to an individual in need thereof, induces an immune response in the individual to HCV genotype 1, HCV genotype 2, HCV genotype 3, HCB genotype 4, HCV genotype 5, HCV genotype 6, and HCV genotype 7.

Variant E1

As noted above, a variant E1 polypeptide of an HCV E1/E2 heterodimer of the present disclosure comprises: i) an HCV E1 polypeptide; and ii) a heterologous polypeptide comprising one or more T cell epitopes (e.g., one or more T-cell epitopes not present in an HCV E1 or an HCV E2 polypeptide; e.g., one or more T-cell epitopes present in an HCV polypeptide other than an HCV E1 or an HCV E2 polypeptide). In some cases, the variant HCV E1 polypeptide comprises, in order from amino terminus (N-terminus) to carboxyl terminus (C-terminus): i) an HCV E1 polypeptide; and ii) a heterologous polypeptide comprising one or more T cell epitopes. In some cases, the variant HCV E1 polypeptide comprises, in order from N-terminus to C-terminus: i) a heterologous polypeptide comprising one or more T cell epitopes; and ii) an HCV E1 polypeptide.

E1

An HCV E1 polypeptide suitable for inclusion in a variant E1 polypeptide of an E1/E2 heterodimer of the present disclosure can have a length of from about 150 amino acids (aa) to about 175 aa, from about 175 aa to about 195 aa, from about 131 aa to about 175 aa, or from about 175 an to about 193 aa. In some cases, an HCV E1 polypeptide suitable for inclusion in a variant E1 polypeptide of an E1/E2 heterodimer of the present disclosure is an HCV E1 ectodomain polypeptide. In some cases, an HCV E1 polypeptide suitable for inclusion in a variant E1 polypeptide of an E1/E2 heterodimer of the present disclosure is a full-length HCV E1 polypeptide.

In FIGS. 1A-1C, the amino acid sequence of E1 is amino acid 192 to amino acid 383. In FIGS. 2A-2C, the amino acid sequence of E1 is amino acid 192 to amino acid 383. In FIGS. 3A-3C, the amino acid sequence of E1 is amino acid 192 to amino acid 384. In FIGS. 4A-4B, the amino acid sequence of E1 is amino acid 192 to amino acid 383. Amino acids at around 170 through approximately 191 serve as a signal sequence for E1. As used herein, "E1 polypeptide" includes a precursor E1 protein, including the signal sequence; includes a mature E1 polypeptide which lacks this sequence; and includes an E1 polypeptide with a heterologous signal sequence. An E1 polypeptide can include a C-terminal membrane anchor sequence which occurs at approximately amino acid positions 360-383 (see, e.g., WO 96/04301). In some cases, a suitable E1 polypeptide lacks a C-terminal portion that includes a transmembrane region. For example, in some cases, a suitable E1 polypeptide lacks the C-terminal portion from amino acid 330 to amino acid 384, or from amino acid 360 to amino acid 384. E1 polypeptides can be an E1 polypeptide of any genotype, subtype or isolate of HCV. E1 polypeptides of genotype 1 and E1 polypeptides of genotype 3 are included in an E1/E2 heterodimer of the present disclosure.

An E1 polypeptide suitable for inclusion in a variant E1 polypeptide of an E1/E2 heterodimer of the present disclosure can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to an amino acid sequence of an E1 polypeptide depicted in FIGS. 1A-1C, FIGS. 2A-2C, FIGS. 3A-3C, or FIGS. 4A-4B.

An E1 polypeptide suitable for inclusion in a variant E1 polypeptide of an E1/E2 heterodimer of the present disclosure can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to an amino acid sequence of an E1 polypeptide depicted in FIGS. 1A-1C. For example, an E1 polypeptide of genotype 1A can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 192-383 of an amino acid sequence identified as 1A and depicted in FIGS. 1A-1C. For example, an E1 polypeptide of genotype 1B can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 192-383 of an amino acid sequence identified as 1B and depicted in FIGS. 1A-1C. For example, an E1 polypeptide of genotype 1C can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 192-383 of an amino acid sequence identified as 1C and depicted in FIGS. 1A-1C.

An E1 polypeptide suitable for inclusion in a variant E1 polypeptide of an E1/E2 heterodimer of the present disclosure can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to an amino acid sequence of an E1 polypeptide depicted in FIGS. 2A-2C. For example, an E1 polypeptide of genotype 2A can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 192-383 of an amino acid sequence identified as 2A and depicted in FIGS. 2A-2C. For example, an E1 polypeptide of genotype 2B can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 192-383 of an amino acid sequence identified as 2B and depicted in FIGS. 2A-2C.

An E1 polypeptide suitable for inclusion in a variant E1 polypeptide of an E1/E2 heterodimer of the present disclosure can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the consensus E1 polypeptide amino acid sequence depicted in FIGS. 3A-3C.

An E1 polypeptide suitable for inclusion in a variant E1 polypeptide of an E1/E2 heterodimer of the present disclosure can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to an amino acid sequence of an E1 polypeptide depicted in FIGS. 4A-4B. For example, an E1 polypeptide of genotype 7A can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 192-383 of the amino acid sequence depicted in FIGS. 4A-4B.

Heterologous Polypeptide

In some cases, the heterologous polypeptide comprises 1, 2, 3, 4, 5, 6, 7, 8, 9, or 10, or more than 10 (e.g., from 10 to 15, from 15 to 20, from 20 to 25, or from 25 to 30, or more than 30), T cell epitopes. T-cell epitopes are epitopes that, when presented with a major histocompatibility complex (MHC) (e.g., a human leukocyte antigen (HLA)) Class I or MHC Class II molecule, are recognized and bound by a T-cell receptor (TCR) present on a T cell surface. T-cell epitopes include epitopes recognized by cytotoxic T cells (e.g., $CD8^+$ T cells), and epitopes recognized by helper T cells (e.g., $CD4^+$ T cells).

The one or more T-cell epitopes can include one or more T-cell epitopes present in: a) an HCV NS3 polypeptide; b) an HCV NS2 polypeptide; c) an HCV NS4A polypeptide; d) an HCV NS4B polypeptide; e) an HCV NS5A polypeptide; f) an HCV NS5B polypeptide; g) an HCV core polypeptide; or h) an HCV p7 polypeptide. In some cases, the one or more T-cell epitopes are T-cell epitopes present in an HCV NS3 polypeptide. In some cases, the heterologous polypeptide further comprises one or more T cell epitopes present in: a) cholera toxin or toxoid; and/or b) tetanus toxin or toxoid; and/or c) diphtheria toxin or toxoid; and/or d) a meningococcal outer membrane protein. Other examples of strong T helper epitopes are diphtheria toxoid, tetanus toxoid, meningococcal outer membrane protein, or mutant diphtheria protein CRM197 (see, e.g.: http://www(dot)medscape(dot)com/viewarticle/431127).

In some cases, the heterologous polypeptide comprises a single T-cell epitope. In some cases, the heterologous polypeptide comprises a single HCV-NS3 T-cell epitope. In some cases, the heterologous polypeptide comprises 2 or more T-cell epitopes. In some cases, the heterologous polypeptide comprises 2 or more HCV-NS3 T-cell epitopes. In some cases, the heterologous polypeptide comprises 3 or more HCV-NS3 T-cell epitopes. In some cases, the heterologous polypeptide comprises 4 or more HCV-NS3 T-cell epitopes. In some cases, the heterologous polypeptide comprises a single HCV-NS3 $CD4^+$ T-cell epitope. In some cases, the heterologous polypeptide comprises 2 or more HCV-NS3 $CD4^+$ T-cell epitopes. In some cases, the heterologous polypeptide comprises one or more HCV $CD8^+$ T cell epitopes. In some cases, the heterologous polypeptide comprises a single HCV-NS3 $CD8^+$ T-cell epitope. In some cases, the heterologous polypeptide comprises 2 or more HCV-NS3 $CD8^+$ T-cell epitopes. In some cases, the heterologous polypeptide comprises at least one HCV $CD4^+$ T cell epitope and at least one HCV $CD8^+$ T cell epitope. In some cases, the heterologous polypeptide comprises at least one HCV-NS3 $CD4^+$ T cell epitope and at least one HCV-NS3 $CD8^+$ T cell epitope. In some cases, heterologous polypeptide comprises 2 or more HCV-NS3 $CD4^+$ T-cell epitopes and 2 or more HCV-NS3 $CD8^+$ T-cell epitopes. In some cases, the heterologous polypeptide comprises 2, 3, 4, or 5 HCV-NS3 $CD4^+$ T-cell epitopes and 2, 3, 4, or 5 HCV-NS3 $CD8^+$ T-cell epitopes.

In some cases, the heterologous polypeptide comprises a single T-cell epitope. In some cases, the heterologous polypeptide comprises a single HCV-NS2 T-cell epitope. In some cases, the heterologous polypeptide comprises 2 or more T-cell epitopes. In some cases, the heterologous polypeptide comprises 2 or more HCV-NS2 T-cell epitopes. In some cases, the heterologous polypeptide comprises 3 or more HCV-NS2 T-cell epitopes. In some cases, the heterologous polypeptide comprises 4 or more HCV-NS2 T-cell epitopes. In some cases, the heterologous polypeptide comprises a single HCV-NS2 $CD4^+$ T-cell epitope. In some cases, the heterologous polypeptide comprises 2 or more HCV-NS2 $CD4^+$ T-cell epitopes. In some cases, the heterologous polypeptide comprises one or more HCV $CD8^+$ T cell epitopes. In some cases, the heterologous polypeptide comprises a single HCV-NS2 $CD8^+$ T-cell epitope. In some cases, the heterologous polypeptide comprises 2 or more HCV-NS2 $CD8^+$ T-cell epitopes. In some cases, the heterologous polypeptide comprises at least one HCV $CD4^+$ T cell epitope and at least one HCV $CD8^+$ T cell epitope. In some cases, the heterologous polypeptide comprises at least one HCV-NS2 $CD4^+$ T cell epitope and at least one HCV-NS2 $CD8^+$ T cell epitope. In some cases, heterologous polypeptide comprises 2 or more HCV-NS2 $CD4^+$ T-cell epitopes and 2 or more HCV-NS2 $CD8^+$ T-cell epitopes. In some cases, the heterologous polypeptide comprises 2, 3, 4, or 5 HCV-NS2 $CD4^+$ T-cell epitopes and 2, 3, 4, or 5 HCV-NS2 $CD8^+$ T-cell epitopes.

In some cases, the heterologous polypeptide comprises a single T-cell epitope. In some cases, the heterologous polypeptide comprises a single HCV-NS4A T-cell epitope. In some cases, the heterologous polypeptide comprises 2 or more T-cell epitopes. In some cases, the heterologous polypeptide comprises 2 or more HCV-NS4A T-cell epitopes. In some cases, the heterologous polypeptide comprises 3 or more HCV-NS4A T-cell epitopes. In some cases, the heterologous polypeptide comprises 4 or more HCV-NS4A T-cell epitopes. In some cases, the heterologous polypeptide comprises a single HCV-NS4A $CD4^+$ T-cell epitope. In some cases, the heterologous polypeptide comprises 2 or more HCV-NS4A $CD4^+$ T-cell epitopes. In some cases, the heterologous polypeptide comprises one or more HCV $CD8^+$ T cell epitopes. In some cases, the heterologous polypeptide comprises a single HCV-NS4A $CD8^+$ T-cell epitope. In some cases, the heterologous polypeptide comprises 2 or more HCV-NS4A $CD8^+$ T-cell epitopes. In some cases, the heterologous polypeptide comprises at least one HCV $CD4^+$ T cell epitope and at least one HCV $CD8^+$ T cell epitope. In some cases, the heterologous polypeptide comprises at least one HCV-NS4A $CD4^+$ T cell epitope and at least one HCV-NS4A $CD8^+$ T cell epitope. In some cases, heterologous polypeptide comprises 2 or more HCV-NS4A $CD4^+$ T-cell epitopes and 2 or more HCV-NS4A $CD8^+$ T-cell epitopes. In some cases, the heterologous polypeptide comprises 2, 3, 4, or 5 HCV-NS4A $CD4^+$ T-cell epitopes and 2, 3, 4, or 5 HCV-NS4A $CD8^+$ T-cell epitopes.

In some cases, the heterologous polypeptide comprises a single T-cell epitope. In some cases, the heterologous polypeptide comprises a single HCV-NS5A T-cell epitope. In some cases, the heterologous polypeptide comprises 2 or more T-cell epitopes. In some cases, the heterologous polypeptide comprises 2 or more HCV-NS5A T-cell epitopes. In some cases, the heterologous polypeptide comprises 3 or more HCV-NS5A T-cell epitopes. In some cases, the heterologous polypeptide comprises 4 or more HCV-NS5A T-cell epitopes. In some cases, the heterologous polypeptide comprises a single HCV-NS5A $CD4^+$ T-cell epitope. In some cases, the heterologous polypeptide comprises 2 or more HCV-NS5A $CD4^+$ T-cell epitopes. In some cases, the heterologous polypeptide comprises one or more HCV $CD8^+$ T cell epitopes. In some cases, the heterologous polypeptide comprises a single HCV-NS5A $CD8^+$ T-cell epitope. In some cases, the heterologous polypeptide comprises 2 or more HCV-NS5A $CD8^+$ T-cell epitopes. In some cases, the heterologous polypeptide comprises at least one HCV $CD4^+$ T cell epitope and at least one HCV $CD8^+$ T cell epitope. In some cases, the heterologous polypeptide comprises at least one HCV-NS5A $CD4^+$ T cell epitope and at least one HCV-NS5A $CD8^+$ T cell epitope. In some cases, heterologous polypeptide comprises 2 or more HCV-NS5A $CD4^+$ T-cell epitopes and 2 or more HCV-NS5A $CD8^+$ T-cell epitopes. In some cases, the heterologous polypeptide comprises 2, 3, 4, or 5 HCV-NS5A $CD4^+$ T-cell epitopes and 2, 3, 4, or 5 HCV-NS5A $CD8^+$ T-cell epitopes.

In some cases, the heterologous polypeptide comprises a single T-cell epitope. In some cases, the heterologous polypeptide comprises a single HCV-NS5B T-cell epitope. In some cases, the heterologous polypeptide comprises 2 or more T-cell epitopes. In some cases, the heterologous polypeptide comprises 2 or more HCV-NS5B T-cell epitopes. In some cases, the heterologous polypeptide comprises 3 or more HCV-NS5B T-cell epitopes. In some cases, the heterologous polypeptide comprises 4 or more HCV-NS5B T-cell epitopes. In some cases, the heterologous polypeptide comprises a single HCV-NS5B $CD4^+$ T-cell epitope. In some cases, the heterologous polypeptide comprises 2 or more HCV-NS5B $CD4^+$ T-cell epitopes. In some cases, the heterologous polypeptide comprises one or more HCV $CD8^+$ T cell epitopes. In some cases, the heterologous polypeptide comprises a single HCV-NS5B $CD8^+$ T-cell epitope. In some cases, the heterologous polypeptide comprises 2 or more HCV-NS5B $CD8^+$ T-cell epitopes. In some cases, the heterologous polypeptide comprises at least one HCV $CD4^+$ T cell epitope and at least one HCV $CD8^+$ T cell epitope. In some cases, the heterologous polypeptide comprises at least one HCV-NS5B $CD4^+$ T cell epitope and at least one HCV-NS5B $CD8^+$ T cell epitope. In some cases, heterologous polypeptide comprises 2 or more HCV-NS5B $CD4^+$ T-cell epitopes and 2 or more HCV-NS5B $CD8^+$ T-cell epitopes. In some cases, the heterologous polypeptide comprises 2, 3, 4, or 5 HCV-NS5B $CD4^+$ T-cell epitopes and 2, 3, 4, or 5 HCV-NS5B $CD8^+$ T-cell epitopes.

In some cases, the heterologous polypeptide comprises a single T-cell epitope. In some cases, the heterologous polypeptide comprises a single HCV-core T-cell epitope. In some cases, the heterologous polypeptide comprises 2 or more T-cell epitopes. In some cases, the heterologous polypeptide comprises 2 or more HCV-core T-cell epitopes. In some cases, the heterologous polypeptide comprises 3 or more HCV-core T-cell epitopes. In some cases, the heterologous polypeptide comprises 4 or more HCV-core T-cell epitopes. In some cases, the heterologous polypeptide comprises a single HCV-core $CD4^+$ T-cell epitope. In some cases, the heterologous polypeptide comprises 2 or more HCV-core $CD4^+$ T-cell epitopes. In some cases, the heterologous polypeptide comprises one or more HCV $CD8^+$ T cell epitopes. In some cases, the heterologous polypeptide comprises a single HCV-core $CD8^+$ T-cell epitope. In some cases, the heterologous polypeptide comprises 2 or more HCV-core $CD8^+$ T-cell epitopes. In some cases, the heterologous polypeptide comprises at least one HCV $CD4^+$ T cell epitope and at least one HCV $CD8^+$ T cell epitope. In some cases, the heterologous polypeptide comprises at least one HCV-core $CD4^+$ T cell epitope and at least one HCV-core $CD8^+$ T cell epitope. In some cases, heterologous polypeptide comprises 2 or more HCV-core $CD4^+$ T-cell epitopes and 2 or more HCV-core $CD8^+$ T-cell epitopes. In some cases, the heterologous polypeptide comprises 2, 3, 4, or 5 HCV-core $CD4^+$ T-cell epitopes and 2, 3, 4, or 5 HCV-core $CD8^+$ T-cell epitopes.

In some cases, the heterologous polypeptide comprises a single T-cell epitope. In some cases, the heterologous polypeptide comprises a single HCV-p7 T-cell epitope. In some cases, the heterologous polypeptide comprises 2 or more T-cell epitopes. In some cases, the heterologous polypeptide comprises 2 or more HCV-p7 T-cell epitopes. In some cases, the heterologous polypeptide comprises 3 or more HCV-p7 T-cell epitopes. In some cases, the heterologous polypeptide comprises 4 or more HCV-p7 T-cell epitopes. In some cases, the heterologous polypeptide comprises a single HCV-p7 $CD4^+$ T-cell epitope. In some cases, the heterologous polypeptide comprises 2 or more HCV-core $CD4^+$ T-cell epitopes. In some cases, the heterologous polypeptide comprises one or more HCV $CD8^+$ T cell epitopes. In some cases, the heterologous polypeptide comprises a single HCV-p7 $CD8^+$ T-cell epitope. In some cases, the heterologous polypeptide comprises 2 or more HCV-p7 $CD8^+$ T-cell epitopes. In some cases, the heterologous polypeptide comprises at least one HCV $CD4^+$ T cell epitope and at least one HCV $CD8^+$ T cell epitope. In some cases, the heterologous polypeptide comprises at least one HCV-p7 $CD4^+$ T cell epitope and at least one HCV-p7 $CD8^+$ T cell epitope. In some cases, heterologous polypeptide comprises 2 or more HCV-p7 $CD4^+$ T-cell epitopes and 2 or more HCV-p7 $CD8^+$ T-cell epitopes. In some cases, the heterologous polypeptide comprises 2, 3, 4, or 5 HCV-p7 $CD4^+$ T-cell epitopes and 2, 3, 4, or 5 HCV-p7 $CD8^+$ T-cell epitopes.

In some cases, the heterologous polypeptide comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, or 63, of the T-cell epitopes set out in FIGS. 13A-13B. In some cases, the heterologous polypeptide comprises from 1 to 3, from 3 to 5, from 5 to 10, from 10 to 15, from 15 to 20, from 20 to 25, or from 25 to 30 of the T-cell epitopes set out in FIGS. 13A-13B. For example, in some cases, the heterologous polypeptide comprises the T-cell epitopes designated NS3-3, NS3-4, and NS3-11 in FIGS. 13A-13B and FIGS. 15A-15N. As another example, in some cases, the heterologous polypeptide comprises the T-cell epitopes designated NS2-1, NS2-2, NS2-3, NS2-7, and NS2-8 in FIGS. 13A-13B and FIGS. 15A-15N. As another example, in some cases, the heterologous polypeptide comprises the T-cell epitopes designated NS3-3, NS3-4, NS3-5, and NS3-11 in FIGS. 13A-13B and FIGS. 15A-15N. As another example, in some cases, the heterologous polypeptide comprises the T-cell epitopes designated NS3-3, NS3-4, NS3-5, NS3-6, NS3-7, NS3-11, NS3-12, and NS3-13 in FIGS. 13A-13B and FIGS. 15A-15N. As another example, in some cases, the heterologous polypeptide comprises the T-cell epitopes designated NS3-3, NS3-4, NS3-5, NS3-6, NS3-7, NS3-10, NS3-11, NS3-12, and NS3-13 in FIGS. 13A-13B and FIGS. 15A-15N. As another example, in some cases, the heterologous polypeptide comprises the T-cell epitopes designated Core-1, Core-2, Core-3, Core-4, Core-5, Core-6, Core-7, Core-8, Core-9, Core-10, Core-11, Core-12, Core-13, Core-14, Core-16, Core-17, Core-18, Core-19, Core-20, Core-21, and Core-22 in FIGS. 13A-13B and FIGS. 15A-15N. As another example, in some cases, the heterologous polypeptide comprises the T-cell epitopes designated NS3-1, NS3-2, NS3-3, NS3-4, NS3-5, NS3-6, NS3-7, NS3-9, NS3-10, NS3-11, NS3-12, and NS3-13 in FIGS. 13A-13B and FIGS. 15A-15N. As another example, in some cases, the heterologous polypeptide comprises the T-cell epitopes designated NS2-1, NS2-2, NS2-3, NS2-4, NS2-5, NS2-6, NS2-7, NS2-8, NS3-1, NS3-2, NS3-3, NS3-4, NS3-5, NS3-6, NS3-7, NS3-9, NS3-10, NS3-11, NS3-12, and NS3-13 in FIGS. 13A-13B and FIGS. 15A-15N. As another example, in some cases, the heterologous polypeptide comprises the T-cell epitopes designated NS3-1, NS3-2, NS3-3, NS3-4, NS3-5, NS3-6, NS3-7, NS3-8, NS3-9, NS3-10, NS3-11, NS3-12, NS3-13, NS3-14, NS4a-1, NS4b-1, NS4b-2, NS4b-3, NS4b-4, NS4b-5, NS4b-6, NS4b-7, NS4b-8, NS4b-9, and NS4b-10 in FIGS. 13A-13B and FIGS. 15A-15N. As another example, in some cases, the heterologous polypeptide comprises the T-cell epitopes designated NS3-1, NS3-2, NS3-3, NS3-4, NS3-5, NS3-6, NS3-7, NS3-8, NS3-9, NS3-10, NS3-11, NS3-12, NS3-13, NS3-14, NS4a-1, NS4b-1, NS4b-2, NS4b-3, NS4b-4, NS4b-5, NS4b-6, NS4b-7, NS4b-8, NS4b-9, NS4b-10, NS5a-1, NS5a-2, NS5b-1, and NS5b-2 in FIGS. 13A-13B and FIGS. 15A-15N. In some cases, the T-cell epitopes are contiguous. In some cases, any two T-cell epitopes are separated by linkers (e.g., a linker having a length of from 1 amino acid to about 50 amino acids, e.g., from 1 amino acid to 5 amino acids (aa), from 5 aa to 10 aa, from 10 aa to 15 aa, from 15 aa to 20 aa, from 20 aa to 25 aa, from 25 aa to 30 aa, from 30 aa to 40 aa, or from 40 aa to 50 aa).

In some cases, the heterologous polypeptide comprises at least one HCV $CD4^+$ T cell epitope and at least one HCV $CD8^+$ T cell epitope, where epitopes are conserved among HCV genotypes 1 and 2. In some cases, the heterologous polypeptide comprises at least one HCV $CD4^+$ T cell epitope and at least one HCV $CD8^+$ T cell epitope, where epitopes are conserved among HCV genotypes 1 and 3. In some cases, the heterologous polypeptide comprises at least one HCV $CD4^+$ T cell epitope and at least one HCV $CD8^+$ T cell epitope, where epitopes are conserved among HCV genotypes 1, 2, and 3. In some cases, the heterologous polypeptide comprises at least one HCV $CD4^+$ T cell epitope and at least one HCV $CD8^+$ T cell epitope, where epitopes are conserved among HCV genotypes 1, 2, 3, and 7. In some cases, the heterologous polypeptide comprises at least one HCV $CD4^+$ T cell epitope and at least one HCV $CD8^+$ T cell epitope, where epitopes are conserved among HCV genotypes 1-7.

The heterologous polypeptide can have a length of from about 10 amino acids to about 2000 amino acids; e.g., the heterologous polypeptide can have a length of from 10 amino acids (aa) to 15 aa, from 15 an to 20 aa, from 20 an to 25 aa, from 25 aa to 50 aa, from 50 aa to 75 aa, from 75 an to 100 aa, from 100 an to 150 aa, from 150 aa to 200 aa, from 200 aa to 250 aa, from 250 aa to 300 aa, from 300 an to 350 aa, from 350 aa to 400 aa, from 450 an to 500 aa, from 500 an to 550 aa, from 550 an to 600 aa, from 600 an to 650 aa, from 650 aa to 700 aa, from 700 aa to 750 aa, or from 750 aa to 800 aa. The heterologous polypeptide can have a length of from about 25 amino acids to about 2000 amino acids, e.g., from about 25 amino acids (aa) to 50 aa, from 50 an to 75 aa, from 75 an to 100 aa, from 100 an to 150 aa, from 150 an to 200 aa, from 200 aa to 250 aa, from 250 an to 300 aa, from 300 aa to 350 aa, from 350 an to 400 aa, from 400 an to 500 aa, from 500 aa to 600 aa, from 600 an to 700 aa, from 700 an to 800 aa, from 800 aa to 900 aa, from 900 an to 1000 aa, from 1000 aa to 1100 aa, from 1100 aa to 1200 aa, from 1200 an to 1300 aa, from 1300 aa to 1400 aa, from 1400 aa to 1500 aa, from 1500 aa to 1600 aa, from 1600 aa to 1700 aa, from 1700 aa to 1800 aa, from 1800 aa to 1900 aa, or from 1900 aa to 2000 aa. The heterologous polypeptide can have a length of from about 25 amino acids to about 3000 amino acids, e.g., from about 25 amino acids (aa) to 50 aa, from 50 aa to 75 aa, from 75 aa to 100 aa, from 100 aa to 150 aa, from 150 aa to 200 aa, from 200 aa to 250 aa, from 250 aa to 300 aa, from 300 aa to 350 aa, from 350 an to 400 aa, from 400 an to 500 aa, from 500 an to 600 aa, from 600 an to 700 aa, from 700 an to 800 aa, from 800 an to 900 aa, from 900 aa to 1000 aa, from 1000 aa to 1100 aa, from 1100 an to 1200 aa, from 1200 aa to 1300 aa, from 1300 an to 1400 aa, from 1400 aa to 1500 aa, from 1500 an to 1600 aa, from 1600 aa to 1700 aa, from 1700 an to 1800 aa, from 1800 aa to 1900 aa, from 1900 aa to 2000 aa, from 2000 aa to 2250 aa, from 2250 aa to 2500 aa, from 2500 an to 2750 aa, or from 2750 an to 3000 aa.

The heterologous polypeptide can have a length of from about 25 amino acids to about 800 amino acids, e.g., from about 25 amino acids (aa) to 50 aa, from 50 an to 75 aa, from 75 aa to 100 aa, from 100 an to 150 aa, from 150 an to 200 aa, from 200 an to 250 aa, from 250 aa to 300 aa, from 300 an to 350 aa, from 350 aa to 400 aa, from 450 an to 500 aa, from 500 an to 550 aa, from 550 aa to 600 aa, from 600 an to 650 aa, from 650 an to 700 aa, from 700 aa to 750 aa, or from 750 an to 800 aa. The heterologous polypeptide can have a length of from about 25 amino acids to about 400 amino acids, e.g., from about 25 amino acids (aa) to 50 aa, from 50 an to 75 aa, from 75 an to 100 aa, from 100 an to 150 aa, from 150 an to 200 aa, from 200 aa to 250 aa, from 250 aa to 300 aa, from 300 an to 350 aa, or from 350 aa to 400 aa. The heterologous polypeptide can have a length of 25 amino acids (aa), 26 aa, 27 aa, 28 aa, 29 aa, 30 aa, 31 aa, 32 aa, 33 aa, 34 aa, 35 aa, 36 aa, 37 aa, 38 aa, 39 aa, 40 aa, 41 aa, 42 aa, 43 aa, 44 aa, 45 aa, 46 aa, 47 aa, 48 aa, 49 aa, or 50 aa. The heterologous polypeptide can have a length of from about 100 amino acids (aa) to 800 aa, e.g., from 100 aa to 150 aa, from 150 aa to 200 aa, from 200 aa to 250 aa, from 250 an to 300 aa, from 300 aa to 350 aa, from 350 an to 400 aa, from 450 an to 500 aa, from 500 aa to 550 aa, from 550 an to 600 aa, from 600 an to 650 aa, from 650 aa to 700 aa, from 700 an to 750 aa, or from 750 aa to 800 aa. The heterologous polypeptide can have a length of from 25 an to 30 aa. The heterologous polypeptide can have a length of from 30 an to 40 aa. The heterologous polypeptide can have a length of from 40 an to 50 aa. The heterologous polypeptide can have a length of from 50 aa to 60 aa (e.g., 50 aa, 51 aa, 52, aa, 53 aa, 54 aa, 55 aa, 56 aa, 57 aa, 58 aa, 59 aa, or 60 aa). The heterologous polypeptide can have a length of from 60 aa to 70 aa. The heterologous polypeptide can have a length of from 65 an to 75 aa (e.g., 65, 66, 67, 68, 69, 70, 71, 72, 7, 74, or 75 aa). The heterologous polypeptide can have a length of 70 aa. The heterologous polypeptide can have a length of from 70 an to 80 aa. The heterologous polypeptide can have a length of from 80 aa to 90 aa. The heterologous polypeptide can have a length of from 90 an to 100 aa. The heterologous polypeptide can have a length of from 100 an to 105 aa (e.g., 100, 101, 102, 103, 104, 105, 106, 107, 108, 109, or 110 aa). The heterologous polypeptide can have a length of 100 aa. The heterologous polypeptide can have a length of from 10 amino acids (aa) to 50 aa; e.g., from 10 an to 15 aa, from 15 an to 20 aa, from 20 an to 25 aa, from 25 an to 30 aa, from 30 an to 35 aa, from 35 aa to 40 aa, from 40 an to 45 aa, or from 45 an to 50 aa. The heterologous polypeptide can have a length of from 10 amino acids (aa) to 20 aa, e.g., 10, 11, 12, 13, 14, 15, 16, 17, 18, 19, or 20 aa.

HCV NS3 T-Cell Epitopes

In some cases, the heterologous polypeptide present in an E2 variant polypeptide of an E1/E2 heterodimer of the present disclosure includes one or more T-cell epitopes present in an HCV NS3 polypeptide. Examples of T-cell epitopes present in NS3 polypeptides are depicted in FIGS. 15A-15N, FIG. 13B, and FIGS. 14A-14B.

The heterologous polypeptide can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence:

AIPLEVIKGGRHLIFCHSKKKCDELAAKL (SEQ ID NO:1). In some cases, the heterologous polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence:

AIPLEVIKGGRHLIFCHSKKKCDELAAKL (SEQ ID NO:1); and has a length of from 25 aa to 35 aa (e.g., 25 aa, 26 aa, 27 aa, 28 aa, 29 aa, 30 aa, 31 aa, 32 aa, 33 aa, 34 aa, or 35 aa). In some cases, the heterologous polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence:

AIPLEVIKGGRHLIFCHSKKKCDELAAKL (SEQ ID NO:1); and has a length of 29 amino acids. Such a polytope can include NS3 T-cell epitopes designated NS3-3, NS3-4, and NS3-11 in FIG. 13B and FIGS. 15A-15N.

The heterologous polypeptide can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence: AIPLEVIKGGRHLIFCHSKKKCDELAAKLVALGI-NAVAYYRGLDVSVIPTSG (SEQ ID NO:2). In some cases, the heterologous polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence: AIPLEV-IKGGRHLIFCHSKKKCDELAAKLVALGI-NAVAYYRGLDVSVIPTSG (SEQ ID NO:2); and has a length of from 45 amino acids to 60 amino acids (e.g., 45 aa, 46 aa, 47 aa, 48 aa, 49 aa, 50 aa, 51 aa, 52 aa, 53 aa, 54 aa, 55 aa, 56 aa, 57 aa, 58 aa, 59 aa, or 60 aa). In some cases, the heterologous polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence: AIPLEVIKGGRHLIFCHSKKKCDELAAKLVALGI-NAVAYYRGLDVSVIPTSG (SEQ ID NO:2); and has a length of 52 amino acids. Such a polytope can include NS3 T-cell epitopes designated NS3-3, NS3-4, NS3-5, and NS3-11 in FIG. 13B and FIGS. 15A-15N.

The heterologous polypeptide can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence: KGGRHLIFCHSKKKCDELAAKLVALGINAVAYYR-GLDVSVIPTSGDVVVVATDALMTG FTGDFD-SVIDCN (SEQ ID NO:3); and has a length of from 65 amino acids to 80 amino acids (e.g., 65 aa, 66 aa, 67 aa, 68 aa, 69 aa, 70 aa, 71 aa, 72 aa, 73 aa, 74 aa, 75 aa, 76 aa, 77 aa, 78 aa, 79 aa, or 80 aa). In some cases, the heterologous polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence: KGGRHLIFCHSKKKCDELAAKLVALGINAVAYYR-GLDVSVIPTSGDVVVVATDALMTG FTGDFDS-VIDCN (SEQ ID NO:3); and has a length of 70 amino acids. Such a polytope can include NS3 T-cell epitopes designated NS3-3, NS3-4, NS3-5, NS3-6, NS3-7, NS3-11, NS3-12, and NS3-13 in FIG. 13B and FIGS. 15A-15N.

The heterologous polypeptide can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence: VALSTTGEIPFYGKAIPLEVIKGGRHLIFCHS-KKKCDELAAKLVALGINAVAYYRGLDVS VIPTSGDVVVVATDALMTGFTGDFDSVID-CNTCVTQTVDF (SEQ ID NO:4); and has a length of from 95 amino acids (aa) to 105 aa (e.g., 95 aa, 96 aa, 97 aa, 98 aa, 99 aa, 100 aa, 101 aa, 102 aa, 103 aa, 104 aa, or 105 aa). In some cases, the heterologous polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence: VALSTTGEIPFYGKAIPLEVIKGGRHLIFCHS-KKKCDELAAKLVALGINAVAYYRGLDVS VIPTSGDVVVVATDALMTGFTGDFDSVID-CNTCVTQTVDF (SEQ ID NO:4); and has a length of 100 amino acids. Such a polytope can include NS3 T-cell epitopes designated NS3-3, NS3-4, NS3-5, NS3-6, NS3-7, NS3-10, NS3-11, NS3-12, and NS3-13 in FIG. 13B and FIGS. 15A-15N.

The heterologous polypeptide can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence: MSTNPKPQRKTKRNTNRRPQDVKFPGGGQI-VGGVYLLPRRGPRLGVRATRKTSERSQP RGRRQPIPKARRPEGRTWAQPGYPWPLYG-NEGCGWAGWLLSPRGSRPSWGPTDPRRRS RNLGKVIDTLTCGFADLMGYIPLVGAPLG-GAARALAHGVRVLEDGVNYATGNLPGCSF SIFLLALLSCLTVPASA (SEQ ID NO:9); and has a length of from 190 amino acids (aa) to 200 an (e.g., 190 aa, 191 aa, 192 aa, 193 aa, 194 aa, 195 aa, 196 aa, 197 aa, 198 aa, 199 aa, or 200 aa. In some cases, the heterologous polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence: MSTNPKPQRKTKRNTNRRPQDVKFPGGGQI-VGGVYLLPRRGPRLGVRATRKTSERSQP RGRRQPIPKARRPEGRTWAQPGYPWPLYG-NEGCGWAGWLLSPRGSRPSWGPTDPRRRS RNLGKVIDTLTCGFADLMGYIPLVGAPLG-GAARALAHGVRVLEDGVNYATGNLPGCSF SIFLLALLSCLTVPASA (SEQ ID NO:9); and has a length of 191 amino acids.

The heterologous polypeptide can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence:

```
                                        (SEQ ID NO: 10)
LHAPTGSGKSTKVPAAYAAQGYKVLVLNPSVAATLGFGAYMSKAHGIDPN

IRTGVRTITTGSPITYSTYGKFLADGGCSGGAYDIIICDECHSTDATSIL

GIGTVLDQAETAGARLVVLATATPPGSVTVPHPNIEEVALSTTGEIPFYG

KAIPLEVIKGGRHLIFCHSKKKCDELAAKLVALGINAVAYYRGLDVSVIP

TSGDVVVVATDALMTGFTGDFDSVIDCN;
```

and has a length of from 215 amino acids (aa) to 235 aa (e.g., 215 aa, 216 aa, 217 11, 218 aa, 219 aa, 220 aa, 221 aa, 222 aa, 223 aa, 224 aa, 225 aa, 226 aa, 227 aa, 228 aa, 229 aa, 230 aa, 231 aa, 232 aa, 233 aa, 234 aa, or 235 aa). In some cases, the heterologous polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence:

```
                                        (SEQ ID NO: 10)
LHAPTGSGKSTKVPAAYAAQGYKVLVLNPSVAATLGFGAYMSKAHGIDPN

IRTGVRTITTGSPITYSTYGKFLADGGCSGGAYDIIICDECHSTDATSIL

GIGTVLDQAETAGARLVVLATATPPGSVTVPHPNIEEVALSTTGEIPFYG

KAIPLEVIKGGRHLIFCHSKKKCDELAAKLVALGINAVAYYRGLDVSVIP

TSGDVVVVATDALMTGFTGDFDSVIDCN;
```

and has a length of 228 amino acids. Such a polytope can include NS3 T-cell epitopes designated NS3-1, NS3-2, NS3-3, NS3-4, NS3-5, NS3-6, NS3-7, NS3-9, NS3-10, NS3-11, NS3-12, and NS3-13 in FIG. 13B and FIGS. 15A-15N.

As another example, the heterologous polypeptide can comprise an HCV NS3 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1265-1279 of the amino acid sequence designated "Consensus" in FIGS. 16A-16L, or a corresponding HCV NS3 amino acid sequence of any HCV genotype; and the HCV NS3 T-cell epitope can have a length of from 15 amino acids (aa) to 20 amino acids (e.g., 15 aa, 16 aa, 17 aa, 18 aa, 19 aa, or 20 aa).

As another example, the heterologous polypeptide can comprise an HCV NS3 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1309-1323 of the amino acid sequence designated "Consensus" in FIGS. 16A-16L, or a corresponding HCV NS3 amino acid sequence of any HCV genotype; and the HCV NS3 T-cell epitope can have a length of from 15 amino acids (aa) to 20 amino acids (e.g., 15 aa, 16 aa, 17 aa, 18 aa, 19 aa, or 20 aa).

As another example, the heterologous polypeptide can comprise an HCV NS3 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1401-1415 of the amino acid sequence designated "Consensus" in FIGS. 16A-16L, or a corresponding HCV NS3 amino acid sequence of any HCV genotype; and the HCV NS3 T-cell epitope can have a length of from 15 amino acids (aa) to 20 amino acids (e.g., 15 aa, 16 aa, 17 aa, 18 aa, 19 aa, or 20 aa).

As another example, the heterologous polypeptide can comprise an HCV NS3 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1402-1412 of the amino acid sequence designated "Consensus" in FIGS. 16A-16L, or a corresponding HCV NS3 amino acid sequence of any HCV genotype; and the HCV NS3 T-cell epitope can have a length of from 11 amino acids (aa) to 16 amino acids (e.g., 11 aa, 12 aa, 13 aa, 14 aa, 15 aa, or 16 aa).

As another example, the heterologous polypeptide can comprise an HCV NS3 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1429-1439 of the amino acid sequence designated "Consensus" in FIGS. 16A-16L, or a corresponding HCV NS3 amino acid sequence of any HCV genotype; and the HCV NS3 T-cell epitope can have a length of from 11 amino acids (aa) to 16 amino acids (e.g., 11 aa, 12 aa, 13 aa, 14 aa, 15 aa, or 16 aa).

As another example, the heterologous polypeptide can comprise an HCV NS3 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1450-1464 of the amino acid sequence designated "Consensus" in FIGS. 16A-16L, or a corresponding HCV NS3 amino acid sequence of any HCV genotype; and the HCV NS3 T-cell epitope can have a length of from 15 amino acids (aa) to 20 amino acids (e.g., 15 aa, 16 aa, 17 aa, 18 aa, 19 aa, or 20 aa).

As another example, the heterologous polypeptide can comprise an HCV NS3 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1453-1467 of the amino acid sequence designated "Consensus" in FIGS. 16A-16L, or a corresponding HCV NS3 amino acid sequence of any HCV genotype; and the HCV NS3 T-cell epitope can have a length of from 15 amino acids (aa) to 20 amino acids (e.g., 15 aa, 16 aa, 17 aa, 18 aa, 19 aa, or 20 aa).

As another example, the heterologous polypeptide can comprise an HCV NS3 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1577-1591 of the amino acid sequence designated "Consensus" in FIGS. 16A-16L, or a corresponding HCV NS3 amino acid sequence of any HCV genotype; and the HCV NS3 T-cell epitope can have a length of from 15 amino acids (aa) to 20 amino acids (e.g., 15 aa, 16 aa, 17 aa, 18 aa, 19 aa, or 20 aa).

As another example, the heterologous polypeptide can comprise an HCV NS3 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1306-1314 of the amino acid sequence designated "Consensus" in FIGS. 16A-16L, or a corresponding HCV NS3 amino acid sequence of any HCV genotype; and the HCV NS3 T-cell epitope can have a length of from 9 amino acids (aa) to 15 amino acids (e.g., 9 aa, 10 aa, 11 aa, 12 aa, 13 aa, 14 aa, or 15 aa).

As another example, the heterologous polypeptide can comprise an HCV NS3 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1387-1394 of the amino acid sequence designated "Consensus" in FIGS. 16A-16L, or a corresponding HCV NS3 amino acid sequence of any HCV genotype; and the HCV NS3 T-cell epitope can have a length of from 1 amino acids (aa) to 15 amino acids (e.g., 8 aa, 9 aa, 10 aa, 11 aa, 12 aa, 13 aa, 14 aa, or 15 aa).

As another example, the heterologous polypeptide can comprise an HCV NS3 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1405-1413 of the amino acid sequence designated "Consensus" in FIGS. 16A-16L, or a corresponding HCV NS3 amino acid sequence of any HCV genotype; and the HCV NS3 T-cell epitope can have a length of from 9 amino acids (aa) to 15 amino acids (e.g., 9 aa, 10 aa, 11 aa, 12 aa, 13 aa, 14 aa, or 15 aa).

As another example, the heterologous polypeptide can comprise an HCV NS3 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1450-1458 of the amino acid sequence designated "Consensus" in FIGS. 16A-16L, or a corresponding HCV NS3 amino acid sequence of any HCV genotype; and the HCV NS3 T-cell epitope can have a length of from 9 amino acids (aa) to 15 amino acids (e.g., 9 aa, 10 aa, 11 aa, 12 aa, 13 aa, 14 aa, or 15 aa).

As another example, the heterologous polypeptide can comprise an HCV NS3 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1457-1465 of the amino acid sequence designated "Consensus" in FIGS. 16A-16L, or a corresponding HCV NS3 amino acid sequence of any HCV genotype; and the HCV NS3 T-cell epitope can have a length of from 9 amino acids (aa) to 15 amino acids (e.g., 9 aa, 10 aa, 11 aa, 12 aa, 13 aa, 14 aa, or 15 aa).

As another example, the heterologous polypeptide can comprise an HCV NS3 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1610-1618 of the amino acid sequence designated "Consensus" in FIGS. 16A-16L, or a corresponding HCV NS3 amino acid sequence of any HCV genotype; and the HCV NS3 T-cell epitope can have a length of from 9 amino acids (aa) to 15 amino acids (e.g., 9 aa, 10 aa, 11 aa, 12 aa, 13 aa, 14 aa, or 15 aa).

HCV NS2 T-Cell Epitopes

In some cases, the heterologous polypeptide present in an E2 variant polypeptide of an E1/E2 heterodimer of the present disclosure includes one or more T-cell epitopes present in an HCV NS2 polypeptide. Examples of T-cell epitopes present in NS2 polypeptides are depicted in FIGS. 15A-15N, and FIG. 13A.

For example, the heterologous polypeptide can comprise an NS2 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 955-974 of the amino acid sequence designated "Consensus" in FIGS. 16A-16L, or a corresponding HCV NS2 amino acid sequence of any HCV genotype; and the NS2 T cell epitope can have a length of from 20 amino acids (aa) to 25 amino acids (e.g., 20 aa, 21 aa, 22 aa, 23 aa, 24 aa, or 25 aa).

As another example, the heterologous polypeptide can comprise an NS2 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 975-994 of the amino acid sequence designated "Consensus" in FIGS. 16A-16L, or a corresponding HCV NS2 amino acid sequence of any HCV genotype; and the NS2 T cell epitope can have a length of from 20 amino acids (aa) to 25 amino acids (e.g., 20 aa, 21 aa, 22 aa, 23 aa, 24 aa, or 25 aa).

As another example, the heterologous polypeptide can comprise an NS2 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 985-1004 of the amino acid sequence designated "Consensus" in FIGS. 16A-16L, or a corresponding HCV NS2 amino acid sequence of any HCV genotype; and the NS2 T cell epitope can have a length of from 20 amino acids (aa) to 25 amino acids (e.g., 20 aa, 21 aa, 22 aa, 23 aa, 24 aa, or 25 aa).

As another example, the heterologous polypeptide can comprise an NS2 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1015-1034 of the amino acid sequence designated "Consensus" in FIGS. 16A-16L, or a corresponding HCV NS2 amino acid sequence of any HCV genotype; and the NS2 T cell epitope can have a length of from 20 amino acids (aa) to 25 amino acids (e.g., 20 aa, 21 aa, 22 aa, 23 aa, 24 aa, or 25 aa).

As another example, the heterologous polypeptide can comprise an NS2 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1035-1054 of the amino acid sequence designated "Consensus" in FIGS. 16A-16L, or a corresponding HCV NS2 amino acid sequence of any HCV genotype; and the NS2 T cell epitope can have a length of from 20 amino acids (aa) to 25 amino acids (e.g., 20 aa, 21 aa, 22 aa, 23 aa, 24 aa, or 25 aa).

As another example, the heterologous polypeptide can comprise an NS2 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 924-933 of the amino acid sequence designated "Consensus" in FIGS. 16A-16L, or a corresponding HCV NS2 amino acid sequence of any HCV genotype; and the NS2 T cell epitope can have a length of from 10 amino acids (aa) to 15 amino acids (e.g., 10 aa, 11 aa, 12 aa, 13 aa, 14 aa, or 15 aa).

As another example, the heterologous polypeptide can comprise an NS2 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 961-970 of the amino acid sequence designated "Consensus" in FIGS. 16A-16L, or a corresponding HCV NS2 amino acid sequence of any HCV genotype; and the NS2 T cell epitope can have a length of from 10 amino acids (aa) to 15 amino acids (e.g., 10 aa, 11 aa, 12 aa, 13 aa, 14 aa, or 15 aa).

As another example, the heterologous polypeptide can comprise an NS2 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 989-997 of the amino acid sequence designated "Consensus" in FIGS. 16A-16L, or a corresponding HCV NS2 amino acid sequence of any HCV genotype; and the NS2 T cell epitope can have a length of from 9 amino acids (aa) to 15 amino acids (e.g., 9 aa, 10 aa, 11 aa, 12 aa, 13 aa, 14 aa, or 15 aa).

In some cases, the heterologous polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to a contiguous stretch of from 10 amino acids (aa) to 50 an (e.g., from 10 aa to 25 aa, or from 25 an to 50 aa) of amino acids 955-1004 of the amino acid sequence designated "Consensus" in FIGS. 16A-16L, or a corresponding HCV NS2 amino acid sequence of any HCV genotype; and has a length of from 10 amino acids (aa) to 25 aa, or from 25 aa to 50 aa. In some cases, the heterologous polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 955-1004 of the amino acid sequence designated "Consensus" in FIGS. 16A-16L, or a corresponding HCV NS2 amino acid sequence of any HCV genotype; and has a length of about 50 amino acids.

In some cases, the heterologous polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to a contiguous stretch of from 10 amino acids (aa) to 553 aa (e.g., from 10 aa to 25 aa, from 25 aa to 50 aa, from 50 aa to 100 aa, from 100 aa to 200 aa, from 200 aa to 300 aa, from 300 aa to 400 aa, from 400 aa to 500 aa, or from 500 aa to 553 aa) of amino acids 917-1469 of the amino acid sequence designated "Consensus" in FIGS. 16A-16L, or a corresponding HCV NS2 and NS3 amino acid sequence of any HCV genotype; and has a length of from 10 amino acids (aa) to 25 aa, from 25 aa to 50 aa, from 50 an to 100 aa, from 100 an to 200 aa, from 200 aa to 300 aa, from 300 aa to 400 aa, from 400 aa to 500 aa, or from 500 an to 553 aa. In some cases, the heterologous polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 917-1469 of the amino acid sequence designated "Consensus" in FIGS. 16A-16L, or a corresponding HCV NS2 and NS3 amino acid sequence of any HCV genotype; and has a length of about 553 amino acids.

The heterologous polypeptide can comprise an amino acid sequence having at least about 20%, at least about 25%, at least about 30%, at least about 35%, at least about 40%, at least about 45%, at least about 50%, at least about 60%, at least about 0%, at least about 75%, at least about 80%, at least about 85%, at least about 90%, at least about 95%, at least about 98%, at least about 99%, or 100%, amino acid sequence identity to the following amino acid sequence:

LGALTGTYVYNHLTPLRDWAHNGLRDLAVAVEPVVFSQMETKLITWGADT (SEQ ID NO:11). In some cases, the heterologous polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence:

LGALTGTYVYNHLTPLRDWAHNGLRDLAVAVEPVVFSQMETKLITWGADT (SEQ ID NO:11); and has a length of from 50 amino acids to 60 amino acids (e.g., 50 aa, 51 aa, 52 aa, 53 aa, 54 aa, 55 aa, 56 aa, 57 aa, 58 aa, 59 aa, or 60 aa). In some cases, the heterologous polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence:

LGALTGTYVYNHLTPLRDWAHNGLRDLAVAVEPVVFSQMETKLITWGADT (SEQ ID NO:11); and has a length of 50 amino acids. Such a polytope can include NS2 T-cell epitopes designated NS2-1, NS2-2, NS2-3, NS2-7, and NS2-8 in FIG. 13A and FIGS. 15A-15N.

HCV NS4A T-Cell Epitopes

In some cases, the heterologous polypeptide present in an E2 variant polypeptide of an E1/E2 heterodimer of the present disclosure includes one or more T-cell epitopes present in an HCV NS4A polypeptide. Examples of T-cell epitopes present in NS4A polypeptides are depicted in FIGS. 15A-15N and FIG. 13B.

The heterologous polypeptide can comprise an NS4A T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1683-1692 of the amino acid sequence designated "Consensus" in FIGS. 16A-16L, or a corresponding HCV NS4A amino acid sequence of any HCV genotype; and the NS4A T-cell epitope can have a length of from 10 amino acids (aa) to 15 amino acids (e.g., 10 aa, 11 aa, 12 aa, 13 aa, 14 aa, or 15 aa).

HCV NS4B T-Cell Epitopes

In some cases, the heterologous polypeptide present in an E2 variant polypeptide of an E1/E2 heterodimer of the present disclosure includes one or more T-cell epitopes present in an HCV NS4B polypeptide. Examples of T-cell epitopes present in NS4B polypeptides are depicted in FIGS. 15A-15N and FIG. 13B.

As one example, the heterologous polypeptide can comprise an NS4B T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1790-1801 of the amino acid sequence designated "Consensus" in FIGS. 16A-16L, or a corresponding HCV NS4B amino acid sequence of any HCV genotype; and the NS4B T-cell epitope can have a length of from 12 amino acids (aa) to 20 amino acids (e.g., 12 aa, 13 aa, 14 aa, 15 aa, 16 aa, 17 aa, 18 aa, 19 aa, or 20 aa).

As another example, the heterologous polypeptide can comprise an NS4B T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1792-1802 of the amino acid sequence designated "Consensus" in FIGS. 16A-16L, or a corresponding HCV NS4B amino acid sequence of any HCV genotype; and the NS4B T-cell epitope can have a length of from 11 amino acids (aa) to 20 amino acids (e.g., 11 aa, 12 aa, 13 aa, 14 aa, 15 aa, 16 aa, 17 aa, 18 aa, 19 aa, or 20 aa).

As another example, the heterologous polypeptide can comprise an NS4B T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1898-1905 of the amino acid sequence designated "Consensus" in FIGS. 16A-16L, or a corresponding HCV NS4B amino acid sequence of any HCV genotype; and the NS4B T-cell epitope can have a length of from 8 amino acids (aa) to 15 amino acids (e.g., 8 aa, 9 aa, 10 aa, 11 aa, 12 aa, 13 aa, 14 aa, or 15 aa).

As another example, the heterologous polypeptide can comprise an NS4B T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1921-1935 of the amino acid sequence designated "Consensus" in FIGS. 16A-16L, or a corresponding HCV NS4B amino acid sequence of any HCV genotype; and the NS4B T-cell epitope can have a length of from 15 amino acids (aa) to 20 amino acids (e.g., 15 aa, 16 aa, 17 aa, 18 aa, 19 aa, or 20 aa).

As another example, the heterologous polypeptide can comprise an NS4B T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1922-1941 of the amino acid sequence designated "Consensus" in FIGS. 16A-16L, or a corresponding HCV NS4B amino acid sequence of any HCV genotype; and the NS4B T-cell epitope can have a length of from 20 amino acids (aa) to 25 amino acids (e.g., 20 aa, 21 aa, 22 aa, 23 aa, 24 aa, or 25 aa).

As another example, the heterologous polypeptide can comprise an NS4B T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1928-1947 of the amino acid sequence designated "Consensus" in FIGS. 16A-16L, or a corresponding HCV NS4B amino acid sequence of any HCV genotype; and the NS4B T-cell epitope can have a length of from 20 amino acids (aa) to 25 amino acids (e.g., 20 aa, 21 aa, 22 aa, 23 aa, 24 aa, or 25 aa).

As another example, the heterologous polypeptide can comprise an NS4B T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1868-1876 of the amino acid sequence designated "Consensus" in FIGS. 16A-16L, or a corresponding HCV NS4B amino acid sequence of any HCV genotype; and the NS4B T-cell epitope can have a length of from 9 amino acids (aa) to 15 amino acids (e.g., 9 aa, 10 aa, 11 aa, 12 aa, 13 aa, 14 aa, or 15 aa).

As another example, the heterologous polypeptide can comprise an NS4B T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1927-1942 of the amino acid sequence designated "Consensus" in FIGS. 16A-16L, or a corresponding HCV NS4B amino acid sequence of any HCV genotype; and the NS4B T-cell epitope can have a length of from 16 amino acids (aa) to 20 amino acids (e.g., 16 aa, 17 aa, 18 aa, 19 aa, or 20 aa).

As another example, the heterologous polypeptide can comprise an NS4B T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1932-1940 of the amino acid sequence designated "Consensus" in FIGS. 16A-16L, or a corresponding HCV NS4B amino acid sequence of any HCV genotype; and the NS4B T-cell epitope can have a length of from 9 amino acids (aa) to 15 amino acids (e.g., 9 aa, 10 aa, 11 aa, 12 aa, 13 aa, 14 aa, or 15 aa).

As another example, the heterologous polypeptide can comprise an NS4B T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1948-1962 of the amino acid sequence designated "Consensus" in FIGS. 16A-16L, or a corresponding HCV NS4B amino acid sequence of any HCV genotype; and the NS4B T-cell epitope can have a length of from 15 amino acids (aa) to 20 amino acids (e.g., 15 aa, 16 aa, 17 aa, 18 aa, 19 aa, or 20 aa).

HCV NS5A T-Cell Epitopes

In some cases, the heterologous polypeptide present in an E2 variant polypeptide of an E1/E2 heterodimer of the present disclosure includes one or more T-cell epitopes present in an HCV NS5A polypeptide. Examples of T-cell epitopes present in NS5A polypeptides are depicted in FIGS. 15A-15N and FIG. 13B.

As one example, the heterologous polypeptide can comprise an NS5A T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 2218-2232 of the amino acid sequence designated "Consensus" in FIGS. 16A-16L, or a corresponding HCV NSSA amino acid sequence of any HCV genotype; and the NSSA T-cell epitope can have a length of from 15 amino acids (aa) to 20 amino acids (e.g., 15 aa, 16 aa, 17 aa, 18 aa, 19 aa, or 20 aa).

As another example, the heterologous polypeptide can comprise an NSSA T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 2309-2317 of the amino acid sequence designated "Consensus" in FIGS. 16A-16L, or a corresponding HCV NSSA amino acid sequence of any HCV genotype; and the NSSA T-cell epitope can have a length of from 9 amino acids (aa) to 15 amino acids (e.g., 9 aa, 10 aa, 11 aa, 12 aa, 13 aa, 14 aa, or 15 aa).

HCV NS5B T-Cell Epitopes

In some cases, the heterologous polypeptide present in an E2 variant polypeptide of an E1/E2 heterodimer of the present disclosure includes one or more T-cell epitopes present in an HCV NS5B polypeptide. Examples of T-cell epitopes present in NS5B polypeptides are depicted in FIGS. 15A-15N and FIG. 13B.

As one example, the heterologous polypeptide can comprise an NS5B T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 2847-2851 of the amino acid sequence designated "Consensus" in FIGS. 16A-16L, or a corresponding HCV NS5B amino acid sequence of any HCV genotype; and the NS5B T-cell epitope can have a length of from 5 amino acids (aa) to 10 amino acids (e.g., 5 aa, 6 aa, 7 aa, 8 aa, 9 aa, or 10 aa).

As another example, the heterologous polypeptide can comprise an NS5B T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 2602-2610 of the amino acid sequence designated "Consensus" in FIGS. 16A-16L, or a corresponding HCV NS5B amino acid sequence of any HCV genotype; and the NS5B T-cell epitope can have a length of from 9 amino acids (aa) to 15 amino acids (e.g., 9 aa, 10 aa, 11 aa, 12 aa, 13 aa, 14 aa, or 15 aa).

HCV Core T-Cell Epitopes

In some cases, the heterologous polypeptide present in an E2 variant polypeptide of an E1/E2 heterodimer of the present disclosure includes one or more T-cell epitopes present in an HCV core polypeptide. Examples of T-cell epitopes present in HCV Core polypeptides are depicted in FIGS. 15A-15N and FIG. 13A.

As one example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1-20 of the amino acid sequence designated "Consensus" in FIGS. 16A-16L, or a corresponding HCV core amino acid sequence of any HCV genotype; and the HCV core T-cell epitope can have a length of from 20 amino acids (aa) to 25 amino acids (e.g., 20 aa, 21 aa, 22 aa, 23 aa, 24 aa, or 25 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 11-30 of the amino acid sequence designated "Consensus" in FIGS. 16A-16L, or a corresponding HCV core amino acid sequence of any HCV genotype; and the HCV core T-cell epitope can have a length of from 20 amino acids (aa) to 25 amino acids (e.g., 20 aa, 21 aa, 22 aa, 23 aa, 24 aa, or 25 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 21-40 of the amino acid sequence designated "Consensus" in FIGS. 16A-16L, or a corresponding HCV core amino acid sequence of any HCV genotype; and the HCV core T-cell epitope can have a length of from 20 amino acids (aa) to 25 amino acids (e.g., 20 aa, 21 aa, 22 aa, 23 aa, 24 aa, or 25 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 39-63 of the amino acid sequence designated "Consensus" in FIGS. 16A-16L, or a corresponding HCV core amino acid sequence of any HCV genotype; and the HCV core T-cell epitope can have a length of from 23 amino acids (aa) to 28 amino acids (e.g., 23 aa, 24 aa, 25 aa, 26 aa, 27 aa, or 28 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 47-70 of the amino acid sequence designated "Consensus" in FIGS. 16A-16L, or a corresponding HCV core amino acid sequence of any HCV genotype; and the HCV core T-cell epitope can have a length of from 24 amino acids (aa) to 29 amino acids (e.g., 24 aa, 25 aa, 26 aa, 27 aa, 28 aa, or 29 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 61-80 of the amino acid sequence designated "Consensus" in FIGS. 16A-16L, or a corresponding HCV core amino acid sequence of any HCV genotype; and the HCV core T-cell epitope can have a length of from 20 amino acids (aa) to 25 amino acids (e.g., 20 aa, 21 aa, 22 aa, 23 aa, 24 aa, or 25 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 71-90 of the amino acid sequence designated "Consensus" in FIGS. 16A-16L, or a corresponding HCV core amino acid sequence of any HCV genotype; and the HCV core T-cell epitope can have a length of from 20 amino acids (aa) to 25 amino acids (e.g., 20 aa, 21 aa, 22 aa, 23 aa, 24 aa, or 25 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 81-100 of the amino acid sequence designated “Consensus” in FIGS. 16A-16L, or a corresponding HCV core amino acid sequence of any HCV genotype; and the HCV core T-cell epitope can have a length of from 20 amino acids (aa) to 25 amino acids (e.g., 20 aa, 21 aa, 22 aa, 23 aa, 24 aa, or 25 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 91-110 of the amino acid sequence designated “Consensus” in FIGS. 16A-16L, or a corresponding HCV core amino acid sequence of any HCV genotype; and the HCV core T-cell epitope can have a length of from 20 amino acids (aa) to 25 amino acids (e.g., 20 aa, 21 aa, 22 aa, 23 aa, 24 aa, or 25 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 101-115 of the amino acid sequence designated “Consensus” in FIGS. 16A-16L, or a corresponding HCV core amino acid sequence of any HCV genotype; and the HCV core T-cell epitope can have a length of from 15 amino acids (aa) to 20 amino acids (e.g., 15 aa, 16 aa, 17 aa, 18 aa, 19 aa, or 20 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 111-130 of the amino acid sequence designated “Consensus” in FIGS. 16A-16L, or a corresponding HCV core amino acid sequence of any HCV genotype; and the HCV core T-cell epitope can have a length of from 20 amino acids (aa) to 25 amino acids (e.g., 20 aa, 21 aa, 22 aa, 23 aa, 24 aa, or 25 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 125-139 of the amino acid sequence designated “Consensus” in FIGS. 16A-16L, or a corresponding HCV core amino acid sequence of any HCV genotype; and the HCV core T-cell epitope can have a length of from 15 amino acids (aa) to 20 amino acids (e.g., 15 aa, 16 aa, 17 aa, 18 aa, 19 aa, or 20 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 131-150 of the amino acid sequence designated “Consensus” in FIGS. 16A-16L, or a corresponding HCV core amino acid sequence of any HCV genotype; and the HCV core T-cell epitope can have a length of from 20 amino acids (aa) to 25 amino acids (e.g., 20 aa, 21 aa, 22 aa, 23 aa, 24 aa, or 25 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 151-170 of the amino acid sequence designated “Consensus” in FIGS. 16A-16L, or a corresponding HCV core amino acid sequence of any HCV genotype; and the HCV core T-cell epitope can have a length of from 20 amino acids (aa) to 25 amino acids (e.g., 20 aa, 21 aa, 22 aa, 23 aa, 24 aa, or 25 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 161-180 of the amino acid sequence designated “Consensus” in FIGS. 16A-16L, or a corresponding HCV core amino acid sequence of any HCV genotype; and the HCV core T-cell epitope can have a length of from 20 amino acids (aa) to 25 amino acids (e.g., 20 aa, 21 aa, 22 aa, 23 aa, 24 aa, or 25 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 35-44 of the amino acid sequence designated “Consensus” in FIGS. 16A-16L, or a corresponding HCV core amino acid sequence of any HCV genotype; and the HCV core T-cell epitope can have a length of from 10 amino acids (aa) to 15 amino acids (e.g., 10 aa, 11 aa, 12 aa, 13 aa, 14 aa, or 15 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 43-51 of the amino acid sequence designated “Consensus” in FIGS. 16A-16L, or a corresponding HCV core amino acid sequence of any HCV genotype; and the HCV core T-cell epitope can have a length of from 9 amino acids (aa) to 15 amino acids (e.g., 9 aa, 10 aa, 11 aa, 12 aa, 13 aa, 14 aa, or 15 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 51-59 of the amino acid sequence designated "Consensus" in FIGS. 16A-16L, or a corresponding HCV core amino acid sequence of any HCV genotype; and the HCV core T-cell epitope can have a length of from 9 amino acids (aa) to 15 amino acids (e.g., 9 aa, 10 aa, 11 aa, 12 aa, 13 aa, 14 aa, or 15 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 129-137 of the amino acid sequence designated "Consensus" in FIGS. 16A-16L, or a corresponding HCV core amino acid sequence of any HCV genotype; and the HCV core T-cell epitope can have a length of from 9 amino acids (aa) to 15 amino acids (e.g., 9 aa, 10 aa, 11 aa, 12 aa, 13 aa, 14 aa, or 15 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 131-140 of the amino acid sequence designated "Consensus" in FIGS. 16A-16L, or a corresponding HCV core amino acid sequence of any HCV genotype; and the HCV core T-cell epitope can have a length of from 10 amino acids (aa) to 15 amino acids (e.g., 10 aa, 11 aa, 12 aa, 13 aa, 14 aa, or 15 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 150-158 of the amino acid sequence designated "Consensus" in FIGS. 16A-16L, or a corresponding HCV core amino acid sequence of any HCV genotype; and the HCV core T-cell epitope can have a length of from 9 amino acids (aa) to 15 amino acids (e.g., 9 aa, 10 aa, 11 aa, 12 aa, 13 aa, 14 aa, or 15 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 154-162 of the amino acid sequence designated "Consensus" in FIGS. 16A-16L, or a corresponding HCV core amino acid sequence of any HCV genotype; and the HCV core T-cell epitope can have a length of from 9 amino acids (aa) to 15 amino acids (e.g., 9 aa, 10 aa, 11 aa, 12 aa, 13 aa, 14 aa, or 15 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 168-176 of the amino acid sequence designated "Consensus" in FIGS. 16A-16L, or a corresponding HCV core amino acid sequence of any HCV genotype; and the HCV core T-cell epitope can have a length of from 9 amino acids (aa) to 15 amino acids (e.g., 9 aa, 10 aa, 11 aa, 12 aa, 13 aa, 14 aa, or 15 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 177-187 of the amino acid sequence designated "Consensus" in FIGS. 16A-16L, or a corresponding HCV core amino acid sequence of any HCV genotype; and the HCV core T-cell epitope can have a length of from 11 amino acids (aa) to 16 amino acids (e.g., 11 aa, 12 aa, 13 aa, 14 aa, 15 aa, or 16 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 178-187 of the amino acid sequence designated "Consensus" in FIGS. 16A-16L, or a corresponding HCV core amino acid sequence of any HCV genotype; and the HCV core T-cell epitope can have a length of from 10 amino acids (aa) to 15 amino acids (e.g., 10 aa, 11 aa, 12 aa, 13 aa, 14 aa, or 15 aa).

In some cases, the heterologous polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to a contiguous stretch of from 10 amino acids (aa) to 191 an (e.g., from 10 aa to 25 aa, from 25 aa to 50 aa, from 50 aa to 75 aa, from 75 aa to 100 aa, from 100 aa to 150 aa, or from 150 aa to 191aa) of amino acids 1-191 of the amino acid sequence designated "Consensus" in FIGS. 16A-16L, or a corresponding HCV core amino acid sequence of any HCV genotype; and has a length of from 10 amino acids (aa) to 25 aa, from 25 an to 50 aa, from 50 an to 100 aa, or from 100 aa to 150 aa, or from 150 an to 191 aa. In some cases, the heterologous polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1-191 of the amino acid sequence designated "Consensus" in FIGS. 16A-16L, or a corresponding HCV core amino acid sequence of any HCV genotype; and has a length of about 191 amino acids.

The heterologous polypeptide can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence: MSTNPKPQRKTKRNTNRRPQDVKFPGGGQI-VGGVYLLPRRGPRLGVRATRKTS ERSQPR-GRRQPIPKARRPEGRTWAQPGYPWPLYG-NEGCGWAGWLLSPRGSRPS WGPTDPRRRSRN-LGKVIDTLTCGFADLMGYIPLVGAPLGGAARAL-AHGVRVLE DGVNYATGNLPG (SEQ ID NO:63); and has a length of from 171 amino acids (aa) to 180 aa (e.g., 171 aa, 172 aa, 173 aa, 174 aa, 175 aa, 176 aa, 177 aa, 178 aa, 179 aa, or 180 aa. In some cases, the heterologous polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence: MSTNPKPQRKTKRNTNRRPQDVKFPGGGQI-VGGVYLLPRRGPRLGVRATRKTS ERSQPR-GRRQPIPKARRPEGRTWAQPGYPWPLYG-NEGCGWAGWLLSPRGSRPS WGPTDPRRR-SRNLGKVIDTLTCGFADLMGYIPLVGAPLG-GAARALAHGVRVLE DGVNYATGNLPG (SEQ ID NO:63); and has a length of 171 amino acids. Such a polytope can include core T-cell epitopes designated Core-1, Core-2, Core-3, Core-4, Core-5, Core-6, Core-7, Core-8, Core-9, Core-10, Core-11, Core-12, Core-13, Core-14, Core-16, Core-17, Core-18, Core-19, Core-20, Core-21, Core-22 in FIG. 13A and FIGS. 15A-15N.

HCV p7 T-Cell Epitopes

In some cases, the heterologous polypeptide present in an E2 variant polypeptide of an E1/E2 heterodimer of the present disclosure includes one or more T-cell epitopes present in an HCV p7 polypeptide. Examples of T-cell epitopes present in HCV p7 polypeptides are depicted in FIGS. 15A-15N or FIG. 13A.

As another example, the heterologous polypeptide can comprise an HCV p7 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 803-811 of the amino acid sequence designated "Consensus" in FIGS. 16A-16L, or a corresponding HCV p7 amino acid sequence of any HCV genotype; and the HCV p7 T-cell epitope can have a length of from 9 amino acids (aa) to 15 amino acids (e.g., 9 aa, 10 aa, 11 aa, 12 aa, 13 aa, 14 aa, or 15 aa).

Polytopes Including HCV T-Cell Epitopes from More than One HCV Polypeptide Other than E1 and E2

As noted above, a heterologous polypeptide can include T-cell epitopes from more than one HCV polypeptide other than E1 and E2.

As one example, a heterologous polypeptide can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence: QASLLKVPYFVRVQGLLRICALARKMAGGHYVQ-MAIIKLGALTGTYVYNALTP LRDWAHNGLRD-LAVAVEPVVFSQMETKLITWGADTAACGDI-INGLPVSARRGR EILLGPADGMVSKGWRLL-APITAYAQQTRGLLGCIITSLTGRDKNQVEG-EVQIVS TAAQTFLATCINGVCWTVYHGAGTR-TIASPKGPVIQMYTNVDQDLVGWPAPQG ARSLTPCTCGSSDLYLVTRHADVIPVRRRGDS-RGSLLSPRPISYLKGSAGGPLLCP AGHAVGI-FRAAVCTRGVAKAVDFIPVENLETTMRSPVFT-DNSSPPAVPQSFQVA HLHAPTGSGKSTKVPA-AYAAQGYKVLVLNPSVAATLGFGAYMSKA-HGIDPNIR TGVRTITTGSPITYSTYGKFLADGGC-SGGAYDIIICDECHSTDATSILGIGTVLDQA ETAGARLVVLATATPPGSVTVPHPNIEEVALSTT-GEIPFYGKAIPLEVIKGGRHLIF CHSKKKCDE-LAAKLVALGINAVAYYRGLDVSVIPTSGDVVV-VATDALMTGFTG DFDSVIDCN (SEQ ID NO:12); and has a length of from 550 amino acids (aa) to 560 aa (e.g., 550 aa, 551 aa, 552 aa, 553 aa, 554 aa, 555 aa, 556 aa, 557 aa, 558 aa, 559 aa, or 560 aa). In some cases, the heterologous polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence: QASLLKVPYFVRVQGLLRICALARKMAGGHYVQ-MAIIKLGALTGTYVYNALTP LRDWAHNGLRD-LAVAVEPVVFSQMETKLITWGADTAACGDI-INGLPVSARRGR EILLGPADGMVSKGWRL-LAPITAYAQQTRGLLGCIITSLTGRDKNQVEG-EVQIVS TAAQTFLATCINGVCWTVYHGAGTR-TIASPKGPVIQMYTNVDQDLVGWPAPQG ARSLTPCTCGSSDLYLVTRHADVIPVRRRGD-SRGSLLSPRPISYLKGSAGGPLLCP AGHAVGI-FRAAVCTRGVAKAVDFIPVENLETTMRSPVFT-DNSSPPAVPQSFQVA HLHAPTGSGKSTKVPAA-YAAQGYKVLVLNPSVAATLGFGAYMSKAHGI-DPNIR TGVRTITTGSPITYSTYGKFLADGGCSG-GAYDIIICDECHSTDATSILGIGTVLDQA ETAG-ARLVVLATATPPGSVTVPHPNIEEVALSTTGEIP-FYGKAIPLEVIKGGRHLIF CHSKKKCDELAAK-LVALGINAVAYYRGLDVSVIPTSGDVVVVATDA-LMTGFTG DFDSVIDCN (SEQ ID NO:12); and has a length of 553 amino acids. Such a polytope can include T-cell epitopes designated NS2-1, NS2-2, NS2-3, NS2-4, NS2-5, NS2-6, NS2-7, NS2-8, NS3-1, NS3-2, NS3-3, NS3-4, NS3-5, NS3-6, NS3-7, NS3-9, NS3-10, NS3-11, NS3-12, and NS3-13 in FIGS. 13A-13B and FIGS. 15A-15N. This polytope is also referred to as "TP553" (FIGS. 14A-14D). In order to prevent self cleavage of the TP553 polytope (amino acids 917-1469) (FIGS. 15E-G) at the NS2-NS3 junction that is mediated by the catalytic domain of the NS2 protease (amino acids 917-1040), the histidine at position 966 (H966), a critical residue for NS2 protease activity, is mutated to alanine (H966A) (FIG. 15E).

As another example, the heterologous polypeptide can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to a contiguous stretch of from 25 amino acids (aa) to 778 aa (e.g., from 25 aa to 50 aa, from 50 aa to 75 aa, from 75 aa to 100 aa, from 100 an to 150 aa, from 150 an to 200 aa, from 200 aa to 250 aa, from 250 an to 300 aa, from 300 an to 350 aa, from 350 an to 400 aa, from 400 aa to 450 aa, from 450 aa to 500 aa, from 500 an to 550 aa, from 550 aa to 600 aa, from 600 an to 650 aa, from 650 an to 700 aa, from 700 aa to 750 aa, or from 750 an to 778 aa) the following amino acid sequence:
LHAPTGSGKSTKVPAAYAAQGYKVLVLNPSVAATLGFGAYMSKAHGIDPNIRTGVRTIT TGSPITYSTYGKFLADGGCSGGAYDIIICDECHSTDATSILGIGTVLDQAETAGARLVVLA TATPPGSVTVPHPNIEEVALSTTGEIPFYGKAIPLEVIKGGRHLIFCHSKKKCDELAAKLV ALGINAVAYYRGLDVSVIPTSGDVVVVATDALMTGFTGDFDSVIDCNTCVTQTVDFSLD PTFTIETITLPQDAVSRTQRRGRTGRGKPGIYRFVAPGERPSGMFDSSVLCECYDAGCA WYELTPAETTVRLRAYMNTPGLPVCQDHLEFWEGVFTGLTHIDAHFLSQTKQSGENLP YLVAYQATVCARAQAPPPSWDQMWKCLIRLKPTLHGPTPLLYRLGAVQNEVTLTHPIT KYIMTCMSADLEVVTSTWVLVGGVLAALAAYCLSTGCVVIVGRIVLSGKPAIIPDREVL YREFDEMEECSQHLPYIEQGMMLAEQFKQKALGLLQTASRQAEVIAPAVQTNWQKLEA FWAKHMWNFISGIQYLAGLSTLPGNPAIASLMAFTAAVTSPLTTSQTLLFNILGGWVAA QLAAPGAATAFVGAGLAGAAIGSVGLGKVLVDILAGYGAGVAGALVAFKIMSGEVPST EDLVNLLPAILSPGALVVGVVCAAILRRHVGPGEGAVQWMNRLIAFASRGNHVSPTHY VPESDAAARVTAILSSLTVTQLLRRLHQWISSECTTPCSGSWLRDIWDWICEVLSDFKTW LKAKLMPQLPG (SEQ ID NO:64). In some cases, the heterologous polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to a contiguous stretch of from 25 amino acids (aa) to 778 an (e.g., from 25 an to 50 aa, from 50 aa to 75 aa, from 75 an to 100 aa, from 100 aa to 150 aa, from 150 aa to 200 aa, from 200 aa to 250 aa, from 250 aa to 300 aa, from 300 aa to 350 aa, from 350 aa to 400 aa, from 400 an to 450 aa, from 450 an to 500 aa, from 500 an to 550 aa, from 550 aa to 600 aa, from 600 aa to 650 aa, from 650 an to 700 aa, from 700 aa to 750 aa, or from 750 an to 778 aa) of the following amino acid sequence:
LHAPTGSGKSTKVPAAYAAQGYKVLVLNPSVAATLGFGAYMSKAHGIDPNIRTGVRTIT TGSPITYSTYGKFLADGGCSGGAYDIIICDECHSTDATSILGIGTVLDQAETAGARLVVLA TATPPGSVTVPHPNIEEVALSTTGEIPFYGKAIPLEVIKGGRHLIFCHSKKKCDELAAKLV ALGINAVAYYRGLDVSVIPTSGDVVVVATDALMTGFTGDFDSVIDCNTCVTQTVDFSLD PTFTIETITLPQDAVSRTQRRGRTGRGKPGIYRFVAPGERPSGMFDSSVLCECYDAGCA WYELTPAETTVRLRAYMNTPGLPVCQDHLEFWEGVFTGLTHIDAHFLSQTKQSGENLP YLVAYQATVCARAQAPPPSWDQMWKCLIRLKPTLHGPTPLLYRLGAVQNEVTLTHPIT KYIMTCMSADLEVVTSTWVLVGGVLAALAAYCLSTGCVVIVGRIVLSGKPAIIPDREVL YREFDEMEECSQHLPYIEQGMMLAEQFKQKALGLLQTASRQAEVIAPAVQTNWQKLEA FWAKHMWNFISGIQYLAGLSTLPGNPAIASLMAFTAAVTSPLTTSQTLLFNILGGWVAA QLAAPGAATAFVGAGLAGAAIGSVGLGKVLVDILAGYGAGVAGALVAFKIMSGEVPST EDLVNLLPAILSPGALVVGVVCAAILRRHVGPGEGAVQWMNRLIAFASRGNHVSPTHY VPESDAAARVTAILSSLTVTQLLRRLHQWISSECTTPCSGSWLRDIWDWICEVLSDFKTW LKAKLMPQLPG (SEQ ID NO:64); and has a length of from 25 amino acids (aa) to 50 aa, from 50 aa to 100 aa, from 100 an to 200 aa, from 200 an to 300 aa, from 300 aa to 400 aa, from 400 an to 500 aa, from 500 an to 600 aa, from 600 an to 700 aa, or from 700 an to 778 aa. In some cases, the heterologous polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence:
LHAPTGSGKSTKVPAAYAAQGYKVLVLNPSVAATLGFGAYMSKAHGIDPNIRTGVRTIT TGSPITYSTYGKFLADGGCSGGAYDIIICDECHSTDATSILGIGTVLDQAETAGARLVVLA TATPPGSVTVPHPNIEEVALSTTGEIPFYGKAIPLEVIKGGRHLIFCHSKKKCDELAAKLV ALGINAVAYYRGLDVSVIPTSGDVVVVATDALMTGFTGDFDSVIDCNTCVTQTVDFSLD FTFTIETITLPQDAVSRTQRRGRTGRGKPGIYRFVAPGERPSGMFDSSVLCECYDAGCA WYELTPAETTVRLRAYMNTPGLPVCQDHLEFWEGVFTGLTHIDAHFLSQTKQSGENLP YLVAYQATVCARAQAPPPSWDQMWKCLIRLKPTLHGPTPLLYRLGAVQNEVTLTHPIT KYIMTCMSADLEVVTSTWVLVGGVLAALAAYCLSTGCVVIVGRIVLSGKPAIIPDREVL YREFDEMEECSQHLPYIEQGMMLAEQFKQKALGLLQTASRQAEVIAPAVQTNWQKLEA FWAKHMWNFISGIQYLAGLSTLPGNPAIASLMAFTAAVTSPLTTSQTLLFNILGGWVAA QLAAPGAATAFVGAGLAGAAIGSVGLGKVLVDILAGYGAGVAGALVAFKIMSGEVPST EDLVNLLPAILSPGALVVGVVCAAILRRHVGPGEGAVQWMNRLIAFASRGNHVSPTHY VPESDAAARVTAILSSLTVTQLLRRLHQWISSECTTPCSGSWLRDIWDWICEVLSDFKTW LKAKLMPQLPG (SEQ ID NO:64); and has a length of 778 amino acids. Such a polytope can include T-cell epitopes designated NS3-

1, NS3-2, NS3-3, NS3-4, NS3-5, NS3-6, NS3-7, NS3-8, NS3-9, NS3-10, NS3-11, NS3-12, NS3-13, NS2-14, NS4a-1, NS4b-1, NS4b-2, NS4b-3, NS4b-4, NS4b-5, NS4b-6, NS4b-7, NS4b-8, NS4b-9, and NS4b-10 in FIG. 13B and FIGS. 15A-15N.

As another example, the heterologous polypeptide can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to a contiguous stretch of from 25 amino acids (aa) to 1985 aa (e.g., from 25 aa to 50 aa, from 50 aa to 75 aa, from 75 aa to 100 aa, from 100 aa to 150 aa, from 150 an to 200 aa, from 200 aa to 250 aa, from 250 aa to 500 aa, from 500 an to 750 aa, from 750 an to 1000 aa, from 1000 aa to 1500 aa, or from 1500 an to 1985 aa) of the following amino acid sequence:

(SEQ ID NO: 13)

APITAYAQQTRGLLGCIITSLTGRDKNQVEGEVQIVSTAAQTFLATCING

VCWTVYHGAGTRTIASPKGPVIQMYTNVDQDLVGWPAPQGARSLTPCTCG

SSDLYLVTRHADVIPVRRRGDSRGSLLSPRPISYLKGSAGGPLLCPAGHA

VGIFRAAVCTRGVAKAVDFIPVENLETTMRSPVFTDNSSPPAVPQSFQVA

HLHAPTGSGKSTKVPAAYAAQGYKVLVLNPSVAATLGFGAYMSKAHGIDP

NIRTGVRTITTGSPITYSTYGKFLADGGCSGGAYDIIICDECHSTDATSI

LGIGTVLDQAETAGARLVVLATATPPGSVTVPHPNIEEVALSTTGEIPFY

GKAIPLEVIKGGRHLIFCHSKKKCDELAAKLVALGINAVAYYRGLDVSVI

PTSGDVVVVATDALMTGFTGDFDSVIDCNTCVTQTVDFSLDPTFTIETTT

LPQDAVSRTQRRGRTGRGKPGIYRFVAPGERPSGMFDSSVLCECYDAGCA

WYELTPAETTVRLRAYMNTPGLPVCQDHLEFWEGVFTGLTHIDAHFLSQT

KQSGENLPYLVAYQATVCARAQAPPPSWDQMWKCLIRLKPTLHGPTPLLY

RLGAVQNEVTLTHPITKYIMTCMSADLEVVTSTWVLVGGVLAALAAYCLS

TGCVVIVGRIVLSGKPAIIPDREVLYREFDEMEECSQHLPYIEQGMMLAE

QFKQKALGLLQTASRQAEVIAPAVQTNWQKLEAFWAKHMWNFISGIQYLA

GLSTLPGNPAIASLMAFTAAVTSPLTTSQTLLFNILGGWVAAQLAAPGAA

TAFVGAGLAGAAIGSVGLGKVLVDILAGYGAGVAGALVAFKIMSGEVPST

EDLVNLLPAILSPGALVVGVVCAAILRRHVGPGEGAVQWMNRLIAFASRG

NHVSPTHYVPESDAAARVTAILSSLTVTQLLRRLHQWISSECTTPCSGSW

LRDIWDWICEVLSDFKTWLKAKLMPQLPGIPFVSCQRGYRGVWRGDGIMH

TRCHCGAEITGHVKNGTMRIVGPRTCRNMWSGTFPINAYTTGPCTPLPAP

NYTFALWRVSAEEYVEIRQVGDFHYVTGMTTDNLKCPCQVPSPEFFTELD

GVRLHRFAPPCKPLLREEVSFRVGLHEYPVGSQLPCEPEPDVAVLTSMLT

DPSHITAEAAGRRLARGSPPSVASSSASQLSAPSLKATCTANHDSPDAEL

IEANLLWRQEMGGNITRVESENKVVILDSFDPLVAEEDEREISVPAEILR

KSRRFAPALPIWARPDYNPPLLETWKKPDYEPPVVHGCPLPPPQSPPVPP

PRKKRTVVLTESTVSTALAELATKSFGSSSTSGITGDNTTTSSEPAPSGC

PPDSDAESYSSMPPLEGEPGDPDLSDGSWSTVSSEADTEDVVCCSMSYSW

-continued

TGALVTPCAAEEQKLPINALSNSLLRHHNLVYSTTSRSACQRQKKVTFDR

LQVLDSHYQDVLKEVKAAASKVKANLLSVEEACSLTPPHSAKSKFGYGAK

DVRCHARKAVNHINSVWKDLLEDSVTPIDTTIMAKNEVFCVQPEKGGRKP

ARLIVFPDLGVRVCEKMALYDVVSKLPLAVMGSSYGFQYSPGQRVEFLVQ

AWKSKKTPMGFSYDTRCFDSTVTESDIRTEEAIYQCCDLDPQARVAIKSL

TERLYVGGPLTNSRGENCGYRRCRASGVLTTSCGNTLTCYIKARAACRAA

GLQDCTMLVCGNNLVVICESAGVQEDAASLRAFTEAMTRYSAPPGDPPQP

EYDLELITSCSSNVSVAHDGAGKRVYYLTRDPTTPLARAAWETARHTPVN

SWLGNIIMFAPTLWARMILMTHFFSVLIARDQLEQALDCEIYGACYSIEP

LDLPPIIQRLHGLSAFSLHSYSPGEINRVAACLRKLGVPPLRAWRHRARS

VRARLLSRGGRAAICGKYLFNWAVRTKLKLTPIAAAGQLDLSGWFTAGYS

GGDIYHSVSHARPRWFWFCLLLLAAGVGIYLLPNR.

In some cases, the heterologous polypeptide can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence:

(SEQ ID NO: 13)

APITAYAQQTRGLLGCIITSLTGRDKNQVEGEVQIVSTAAQTFLATCING

VCWTVYHGAGTRTIASPKGPVIQMYTNVDQDLVGWPAPQGARSLTPCTCG

SSDLYLVTRHADVIPVRRRGDSRGSLLSPRPISYLKGSAGGPLLCPAGHA

VGIFRAAVCTRGVAKAVDFIPVENLETTMRSPVFTDNSSPPAVPQSFQVA

HLHAPTGSGKSTKVPAAYAAQGYKVLVLNPSVAATLGFGAYMSKAHGIDP

NIRTGVRTITTGSPITYSTYGKFLADGGCSGGAYDIIICDECHSTDATSI

LGIGTVLDQAETAGARLVVLATATPPGSVTVPHPNIEEVALSTTGEIPFY

GKAIPLEVIKGGRHLIFCHSKKKCDELAAKLVALGINAVAYYRGLDVSVI

PTSGDVVVVATDALMTGFTGDFDSVIDCNTCVTQTVDFSLDPTFTIETTT

LPQDAVSRTQRRGRTGRGKPGIYRFVAPGERPSGMFDSSVLCECYDAGCA

WYELTPAETTVRLRAYMNTPGLPVCQDHLEFWEGVFTGLTHIDAHFLSQT

KQSGENLPYLVAYQATVCARAQAPPPSWDQMWKCLIRLKPTLHGPTPLLY

RLGAVQNEVTLTHPITKYIMTCMSADLEVVTSTWVLVGGVLAALAAYCLS

TGCVVIVGRIVLSGKPAIIPDREVLYREFDEMEECSQHLPYIEQGMMLAE

QFKQKALGLLQTASRQAEVIAPAVQTNWQKLEAFWAKHMWNFISGIQYLA

GLSTLPGNPAIASLMAFTAAVTSPLTTSQTLLFNILGGWVAAQLAAPGAA

TAFVGAGLAGAAIGSVGLGKVLVDILAGYGAGVAGALVAFKIMSGEVPST

EDLVNLLPAILSPGALVVGVVCAAILRRHVGPGEGAVQWMNRLIAFASRG

NHVSPTHYVPESDAAARVTAILSSLTVTQLLRRLHQWISSECTTPCSGSW

LRDIWDWICEVLSDFKTWLKAKLMPQLPGIPFVSCQRGYRGVWRGDGIMH

TRCHCGAEITGHVKNGTMRIVGPRTCRNMWSGTFPINAYTTGPCTPLPAP

-continued

```
NYTFALWRVSAEEYVEIRQVGDFHYVTGMTTDNLKCPCQVPSPEFFTELD

GVRLHRFAPPCKPLLREEVSFRVGLHEYPVGSQLPCEPEPDVAVLTSMLT

DPSHITAEAAGRRLARGSPPSVASSSASQLSAPSLKATCTANHDSPDAEL

IEANLLWRQEMGGNITRVESENKVVILDSFDPLVAEEDEREISVPAEILR

KSRRFAPALPIWARPDYNPPLLETWKKPDYEPPVVHGCPLPPPQSPPVPP

PRKKRTVVLTESTVSTALAELATKSFGSSSTSGITGDNTTTSSEPAPSGC

PPDSDAESYSSMPPLEGEPGDPDLSDGSWSTVSSEADTEDVVCCSMSYSW

TGALVTPCAAEEQKLPINALSNSLLRHHNLVYSTTSRSACQRQKKVTFDR

LQVLDSHYQDVLKEVKAAASKVKANLLSVEEACSLTPPHSAKSKFGYGAK

DVRCHARKAVNHINSVWKDLLEDSVTPIDTTIMAKNEVFCVQPEKGGRKP

ARLIVFPDLGVRVCEKMALYDVVSKLPLAVMGSSYGFQYSPGQRVEFLVQ

AWKSKKTPMGFSYDTRCFDSTVTESDIRTEEAIYQCCDLDPQARVAIKSL

TERLYVGGPLTNSRGENCGYRRCRASGVLTTSCGNTLTCYIKARAACRAA

GLQDCTMLVCGNNLVVICESAGVQEDAASLRAFTEAMTRYSAPPGDPPQP

EYDLELITSCSSNVSVAHDGAGKRVYYLTRDPTTPLARAAWETARHTPVN

SWLGNIIMFAPTLWARMILMTHFFSVLIARDQLEQALDCEIYGACYSIEP

LDLPPIIQRLHGLSAFSLHSYSPGEINRVAACLRKLGVPPLRAWRHRARS

VRARLLSRGGRAAICGKYLFNWAVRTKLKLTPIAAAGQLDLSGWFTAGYS

GGDIYHSVSHARPRWFWFCLLLLAAGVGIYLLPNR;
```

and has a length of 1985 amino acids. Such a polytope can include T-cell epitopes designated NS3-1, NS3-2, NS3-3, NS3-4, NS3-5, NS3-6, NS3-7, NS3-8, NS3-9, NS3-10, NS3-11, NS3-12, NS3-13, NS3-14, NS4a-1, NS4b-1, NS4b-2, NS4b-3, NS4b-4, NS4b-5, NS4b-6, NS4b-7, NS4b-8, NS4b-9, NS4b-10, NS5a-1, NS5a-2, NS5b-1, NS5b-2 in FIGS. 13A-13B and FIGS. 15A-15N.

Additional T-Cell Epitopes

As discussed above, an E1/E2 a heterodimeric polypeptide of the present disclosure includes: a) an HCV E2 polypeptide; and b) a variant HCV E1 polypeptide comprising: i) an HCV E1 polypeptide; and ii) a heterologous polypeptide that comprises one or more T-cell epitopes (e.g., one or more T cell epitopes present in an HCV polypeptide other than an HCV E1 polypeptide or an HCV E2 polypeptide). The one or more T-cell epitopes can include one or more T-cell epitopes present in: a) an HCV NS3 polypeptide; b) an HCV NS2 polypeptide; c) an HCV NS4A polypeptide; d) an HCV NS4B polypeptide; e) an HCV NS5A polypeptide; f) an HCV NS5B polypeptide; g) an HCV core polypeptide; or h) an HCV p7 polypeptide. In some cases, the one or more T-cell epitopes are T-cell epitopes present in an HCV NS3 polypeptide. In some cases, the heterologous polypeptide further comprises one or more T cell epitopes present in: a) cholera toxin or toxoid; and/or b) tetanus toxin or toxoid; and/or c) diphtheria toxin or toxoid; and/or d) a meningococcal outer membrane protein.

Thus, in some cases, a variant HCV E1 polypeptide of an E1/E2 heterodimer of the present disclosure includes: a) an HCV E1 polypeptide; and b) a heterologous polypeptide that comprises one or more T-cell epitopes, where the one or more T-cell epitopes are T-cell epitopes present in: i) one or more of an HCV NS3 polypeptide, an HCV NS2 polypeptide, an HCV NS4A polypeptide, an HCV NS4B polypeptide, an HCV NS5A polypeptide, an HCV NS5B polypeptide, an HCV core polypeptide, and an HCV p7 polypeptide; and ii) one or more of cholera toxin or toxoid, tetanus toxin or toxoid, diphtheria toxin or toxoid, and a meningococcal outer membrane protein.

Additional T-Cell Epitopes

As discussed above, an E1/E2 a heterodimeric polypeptide of the present disclosure includes: a) an HCV E1 polypeptide; and b) a variant HCV E2 polypeptide comprising: i) an HCV E2 polypeptide; and ii) a heterologous polypeptide that comprises one or more T-cell epitopes (e.g., one or more T cell epitopes present in an HCV polypeptide other than an HCV E1 polypeptide or an HCV E2 polypeptide). The one or more T-cell epitopes can include one or more T-cell epitopes present in: a) an HCV NS3 polypeptide; b) an HCV NS2 polypeptide; c) an HCV NS4A polypeptide; d) an HCV NS4B polypeptide; e) an HCV NS5A polypeptide; f) an HCV NS5B polypeptide; g) an HCV core polypeptide; or h) an HCV p7 polypeptide. In some cases, the one or more T-cell epitopes are T-cell epitopes present in an HCV NS3 polypeptide. In some cases, the heterologous polypeptide further comprises one or more T cell epitopes present in: a) cholera toxin or toxoid; and/or b) tetanus toxin or toxoid; and/or c) diphtheria toxin or toxoid; and/or d) a meningococcal outer membrane protein.

Thus, in some cases, a variant HCV polypeptide of an E1/E2 heterodimer of the present disclosure includes: a) an HCV E2 polypeptide; and b) a heterologous polypeptide that comprises one or more T-cell epitopes, where the one or more T-cell epitopes are T-cell epitopes present in: i) one or more of an HCV NS3 polypeptide, an HCV NS2 polypeptide, an HCV NS4A polypeptide, an HCV NS4B polypeptide, an HCV NS5A polypeptide, an HCV NS5B polypeptide, an HCV core polypeptide, and an HCV p7 polypeptide; and ii) one or more of cholera toxin or toxoid, tetanus toxin or toxoid, diphtheria toxin or toxoid, and a meningococcal outer membrane protein.

A T helper tetanus toxin epitope or other bacterial T-cell epitope could be fused (e.g., by recombinant expression) or chemically conjugated to the HCV polytope/E2 fusion protein and/or to the HCV polytope E1 fusion protein of an E1/E2 heterodimer of the present disclosure to further enhance both T and B cell responses to both the HCV polytope and E1/E2 moieties. Alternatively, the whole or part of the detoxified toxin ("toxoid") could be fused (e.g., by recombinant expression) or chemically conjugated to the HCV polytope/E1E2 protein, wherein specific amino acids of the toxins are mutated to render the toxins inactive, thereby generating toxoids. Methods of generating toxoids are well known in the art. Examples of bacterial epitopes include the use of diphtheria toxoid, meningococcal outer membrane protein, or mutant diphtheria protein CRM197 (see, e.g.: http://www(dot)medscape(dot)com/viewarticle/431127)

In some cases, a suitable tetanus toxoid polypeptide comprises the amino acid sequence QYIKANSKFIGIFE (SEQ ID NO:14). In some cases, a suitable tetanus toxoid polypeptide comprises the amino acid sequence QYIKANSKFIGITE (SEQ ID NO:65).

In some cases, a heterologous polypeptide can comprise cholera toxin (or toxoid) epitope. In some cases, a suitable heterologous polypeptide comprising a cholera toxoid epitope comprises a fragment of cholera toxin-B subunit (CT-B), e.g., a fragment of from 5 amino acids to 25 amino acids, or from 25 amino acids to 50 amino acids, of the following amino acid sequence: MIKLKFGVFF TVLLSSAYAH GTPQNITDLC AEYHNTQIHT LNDKIFSYTE SLAGKREMAI ITFKNGATFQ VEVPGSQHID SQKKAI-ERMK DTLRIAYLTE AKVEKLCVWN NKTPHAIAAI SMAN (SEQ ID NO:15).

In some cases, a heterologous polypeptide can comprise a tetanus toxin (or toxoid) T-cell epitope. In some cases, a suitable heterologous polypeptide comprising a tetanus toxin T-cell epitope comprises the amino acid sequence: ILMQYIKANSKFIGI (SEQ ID NO:16); and has a length of from 15 amino acids to 20 amino acids. In some cases, a suitable heterologous polypeptide comprising a tetanus toxin T-cell epitope comprises the amino acid sequence: VNNESSE (SEQ ID NO:17). In some cases, a suitable heterologous polypeptide comprising a tetanus toxin T-cell epitope comprises the amino acid sequence: PGINGKAIHLVNNESSE (SEQ ID NO:18). In some cases, a suitable heterologous polypeptide comprising a tetanus toxin T-cell epitope comprises the amino acid sequence: PNRDIL (SEQ ID NO:19). In some cases, a suitable heterologous polypeptide comprising a tetanus toxin T-cell epitope comprises the amino acid sequence: FIGITEL (SEQ ID NO:20). In some cases, a suitable tetanus toxin T-cell epitope comprises the amino acid sequence: SYFPSV (SEQ ID NO:21). In some cases, a suitable heterologous polypeptide comprising a tetanus toxin T-cell epitope comprises the amino acid sequence: NSVDDALINSTKIYSYFPSV (SEQ ID NO:22). In some cases, a suitable heterologous polypeptide comprising a tetanus toxin T-cell epitope comprises the amino acid sequence: IDKISDVSTIVPYIGPALNI (SEQ ID NO:23).

In some cases, a heterologous polypeptide can comprise a diphtheria toxin T-cell epitope In some cases, a suitable heterologous polypeptide comprising a diphtheria toxin T-cell epitope comprises the amino acid sequence: QSIALSSLMVAQAIP (SEQ ID NO:24); and has a length of from 15 amino acids to 20 amino acids. In some cases, a suitable heterologous polypeptide comprising a diphtheria toxin T-cell epitope comprises the amino acid sequence:

PVFAGANYAAWAVNVAQVI (SEQ ID NO:25). In some cases, a suitable heterologous polypeptide comprising a diphtheria toxin T-cell epitope comprises the amino acid sequence:

VHHNTEEIVAQSIALSSLMV (SEQ ID NO:26). In some cases, a suitable heterologous polypeptide comprising a diphtheria toxin T-cell epitope comprises the amino acid sequence: QSIALSSLMVAQAIPLVGEL (SEQ ID NO:66). In some cases, a suitable heterologous polypeptide comprising a diphtheria toxin T-cell epitope comprises the amino acid sequence:

VDIGFAAYNFVESIINLFQV (SEQ ID NO:67). In some cases, a suitable heterologous polypeptide comprising a diphtheria toxin T-cell epitope comprises the amino acid sequence:

QGESGHDIKITAENTPLPIA (SEQ ID NO:68). In some cases, a suitable heterologous polypeptide comprising a diphtheria toxin T-cell epitope comprises the amino acid sequence:

GVLLPTIPGKLDVNKSKTHI (SEQ ID NO:69). In some cases, a suitable heterologous polypeptide comprising a diphtheria toxin T-cell epitope comprises the amino acid sequence of CRM197 (see, e.g., Giannini et al. (1984) Nucl. Acids. Res. 12:4063). The amino acid sequence of CRM197 is provided above.

In some cases, a heterologous polypeptide can comprise a tetanus toxin T-cell epitope and a diphtheria toxin T-cell epitope. In some of these cases, the heterologous polypeptide can comprise the amino acid sequence: IMQYIKAN-SKFIGIQSIALSSLMVAQ (SEQ ID NO:28); and can have a length of from 26 amino acids to 30 amino acids.

E2

An E2 polypeptide suitable for inclusion in an E1/E2 heterodimer of the present disclosure can have a length of from about 200 amino acids (aa) to about 250 aa, from about 250 aa to about 275 aa, from about 275 aa to about 300 aa, from about 300 aa to about 325 aa, from about 325 aa to about 350 aa, or from about 350 aa to about 365 aa. In some cases, an E2 polypeptide suitable for inclusion in an E1/E2 heterodimer of the present disclosure is a full-length HCV E2 polypeptide. In some cases, an E2 polypeptide suitable for inclusion in an E1/E2 heterodimer of the present disclosure is an HCV E2 ectodomain polypeptide.

In FIGS. 1A-AC, the amino acid sequence of E2 is amino acid 384 to amino acid 746. In FIGS. 2A-2B, the amino acid sequence of E2 is amino acid 384 to amino acid 751. In FIGS. 3A-3C, the amino acid sequence of E2 is amino acid 385 to amino acid 754. In FIGS. 4A-4B, the amino acid sequence of E2 is amino acid 384 to amino acid 750. As used herein, an "E2 polypeptide" includes a precursor E2 protein, including the signal sequence; includes a mature E2 polypeptide which lacks this sequence; and includes an E2 polypeptide with a heterologous signal sequence. An E2 polypeptide can include a C-terminal membrane anchor sequence which occurs at approximately amino acid positions 715-730 and may extend as far as approximately amino acid residue 746 (see, Lin et al., J. Virol. (1994) 68:5063-5073).

In some cases, a E2 polypeptide suitable for inclusion in an E1/E2 heterodimer of the present disclosure lacks a portion of its C-terminal region, e.g., from about amino acid 715 to the C-terminus; from about amino acid 625 to the C-terminus; from about amino acid 661 to the C-terminus; from about amino acid 655 to the C-terminus; from about amino acid 500 to the C-terminus, where the amino acid numbering is with reference to the numbering in FIGS. 1A-1C. See, e.g., U.S. Pat. No. 6,521,423.

An E2 polypeptide suitable for inclusion in an E1/E2 heterodimer of the present disclosure can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to an amino acid sequence of an E2 polypeptide depicted in FIGS. 1A-1C, FIGS. 2A-2C, FIGS. 3A-3C, or FIGS. 4A-4B.

An E2 polypeptide suitable for inclusion in an E1/E2 heterodimer of the present disclosure can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to an amino acid sequence of an E2 polypeptide depicted in FIGS. 1A-1C. For example, an E2 polypeptide of genotype 1 can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 384-746 of an amino acid sequence depicted in FIGS. 1A-1C. For example, an E2 polypeptide of genotype 1A can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 384-746 of an amino acid sequence identified as 1A and depicted in FIGS. 1A-1C. For example, an E2 polypeptide of genotype 1B can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 384-746 of an amino acid sequence identified as 1B and depicted in FIGS. 1A-1C. For example, an E2 polypeptide of genotype 1C can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 384-746 of an amino acid sequence identified as 1C and depicted in FIGS. 1A-1C.

An E2 polypeptide suitable for inclusion in an E1/E2 heterodimer of the present disclosure can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to an amino acid sequence of an E2 polypeptide depicted in FIGS. 2A-2C. For example, an E2 polypeptide can comprise an amino acid sequence having having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 384-746 of an amino acid sequence depicted in FIGS. 2A-2C. For example, an E2 polypeptide of genotype 2A can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 384-751 of the "consensus" amino acid sequence depicted in FIGS. 2A-2C. For example, an E2 polypeptide of genotype 2B can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 384-751 of the "consensus" amino acid sequence depicted in FIGS. 2A-2C.

An E2 polypeptide suitable for inclusion in an E1/E2 heterodimer of the present disclosure can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to an amino acid sequence of an E2 polypeptide depicted in FIGS. 3A-3C. For example, an E2 polypeptide of genotype 3 can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 385-754 of an amino acid sequence depicted in FIGS. 3A-3C. For example, an E2 polypeptide of genotype 3A can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 385-754 of an amino acid sequence identified as 3A and depicted in FIGS. 3A-3C. For example, an E2 polypeptide of genotype 3B can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 385-754 of the amino acid sequence identified as 3B and depicted in FIGS. 3A-3C. For example, an E2 polypeptide of genotype 3K can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 385-754 of the amino acid sequence identified as 3K and depicted in FIGS. 3A-3C.

An E2 polypeptide suitable for inclusion in an E1/E2 heterodimer of the present disclosure can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the amino acid sequence of the E2 polypeptide depicted in FIGS. 4A-4B. For example, an E2 polypeptide of genotype 7A can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 384-750 of the amino acid sequence depicted in FIGS. 4A-4B.

Additional Polypeptides

In any of the above-described embodiments, one or both of the polypeptide chains of the E1/E2 heterodimer can include one or more additional polypeptides. For example, in some cases, the variant E1 polypeptide or the E2 polypeptide can include an Ig Fc polypeptide at the C-terminus of the variant E1 polypeptide or the E2 polypeptide. As another example, in some cases, the variant E1 polypeptide or the E2 polypeptide can include an Ig Fc polypeptide at the N-terminus of the variant E1 polypeptide or the E2 polypeptide. Ig Fc polypeptides are known in the art, and are described elsewhere herein.

IC. E1E2 Heterodimers Comprising a Variant HCV E1 and a Variant HCV E2

The present disclosure provides an E1/E2 heterodimer, where the E1/E2 heterodimer includes both a variant E1 polypeptide and a variant E2 polypeptide.

Thus, in some cases, a heterodimeric polypeptide of the present disclosure includes: a) a variant HCV E1 polypeptide comprising: i) an HCV E1 polypeptide; and ii) a heterologous polypeptide that comprises one or more T-cell epitopes (e.g., one or more T cell epitopes present in an HCV polypeptide other than an HCV E1 polypeptide or an HCV E2 polypeptide); and b) a variant HCV E2 polypeptide comprising: i) an HCV E2 polypeptide; and ii) a heterologous polypeptide that comprises one or more T-cell epitopes (e.g., one or more T cell epitopes present in an HCV polypeptide other than an HCV E1 polypeptide or an HCV E2 polypeptide). The one or more T-cell epitopes can include one or more T-cell epitopes present in: a) an HCV NS3 polypeptide; b) an HCV NS2 polypeptide; c) an HCV NS4A polypeptide; d) an HCV NS4B polypeptide; e) an HCV NS5A polypeptide; f) an HCV NS5B polypeptide; g) an HCV core polypeptide; or h) an HCV p7 polypeptide. In some cases, the one or more T-cell epitopes are T-cell epitopes present in an HCV NS3 polypeptide. In some cases, the heterologous polypeptide further comprises one or more T cell epitopes present in: a) cholera toxin or toxoid; and/or b) tetanus toxin or toxoid; and/or c) diphtheria toxin or toxoid; and/or d) a meningococcal outer membrane protein. In some cases, a variant HCV E2 and a variant HCV E1 polypeptide of an E1/E2 heterodimer of the present disclosure includes: 1) a) an HCV E2 polypeptide; and b) a heterologous polypeptide that comprises one or more T-cell epitopes, where the one or more T-cell epitopes are T-cell epitopes present in: i) one or more of an HCV NS3 polypeptide, an HCV NS2 polypeptide, an HCV NS4A polypeptide, an HCV NS4B polypeptide, an HCV NS5A polypeptide, an HCV NS5B polypeptide, an HCV core polypeptide, and an HCV p7 polypeptide; and ii) one or more of cholera toxin or toxoid, tetanus toxin or toxoid, diphtheria toxin or toxoid, and a meningococcal outer membrane protein; and 2) a) an HCV E1 polypeptide; and b) a heterologous polypeptide that comprises one or more T-cell epitopes, where the one or more T-cell epitopes are T-cell epitopes present in: i) one or more of an HCV NS3 polypeptide, an HCV NS2 polypeptide, an HCV NS4A polypeptide, an HCV NS4B polypeptide, an HCV NS5A polypeptide, an HCV NS5B polypeptide, an HCV core polypeptide, and an HCV p7 polypeptide; and ii) one or more of cholera toxin or toxoid, tetanus toxin or toxoid, diphtheria toxin or toxoid, and a meningococcal outer membrane protein.

In some cases, a variant E2 polypeptide present in an E1/E2 heterodimer of the present disclosure comprises, in order from N-terminus to C-terminus: i) an HCV E2 polypeptide; and ii) a heterologous polypeptide comprising one or more T cell epitopes. In some cases, a variant HCV E2 polypeptide present in an E1/E2 heterodimer of the present disclosure comprises, in order from N-terminus to C-terminus: i) a heterologous polypeptide comprising one or more T cell epitopes; and ii) an HCV E2 polypeptide. In some cases, a variant E1 polypeptide present in an E1/E2 heterodimer of the present disclosure comprises, in order from N-terminus to C-terminus: i) an HCV E1 polypeptide; and ii) a heterologous polypeptide comprising one or more T cell epitopes. In some cases, a variant HCV E1 polypeptide present in an E1/E2 heterodimer of the present disclosure comprises, in order from N-terminus to C-terminus: i) a heterologous polypeptide comprising one or more T cell epitopes; and ii) an HCV E1 polypeptide. In some cases, both the variant E1 and the variant E2 polypeptide include the heterologous polypeptide at the N-terminus of the E1 and E2 polypeptides. In some cases, both the variant E1 and the variant E2 polypeptide include the heterologous polypeptide at the C-terminus of the E1 and E2 polypeptides. In some cases, the variant E1 polypeptide comprises the heterologous polypeptide at the N-terminus of the E1 polypeptide; and the variant E2 polypeptide comprises the heterologous polypeptide at the C-terminus of the E2 polypeptide. In some cases, the variant E1 polypeptide comprises the heterologous polypeptide at the C-terminus of the E1 polypeptide; and the variant E2 polypeptide comprises the heterologous polypeptide at the N-terminus of the E2 polypeptide.

Variant E1

As noted above, a variant E1 polypeptide of an HCV E1/E2 heterodimer of the present disclosure comprises: i) an HCV E1 polypeptide; and ii) a heterologous polypeptide comprising one or more T cell epitopes (e.g., one or more T-cell epitopes not present in an HCV E1 or an HCV E2 polypeptide; e.g., one or more T-cell epitopes present in an HCV polypeptide other than an HCV E1 or an HCV E2 polypeptide). In some cases, the variant HCV E1 polypeptide comprises, in order from amino terminus (N-terminus) to carboxyl terminus (C-terminus): i) an HCV E1 polypeptide; and ii) a heterologous polypeptide comprising one or more T cell epitopes. In some cases, the variant HCV E1 polypeptide comprises, in order from N-terminus to C-terminus: i) a heterologous polypeptide comprising one or more T cell epitopes; and ii) an HCV E1 polypeptide.

E1

An HCV E1 polypeptide suitable for inclusion in a variant E1 polypeptide of an E1/E2 heterodimer of the present disclosure can have a length of from about 150 amino acids (aa) to about 175 aa, from about 175 aa to about 195 aa, from about 131 an to about 175 aa, or from about 175 aa to about 193 aa. In some cases, an E1 polypeptide suitable for inclusion in a variant E1 polypeptide of an HCV E1/E2 heterodimer of the present disclosure is a full-length HCV E1 polypeptide. In some cases, an E1 polypeptide suitable for inclusion in a variant E1 polypeptide of an HCV E1/E2 heterodimer of the present disclosure is an HCV E1 ectodomain polypeptide.

In FIGS. 1A-1C, the amino acid sequence of E1 is amino acid 192 to amino acid 383. In FIGS. 2A-2C, the amino acid sequence of E1 is amino acid 192 to amino acid 383. In FIGS. 3A-3C, the amino acid sequence of E1 is amino acid 192 to amino acid 384. In FIGS. 4A-4B, the amino acid sequence of E1 is amino acid 192 to amino acid 383. Amino acids at around 170 through approximately 191 serve as a signal sequence for E1. As used herein, "E1 polypeptide" includes a precursor E1 protein, including the signal sequence; includes a mature E1 polypeptide which lacks this sequence; and includes an E1 polypeptide with a heterologous signal sequence. An E1 polypeptide can include a C-terminal membrane anchor sequence which occurs at approximately amino acid positions 360-383 (see, e.g., WO 96/04301). In some cases, a suitable E1 polypeptide lacks a C-terminal portion that includes a transmembrane region. For example, in some cases, a suitable E1 polypeptide lacks the C-terminal portion from amino acid 330 to amino acid 384, or from amino acid 360 to amino acid 384. E1 polypeptides can be an E1 polypeptide of any genotype, subtype or isolate of HCV. E1 polypeptides of genotype 1 and E1 polypeptides of genotype 3 are included in an E1/E2 heterodimer of the present disclosure.

An E1 polypeptide suitable for inclusion in a variant E1 polypeptide of an E1/E2 heterodimer of the present disclosure can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to an amino acid sequence of an E1 polypeptide depicted in FIGS. 1A-1C, FIGS. 2A-2C, FIGS. 3A-3C, or FIGS. 4A-4B.

An E1 polypeptide suitable for inclusion in a variant E1 polypeptide of an E1/E2 heterodimer of the present disclosure can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to an amino acid sequence of an E1 polypeptide depicted in FIGS. 1A-1C. For example, an E1 polypeptide of genotype 1A can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 192-383 of an amino acid sequence identified as 1A and depicted in FIGS. 1A-1C. For example, an E1 polypeptide of genotype 1B can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 192-383 of an amino acid sequence identified as 1B and depicted in FIGS. 1A-1C. For example, an E1 polypeptide of genotype 1C can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 192-383 of an amino acid sequence identified as 1C and depicted in FIGS. 1A-1C.

An E1 polypeptide suitable for inclusion in a variant E1 polypeptide of an E1/E2 heterodimer of the present disclosure can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to an amino acid sequence of an E1 polypeptide depicted in FIGS. 2A-2C. For example, an E1 polypeptide of genotype 2A can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 192-383 of an amino acid sequence identified as 2A and depicted in FIGS. 2A-2C. For example, an E1 polypeptide of genotype 2B can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 192-383 of an amino acid sequence identified as 2B and depicted in FIGS. 2A-2C.

An E1 polypeptide suitable for inclusion in a variant E1 polypeptide of an E1/E2 heterodimer of the present disclosure can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the consensus E1 polypeptide amino acid sequence depicted in FIGS. 3A-3C.

An E1 polypeptide suitable for inclusion in a variant E1 polypeptide of an E1/E2 heterodimer of the present disclosure can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to an amino acid sequence of an E1 polypeptide depicted in FIGS. 4A-4B. For example, an E1 polypeptide of genotype 7A can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 192-383 of the amino acid sequence depicted in FIGS. 4A-4B.

Variant E2

As noted above, a variant E2 polypeptide of an HCV E1/E2 heterodimer of the present disclosure comprises: i) an HCV E2 polypeptide; and ii) a heterologous polypeptide comprising one or more T cell epitopes (e.g., one or more T-cell epitopes not present in an HCV E1 or an HCV E2 polypeptide; e.g., one or more T-cell epitopes present in an HCV polypeptide other than an HCV E1 or an HCV E2 polypeptide). In some cases, the variant HCV E2 polypeptide comprises, in order from amino terminus (N-terminus) to carboxyl terminus (C-terminus): i) an HCV E2 polypeptide; and ii) a heterologous polypeptide comprising one or more T cell epitopes. In some cases, the variant HCV E2 polypeptide comprises, in order from N-terminus to C-terminus: i) a heterologous polypeptide comprising one or more T cell epitopes; and ii) an HCV E2 polypeptide.

In some cases, a variant E2 polypeptide of an HCV E1/E2 heterodimer of the present disclosure comprises from 1 to 10 amino acids at the N-terminus of the variant E2 polypeptide, which 1 to 10 amino acids are part of a cleavable linker that remains following cleavage of a polyprotein precursor, as described below. For example, where the cleavable linker comprises the amino acid sequence LEVLFQGP (SEQ ID NO:5), the variant E2 polypeptide can comprise Gly-Pro residues at the N-terminus of the polypeptide, e.g., as depicted in FIG. 5A.

E2

An E2 polypeptide suitable for inclusion in a variant E2 polypeptide of an E1/E2 heterodimer of the present disclosure can have a length of from about 200 amino acids (aa) to about 250 aa, from about 250 aa to about 275 aa, from about 275 aa to about 300 aa, from about 300 aa to about 325 aa, from about 325 aa to about 350 aa, or from about 350 aa to about 365 aa. In some cases, an E2 polypeptide suitable for inclusion in a variant E2 polypeptide of an HCV E1/E2 heterodimer of the present disclosure is a full-length HCV E1 polypeptide. In some cases, an E2 polypeptide suitable for inclusion in a variant E1 polypeptide of an HCV E1/E2 heterodimer of the present disclosure is an HCV E2 ectodomain polypeptide.

In FIGS. 1A-AC, the amino acid sequence of E2 is amino acid 384 to amino acid 746. In FIGS. 2A-2B, the amino acid sequence of E2 is amino acid 384 to amino acid 751. In FIGS. 3A-3C, the amino acid sequence of E2 is amino acid 385 to amino acid 754. In FIGS. 4A-4B, the amino acid sequence of E2 is amino acid 384 to amino acid 750. As used herein, an "E2 polypeptide" includes a precursor E2 protein, including the signal sequence; includes a mature E2 polypeptide which lacks this sequence; and includes an E2 polypeptide with a heterologous signal sequence. An E2 polypeptide can include a C-terminal membrane anchor sequence which occurs at approximately amino acid positions 715-730 and may extend as far as approximately amino acid residue 746 (see, Lin et al., J. Virol. (1994) 68:5063-5073).

In some cases, a E2 polypeptide suitable for inclusion in a variant E2 polypeptide of an E1/E2 heterodimer of the present disclosure lacks a portion of its C-terminal region, e.g., from about amino acid 715 to the C-terminus; from about amino acid 625 to the C-terminus; from about amino acid 661 to the C-terminus; from about amino acid 655 to the C-terminus; from about amino acid 500 to the C-terminus, where the amino acid numbering is with reference to the numbering in FIGS. 1A-1C. See, e.g., U.S. Pat. No. 6,521,423.

An E2 polypeptide suitable for inclusion in a variant E2 polypeptide of an E1/E2 heterodimer of the present disclosure can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to an amino acid sequence of an E2 polypeptide depicted in FIGS. 1A-1C, FIGS. 2A-2C, FIGS. 3A-3C, or FIGS. 4A-4B.

An E2 polypeptide suitable for inclusion in a variant E2 polypeptide of an E1/E2 heterodimer of the present disclosure can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to an amino acid sequence of an E2 polypeptide depicted in FIGS. 1A-1C. For example, an E2 polypeptide of genotype 1 can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 384-746 of an amino acid sequence depicted in FIGS. 1A-1C. For example, an E2 polypeptide of genotype 1A can comprise an amino acid sequence having having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 384-746 of an amino acid sequence identified as 1A and depicted in FIGS. 1A-1C. For example, an E2 polypeptide of genotype 1B can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 384-746 of an amino acid sequence identified as 1B and depicted in FIGS. 1A-1C. For example, an E2 polypeptide of genotype 1C can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 384-746 of an amino acid sequence identified as 1C and depicted in FIGS. 1A-1C.

An E2 polypeptide suitable for inclusion in a variant E2 polypeptide of an E1/E2 heterodimer of the present disclosure can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to an amino acid sequence of an E2 polypeptide depicted in FIGS. 2A-2C. For example, an E2 polypeptide can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 384-746 of an amino acid sequence depicted in FIGS. 2A-2C. For example, an E2 polypeptide of genotype 2A can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 384-751 of the "consensus" amino acid sequence depicted in FIGS. 2A-2C. For example, an E2 polypeptide of genotype 2B can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 384-751 of the "consensus" amino acid sequence depicted in FIGS. 2A-2C.

An E2 polypeptide suitable for inclusion in a variant E2 polypeptide of an E1/E2 heterodimer of the present disclosure can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to an amino acid sequence of an E2 polypeptide depicted in FIGS. 3A-3C. For example, an E2 polypeptide of genotype 3 can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 385-754 of an amino acid sequence depicted in FIGS. 3A-3C. For example, an E2 polypeptide of genotype 3A can comprise an amino acid sequence having having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 385-754 of an amino acid sequence identified as 3A and depicted in FIGS. 3A-3C. For example, an E2 polypeptide of genotype 3B can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 385-754 of the amino acid sequence identified as 3B and depicted in FIGS. 3A-3C. For example, an E2 polypeptide of genotype 3K can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 385-754 of the amino acid sequence identified as 3K and depicted in FIGS. 3A-3C.

An E2 polypeptide suitable for inclusion in a variant E2 polypeptide of an E1/E2 heterodimer of the present disclosure can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the amino acid sequence of the E2 polypeptide depicted in FIGS. 4A-4B. For example, an E2 polypeptide of genotype 7A can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 384-750 of the amino acid sequence depicted in FIGS. 4A-4B.

Heterologous Polypeptide

As noted above, in some embodiments, an E1/E2 heterodimer of the present disclosure comprises: a) a variant E1 polypeptide comprising: i) an HCV E1 polypeptide; and 2) a heterologous polypeptide comprising one or more T cell epitopes (e.g., one or more T-cell epitopes not present in an HCV E1 or an HCV E2 polypeptide; e.g., one or more T-cell epitopes present in an HCV polypeptide other than an HCV E1 or an HCV E2 polypeptide); and b) a variant E2 polypeptide comprising: i) an HCV E2 polypeptide; and 2) a heterologous polypeptide comprising one or more T cell epitopes (e.g., one or more T-cell epitopes not present in an HCV E1 or an HCV E2 polypeptide; e.g., one or more T-cell epitopes present in an HCV polypeptide other than an HCV E1 or an HCV E2 polypeptide).

In some cases, the heterologous polypeptide comprises 1, 2, 3, 4, 5, 6, 7, 8, 9, or 10, or more than 10 (e.g., from 10 to 15, from 15 to 20, from 20 to 25, or from 25 to 30, or more than 30), T cell epitopes. T-cell epitopes are epitopes that, when presented with a major histocompatibility complex (MHC) (e.g., a human leukocyte antigen (HLA)) Class I or MHC Class II molecule, are recognized and bound by a T-cell receptor (TCR) present on a T cell surface. T-cell epitopes include epitopes recognized by cytotoxic T cells (e.g., $CD8^+$ T cells), and epitopes recognized by helper T cells (e.g., $CD4^+$ T cells).

The one or more T-cell epitopes can include one or more T-cell epitopes present in: a) an HCV NS3 polypeptide; b) an HCV NS2 polypeptide; c) an HCV NS4A polypeptide; d) an HCV NS4B polypeptide; e) an HCV NS5A polypeptide; f) an HCV NS5B polypeptide; g) an HCV core polypeptide; or h) an HCV p7 polypeptide. In some cases, the one or more T-cell epitopes are T-cell epitopes present in an HCV NS3 polypeptide. In some cases, the heterologous polypeptide further comprises one or more T cell epitopes present in: a) cholera toxin or toxoid; and/or b) tetanus toxin or toxoid; and/or c) diphtheria toxin or toxoid; and/or d) a meningococcal outer membrane protein. Other examples of strong T helper epitopes are diphtheria toxoid, tetanus toxoid, meningococcal outer membrane protein, or mutant diphtheria protein CRM197 (see, e.g.: http://www(dot)medscape(dot)com/viewarticle/431127).

In some cases, the heterologous polypeptide comprises a single T-cell epitope. In some cases, the heterologous polypeptide comprises a single HCV-NS3 T-cell epitope. In some cases, the heterologous polypeptide comprises 2 or more T-cell epitopes. In some cases, the heterologous polypeptide comprises 2 or more HCV-NS3 T-cell epitopes. In some cases, the heterologous polypeptide comprises 3 or more HCV-NS3 T-cell epitopes. In some cases, the heterologous polypeptide comprises 4 or more HCV-NS3 T-cell epitopes. In some cases, the heterologous polypeptide comprises a single HCV-NS3 $CD4^+$ T-cell epitope. In some cases, the heterologous polypeptide comprises 2 or more HCV-NS3

$CD4^+$ T-cell epitopes. In some cases, the heterologous polypeptide comprises one or more HCV $CD8^+$ T cell epitopes. In some cases, the heterologous polypeptide comprises a single HCV-NS3 $CD8^+$ T-cell epitope. In some cases, the heterologous polypeptide comprises 2 or more HCV-NS3 $CD8^+$ T-cell epitopes. In some cases, the heterologous polypeptide comprises at least one HCV $CD4^+$ T cell epitope and at least one HCV $CD8^+$ T cell epitope. In some cases, the heterologous polypeptide comprises at least one HCV-NS3 $CD4^+$ T cell epitope and at least one HCV-NS3 $CD8^+$ T cell epitope. In some cases, heterologous polypeptide comprises 2 or more HCV-NS3 $CD4^+$ T-cell epitopes and 2 or more HCV-NS3 $CD8^+$ T-cell epitopes. In some cases, the heterologous polypeptide comprises 2, 3, 4, or 5 HCV-NS3 $CD4^+$ T-cell epitopes and 2, 3, 4, or 5 HCV-NS3 $CD8^+$ T-cell epitopes.

In some cases, the heterologous polypeptide comprises a single T-cell epitope. In some cases, the heterologous polypeptide comprises a single HCV-NS2 T-cell epitope. In some cases, the heterologous polypeptide comprises 2 or more T-cell epitopes. In some cases, the heterologous polypeptide comprises 2 or more HCV-NS2 T-cell epitopes. In some cases, the heterologous polypeptide comprises 3 or more HCV-NS2 T-cell epitopes. In some cases, the heterologous polypeptide comprises 4 or more HCV-NS2 T-cell epitopes. In some cases, the heterologous polypeptide comprises a single HCV-NS2 $CD4^+$ T-cell epitope. In some cases, the heterologous polypeptide comprises 2 or more HCV-NS2 $CD4^+$ T-cell epitopes. In some cases, the heterologous polypeptide comprises one or more HCV $CD8^+$ T cell epitopes. In some cases, the heterologous polypeptide comprises a single HCV-NS2 $CD8^+$ T-cell epitope. In some cases, the heterologous polypeptide comprises 2 or more HCV-NS2 $CD8^+$ T-cell epitopes. In some cases, the heterologous polypeptide comprises at least one HCV $CD4^+$ T cell epitope and at least one HCV $CD8^+$ T cell epitope. In some cases, the heterologous polypeptide comprises at least one HCV-NS2 $CD4^+$ T cell epitope and at least one HCV-NS2 $CD8^+$ T cell epitope. In some cases, heterologous polypeptide comprises 2 or more HCV-NS2 $CD4^+$ T-cell epitopes and 2 or more HCV-NS2 $CD8^+$ T-cell epitopes. In some cases, the heterologous polypeptide comprises 2, 3, 4, or 5 HCV-NS2 $CD4^+$ T-cell epitopes and 2, 3, 4, or 5 HCV-NS2 $CD8^+$ T-cell epitopes.

In some cases, the heterologous polypeptide comprises a single T-cell epitope. In some cases, the heterologous polypeptide comprises a single HCV-NS4A T-cell epitope. In some cases, the heterologous polypeptide comprises 2 or more T-cell epitopes. In some cases, the heterologous polypeptide comprises 2 or more HCV-NS4A T-cell epitopes. In some cases, the heterologous polypeptide comprises 3 or more HCV-NS4A T-cell epitopes. In some cases, the heterologous polypeptide comprises 4 or more HCV-NS4A T-cell epitopes. In some cases, the heterologous polypeptide comprises a single HCV-NS4A $CD4^+$ T-cell epitope. In some cases, the heterologous polypeptide comprises 2 or more HCV-NS4A $CD4^+$ T-cell epitopes. In some cases, the heterologous polypeptide comprises one or more HCV $CD8^+$ T cell epitopes. In some cases, the heterologous polypeptide comprises a single HCV-NS4A $CD8^+$ T-cell epitope. In some cases, the heterologous polypeptide comprises 2 or more HCV-NS4A $CD8^+$ T-cell epitopes. In some cases, the heterologous polypeptide comprises at least one HCV $CD4^+$ T cell epitope and at least one HCV $CD8^+$ T cell epitope. In some cases, the heterologous polypeptide comprises at least one HCV-NS4A $CD4^+$ T cell epitope and at least one HCV-NS4A $CD8^+$ T cell epitope. In some cases, heterologous polypeptide comprises 2 or more HCV-NS4A $CD4^+$ T-cell epitopes and 2 or more HCV-NS4A $CD8^+$ T-cell epitopes. In some cases, the heterologous polypeptide comprises 2, 3, 4, or 5 HCV-NS4A $CD4^+$ T-cell epitopes and 2, 3, 4, or 5 HCV-NS4A $CD8^+$ T-cell epitopes.

In some cases, the heterologous polypeptide comprises a single T-cell epitope. In some cases, the heterologous polypeptide comprises a single HCV-NS5A T-cell epitope. In some cases, the heterologous polypeptide comprises 2 or more T-cell epitopes. In some cases, the heterologous polypeptide comprises 2 or more HCV-NS5A T-cell epitopes. In some cases, the heterologous polypeptide comprises 3 or more HCV-NS5A T-cell epitopes. In some cases, the heterologous polypeptide comprises 4 or more HCV-NS5A T-cell epitopes. In some cases, the heterologous polypeptide comprises a single HCV-NS5A $CD4^+$ T-cell epitope. In some cases, the heterologous polypeptide comprises 2 or more HCV-NS5A $CD4^+$ T-cell epitopes. In some cases, the heterologous polypeptide comprises one or more HCV $CD8^+$ T cell epitopes. In some cases, the heterologous polypeptide comprises a single HCV-NS5A $CD8^+$ T-cell epitope. In some cases, the heterologous polypeptide comprises 2 or more HCV-NS5A $CD8^+$ T-cell epitopes. In some cases, the heterologous polypeptide comprises at least one HCV $CD4^+$ T cell epitope and at least one HCV $CD8^+$ T cell epitope. In some cases, the heterologous polypeptide comprises at least one HCV-NS5A $CD4^+$ T cell epitope and at least one HCV-NS5A $CD8^+$ T cell epitope. In some cases, heterologous polypeptide comprises 2 or more HCV-NS5A $CD4^+$ T-cell epitopes and 2 or more HCV-NS5A $CD8^+$ T-cell epitopes. In some cases, the heterologous polypeptide comprises 2, 3, 4, or 5 HCV-NS5A $CD4^+$ T-cell epitopes and 2, 3, 4, or 5 HCV-NS5A $CD8^+$ T-cell epitopes.

In some cases, the heterologous polypeptide comprises a single T-cell epitope. In some cases, the heterologous polypeptide comprises a single HCV-NS5B T-cell epitope. In some cases, the heterologous polypeptide comprises 2 or more T-cell epitopes. In some cases, the heterologous polypeptide comprises 2 or more HCV-NS5B T-cell epitopes. In some cases, the heterologous polypeptide comprises 3 or more HCV-NS5B T-cell epitopes. In some cases, the heterologous polypeptide comprises 4 or more HCV-NS5B T-cell epitopes. In some cases, the heterologous polypeptide comprises a single HCV-NS5B $CD4^+$ T-cell epitope. In some cases, the heterologous polypeptide comprises 2 or more HCV-NS5B $CD4^+$ T-cell epitopes. In some cases, the heterologous polypeptide comprises one or more HCV $CD8^+$ T cell epitopes. In some cases, the heterologous polypeptide comprises a single HCV-NS5B $CD8^+$ T-cell epitope. In some cases, the heterologous polypeptide comprises 2 or more HCV-NS5B $CD8^+$ T-cell epitopes. In some cases, the heterologous polypeptide comprises at least one HCV $CD4^+$ T cell epitope and at least one HCV $CD8^+$ T cell epitope. In some cases, the heterologous polypeptide comprises at least one HCV-NS5B $CD4^+$ T cell epitope and at least one HCV-NS5B $CD8^+$ T cell epitope. In some cases, heterologous polypeptide comprises 2 or more HCV-NS5B $CD4^+$ T-cell epitopes and 2 or more HCV-NS5B $CD8^+$ T-cell epitopes. In some cases, the heterologous polypeptide comprises 2, 3, 4, or 5 HCV-NS5B $CD4^+$ T-cell epitopes and 2, 3, 4, or 5 HCV-NS5B $CD8^+$ T-cell epitopes.

In some cases, the heterologous polypeptide comprises a single T-cell epitope. In some cases, the heterologous polypeptide comprises a single HCV-core T-cell epitope. In some cases, the heterologous polypeptide comprises 2 or more T-cell epitopes. In some cases, the heterologous polypeptide comprises 2 or more HCV-core T-cell epitopes. In some cases, the heterologous polypeptide comprises 3 or more HCV-core T-cell epitopes. In some cases, the heterologous polypeptide comprises 4 or more HCV-core T-cell epitopes. In some cases, the heterologous polypeptide comprises a single HCV-core $CD4^+$ T-cell epitope. In some cases, the heterologous polypeptide comprises 2 or more HCV-core $CD4^+$ T-cell epitopes. In some cases, the heterologous polypeptide comprises one or more HCV $CD8^+$ T cell epitopes. In some cases, the heterologous polypeptide comprises a single HCV-core $CD8^+$ T-cell epitope. In some cases, the heterologous polypeptide comprises 2 or more HCV-core $CD8^+$ T-cell epitopes. In some cases, the heterologous polypeptide comprises at least one HCV $CD4^+$ T cell epitope and at least one HCV $CD8^+$ T cell epitope. In some cases, the heterologous polypeptide comprises at least one HCV-core $CD4^+$ T cell epitope and at least one HCV-core $CD8^+$ T cell epitope. In some cases, heterologous polypeptide comprises 2 or more HCV-core $CD4^+$ T-cell epitopes and 2 or more HCV-core $CD8^+$ T-cell epitopes. In some cases, the heterologous polypeptide comprises 2, 3, 4, or 5 HCV-core $CD4^+$ T-cell epitopes and 2, 3, 4, or 5 HCV-core $CD8^+$ T-cell epitopes.

In some cases, the heterologous polypeptide comprises a single T-cell epitope. In some cases, the heterologous polypeptide comprises a single HCV-p7 T-cell epitope. In some cases, the heterologous polypeptide comprises 2 or more T-cell epitopes. In some cases, the heterologous polypeptide comprises 2 or more HCV-p7 T-cell epitopes. In some cases, the heterologous polypeptide comprises 3 or more HCV-p7 T-cell epitopes. In some cases, the heterologous polypeptide comprises 4 or more HCV-p7 T-cell epitopes. In some cases, the heterologous polypeptide comprises a single HCV-p7 $CD4^+$ T-cell epitope. In some cases, the heterologous polypeptide comprises 2 or more HCV-core $CD4^+$ T-cell epitopes. In some cases, the heterologous polypeptide comprises one or more HCV $CD8^+$ T cell epitopes. In some cases, the heterologous polypeptide comprises a single HCV-p7 $CD8^+$ T-cell epitope. In some cases, the heterologous polypeptide comprises 2 or more HCV-p7 $CD8^+$ T-cell epitopes. In some cases, the heterologous polypeptide comprises at least one HCV $CD4^+$ T cell epitope and at least one HCV $CD8^+$ T cell epitope. In some cases, the heterologous polypeptide comprises at least one HCV-p7 $CD4^+$ T cell epitope and at least one HCV-p7 $CD8^+$ T cell epitope. In some cases, heterologous polypeptide comprises 2 or more HCV-p7 $CD4^+$ T-cell epitopes and 2 or more HCV-p7 $CD8^+$ T-cell epitopes. In some cases, the heterologous polypeptide comprises 2, 3, 4, or 5 HCV-p7 $CD4^+$ T-cell epitopes and 2, 3, 4, or 5 HCV-p7 $CD8^+$ T-cell epitopes.

In some cases, the heterologous polypeptide comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, or 63, of the T-cell epitopes set out in FIGS. 13A-13B. In some cases, the heterologous polypeptide comprises from 1 to 3, from 3 to 5, from 5 to 10, from 10 to 15, from 15 to 20, from 20 to 25, or from 25 to 30 of the T-cell epitopes set out in FIGS. 13A-13B. For example, in some cases, the heterologous polypeptide comprises the T-cell epitopes designated NS3-3, NS3-4, and NS3-11 in FIGS. 13A-13B and FIGS. 15A-15N. As another example, in some cases, the heterologous polypeptide comprises the T-cell epitopes designated NS2-1, NS2-2, NS2-3, NS2-7, and NS2-8 in FIGS. 13A-13B and FIGS. 15A-15N. As another example, in some cases, the heterologous polypeptide comprises the T-cell epitopes designated NS3-3, NS3-4, NS3-5, and NS3-11 in FIGS. 13A-13B and FIGS. 15A-15N. As another example, in some cases, the heterologous polypeptide comprises the T-cell epitopes designated NS3-3, NS3-4, NS3-5, NS3-6, NS3-7, NS3-11, NS3-12, and NS3-13 in FIGS. 13A-13B and FIGS. 15A-15N. As another example, in some cases, the heterologous polypeptide comprises the T-cell epitopes designated NS3-3, NS3-4, NS3-5, NS3-6, NS3-7, NS3-10, NS3-11, NS3-12, and NS3-13 in FIGS. 13A-13B and FIGS. 15A-15N. As another example, in some cases, the heterologous polypeptide comprises the T-cell epitopes designated Core-1, Core-2, Core-3, Core-4, Core-5, Core-6, Core-7, Core-8, Core-9, Core-10, Core-11, Core-12, Core-13, Core-14, Core-16, Core-17, Core-18, Core-19, Core-20, Core-21, and Core-22 in FIGS. 13A-13B and FIGS. 15A-15N. As another example, in some cases, the heterologous polypeptide comprises the T-cell epitopes designated NS3-1, NS3-2, NS3-3, NS3-4, NS3-5, NS3-6, NS3-7, NS3-9, NS3-10, NS3-11, NS3-12, and NS3-13 in FIGS. 13A-13B and FIGS. 15A-15N. As another example, in some cases, the heterologous polypeptide comprises the T-cell epitopes designated NS2-1, NS2-2, NS2-3, NS2-4, NS2-5, NS2-6, NS2-7, NS2-8, NS3-1, NS3-2, NS3-3, NS3-4, NS3-5, NS3-6, NS3-7, NS3-9, NS3-10, NS3-11, NS3-12, and NS3-13 in FIGS. 13A-13B and FIGS. 15A-15N. As another example, in some cases, the heterologous polypeptide comprises the T-cell epitopes designated NS3-1, NS3-2, NS3-3, NS3-4, NS3-5, NS3-6, NS3-7, NS3-8, NS3-9, NS3-10, NS3-11, NS3-12, NS3-13, NS3-14, NS4a-1, NS4b-1, NS4b-2, NS4b-3, NS4b-4, NS4b-5, NS4b-6, NS4b-7, NS4b-8, NS4b-9, and NS4b-10 in FIGS. 13A-13B and FIGS. 15A-15N. As another example, in some cases, the heterologous polypeptide comprises the T-cell epitopes designated NS3-1, NS3-2, NS3-3, NS3-4, NS3-5, NS3-6, NS3-7, NS3-8, NS3-9, NS3-10, NS3-11, NS3-12, NS3-13, NS3-14, NS4a-1, NS4b-1, NS4b-2, NS4b-3, NS4b-4, NS4b-5, NS4b-6, NS4b-7, NS4b-8, NS4b-9, NS4b-10, NS5a-1, NS5a-2, NS5b-1, and NS5b-2 in FIGS. 13A-13B and FIGS. 15A-15N. In some cases, the T-cell epitopes are contiguous. In some cases, any two T-cell epitopes are separated by linkers (e.g., a linker having a length of from 1 amino acid to about 50 amino acids, e.g., from 1 amino acid to 5 amino acids (aa), from 5 aa to 10 aa, from 10 aa to 15 aa, from 15 aa to 20 aa, from 20 aa to 25 aa, from 25 aa to 30 aa, from 30 aa to 40 aa, or from 40 aa to 50 aa).

In some cases, the heterologous polypeptide comprises at least one HCV $CD4^+$ T cell epitope and at least one HCV $CD8^+$ T cell epitope, where epitopes are conserved among HCV genotypes 1 and 2. In some cases, the heterologous polypeptide comprises at least one HCV $CD4^+$ T cell epitope and at least one HCV $CD8^+$ T cell epitope, where epitopes are conserved among HCV genotypes 1 and 3. In some cases, the heterologous polypeptide comprises at least one HCV $CD4^+$ T cell epitope and at least one HCV $CD8^+$ T cell epitope, where epitopes are conserved among HCV genotypes 1, 2, and 3. In some cases, the heterologous polypeptide comprises at least one HCV $CD4^+$ T cell epitope and at least one HCV $CD8^+$ T cell epitope, where epitopes are conserved among HCV genotypes 1, 2, 3, and 7. In some cases, the heterologous polypeptide comprises at least one HCV $CD4^+$ T cell epitope and at least one HCV $CD8^+$ T cell epitope, where epitopes are conserved among HCV genotypes 1-7.

The heterologous polypeptide can have a length of from about 10 amino acids to about 2000 amino acids; e.g., the heterologous polypeptide can have a length of from 10 amino acids (aa) to 15 aa, from 15 aa to 20 aa, from 20 aa to 25 aa, from 25 an to 50 aa, from 50 aa to 75 aa, from 75 aa to 100 aa, from 100 aa to 150 aa, from 150 aa to 200 aa, from 200 aa to 250 aa, from 250 aa to 300 aa, from 300 aa to 350 aa, from 350 aa to 400 aa, from 450 aa to 500 aa, from 500 an to 550 aa, from 550 an to 600 aa, from 600 an to 650 aa, from 650 aa to 700 aa, from 700 aa to 750 aa, or from 750 aa to 800 aa. The heterologous polypeptide can have a length of from about 25 amino acids to about 2000 amino acids, e.g., from about 25 amino acids (aa) to 50 aa, from 50 an to 75 aa, from 75 an to 100 aa, from 100 an to 150 aa, from 150 an to 200 aa, from 200 aa to 250 aa, from 250 an to 300 aa, from 300 aa to 350 aa, from 350 an to 400 aa, from 400 an to 500 aa, from 500 aa to 600 aa, from 600 an to 700 aa, from 700 an to 800 aa, from 800 aa to 900 aa, from 900 an to 1000 aa, from 1000 aa to 1100 aa, from 1100 aa to 1200 aa, from 1200 an to 1300 aa, from 1300 aa to 1400 aa, from 1400 aa to 1500 aa, from 1500 aa to 1600 aa, from 1600 aa to 1700 aa, from 1700 aa to 1800 aa, from 1800 aa to 1900 aa, or from 1900 aa to 2000 aa. The heterologous polypeptide can have a length of from about 25 amino acids to about 3000 amino acids, e.g., from about 25 amino acids (aa) to 50 aa, from 50 aa to 75 aa, from 75 aa to 100 aa, from 100 aa to 150 aa, from 150 aa to 200 aa, from 200 aa to 250 aa, from 250 aa to 300 aa, from 300 aa to 350 aa, from 350 an to 400 aa, from 400 an to 500 aa, from 500 an to 600 aa, from 600 an to 700 aa, from 700 an to 800 aa, from 800 an to 900 aa, from 900 aa to 1000 aa, from 1000 aa to 1100 aa, from 1100 an to 1200 aa, from 1200 aa to 1300 aa, from 1300 an to 1400 aa, from 1400 aa to 1500 aa, from 1500 an to 1600 aa, from 1600 aa to 1700 aa, from 1700 an to 1800 aa, from 1800 an to 1900 aa, from 1900 aa to 2000 aa, from 2000 an to 2250 aa, from 2250 an to 2500 aa, from 2500 an to 2750 aa, or from 2750 an to 3000 aa.

The heterologous polypeptide can have a length of from about 25 amino acids to about 800 amino acids, e.g., from about 25 amino acids (aa) to 50 aa, from 50 an to 75 aa, from 75 an to 100 aa, from 100 an to 150 aa, from 150 an to 200 aa, from 200 an to 250 aa, from 250 aa to 300 aa, from 300 an to 350 aa, from 350 aa to 400 aa, from 450 an to 500 aa, from 500 an to 550 aa, from 550 aa to 600 aa, from 600 an to 650 aa, from 650 an to 700 aa, from 700 aa to 750 aa, or from 750 an to 800 aa. The heterologous polypeptide can have a length of from about 25 amino acids to about 400 amino acids, e.g., from about 25 amino acids (aa) to 50 aa, from 50 an to 75 aa, from 75 an to 100 aa, from 100 an to 150 aa, from 150 an to 200 aa, from 200 aa to 250 aa, from 250 aa to 300 aa, from 300 an to 350 aa, or from 350 aa to 400 aa. The heterologous polypeptide can have a length of 25 amino acids (aa), 26 aa, 27 aa, 28 aa, 29 aa, 30 aa, 31 aa, 32 aa, 33 aa, 34 aa, 35 aa, 36 aa, 37 aa, 38 aa, 39 aa, 40 aa, 41 aa, 42 aa, 43 aa, 44 aa, 45 aa, 46 aa, 47 aa, 48 aa, 49 aa, or 50 aa. The heterologous polypeptide can have a length of from about 100 amino acids (aa) to 800 aa, e.g., from 100 aa to 150 aa, from 150 aa to 200 aa, from 200 aa to 250 aa, from 250 an to 300 aa, from 300 aa to 350 aa, from 350 an to 400 aa, from 450 an to 500 aa, from 500 aa to 550 aa, from 550 an to 600 aa, from 600 an to 650 aa, from 650 aa to 700 aa, from 700 an to 750 aa, or from 750 aa to 800 aa. The heterologous polypeptide can have a length of from 25 aa to 30 aa. The heterologous polypeptide can have a length of from 30 aa to 40 aa. The heterologous polypeptide can have a length of from 40 aa to 50 aa. The heterologous polypeptide can have a length of from 50 aa to 60 aa (e.g., 50 aa, 51 aa, 52, aa, 53 aa, 54 aa, 55 aa, 56 aa, 57 aa, 58 aa, 59 aa, or 60 aa). The heterologous polypeptide can have a length of from 60 aa to 70 aa. The heterologous polypeptide can have a length of from 65 an to 75 aa (e.g., 65, 66, 67, 68, 69, 70, 71, 72, 7, 74, or 75 aa). The heterologous polypeptide can have a length of 70 aa. The heterologous polypeptide can have a length of from 70 an to 80 aa. The heterologous polypeptide can have a length of from 80 aa to 90 aa. The heterologous polypeptide can have a length of from 90 an to 100 aa. The heterologous polypeptide can have a length of from 100 an to 105 aa (e.g., 100, 101, 102, 103, 104, 105, 106, 107, 108, 109, or 110 aa). The heterologous polypeptide can have a length of 100 aa. The heterologous polypeptide can have a length of from 10 amino acids (aa) to 50 aa; e.g., from 10 aa to 15 aa, from 15 an to 20 aa, from 20 an to 25 aa, from 25 an to 30 aa, from 30 an to 35 aa, from 35 aa to 40 aa, from 40 an to 45 aa, or from 45 an to 50 aa. The heterologous polypeptide can have a length of from 10 amino acids (aa) to 20 aa, e.g., 10, 11, 12, 13, 14, 15, 16, 17, 18, 19, or 20 aa.

HCV NS3 T-Cell Epitopes

In some cases, the heterologous polypeptide present in an E2 variant polypeptide of an E1/E2 heterodimer of the present disclosure includes one or more T-cell epitopes present in an HCV NS3 polypeptide. Examples of T-cell epitopes present in NS3 polypeptides are depicted in FIGS. 15A-15N, FIG. 13B, and FIGS. 14A-14B.

The heterologous polypeptide can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence:

AIPLEVIKGGRHLIFCHSKKKCDELAAKL (SEQ ID NO:1). In some cases, the heterologous polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence:

AIPLEVIKGGRHLIFCHSKKKCDELAAKL (SEQ ID NO:1); and has a length of from 25 an to 35 aa (e.g., 25 aa, 26 aa, 27 aa, 28 aa, 29 aa, 30 aa, 31 aa, 32 aa, 33 aa, 34 aa, or 35 aa). In some cases, the heterologous polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence:

AIPLEVIKGGRHLIFCHSKKKCDELAAKL (SEQ ID NO:1); and has a length of 29 amino acids. Such a polytope can include NS3 T-cell epitopes designated NS3-3, NS3-4, and NS3-11 in FIG. 13B and FIGS. 15A-15N.

The heterologous polypeptide can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence:

AIPLEVIKGGRHLIFCHSKKKCDELAAKLVALGINAVAYYRGLDVSVIPTSG (SEQ ID NO:2). In some cases, the heterologous polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence: AIPLEVIKGGRHLIFCHSKKKCDELAAKLVALGINAVAYYRGLDVSVIPTSG (SEQ ID NO:2); and has a length of from 45 amino acids to 60 amino acids (e.g., 45 aa, 46 aa, 47 aa, 48 aa, 49 aa, 50 aa, 51 aa, 52 aa, 53 aa, 54 aa, 55 aa, 56 aa, 57 aa, 58 aa, 59 aa, or 60 aa). In some cases, the heterologous polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence: AIPLEVIKGGRHLIFCHSKKKCDELAAKLVALGINAVAYYRGLDVSVIPTSG (SEQ ID NO:2); and has a length of 52 amino acids. Such a polytope can include NS3 T-cell epitopes designated NS3-3, NS3-4, NS3-5, and NS3-11 in FIG. 13B and FIGS. 15A-15N.

The heterologous polypeptide can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence: KGGRHLIFCHSKKKCDELAAKLVALGINAVAYYRGLDVSVIPTSGDVVVVATDALMTG FTGDFDSVIDCN (SEQ ID NO:3); and has a length of from 65 amino acids to 80 amino acids (e.g., 65 aa, 66 aa, 67 aa, 68 aa, 69 aa, 70 aa, 71 aa, 72 aa, 73 aa, 74 aa, 75 aa, 76 aa, 77 aa, 78 aa, 79 aa, or 80 aa). In some cases, the heterologous polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence: KGGRHLIFCHSKKKCDELAAKLVALGINAVAYYRGLDVSVIPTSGDVVVVATDALMTG FTGDFDSVIDCN (SEQ ID NO:3); and has a length of 70 amino acids. Such a polytope can include NS3 T-cell epitopes designated NS3-3, NS3-4, NS3-5, NS3-6, NS3-7, NS3-11, NS3-12, and NS3-13 in FIG. 13B and FIGS. 15A-15N.

The heterologous polypeptide can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence: VALSTTGEIPFYGKAIPLEVIKGGRHLIFCHSKKKCDELAAKLVALGINAVAYYRGLDVS VIPTSGDVVVVATDALMTGFTGDFDSVIDCNTCVTQTVDF (SEQ ID NO:4); and has a length of from 95 amino acids (aa) to 105 an (e.g., 95 aa, 96 aa, 97 aa, 98 aa, 99 aa, 100 aa, 101 aa, 102 aa, 103 aa, 104 aa, or 105 aa). In some cases, the heterologous polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence: VALSTTGEIPFYGKAIPLEVIKGGRHLIFCHSKKKCDELAAKLVALGINAVAYYRGLDVS VIPTSGDVVVVATDALMTGFTGDFDSVIDCNTCVTQTVDF (SEQ ID NO:4); and has a length of 100 amino acids. Such a polytope can include NS3 T-cell epitopes designated NS3-3, NS3-4, NS3-5, NS3-6, NS3-7, NS3-10, NS3-11, NS3-12, and NS3-13 in FIG. 13B and FIGS. 15A-15N.

The heterologous polypeptide can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence: MSTNPKPQRKTKRNTNRRPQDVKFPGGGQIVGGVYLLPRRGPRLGVRATRKTSERSQP RGRRQPIPKARRPEGRTWAQPGYPWPLYGNEGCGWAGWLLSPRGSRPSWGPTDPRRRS RNLGKVIDTLTCGFADLMGYIPLVGAPLGGAARALAHGVRVLEDGVNYATGNLPGCSF SIFLLALLSCLTVPASA (SEQ ID NO:9); and has a length of from 190 amino acids (aa) to 200 aa (e.g., 190 aa, 191 aa, 192 aa, 193 aa, 194 aa, 195 aa, 196 aa, 197 aa, 198 aa, 199 aa, or 200 aa. In some cases, the heterologous polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence:

(SEQ ID NO: 10)

LHAPTGSGKSTKVPAAYAAQGYKVLVLNPSVAATLGFGAYMSKAHGIDPN

IRTGVRTITTGSPITYSTYGKFLADGGCSGGAYDIIICDECHSTDATSIL

GIGTVLDQAETAGARLVVLATATPPGSVTVPHPNIEEVALSTTGEIPFYG

KAIPLEVIKGGRHLIFCHSKKKCDELAAKLVALGINAVAYYRGLDVSVIP

TSGDVVVVATDALMTGFTGDFDSVIDCN;

and has a length of from 215 amino acids (aa) to 235 an (e.g., 215 aa, 216 aa, 217 11, 218 aa, 219 aa, 220 aa, 221 aa, 222 aa, 223 aa, 224 aa, 225 aa, 226 aa, 227 aa, 228 aa, 229 aa, 230 aa, 231 aa, 232 aa, 233 aa, 234 aa, or 235 aa). In some cases, the heterologous polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence:

```
                                (SEQ ID NO: 10)
LHAPTGSGKSTKVPAAYAAQGYKVLVLNPSVAATLGFGAYMSKAHGIDPN

IRTGVRTITTGSPITYSTYGKFLADGGCSGGAYDIIICDECHSTDATSIL

GIGTVLDQAETAGARLVVLATATPPGSVTVPHPNIEEVALSTTGEIPFYG

KAIPLEVIKGGRHLIFCHSKKKCDELAAKLVALGINAVAYYRGLDVSVIP

TSGDVVVVATDALMTGFTGDFDSVIDCN;
```

and has a length of 228 amino acids. Such a polytope can include NS3 T-cell epitopes designated NS3-1, NS3-2, NS3-3, NS3-4, NS3-5, NS3-6, NS3-7, NS3-9, NS3-10, NS3-11, NS3-12, and NS3-13 in FIG. 13B and FIGS. 15A-15N.

As another example, the heterologous polypeptide can comprise an HCV NS3 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1265-1279 of the amino acid sequence designated "Consensus" in FIGS. 16A-16L, or a corresponding HCV NS3 amino acid sequence of any HCV genotype; and the HCV NS3 T-cell epitope can have a length of from 15 amino acids (aa) to 20 amino acids (e.g., 15 aa, 16 aa, 17 aa, 18 aa, 19 aa, or 20 aa).

As another example, the heterologous polypeptide can comprise an HCV NS3 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1309-1323 of the amino acid sequence designated "Consensus" in FIGS. 16A-16L, or a corresponding HCV NS3 amino acid sequence of any HCV genotype; and the HCV NS3 T-cell epitope can have a length of from 15 amino acids (aa) to 20 amino acids (e.g., 15 aa, 16 aa, 17 aa, 18 aa, 19 aa, or 20 aa).

As another example, the heterologous polypeptide can comprise an HCV NS3 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1401-1415 of the amino acid sequence designated "Consensus" in FIGS. 16A-16L, or a corresponding HCV NS3 amino acid sequence of any HCV genotype; and the HCV NS3 T-cell epitope can have a length of from 15 amino acids (aa) to 20 amino acids (e.g., 15 aa, 16 aa, 17 aa, 18 aa, 19 aa, or 20 aa).

As another example, the heterologous polypeptide can comprise an HCV NS3 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1402-1412 of the amino acid sequence designated "Consensus" in FIGS. 16A-16L, or a corresponding HCV NS3 amino acid sequence of any HCV genotype; and the HCV NS3 T-cell epitope can have a length of from 11 amino acids (aa) to 16 amino acids (e.g., 11 aa, 12 aa, 13 aa, 14 aa, 15 aa, or 16 aa).

As another example, the heterologous polypeptide can comprise an HCV NS3 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1429-1439 of the amino acid sequence designated "Consensus" in FIGS. 16A-16L, or a corresponding HCV NS3 amino acid sequence of any HCV genotype; and the HCV NS3 T-cell epitope can have a length of from 11 amino acids (aa) to 16 amino acids (e.g., 11 aa, 12 aa, 13 aa, 14 aa, 15 aa, or 16 aa).

As another example, the heterologous polypeptide can comprise an HCV NS3 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1450-1464 of the amino acid sequence designated "Consensus" in FIGS. 16A-16L, or a corresponding HCV NS3 amino acid sequence of any HCV genotype; and the HCV NS3 T-cell epitope can have a length of from 15 amino acids (aa) to 20 amino acids (e.g., 15 aa, 16 aa, 17 aa, 18 aa, 19 aa, or 20 aa).

As another example, the heterologous polypeptide can comprise an HCV NS3 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1453-1467 of the amino acid sequence designated "Consensus" in FIGS. 16A-16L, or a corresponding HCV NS3 amino acid sequence of any HCV genotype; and the HCV NS3 T-cell epitope can have a length of from 15 amino acids (aa) to 20 amino acids (e.g., 15 aa, 16 aa, 17 aa, 18 aa, 19 aa, or 20 aa).

As another example, the heterologous polypeptide can comprise an HCV NS3 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1577-1591 of the amino acid sequence designated "Consensus" in FIGS. 16A-16L, or a corresponding HCV NS3 amino acid sequence of any HCV genotype; and the HCV NS3 T-cell epitope can have a length of from 15 amino acids (aa) to 20 amino acids (e.g., 15 aa, 16 aa, 17 aa, 18 aa, 19 aa, or 20 aa).

As another example, the heterologous polypeptide can comprise an HCV NS3 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1306-1314 of the amino acid sequence designated "Consensus" in FIGS. 16A-16L, or a corresponding HCV NS3 amino acid sequence of any HCV genotype; and the HCV NS3 T-cell epitope can have a length of from 9 amino acids (aa) to 15 amino acids (e.g., 9 aa, 10 aa, 11 aa, 12 aa, 13 aa, 14 aa, or 15 aa).

As another example, the heterologous polypeptide can comprise an HCV NS3 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1387-1394 of the amino acid sequence designated "Consensus" in FIGS. 16A-16L, or a corresponding HCV NS3 amino acid sequence of any HCV genotype; and the HCV NS3 T-cell epitope can have a length of from 1 amino acids (aa) to 15 amino acids (e.g., 8 aa, 9 aa, 10 aa, 11 aa, 12 aa, 13 aa, 14 aa, or 15 aa).

As another example, the heterologous polypeptide can comprise an HCV NS3 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1405-1413 of the amino acid sequence designated "Consensus" in FIGS. 16A-16L, or a corresponding HCV NS3 amino acid sequence of any HCV genotype; and the HCV NS3 T-cell epitope can have a length of from 9 amino acids (aa) to 15 amino acids (e.g., 9 aa, 10 aa, 11 aa, 12 aa, 13 aa, 14 aa, or 15 aa).

As another example, the heterologous polypeptide can comprise an HCV NS3 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1450-1458 of the amino acid sequence designated "Consensus" in FIGS. 16A-16L, or a corresponding HCV NS3 amino acid sequence of any HCV genotype; and the HCV NS3 T-cell epitope can have a length of from 9 amino acids (aa) to 15 amino acids (e.g., 9 aa, 10 aa, 11 aa, 12 aa, 13 aa, 14 aa, or 15 aa).

As another example, the heterologous polypeptide can comprise an HCV NS3 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1457-1465 of the amino acid sequence designated "Consensus" in FIGS. 16A-16L, or a corresponding HCV NS3 amino acid sequence of any HCV genotype; and the HCV NS3 T-cell epitope can have a length of from 9 amino acids (aa) to 15 amino acids (e.g., 9 aa, 10 aa, 11 aa, 12 aa, 13 aa, 14 aa, or 15 aa).

As another example, the heterologous polypeptide can comprise an HCV NS3 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1610-1618 of the amino acid sequence designated "Consensus" in FIGS. 16A-16L, or a corresponding HCV NS3 amino acid sequence of any HCV genotype; and the HCV NS3 T-cell epitope can have a length of from 9 amino acids (aa) to 15 amino acids (e.g., 9 aa, 10 aa, 11 aa, 12 aa, 13 aa, 14 aa, or 15 aa).

HCV NS2 T-Cell Epitopes

In some cases, the heterologous polypeptide present in an E2 variant polypeptide of an E1/E2 heterodimer of the present disclosure includes one or more T-cell epitopes present in an HCV NS2 polypeptide. Examples of T-cell epitopes present in NS2 polypeptides are depicted in FIGS. 15A-15N, and FIG. 13A.

For example, the heterologous polypeptide can comprise an NS2 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 955-974 of the amino acid sequence designated "Consensus" in FIGS. 16A-16L, or a corresponding HCV NS2 amino acid sequence of any HCV genotype; and the NS2 T cell epitope can have a length of from 20 amino acids (aa) to 25 amino acids (e.g., 20 aa, 21 aa, 22 aa, 23 aa, 24 aa, or 25 aa).

As another example, the heterologous polypeptide can comprise an NS2 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 975-994 of the amino acid sequence designated "Consensus" in FIGS. 16A-16L, or a corresponding HCV NS2 amino acid sequence of any HCV genotype; and the NS2 T cell epitope can have a length of from 20 amino acids (aa) to 25 amino acids (e.g., 20 aa, 21 aa, 22 aa, 23 aa, 24 aa, or 25 aa).

As another example, the heterologous polypeptide can comprise an NS2 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 985-1004 of the amino acid sequence designated "Consensus" in FIGS. 16A-16L, or a corresponding HCV NS2 amino acid sequence of any HCV genotype; and the NS2 T cell epitope can have a length of from 20 amino acids (aa) to 25 amino acids (e.g., 20 aa, 21 aa, 22 aa, 23 aa, 24 aa, or 25 aa).

As another example, the heterologous polypeptide can comprise an NS2 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1015-1034 of the amino acid sequence designated "Consensus" in FIGS. 16A-16L, or a corresponding HCV NS2 amino acid sequence of any HCV genotype; and the NS2 T cell epitope can have a length of from 20 amino acids (aa) to 25 amino acids (e.g., 20 aa, 21 aa, 22 aa, 23 aa, 24 aa, or 25 aa).

As another example, the heterologous polypeptide can comprise an NS2 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1035-1054 of the amino acid sequence designated "Consensus" in FIGS. 16A-16L, or a corresponding HCV NS2 amino acid sequence of any HCV genotype; and the NS2 T cell epitope can have a length of from 20 amino acids (aa) to 25 amino acids (e.g., 20 aa, 21 aa, 22 aa, 23 aa, 24 aa, or 25 aa).

As another example, the heterologous polypeptide can comprise an NS2 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 924-933 of the amino acid sequence designated "Consensus" in FIGS. 16A-16L, or a corresponding HCV NS2 amino acid sequence of any HCV genotype; and the NS2 T cell epitope can have a length of from 10 amino acids (aa) to 15 amino acids (e.g., 10 aa, 11 aa, 12 aa, 13 aa, 14 aa, or 15 aa).

As another example, the heterologous polypeptide can comprise an NS2 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 961-970 of the amino acid sequence designated "Consensus" in FIGS. 16A-16L, or a corresponding HCV NS2 amino acid sequence of any HCV genotype; and the NS2 T cell epitope can have a length of from 10 amino acids (aa) to 15 amino acids (e.g., 10 aa, 11 aa, 12 aa, 13 aa, 14 aa, or 15 aa).

As another example, the heterologous polypeptide can comprise an NS2 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 989-997 of the amino acid sequence designated "Consensus" in FIGS. 16A-16L, or a corresponding HCV NS2 amino acid sequence of any HCV genotype; and the NS2 T cell epitope can have a length of from 9 amino acids (aa) to 15 amino acids (e.g., 9 aa, 10 aa, 11 aa, 12 aa, 13 aa, 14 aa, or 15 aa).

In some cases, the heterologous polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to a contiguous stretch of from 10 amino acids (aa) to 50 an (e.g., from 10 aa to 25 aa, or from 25 an to 50 aa) of amino acids 955-1004 of the amino acid sequence designated "Consensus" in FIGS. 16A-16L, or a corresponding HCV NS2 amino acid sequence of any HCV genotype; and has a length of from 10 amino acids (aa) to 25 aa, or from 25 aa to 50 aa. In some cases, the heterologous polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 955-1004 of the amino acid sequence designated "Consensus" in FIGS. 16A-16L, or a corresponding HCV NS2 amino acid sequence of any HCV genotype; and has a length of about 50 amino acids.

In some cases, the heterologous polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to a contiguous stretch of from 10 amino acids (aa) to 553 an (e.g., from 10 aa to 25 aa, from 25 aa to 50 aa, from 50 aa to 100 aa, from 100 aa to 200 aa, from 200 aa to 300 aa, from 300 aa to 400 aa, from 400 aa to 500 aa, or from 500 an to 553 aa) of amino acids 917-1469 of the amino acid sequence designated "Consensus" in FIGS. 16A-16L, or a corresponding HCV NS2 and NS3 amino acid sequence of any HCV genotype; and has a length of from 10 amino acids (aa) to 25 aa, from 25 an to 50 aa, from 50 an to 100 aa, from 100 an to 200 aa, from 200 aa to 300 aa, from 300 aa to 400 aa, from 400 aa to 500 aa, or from 500 an to 553 aa. In some cases, the heterologous polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 917-1469 of the amino acid sequence designated "Consensus" in FIGS. 16A-16L, or a corresponding HCV NS2 and NS3 amino acid sequence of any HCV genotype; and has a length of about 553 amino acids.

The heterologous polypeptide can comprise an amino acid sequence having at least about 20%, at least about 25%, at least about 30%, at least about 35%, at least about 40%, at least about 45%, at least about 50%, at least about 60%, at least about 0%, at least about 75%, at least about 80%, at least about 85%, at least about 90%, at least about 95%, at least about 98%, at least about 99%, or 100%, amino acid sequence identity to the following amino acid sequence:

LGALTGTYVYNHLTPLRDWAHNGLRDLAVAVEPVVFSQMETKLITWGADT (SEQ ID NO:11). In some cases, the heterologous polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence:

LGALTGTYVYNHLTPLRDWAHNGLRDLAVAVEPVVFSQMETKLITWGADT (SEQ ID NO:11); and has a length of from 50 amino acids to 60 amino acids (e.g., 50 aa, 51 aa, 52 aa, 53 aa, 54 aa, 55 aa, 56 aa, 57 aa, 58 aa, 59 aa, or 60 aa). In some cases, the heterologous polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence:

LGALTGTYVYNHLTPLRDWAHNGLRDLAVAVEPVVFSQMETKLITWGADT (SEQ ID NO:11); and has a length of 50 amino acids. Such a polytope can include NS2 T-cell epitopes designated NS2-1, NS2-2, NS2-3, NS2-7, and NS2-8 in FIG. 13A and FIGS. 15A-15N.

HCV NS4A T-Cell Epitopes

In some cases, the heterologous polypeptide present in an E2 variant polypeptide of an E1/E2 heterodimer of the present disclosure includes one or more T-cell epitopes present in an HCV NS4A polypeptide. Examples of T-cell epitopes present in NS4A polypeptides are depicted in FIGS. 15A-15N and FIG. 13B.

The heterologous polypeptide can comprise an NS4A T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1683-1692 of the amino acid sequence designated "Consensus" in FIGS. 16A-16L, or a corresponding HCV NS4A amino acid sequence of any HCV genotype; and the NS4A T-cell epitope can have a length of from 10 amino acids (aa) to 15 amino acids (e.g., 10 aa, 11 aa, 12 aa, 13 aa, 14 aa, or 15 aa).

HCV NS4B T-Cell Epitopes

In some cases, the heterologous polypeptide present in an E2 variant polypeptide of an E1/E2 heterodimer of the present disclosure includes one or more T-cell epitopes present in an HCV NS4B polypeptide. Examples of T-cell epitopes present in NS4B polypeptides are depicted in FIGS. 15A-15N and FIG. 13B.

As one example, the heterologous polypeptide can comprise an NS4B T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1790-1801 of the amino acid sequence designated "Consensus" in FIGS. 16A-16L, or a corresponding HCV NS4B amino acid sequence of any HCV genotype; and the NS4B T-cell epitope can have a length of from 12 amino acids (aa) to 20 amino acids (e.g., 12 aa, 13 aa, 14 aa, 15 aa, 16 aa, 17 aa, 18 aa, 19 aa, or 20 aa).

As another example, the heterologous polypeptide can comprise an NS4B T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1792-1802 of the amino acid sequence designated "Consensus" in FIGS. 16A-16L, or a corresponding HCV NS4B amino acid sequence of any HCV genotype; and the NS4B T-cell epitope can have a length of from 11 amino acids (aa) to 20 amino acids (e.g., 11 aa, 12 aa, 13 aa, 14 aa, 15 aa, 16 aa, 17 aa, 18 aa, 19 aa, or 20 aa).

As another example, the heterologous polypeptide can comprise an NS4B T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1898-1905 of the amino acid sequence designated "Consensus" in FIGS. 16A-16L, or a corresponding HCV NS4B amino acid sequence of any HCV genotype; and the NS4B T-cell epitope can have a length of from 8 amino acids (aa) to 15 amino acids (e.g., 8 aa, 9 aa, 10 aa, 11 aa, 12 aa, 13 aa, 14 aa, or 15 aa).

As another example, the heterologous polypeptide can comprise an NS4B T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1921-1935 of the amino acid sequence designated "Consensus" in FIGS. 16A-16L, or a corresponding HCV NS4B amino acid sequence of any HCV genotype; and the NS4B T-cell epitope can have a length of from 15 amino acids (aa) to 20 amino acids (e.g., 15 aa, 16 aa, 17 aa, 18 aa, 19 aa, or 20 aa).

As another example, the heterologous polypeptide can comprise an NS4B T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1922-1941 of the amino acid sequence designated "Consensus" in FIGS. 16A-16L, or a corresponding HCV NS4B amino acid sequence of any HCV genotype; and the NS4B T-cell epitope can have a length of from 20 amino acids (aa) to 25 amino acids (e.g., 20 aa, 21 aa, 22 aa, 23 aa, 24 aa, or 25 aa).

As another example, the heterologous polypeptide can comprise an NS4B T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1928-1947 of the amino acid sequence designated "Consensus" in FIGS. 16A-16L, or a corresponding HCV NS4B amino acid sequence of any HCV genotype; and the NS4B T-cell epitope can have a length of from 20 amino acids (aa) to 25 amino acids (e.g., 20 aa, 21 aa, 22 aa, 23 aa, 24 aa, or 25 aa).

As another example, the heterologous polypeptide can comprise an NS4B T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1868-1876 of the amino acid sequence designated "Consensus" in FIGS. 16A-16L, or a corresponding HCV NS4B amino acid sequence of any HCV genotype; and the NS4B T-cell epitope can have a length of from 9 amino acids (aa) to 15 amino acids (e.g., 9 aa, 10 aa, 11 aa, 12 aa, 13 aa, 14 aa, or 15 aa).

As another example, the heterologous polypeptide can comprise an NS4B T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1927-1942 of the amino acid sequence designated "Consensus" in FIGS. 16A-16L, or a corresponding HCV NS4B amino acid sequence of any HCV genotype; and the NS4B T-cell epitope can have a length of from 16 amino acids (aa) to 20 amino acids (e.g., 16 aa, 17 aa, 18 aa, 19 aa, or 20 aa).

As another example, the heterologous polypeptide can comprise an NS4B T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1932-1940 of the amino acid sequence designated "Consensus" in FIGS. 16A-16L, or a corresponding HCV NS4B amino acid sequence of any HCV genotype; and the NS4B T-cell epitope can have a length of from 9 amino acids (aa) to 15 amino acids (e.g., 9 aa, 10 aa, 11 aa, 12 aa, 13 aa, 14 aa, or 15 aa).

As another example, the heterologous polypeptide can comprise an NS4B T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1948-1962 of the amino acid sequence designated "Consensus" in FIGS. 16A-16L, or a corresponding HCV NS4B amino acid sequence of any HCV genotype; and the NS4B T-cell epitope can have a length of from 15 amino acids (aa) to 20 amino acids (e.g., 15 aa, 16 aa, 17 aa, 18 aa, 19 aa, or 20 aa).

HCV NS5A T-Cell Epitopes

In some cases, the heterologous polypeptide present in an E2 variant polypeptide of an E1/E2 heterodimer of the present disclosure includes one or more T-cell epitopes present in an HCV NS5A polypeptide. Examples of T-cell epitopes present in NS5A polypeptides are depicted in FIGS. 15A-15N and FIG. 13B.

As one example, the heterologous polypeptide can comprise an NSSA T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 2218-2232 of the amino acid sequence designated "Consensus" in FIGS. 16A-16L, or a corresponding HCV NS5A amino acid sequence of any HCV genotype; and the NSSA T-cell epitope can have a length of from 15 amino acids (aa) to 20 amino acids (e.g., 15 aa, 16 aa, 17 aa, 18 aa, 19 aa, or 20 aa).

As another example, the heterologous polypeptide can comprise an NSSA T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 2309-2317 of the amino acid sequence designated "Consensus" in FIGS. 16A-16L, or a corresponding HCV NSSA amino acid sequence of any HCV genotype; and the NSSA T-cell epitope can have a length of from 9 amino acids (aa) to 15 amino acids (e.g., 9 aa, 10 aa, 11 aa, 12 aa, 13 aa, 14 aa, or 15 aa).

HCV NS5B T-Cell Epitopes

In some cases, the heterologous polypeptide present in an E2 variant polypeptide of an E1/E2 heterodimer of the present disclosure includes one or more T-cell epitopes present in an HCV NS5B polypeptide. Examples of T-cell epitopes present in NS5B polypeptides are depicted in FIGS. 15A-15N and FIG. 13B.

As one example, the heterologous polypeptide can comprise an NS5B T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 2847-2851 of the amino acid sequence designated "Consensus" in FIGS. 16A-16L, or a corresponding HCV NS5B amino acid sequence of any HCV genotype; and the NS5B T-cell epitope can have a length of from 5 amino acids (aa) to 10 amino acids (e.g., 5 aa, 6 aa, 7 aa, 8 aa, 9 aa, or 10 aa).

As another example, the heterologous polypeptide can comprise an NS5B T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 2602-2610 of the amino acid sequence designated "Consensus" in FIGS. 16A-16L, or a corresponding HCV NS5B amino acid sequence of any HCV genotype; and the NS5B T-cell epitope can have a length of from 9 amino acids (aa) to 15 amino acids (e.g., 9 aa, 10 aa, 11 aa, 12 aa, 13 aa, 14 aa, or 15 aa).

HCV Core T-Cell Epitopes

In some cases, the heterologous polypeptide present in an E2 variant polypeptide of an E1/E2 heterodimer of the present disclosure includes one or more T-cell epitopes present in an HCV core polypeptide. Examples of T-cell epitopes present in HCV Core polypeptides are depicted in FIGS. 15A-15N and FIG. 13A.

As one example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1-20 of the amino acid sequence designated "Consensus" in FIGS. 16A-16L, or a corresponding HCV core amino acid sequence of any HCV genotype; and the HCV core T-cell epitope can have a length of from 20 amino acids (aa) to 25 amino acids (e.g., 20 aa, 21 aa, 22 aa, 23 aa, 24 aa, or 25 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 11-30 of the amino acid sequence designated "Consensus" in FIGS. 16A-16L, or a corresponding HCV core amino acid sequence of any HCV genotype; and the HCV core T-cell epitope can have a length of from 20 amino acids (aa) to 25 amino acids (e.g., 20 aa, 21 aa, 22 aa, 23 aa, 24 aa, or 25 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 21-40 of the amino acid sequence designated "Consensus" in FIGS. 16A-16L, or a corresponding HCV core amino acid sequence of any HCV genotype; and the HCV core T-cell epitope can have a length of from 20 amino acids (aa) to 25 amino acids (e.g., 20 aa, 21 aa, 22 aa, 23 aa, 24 aa, or 25 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 39-63 of the amino acid sequence designated "Consensus" in FIGS. 16A-16L, or a corresponding HCV core amino acid sequence of any HCV genotype; and the HCV core T-cell epitope can have a length of from 23 amino acids (aa) to 28 amino acids (e.g., 23 aa, 24 aa, 25 aa, 26 aa, 27 aa, or 28 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 47-70 of the amino acid sequence designated "Consensus" in FIGS. 16A-16L, or a corresponding HCV core amino acid sequence of any HCV genotype; and the HCV core T-cell epitope can have a length of from 24 amino acids (aa) to 29 amino acids (e.g., 24 aa, 25 aa, 26 aa, 27 aa, 28 aa, or 29 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 61-80 of the amino acid sequence designated "Consensus" in FIGS. 16A-16L, or a corresponding HCV core amino acid sequence of any HCV genotype; and the HCV core T-cell epitope can have a length of from 20 amino acids (aa) to 25 amino acids (e.g., 20 aa, 21 aa, 22 aa, 23 aa, 24 aa, or 25 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 71-90 of the amino acid sequence designated "Consensus" in FIGS. 16A-16L, or a corresponding HCV core amino acid sequence of any HCV genotype; and the HCV core T-cell epitope can have a length of from 20 amino acids (aa) to 25 amino acids (e.g., 20 aa, 21 aa, 22 aa, 23 aa, 24 aa, or 25 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 81-100 of the amino acid sequence designated "Consensus" in FIGS. 16A-16L, or a corresponding HCV core amino acid sequence of any HCV genotype; and the HCV core T-cell epitope can have a length of from 20 amino acids (aa) to 25 amino acids (e.g., 20 aa, 21 aa, 22 aa, 23 aa, 24 aa, or 25 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 91-110 of the amino acid sequence designated "Consensus" in FIGS. 16A-16L, or a corresponding HCV core amino acid sequence of any HCV genotype; and the HCV core T-cell epitope can have a length of from 20 amino acids (aa) to 25 amino acids (e.g., 20 aa, 21 aa, 22 aa, 23 aa, 24 aa, or 25 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 101-115 of the amino acid sequence designated "Consensus" in FIGS. 16A-16L, or a corresponding HCV core amino acid sequence of any HCV genotype; and the HCV core T-cell epitope can have a length of from 15 amino acids (aa) to 20 amino acids (e.g., 15 aa, 16 aa, 17 aa, 18 aa, 19 aa, or 20 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 111-130 of the amino acid sequence designated "Consensus" in FIGS. 16A-16L, or a corresponding HCV core amino acid sequence of any HCV genotype; and the HCV core T-cell epitope can have a length of from 20 amino acids (aa) to 25 amino acids (e.g., 20 aa, 21 aa, 22 aa, 23 aa, 24 aa, or 25 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 125-139 of the amino acid sequence designated "Consensus" in FIGS. 16A-16L, or a corresponding HCV core amino acid sequence of any HCV genotype; and the HCV core T-cell epitope can have a length of from 15 amino acids (aa) to 20 amino acids (e.g., 15 aa, 16 aa, 17 aa, 18 aa, 19 aa, or 20 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 131-150 of the amino acid sequence designated "Consensus" in FIGS. 16A-16L, or a corresponding HCV core amino acid sequence of any HCV genotype; and the HCV core T-cell epitope can have a length of from 20 amino acids (aa) to 25 amino acids (e.g., 20 aa, 21 aa, 22 aa, 23 aa, 24 aa, or 25 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 151-170 of the amino acid sequence designated "Consensus" in FIGS. 16A-16L, or a corresponding HCV core amino acid sequence of any HCV genotype; and the HCV core T-cell epitope can have a length of from 20 amino acids (aa) to 25 amino acids (e.g., 20 aa, 21 aa, 22 aa, 23 aa, 24 aa, or 25 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 161-180 of the amino acid sequence designated "Consensus" in FIGS. 16A-16L, or a corresponding HCV core amino acid sequence of any HCV genotype; and the HCV core T-cell epitope can have a length of from 20 amino acids (aa) to 25 amino acids (e.g., 20 aa, 21 aa, 22 aa, 23 aa, 24 aa, or 25 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 35-44 of the amino acid sequence designated "Consensus" in FIGS. 16A-16L, or a corresponding HCV core amino acid sequence of any HCV genotype; and the HCV core T-cell epitope can have a length of from 10 amino acids (aa) to 15 amino acids (e.g., 10 aa, 11 aa, 12 aa, 13 aa, 14 aa, or 15 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 43-51 of the amino acid sequence designated "Consensus" in FIGS. 16A-16L, or a corresponding HCV core amino acid sequence of any HCV genotype; and the HCV core T-cell epitope can have a length of from 9 amino acids (aa) to 15 amino acids (e.g., 9 aa, 10 aa, 11 aa, 12 aa, 13 aa, 14 aa, or 15 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 51-59 of the amino acid sequence designated "Consensus" in FIGS. 16A-16L, or a corresponding HCV core amino acid sequence of any HCV genotype; and the HCV core T-cell epitope can have a length of from 9 amino acids (aa) to 15 amino acids (e.g., 9 aa, 10 aa, 11 aa, 12 aa, 13 aa, 14 aa, or 15 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 129-137 of the amino acid sequence designated "Consensus" in FIGS. 16A-16L, or a corresponding HCV core amino acid sequence of any HCV genotype; and the HCV core T-cell epitope can have a length of from 9 amino acids (aa) to 15 amino acids (e.g., 9 aa, 10 aa, 11 aa, 12 aa, 13 aa, 14 aa, or 15 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 131-140 of the amino acid sequence designated "Consensus" in FIGS. 16A-16L, or a corresponding HCV core amino acid sequence of any HCV genotype; and the HCV core T-cell epitope can have a length of from 10 amino acids (aa) to 15 amino acids (e.g., 10 aa, 11 aa, 12 aa, 13 aa, 14 aa, or 15 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 150-158 of the amino acid sequence designated "Consensus" in FIGS. 16A-16L, or a corresponding HCV core amino acid sequence of any HCV genotype; and the HCV core T-cell epitope can have a length of from 9 amino acids (aa) to 15 amino acids (e.g., 9 aa, 10 aa, 11 aa, 12 aa, 13 aa, 14 aa, or 15 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 154-162 of the amino acid sequence designated "Consensus" in FIGS. 16A-16L, or a corresponding HCV core amino acid sequence of any HCV genotype; and the HCV core T-cell epitope can have a length of from 9 amino acids (aa) to 15 amino acids (e.g., 9 aa, 10 aa, 11 aa, 12 aa, 13 aa, 14 aa, or 15 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 168-176 of the amino acid sequence designated "Consensus" in FIGS. 16A-16L, or a corresponding HCV core amino acid sequence of any HCV genotype; and the HCV core T-cell epitope can have a length of from 9 amino acids (aa) to 15 amino acids (e.g., 9 aa, 10 aa, 11 aa, 12 aa, 13 aa, 14 aa, or 15 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 177-187 of the amino acid sequence designated "Consensus" in FIGS. 16A-16L, or a corresponding HCV core amino acid sequence of any HCV genotype; and the HCV core T-cell epitope can have a length of from 11 amino acids (aa) to 16 amino acids (e.g., 11 aa, 12 aa, 13 aa, 14 aa, 15 aa, or 16 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 178-187 of the amino acid sequence designated "Consensus" in FIGS. 16A-16L, or a corresponding HCV core amino acid sequence of any HCV genotype; and the HCV core T-cell epitope can have a length of from 10 amino acids (aa) to 15 amino acids (e.g., 10 aa, 11 aa, 12 aa, 13 aa, 14 aa, or 15 aa).

In some cases, the heterologous polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to a contiguous stretch of from 10 amino acids (aa) to 191 aa (e.g., from 10 aa to 25 aa, from 25 aa to 50 aa, from 50 aa to 75 aa, from 75 aa to 100 aa, from 100 aa to 150 aa, or from 150 aa to 191aa) of amino acids 1-191 of the amino acid sequence designated "Consensus" in FIGS. 16A-16L, or a corresponding HCV core amino acid sequence of any HCV genotype; and has a length of from 10 amino acids (aa) to 25 aa, from 25 an to 50 aa, from 50 an to 100 aa, or from 100 aa to 150 aa, or from 150 an to 191 aa. In some cases, the heterologous polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1-191 of the amino acid sequence designated "Consensus" in FIGS. 16A-16L, or a corresponding HCV core amino acid sequence of any HCV genotype; and has a length of about 191 amino acids.

The heterologous polypeptide can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence:

MSTNPKPQRKTKRNTNRRPQDVKFPGGGQI-VGGVYLLPRRGPRLGVRATRKTS ERSQPR-GRRQPIPKARRPEGRTWAQPGYPWPLYG-

NEGCGWAGWLLSPRGSRPS WGPTDPRRRSRNLGKVIDTLTCGFADLMGYIPLVGAPLGGAARALAHGVRVLE DGVNYATGNLPG (SEQ ID NO:63); and has a length of from 171 amino acids (aa) to 180 an (e.g., 171 aa, 172 aa, 173 aa, 174 aa, 175 aa, 176 aa, 177 aa, 178 aa, 179 aa, or 180 aa. In some cases, the heterologous polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence:

MSTNPKPQRKTKRNTNRRPQDVKFPGGGQIVGGVYLLPRRGPRLGVRATRKTS ERSQPRGRRQPIPKARRPEGRTWAQPGYPWPLYGNEGCGWAGWLLSPRGSRPS WGPTDPRRRSRNLGKVIDTLTCGFADLMGYIPLVGAPLGGAARALAHGVRVLE DGVNYATGNLPG (SEQ ID NO:63); and has a length of 171 amino acids. Such a polytope can include core T-cell epitopes designated Core-1, Core-2, Core-3, Core-4, Core-5, Core-6, Core-7, Core-8, Core-9, Core-10, Core-11, Core-12, Core-13, Core-14, Core-16, Core-17, Core-18, Core-19, Core-20, Core-21, Core-22 in FIG. 13A and FIGS. 15A-15N.

HCV p7 T-Cell Epitopes

In some cases, the heterologous polypeptide present in an E2 variant polypeptide of an E1/E2 heterodimer of the present disclosure includes one or more T-cell epitopes present in an HCV p7 polypeptide. Examples of T-cell epitopes present in HCV p7 polypeptides are depicted in FIGS. 15A-15N or FIG. 13A.

As another example, the heterologous polypeptide can comprise an HCV p7 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 803-811 of the amino acid sequence designated "Consensus" in FIGS. 16A-16L, or a corresponding HCV p7 amino acid sequence of any HCV genotype; and the HCV p7 T-cell epitope can have a length of from 9 amino acids (aa) to 15 amino acids (e.g., 9 aa, 10 aa, 11 aa, 12 aa, 13 aa, 14 aa, or 15 aa).

Polytopes Including HCV T-Cell Epitopes from More than One HCV Polypeptide Other than E1 and E2

As noted above, a heterologous polypeptide can include T-cell epitopes from more than one HCV polypeptide other than E1 and E2.

As one example, a heterologous polypeptide can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence:

QASLLKVPYFVRVQGLLRICALARKMAGGHYVQMAIIKLGALTGTYVYNALTP LRDWAHNGLRDLAVAVEPVVFSQMETKLITWGADTAACGDIINGLPVSARRGR EILLGPADGMVSKGWRLLAPITAYAQQTRGLLGCIITSLTGRDKNQVEGEVQIVS TAAQTFLATCINGVCWTVYHGAGTRTIASPKGPVIQMYTNVDQDLVGWPAPQG ARSLTPCTCGSSDLYLVTRHADVIPVRRRGDSRGSLLSPRPISYLKGSAGGPLLCP AGHAVGIFRAAVCTRGVAKAVDFIPVENLETTMRSPVFTDNSSPPAVPQSFQVA HLHAPTGSGKSTKVPAAYAAQGYKVLVLNPSVAATLGFGAYMSKAHGIDPNIR TGVRTITTGSPITYSTYGKFLADGGCSGGAYDIIICDECHSTDATSILGIGTVLDQA ETAGARLVVLATATPPGSVTVPHPNIEEVALSTTGEIPFYGKAIPLEVIKGGRHLIF CHSKKKCDELAAKLVALGINAVAYYRGLDVSVIPTSGDVVVVATDALMTGFTG DFDSVIDCN (SEQ ID NO:12); and has a length of from 550 amino acids (aa) to 560 aa (e.g., 550 aa, 551 aa, 552 aa, 553 aa, 554 aa, 555 aa, 556 aa, 557 aa, 558 aa, 559 aa, or 560 aa). In some cases, the heterologous polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence:

QASLLKVPYFVRVQGLLRICALARKMAGGHYVQMAIIKLGALTGTYVYNALTP LRDWAHNGLRDLAVAVEPVVFSQMETKLITWGADTAACGDIINGLPVSARRGR EILLGPADGMVSKGWRLLAPITAYAQQTRGLLGCIITSLTGRDKNQVEGEVQIVS TAAQTFLATCINGVCWTVYHGAGTRTIASPKGPVIQMYTNVDQDLVGWPAPQG ARSLTPCTCGSSDLYLVTRHADVIPVRRRGDSRGSLLSPRPISYLKGSAGGPLLCP AGHAVGIFRAAVCTRGVAKAVDFIPVENLETTMRSPVFTDNSSPPAVPQSFQVA HLHAPTGSGKSTKVPAAYAAQGYKVLVLNPSVAATLGFGAYMSKAHGIDPNIR TGVRTITTGSPITYSTYGKFLADGGCSGGAYDIIICDECHSTDATSILGIGTVLDQA ETAGARLVVLATATPPGSVTVPHPNIEEVALSTTGEIPFYGKAIPLEVIKGGRHLIF CHSKKKCDELAAKLVALGINAVAYYRGLDVSVIPTSGDVVVVATDALMTGFTG DFDSVIDCN (SEQ ID NO:12); and has a length of 553 amino acids. Such a polytope can include T-cell epitopes designated NS2-1, NS2-2, NS2-3, NS2-4, NS2-5, NS2-6, NS2-7, NS2-8, NS3-1, NS3-2, NS3-3, NS3-4, NS3-5, NS3-6, NS3-7, NS3-9, NS3-10, NS3-11, NS3-12, and NS3-13 in FIGS. 13A-13B and FIGS. 15A-15N. This polytope is also referred to as "TP553" (FIGS. 14A-14D). In order to prevent self cleavage of the TP553 polytope (amino acids 917-1469) (FIGS. 15E-G) at the NS2-NS3 junction that is mediated by the catalytic domain of the NS2 protease (amino acids 917-1040), the histidine at position 966 (H966), a critical residue for NS2 protease activity, is mutated to alanine (H966A) (FIG. 15E).

As another example, the heterologous polypeptide can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to a contiguous stretch of from 25 amino acids (aa) to 778 an (e.g., from 25 an to 50 aa, from 50 an to 75 aa, from 75 aa to 100 aa, from 100 aa to 150 aa, from 150 aa to 200 aa, from 200 aa to 250 aa, from 250 an to 300 aa, from 300 an to 350 aa, from 350 an to 400 aa, from 400 aa to 450 aa, from 450 aa to 500 aa, from 500 an to 550 aa, from 550 aa to 600 aa, from 600 an to 650 aa, from 650 an to 700 aa, from 700 aa to 750 aa, or from 750 an to 778 aa) the following amino acid sequence:

LHAPTGSGKSTKVPAAYAAQGYKVLVL-NPSVAATLGFGAYMSKAHGIDPNIRTGVRTIT TGSPITYSTYGKFLADGGCSGGAYDIIICDECH-STDATSILGIGTVLDQAETAGARLVVLA TATPPGSVTVPHPNIEEVALSTTGEIPFYG-KAIPLEVIKGGRHLIFCHSKKKCDELAAKLV ALGINAVAYYRGLDVSVIPTSGDVVVVATDA-LMTGFTGDFDSVIDCNTCVTQTVDFSLD PTFTI-ETITLPQDAVSRTQRRGRTGRGKPGIYRFV-APGERPSGMFDSSVLCECYDAGCA WYELT-PAETTVRLRAYMNTPGLPVCQDHLEFW-EGVFTGLTHIDAHFLSQTKQSGENLP YLVAY-QATVCARAQAPPPSWDQMWKCLIRLKPTL-HGPTPLLYRLGAVQNEVTLTHPIT KYIMTCMSA-DLEVVTSTWVLVGGVLAALAAYCLSTGCV-VIVGRIVLSGKPAIIPDREVL YREFDEMEECS-QHLPYIEQGMMLAEQFKQKALGLLQTASRQAE-VIAPAVQTNWQKLEA FWAKHMWNFISGIQY-LAGLSTLPGNPAIASLMAFTAAVTSPLTTSQTLL-FNILGGWVAA QLAAPGAATAFVGAGLAGAAI-GSVGLGKVLVDILAGYGAGVAGALVAFKIMS-GEVPST EDLVNLLPAILSPGALVVGVVCAAILR-RHVGPGEGAVQWMNRLIAFASRGNHVSPTHY VPESDAAARVTAILSSLTVTQLLRRLHQWISSE-CTTPCSGSWLRDIWDWICEVLSDFKTW LKAK-LMPQLPG (SEQ ID NO:64). In some cases, the heterologous polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to a contiguous stretch of from 25 amino acids (aa) to 778 an (e.g., from 25 an to 50 aa, from 50 aa to 75 aa, from 75 aa to 100 aa, from 100 aa to 150 aa, from 150 aa to 200 aa, from 200 aa to 250 aa, from 250 aa to 300 aa, from 300 aa to 350 aa, from 350 aa to 400 aa, from 400 an to 450 aa, from 450 an to 500 aa, from 500 an to 550 aa, from 550 aa to 600 aa, from 600 aa to 650 aa, from 650 an to 700 aa, from 700 aa to 750 aa, or from 750 an to 778 aa) of the following amino acid sequence:

LHAPTGSGKSTKVPAAYAAQGYKVLVLNPSVA-ATLGFGAYMSKAHGIDPNIRTGVRTIT TGSPI-TYSTYGKFLADGGCSGGAYDIIICDECHSTDAT-SILGIGTVLDQAETAGARLVVLA TATPPGSV-TVPHPNIEEVALSTTGEIPFYGKAIPLEVIKG-GRHLIFCHSKKKCDELAAKLV ALGINAVAYYR-GLDVSVIPTSGDVVVVATDALMTGFTGDFDS-VIDCNTCVTQTVDFSLD PTFTIETITLPQDAVS-RTQRRGRTGRGKPGIYRFVAPGERPSGMFD-SSVLCECYDAGCA WYELTPAETTVRLRAYMN-TPGLPVCQDHLEFWEGVFTGLTHIDAHFLSQ-TKQSGENLP YLVAYQATVCARAQAPPPSWDQM-WKCLIRLKPTLHGPTPLLYRLGAVQNEVTLTH-PIT KYIMTCMSADLEVVTSTWVLVGGVLAA-LAAYCLSTGCVVIVGRIVLSGKPAIIPDREVL YREFDEMEECSQHLPYIEQGMMLAEQFKQKAL-GLLQTASRQAEVIAPAVQTNWQKLEA FWAKH-MWNFISGIQYLAGLSTLPGNPAIASLMAFTAAVT-SPLTTSQTLLFNILGGWVAA QLAAPGAATAF-VGAGLAGAAIGSVGLGKVLVDILAGYGAGV-AGALVAFKIMSGEVPST EDLVNLLPAILSP-GALVVGVVCAAILRRHVGPGEGAVQWMNRLIA-FASRGNHVSPTHY VPESDAAARVTAILSSLT-VTQLLRRLHQWISSECTTPCSGSWLRDIWD-WICEVLSDFKTW LKAKLMPQLPG (SEQ ID NO:64); and has a length of from 25 amino acids (aa) to 50 aa, from 50 aa to 100 aa, from 100 aa to 200 aa, from 200 aa to 300 aa, from 300 aa to 400 aa, from 400 aa to 500 aa, from 500 aa to 600 aa, from 600 an to 700 aa, or from 700 an to 778 aa. In some cases, the heterologous polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence:

LHAPTGSGKSTKVPAAYAAQGYKVLVLNPSVAA-TLGFGAYMSKAHGIDPNIRTGVRTIT TGSPI-TYSTYGKFLADGGCSGGAYDIIICDECHSTDAT-SILGIGTVLDQAETAGARLVVLA TATPPGS-VTVPHPNIEEVALSTTGEIPFYGKAIPLEVIKG-GRHLIFCHSKKKCDELAAKLV ALGINAVAYYR-GLDVSVIPTSGDVVVVATDALMTGFTGDFD-SVIDCNTCVTQTVDFSLD PTFTIETITLPQDAVS-RTQRRGRTGRGKPGIYRFVAPGERPSGMFDSS-VLCECYDAGCA WYELTPAETTVRLRAYMNTP-GLPVCQDHLEFWEGVFTGLTHIDAHFLSQTKQS-GENLP YLVAYQATVCARAQAPPPSWDQMWKC-LIRLKPTLHGPTPLLYRLGAVQNEVTLTHPIT KYIMTCMSADLEVVTSTWVLVGGVLAALAAY-CLSTGCVVIVGRIVLSGKPAIIPDREVL YREFDE-MEECSQHLPYIEQGMMLAEQFKQKALGLLQ-TASRQAEVIAPAVQTNWQKLEA FWAKHM-WNFISGIQYLAGLSTLPGNPAIASLMAFTAAVT-SPLTTSQTLLFNILGGWVAA QLAAPGAATAF-VGAGLAGAAIGSVGLGKVLVDILAGYGAGV-AGALVAFKIMSGEVPST EDLVNLLPAILSP-GALVVGVVCAAILRRHVGPGEGAVQWMNRLIA-FASRGNHVSPTHY VPESDAAARVTAILSSLTV-TQLLRRLHQWISSECTTPCSGSWLRDIWDWICE-VLSDFKTW LKAKLMPQLPG (SEQ ID NO:64); and has a length of 778 amino acids. Such a polytope can include T-cell epitopes designated NS3-1, NS3-2, NS3-3, NS3-4, NS3-5, NS3-6, NS3-7, NS3-8, NS3-9, NS3-10, NS3-11, NS3-12, NS3-13, NS2-14, NS4a-1, NS4b-1, NS4b-2, NS4b-3, NS4b-4, NS4b-5, NS4b-6, NS4b-7, NS4b-8, NS4b-9, and NS4b-10 in FIG. 13B and FIGS. 15A-15N.

As another example, the heterologous polypeptide can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to a contiguous stretch of from 25 amino acids (aa) to 1985 aa (e.g., from 25 aa to 50 aa, from 50 aa to 75 aa, from 75 an to 100 aa, from 100 an to 150 aa, from 150 an to 200 aa, from 200 aa to 250 aa, from 250 aa to 500 aa, from 500 an to 750 aa, from 750 an to 1000 aa, from 1000 aa to 1500 aa, or from 1500 an to 1985 aa) of the following amino acid sequence:

(SEQ ID NO: 13)

APITAYAQQTRGLLGCIITSLTGRDKNQVEGEVQIVSTAAQTFLATCING
VCWTVYHGAGTRTIASPKGPVIQMYTNVDQDLVGWPAPQGARSLTPCTCG
SSDLYLVTRHADVIPVRRRGDSRGSLLSPRPISYLKGSAGGPLLCPAGHA
VGIFRAAVCTRGVAKAVDFIPVENLETTMRSPVFTDNSSPPAVPQSFQVA
HLHAPTGSGKSTKVPAAYAAQGYKVLVLNPSVAATLGFGAYMSKAHGIDP
NIRTGVRTITTGSPITYSTYGKFLADGGCSGGAYDIIICDECHSTDATSI
LGIGTVLDQAETAGARLVVLATATPPGSVTVPHPNIEEVALSTTGEIPFY
GKAIPLEVIKGGRHLIFCHSKKKCDELAAKLVALGINAVAYYRGLDVSVI
PTSGDVVVVATDALMTGFTGDFDSVIDCNTCVTQTVDFSLDPTFTIETTT
LPQDAVSRTQRRGRTGRGKPGIYRFVAPGERPSGMFDSSVLCECYDAGCA
WYELTPAETTVRLRAYMNTPGLPVCQDHLEFWEGVFTGLTHIDAHFLSQT
KQSGENLPYLVAYQATVCARAQAPPPSWDQMWKCLIRLKPTLHGPTPLLY
RLGAVQNEVTLTHPITKYIMTCMSADLEVVTSTWVLVGGVLAALAAYCLS
TGCVVIVGRIVLSGKPAIIPDREVLYREFDEMEECSQHLPYIEQGMMLAE
QFKQKALGLLQTASRQAEVIAPAVQTNWQKLEAFWAKHMWNFISGIQYLA
GLSTLPGNPAIASLMAFTAAVTSPLTTSQTLLFNILGGWVAAQLAAPGAA
TAFVGAGLAGAAIGSVGLGKVLVDILAGYGAGVAGALVAFKIMSGEVPST
EDLVNLLPAILSPGALVVGVVCAAILRRHVGPGEGAVQWMNRLIAFASRG
NHVSPTHYVPESDAAARVTAILSSLTVTQLLRRLHQWISSECTTPCSGSW
LRDIWDWICEVLSDFKTWLKAKLMPQLPGIPFVSCQRGYRGVWRGDGIMH
TRCHCGAEITGHVKNGTMRIVGPRTCRNMWSGTFPINAYTTGPCTPLPAP
NYTFALWRVSAEEYVEIRQVGDFHYVTGMTTDNLKCPCQVPSPEFFTELD
GVRLHRFAPPCKPLLREEVSFRVGLHEYPVGSQLPCEPEPDVAVLTSMLT
DPSHITAEAAGRRLARGSPPSVASSSASQLSAPSLKATCTANHDSPDAEL
IEANLLWRQEMGGNITRVESENKVVILDSFDPLVAEEDEREISVPAEILR
KSRRFAPALPIWARPDYNPPLLETWKKPDYEPPVVHGCPLPPPQSPPVPP
PRKKRTVVLTESTVSTALAELATKSFGSSSTSGITGDNTTTSSEPAPSGC
PPDSDAESYSSMPPLEGEPGDPDLSDGSWSTVSSEADTEDVVCCSMSYSW
TGALVTPCAAEEQKLPINALSNSLLRHHNLVYSTTSRSACQRQKKVTFDR
LQVLDSHYQDVLKEVKAAASKVKANLLSVEEACSLTPPHSAKSKFGYGAK
DVRCHARKAVNHINSVWKDLLEDSVTPIDTTIMAKNEVFCVQPEKGGRKP
ARLIVFPDLGVRVCEKMALYDVVSKLPLAVMGSSYGFQYSPGQRVEFLVQ
AWKSKKTPMGFSYDTRCFDSTVTESDIRTEEAIYQCCDLDPQARVAIKSL
TERLYVGGPLTNSRGENCGYRRCRASGVLTTSCGNTLTCYIKARAACRAA
GLQDCTMLVCGNNLVVICESAGVQEDAASLRAFTEAMTRYSAPPGDPPQP
EYDLELITSCSSNVSVAHDGAGKRVYYLTRDPTTPLARAAWETARHTPVN
SWLGNIIMFAPTLWARMILMTHFFSVLIARDQLEQALDCEIYGACYSIEP
LDLPPIIQRLHGLSAFSLHSYSPGEINRVAACLRKLGVPPLRAWRHRARS
VRARLLSRGGRAAICGKYLFNWAVRTKLKLTPIAAAGQLDLSGWFTAGYS
GGDIYHSVSHARPRWFWFCLLLLAAGVGIYLLPNR.

In some cases, the heterologous polypeptide can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence:

(SEQ ID NO: 13)

APITAYAQQTRGLLGCIITSLTGRDKNQVEGEVQIVSTAAQTFLATCING
VCWTVYHGAGTRTIASPKGPVIQMYTNVDQDLVGWPAPQGARSLTPCTCG
SSDLYLVTRHADVIPVRRRGDSRGSLLSPRPISYLKGSAGGPLLCPAGHA
VGIFRAAVCTRGVAKAVDFIPVENLETTMRSPVFTDNSSPPAVPQSFQVA
HLHAPTGSGKSTKVPAAYAAQGYKVLVLNPSVAATLGFGAYMSKAHGIDP
NIRTGVRTITTGSPITYSTYGKFLADGGCSGGAYDIIICDECHSTDATSI
LGIGTVLDQAETAGARLVVLATATPPGSVTVPHPNIEEVALSTTGEIPFY
GKAIPLEVIKGGRHLIFCHSKKKCDELAAKLVALGINAVAYYRGLDVSVI
PTSGDVVVVATDALMTGFTGDFDSVIDCNTCVTQTVDFSLDPTFTIETTT
LPQDAVSRTQRRGRTGRGKPGIYRFVAPGERPSGMFDSSVLCECYDAGCA
WYELTPAETTVRLRAYMNTPGLPVCQDHLEFWEGVFTGLTHIDAHFLSQT
KQSGENLPYLVAYQATVCARAQAPPPSWDQMWKCLIRLKPTLHGPTPLLY
RLGAVQNEVTLTHPITKYIMTCMSADLEVVTSTWVLVGGVLAALAAYCLS
TGCVVIVGRIVLSGKPAIIPDREVLYREFDEMEECSQHLPYIEQGMMLAE
QFKQKALGLLQTASRQAEVIAPAVQTNWQKLEAFWAKHMWNFISGIQYLA
GLSTLPGNPAIASLMAFTAAVTSPLTTSQTLLFNILGGWVAAQLAAPGAA
TAFVGAGLAGAAIGSVGLGKVLVDILAGYGAGVAGALVAFKIMSGEVPST
EDLVNLLPAILSPGALVVGVVCAAILRRHVGPGEGAVQWMNRLIAFASRG
NHVSPTHYVPESDAAARVTAILSSLTVTQLLRRLHQWISSECTTPCSGSW
LRDIWDWICEVLSDFKTWLKAKLMPQLPGIPFVSCQRGYRGVWRGDGIMH
TRCHCGAEITGHVKNGTMRIVGPRTCRNMWSGTFPINAYTTGPCTPLPAP
NYTFALWRVSAEEYVEIRQVGDFHYVTGMTTDNLKCPCQVPSPEFFTELD
GVRLHRFAPPCKPLLREEVSFRVGLHEYPVGSQLPCEPEPDVAVLTSMLT
DPSHITAEAAGRRLARGSPPSVASSSASQLSAPSLKATCTANHDSPDAEL
IEANLLWRQEMGGNITRVESENKVVILDSFDPLVAEEDEREISVPAEILR
KSRRFAPALPIWARPDYNPPLLETWKKPDYEPPVVHGCPLPPPQSPPVPP
PRKKRTVVLTESTVSTALAELATKSFGSSSTSGITGDNTTTSSEPAPSGC
PPDSDAESYSSMPPLEGEPGDPDLSDGSWSTVSSEADTEDVVCCSMSYSW
TGALVTPCAAEEQKLPINALSNSLLRHHNLVYSTTSRSACQRQKKVTFDR
LQVLDSHYQDVLKEVKAAASKVKANLLSVEEACSLTPPHSAKSKFGYGAK
DVRCHARKAVNHINSVWKDLLEDSVTPIDTTIMAKNEVFCVQPEKGGRKP
ARLIVFPDLGVRVCEKMALYDVVSKLPLAVMGSSYGFQYSPGQRVEFLVQ
AWKSKKTPMGFSYDTRCFDSTVTESDIRTEEAIYQCCDLDPQARVAIKSL
TERLYVGGPLTNSRGENCGYRRCRASGVLTTSCGNTLTCYIKARAACRAA

-continued

```
GLQDCTMLVCGNNLVVICESAGVQEDAASLRAFTEAMTRYSAPPGDPPQP

EYDLELITSCSSNVSVAHDGAGKRVYYLTRDPTTPLARAAWETARHTPVN

SWLGNIIMFAPTLWARMILMTHFFSVLIARDQLEQALDCEIYGACYSIEP

LDLPPIIQRLHGLSAFSLHSYSPGEINRVAACLRKLGVPPLRAWRHRARS

VRARLLSRGGRAAICGKYLFNWAVRTKLKLTPIAAAGQLDLSGWFTAGYS

GGDIYHSVSHARPRWFWFCLLLLAAGVGIYLLPNR;
```

and has a length of 1985 amino acids. Such a polytope can include T-cell epitopes designated NS3-1, NS3-2, NS3-3, NS3-4, NS3-5, NS3-6, NS3-7, NS3-8, NS3-9, NS3-10, NS3-11, NS3-12, NS3-13, NS3-14, NS4a-1, NS4b-1, NS4b-2, NS4b-3, NS4b-4, NS4b-5, NS4b-6, NS4b-7, NS4b-8, NS4b-9, NS4b-10, NS5a-1, NS5a-2, NS5b-1, NS5b-2 in FIGS. 13A-13B and FIGS. 15A-15N.

Additional T-Cell Epitopes

As discussed above, an E1/E2 a heterodimeric polypeptide of the present disclosure includes: a) an HCV E2 polypeptide; and b) a variant HCV E1 polypeptide comprising: i) an HCV E1 polypeptide; and ii) a heterologous polypeptide that comprises one or more T-cell epitopes (e.g., one or more T cell epitopes present in an HCV polypeptide other than an HCV E1 polypeptide or an HCV E2 polypeptide). The one or more T-cell epitopes can include one or more T-cell epitopes present in: a) an HCV NS3 polypeptide; b) an HCV NS2 polypeptide; c) an HCV NS4A polypeptide; d) an HCV NS4B polypeptide; e) an HCV NS5A polypeptide; f) an HCV NS5B polypeptide; g) an HCV core polypeptide; or h) an HCV p7 polypeptide. In some cases, the one or more T-cell epitopes are T-cell epitopes present in an HCV NS3 polypeptide. In some cases, the heterologous polypeptide comprises one or more T cell epitopes present in: a) cholera toxin; and/or b) tetanus toxin; and/or c) diphtheria toxin; and/or d) a meningococcal outer membrane protein.

Thus, in some cases, a variant HCV E1 polypeptide of an E1/E2 heterodimer of the present disclosure includes: a) an HCV E1 polypeptide; and b) a heterologous polypeptide that comprises one or more T-cell epitopes, where the one or more T-cell epitopes are T-cell epitopes present in: i) one or more of an HCV NS3 polypeptide, an HCV NS2 polypeptide, an HCV NS4A polypeptide, an HCV NS4B polypeptide, an HCV NS5A polypeptide, an HCV NS5B polypeptide, an HCV core polypeptide, and an HCV p7 polypeptide; and ii) one or more of cholera toxin or toxoid, tetanus toxin or toxoid, diphtheria toxin or toxoid, and a meningococcal outer membrane protein.

A T helper tetanus toxin epitope or other bacterial T-cell epitope could be fused (e.g., by recombinant expression) or chemically conjugated to the HCV polytope/E2 fusion protein and/or to the HCV polytope E1 fusion protein of an E1/E2 heterodimer of the present disclosure to further enhance both T and B cell responses to both the HCV polytope and E1/E2 moieties. Alternatively, the whole or part of the detoxified toxin ("toxoid") could be fused (e.g., by recombinant expression) or chemically conjugated to the HCV polytope/E1E2 protein, wherein specific amino acids of the toxins are mutated to render the toxins inactive, thereby generating toxoids. Methods of generating toxoids are well known in the art. Examples of bacterial epitopes include the use of diphtheria toxoid, meningococcal outer membrane protein, or mutant diphtheria protein CRM197 (see, e.g.: http://www(dot)medscape(dot)com/viewarticle/431127)

In some cases, a suitable tetanus toxoid polypeptide comprises the amino acid sequence QYIKANSKFIGIFE (SEQ ID NO:14). In some cases, a suitable tetanus toxoid polypeptide comprises the amino acid sequence QYIKANSKFIGITE (SEQ ID NO:65).

In some cases, a heterologous polypeptide can comprise cholera toxin (or toxoid) epitope. In some cases, a suitable heterologous polypeptide comprising a cholera toxoid epitope comprises a fragment of cholera toxin-B subunit (CT-B), e.g., a fragment of from 5 amino acids to 25 amino acids, or from 25 amino acids to 50 amino acids, of the following amino acid sequence: MIKLKFGVFF TVLLSSAYAH GTPQNITDLC AEYHNTQIHT LNDKIFSYTE SLAGKREMAI ITFKNGATFQ VEVPGSQHID SQKKAIERMK DTLRIAYLTE AKVEKLCVWN NKTPHAIAAI SMAN (SEQ ID NO:15). In some cases, a suitable heterologous polypeptide comprising a cholera toxoid epitope comprises the following amino acid sequence: SLAGKREMAIITFKNGATFQVEVPG (SEQ ID NO:29).

In some cases, a heterologous polypeptide can comprise a tetanus toxin (or toxoid) T-cell epitope. In some cases, a suitable heterologous polypeptide comprising a tetanus toxin T-cell epitope comprises the amino acid sequence: ILMQYIKANSKFIGI (SEQ ID NO:16); and has a length of from 15 amino acids to 20 amino acids. In some cases, a suitable heterologous polypeptide comprising a tetanus toxin T-cell epitope comprises the amino acid sequence:

VNNESSE (SEQ ID NO:17). In some cases, a suitable heterologous polypeptide comprising a tetanus toxin T-cell epitope comprises the amino acid sequence: PGINGKAIHLVNNESSE (SEQ ID NO:18). In some cases, a suitable heterologous polypeptide comprising a tetanus toxin T-cell epitope comprises the amino acid sequence: PNRDIL (SEQ ID NO:19). In some cases, a suitable heterologous polypeptide comprising a tetanus toxin T-cell epitope comprises the amino acid sequence: FIGITEL (SEQ ID NO:20). In some cases, a suitable tetanus toxin T-cell epitope comprises the amino acid sequence: SYFPSV (SEQ ID NO:21). In some cases, a suitable heterologous polypeptide comprising a tetanus toxin T-cell epitope comprises the amino acid sequence: NSVDDALINSTKIYSYFPSV (SEQ ID NO:22). In some cases, a suitable heterologous polypeptide comprising a tetanus toxin T-cell epitope comprises the amino acid sequence: IDKISDVSTIVPYIGPALNI (SEQ ID NO:23).

In some cases, a heterologous polypeptide can comprise a diphtheria toxin T-cell epitope In some cases, a suitable heterologous polypeptide comprising a diphtheria toxin T-cell epitope comprises the amino acid sequence: QSIALSSLMVAQAIP (SEQ ID NO:24); and has a length of from 15 amino acids to 20 amino acids. In some cases, a suitable heterologous polypeptide comprising a diphtheria toxin T-cell epitope comprises the amino acid sequence:

PVFAGANYAAWAVNVAQVI (SEQ ID NO:25). In some cases, a suitable heterologous polypeptide comprising a diphtheria toxin T-cell epitope comprises the amino acid sequence:

VHHNTEEIVAQSIALSSLMV (SEQ ID NO:26). In some cases, a suitable heterologous polypeptide comprising a diphtheria toxin T-cell epitope comprises the amino acid sequence:

QSIALSSLMVAQAIPLVGEL (SEQ ID NO:66). In some cases, a suitable heterologous polypeptide comprising a diphtheria toxin T-cell epitope comprises the amino acid sequence:

VDIGFAAYNFVESIINLFQV (SEQ ID NO:67). In some cases, a suitable heterologous polypeptide comprising a diphtheria toxin T-cell epitope comprises the amino acid sequence:

QGESGHDIKITAENTPLPIA (SEQ ID NO:68). In some cases, a suitable heterologous polypeptide comprising a diphtheria toxin T-cell epitope comprises the amino acid sequence: GVLLPTIPGKLDVNKSKTHI (SEQ ID NO:69). In some cases, a suitable heterologous polypeptide comprising a diphtheria toxin T-cell epitope comprises the amino acid sequence of CRM197 (see, e.g., Giannini et al. (1984) Nucl. Acids. Res. 12:4063). The amino acid sequence of CRM197 is provided above.

In some cases, a heterologous polypeptide can comprise a tetanus toxin T-cell epitope and a diphtheria toxin T-cell epitope. In some of these cases, the heterologous polypeptide can comprise the amino acid sequence: IMQYIKANSKFIGIQSIALSSLMVAQ (SEQ ID NO:28); and can have a length of from 26 amino acids to 30 amino acids.

Additional Polypeptides

In any of the above-described embodiments, one or both of the polypeptide chains of the E1/E2 heterodimer can include one or more additional polypeptides. For example, in some cases, the variant E1 polypeptide or the variant E2 polypeptide can include an Ig Fc polypeptide at the C-terminus of the variant E1 polypeptide or the variant E2 polypeptide. Ig Fc polypeptides are known in the art, and are described elsewhere herein.

II. Variant E2 Polypeptides

The present disclosure provides a variant HCV E2 polypeptide that comprises: a) an HCV E2 polypeptide; and b) a heterologous polypeptide that comprises one or more T-cell epitopes (e.g., one or more T cell epitopes present in an HCV polypeptide other than an HCV E1 polypeptide or an HCV E2 polypeptide). The heterologous polypeptide is also referred to as a "polytope." A variant E2 polypeptide of the present disclosure is useful for inclusion in an E1/E2 heterodimer of the present disclosure.

The one or more T-cell epitopes can include one or more T-cell epitopes present in: a) an HCV NS3 polypeptide; b) an HCV NS2 polypeptide; c) an HCV NS4A polypeptide; d) an HCV NS4B polypeptide; e) an HCV NS5A polypeptide; f) an HCV NS5B polypeptide; g) an HCV core polypeptide; or h) an HCV p7 polypeptide. In some cases, the one or more T-cell epitopes are T-cell epitopes present in an HCV NS3 polypeptide. In some cases, the heterologous polypeptide further comprises one or more T cell epitopes present in: a) cholera toxin or toxoid; and/or b) tetanus toxin or toxoid; and/or c) diphtheria toxin or toxoid; and/or d) a meningococcal outer membrane protein. In some cases, a variant HCV E2 polypeptide of the present disclosure includes: a) an HCV E2 polypeptide; and b) a heterologous polypeptide that comprises one or more T-cell epitopes, where the one or more T-cell epitopes are T-cell epitopes present in: i) one or more of an HCV NS3 polypeptide, an HCV NS2 polypeptide, an HCV NS4A polypeptide, an HCV NS4B polypeptide, an HCV NS5A polypeptide, an HCV NS5B polypeptide, an HCV core polypeptide, and an HCV p7 polypeptide; and ii) one or more of cholera toxin or toxoid, tetanus toxin or toxoid, diphtheria toxin or toxoid, and a meningococcal outer membrane protein.

In some cases, the variant HCV E2 polypeptide comprises, in order from N-terminus to C-terminus: i) an HCV E2 polypeptide; and ii) a heterologous polypeptide comprising one or more T cell epitopes. In some cases, the variant HCV E2 polypeptide comprises, in order from N-terminus to C-terminus: i) a heterologous polypeptide comprising one or more T cell epitopes; and ii) an HCV E2 polypeptide.

E2

An E2 polypeptide suitable for inclusion in a variant E2 polypeptide of the present disclosure can have a length of from about 200 amino acids (aa) to about 250 aa, from about 250 aa to about 275 aa, from about 275 aa to about 300 aa, from about 300 aa to about 325 aa, from about 325 aa to about 350 aa, or from about 350 aa to about 365 aa. The E2 polypeptide can be a full-length HCV E2 polypeptide. The E2 polypeptide can be an HCV E2 ectodomain polypeptide.

In FIGS. 1A-AC, the amino acid sequence of E2 is amino acid 384 to amino acid 746. In FIGS. 2A-2B, the amino acid sequence of E2 is amino acid 384 to amino acid 751. In FIGS. 3A-3C, the amino acid sequence of E2 is amino acid 385 to amino acid 754. In FIGS. 4A-4B, the amino acid sequence of E2 is amino acid 384 to amino acid 750. As used herein, an "E2 polypeptide" includes a precursor E2 protein, including the signal sequence; includes a mature E2 polypeptide which lacks this sequence; and includes an E2 polypeptide with a heterologous signal sequence. An E2 polypeptide can include a C-terminal membrane anchor sequence which occurs at approximately amino acid positions 715-730 and may extend as far as approximately amino acid residue 746 (see, Lin et al., J. Virol. (1994) 68:5063-5073).

In some cases, a E2 polypeptide suitable for inclusion in a variant E2 polypeptide of the present disclosure lacks a portion of its C-terminal region, e.g., from about amino acid 715 to the C-terminus; from about amino acid 625 to the C-terminus; from about amino acid 661 to the C-terminus; from about amino acid 655 to the C-terminus; from about amino acid 500 to the C-terminus, where the amino acid numbering is with reference to the numbering in FIGS. 1A-1C. See, e.g., U.S. Pat. No. 6,521,423.

An E2 polypeptide suitable for inclusion in a variant E2 polypeptide of an E1/E2 heterodimer of the present disclosure can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to an amino acid sequence of an E2 polypeptide depicted in FIGS. 1A-1C, FIGS. 2A-2C, FIGS. 3A-3C, or FIGS. 4A-4B.

An E2 polypeptide suitable for inclusion in a variant E2 polypeptide of the present disclosure can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to an amino acid sequence of an E2 polypeptide depicted in FIGS. 1A-1C. For example, an E2 polypeptide of genotype 1 can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 384-746 of an amino acid sequence depicted in FIGS. 1A-1C. For example, an E2 polypeptide of genotype 1A can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 384-746 of an amino acid sequence identified as 1A and depicted in FIGS. 1A-1C. For example, an E2 polypeptide of genotype 1B can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 384-746 of an amino acid sequence identified as 1B and depicted in FIGS. 1A-1C. For example, an E2 polypeptide of genotype 1C can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 384-746 of an amino acid sequence identified as 1C and depicted in FIGS. 1A-1C.

An E2 polypeptide suitable for inclusion in a variant E2 polypeptide of the present disclosure can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to an amino acid sequence of an E2 polypeptide depicted in FIGS. 2A-2C. For example, an E2 polypeptide can comprise an amino acid sequence having having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 384-746 of an amino acid sequence depicted in FIGS. 2A-2C. For example, an E2 polypeptide of genotype 2A can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 384-751 of the "consensus" amino acid sequence depicted in FIGS. 2A-2C. For example, an E2 polypeptide of genotype 2B can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 384-751 of the "consensus" amino acid sequence depicted in FIGS. 2A-2C.

An E2 polypeptide suitable for inclusion in a variant E2 polypeptide of an E1/E2 heterodimer of the present disclosure can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to an amino acid sequence of an E2 polypeptide depicted in FIGS. 3A-3C. For example, an E2 polypeptide of genotype 3 can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 385-754 of an amino acid sequence depicted in FIGS. 3A-3C. For example, an E2 polypeptide of genotype 3A can comprise an amino acid sequence having having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 385-754 of an amino acid sequence identified as 3A and depicted in FIGS. 3A-3C. For example, an E2 polypeptide of genotype 3B can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 385-754 of the amino acid sequence identified as 3B and depicted in FIGS. 3A-3C. For example, an E2 polypeptide of genotype 3K can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 385-754 of the amino acid sequence identified as 3K and depicted in FIGS. 3A-3C.

An E2 polypeptide suitable for inclusion in a variant E2 polypeptide of the present disclosure can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the amino acid sequence of the E2 polypeptide depicted in FIGS. 4A-4B. For example, an E2 polypeptide of genotype 7A can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 384-750 of the amino acid sequence depicted in FIGS. 4A-4B.

Heterologous Polypeptide

The heterologous polypeptide present in an E2 variant polypeptide of the present disclosure includes one or more T-cell epitopes.

In some cases, the heterologous polypeptide comprises 1, 2, 3, 4, 5, 6, 7, 8, 9, or 10, or more than 10 (e.g., from 10 to 15, from 15 to 20, from 20 to 25, or from 25 to 30, or more than 30), T cell epitopes. T-cell epitopes are epitopes that, when presented with a major histocompatibility complex (MHC) (e.g., a human leukocyte antigen (HLA)) Class I or MHC Class II molecule, are recognized and bound by a T-cell receptor (TCR) present on a T cell surface. T-cell epitopes include epitopes recognized by cytotoxic T cells (e.g., $CD8^+$ T cells), and epitopes recognized by helper T cells (e.g., $CD4^+$ T cells).

The one or more T-cell epitopes can include one or more T-cell epitopes present in: a) an HCV NS3 polypeptide; b) an HCV NS2 polypeptide; c) an HCV NS4A polypeptide; d) an HCV NS4B polypeptide; e) an HCV NS5A polypeptide; f) an HCV NS5B polypeptide; g) an HCV core polypeptide; or h) an HCV p7 polypeptide. In some cases, the one or more T-cell epitopes are T-cell epitopes present in an HCV NS3 polypeptide. In some cases, the heterologous polypeptide further comprises one or more T cell epitopes present in: a) cholera toxin or toxoid; and/or b) tetanus toxin or toxoid; and/or c) diphtheria toxin or toxoid; and/or d) a meningococcal outer membrane protein. Other examples of strong T helper epitopes are diphtheria toxoid, tetanus toxoid, meningococcal outer membrane protein, or mutant diphtheria protein CRM197 (see, e.g.: http://www(dot)medscape(dot)com/viewarticle/431127).

In some cases, the heterologous polypeptide comprises a single T-cell epitope. In some cases, the heterologous polypeptide comprises a single HCV-NS3 T-cell epitope. In some cases, the heterologous polypeptide comprises 2 or more T-cell epitopes. In some cases, the heterologous polypeptide comprises 2 or more HCV-NS3 T-cell epitopes. In some cases, the heterologous polypeptide comprises 3 or more HCV-NS3 T-cell epitopes. In some cases, the heterologous polypeptide comprises 4 or more HCV-NS3 T-cell epitopes. In some cases, the heterologous polypeptide comprises a single HCV-NS3 $CD4^+$ T-cell epitope. In some cases, the heterologous polypeptide comprises 2 or more HCV-NS3 $CD4^+$ T-cell epitopes. In some cases, the heterologous polypeptide comprises one or more HCV $CD8^+$ T cell epitopes. In some cases, the heterologous polypeptide comprises a single HCV-NS3 $CD8^+$ T-cell epitope. In some cases, the heterologous polypeptide comprises 2 or more HCV-NS3 $CD8^+$ T-cell epitopes. In some cases, the heterologous polypeptide comprises at least one HCV $CD4^+$ T cell epitope and at least one HCV $CD8^+$ T cell epitope. In some cases, the heterologous polypeptide comprises at least one HCV-NS3 $CD4^+$ T cell epitope and at least one HCV-NS3 $CD8^+$ T cell epitope. In some cases, heterologous polypeptide comprises 2 or more HCV-NS3 $CD4^+$ T-cell epitopes and 2 or more HCV-NS3 $CD8^+$ T-cell epitopes. In some cases, the heterologous polypeptide comprises 2, 3, 4, or 5 HCV-NS3 $CD4^+$ T-cell epitopes and 2, 3, 4, or 5 HCV-NS3 $CD8^+$ T-cell epitopes.

In some cases, the heterologous polypeptide comprises a single T-cell epitope. In some cases, the heterologous polypeptide comprises a single HCV-NS2 T-cell epitope. In some cases, the heterologous polypeptide comprises 2 or more T-cell epitopes. In some cases, the heterologous polypeptide comprises 2 or more HCV-NS2 T-cell epitopes. In some cases, the heterologous polypeptide comprises 3 or more HCV-NS2 T-cell epitopes. In some cases, the heterologous polypeptide comprises 4 or more HCV-NS2 T-cell epitopes. In some cases, the heterologous polypeptide comprises a single HCV-NS2 $CD4^+$ T-cell epitope. In some cases, the heterologous polypeptide comprises 2 or more HCV-NS2 $CD4^+$ T-cell epitopes. In some cases, the heterologous polypeptide comprises one or more HCV $CD8^+$ T cell epitopes. In some cases, the heterologous polypeptide comprises a single HCV-NS2 $CD8^+$ T-cell epitope. In some cases, the heterologous polypeptide comprises 2 or more HCV-NS2 $CD8^+$ T-cell epitopes. In some cases, the heterologous polypeptide comprises at least one HCV $CD4^+$ T cell epitope and at least one HCV $CD8^+$ T cell epitope. In some cases, the heterologous polypeptide comprises at least one HCV-NS2 $CD4^+$ T cell epitope and at least one HCV-NS2 $CD8^+$ T cell epitope. In some cases, heterologous polypeptide comprises 2 or more HCV-NS2 $CD4^+$ T-cell epitopes and 2 or more HCV-NS2 $CD8^+$ T-cell epitopes. In some cases, the heterologous polypeptide comprises 2, 3, 4, or 5 HCV-NS2 $CD4^+$ T-cell epitopes and 2, 3, 4, or 5 HCV-NS2 $CD8^+$ T-cell epitopes.

In some cases, the heterologous polypeptide comprises a single T-cell epitope. In some cases, the heterologous polypeptide comprises a single HCV-NS4A T-cell epitope. In some cases, the heterologous polypeptide comprises 2 or more T-cell epitopes. In some cases, the heterologous polypeptide comprises 2 or more HCV-NS4A T-cell epitopes. In some cases, the heterologous polypeptide comprises 3 or more HCV-NS4A T-cell epitopes. In some cases, the heterologous polypeptide comprises 4 or more HCV-NS4A T-cell epitopes. In some cases, the heterologous polypeptide comprises a single HCV-NS4A $CD4^+$ T-cell epitope. In some cases, the heterologous polypeptide comprises 2 or more HCV-NS4A $CD4^+$ T-cell epitopes. In some cases, the heterologous polypeptide comprises one or more HCV $CD8^+$ T cell epitopes. In some cases, the heterologous polypeptide comprises a single HCV-NS4A $CD8^+$ T-cell epitope. In some cases, the heterologous polypeptide comprises 2 or more HCV-NS4A $CD8^+$ T-cell epitopes. In some cases, the heterologous polypeptide comprises at least one HCV $CD4^+$ T cell epitope and at least one HCV $CD8^+$ T cell epitope. In some cases, the heterologous polypeptide comprises at least one HCV-NS4A $CD4^+$ T cell epitope and at least one HCV-NS4A $CD8^+$ T cell epitope. In some cases, heterologous polypeptide comprises 2 or more HCV-NS4A $CD4^+$ T-cell epitopes and 2 or more HCV-NS4A $CD8^+$ T-cell epitopes. In some cases, the heterologous polypeptide comprises 2, 3, 4, or 5 HCV-NS4A $CD4^+$ T-cell epitopes and 2, 3, 4, or 5 HCV-NS4A $CD8^+$ T-cell epitopes.

In some cases, the heterologous polypeptide comprises a single T-cell epitope. In some cases, the heterologous polypeptide comprises a single HCV-NS5A T-cell epitope. In some cases, the heterologous polypeptide comprises 2 or more T-cell epitopes. In some cases, the heterologous polypeptide comprises 2 or more HCV-NS5A T-cell epitopes. In some cases, the heterologous polypeptide comprises 3 or more HCV-NS5A T-cell epitopes. In some cases, the heterologous polypeptide comprises 4 or more HCV-NS5A T-cell epitopes. In some cases, the heterologous polypeptide comprises a single HCV-NS5A $CD4^+$ T-cell epitope. In some cases, the heterologous polypeptide comprises 2 or more HCV-NS5A $CD4^+$ T-cell epitopes. In some cases, the heterologous polypeptide comprises one or more HCV $CD8^+$ T cell epitopes. In some cases, the heterologous polypeptide comprises a single HCV-NS5A $CD8^+$ T-cell epitope. In some cases, the heterologous polypeptide comprises 2 or more HCV-NS5A $CD8^+$ T-cell epitopes. In some cases, the heterologous polypeptide comprises at least one HCV $CD4^+$ T cell epitope and at least one HCV $CD8^+$ T cell epitope. In some cases, the heterologous polypeptide comprises at least one HCV-NS5A $CD4^+$ T cell epitope and at least one HCV-NS5A $CD8^+$ T cell epitope. In some cases, heterologous polypeptide comprises 2 or more HCV-NS5A $CD4^+$ T-cell epitopes and 2 or more HCV-NS5A $CD8^+$ T-cell epitopes. In some cases, the heterologous polypeptide comprises 2, 3, 4, or 5 HCV-NS5A $CD4^+$ T-cell epitopes and 2, 3, 4, or 5 HCV-NS5A $CD8^+$ T-cell epitopes.

In some cases, the heterologous polypeptide comprises a single T-cell epitope. In some cases, the heterologous polypeptide comprises a single HCV-NS5B T-cell epitope. In some cases, the heterologous polypeptide comprises 2 or more T-cell epitopes. In some cases, the heterologous polypeptide comprises 2 or more HCV-NS5B T-cell epitopes. In some cases, the heterologous polypeptide comprises 3 or more HCV-NS5B T-cell epitopes. In some cases, the heterologous polypeptide comprises 4 or more HCV-NS5B T-cell epitopes. In some cases, the heterologous polypeptide comprises a single HCV-NS5B $CD4^+$ T-cell epitope. In some cases, the heterologous polypeptide comprises 2 or more HCV-NS5B $CD4^+$ T-cell epitopes. In some cases, the heterologous polypeptide comprises one or more HCV $CD8^+$ T cell epitopes. In some cases, the heterologous polypeptide comprises a single HCV-NS5B $CD8^+$ T-cell epitope. In some cases, the heterologous polypeptide comprises 2 or more HCV-NS5B $CD8^+$ T-cell epitopes. In some cases, the heterologous polypeptide comprises at least one HCV $CD4^+$ T cell epitope and at least one HCV $CD8^+$ T cell epitope. In some cases, the heterologous polypeptide comprises at least one HCV-NS5B $CD4^+$ T cell epitope and at least one HCV-NS5B $CD8^+$ T cell epitope. In some cases, heterologous polypeptide comprises 2 or more HCV-NS5B $CD4^+$ T-cell epitopes and 2 or more HCV-NS5B $CD8^+$ T-cell epitopes. In some cases, the heterologous polypeptide comprises 2, 3, 4, or 5 HCV-NS5B $CD4^+$ T-cell epitopes and 2, 3, 4, or 5 HCV-NS5B $CD8^+$ T-cell epitopes.

In some cases, the heterologous polypeptide comprises a single T-cell epitope. In some cases, the heterologous polypeptide comprises a single HCV-core T-cell epitope. In some cases, the heterologous polypeptide comprises 2 or more T-cell epitopes. In some cases, the heterologous polypeptide comprises 2 or more HCV-core T-cell epitopes. In some cases, the heterologous polypeptide comprises 3 or more HCV-core T-cell epitopes. In some cases, the heterologous polypeptide comprises 4 or more HCV-core T-cell epitopes. In some cases, the heterologous polypeptide comprises a single HCV-core $CD4^+$ T-cell epitope. In some cases, the heterologous polypeptide comprises 2 or more HCV-core $CD4^+$ T-cell epitopes. In some cases, the heterologous polypeptide comprises one or more HCV $CD8^+$ T cell epitopes. In some cases, the heterologous polypeptide comprises a single HCV-core $CD8^+$ T-cell epitope. In some cases, the heterologous polypeptide comprises 2 or more HCV-core $CD8^+$ T-cell epitopes. In some cases, the heterologous polypeptide comprises at least one HCV $CD4^+$ T cell epitope and at least one HCV $CD8^+$ T cell epitope. In some cases, the heterologous polypeptide comprises at least one HCV-core $CD4^+$ T cell epitope and at least one HCV-core $CD8^+$ T cell epitope. In some cases, heterologous polypeptide comprises 2 or more HCV-core $CD4^+$ T-cell epitopes and 2 or more HCV-core $CD8^+$ T-cell epitopes. In some cases, the heterologous polypeptide comprises 2, 3, 4, or 5 HCV-core $CD4^+$ T-cell epitopes and 2, 3, 4, or 5 HCV-core $CD8^+$ T-cell epitopes.

In some cases, the heterologous polypeptide comprises a single T-cell epitope. In some cases, the heterologous polypeptide comprises a single HCV-p7 T-cell epitope. In some cases, the heterologous polypeptide comprises 2 or more T-cell epitopes. In some cases, the heterologous polypeptide comprises 2 or more HCV-p7 T-cell epitopes. In some cases, the heterologous polypeptide comprises 3 or more HCV-p7 T-cell epitopes. In some cases, the heterologous polypeptide comprises 4 or more HCV-p7 T-cell epitopes. In some cases, the heterologous polypeptide comprises a single HCV-p7 $CD4^+$ T-cell epitope. In some cases, the heterologous polypeptide comprises 2 or more HCV-core $CD4^+$ T-cell epitopes. In some cases, the heterologous polypeptide comprises one or more HCV $CD8^+$ T cell epitopes. In some cases, the heterologous polypeptide comprises a single HCV-p7 $CD8^+$ T-cell epitope. In some cases, the heterologous polypeptide comprises 2 or more HCV-p7 $CD8^+$ T-cell epitopes. In some cases, the heterologous polypeptide comprises at least one HCV $CD4^+$ T cell epitope and at least one HCV $CD8^+$ T cell epitope. In some cases, the heterologous polypeptide comprises at least one HCV-p7 $CD4^+$ T cell epitope and at least one HCV-p7 $CD8^+$ T cell epitope. In some cases, heterologous polypeptide comprises 2 or more HCV-p7 $CD4^+$ T-cell epitopes and 2 or more HCV-p7 $CD8^+$ T-cell epitopes. In some cases, the heterologous polypeptide comprises 2, 3, 4, or 5 HCV-p7 $CD4^+$ T-cell epitopes and 2, 3, 4, or 5 HCV-p7 $CD8^+$ T-cell epitopes.

In some cases, the heterologous polypeptide comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, or 63, of the T-cell epitopes set out in FIGS. 13A-13B. In some cases, the heterologous polypeptide comprises from 1 to 3, from 3 to 5, from 5 to 10, from 10 to 15, from 15 to 20, from 20 to 25, or from 25 to 30 of the T-cell epitopes set out in FIGS. 13A-13B. For example, in some cases, the heterologous polypeptide comprises the T-cell epitopes designated NS3-3, NS3-4, and NS3-11 in FIGS. 13A-13B and FIGS. 15A-15N. As another example, in some cases, the heterologous polypeptide comprises the T-cell epitopes designated NS2-1, NS2-2, NS2-3, NS2-7, and NS2-8 in FIGS. 13A-13B and FIGS. 15A-15N. As another example, in some cases, the heterologous polypeptide comprises the T-cell epitopes designated NS3-3, NS3-4, NS3-5, and NS3-11 in FIGS. 13A-13B and FIGS. 15A-15N. As another example, in some cases, the heterologous polypeptide comprises the T-cell epitopes designated NS3-3, NS3-4, NS3-5, NS3-6, NS3-7, NS3-11, NS3-12, and NS3-13 in FIGS. 13A-13B and FIGS. 15A-15N. As another example, in some cases, the heterologous polypeptide comprises the T-cell epitopes designated NS3-3, NS3-4, NS3-5, NS3-6, NS3-7, NS3-10, NS3-11, NS3-12, and NS3-13 in FIGS. 13A-13B and FIGS. 15A-15N. As another example, in some cases, the heterologous polypeptide comprises the T-cell epitopes designated Core-1, Core-2, Core-3, Core-4, Core-5, Core-6, Core-7, Core-8, Core-9, Core-10, Core-11, Core-12, Core-13, Core-14, Core-16, Core-17, Core-18, Core-19, Core-20, Core-21, and Core-22 in FIGS. 13A-13B and FIGS. 15A-15N. As another example, in some cases, the heterologous polypeptide comprises the T-cell epitopes designated NS3-1, NS3-2, NS3-3, NS3-4, NS3-5, NS3-6, NS3-7, NS3-9, NS3-10, NS3-11, NS3-12, and NS3-13 in FIGS. 13A-13B and FIGS. 15A-15N. As another example, in some cases, the heterologous polypeptide comprises the T-cell epitopes designated NS2-1, NS2-2, NS2-3, NS2-4, NS2-5, NS2-6, NS2-7, NS2-8, NS3-1, NS3-2, NS3-3, NS3-4, NS3-5, NS3-6, NS3-7, NS3-9, NS3-10, NS3-11, NS3-12, and NS3-13 in FIGS. 13A-13B and FIGS. 15A-15N. As another example, in some cases, the heterologous polypeptide comprises the T-cell epitopes designated NS3-1, NS3-2, NS3-3, NS3-4, NS3-5, NS3-6, NS3-7, NS3-8, NS3-9, NS3-10, NS3-11, NS3-12, NS3-13, NS3-14, NS4a-1, NS4b-1, NS4b-2, NS4b-3, NS4b-4, NS4b-5, NS4b-6, NS4b-7, NS4b-8, NS4b-9, and NS4b-10 in FIGS. 13A-13B and FIGS. 15A-15N. As another example, in some cases, the heterologous polypeptide comprises the T-cell epitopes designated NS3-1, NS3-2, NS3-3, NS3-4, NS3-5, NS3-6, NS3-7, NS3-8, NS3-9, NS3-10, NS3-11, NS3-12, NS3-13, NS3-14, NS4a-1, NS4b-1, NS4b-2, NS4b-3, NS4b-4, NS4b-5, NS4b-6, NS4b-7, NS4b-8, NS4b-9, NS4b-10, NS5a-1, NS5a-2, NS5b-1, and NS5b-2 in FIGS. 13A-13B and FIGS. 15A-15N. In some cases, the T-cell epitopes are contiguous. In some cases, any two T-cell epitopes are separated by linkers (e.g., a linker having a length of from 1 amino acid to about 50 amino acids, e.g., from 1 amino acid to 5 amino acids (aa), from 5 aa to 10 aa, from 10 aa to 15 aa, from 15 aa to 20 aa, from 20 aa to 25 aa, from 25 aa to 30 aa, from 30 aa to 40 aa, or from 40 aa to 50 aa).

In some cases, the heterologous polypeptide comprises at least one HCV $CD4^+$ T cell epitope and at least one HCV $CD8^+$ T cell epitope, where epitopes are conserved among HCV genotypes 1 and 2. In some cases, the heterologous polypeptide comprises at least one HCV $CD4^+$ T cell epitope and at least one HCV $CD8^+$ T cell epitope, where epitopes are conserved among HCV genotypes 1 and 3. In some cases, the heterologous polypeptide comprises at least one HCV $CD4^+$ T cell epitope and at least one HCV $CD8^+$ T cell epitope, where epitopes are conserved among HCV genotypes 1, 2, and 3. In some cases, the heterologous polypeptide comprises at least one HCV $CD4^+$ T cell epitope and at least one HCV $CD8^+$ T cell epitope, where epitopes are conserved among HCV genotypes 1, 2, 3, and 7. In some cases, the heterologous polypeptide comprises at least one HCV $CD4^+$ T cell epitope and at least one HCV $CD8^+$ T cell epitope, where epitopes are conserved among HCV genotypes 1-7.

The heterologous polypeptide can have a length of from about 10 amino acids to about 2000 amino acids; e.g., the heterologous polypeptide can have a length of from 10 amino acids (aa) to 15 aa, from 15 an to 20 aa, from 20 an to 25 aa, from 25 aa to 50 aa, from 50 aa to 75 aa, from 75 an to 100 aa, from 100 an to 150 aa, from 150 aa to 200 aa, from 200 aa to 250 aa, from 250 aa to 300 aa, from 300 an to 350 aa, from 350 aa to 400 aa, from 450 an to 500 aa, from 500 an to 550 aa, from 550 an to 600 aa, from 600 an to 650 aa, from 650 aa to 700 aa, from 700 aa to 750 aa, or from 750 aa to 800 aa. The heterologous polypeptide can have a length of from about 25 amino acids to about 2000 amino acids, e.g., from about 25 amino acids (aa) to 50 aa, from 50 an to 75 aa, from 75 an to 100 aa, from 100 an to 150 aa, from 150 an to 200 aa, from 200 aa to 250 aa, from 250 an to 300 aa, from 300 aa to 350 aa, from 350 an to 400 aa, from 400 an to 500 aa, from 500 aa to 600 aa, from 600 an to 700 aa, from 700 an to 800 aa, from 800 aa to 900 aa, from 900 an to 1000 aa, from 1000 aa to 1100 aa, from 1100 aa to 1200 aa, from 1200 an to 1300 aa, from 1300 aa to 1400 aa, from 1400 aa to 1500 aa, from 1500 aa to 1600 aa, from 1600 aa to 1700 aa, from 1700 aa to 1800 aa, from 1800 aa to 1900 aa, or from 1900 aa to 2000 aa. The heterologous polypeptide can have a length of from about 25 amino acids to about 3000 amino acids, e.g., from about 25 amino acids (aa) to 50 aa, from 50 aa to 75 aa, from 75 aa to 100 aa, from 100 aa to 150 aa, from 150 aa to 200 aa, from 200 aa to 250 aa, from 250 aa to 300 aa, from 300 aa to 350 aa, from 350 an to 400 aa, from 400 an to 500 aa, from 500 an to 600 aa, from 600 an to 700 aa, from 700 an to 800 aa, from 800 an to 900 aa, from 900 aa to 1000 aa, from 1000 aa to 1100 aa, from 1100 aa to 1200 aa, from 1200 aa to 1300 aa, from 1300 aa to 1400 aa, from 1400 aa to 1500 aa, from 1500 an to 1600 aa, from 1600 aa to 1700 aa, from 1700 aa to 1800 aa, from 1800 an to 1900 aa, from 1900 aa to 2000 aa, from 2000 an to 2250 aa, from 2250 an to 2500 aa, from 2500 an to 2750 aa, or from 2750 an to 3000 aa.

The heterologous polypeptide can have a length of from about 25 amino acids to about 800 amino acids, e.g., from about 25 amino acids (aa) to 50 aa, from 50 an to 75 aa, from 75 aa to 100 aa, from 100 an to 150 aa, from 150 an to 200 aa, from 200 an to 250 aa, from 250 aa to 300 aa, from 300 aa to 350 aa, from 350 aa to 400 aa, from 450 an to 500 aa, from 500 an to 550 aa, from 550 aa to 600 aa, from 600 an to 650 aa, from 650 an to 700 aa, from 700 aa to 750 aa, or from 750 an to 800 aa. The heterologous polypeptide can have a length of from about 25 amino acids to about 400 amino acids, e.g., from about 25 amino acids (aa) to 50 aa, from 50 an to 75 aa, from 75 an to 100 aa, from 100 an to 150 aa, from 150 an to 200 aa, from 200 aa to 250 aa, from 250 aa to 300 aa, from 300 an to 350 aa, or from 350 aa to 400 aa. The heterologous polypeptide can have a length of 25 amino acids (aa), 26 aa, 27 aa, 28 aa, 29 aa, 30 aa, 31 aa, 32 aa, 33 aa, 34 aa, 35 aa, 36 aa, 37 aa, 38 aa, 39 aa, 40 aa, 41 aa, 42 aa, 43 aa, 44 aa, 45 aa, 46 aa, 47 aa, 48 aa, 49 aa, or 50 aa. The heterologous polypeptide can have a length of from about 100 amino acids (aa) to 800 aa, e.g., from 100 aa to 150 aa, from 150 aa to 200 aa, from 200 aa to 250 aa, from 250 an to 300 aa, from 300 aa to 350 aa, from 350 an to 400 aa, from 450 an to 500 aa, from 500 aa to 550 aa, from 550 an to 600 aa, from 600 an to 650 aa, from 650 aa to 700 aa, from 700 an to 750 aa, or from 750 aa to 800 aa. The heterologous polypeptide can have a length of from 25 an to 30 aa. The heterologous polypeptide can have a length of from 30 an to 40 aa. The heterologous polypeptide can have a length of from 40 an to 50 aa. The heterologous polypeptide can have a length of from 50 aa to 60 aa (e.g., 50 aa, 51 aa, 52, aa, 53 aa, 54 aa, 55 aa, 56 aa, 57 aa, 58 aa, 59 aa, or 60 aa). The heterologous polypeptide can have a length of from 60 aa to 70 aa. The heterologous polypeptide can have a length of from 65 an to 75 aa (e.g., 65, 66, 67, 68, 69, 70, 71, 72, 7, 74, or 75 aa). The heterologous polypeptide can have a length of 70 aa. The heterologous polypeptide can have a length of from 70 an to 80 aa. The heterologous polypeptide can have a length of from 80 aa to 90 aa. The heterologous polypeptide can have a length of from 90 an to 100 aa. The heterologous polypeptide can have a length of from 100 an to 105 aa (e.g., 100, 101, 102, 103, 104, 105, 106, 107, 108, 109, or 110 aa). The heterologous polypeptide can have a length of 100 aa. The heterologous polypeptide can have a length of from 10 amino acids (aa) to 50 aa; e.g., from 10 an to 15 aa, from 15 an to 20 aa, from 20 an to 25 aa, from 25 an to 30 aa, from 30 an to 35 aa, from 35 aa to 40 aa, from 40 an to 45 aa, or from 45 an to 50 aa. The heterologous polypeptide can have a length of from 10 amino acids (aa) to 20 aa, e.g., 10, 11, 12, 13, 14, 15, 16, 17, 18, 19, or 20 aa.

HCV NS3 T-Cell Epitopes

In some cases, the heterologous polypeptide present in an E2 variant polypeptide of an E1/E2 heterodimer of the present disclosure includes one or more T-cell epitopes present in an HCV NS3 polypeptide. Examples of T-cell epitopes present in NS3 polypeptides are depicted in FIGS. 15A-15N, FIG. 13B, and FIGS. 14A-14B.

The heterologous polypeptide can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence: AIPLEVIKGGRHLIFCHSKKKCDELAAKL (SEQ ID NO:1). In some cases, the heterologous polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence: AIPLEVIKGGRHLIFCHSKKKCDELAAKL (SEQ ID NO:1); and has a length of from 25 aa to 35 aa (e.g., 25 aa, 26 aa, 27 aa, 28 aa, 29 aa, 30 aa, 31 aa, 32 aa, 33 aa, 34 aa, or 35 aa). In some cases, the heterologous polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence: AIPLEVIKGGRHLIFCHSKKKCDELAAKL (SEQ ID NO:1); and has a length of 29 amino acids. Such a polytope can include NS3 T-cell epitopes designated NS3-3, NS3-4, and NS3-11 in FIG. 13B and FIGS. 15A-15N.

The heterologous polypeptide can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence: AIPLEVIKGGRHLIFCHSKKKCDELAAKLVALGI-NAVAYYRGLDVSVIPTSG (SEQ ID NO:2). In some cases, the heterologous polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence: AIPLEV-IKGGRHLIFCHSKKKCDELAAKLVALGI-NAVAYYRGLDVSVIPTSG (SEQ ID NO:2); and has a length of from 45 amino acids to 60 amino acids (e.g., 45 aa, 46 aa, 47 aa, 48 aa, 49 aa, 50 aa, 51 aa, 52 aa, 53 aa, 54 aa, 55 aa, 56 aa, 57 aa, 58 aa, 59 aa, or 60 aa). In some cases, the heterologous polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence: AIPLEVIKGGRHLIFCHSKKKCDELAAKLVALGI-NAVAYYRGLDVSVIPTSG (SEQ ID NO:2); and has a length of 52 amino acids. Such a polytope can include NS3 T-cell epitopes designated NS3-3, NS3-4, NS3-5, and NS3-11 in FIG. 13B and FIGS. 15A-15N.

The heterologous polypeptide can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence: KGGRHLIFCHSKKKCDELAAKLVALGINAVAYYR-GLDVSVIPTSGDVVVVATDALMTG FTGDFDSVIDCN (SEQ ID NO:3); and has a length of from 65 amino acids to 80 amino acids (e.g., 65 aa, 66 aa, 67 aa, 68 aa, 69 aa, 70 aa, 71 aa, 72 aa, 73 aa, 74 aa, 75 aa, 76 aa, 77 aa, 78 aa, 79 aa, or 80 aa). In some cases, the heterologous polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence: KGGRHLIFCHSKKKCDELAAKLVALGINAVAYYR-GLDVSVIPTSGDVVVVATDALMTG FTGDFDSVIDCN (SEQ ID NO:3); and has a length of 70 amino acids. Such a polytope can include NS3 T-cell epitopes designated NS3-3, NS3-4, NS3-5, NS3-6, NS3-7, NS3-11, NS3-12, and NS3-13 in FIG. 13B and FIGS. 15A-15N.

The heterologous polypeptide can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence: VALSTTGEIPFYGKAIPLEVIKGGRHLIFCHS-KKKCDELAAKLVALGINAVAYYRGLDVS VIPTSGDVVVVATDALMTGFTGDFDSVID-CNTCVTQTVDF (SEQ ID NO:4); and has a length of from 95 amino acids (aa) to 105 aa (e.g., 95 aa, 96 aa, 97 aa, 98 aa, 99 aa, 100 aa, 101 aa, 102 aa, 103 aa, 104 aa, or 105 aa). In some cases, the heterologous polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence: VALSTTGEIPFYGKAIPLEVIKGGRHLIFCHS-KKKCDELAAKLVALGINAVAYYRGLDVS VIPTSGDVVVVATDALMTGFTGDFDSVID-CNTCVTQTVDF (SEQ ID NO:4); and has a length of 100 amino acids. Such a polytope can include NS3 T-cell epitopes designated NS3-3, NS3-4, NS3-5, NS3-6, NS3-7, NS3-10, NS3-11, NS3-12, and NS3-13 in FIG. 13B and FIGS. 15A-15N.

The heterologous polypeptide can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence:

MSTNPKPQRKTKRNTNRRPQDVKFPGGGQI-VGGVYLLPRRGPRLGVRATRKTSERSQP RGRRQPIPKARRPEGRTWAQPGYPWPLYG-NEGCGWAGWLLSPRGSRPSWGPTDPRRRS RNLGKVIDTLTCGFADLMGYIPLVGAPLG-GAARALAHGVRVLEDGVNYATGNLPGCSF SIFLLALLSCLTVPASA (SEQ ID NO:9); and has a length of from 190 amino acids (aa) to 200 an (e.g., 190 aa, 191 aa, 192 aa, 193 aa, 194 aa, 195 aa, 196 aa, 197 aa, 198 aa, 199 aa, or 200 aa. In some cases, the heterologous polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence:

MSTNPKPQRKTKRNTNRRPQDVKFPGGGQI-VGGVYLLPRRGPRLGVRATRKTSERSQP RGRRQPIPKARRPEGRTWAQPGYPWPLYG-NEGCGWAGWLLSPRGSRPSWGPTDPRRRS RNLGKVIDTLTCGFADLMGYIPLVGAPLG-GAARALAHGVRVLEDGVNYATGNLPGCSF SIFLLALLSCLTVPASA (SEQ ID NO:9); and has a length of 191 amino acids.

The heterologous polypeptide can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence:

(SEQ ID NO: 10)
LHAPTGSGKSTKVPAAYAAQGYKVLVLNPSVAATLGFGAYMSKAHGIDPN

IRTGVRTITTGSPITYSTYGKFLADGGCSGGAYDIIICDECHSTDATSIL

GIGTVLDQAETAGARLVVLATATPPGSVTVPHPNIEEVALSTTGEIPFYG

KAIPLEVIKGGRHLIFCHSKKKCDELAAKLVALGINAVAYYRGLDVSVIP

TSGDVVVVATDALMTGFTGDFDSVIDCN;

and has a length of from 215 amino acids (aa) to 235 aa (e.g., 215 aa, 216 aa, 217 11, 218 aa, 219 aa, 220 aa, 221 aa, 222 aa, 223 aa, 224 aa, 225 aa, 226 aa, 227 aa, 228 aa, 229 aa, 230 aa, 231 aa, 232 aa, 233 aa, 234 aa, or 235 aa). In some cases, the heterologous polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence:

(SEQ ID NO: 10)
LHAPTGSGKSTKVPAAYAAQGYKVLVLNPSVAATLGFGAYMSKAHGIDPN

IRTGVRTITTGSPITYSTYGKFLADGGCSGGAYDIIICDECHSTDATSIL

GIGTVLDQAETAGARLVVLATATPPGSVTVPHPNIEEVALSTTGEIPFYG

KAIPLEVIKGGRHLIFCHSKKKCDELAAKLVALGINAVAYYRGLDVSVIP

TSGDVVVVATDALMTGFTGDFDSVIDCN;

and has a length of 228 amino acids. Such a polytope can include NS3 T-cell epitopes designated NS3-1, NS3-2, NS3-3, NS3-4, NS3-5, NS3-6, NS3-7, NS3-9, NS3-10, NS3-11, NS3-12, and NS3-13 in FIG. 13B and FIGS. 15A-15N.

As another example, the heterologous polypeptide can comprise an HCV NS3 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1265-1279 of the amino acid sequence designated "Consensus" in FIGS. 16A-16L, or a corresponding HCV NS3 amino acid sequence of any HCV genotype; and the HCV NS3 T-cell epitope can have a length of from 15 amino acids (aa) to 20 amino acids (e.g., 15 aa, 16 aa, 17 aa, 18 aa, 19 aa, or 20 aa).

As another example, the heterologous polypeptide can comprise an HCV NS3 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1309-1323 of the amino acid sequence designated "Consensus" in FIGS. 16A-16L, or a corresponding HCV NS3 amino acid sequence of any HCV genotype; and the HCV NS3 T-cell epitope can have a length of from 15 amino acids (aa) to 20 amino acids (e.g., 15 aa, 16 aa, 17 aa, 18 aa, 19 aa, or 20 aa).

As another example, the heterologous polypeptide can comprise an HCV NS3 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1401-1415 of the amino acid sequence designated "Consensus" in FIGS. 16A-16L, or a corresponding HCV NS3 amino acid sequence of any HCV genotype; and the HCV NS3 T-cell epitope can have a length of from 15 amino acids (aa) to 20 amino acids (e.g., 15 aa, 16 aa, 17 aa, 18 aa, 19 aa, or 20 aa).

As another example, the heterologous polypeptide can comprise an HCV NS3 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1402-1412 of the amino acid sequence designated "Consensus" in FIGS. 16A-16L, or a corresponding HCV NS3 amino acid sequence of any HCV genotype; and the HCV NS3 T-cell epitope can have a length of from 11 amino acids (aa) to 16 amino acids (e.g., 11 aa, 12 aa, 13 aa, 14 aa, 15 aa, or 16 aa).

As another example, the heterologous polypeptide can comprise an HCV NS3 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1429-1439 of the amino acid sequence designated "Consensus" in FIGS. 16A-16L, or a corresponding HCV NS3 amino acid sequence of any HCV genotype; and the HCV NS3 T-cell epitope can have a length of from 11 amino acids (aa) to 16 amino acids (e.g., 11 aa, 12 aa, 13 aa, 14 aa, 15 aa, or 16 aa).

As another example, the heterologous polypeptide can comprise an HCV NS3 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1450-1464 of the amino acid sequence designated "Consensus" in FIGS. 16A-16L, or a corresponding HCV NS3 amino acid sequence of any HCV genotype; and the HCV NS3 T-cell epitope can have a length of from 15 amino acids (aa) to 20 amino acids (e.g., 15 aa, 16 aa, 17 aa, 18 aa, 19 aa, or 20 aa).

As another example, the heterologous polypeptide can comprise an HCV NS3 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1453-1467 of the amino acid sequence designated "Consensus" in FIGS. 16A-16L, or a corresponding HCV NS3 amino acid sequence of any HCV genotype; and the HCV NS3 T-cell epitope can have a length of from 15 amino acids (aa) to 20 amino acids (e.g., 15 aa, 16 aa, 17 aa, 18 aa, 19 aa, or 20 aa).

As another example, the heterologous polypeptide can comprise an HCV NS3 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1577-1591 of the amino acid sequence designated "Consensus" in FIGS. 16A-16L, or a corresponding HCV NS3 amino acid sequence of any HCV genotype; and the HCV NS3 T-cell epitope can have a length of from 15 amino acids (aa) to 20 amino acids (e.g., 15 aa, 16 aa, 17 aa, 18 aa, 19 aa, or 20 aa).

As another example, the heterologous polypeptide can comprise an HCV NS3 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1306-1314 of the amino acid sequence designated "Consensus" in FIGS. 16A-16L, or a corresponding HCV NS3 amino acid sequence of any HCV genotype; and the HCV NS3 T-cell epitope can have a length of from 9 amino acids (aa) to 15 amino acids (e.g., 9 aa, 10 aa, 11 aa, 12 aa, 13 aa, 14 aa, or 15 aa).

As another example, the heterologous polypeptide can comprise an HCV NS3 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1387-1394 of the amino acid sequence designated "Consensus" in FIGS. 16A-16L, or a corresponding HCV NS3 amino acid sequence of any HCV genotype; and the HCV NS3 T-cell epitope can have a length of from 1 amino acids (aa) to 15 amino acids (e.g., 8 aa, 9 aa, 10 aa, 11 aa, 12 aa, 13 aa, 14 aa, or 15 aa).

As another example, the heterologous polypeptide can comprise an HCV NS3 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1405-1413 of the amino acid sequence designated "Consensus" in FIGS. 16A-16L, or a corresponding HCV NS3 amino acid sequence of any HCV genotype; and the HCV NS3 T-cell epitope can have a length of from 9 amino acids (aa) to 15 amino acids (e.g., 9 aa, 10 aa, 11 aa, 12 aa, 13 aa, 14 aa, or 15 aa).

As another example, the heterologous polypeptide can comprise an HCV NS3 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1450-1458 of the amino acid sequence designated "Consensus" in FIGS. 16A-16L, or a corresponding HCV NS3 amino acid sequence of any HCV genotype; and the HCV NS3 T-cell epitope can have a length of from 9 amino acids (aa) to 15 amino acids (e.g., 9 aa, 10 aa, 11 aa, 12 aa, 13 aa, 14 aa, or 15 aa).

As another example, the heterologous polypeptide can comprise an HCV NS3 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1457-1465 of the amino acid sequence designated "Consensus" in FIGS. 16A-16L, or a corresponding HCV NS3 amino acid sequence of any HCV genotype; and the HCV NS3 T-cell epitope can have a length of from 9 amino acids (aa) to 15 amino acids (e.g., 9 aa, 10 aa, 11 aa, 12 aa, 13 aa, 14 aa, or 15 aa).

As another example, the heterologous polypeptide can comprise an HCV NS3 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1610-1618 of the amino acid sequence designated "Consensus" in FIGS. 16A-16L, or a corresponding HCV NS3 amino acid sequence of any HCV genotype; and the HCV NS3 T-cell epitope can have a length of from 9 amino acids (aa) to 15 amino acids (e.g., 9 aa, 10 aa, 11 aa, 12 aa, 13 aa, 14 aa, or 15 aa).

HCV NS2 T-Cell Epitopes

In some cases, the heterologous polypeptide present in an E2 variant polypeptide of an E1/E2 heterodimer of the present disclosure includes one or more T-cell epitopes present in an HCV NS2 polypeptide. Examples of T-cell epitopes present in NS2 polypeptides are depicted in FIGS. 15A-15N, and FIG. 13A.

For example, the heterologous polypeptide can comprise an NS2 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 955-974 of the amino acid sequence designated "Consensus" in FIGS. 16A-16L, or a corresponding HCV NS2 amino acid sequence of any HCV genotype; and the NS2 T cell epitope can have a length of from 20 amino acids (aa) to 25 amino acids (e.g., 20 aa, 21 aa, 22 aa, 23 aa, 24 aa, or 25 aa).

As another example, the heterologous polypeptide can comprise an NS2 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 975-994 of the amino acid sequence designated "Consensus" in FIGS. 16A-16L, or a corresponding HCV NS2 amino acid sequence of any HCV genotype; and the NS2 T cell epitope can have a length of from 20 amino acids (aa) to 25 amino acids (e.g., 20 aa, 21 aa, 22 aa, 23 aa, 24 aa, or 25 aa).

As another example, the heterologous polypeptide can comprise an NS2 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 985-1004 of the amino acid sequence designated "Consensus" in FIGS. 16A-16L, or a corresponding HCV NS2 amino acid sequence of any HCV genotype; and the NS2 T cell epitope can have a length of from 20 amino acids (aa) to 25 amino acids (e.g., 20 aa, 21 aa, 22 aa, 23 aa, 24 aa, or 25 aa).

As another example, the heterologous polypeptide can comprise an NS2 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1015-1034 of the amino acid sequence designated "Consensus" in FIGS. 16A-16L, or a corresponding HCV NS2 amino acid sequence of any HCV genotype; and the NS2 T cell epitope can have a length of from 20 amino acids (aa) to 25 amino acids (e.g., 20 aa, 21 aa, 22 aa, 23 aa, 24 aa, or 25 aa).

As another example, the heterologous polypeptide can comprise an NS2 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1035-1054 of the amino acid sequence designated "Consensus" in FIGS. 16A-16L, or a corresponding HCV NS2 amino acid sequence of any HCV genotype; and the NS2 T cell epitope can have a length of from 20 amino acids (aa) to 25 amino acids (e.g., 20 aa, 21 aa, 22 aa, 23 aa, 24 aa, or 25 aa).

As another example, the heterologous polypeptide can comprise an NS2 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 924-933 of the amino acid sequence designated "Consensus" in FIGS. 16A-16L, or a corresponding HCV NS2 amino acid sequence of any HCV genotype; and the NS2 T cell epitope can have a length of from 10 amino acids (aa) to 15 amino acids (e.g., 10 aa, 11 aa, 12 aa, 13 aa, 14 aa, or 15 aa).

As another example, the heterologous polypeptide can comprise an NS2 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 961-970 of the amino acid sequence designated "Consensus" in FIGS. 16A-16L, or a corresponding HCV NS2 amino acid sequence of any HCV genotype; and the NS2 T cell epitope can have a length of from 10 amino acids (aa) to 15 amino acids (e.g., 10 aa, 11 aa, 12 aa, 13 aa, 14 aa, or 15 aa).

As another example, the heterologous polypeptide can comprise an NS2 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 989-997 of the amino acid sequence designated "Consensus" in FIGS. 16A-16L, or a corresponding HCV NS2 amino acid sequence of any HCV genotype; and the NS2 T cell epitope can have a length of from 9 amino acids (aa) to 15 amino acids (e.g., 9 aa, 10 aa, 11 aa, 12 aa, 13 aa, 14 aa, or 15 aa).

In some cases, the heterologous polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to a contiguous stretch of from 10 amino acids (aa) to 50 an (e.g., from 10 aa to 25 aa, or from 25 an to 50 aa) of amino acids 955-1004 of the amino acid sequence designated "Consensus" in FIGS. 16A-16L, or a corresponding HCV NS2 amino acid sequence of any HCV genotype; and has a length of from 10 amino acids (aa) to 25 aa, or from 25 aa to 50 aa. In some cases, the heterologous polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 955-1004 of the amino acid sequence designated "Consensus" in FIGS. 16A-16L, or a corresponding HCV NS2 amino acid sequence of any HCV genotype; and has a length of about 50 amino acids.

In some cases, the heterologous polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to a contiguous stretch of from 10 amino acids (aa) to 553 aa (e.g., from 10 aa to 25 aa, from 25 aa to 50 aa, from 50 aa to 100 aa, from 100 aa to 200 aa, from 200 aa to 300 aa, from 300 aa to 400 aa, from 400 aa to 500 aa, or from 500 aa to 553 aa) of amino acids 917-1469 of the amino acid sequence designated "Consensus" in FIGS. 16A-16L, or a corresponding HCV NS2 and NS3 amino acid sequence of any HCV genotype; and has a length of from 10 amino acids (aa) to 25 aa, from 25 aa to 50 aa, from 50 an to 100 aa, from 100 an to 200 aa, from 200 aa to 300 aa, from 300 aa to 400 aa, from 400 aa to 500 aa, or from 500 an to 553 aa. In some cases, the heterologous polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 917-1469 of the amino acid sequence designated "Consensus" in FIGS. 16A-16L, or a corresponding HCV NS2 and NS3 amino acid sequence of any HCV genotype; and has a length of about 553 amino acids.

The heterologous polypeptide can comprise an amino acid sequence having at least about 20%, at least about 25%, at least about 30%, at least about 35%, at least about 40%, at least about 45%, at least about 50%, at least about 60%, at least about 0%, at least about 75%, at least about 80%, at least about 85%, at least about 90%, at least about 95%, at least about 98%, at least about 99%, or 100%, amino acid sequence identity to the following amino acid sequence:

LGALTGTYVYNHLTPLRDWAHNGLRDLAVAVE-PVVFSQMETKLITWGADT (SEQ ID NO:11). In some cases, the heterologous polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence:

LGALTGTYVYNHLTPLRDWAHNGLRDLAVAVE-PVVFSQMETKLITWGADT (SEQ ID NO:11); and has a length of from 50 amino acids to 60 amino acids (e.g., 50 aa, 51 aa, 52 aa, 53 aa, 54 aa, 55 aa, 56 aa, 57 aa, 58 aa, 59 aa, or 60 aa). In some cases, the heterologous polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence:

LGALTGTYVYNHLTPLRDWAHNGLRDLAVAVE-PVVFSQMETKLITWGADT (SEQ ID NO:11); and has a length of 50 amino acids. Such a polytope can include NS2 T-cell epitopes designated NS2-1, NS2-2, NS2-3, NS2-7, and NS2-8 in FIG. 13A and FIGS. 15A-15N.

HCV NS4A T-Cell Epitopes

In some cases, the heterologous polypeptide present in an E2 variant polypeptide of an E1/E2 heterodimer of the present disclosure includes one or more T-cell epitopes present in an HCV NS4A polypeptide. Examples of T-cell epitopes present in NS4A polypeptides are depicted in FIGS. 15A-15N and FIG. 13B.

The heterologous polypeptide can comprise an NS4A T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1683-1692 of the amino acid sequence designated "Consensus" in FIGS. 16A-16L, or a corresponding HCV NS4A amino acid sequence of any HCV genotype; and the NS4A T-cell epitope can have a length of from 10 amino acids (aa) to 15 amino acids (e.g., 10 aa, 11 aa, 12 aa, 13 aa, 14 aa, or 15 aa).

HCV NS4B T-Cell Epitopes

In some cases, the heterologous polypeptide present in an E2 variant polypeptide of an E1/E2 heterodimer of the present disclosure includes one or more T-cell epitopes present in an HCV NS4B polypeptide. Examples of T-cell epitopes present in NS4B polypeptides are depicted in FIGS. 15A-15N and FIG. 13B.

As one example, the heterologous polypeptide can comprise an NS4B T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1790-1801 of the amino acid sequence designated "Consensus" in FIGS. 16A-16L, or a corresponding HCV NS4B amino acid sequence of any HCV genotype; and the NS4B T-cell epitope can have a length of from 12 amino acids (aa) to 20 amino acids (e.g., 12 aa, 13 aa, 14 aa, 15 aa, 16 aa, 17 aa, 18 aa, 19 aa, or 20 aa).

As another example, the heterologous polypeptide can comprise an NS4B T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1792-1802 of the amino acid sequence designated "Consensus" in FIGS. 16A-16L, or a corresponding HCV NS4B amino acid sequence of any HCV genotype; and the NS4B T-cell epitope can have a length of from 11 amino acids (aa) to 20 amino acids (e.g., 11 aa, 12 aa, 13 aa, 14 aa, 15 aa, 16 aa, 17 aa, 18 aa, 19 aa, or 20 aa).

As another example, the heterologous polypeptide can comprise an NS4B T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1898-1905 of the amino acid sequence designated "Consensus" in FIGS. 16A-16L, or a corresponding HCV NS4B amino acid sequence of any HCV genotype; and the NS4B T-cell epitope can have a length of from 8 amino acids (aa) to 15 amino acids (e.g., 8 aa, 9 aa, 10 aa, 11 aa, 12 aa, 13 aa, 14 aa, or 15 aa).

As another example, the heterologous polypeptide can comprise an NS4B T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1921-1935 of the amino acid sequence designated "Consensus" in FIGS. 16A-16L, or a corresponding HCV NS4B amino acid sequence of any HCV genotype; and the NS4B T-cell epitope can have a length of from 15 amino acids (aa) to 20 amino acids (e.g., 15 aa, 16 aa, 17 aa, 18 aa, 19 aa, or 20 aa).

As another example, the heterologous polypeptide can comprise an NS4B T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1922-1941 of the amino acid sequence designated "Consensus" in FIGS. 16A-16L, or a corresponding HCV NS4B amino acid sequence of any HCV genotype; and the NS4B T-cell epitope can have a length of from 20 amino acids (aa) to 25 amino acids (e.g., 20 aa, 21 aa, 22 aa, 23 aa, 24 aa, or 25 aa).

As another example, the heterologous polypeptide can comprise an NS4B T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1928-1947 of the amino acid sequence designated "Consensus" in FIGS. 16A-16L, or a corresponding HCV NS4B amino acid sequence of any HCV genotype; and the NS4B T-cell epitope can have a length of from 20 amino acids (aa) to 25 amino acids (e.g., 20 aa, 21 aa, 22 aa, 23 aa, 24 aa, or 25 aa).

As another example, the heterologous polypeptide can comprise an NS4B T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1868-1876 of the amino acid sequence designated "Consensus" in FIGS. 16A-16L, or a corresponding HCV NS4B amino acid sequence of any HCV genotype; and the NS4B T-cell epitope can have a length of from 9 amino acids (aa) to 15 amino acids (e.g., 9 aa, 10 aa, 11 aa, 12 aa, 13 aa, 14 aa, or 15 aa).

As another example, the heterologous polypeptide can comprise an NS4B T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1927-1942 of the amino acid sequence designated "Consensus" in FIGS. 16A-16L, or a corresponding HCV NS4B amino acid sequence of any HCV genotype; and the NS4B T-cell epitope can have a length of from 16 amino acids (aa) to 20 amino acids (e.g., 16 aa, 17 aa, 18 aa, 19 aa, or 20 aa).

As another example, the heterologous polypeptide can comprise an NS4B T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1932-1940 of the amino acid sequence designated "Consensus" in FIGS. 16A-16L, or a corresponding HCV NS4B amino acid sequence of any HCV genotype; and the NS4B T-cell epitope can have a length of from 9 amino acids (aa) to 15 amino acids (e.g., 9 aa, 10 aa, 11 aa, 12 aa, 13 aa, 14 aa, or 15 aa).

As another example, the heterologous polypeptide can comprise an NS4B T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1948-1962 of the amino acid sequence designated "Consensus" in FIGS. 16A-16L, or a corresponding HCV NS4B amino acid sequence of any HCV genotype; and the NS4B T-cell epitope can have a length of from 15 amino acids (aa) to 20 amino acids (e.g., 15 aa, 16 aa, 17 aa, 18 aa, 19 aa, or 20 aa).

HCV NS5A T-Cell Epitopes

In some cases, the heterologous polypeptide present in an E2 variant polypeptide of an E1/E2 heterodimer of the present disclosure includes one or more T-cell epitopes present in an HCV NS5A polypeptide. Examples of T-cell epitopes present in NS5A polypeptides are depicted in FIGS. 15A-15N and FIG. 13B.

As one example, the heterologous polypeptide can comprise an NS5A T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 2218-2232 of the amino acid sequence designated "Consensus" in FIGS. 16A-16L, or a corresponding HCV NSSA amino acid sequence of any HCV genotype; and the NSSA T-cell epitope can have a length of from 15 amino acids (aa) to 20 amino acids (e.g., 15 aa, 16 aa, 17 aa, 18 aa, 19 aa, or 20 aa).

As another example, the heterologous polypeptide can comprise an NSSA T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 2309-2317 of the amino acid sequence designated "Consensus" in FIGS. 16A-16L, or a corresponding HCV NSSA amino acid sequence of any HCV genotype; and the NSSA T-cell epitope can have a length of from 9 amino acids (aa) to 15 amino acids (e.g., 9 aa, 10 aa, 11 aa, 12 aa, 13 aa, 14 aa, or 15 aa).

HCV NS5B T-Cell Epitopes

In some cases, the heterologous polypeptide present in an E2 variant polypeptide of an E1/E2 heterodimer of the present disclosure includes one or more T-cell epitopes present in an HCV NS5B polypeptide. Examples of T-cell epitopes present in NS5B polypeptides are depicted in FIGS. 15A-15N and FIG. 13B.

As one example, the heterologous polypeptide can comprise an NS5B T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 2847-2851 of the amino acid sequence designated "Consensus" in FIGS. 16A-16L, or a corresponding HCV NS5B amino acid sequence of any HCV genotype; and the NS5B T-cell epitope can have a length of from 5 amino acids (aa) to 10 amino acids (e.g., 5 aa, 6 aa, 7 aa, 8 aa, 9 aa, or 10 aa).

As another example, the heterologous polypeptide can comprise an NS5B T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 2602-2610 of the amino acid sequence designated "Consensus" in FIGS. 16A-16L, or a corresponding HCV NS5B amino acid sequence of any HCV genotype; and the NS5B T-cell epitope can have a length of from 9 amino acids (aa) to 15 amino acids (e.g., 9 aa, 10 aa, 11 aa, 12 aa, 13 aa, 14 aa, or 15 aa).

HCV Core T-Cell Epitopes

In some cases, the heterologous polypeptide present in an E2 variant polypeptide of an E1/E2 heterodimer of the present disclosure includes one or more T-cell epitopes present in an HCV core polypeptide. Examples of T-cell epitopes present in HCV Core polypeptides are depicted in FIGS. 15A-15N and FIG. 13A.

As one example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1-20 of the amino acid sequence designated "Consensus" in FIGS. 16A-16L, or a corresponding HCV core amino acid sequence of any HCV genotype; and the HCV core T-cell epitope can have a length of from 20 amino acids (aa) to 25 amino acids (e.g., 20 aa, 21 aa, 22 aa, 23 aa, 24 aa, or 25 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 11-30 of the amino acid sequence designated "Consensus" in FIGS. 16A-16L, or a corresponding HCV core amino acid sequence of any HCV genotype; and the HCV core T-cell epitope can have a length of from 20 amino acids (aa) to 25 amino acids (e.g., 20 aa, 21 aa, 22 aa, 23 aa, 24 aa, or 25 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 21-40 of the amino acid sequence designated "Consensus" in FIGS. 16A-16L, or a corresponding HCV core amino acid sequence of any HCV genotype; and the HCV core T-cell epitope can have a length of from 20 amino acids (aa) to 25 amino acids (e.g., 20 aa, 21 aa, 22 aa, 23 aa, 24 aa, or 25 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 39-63 of the amino acid sequence designated "Consensus" in FIGS. 16A-16L, or a corresponding HCV core amino acid sequence of any HCV genotype; and the HCV core T-cell epitope can have a length of from 23 amino acids (aa) to 28 amino acids (e.g., 23 aa, 24 aa, 25 aa, 26 aa, 27 aa, or 28 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 47-70 of the amino acid sequence designated "Consensus" in FIGS. 16A-16L, or a corresponding HCV core amino acid sequence of any HCV genotype; and the HCV core T-cell epitope can have a length of from 24 amino acids (aa) to 29 amino acids (e.g., 24 aa, 25 aa, 26 aa, 27 aa, 28 aa, or 29 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 61-80 of the amino acid sequence designated "Consensus" in FIGS. 16A-16L, or a corresponding HCV core amino acid sequence of any HCV genotype; and the HCV core T-cell epitope can have a length of from 20 amino acids (aa) to 25 amino acids (e.g., 20 aa, 21 aa, 22 aa, 23 aa, 24 aa, or 25 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 71-90 of the amino acid sequence designated "Consensus" in FIGS. 16A-16L, or a corresponding HCV core amino acid sequence of any HCV genotype; and the HCV core T-cell epitope can have a length of from 20 amino acids (aa) to 25 amino acids (e.g., 20 aa, 21 aa, 22 aa, 23 aa, 24 aa, or 25 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 81-100 of the amino acid sequence designated "Consensus" in FIGS. 16A-16L, or a corresponding HCV core amino acid sequence of any HCV genotype; and the HCV core T-cell epitope can have a length of from 20 amino acids (aa) to 25 amino acids (e.g., 20 aa, 21 aa, 22 aa, 23 aa, 24 aa, or 25 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 91-110 of the amino acid sequence designated "Consensus" in FIGS. 16A-16L, or a corresponding HCV core amino acid sequence of any HCV genotype; and the HCV core T-cell epitope can have a length of from 20 amino acids (aa) to 25 amino acids (e.g., 20 aa, 21 aa, 22 aa, 23 aa, 24 aa, or 25 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 101-115 of the amino acid sequence designated "Consensus" in FIGS. 16A-16L, or a corresponding HCV core amino acid sequence of any HCV genotype; and the HCV core T-cell epitope can have a length of from 15 amino acids (aa) to 20 amino acids (e.g., 15 aa, 16 aa, 17 aa, 18 aa, 19 aa, or 20 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 111-130 of the amino acid sequence designated "Consensus" in FIGS. 16A-16L, or a corresponding HCV core amino acid sequence of any HCV genotype; and the HCV core T-cell epitope can have a length of from 20 amino acids (aa) to 25 amino acids (e.g., 20 aa, 21 aa, 22 aa, 23 aa, 24 aa, or 25 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 125-139 of the amino acid sequence designated "Consensus" in FIGS. 16A-16L, or a corresponding HCV core amino acid sequence of any HCV genotype; and the HCV core T-cell epitope can have a length of from 15 amino acids (aa) to 20 amino acids (e.g., 15 aa, 16 aa, 17 aa, 18 aa, 19 aa, or 20 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 131-150 of the amino acid sequence designated "Consensus" in FIGS. 16A-16L, or a corresponding HCV core amino acid sequence of any HCV genotype; and the HCV core T-cell epitope can have a length of from 20 amino acids (aa) to 25 amino acids (e.g., 20 aa, 21 aa, 22 aa, 23 aa, 24 aa, or 25 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 151-170 of the amino acid sequence designated "Consensus" in FIGS. 16A-16L, or a corresponding HCV core amino acid sequence of any HCV genotype; and the HCV core T-cell epitope can have a length of from 20 amino acids (aa) to 25 amino acids (e.g., 20 aa, 21 aa, 22 aa, 23 aa, 24 aa, or 25 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 161-180 of the amino acid sequence designated "Consensus" in FIGS. 16A-16L, or a corresponding HCV core amino acid sequence of any HCV genotype; and the HCV core T-cell epitope can have a length of from 20 amino acids (aa) to 25 amino acids (e.g., 20 aa, 21 aa, 22 aa, 23 aa, 24 aa, or 25 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 35-44 of the amino acid sequence designated "Consensus" in FIGS. 16A-16L, or a corresponding HCV core amino acid sequence of any HCV genotype; and the HCV core T-cell epitope can have a length of from 10 amino acids (aa) to 15 amino acids (e.g., 10 aa, 11 aa, 12 aa, 13 aa, 14 aa, or 15 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 43-51 of the amino acid sequence designated "Consensus" in FIGS. 16A-16L, or a corresponding HCV core amino acid sequence of any HCV genotype; and the HCV core T-cell epitope can have a length of from 9 amino acids (aa) to 15 amino acids (e.g., 9 aa, 10 aa, 11 aa, 12 aa, 13 aa, 14 aa, or 15 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 51-59 of the amino acid sequence designated "Consensus" in FIGS. 16A-16L, or a corresponding HCV core amino acid sequence of any HCV genotype; and the HCV core T-cell epitope can have a length of from 9 amino acids (aa) to 15 amino acids (e.g., 9 aa, 10 aa, 11 aa, 12 aa, 13 aa, 14 aa, or 15 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 129-137 of the amino acid sequence designated "Consensus" in FIGS. 16A-16L, or a corresponding HCV core amino acid sequence of any HCV genotype; and the HCV core T-cell epitope can have a length of from 9 amino acids (aa) to 15 amino acids (e.g., 9 aa, 10 aa, 11 aa, 12 aa, 13 aa, 14 aa, or 15 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 131-140 of the amino acid sequence designated "Consensus" in FIGS. 16A-16L, or a corresponding HCV core amino acid sequence of any HCV genotype; and the HCV core T-cell epitope can have a length of from 10 amino acids (aa) to 15 amino acids (e.g., 10 aa, 11 aa, 12 aa, 13 aa, 14 aa, or 15 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 150-158 of the amino acid sequence designated "Consensus" in FIGS. 16A-16L, or a corresponding HCV core amino acid sequence of any HCV genotype; and the HCV core T-cell epitope can have a length of from 9 amino acids (aa) to 15 amino acids (e.g., 9 aa, 10 aa, 11 aa, 12 aa, 13 aa, 14 aa, or 15 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 154-162 of the amino acid sequence designated "Consensus" in FIGS. 16A-16L, or a corresponding HCV core amino acid sequence of any HCV genotype; and the HCV core T-cell epitope can have a length of from 9 amino acids (aa) to 15 amino acids (e.g., 9 aa, 10 aa, 11 aa, 12 aa, 13 aa, 14 aa, or 15 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 168-176 of the amino acid sequence designated "Consensus" in FIGS. 16A-16L, or a corresponding HCV core amino acid sequence of any HCV genotype; and the HCV core T-cell epitope can have a length of from 9 amino acids (aa) to 15 amino acids (e.g., 9 aa, 10 aa, 11 aa, 12 aa, 13 aa, 14 aa, or 15 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 177-187 of the amino acid sequence designated "Consensus" in FIGS. 16A-16L, or a corresponding HCV core amino acid sequence of any HCV genotype; and the HCV core T-cell epitope can have a length of from 11 amino acids (aa) to 16 amino acids (e.g., 11 aa, 12 aa, 13 aa, 14 aa, 15 aa, or 16 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 178-187 of the amino acid sequence designated “Consensus” in FIGS. 16A-16L, or a corresponding HCV core amino acid sequence of any HCV genotype; and the HCV core T-cell epitope can have a length of from 10 amino acids (aa) to 15 amino acids (e.g., 10 aa, 11 aa, 12 aa, 13 aa, 14 aa, or 15 aa).

In some cases, the heterologous polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to a contiguous stretch of from 10 amino acids (aa) to 191 an (e.g., from 10 aa to 25 aa, from 25 aa to 50 aa, from 50 aa to 75 aa, from 75 aa to 100 aa, from 100 aa to 150 aa, or from 150 aa to 191aa) of amino acids 1-191 of the amino acid sequence designated “Consensus” in FIGS. 16A-16L, or a corresponding HCV core amino acid sequence of any HCV genotype; and has a length of from 10 amino acids (aa) to 25 aa, from 25 an to 50 aa, from 50 an to 100 aa, or from 100 aa to 150 aa, or from 150 an to 191 aa. In some cases, the heterologous polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1-191 of the amino acid sequence designated “Consensus” in FIGS. 16A-16L, or a corresponding HCV core amino acid sequence of any HCV genotype; and has a length of about 191 amino acids.

The heterologous polypeptide can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence:

MSTNPKPQRKTKRNTNRRPQDVKFPGGGQI-VGGVYLLPRRGPRLGVRATRKTS ERSQPR-GRRQPIPKARRPEGRTWAQPGYPWPLYG-NEGCGWAGWLLSPRGSRPS WGPTDPRRRS-RNLGKVIDTLTCGFADLMGYIPLVGAPLG-GAARALAHGVRVLE DGVNYATGNLPG (SEQ ID NO:63); and has a length of from 171 amino acids (aa) to 180 aa (e.g., 171 aa, 172 aa, 173 aa, 174 aa, 175 aa, 176 aa, 177 aa, 178 aa, 179 aa, or 180 aa. In some cases, the heterologous polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence:

MSTNPKPQRKTKRNTNRRPQDVKFPGGGQI-VGGVYLLPRRGPRLGVRATRKTS ERSQPR-GRRQPIPKARRPEGRTWAQPGYPWPLYG-NEGCGWAGWLLSPRGSRPS WGPTDPRRR-SRNLGKVIDTLTCGFADLMGYIPLVGAPLG-GAARALAHGVRVLE DGVNYATGNLPG (SEQ ID NO:63); and has a length of 171 amino acids. Such a polytope can include core T-cell epitopes designated Core-1, Core-2, Core-3, Core-4, Core-5, Core-6, Core-7, Core-8, Core-9, Core-10, Core-11, Core-12, Core-13, Core-14, Core-16, Core-17, Core-18, Core-19, Core-20, Core-21, Core-22 in FIG. 13A and FIGS. 15A-15N.

HCV p7 T-Cell Epitopes

In some cases, the heterologous polypeptide present in an E2 variant polypeptide of an E1/E2 heterodimer of the present disclosure includes one or more T-cell epitopes present in an HCV p7 polypeptide. Examples of T-cell epitopes present in HCV p7 polypeptides are depicted in FIGS. 15A-15N or FIG. 13A.

As another example, the heterologous polypeptide can comprise an HCV p7 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 803-811 of the amino acid sequence designated “Consensus” in FIGS. 16A-16L, or a corresponding HCV p7 amino acid sequence of any HCV genotype; and the HCV p7 T-cell epitope can have a length of from 9 amino acids (aa) to 15 amino acids (e.g., 9 aa, 10 aa, 11 aa, 12 aa, 13 aa, 14 aa, or 15 aa).

Polytopes Including HCV T-Cell Epitopes from More than One HCV Polypeptide Other than E1 and E2

As noted above, a heterologous polypeptide can include T-cell epitopes from more than one HCV polypeptide other than E1 and E2.

As one example, a heterologous polypeptide can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence:

QASLLKVPYFVRVQGLLRICALARKMAGGHYVQ-MAIIKLGALTGTYVYNALTP LRDWAHNGLRD-LAVAVEPVVFSQMETKLITWGADTAACGDI-INGLPVSARRGR EILLGPADGMVSKGWRL-LAPITAYAQQTRGLLGCIITSLTGRDKNQVEG-EVQIVS TAAQTFLATCINGVCWTVYHGAGTR-TIASPKGPVIQMYTNVDQDLVGWPAPQG ARSLTPCTCGSSDLYLVTRHADVIPVRRRGD-SRGSLLSPRPISYLKGSAGGPLLCP AGHAVGI-FRAAVCTRGVAKAVDFIPVENLETTMRSPVFT-DNSSPPAVPQSFQVA HLHAPTGSGKSTKVPA-AYAAQGYKVLVLNPSVAATLGFGAYMSKAHG-IDPNIR TGVRTITTGSPITYSTYGKFLADGGCSG-GAYDIIICDECHSTDATSILGIGTVLDQA ETAG-ARLVVLATATPPGSVTVPHPNIEEVALSTT-GEIPFYGKAIPLEVIKGGRHLIF CHSKKKCDE-

LAAKLVALGINAVAYYRGLDVSVIPTSGDVVV-
VATDALMTGFTG DFDSVIDCN (SEQ ID NO:12); and has a length of from 550 amino acids (aa) to 560 aa (e.g., 550 aa, 551 aa, 552 aa, 553 aa, 554 aa, 555 aa, 556 aa, 557 aa, 558 aa, 559 aa, or 560 aa). In some cases, the heterologous polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence:

QASLLKVPYFVRVQGLLRICALARKMAGGHYVQ-
MAIIKLGALTGTYVYNALTP LRDWAHNGLRD-
LAVAVEPVVFSQMETKLITWGADTAACGDI-
INGLPVSARRGR EILLGPADGMVSKGWRL-
LAPITAYAQQTRGLLGCIITSLTGRDKNQVEG-
EVQIVS TAAQTFLATCINGVCWTVYHGAGTR-
TIASPKGPVIQMYTNVDQDLVGWPAPQG
ARSLTPCTCGSSDLYLVTRHADVIPVRRRG-
DSRGSLLSPRPISYLKGSAGGPLLCP AGHAVGI-
FRAAVCTRGVAKAVDFIPVENLETTMRSPVFT-
DNSSPPAVPQSFQVA HLHAPTGSGKSTKVPAAY-
AAQGYKVLVLNPSVAATLGFGAYMSKAHGID-
PNIR TGVRTITTGSPITYSTYGKFLADGGCSG-
GAYDIIICDECHSTDATSILGIGTVLDQA
ETAGARLVVLATATPPGSVTVPHPNIEEVALSTT-
GEIPFYGKAIPLEVIKGGRHLIF CHSKKKCDE-
LAAKLVALGINAVAYYRGLDVSVIPTSGDVVV-
VATDALMTGFTG DFDSVIDCN (SEQ ID NO:12); and has a length of 553 amino acids. Such a polytope can include T-cell epitopes designated NS2-1, NS2-2, NS2-3, NS2-4, NS2-5, NS2-6, NS2-7, NS2-8, NS3-1, NS3-2, NS3-3, NS3-4, NS3-5, NS3-6, NS3-7, NS3-9, NS3-10, NS3-11, NS3-12, and NS3-13 in FIGS. 13A-13B and FIGS. 15A-15N. This polytope is also referred to as "TP553" (FIGS. 14A-14D). In order to prevent self cleavage of the TP553 polytope (amino acids 917-1469) (FIGS. 15E-G) at the NS2-NS3 junction that is mediated by the catalytic domain of the NS2 protease (amino acids 917-1040), the histidine at position 966 (H966), a critical residue for NS2 protease activity, is mutated to alanine (H966A) (FIG. 15E).

As another example, the heterologous polypeptide can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to a contiguous stretch of from 25 amino acids (aa) to 778 aa (e.g., from 25 aa to 50 aa, from 50 aa to 75 aa, from 75 aa to 100 aa, from 100 an to 150 aa, from 150 an to 200 aa, from 200 aa to 250 aa, from 250 an to 300 aa, from 300 an to 350 aa, from 350 an to 400 aa, from 400 aa to 450 aa, from 450 aa to 500 aa, from 500 an to 550 aa, from 550 aa to 600 aa, from 600 an to 650 aa, from 650 an to 700 aa, from 700 aa to 750 aa, or from 750 an to 778 aa) the following amino acid sequence:

LHAPTGSGKSTKVPAAYAAQGYKVLVLN-
PSVAATLGFGAYMSKAHGIDPNIRTGVRTIT
TGSPITYSTYGKFLADGGCSGGAYDIIICDECH-
STDATSILGIGTVLDQAETAGARLVVLA
TATPPGSVTVPHPNIEEVALSTTGEIPFYG-
KAIPLEVIKGGRHLIFCHSKKKCDELAAKLV
ALGINAVAYYRGLDVSVIPTSGDVVVVATDAL-
MTGFTGDFDSVIDCNTCVTQTVDFSLD PTFTI-
ETITLPQDAVSRTQRRGRTGRGKPGIYRF-
VAPGERPSGMFDSSVLCECYDAGCA WYELT-
PAETTVRLRAYMNTPGLPVCQDHLEF-
WEGVFTGLTHIDAHFLSQTKQSGENLP
YLVAYQATVCARAQAPPPSWDQMWKC-
LIRLKPTLHGPTPLLYRLGAVQNEVTLTHPIT
KYIMTCMSADLEVVTSTWVLVGGVLAALAAY-
CLSTGCVVIVGRIVLSGKPAIIPDREVL YREFDE-
MEECSQHLPYIEQGMMLAEQFKQKALGLLQ-
TASRQAEVIAPAVQTNWQKLEA FWAKHM-
WNFISGIQYLAGLSTLPGNPAIASLMAFTAAVT-
SPLTTSQTLLFNILGGWVAA QLAAPGAATAF-
VGAGLAGAAIGSVGLGKVLVDILAGYGAGVA-
GALVAFKIMSGEVPST EDLVNLLPAILSP-
GALVVGVVCAAILRRHVGPGEGAVQWMNRLIA-
FASRGNHVSPTHY VPESDAAARVTAILSSLTV-
TQLLRRLHQWISSECTTPCSGSWLRDIWDWICE-
VLSDFKTW LKAKLMPQLPG (SEQ ID NO:64). In some cases, the heterologous polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to a contiguous stretch of from 25 amino acids (aa) to 778 an (e.g., from 25 an to 50 aa, from 50 aa to 75 aa, from 75 an to 100 aa, from 100 aa to 150 aa, from 150 aa to 200 aa, from 200 aa to 250 aa, from 250 aa to 300 aa, from 300 aa to 350 aa, from 350 aa to 400 aa, from 400 an to 450 aa, from 450 an to 500 aa, from 500 an to 550 aa, from 550 aa to 600 aa, from 600 aa to 650 aa, from 650 an to 700 aa, from 700 aa to 750 aa, or from 750 an to 778 aa) of the following amino acid sequence:

LHAPTGSGKSTKVPAAYAAQGYKVLVLNPSVA-
ATLGFGAYMSKAHGIDPNIRTGVRTIT TGSPI-
TYSTYGKFLADGGCSGGAYDIIICDECHSTDAT-
SILGIGTVLDQAETAGARLVVLA TATPPGS-
VTVPHPNIEEVALSTTGEIPFYGKAIPLEVIKG-
GRHLIFCHSKKKCDELAAKLV ALGINAVAYYR-
GLDVSVIPTSGDVVVVATDALMTGFTGD-
FDSVIDCNTCVTQTVDFSLD PTFTIETITLPQ-
DAVSRTQRRGRTGRGKPGIYRFVAPGER-
PSGMFDSSVLCECYDAGCA WYELTPAETTVRL-
RAYMNTPGLPVCQDHLEFWEGVFTGLTHI-
DAHFLSQTKQSGENLP YLVAYQATVCAR-
AQAPPPSWDQMWKCLIRLKPTLHGPTPLLYRL-
GAVQNEVTLTHPIT KYIMTCMSADLEVVT-
STWVLVGGVLAALAAYCLSTGCVVIVGRIVL-
SGKPAIIPDREVL YREFDEMEECSQHLPYIEQGM-
MLAEQFKQKALGLLQTASRQAEVIAPAVQTN-
WQKLEA FWAKHMWNFISGIQYLAGLSTLPGN-
PAIASLMAFTAAVTSPLTTSQTLLFNILGGWVAA
QLAAPGAATAFVGAGLAGAAIGSVGLGK-
VLVDILAGYGAGVAGALVAFKIMSGEVPST
EDLVNLLPAILSPGALVVGVVCAAILR-
RHVGPGEGAVQWMNRLIAFASRGNHVSPTHY
VPESDAAARVTAILSSLTVTQLLRRLHQWISS-
ECTTPCSGSWLRDIWDWICEVLSDFKTW LKAK-
LMPQLPG (SEQ ID NO:64); and has a length of from 25 amino acids (aa) to 50 aa, from 50 aa to 100 aa, from 100 an to 200 aa, from 200 an to 300 aa, from 300 aa to 400 aa, from 400 an to 500 aa, from 500 an to 600 aa, from 600 an to 700 aa, or from 700 an to 778 aa. In some cases, the heterologous polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence:

LHAPTGSGKSTKVPAAYAAQGYKVLVLNPSVAA-TLGFGAYMSKAHGIDPNIRTGVRTIT TGSPI-TYSTYGKFLADGGCSGGAYDIIICDECHSTDAT-SILGIGTVLDQAETAGARLVVLA TATPPGS-VTVPHPNIEEVALSTTGEIPFYGKAIPLEVIKG-GRHLIFCHSKKKCDELAAKLV ALGINAVAYYR-GLDVSVIPTSGDVVVVATDALMTGFTGDFDSVI-DCNTCVTQTVDFSLD FTFTIETITLPQDAVSRTQ-RRGRTGRGKPGIYRFVAPGERPSGMFDSSVL-CECYDAGCA WYELTPAETTVRLRAYMNTPG-LPVCQDHLEFWEGVFTGLTHIDAHFLSQTKQS-GENLP YLVAYQATVCARAQAPPPSWDQMWKC-LIRLKPTLHGPTPLLYRLGAVQNEVTLTHPIT KYIMTCMSADLEVVTSTWVLVGGVLAALAAY-CLSTGCVVIVGRIVLSGKPAIIPDREVL YREFDE-MEECSQHLPYIEQGMMLAEQFKQKALGLLQ-TASRQAEVIAPAVQTNWQKLEA FWAKHMWNF-ISGIQYLAGLSTLPGNPAIASLMAFTAAVT-SPLTTSQTLLFNILGGWVAA QLAAPGAATAFV-GAGLAGAAIGSVGLGKVLVDILAGYGAGVAGA-LVAFKIMSGEVPST EDLVNLLPAILSPGALVVGV-VCAAILRRHVGPGEGAVQWMNRLIAFAS-RGNHVSPTHY VPESDAAARVTAILSSLTVT-QLLRRLHQWISSECTTPCSGSWLRDIWDWICE-VLSDFKTW LKAKLMPQLPG (SEQ ID NO:64); and has a length of 778 amino acids. Such a polytope can include T-cell epitopes designated NS3-1, NS3-2, NS3-3, NS3-4, NS3-5, NS3-6, NS3-7, NS3-8, NS3-9, NS3-10, NS3-11, NS3-12, NS3-13, NS2-14, NS4a-1, NS4b-1, NS4b-2, NS4b-3, NS4b-4, NS4b-5, NS4b-6, NS4b-7, NS4b-8, NS4b-9, and NS4b-10 in FIG. 13B and FIGS. 15A-15N.

As another example, the heterologous polypeptide can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to a contiguous stretch of from 25 amino acids (aa) to 1985 aa (e.g., from 25 aa to 50 aa, from 50 aa to 75 aa, from 75 aa to 100 aa, from 100 aa to 150 aa, from 150 an to 200 aa, from 200 aa to 250 aa, from 250 aa to 500 aa, from 500 an to 750 aa, from 750 an to 1000 aa, from 1000 aa to 1500 aa, or from 1500 an to 1985 aa) of the following amino acid sequence:

(SEQ ID NO: 13)

APITAYAQQTRGLLGCIITSLTGRDKNQVEGEVQIVSTAAQTFLATCING

VCWTVYHGAGTRTIASPKGPVIQMYTNVDQDLVGWPAPQGARSLTPCTCG

SSDLYLVTRHADVIPVRRRGDSRGSLLSPRPISYLKGSAGGPLLCPAGHA

VGIFRAAVCTRGVAKAVDFIPVENLETTMRSPVFTDNSSPPAVPQSFQVA

HLHAPTGSGKSTKVPAAYAAQGYKVLVLNPSVAATLGFGAYMSKAHGIDP

-continued

NIRTGVRTITTGSPITYSTYGKFLADGGCSGGAYDIIICDECHSTDATSI

LGIGTVLDQAETAGARLVVLATATPPGSVTVPHPNIEEVALSTTGEIPFY

GKAIPLEVIKGGRHLIFCHSKKKCDELAAKLVALGINAVAYYRGLDVSVI

PTSGDVVVVATDALMTGFTGDFDSVIDCNTCVTQTVDFSLDPTFTIETTT

LPQDAVSRTQRRGRTGRGKPGIYRFVAPGERPSGMFDSSVLCECYDAGCA

WYELTPAETTVRLRAYMNTPGLPVCQDHLEFWEGVFTGLTHIDAHFLSQT

KQSGENLPYLVAYQATVCARAQAPPPSWDQMWKCLIRLKPTLHGPTPLLY

RLGAVQNEVTLTHPITKYIMTCMSADLEVVTSTWVLVGGVLAALAAYCLS

TGCVVIVGRIVLSGKPAIIPDREVLYREFDEMEECSQHLPYIEQGMMLAE

QFKQKALGLLQTASRQAEVIAPAVQTNWQKLEAFWAKHMWNFISGIQYLA

GLSTLPGNPAIASLMAFTAAVTSPLTTSQTLLFNILGGWVAAQLAAPGAA

TAFVGAGLAGAAIGSVGLGKVLVDILAGYGAGVAGALVAFKIMSGEVPST

EDLVNLLPAILSPGALVVGVVCAAILRRHVGPGEGAVQWMNRLIAFASRG

NHVSPTHYVPESDAAARVTAILSSLTVTQLLRRLHQWISSECTTPCSGSW

LRDIWDWICEVLSDFKTWLKAKLMPQLPGIPFVSCQRGYRGVWRGDGIMH

TRCHCGAEITGHVKNGTMRIVGPRTCRNMWSGTFPINAYTTGPCTPLPAP

NYTFALWRVSAEEYVEIRQVGDFHYVTGMTTDNLKCPCQVPSPEFFTELD

GVRLHRFAPPCKPLLREEVSFRVGLHEYPVGSQLPCEPEPDVAVLTSMLT

DPSHITAEAAGRRLARGSPPSVASSSASQLSAPSLKATCTANHDSPDAEL

IEANLLWRQEMGGNITRVESENKVVILDSFDPLVAEEDEREISVPAEILR

KSRRFAPALPIWARPDYNPPLLETWKKPDYEPPVVHGCPLPPPQSPPVPP

PRKKRTVVLTESTVSTALAELATKSFGSSSTSGITGDNTTTSSEPAPSGC

PPDSDAESYSSMPPLEGEPGDPDLSDGSWSTVSSEADTEDVVCCSMSYSW

TGALVTPCAAEEQKLPINALSNSLLRHHNLVYSTTSRSACQRQKKVTFDR

LQVLDSHYQDVLKEVKAAASKVKANLLSVEEACSLTPPHSAKSKFGYGAK

DVRCHARKAVNHINSVWKDLLEDSVTPIDTTIMAKNEVFCVQPEKGGRKP

ARLIVFPDLGVRVCEKMALYDVVSKLPLAVMGSSYGFQYSPGQRVEFLVQ

AWKSKKTPMGFSYDTRCFDSTVTESDIRTEEAIYQCCDLDPQARVAIKSL

TERLYVGGPLTNSRGENCGYRRCRASGVLTTSCGNTLTCYIKARAACRAA

GLQDCTMLVCGNNLVVICESAGVQEDAASLRAFTEAMTRYSAPPGDPPQP

EYDLELITSCSSNVSVAHDGAGKRVYYLTRDPTTPLARAAWETARHTPVN

SWLGNIIMFAPTLWARMILMTHFFSVLIARDQLEQALDCEIYGACYSIEP

LDLPPIIQRLHGLSAFSLHSYSPGEINRVAACLRKLGVPPLRAWRHRARS

VRARLLSRGGRAAICGKYLFNWAVRTKLKLTPIAAAGQLDLSGWFTAGYS

GGDIYHSVSHARPRWFWFCLLLLAAGVGIYLLPNR.

In some cases, the heterologous polypeptide can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence:

```
                                              (SEQ ID NO: 13)
APITAYAQQTRGLLGCIITSLTGRDKNQVEGEVQIVSTAAQTFLATCING

VCWTVYHGAGTRTIASPKGPVIQMYTNVDQDLVGWPAPQGARSLTPCTCG

SSDLYLVTRHADVIPVRRRGDSRGSLLSPRPISYLKGSAGGPLLCPAGHA

VGIFRAAVCTRGVAKAVDFIPVENLETTMRSPVFTDNSSPPAVPQSFQVA

HLHAPTGSGKSTKVPAAYAAQGYKVLVLNPSVAATLGFGAYMSKAHGIDP

NIRTGVRTITTGSPITYSTYGKFLADGGCSGGAYDIIICDECHSTDATSI

LGIGTVLDQAETAGARLVVLATATPPGSVTVPHPNIEEVALSTTGEIPFY

GKAIPLEVIKGGRHLIFCHSKKKCDELAAKLVALGINAVAYYRGLDVSVI

PTSGDVVVVATDALMTGFTGDFDSVIDCNTCVTQTVDFSLDPTFTIETTT

LPQDAVSRTQRRGRTGRGKPGIYRFVAPGERPSGMFDSSVLCECYDAGCA

WYELTPAETTVRLRAYMNTPGLPVCQDHLEFWEGVFTGLTHIDAHFLSQT

KQSGENLPYLVAYQATVCARAQAPPPSWDQMWKCLIRLKPTLHGPTPLLY

RLGAVQNEVTLTHPITKYIMTCMSADLEVVTSTWVLVGGVLAALAAYCLS

TGCVVIVGRIVLSGKPAIIPDREVLYREFDEMEECSQHLPYIEQGMMLAE

QFKQKALGLLQTASRQAEVIAPAVQTNWQKLEAFWAKHMWNFISGIQYLA

GLSTLPGNPAIASLMAFTAAVTSPLTTSQTLLFNILGGWVAAQLAAPGAA

TAFVGAGLAGAAIGSVGLGKVLVDILAGYGAGVAGALVAFKIMSGEVPST

EDLVNLLPAILSPGALVVGVVCAAILRRHVGPGEGAVQWMNRLIAFASRG

NHVSPTHYVPESDAAARVTAILSSLTVTQLLRRLHQWISSECTTPCSGSW

LRDIWDWICEVLSDFKTWLKAKLMPQLPGIPFVSCQRGYRGVWRGDGIMH

TRCHCGAEITGHVKNGTMRIVGPRTCRNMWSGTFPINAYTTGPCTPLPAP

NYTFALWRVSAEEYVEIRQVGDFHYVTGMTTDNLKCPCQVPSPEFFTELD

GVRLHRFAPPCKPLLREEVSFRVGLHEYPVGSQLPCEPEPDVAVLTSMLT

DPSHITAEAAGRRLARGSPPSVASSSASQLSAPSLKATCTANHDSPDAEL

IEANLLWRQEMGGNITRVESENKVVILDSFDPLVAEEDEREISVPAEILR

KSRRFAPALPIWARPDYNPPLLETWKKPDYEPPVVHGCPLPPPQSPPVPP

PRKKRTVVLTESTVSTALAELATKSFGSSSTSGITGDNTTTSSEPAPSGC

PPDSDAESYSSMPPLEGEPGDPDLSDGSWSTVSSEADTEDVVCCSMSYSW

TGALVTPCAAEEQKLPINALSNSLLRHHNLVYSTTSRSACQRQKKVTFDR

LQVLDSHYQDVLKEVKAAASKVKANLLSVEEACSLTPPHSAKSKFGYGAK

DVRCHARKAVNHINSVWKDLLEDSVTPIDTTIMAKNEVFCVQPEKGGRKP

ARLIVFPDLGVRVCEKMALYDVVSKLPLAVMGSSYGFQYSPGQRVEFLVQ

AWKSKKTPMGFSYDTRCFDSTVTESDIRTEEAIYQCCDLDPQARVAIKSL

TERLYVGGPLTNSRGENCGYRRCRASGVLTTSCGNTLTCYIKARAACRAA

GLQDCTMLVCGNNLVVICESAGVQEDAASLRAFTEAMTRYSAPPGDPPQP

EYDLELITSCSSNVSVAHDGAGKRVYYLTRDPTTPLARAAWETARHTPVN

SWLGNIIMFAPTLWARMILMTHFFSVLIARDQLEQALDCEIYGACYSIEP

                     -continued
LDLPPIIQRLHGLSAFSLHSYSPGEINRVAACLRKLGVPPLRAWRHRARS

VRARLLSRGGRAAICGKYLFNWAVRTKLKLTPIAAAGQLDLSGWFTAGYS

GGDIYHSVSHARPRWFWFCLLLLAAGVGIYLLPNR;
```

and has a length of 1985 amino acids. Such a polytope can include T-cell epitopes designated NS3-1, NS3-2, NS3-3, NS3-4, NS3-5, NS3-6, NS3-7, NS3-8, NS3-9, NS3-10, NS3-11, NS3-12, NS3-13, NS3-14, NS4a-1, NS4b-1, NS4b-2, NS4b-3, NS4b-4, NS4b-5, NS4b-6, NS4b-7, NS4b-8, NS4b-9, NS4b-10, NS5a-1, NS5a-2, NS5b-1, NS5b-2 in FIGS. 13A-13B and FIGS. 15A-15N.

Additional T-Cell Epitopes

As discussed above, an E1/E2 a heterodimeric polypeptide of the present disclosure includes: a) an HCV E1 polypeptide; and b) a variant HCV E2 polypeptide comprising: i) an HCV E2 polypeptide; and ii) a heterologous polypeptide that comprises one or more T-cell epitopes (e.g., one or more T cell epitopes present in an HCV polypeptide other than an HCV E1 polypeptide or an HCV E2 polypeptide). The one or more T-cell epitopes can include one or more T-cell epitopes present in: a) an HCV NS3 polypeptide; b) an HCV NS2 polypeptide; c) an HCV NS4A polypeptide; d) an HCV NS4B polypeptide; e) an HCV NS5A polypeptide; f) an HCV NS5B polypeptide; g) an HCV core polypeptide; or h) an HCV p7 polypeptide. In some cases, the one or more T-cell epitopes are T-cell epitopes present in an HCV NS3 polypeptide. In some cases, the heterologous polypeptide comprises one or more T cell epitopes present in: a) cholera toxin; and/or b) tetanus toxin; and/or c) diphtheria toxin.

Thus, in some cases, a variant HCV polypeptide of an E1/E2 heterodimer of the present disclosure includes: a) an HCV E2 polypeptide; and b) a heterologous polypeptide that comprises one or more T-cell epitopes, where the one or more T-cell epitopes are T-cell epitopes present in: i) one or more of an HCV NS3 polypeptide, an HCV NS2 polypeptide, an HCV NS4A polypeptide, an HCV NS4B polypeptide, an HCV NS5A polypeptide, an HCV NS5B polypeptide, an HCV core polypeptide, and an HCV p7 polypeptide; and ii) one or more of cholera toxin or toxoid, tetanus toxin or toxoid, diphtheria toxin or toxoid, and a meningococcal outer membrane protein.

In some cases, a heterologous polypeptide can comprise a tetanus toxin T-cell epitope. In some cases, a suitable heterologous polypeptide comprising a tetanus toxin T-cell epitope comprises the amino acid sequence: ILMQYIKANSKFIGI (SEQ ID NO:16); and has a length of from 15 amino acids to 20 amino acids. In some cases, a suitable heterologous polypeptide comprising a tetanus toxin T-cell epitope comprises the amino acid sequence: VNNESSE (SEQ ID NO:17). In some cases, a suitable heterologous polypeptide comprising a tetanus toxin T-cell epitope comprises the amino acid sequence: PGINGKAIHLVNNESSE (SEQ ID NO:18). In some cases, a suitable heterologous polypeptide comprising a tetanus toxin T-cell epitope comprises the amino acid sequence: PNRDIL (SEQ ID NO:19). In some cases, a suitable heterologous polypeptide comprising a tetanus toxin T-cell epitope comprises the amino acid sequence: FIGITEL (SEQ ID NO:20). In some cases, a suitable tetanus toxin T-cell epitope comprises the amino acid sequence: SYFPSV (SEQ ID NO:21). In some cases, a suitable heterologous polypeptide comprising a tetanus toxin T-cell epitope comprises the amino acid sequence: NSVDDALINSTKIYSYFPSV (SEQ ID NO:22). In some cases, a suitable heterologous polypeptide comprising a tetanus toxin T-cell epitope comprises the amino acid sequence: IDKISDVSTIVPYIGPALNI (SEQ ID NO:23).

In some cases, a heterologous polypeptide can comprise a diphtheria toxin T-cell epitope In some cases, a suitable heterologous polypeptide comprising a diphtheria toxin T-cell epitope comprises the amino acid sequence: QSIALSSLMVAQAIP (SEQ ID NO:24); and has a length of from 15 amino acids to 20 amino acids. In some cases, a suitable heterologous polypeptide comprising a diphtheria toxin T-cell epitope comprises the amino acid sequence:

PVFAGANYAAWAVNVAQVI (SEQ ID NO:25). In some cases, a suitable heterologous polypeptide comprising a diphtheria toxin T-cell epitope comprises the amino acid sequence:

VHHNTEEIVAQSIALSSLMV (SEQ ID NO:26). In some cases, a suitable heterologous polypeptide comprising a diphtheria toxin T-cell epitope comprises the amino acid sequence:

QSIALSSLMVAQAIPLVGEL (SEQ ID NO:66). In some cases, a suitable heterologous polypeptide comprising a diphtheria toxin T-cell epitope comprises the amino acid sequence:

VDIGFAAYNFVESIINLFQV (SEQ ID NO:67). In some cases, a suitable heterologous polypeptide comprising a diphtheria toxin T-cell epitope comprises the amino acid sequence:

QGESGHDIKITAENTPLPIA (SEQ ID NO:68). In some cases, a suitable heterologous polypeptide comprising a diphtheria toxin T-cell epitope comprises the amino acid sequence:

GVLLPTIPGKLDVNKSKTHI (SEQ ID NO:69).

In some cases, a heterologous polypeptide can comprise a tetanus toxin T-cell epitope and a diphtheria toxin T-cell epitope. In some of these cases, the heterologous polypeptide can comprise the amino acid sequence: IMQYIKANSKFIGIQSIALSSLMVAQ (SEQ ID NO:28); and can have a length of from 26 amino acids to 30 amino acids.

Additional Polypeptides

In any of the above-described embodiments, the variant E2 polypeptide can include one or more additional polypeptides. For example, in some cases, the variant E2 polypeptide includes an Ig Fc polypeptide at the C-terminus of variant E2 polypeptide. As another example, in some cases, the variant E2 polypeptide includes an Ig Fc polypeptide at the N-terminus of variant E2 polypeptide. Ig Fc polypeptides are known in the art, and are described elsewhere herein.

III. Variant E1 Polypeptides

The present disclosure provides a variant HCV E1 polypeptide that comprises: a) an HCV E1 polypeptide; and b) a heterologous polypeptide that comprises one or more T-cell epitopes (e.g., one or more T cell epitopes present in an HCV polypeptide other than an HCV E1 polypeptide or an HCV E2 polypeptide). The heterologous polypeptide is also referred to as a "polytope." A variant E1 polypeptide of the present disclosure is useful for including in an E1/E2 heterodimer of the present disclosure.

The one or more T-cell epitopes can include one or more T-cell epitopes present in: a) an HCV NS3 polypeptide; b) an HCV NS2 polypeptide; c) an HCV NS4A polypeptide; d) an HCV NS4B polypeptide; e) an HCV NS5A polypeptide; f) an HCV NS5B polypeptide; g) an HCV core polypeptide; or h) an HCV p7 polypeptide. In some cases, the one or more T-cell epitopes are T-cell epitopes present in an HCV NS3 polypeptide. In some cases, the heterologous polypeptide further comprises one or more T cell epitopes present in: a) cholera toxin or toxoid; and/or b) tetanus toxin or toxoid; and/or c) diphtheria toxin or toxoid; and/or d) a meningococcal outer membrane protein. In some cases, a variant HCV E1 polypeptide of the present disclosure includes: a) an HCV E1 polypeptide; and b) a heterologous polypeptide that comprises one or more T-cell epitopes, where the one or more T-cell epitopes are T-cell epitopes present in: i) one or more of an HCV NS3 polypeptide, an HCV NS2 polypeptide, an HCV NS4A polypeptide, an HCV NS4B polypeptide, an HCV NS5A polypeptide, an HCV NS5B polypeptide, an HCV core polypeptide, and an HCV p7 polypeptide; and ii) one or more of cholera toxin or toxoid, tetanus toxin or toxoid, diphtheria toxin or toxoid, and a meningococcal outer membrane protein.

In some cases, the variant HCV E1 polypeptide comprises, in order from N-terminus to C-terminus: i) an HCV E1 polypeptide; and ii) a heterologous polypeptide comprising one or more T cell epitopes. In some cases, the variant HCV E1 polypeptide comprises, in order from N-terminus to C-terminus: i) a heterologous polypeptide comprising one or more T cell epitopes; and ii) an HCV E1 polypeptide.

E1

An HCV E1 polypeptide suitable for inclusion in a variant E1 polypeptide of the present disclosure can have a length of from about 150 amino acids (aa) to about 175 aa, from about 175 aa to about 195 aa, from about 131 aa to about 175 aa, or from about 175 aa to about 193 aa. The E1 polypeptide can be a full-length HCV E1 polypeptide. The E1 polypeptide can be an HCV E1 ectodomain polypeptide.

In FIGS. 1A-1C, the amino acid sequence of E1 is amino acid 192 to amino acid 383. In FIGS. 2A-2C, the amino acid sequence of E1 is amino acid 192 to amino acid 383. In FIGS. 3A-3C, the amino acid sequence of E1 is amino acid 192 to amino acid 384. In FIGS. 4A-4B, the amino acid sequence of E1 is amino acid 192 to amino acid 383. Amino acids at around 170 through approximately 191 serve as a signal sequence for E1. As used herein, "E1 polypeptide" includes a precursor E1 protein, including the signal sequence; includes a mature E1 polypeptide which lacks this sequence; and includes an E1 polypeptide with a heterologous signal sequence. An E1 polypeptide can include a C-terminal membrane anchor sequence which occurs at approximately amino acid positions 360-383 (see, e.g., WO 96/04301). In some cases, a suitable E1 polypeptide lacks a C-terminal portion that includes a transmembrane region. For example, in some cases, a suitable E1 polypeptide lacks the C-terminal portion from amino acid 330 to amino acid 384, or from amino acid 360 to amino acid 384. E1 polypeptides can be an E1 polypeptide of any genotype, subtype or isolate of HCV. E1 polypeptides of genotype 1 and E1 polypeptides of genotype 3 are included in an E1/E2 heterodimer of the present disclosure.

An E1 polypeptide suitable for inclusion in a variant E1 polypeptide of the present disclosure can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to an amino acid sequence of an E1 polypeptide depicted in FIGS. 1A-1C, FIGS. 2A-2C, FIGS. 3A-3C, or FIGS. 4A-4B.

An E1 polypeptide suitable for inclusion in a variant E1 polypeptide of the present disclosure can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to an amino acid sequence of an E1 polypeptide depicted in FIGS. 1A-1C. For example, an E1 polypeptide of genotype 1A can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 192-383 of an amino acid sequence identified as 1A and depicted in FIGS. 1A-1C. For example, an E1 polypeptide of genotype 1B can comprise an amino acid sequence having having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 192-383 of an amino acid sequence identified as 1B and depicted in FIGS. 1A-1C. For example, an E1 polypeptide of genotype 1C can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 192-383 of an amino acid sequence identified as 1C and depicted in FIGS. 1A-1C.

An E1 polypeptide suitable for inclusion in a variant E1 polypeptide of the present disclosure can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to an amino acid sequence of an E1 polypeptide depicted in FIGS. 2A-2C. For example, an E1 polypeptide of genotype 2A can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 192-383 of an amino acid sequence identified as 2A and depicted in FIGS. 2A-2C. For example, an E1 polypeptide of genotype 2B can comprise an amino acid sequence having having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 192-383 of an amino acid sequence identified as 2B and depicted in FIGS. 2A-2C.

An E1 polypeptide suitable for inclusion in a variant E1 polypeptide of the present disclosure can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the consensus E1 polypeptide amino acid sequence depicted in FIGS. 3A-3C.

An E1 polypeptide suitable for inclusion in a variant E1 polypeptide of the present disclosure can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to an amino acid sequence of an E1 polypeptide depicted in FIGS. 4A-4B. For example, an E1 polypeptide of genotype 7A can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 192-383 of the amino acid sequence depicted in FIGS. 4A-4B.

Heterologous Polypeptide

The heterologous polypeptide present in an E1 variant polypeptide of the present disclosure includes one or more T-cell epitopes.

In some cases, the heterologous polypeptide comprises 1, 2, 3, 4, 5, 6, 7, 8, 9, or 10, or more than 10 (e.g., from 10 to 15, from 15 to 20, from 20 to 25, or from 25 to 30, or more than 30), T cell epitopes. T-cell epitopes are epitopes that, when presented with a major histocompatibility complex (MHC) (e.g., a human leukocyte antigen (HLA)) Class I or MHC Class II molecule, are recognized and bound by a T-cell receptor (TCR) present on a T cell surface. T-cell epitopes include epitopes recognized by cytotoxic T cells (e.g., $CD8^+$ T cells), and epitopes recognized by helper T cells (e.g., $CD4^+$ T cells).

The one or more T-cell epitopes can include one or more T-cell epitopes present in: a) an HCV NS3 polypeptide; b) an HCV NS2 polypeptide; c) an HCV NS4A polypeptide; d) an HCV NS4B polypeptide; e) an HCV NS5A polypeptide; f) an HCV NS5B polypeptide; g) an HCV core polypeptide; or h) an HCV p7 polypeptide. In some cases, the one or more T-cell epitopes are T-cell epitopes present in an HCV NS3 polypeptide. In some cases, the heterologous polypeptide further comprises one or more T cell epitopes present in: a) cholera toxin or toxoid; and/or b) tetanus toxin or toxoid; and/or c) diphtheria toxin or toxoid; and/or d) a meningococcal outer membrane protein. Other examples of strong T helper epitopes are diphtheria toxoid, tetanus toxoid, meningococcal outer membrane protein, or mutant diphtheria protein CRM197 (see, e.g.: http://www(dot)medscape(dot)com/viewarticle/431127).

In some cases, the heterologous polypeptide comprises a single T-cell epitope. In some cases, the heterologous polypeptide comprises a single HCV-NS3 T-cell epitope. In some cases, the heterologous polypeptide comprises 2 or more T-cell epitopes. In some cases, the heterologous polypeptide comprises 2 or more HCV-NS3 T-cell epitopes. In some cases, the heterologous polypeptide comprises 3 or more HCV-NS3 T-cell epitopes. In some cases, the heterologous polypeptide comprises 4 or more HCV-NS3 T-cell epitopes. In some cases, the heterologous polypeptide comprises a single HCV-NS3 $CD4^+$ T-cell epitope. In some cases, the heterologous polypeptide comprises 2 or more HCV-NS3

$CD4^+$ T-cell epitopes. In some cases, the heterologous polypeptide comprises one or more HCV $CD8^+$ T cell epitopes. In some cases, the heterologous polypeptide comprises a single HCV-NS3 $CD8^+$ T-cell epitope. In some cases, the heterologous polypeptide comprises 2 or more HCV-NS3 $CD8^+$ T-cell epitopes. In some cases, the heterologous polypeptide comprises at least one HCV $CD4^+$ T cell epitope and at least one HCV $CD8^+$ T cell epitope. In some cases, the heterologous polypeptide comprises at least one HCV-NS3 $CD4^+$ T cell epitope and at least one HCV-NS3 $CD8^+$ T cell epitope. In some cases, heterologous polypeptide comprises 2 or more HCV-NS3 $CD4^+$ T-cell epitopes and 2 or more HCV-NS3 $CD8^+$ T-cell epitopes. In some cases, the heterologous polypeptide comprises 2, 3, 4, or 5 HCV-NS3 $CD4^+$ T-cell epitopes and 2, 3, 4, or 5 HCV-NS3 $CD8^+$ T-cell epitopes.

In some cases, the heterologous polypeptide comprises a single T-cell epitope. In some cases, the heterologous polypeptide comprises a single HCV-NS2 T-cell epitope. In some cases, the heterologous polypeptide comprises 2 or more T-cell epitopes. In some cases, the heterologous polypeptide comprises 2 or more HCV-NS2 T-cell epitopes. In some cases, the heterologous polypeptide comprises 3 or more HCV-NS2 T-cell epitopes. In some cases, the heterologous polypeptide comprises 4 or more HCV-NS2 T-cell epitopes. In some cases, the heterologous polypeptide comprises a single HCV-NS2 $CD4^+$ T-cell epitope. In some cases, the heterologous polypeptide comprises 2 or more HCV-NS2 $CD4^+$ T-cell epitopes. In some cases, the heterologous polypeptide comprises one or more HCV $CD8^+$ T cell epitopes. In some cases, the heterologous polypeptide comprises a single HCV-NS2 $CD8^+$ T-cell epitope. In some cases, the heterologous polypeptide comprises 2 or more HCV-NS2 $CD8^+$ T-cell epitopes. In some cases, the heterologous polypeptide comprises at least one HCV $CD4^+$ T cell epitope and at least one HCV $CD8^+$ T cell epitope. In some cases, the heterologous polypeptide comprises at least one HCV-NS2 $CD4^+$ T cell epitope and at least one HCV-NS2 $CD8^+$ T cell epitope. In some cases, heterologous polypeptide comprises 2 or more HCV-NS2 $CD4^+$ T-cell epitopes and 2 or more HCV-NS2 $CD8^+$ T-cell epitopes. In some cases, the heterologous polypeptide comprises 2, 3, 4, or 5 HCV-NS2 $CD4^+$ T-cell epitopes and 2, 3, 4, or 5 HCV-NS2 $CD8^+$ T-cell epitopes.

In some cases, the heterologous polypeptide comprises a single T-cell epitope. In some cases, the heterologous polypeptide comprises a single HCV-NS4A T-cell epitope. In some cases, the heterologous polypeptide comprises 2 or more T-cell epitopes. In some cases, the heterologous polypeptide comprises 2 or more HCV-NS4A T-cell epitopes. In some cases, the heterologous polypeptide comprises 3 or more HCV-NS4A T-cell epitopes. In some cases, the heterologous polypeptide comprises 4 or more HCV-NS4A T-cell epitopes. In some cases, the heterologous polypeptide comprises a single HCV-NS4A $CD4^+$ T-cell epitope. In some cases, the heterologous polypeptide comprises 2 or more HCV-NS4A $CD4^+$ T-cell epitopes. In some cases, the heterologous polypeptide comprises one or more HCV $CD8^+$ T cell epitopes. In some cases, the heterologous polypeptide comprises a single HCV-NS4A $CD8^+$ T-cell epitope. In some cases, the heterologous polypeptide comprises 2 or more HCV-NS4A $CD8^+$ T-cell epitopes. In some cases, the heterologous polypeptide comprises at least one HCV $CD4^+$ T cell epitope and at least one HCV $CD8^+$ T cell epitope. In some cases, the heterologous polypeptide comprises at least one HCV-NS4A $CD4^+$ T cell epitope and at least one HCV-NS4A $CD8^+$ T cell epitope. In some cases, heterologous polypeptide comprises 2 or more HCV-NS4A $CD4^+$ T-cell epitopes and 2 or more HCV-NS4A $CD8^+$ T-cell epitopes. In some cases, the heterologous polypeptide comprises 2, 3, 4, or 5 HCV-NS4A $CD4^+$ T-cell epitopes and 2, 3, 4, or 5 HCV-NS4A $CD8^+$ T-cell epitopes.

In some cases, the heterologous polypeptide comprises a single T-cell epitope. In some cases, the heterologous polypeptide comprises a single HCV-NS5A T-cell epitope. In some cases, the heterologous polypeptide comprises 2 or more T-cell epitopes. In some cases, the heterologous polypeptide comprises 2 or more HCV-NS5A T-cell epitopes. In some cases, the heterologous polypeptide comprises 3 or more HCV-NS5A T-cell epitopes. In some cases, the heterologous polypeptide comprises 4 or more HCV-NS5A T-cell epitopes. In some cases, the heterologous polypeptide comprises a single HCV-NS5A $CD4^+$ T-cell epitope. In some cases, the heterologous polypeptide comprises 2 or more HCV-NS5A $CD4^+$ T-cell epitopes. In some cases, the heterologous polypeptide comprises one or more HCV $CD8^+$ T cell epitopes. In some cases, the heterologous polypeptide comprises a single HCV-NS5A $CD8^+$ T-cell epitope. In some cases, the heterologous polypeptide comprises 2 or more HCV-NS5A $CD8^+$ T-cell epitopes. In some cases, the heterologous polypeptide comprises at least one HCV $CD4^+$ T cell epitope and at least one HCV $CD8^+$ T cell epitope. In some cases, the heterologous polypeptide comprises at least one HCV-NS5A $CD4^+$ T cell epitope and at least one HCV-NS5A $CD8^+$ T cell epitope. In some cases, heterologous polypeptide comprises 2 or more HCV-NS5A $CD4^+$ T-cell epitopes and 2 or more HCV-NS5A $CD8^+$ T-cell epitopes. In some cases, the heterologous polypeptide comprises 2, 3, 4, or 5 HCV-NS5A $CD4^+$ T-cell epitopes and 2, 3, 4, or 5 HCV-NS5A $CD8^+$ T-cell epitopes.

In some cases, the heterologous polypeptide comprises a single T-cell epitope. In some cases, the heterologous polypeptide comprises a single HCV-NS5B T-cell epitope. In some cases, the heterologous polypeptide comprises 2 or more T-cell epitopes. In some cases, the heterologous polypeptide comprises 2 or more HCV-NS5B T-cell epitopes. In some cases, the heterologous polypeptide comprises 3 or more HCV-NS5B T-cell epitopes. In some cases, the heterologous polypeptide comprises 4 or more HCV-NS5B T-cell epitopes. In some cases, the heterologous polypeptide comprises a single HCV-NS5B $CD4^+$ T-cell epitope. In some cases, the heterologous polypeptide comprises 2 or more HCV-NS5B $CD4^+$ T-cell epitopes. In some cases, the heterologous polypeptide comprises one or more HCV $CD8^+$ T cell epitopes. In some cases, the heterologous polypeptide comprises a single HCV-NS5B $CD8^+$ T-cell epitope. In some cases, the heterologous polypeptide comprises 2 or more HCV-NS5B $CD8^+$ T-cell epitopes. In some cases, the heterologous polypeptide comprises at least one HCV $CD4^+$ T cell epitope and at least one HCV $CD8^+$ T cell epitope. In some cases, the heterologous polypeptide comprises at least one HCV-NS5B $CD4^+$ T cell epitope and at least one HCV-NS5B $CD8^+$ T cell epitope. In some cases, heterologous polypeptide comprises 2 or more HCV-NS5B $CD4^+$ T-cell epitopes and 2 or more HCV-NS5B $CD8^+$ T-cell epitopes. In some cases, the heterologous polypeptide comprises 2, 3, 4, or 5 HCV-NS5B $CD4^+$ T-cell epitopes and 2, 3, 4, or 5 HCV-NS5B $CD8^+$ T-cell epitopes.

In some cases, the heterologous polypeptide comprises a single T-cell epitope. In some cases, the heterologous polypeptide comprises a single HCV-core T-cell epitope. In some cases, the heterologous polypeptide comprises 2 or more T-cell epitopes. In some cases, the heterologous polypeptide comprises 2 or more HCV-core T-cell epitopes. In some cases, the heterologous polypeptide comprises 3 or more HCV-core T-cell epitopes. In some cases, the heterologous polypeptide comprises 4 or more HCV-core T-cell epitopes. In some cases, the heterologous polypeptide comprises a single HCV-core $CD4^+$ T-cell epitope. In some cases, the heterologous polypeptide comprises 2 or more HCV-core $CD4^+$ T-cell epitopes. In some cases, the heterologous polypeptide comprises one or more HCV $CD8^+$ T cell epitopes. In some cases, the heterologous polypeptide comprises a single HCV-core $CD8^+$ T-cell epitope. In some cases, the heterologous polypeptide comprises 2 or more HCV-core $CD8^+$ T-cell epitopes. In some cases, the heterologous polypeptide comprises at least one HCV $CD4^+$ T cell epitope and at least one HCV $CD8^+$ T cell epitope. In some cases, the heterologous polypeptide comprises at least one HCV-core $CD4^+$ T cell epitope and at least one HCV-core $CD8^+$ T cell epitope. In some cases, heterologous polypeptide comprises 2 or more HCV-core $CD4^+$ T-cell epitopes and 2 or more HCV-core $CD8^+$ T-cell epitopes. In some cases, the heterologous polypeptide comprises 2, 3, 4, or 5 HCV-core $CD4^+$ T-cell epitopes and 2, 3, 4, or 5 HCV-core $CD8^+$ T-cell epitopes.

In some cases, the heterologous polypeptide comprises a single T-cell epitope. In some cases, the heterologous polypeptide comprises a single HCV-p7 T-cell epitope. In some cases, the heterologous polypeptide comprises 2 or more T-cell epitopes. In some cases, the heterologous polypeptide comprises 2 or more HCV-p7 T-cell epitopes. In some cases, the heterologous polypeptide comprises 3 or more HCV-p7 T-cell epitopes. In some cases, the heterologous polypeptide comprises 4 or more HCV-p7 T-cell epitopes. In some cases, the heterologous polypeptide comprises a single HCV-p7 $CD4^+$ T-cell epitope. In some cases, the heterologous polypeptide comprises 2 or more HCV-core $CD4^+$ T-cell epitopes. In some cases, the heterologous polypeptide comprises one or more HCV $CD8^+$ T cell epitopes. In some cases, the heterologous polypeptide comprises a single HCV-p7 $CD8^+$ T-cell epitope. In some cases, the heterologous polypeptide comprises 2 or more HCV-p7 $CD8^+$ T-cell epitopes. In some cases, the heterologous polypeptide comprises at least one HCV $CD4^+$ T cell epitope and at least one HCV $CD8^+$ T cell epitope. In some cases, the heterologous polypeptide comprises at least one HCV-p7 $CD4^+$ T cell epitope and at least one HCV-p7 $CD8^+$ T cell epitope. In some cases, heterologous polypeptide comprises 2 or more HCV-p7 $CD4^+$ T-cell epitopes and 2 or more HCV-p7 $CD8^+$ T-cell epitopes. In some cases, the heterologous polypeptide comprises 2, 3, 4, or 5 HCV-p7 $CD4^+$ T-cell epitopes and 2, 3, 4, or 5 HCV-p7 $CD8^+$ T-cell epitopes.

In some cases, the heterologous polypeptide comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, or 63, of the T-cell epitopes set out in FIGS. 13A-13B. In some cases, the heterologous polypeptide comprises from 1 to 3, from 3 to 5, from 5 to 10, from 10 to 15, from 15 to 20, from 20 to 25, or from 25 to 30 of the T-cell epitopes set out in FIGS. 13A-13B. For example, in some cases, the heterologous polypeptide comprises the T-cell epitopes designated NS3-3, NS3-4, and NS3-11 in FIGS. 13A-13B and FIGS. 15A-15N. As another example, in some cases, the heterologous polypeptide comprises the T-cell epitopes designated NS2-1, NS2-2, NS2-3, NS2-7, and NS2-8 in FIGS. 13A-13B and FIGS. 15A-15N. As another example, in some cases, the heterologous polypeptide comprises the T-cell epitopes designated NS3-3, NS3-4, NS3-5, and NS3-11 in FIGS. 13A-13B and FIGS. 15A-15N. As another example, in some cases, the heterologous polypeptide comprises the T-cell epitopes designated NS3-3, NS3-4, NS3-5, NS3-6, NS3-7, NS3-11, NS3-12, and NS3-13 in FIGS. 13A-13B and FIGS. 15A-15N. As another example, in some cases, the heterologous polypeptide comprises the T-cell epitopes designated NS3-3, NS3-4, NS3-5, NS3-6, NS3-7, NS3-10, NS3-11, NS3-12, and NS3-13 in FIGS. 13A-13B and FIGS. 15A-15N. As another example, in some cases, the heterologous polypeptide comprises the T-cell epitopes designated Core-1, Core-2, Core-3, Core-4, Core-5, Core-6, Core-7, Core-8, Core-9, Core-10, Core-11, Core-12, Core-13, Core-14, Core-16, Core-17, Core-18, Core-19, Core-20, Core-21, and Core-22 in FIGS. 13A-13B and FIGS. 15A-15N. As another example, in some cases, the heterologous polypeptide comprises the T-cell epitopes designated NS3-1, NS3-2, NS3-3, NS3-4, NS3-5, NS3-6, NS3-7, NS3-9, NS3-10, NS3-11, NS3-12, and NS3-13 in FIGS. 13A-13B and FIGS. 15A-15N. As another example, in some cases, the heterologous polypeptide comprises the T-cell epitopes designated NS2-1, NS2-2, NS2-3, NS2-4, NS2-5, NS2-6, NS2-7, NS2-8, NS3-1, NS3-2, NS3-3, NS3-4, NS3-5, NS3-6, NS3-7, NS3-9, NS3-10, NS3-11, NS3-12, and NS3-13 in FIGS. 13A-13B and FIGS. 15A-15N. As another example, in some cases, the heterologous polypeptide comprises the T-cell epitopes designated NS3-1, NS3-2, NS3-3, NS3-4, NS3-5, NS3-6, NS3-7, NS3-8, NS3-9, NS3-10, NS3-11, NS3-12, NS3-13, NS3-14, NS4a-1, NS4b-1, NS4b-2, NS4b-3, NS4b-4, NS4b-5, NS4b-6, NS4b-7, NS4b-8, NS4b-9, and NS4b-10 in FIGS. 13A-13B and FIGS. 15A-15N. As another example, in some cases, the heterologous polypeptide comprises the T-cell epitopes designated NS3-1, NS3-2, NS3-3, NS3-4, NS3-5, NS3-6, NS3-7, NS3-8, NS3-9, NS3-10, NS3-11, NS3-12, NS3-13, NS3-14, NS4a-1, NS4b-1, NS4b-2, NS4b-3, NS4b-4, NS4b-5, NS4b-6, NS4b-7, NS4b-8, NS4b-9, NS4b-10, NS5a-1, NS5a-2, NS5b-1, and NS5b-2 in FIGS. 13A-13B and FIGS. 15A-15N. In some cases, the T-cell epitopes are contiguous. In some cases, any two T-cell epitopes are separated by linkers (e.g., a linker having a length of from 1 amino acid to about 50 amino acids, e.g., from 1 amino acid to 5 amino acids (aa), from 5 aa to 10 aa, from 10 aa to 15 aa, from 15 aa to 20 aa, from 20 aa to 25 aa, from 25 aa to 30 aa, from 30 aa to 40 aa, or from 40 aa to 50 aa).

In some cases, the heterologous polypeptide comprises at least one HCV $CD4^+$ T cell epitope and at least one HCV $CD8^+$ T cell epitope, where epitopes are conserved among HCV genotypes 1 and 2. In some cases, the heterologous polypeptide comprises at least one HCV $CD4^+$ T cell epitope and at least one HCV $CD8^+$ T cell epitope, where epitopes are conserved among HCV genotypes 1 and 3. In some cases, the heterologous polypeptide comprises at least one HCV $CD4^+$ T cell epitope and at least one HCV $CD8^+$ T cell epitope, where epitopes are conserved among HCV genotypes 1, 2, and 3. In some cases, the heterologous polypeptide comprises at least one HCV $CD4^+$ T cell epitope and at least one HCV $CD8^+$ T cell epitope, where epitopes are conserved among HCV genotypes 1, 2, 3, and 7. In some cases, the heterologous polypeptide comprises at least one HCV $CD4^+$ T cell epitope and at least one HCV $CD8^+$ T cell epitope, where epitopes are conserved among HCV genotypes 1-7.

The heterologous polypeptide can have a length of from about 10 amino acids to about 2000 amino acids; e.g., the heterologous polypeptide can have a length of from 10 amino acids (aa) to 15 aa, from 15 aa to 20 aa, from 20 aa to 25 aa, from 25 aa to 50 aa, from 50 an to 75 aa, from 75 an to 100 aa, from 100 an to 150 aa, from 150 aa to 200 aa, from 200 aa to 250 aa, from 250 aa to 300 aa, from 300 an to 350 aa, from 350 aa to 400 aa, from 450 aa to 500 aa, from 500 an to 550 aa, from 550 an to 600 aa, from 600 an to 650 aa, from 650 aa to 700 aa, from 700 aa to 750 aa, or from 750 aa to 800 aa. The heterologous polypeptide can have a length of from about 25 amino acids to about 2000 amino acids, e.g., from about 25 amino acids (aa) to 50 aa, from 50 an to 75 aa, from 75 an to 100 aa, from 100 an to 150 aa, from 150 an to 200 aa, from 200 aa to 250 aa, from 250 an to 300 aa, from 300 aa to 350 aa, from 350 an to 400 aa, from 400 an to 500 aa, from 500 aa to 600 aa, from 600 an to 700 aa, from 700 an to 800 aa, from 800 aa to 900 aa, from 900 an to 1000 aa, from 1000 aa to 1100 aa, from 1100 aa to 1200 aa, from 1200 an to 1300 aa, from 1300 aa to 1400 aa, from 1400 aa to 1500 aa, from 1500 aa to 1600 aa, from 1600 aa to 1700 aa, from 1700 aa to 1800 aa, from 1800 aa to 1900 aa, or from 1900 aa to 2000 aa. The heterologous polypeptide can have a length of from about 25 amino acids to about 3000 amino acids, e.g., from about 25 amino acids (aa) to 50 aa, from 50 aa to 75 aa, from 75 aa to 100 aa, from 100 aa to 150 aa, from 150 aa to 200 aa, from 200 aa to 250 aa, from 250 aa to 300 aa, from 300 aa to 350 aa, from 350 an to 400 aa, from 400 an to 500 aa, from 500 an to 600 aa, from 600 an to 700 aa, from 700 an to 800 aa, from 800 an to 900 aa, from 900 aa to 1000 aa, from 1000 aa to 1100 aa, from 1100 an to 1200 aa, from 1200 aa to 1300 aa, from 1300 an to 1400 aa, from 1400 aa to 1500 aa, from 1500 an to 1600 aa, from 1600 aa to 1700 aa, from 1700 an to 1800 aa, from 1800 an to 1900 aa, from 1900 aa to 2000 aa, from 2000 an to 2250 aa, from 2250 an to 2500 aa, from 2500 an to 2750 aa, or from 2750 an to 3000 aa.

The heterologous polypeptide can have a length of from about 25 amino acids to about 800 amino acids, e.g., from about 25 amino acids (aa) to 50 aa, from 50 an to 75 aa, from 75 an to 100 aa, from 100 an to 150 aa, from 150 an to 200 aa, from 200 an to 250 aa, from 250 aa to 300 aa, from 300 aa to 350 aa, from 350 aa to 400 aa, from 450 aa to 500 aa, from 500 an to 550 aa, from 550 aa to 600 aa, from 600 an to 650 aa, from 650 an to 700 aa, from 700 aa to 750 aa, or from 750 an to 800 aa. The heterologous polypeptide can have a length of from about 25 amino acids to about 400 amino acids, e.g., from about 25 amino acids (aa) to 50 aa, from 50 an to 75 aa, from 75 an to 100 aa, from 100 an to 150 aa, from 150 an to 200 aa, from 200 aa to 250 aa, from 250 aa to 300 aa, from 300 an to 350 aa, or from 350 aa to 400 aa. The heterologous polypeptide can have a length of 25 amino acids (aa), 26 aa, 27 aa, 28 aa, 29 aa, 30 aa, 31 aa, 32 aa, 33 aa, 34 aa, 35 aa, 36 aa, 37 aa, 38 aa, 39 aa, 40 aa, 41 aa, 42 aa, 43 aa, 44 aa, 45 aa, 46 aa, 47 aa, 48 aa, 49 aa, or 50 aa. The heterologous polypeptide can have a length of from about 100 amino acids (aa) to 800 aa, e.g., from 100 aa to 150 aa, from 150 aa to 200 aa, from 200 aa to 250 aa, from 250 an to 300 aa, from 300 aa to 350 aa, from 350 an to 400 aa, from 450 an to 500 aa, from 500 aa to 550 aa, from 550 an to 600 aa, from 600 an to 650 aa, from 650 aa to 700 aa, from 700 an to 750 aa, or from 750 aa to 800 aa. The heterologous polypeptide can have a length of from 25 an to 30 aa. The heterologous polypeptide can have a length of from 30 an to 40 aa. The heterologous polypeptide can have a length of from 40 an to 50 aa. The heterologous polypeptide can have a length of from 50 aa to 60 aa (e.g., 50 aa, 51 aa, 52, aa, 53 aa, 54 aa, 55 aa, 56 aa, 57 aa, 58 aa, 59 aa, or 60 aa). The heterologous polypeptide can have a length of from 60 aa to 70 aa. The heterologous polypeptide can have a length of from 65 an to 75 aa (e.g., 65, 66, 67, 68, 69, 70, 71, 72, 7, 74, or 75 aa). The heterologous polypeptide can have a length of 70 aa. The heterologous polypeptide can have a length of from 70 an to 80 aa. The heterologous polypeptide can have a length of from 80 aa to 90 aa. The heterologous polypeptide can have a length of from 90 an to 100 aa. The heterologous polypeptide can have a length of from 100 an to 105 aa (e.g., 100, 101, 102, 103, 104, 105, 106, 107, 108, 109, or 110 aa). The heterologous polypeptide can have a length of 100 aa. The heterologous polypeptide can have a length of from 10 amino acids (aa) to 50 aa; e.g., from 10 an to 15 aa, from 15 an to 20 aa, from 20 an to 25 aa, from 25 an to 30 aa, from 30 an to 35 aa, from 35 aa to 40 aa, from 40 an to 45 aa, or from 45 an to 50 aa. The heterologous polypeptide can have a length of from 10 amino acids (aa) to 20 aa, e.g., 10, 11, 12, 13, 14, 15, 16, 17, 18, 19, or 20 aa.

HCV NS3 T-Cell Epitopes

In some cases, the heterologous polypeptide present in an E2 variant polypeptide of an E1/E2 heterodimer of the present disclosure includes one or more T-cell epitopes present in an HCV NS3 polypeptide. Examples of T-cell epitopes present in NS3 polypeptides are depicted in FIGS. 15A-15N, FIG. 13B, and FIGS. 14A-14B.

The heterologous polypeptide can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence:

AIPLEVIKGGRHLIFCHSKKKCDELAAKL (SEQ ID NO:1). In some cases, the heterologous polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence:

AIPLEVIKGGRHLIFCHSKKKCDELAAKL (SEQ ID NO:1); and has a length of from 25 aa to 35 aa (e.g., 25 aa, 26 aa, 27 aa, 28 aa, 29 aa, 30 aa, 31 aa, 32 aa, 33 aa, 34 aa, or 35 aa). In some cases, the heterologous polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence:

AIPLEVIKGGRHLIFCHSKKKCDELAAKL (SEQ ID NO:1); and has a length of 29 amino acids. Such a polytope can include NS3 T-cell epitopes designated NS3-3, NS3-4, and NS3-11 in FIG. 13B and FIGS. 15A-15N.

The heterologous polypeptide can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence:

AIPLEVIKGGRHLIFCHSKKKCDELAAKLVALGI-NAVAYYRGLDVSVIPTSG (SEQ ID NO:2). In some cases, the heterologous polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence: AIPLEV-IKGGRHLIFCHSKKKCDELAAKLVALGI-NAVAYYRGLDVSVIPTSG (SEQ ID NO:2); and has a length of from 45 amino acids to 60 amino acids (e.g., 45 aa, 46 aa, 47 aa, 48 aa, 49 aa, 50 aa, 51 aa, 52 aa, 53 aa, 54 aa, 55 aa, 56 aa, 57 aa, 58 aa, 59 aa, or 60 aa). In some cases, the heterologous polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence:

AIPLEVIKGGRHLIFCHSKKKCDELAAKLVALGI-NAVAYYRGLDVSVIPTSG (SEQ ID NO:2); and has a length of 52 amino acids. Such a polytope can include NS3 T-cell epitopes designated NS3-3, NS3-4, NS3-5, and NS3-11 in FIG. 13B and FIGS. 15A-15N.

The heterologous polypeptide can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence:

KGGRHLIFCHSKKKCDELAAKLVALGINAVAYYR-GLDVSVIPTSGDVVVVATDALMTG FTGDFDSVIDCN (SEQ ID NO:3); and has a length of from 65 amino acids to 80 amino acids (e.g., 65 aa, 66 aa, 67 aa, 68 aa, 69 aa, 70 aa, 71 aa, 72 aa, 73 aa, 74 aa, 75 aa, 76 aa, 77 aa, 78 aa, 79 aa, or 80 aa). In some cases, the heterologous polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence:

KGGRHLIFCHSKKKCDELAAKLVALGINAVAYYR-GLDVSVIPTSGDVVVVATDALMTG FTGDFDSVIDCN (SEQ ID NO:3); and has a length of 70 amino acids. Such a polytope can include NS3 T-cell epitopes designated NS3-3, NS3-4, NS3-5, NS3-6, NS3-7, NS3-11, NS3-12, and NS3-13 in FIG. 13B and FIGS. 15A-15N.

The heterologous polypeptide can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence:

VALSTTGEIPFYGKAIPLEVIKGGRHLIFCHS-KKKCDELAAKLVALGINAVAYYRGLDVS VIPTSGDVVVVATDALMTGFTGDFDSVID-CNTCVTQTVDF (SEQ ID NO:4); and has a length of from 95 amino acids (aa) to 105 an (e.g., 95 aa, 96 aa, 97 aa, 98 aa, 99 aa, 100 aa, 101 aa, 102 aa, 103 aa, 104 aa, or 105 aa). In some cases, the heterologous polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence:

VALSTTGEIPFYGKAIPLEVIKGGRHLIFCHS-KKKCDELAAKLVALGINAVAYYRGLDVS VIPTSGDVVVVATDALMTGFTGDFDSVIDC-NTCVTQTVDF (SEQ ID NO:4); and has a length of 100 amino acids. Such a polytope can include NS3 T-cell epitopes designated NS3-3, NS3-4, NS3-5, NS3-6, NS3-7, NS3-10, NS3-11, NS3-12, and NS3-13 in FIG. 13B and FIGS. 15A-15N.

The heterologous polypeptide can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence:

MSTNPKPQRKTKRNTNRRPQDVKFPGGGQI-VGGVYLLPRRGPRLGVRATRKTSERSQP RGRRQPIPKARRPEGRTWAQPGYPWPLYG-NEGCGWAGWLLSPRGSRPSWGPTDPRRRS RNLGKVIDTLTCGFADLMGYIPLVGAPLG-GAARALAHGVRVLEDGVNYATGNLPGCSF SIFLLALLSCLTVPASA (SEQ ID NO:9); and has a length of from 190 amino acids (aa) to 200 aa (e.g., 190 aa, 191 aa, 192 aa, 193 aa, 194 aa, 195 aa, 196 aa, 197 aa, 198 aa, 199 aa, or 200 aa. In some cases, the heterologous polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence:

MSTNPKPQRKTKRNTNRRPQDVKFPGGGQI-VGGVYLLPRRGPRLGVRATRKTSERSQP RGRRQPIPKARRPEGRTWAQPGYPWPLYG-NEGCGWAGWLLSPRGSRPSWGPTDPRRRS RNLGKVIDTLTCGFADLMGYIPLVGAPLG-GAARALAHGVRVLEDGVNYATGNLPGCSF SIFLLALLSCLTVPASA (SEQ ID NO:9); and has a length of 191 amino acids.

The heterologous polypeptide can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence:

(SEQ ID NO: 10)
LHAPTGSGKSTKVPAAYAAQGYKVLVLNPSVAATLGFGAYMSKAHGIDPN

IRTGVRTITTGSPITYSTYGKFLADGGCSGGAYDIIICDECHSTDATSIL

GIGTVLDQAETAGARLVVLATATPPGSVTVPHPNIEEVALSTTGEIPFYG

KAIPLEVIKGGRHLIFCHSKKKCDELAAKLVALGINAVAYYRGLDVSVIP

TSGDVVVVATDALMTGFTGDFDSVIDCN;

and has a length of from 215 amino acids (aa) to 235 aa (e.g., 215 aa, 216 aa, 217 11, 218 aa, 219 aa, 220 aa, 221 aa, 222 aa, 223 aa, 224 aa, 225 aa, 226 aa, 227 aa, 228 aa, 229 aa, 230 aa, 231 aa, 232 aa, 233 aa, 234 aa, or 235 aa). In some cases, the heterologous polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence:

(SEQ ID NO: 10)
LHAPTGSGKSTKVPAAYAAQGYKVLVLNPSVAATLGFGAYMSKAHGIDPN

IRTGVRTITTGSPITYSTYGKFLADGGCSGGAYDIIICDECHSTDATSIL

GIGTVLDQAETAGARLVVLATATPPGSVTVPHPNIEEVALSTTGEIPFYG

KAIPLEVIKGGRHLIFCHSKKKCDELAAKLVALGINAVAYYRGLDVSVIP

TSGDVVVVATDALMTGFTGDFDSVIDCN;

and has a length of 228 amino acids. Such a polytope can include NS3 T-cell epitopes designated NS3-1, NS3-2, NS3-3, NS3-4, NS3-5, NS3-6, NS3-7, NS3-9, NS3-10, NS3-11, NS3-12, and NS3-13 in FIG. 13B and FIGS. 15A-15N.

As another example, the heterologous polypeptide can comprise an HCV NS3 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1265-1279 of the amino acid sequence designated "Consensus" in FIGS. 16A-16L, or a corresponding HCV NS3 amino acid sequence of any HCV genotype; and the HCV NS3 T-cell epitope can have a length of from 15 amino acids (aa) to 20 amino acids (e.g., 15 aa, 16 aa, 17 aa, 18 aa, 19 aa, or 20 aa).

As another example, the heterologous polypeptide can comprise an HCV NS3 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1309-1323 of the amino acid sequence designated "Consensus" in FIGS. 16A-16L, or a corresponding HCV NS3 amino acid sequence of any HCV genotype; and the HCV NS3 T-cell epitope can have a length of from 15 amino acids (aa) to 20 amino acids (e.g., 15 aa, 16 aa, 17 aa, 18 aa, 19 aa, or 20 aa).

As another example, the heterologous polypeptide can comprise an HCV NS3 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1401-1415 of the amino acid sequence designated "Consensus" in FIGS. 16A-16L, or a corresponding HCV NS3 amino acid sequence of any HCV genotype; and the HCV NS3 T-cell epitope can have a length of from 15 amino acids (aa) to 20 amino acids (e.g., 15 aa, 16 aa, 17 aa, 18 aa, 19 aa, or 20 aa).

As another example, the heterologous polypeptide can comprise an HCV NS3 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1402-1412 of the amino acid sequence designated "Consensus" in FIGS. 16A-16L, or a corresponding HCV NS3 amino acid sequence of any HCV genotype; and the HCV NS3 T-cell epitope can have a length of from 11 amino acids (aa) to 16 amino acids (e.g., 11 aa, 12 aa, 13 aa, 14 aa, 15 aa, or 16 aa).

As another example, the heterologous polypeptide can comprise an HCV NS3 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1429-1439 of the amino acid sequence designated "Consensus" in FIGS. 16A-16L, or a corresponding HCV NS3 amino acid sequence of any HCV genotype; and the HCV NS3 T-cell epitope can have a length of from 11 amino acids (aa) to 16 amino acids (e.g., 11 aa, 12 aa, 13 aa, 14 aa, 15 aa, or 16 aa).

As another example, the heterologous polypeptide can comprise an HCV NS3 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1450-1464 of the amino acid sequence designated "Consensus" in FIGS. 16A-16L, or a corresponding HCV NS3 amino acid sequence of any HCV genotype; and the HCV NS3 T-cell epitope can have a length of from 15 amino acids (aa) to 20 amino acids (e.g., 15 aa, 16 aa, 17 aa, 18 aa, 19 aa, or 20 aa).

As another example, the heterologous polypeptide can comprise an HCV NS3 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1453-1467 of the amino acid sequence designated "Consensus" in FIGS. 16A-16L, or a corresponding HCV NS3 amino acid sequence of any HCV genotype; and the HCV NS3 T-cell epitope can have a length of from 15 amino acids (aa) to 20 amino acids (e.g., 15 aa, 16 aa, 17 aa, 18 aa, 19 aa, or 20 aa).

As another example, the heterologous polypeptide can comprise an HCV NS3 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1577-1591 of the amino acid sequence designated "Consensus" in FIGS. 16A-16L, or a corresponding HCV NS3 amino acid sequence of any HCV genotype; and the HCV NS3 T-cell epitope can have a length of from 15 amino acids (aa) to 20 amino acids (e.g., 15 aa, 16 aa, 17 aa, 18 aa, 19 aa, or 20 aa).

As another example, the heterologous polypeptide can comprise an HCV NS3 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1306-1314 of the amino acid sequence designated "Consensus" in FIGS. 16A-16L, or a corresponding HCV NS3 amino acid sequence of any HCV genotype; and the HCV NS3 T-cell epitope can have a length of from 9 amino acids (aa) to 15 amino acids (e.g., 9 aa, 10 aa, 11 aa, 12 aa, 13 aa, 14 aa, or 15 aa).

As another example, the heterologous polypeptide can comprise an HCV NS3 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1387-1394 of the amino acid sequence designated "Consensus" in FIGS. 16A-16L, or a corresponding HCV NS3 amino acid sequence of any HCV genotype; and the HCV NS3 T-cell epitope can have a length of from 1 amino acids (aa) to 15 amino acids (e.g., 8 aa, 9 aa, 10 aa, 11 aa, 12 aa, 13 aa, 14 aa, or 15 aa).

As another example, the heterologous polypeptide can comprise an HCV NS3 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1405-1413 of the amino acid sequence designated "Consensus" in FIGS. 16A-16L, or a corresponding HCV NS3 amino acid sequence of any HCV genotype; and the HCV NS3 T-cell epitope can have a length of from 9 amino acids (aa) to 15 amino acids (e.g., 9 aa, 10 aa, 11 aa, 12 aa, 13 aa, 14 aa, or 15 aa).

As another example, the heterologous polypeptide can comprise an HCV NS3 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1450-1458 of the amino acid sequence designated "Consensus" in FIGS. 16A-16L, or a corresponding HCV NS3 amino acid sequence of any HCV genotype; and the HCV NS3 T-cell epitope can have a length of from 9 amino acids (aa) to 15 amino acids (e.g., 9 aa, 10 aa, 11 aa, 12 aa, 13 aa, 14 aa, or 15 aa).

As another example, the heterologous polypeptide can comprise an HCV NS3 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1457-1465 of the amino acid sequence designated "Consensus" in FIGS. 16A-16L, or a corresponding HCV NS3 amino acid sequence of any HCV genotype; and the HCV NS3 T-cell epitope can have a length of from 9 amino acids (aa) to 15 amino acids (e.g., 9 aa, 10 aa, 11 aa, 12 aa, 13 aa, 14 aa, or 15 aa).

As another example, the heterologous polypeptide can comprise an HCV NS3 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1610-1618 of the amino acid sequence designated "Consensus" in FIGS. 16A-16L, or a corresponding HCV NS3 amino acid sequence of any HCV genotype; and the HCV NS3 T-cell epitope can have a length of from 9 amino acids (aa) to 15 amino acids (e.g., 9 aa, 10 aa, 11 aa, 12 aa, 13 aa, 14 aa, or 15 aa).

HCV NS2 T-Cell Epitopes

In some cases, the heterologous polypeptide present in an E2 variant polypeptide of an E1/E2 heterodimer of the present disclosure includes one or more T-cell epitopes present in an HCV NS2 polypeptide. Examples of T-cell epitopes present in NS2 polypeptides are depicted in FIGS. 15A-15N, and FIG. 13A.

For example, the heterologous polypeptide can comprise an NS2 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 955-974 of the amino acid sequence designated "Consensus" in FIGS. 16A-16L, or a corresponding HCV NS2 amino acid sequence of any HCV genotype; and the NS2 T cell epitope can have a length of from 20 amino acids (aa) to 25 amino acids (e.g., 20 aa, 21 aa, 22 aa, 23 aa, 24 aa, or 25 aa).

As another example, the heterologous polypeptide can comprise an NS2 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 975-994 of the amino acid sequence designated "Consensus" in FIGS. 16A-16L, or a corresponding HCV NS2 amino acid sequence of any HCV genotype; and the NS2 T cell epitope can have a length of from 20 amino acids (aa) to 25 amino acids (e.g., 20 aa, 21 aa, 22 aa, 23 aa, 24 aa, or 25 aa).

As another example, the heterologous polypeptide can comprise an NS2 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 985-1004 of the amino acid sequence designated "Consensus" in FIGS. 16A-16L, or a corresponding HCV NS2 amino acid sequence of any HCV genotype; and the NS2 T cell epitope can have a length of from 20 amino acids (aa) to 25 amino acids (e.g., 20 aa, 21 aa, 22 aa, 23 aa, 24 aa, or 25 aa).

As another example, the heterologous polypeptide can comprise an NS2 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1015-1034 of the amino acid sequence designated "Consensus" in FIGS. 16A-16L, or a corresponding HCV NS2 amino acid sequence of any HCV genotype; and the NS2 T cell epitope can have a length of from 20 amino acids (aa) to 25 amino acids (e.g., 20 aa, 21 aa, 22 aa, 23 aa, 24 aa, or 25 aa).

As another example, the heterologous polypeptide can comprise an NS2 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1035-1054 of the amino acid sequence designated "Consensus" in FIGS. 16A-16L, or a corresponding HCV NS2 amino acid sequence of any HCV genotype; and the NS2 T cell epitope can have a length of from 20 amino acids (aa) to 25 amino acids (e.g., 20 aa, 21 aa, 22 aa, 23 aa, 24 aa, or 25 aa).

As another example, the heterologous polypeptide can comprise an NS2 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 924-933 of the amino acid sequence designated "Consensus" in FIGS. 16A-16L, or a corresponding HCV NS2 amino acid sequence of any HCV genotype; and the NS2 T cell epitope can have a length of from 10 amino acids (aa) to 15 amino acids (e.g., 10 aa, 11 aa, 12 aa, 13 aa, 14 aa, or 15 aa).

As another example, the heterologous polypeptide can comprise an NS2 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 961-970 of the amino acid sequence designated "Consensus" in FIGS. 16A-16L, or a corresponding HCV NS2 amino acid sequence of any HCV genotype; and the NS2 T cell epitope can have a length of from 10 amino acids (aa) to 15 amino acids (e.g., 10 aa, 11 aa, 12 aa, 13 aa, 14 aa, or 15 aa).

As another example, the heterologous polypeptide can comprise an NS2 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 989-997 of the amino acid sequence designated "Consensus" in FIGS. 16A-16L, or a corresponding HCV NS2 amino acid sequence of any HCV genotype; and the NS2 T cell epitope can have a length of from 9 amino acids (aa) to 15 amino acids (e.g., 9 aa, 10 aa, 11 aa, 12 aa, 13 aa, 14 aa, or 15 aa).

In some cases, the heterologous polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to a contiguous stretch of from 10 amino acids (aa) to 50 an (e.g., from 10 aa to 25 aa, or from 25 an to 50 aa) of amino acids 955-1004 of the amino acid sequence designated "Consensus" in FIGS. 16A-16L, or a corresponding HCV NS2 amino acid sequence of any HCV genotype; and has a length of from 10 amino acids (aa) to 25 aa, or from 25 aa to 50 aa. In some cases, the heterologous polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 955-1004 of the amino acid sequence designated "Consensus" in FIGS. 16A-16L, or a corresponding HCV NS2 amino acid sequence of any HCV genotype; and has a length of about 50 amino acids.

In some cases, the heterologous polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to a contiguous stretch of from 10 amino acids (aa) to 553 an (e.g., from 10 aa to 25 aa, from 25 aa to 50 aa, from 50 aa to 100 aa, from 100 aa to 200 aa, from 200 aa to 300 aa, from 300 aa to 400 aa, from 400 aa to 500 aa, or from 500 aa to 553 aa) of amino acids 917-1469 of the amino acid sequence designated "Consensus" in FIGS. 16A-16L, or a corresponding HCV NS2 and NS3 amino acid sequence of any HCV genotype; and has a length of from 10 amino acids (aa) to 25 aa, from 25 aa to 50 aa, from 50 aa to 100 aa, from 100 aa to 200 aa, from 200 aa to 300 aa, from 300 aa to 400 aa, from 400 aa to 500 aa, or from 500 aa to 553 aa. In some cases, the heterologous polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 917-1469 of the amino acid sequence designated “Consensus” in FIGS. 16A-16L, or a corresponding HCV NS2 and NS3 amino acid sequence of any HCV genotype; and has a length of about 553 amino acids.

The heterologous polypeptide can comprise an amino acid sequence having at least about 20%, at least about 25%, at least about 30%, at least about 35%, at least about 40%, at least about 45%, at least about 50%, at least about 60%, at least about 0%, at least about 75%, at least about 80%, at least about 85%, at least about 90%, at least about 95%, at least about 98%, at least about 99%, or 100%, amino acid sequence identity to the following amino acid sequence:

LGALTGTYVYNHLTPLRDWAHNGLRDLAVAVEPVVFSQMETKLITWGADT (SEQ ID NO:11). In some cases, the heterologous polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence:

LGALTGTYVYNHLTPLRDWAHNGLRDLAVAVEPVVFSQMETKLITWGADT (SEQ ID NO:11); and has a length of from 50 amino acids to 60 amino acids (e.g., 50 aa, 51 aa, 52 aa, 53 aa, 54 aa, 55 aa, 56 aa, 57 aa, 58 aa, 59 aa, or 60 aa). In some cases, the heterologous polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence:

LGALTGTYVYNHLTPLRDWAHNGLRDLAVAVEPVVFSQMETKLITWGADT (SEQ ID NO:11); and has a length of 50 amino acids. Such a polytope can include NS2 T-cell epitopes designated NS2-1, NS2-2, NS2-3, NS2-7, and NS2-8 in FIG. 13A and FIGS. 15A-15N.

HCV NS4A T-Cell Epitopes

In some cases, the heterologous polypeptide present in an E2 variant polypeptide of an E1/E2 heterodimer of the present disclosure includes one or more T-cell epitopes present in an HCV NS4A polypeptide. Examples of T-cell epitopes present in NS4A polypeptides are depicted in FIGS. 15A-15N and FIG. 13B.

The heterologous polypeptide can comprise an NS4A T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1683-1692 of the amino acid sequence designated “Consensus” in FIGS. 16A-16L, or a corresponding HCV NS4A amino acid sequence of any HCV genotype; and the NS4A T-cell epitope can have a length of from 10 amino acids (aa) to 15 amino acids (e.g., 10 aa, 11 aa, 12 aa, 13 aa, 14 aa, or 15 aa).

HCV NS4B T-Cell Epitopes

In some cases, the heterologous polypeptide present in an E2 variant polypeptide of an E1/E2 heterodimer of the present disclosure includes one or more T-cell epitopes present in an HCV NS4B polypeptide. Examples of T-cell epitopes present in NS4B polypeptides are depicted in FIGS. 15A-15N and FIG. 13B.

As one example, the heterologous polypeptide can comprise an NS4B T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1790-1801 of the amino acid sequence designated “Consensus” in FIGS. 16A-16L, or a corresponding HCV NS4B amino acid sequence of any HCV genotype; and the NS4B T-cell epitope can have a length of from 12 amino acids (aa) to 20 amino acids (e.g., 12 aa, 13 aa, 14 aa, 15 aa, 16 aa, 17 aa, 18 aa, 19 aa, or 20 aa).

As another example, the heterologous polypeptide can comprise an NS4B T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1792-1802 of the amino acid sequence designated “Consensus” in FIGS. 16A-16L, or a corresponding HCV NS4B amino acid sequence of any HCV genotype; and the NS4B T-cell epitope can have a length of from 11 amino acids (aa) to 20 amino acids (e.g., 11 aa, 12 aa, 13 aa, 14 aa, 15 aa, 16 aa, 17 aa, 18 aa, 19 aa, or 20 aa).

As another example, the heterologous polypeptide can comprise an NS4B T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1898-1905 of the amino acid sequence designated “Consensus” in FIGS. 16A-16L, or a corresponding HCV NS4B amino acid sequence of any HCV genotype; and the NS4B T-cell epitope can have a length of from 8 amino acids (aa) to 15 amino acids (e.g., 8 aa, 9 aa, 10 aa, 11 aa, 12 aa, 13 aa, 14 aa, or 15 aa).

As another example, the heterologous polypeptide can comprise an NS4B T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1921-1935 of the amino acid sequence designated “Consensus” in FIGS. 16A-16L, or a corresponding HCV NS4B amino acid sequence of any HCV genotype; and the NS4B T-cell epitope can have a length of from 15 amino acids (aa) to 20 amino acids (e.g., 15 aa, 16 aa, 17 aa, 18 aa, 19 aa, or 20 aa).

As another example, the heterologous polypeptide can comprise an NS4B T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1922-1941 of the amino acid sequence designated "Consensus" in FIGS. 16A-16L, or a corresponding HCV NS4B amino acid sequence of any HCV genotype; and the NS4B T-cell epitope can have a length of from 20 amino acids (aa) to 25 amino acids (e.g., 20 aa, 21 aa, 22 aa, 23 aa, 24 aa, or 25 aa).

As another example, the heterologous polypeptide can comprise an NS4B T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1928-1947 of the amino acid sequence designated "Consensus" in FIGS. 16A-16L, or a corresponding HCV NS4B amino acid sequence of any HCV genotype; and the NS4B T-cell epitope can have a length of from 20 amino acids (aa) to 25 amino acids (e.g., 20 aa, 21 aa, 22 aa, 23 aa, 24 aa, or 25 aa).

As another example, the heterologous polypeptide can comprise an NS4B T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1868-1876 of the amino acid sequence designated "Consensus" in FIGS. 16A-16L, or a corresponding HCV NS4B amino acid sequence of any HCV genotype; and the NS4B T-cell epitope can have a length of from 9 amino acids (aa) to 15 amino acids (e.g., 9 aa, 10 aa, 11 aa, 12 aa, 13 aa, 14 aa, or 15 aa).

As another example, the heterologous polypeptide can comprise an NS4B T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1927-1942 of the amino acid sequence designated "Consensus" in FIGS. 16A-16L, or a corresponding HCV NS4B amino acid sequence of any HCV genotype; and the NS4B T-cell epitope can have a length of from 16 amino acids (aa) to 20 amino acids (e.g., 16 aa, 17 aa, 18 aa, 19 aa, or 20 aa).

As another example, the heterologous polypeptide can comprise an NS4B T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1932-1940 of the amino acid sequence designated "Consensus" in FIGS. 16A-16L, or a corresponding HCV NS4B amino acid sequence of any HCV genotype; and the NS4B T-cell epitope can have a length of from 9 amino acids (aa) to 15 amino acids (e.g., 9 aa, 10 aa, 11 aa, 12 aa, 13 aa, 14 aa, or 15 aa).

As another example, the heterologous polypeptide can comprise an NS4B T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1948-1962 of the amino acid sequence designated "Consensus" in FIGS. 16A-16L, or a corresponding HCV NS4B amino acid sequence of any HCV genotype; and the NS4B T-cell epitope can have a length of from 15 amino acids (aa) to 20 amino acids (e.g., 15 aa, 16 aa, 17 aa, 18 aa, 19 aa, or 20 aa).

HCV NS5A T-Cell Epitopes

In some cases, the heterologous polypeptide present in an E2 variant polypeptide of an E1/E2 heterodimer of the present disclosure includes one or more T-cell epitopes present in an HCV NS5A polypeptide. Examples of T-cell epitopes present in NS5A polypeptides are depicted in FIGS. 15A-15N and FIG. 13B.

As one example, the heterologous polypeptide can comprise an NS5A T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 2218-2232 of the amino acid sequence designated "Consensus" in FIGS. 16A-16L, or a corresponding HCV NS5A amino acid sequence of any HCV genotype; and the NS5A T-cell epitope can have a length of from 15 amino acids (aa) to 20 amino acids (e.g., 15 aa, 16 aa, 17 aa, 18 aa, 19 aa, or 20 aa).

As another example, the heterologous polypeptide can comprise an NS5A T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 2309-2317 of the amino acid sequence designated "Consensus" in FIGS. 16A-16L, or a corresponding HCV NS5A amino acid sequence of any HCV genotype; and the NSSA T-cell epitope can have a length of from 9 amino acids (aa) to 15 amino acids (e.g., 9 aa, 10 aa, 11 aa, 12 aa, 13 aa, 14 aa, or 15 aa).

HCV NS5B T-Cell Epitopes

In some cases, the heterologous polypeptide present in an E2 variant polypeptide of an E1/E2 heterodimer of the present disclosure includes one or more T-cell epitopes present in an HCV NS5B polypeptide. Examples of T-cell epitopes present in NS5B polypeptides are depicted in FIGS. 15A-15N and FIG. 13B.

As one example, the heterologous polypeptide can comprise an NS5B T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 2847-2851 of the amino acid sequence designated "Consensus" in FIGS. 16A-16L, or a corresponding HCV NS5B amino acid sequence of any HCV genotype; and the NS5B T-cell epitope can have a length of from 5 amino acids (aa) to 10 amino acids (e.g., 5 aa, 6 aa, 7 aa, 8 aa, 9 aa, or 10 aa).

As another example, the heterologous polypeptide can comprise an NS5B T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 2602-2610 of the amino acid sequence designated "Consensus" in FIGS. 16A-16L, or a corresponding HCV NS5B amino acid sequence of any HCV genotype; and the NS5B T-cell epitope can have a length of from 9 amino acids (aa) to 15 amino acids (e.g., 9 aa, 10 aa, 11 aa, 12 aa, 13 aa, 14 aa, or 15 aa).

HCV Core T-Cell Epitopes

In some cases, the heterologous polypeptide present in an E2 variant polypeptide of an E1/E2 heterodimer of the present disclosure includes one or more T-cell epitopes present in an HCV core polypeptide. Examples of T-cell epitopes present in HCV Core polypeptides are depicted in FIGS. 15A-15N and FIG. 13A.

As one example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1-20 of the amino acid sequence designated "Consensus" in FIGS. 16A-16L, or a corresponding HCV core amino acid sequence of any HCV genotype; and the HCV core T-cell epitope can have a length of from 20 amino acids (aa) to 25 amino acids (e.g., 20 aa, 21 aa, 22 aa, 23 aa, 24 aa, or 25 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 11-30 of the amino acid sequence designated "Consensus" in FIGS. 16A-16L, or a corresponding HCV core amino acid sequence of any HCV genotype; and the HCV core T-cell epitope can have a length of from 20 amino acids (aa) to 25 amino acids (e.g., 20 aa, 21 aa, 22 aa, 23 aa, 24 aa, or 25 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 21-40 of the amino acid sequence designated "Consensus" in FIGS. 16A-16L, or a corresponding HCV core amino acid sequence of any HCV genotype; and the HCV core T-cell epitope can have a length of from 20 amino acids (aa) to 25 amino acids (e.g., 20 aa, 21 aa, 22 aa, 23 aa, 24 aa, or 25 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 39-63 of the amino acid sequence designated "Consensus" in FIGS. 16A-16L, or a corresponding HCV core amino acid sequence of any HCV genotype; and the HCV core T-cell epitope can have a length of from 23 amino acids (aa) to 28 amino acids (e.g., 23 aa, 24 aa, 25 aa, 26 aa, 27 aa, or 28 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 47-70 of the amino acid sequence designated "Consensus" in FIGS. 16A-16L, or a corresponding HCV core amino acid sequence of any HCV genotype; and the HCV core T-cell epitope can have a length of from 24 amino acids (aa) to 29 amino acids (e.g., 24 aa, 25 aa, 26 aa, 27 aa, 28 aa, or 29 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 61-80 of the amino acid sequence designated "Consensus" in FIGS. 16A-16L, or a corresponding HCV core amino acid sequence of any HCV genotype; and the HCV core T-cell epitope can have a length of from 20 amino acids (aa) to 25 amino acids (e.g., 20 aa, 21 aa, 22 aa, 23 aa, 24 aa, or 25 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 71-90 of the amino acid sequence designated "Consensus" in FIGS. 16A-16L, or a corresponding HCV core amino acid sequence of any HCV genotype; and the HCV core T-cell epitope can have a length of from 20 amino acids (aa) to 25 amino acids (e.g., 20 aa, 21 aa, 22 aa, 23 aa, 24 aa, or 25 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 81-100 of the amino acid sequence designated "Consensus" in FIGS. 16A-16L, or a corresponding HCV core amino acid sequence of any HCV genotype; and the HCV core T-cell epitope can have a length of from 20 amino acids (aa) to 25 amino acids (e.g., 20 aa, 21 aa, 22 aa, 23 aa, 24 aa, or 25 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 91-110 of the amino acid sequence designated "Consensus" in FIGS. 16A-16L, or a corresponding HCV core amino acid sequence of any HCV genotype; and the HCV core T-cell epitope can have a length of from 20 amino acids (aa) to 25 amino acids (e.g., 20 aa, 21 aa, 22 aa, 23 aa, 24 aa, or 25 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 101-115 of the amino acid sequence designated "Consensus" in FIGS. 16A-16L, or a corresponding HCV core amino acid sequence of any HCV genotype; and the HCV core T-cell epitope can have a length of from 15 amino acids (aa) to 20 amino acids (e.g., 15 aa, 16 aa, 17 aa, 18 aa, 19 aa, or 20 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 111-130 of the amino acid sequence designated "Consensus" in FIGS. 16A-16L, or a corresponding HCV core amino acid sequence of any HCV genotype; and the HCV core T-cell epitope can have a length of from 20 amino acids (aa) to 25 amino acids (e.g., 20 aa, 21 aa, 22 aa, 23 aa, 24 aa, or 25 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 125-139 of the amino acid sequence designated "Consensus" in FIGS. 16A-16L, or a corresponding HCV core amino acid sequence of any HCV genotype; and the HCV core T-cell epitope can have a length of from 15 amino acids (aa) to 20 amino acids (e.g., 15 aa, 16 aa, 17 aa, 18 aa, 19 aa, or 20 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 131-150 of the amino acid sequence designated "Consensus" in FIGS. 16A-16L, or a corresponding HCV core amino acid sequence of any HCV genotype; and the HCV core T-cell epitope can have a length of from 20 amino acids (aa) to 25 amino acids (e.g., 20 aa, 21 aa, 22 aa, 23 aa, 24 aa, or 25 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 151-170 of the amino acid sequence designated "Consensus" in FIGS. 16A-16L, or a corresponding HCV core amino acid sequence of any HCV genotype; and the HCV core T-cell epitope can have a length of from 20 amino acids (aa) to 25 amino acids (e.g., 20 aa, 21 aa, 22 aa, 23 aa, 24 aa, or 25 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 161-180 of the amino acid sequence designated "Consensus" in FIGS. 16A-16L, or a corresponding HCV core amino acid sequence of any HCV genotype; and the HCV core T-cell epitope can have a length of from 20 amino acids (aa) to 25 amino acids (e.g., 20 aa, 21 aa, 22 aa, 23 aa, 24 aa, or 25 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 35-44 of the amino acid sequence designated "Consensus" in FIGS. 16A-16L, or a corresponding HCV core amino acid sequence of any HCV genotype; and the HCV core T-cell epitope can have a length of from 10 amino acids (aa) to 15 amino acids (e.g., 10 aa, 11 aa, 12 aa, 13 aa, 14 aa, or 15 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 43-51 of the amino acid sequence designated "Consensus" in FIGS. 16A-16L, or a corresponding HCV core amino acid sequence of any HCV genotype; and the HCV core T-cell epitope can have a length of from 9 amino acids (aa) to 15 amino acids (e.g., 9 aa, 10 aa, 11 aa, 12 aa, 13 aa, 14 aa, or 15 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 51-59 of the amino acid sequence designated "Consensus" in FIGS. 16A-16L, or a corresponding HCV core amino acid sequence of any HCV genotype; and the HCV core T-cell epitope can have a length of from 9 amino acids (aa) to 15 amino acids (e.g., 9 aa, 10 aa, 11 aa, 12 aa, 13 aa, 14 aa, or 15 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 129-137 of the amino acid sequence designated "Consensus" in FIGS. 16A-16L, or a corresponding HCV core amino acid sequence of any HCV genotype; and the HCV core T-cell epitope can have a length of from 9 amino acids (aa) to 15 amino acids (e.g., 9 aa, 10 aa, 11 aa, 12 aa, 13 aa, 14 aa, or 15 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 131-140 of the amino acid sequence designated "Consensus" in FIGS. 16A-16L, or a corresponding HCV core amino acid sequence of any HCV genotype; and the HCV core T-cell epitope can have a length of from 10 amino acids (aa) to 15 amino acids (e.g., 10 aa, 11 aa, 12 aa, 13 aa, 14 aa, or 15 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 150-158 of the amino acid sequence designated "Consensus" in FIGS. 16A-16L, or a corresponding HCV core amino acid sequence of any HCV genotype; and the HCV core T-cell epitope can have a length of from 9 amino acids (aa) to 15 amino acids (e.g., 9 aa, 10 aa, 11 aa, 12 aa, 13 aa, 14 aa, or 15 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 154-162 of the amino acid sequence designated "Consensus" in FIGS. 16A-16L, or a corresponding HCV core amino acid sequence of any HCV genotype; and the HCV core T-cell epitope can have a length of from 9 amino acids (aa) to 15 amino acids (e.g., 9 aa, 10 aa, 11 aa, 12 aa, 13 aa, 14 aa, or 15 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 168-176 of the amino acid sequence designated "Consensus" in FIGS. 16A-16L, or a corresponding HCV core amino acid sequence of any HCV genotype; and the HCV core T-cell epitope can have a length of from 9 amino acids (aa) to 15 amino acids (e.g., 9 aa, 10 aa, 11 aa, 12 aa, 13 aa, 14 aa, or 15 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 177-187 of the amino acid sequence designated "Consensus" in FIGS. 16A-16L, or a corresponding HCV core amino acid sequence of any HCV genotype; and the HCV core T-cell epitope can have a length of from 11 amino acids (aa) to 16 amino acids (e.g., 11 aa, 12 aa, 13 aa, 14 aa, 15 aa, or 16 aa).

As another example, the heterologous polypeptide can comprise an HCV core T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 178-187 of the amino acid sequence designated "Consensus" in FIGS. 16A-16L, or a corresponding HCV core amino acid sequence of any HCV genotype; and the HCV core T-cell epitope can have a length of from 10 amino acids (aa) to 15 amino acids (e.g., 10 aa, 11 aa, 12 aa, 13 aa, 14 aa, or 15 aa).

In some cases, the heterologous polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to a contiguous stretch of from 10 amino acids (aa) to 191 an (e.g., from 10 aa to 25 aa, from 25 aa to 50 aa, from 50 aa to 75 aa, from 75 aa to 100 aa, from 100 aa to 150 aa, or from 150 aa to 191aa) of amino acids 1-191 of the amino acid sequence designated "Consensus" in FIGS. 16A-16L, or a corresponding HCV core amino acid sequence of any HCV genotype; and has a length of from 10 amino acids (aa) to 25 aa, from 25 an to 50 aa, from 50 an to 100 aa, or from 100 aa to 150 aa, or from 150 an to 191 aa. In some cases, the heterologous polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 1-191 of the amino acid sequence designated "Consensus" in FIGS. 16A-16L, or a corresponding HCV core amino acid sequence of any HCV genotype; and has a length of about 191 amino acids.

The heterologous polypeptide can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence:

MSTNPKPQRKTKRNTNRRPQDVKFPGGGQI-VGGVYLLPRRGPRLGVRATRKTS ERSQPR-GRRQPIPKARRPEGRTWAQPGYPWPLYG-NEGCGWAGWLLSPRGSRPS WGPTDPRRRSRN-LGKVIDTLTCGFADLMGYIPLVGAPLGGAARAL-AHGVRVLE DGVNYATGNLPG (SEQ ID NO:63); and has a length of from 171 amino acids (aa) to 180 an (e.g., 171 aa, 172 aa, 173 aa, 174 aa, 175 aa, 176 aa, 177 aa, 178 aa, 179 aa, or 180 aa. In some cases, the heterologous polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence:

MSTNPKPQRKTKRNTNRRPQDVKFPGGGQI-VGGVYLLPRRGPRLGVRATRKTS ERSQPR-GRRQPIPKARRPEGRTWAQPGYPWPLYG-NEGCGWAGWLLSPRGSRPS WGPTDPRRRSR-NLGKVIDTLTCGFADLMGYIPLVGAPLG-GAARALAHGVRVLE DGVNYATGNLPG (SEQ ID NO:63); and has a length of 171 amino acids. Such a polytope can include core T-cell epitopes designated Core-1, Core-2, Core-3, Core-4, Core-5, Core-6, Core-7, Core-8, Core-9, Core-10, Core-11, Core-12, Core-13, Core-14, Core-16, Core-17, Core-18, Core-19, Core-20, Core-21, Core-22 in FIG. 13A and FIGS. 15A-15N.

HCV p7 T-Cell Epitopes

In some cases, the heterologous polypeptide present in an E2 variant polypeptide of an E1/E2 heterodimer of the present disclosure includes one or more T-cell epitopes present in an HCV p7 polypeptide. Examples of T-cell epitopes present in HCV p7 polypeptides are depicted in FIGS. 15A-15N or FIG. 13A.

As another example, the heterologous polypeptide can comprise an HCV p7 T cell epitope comprising an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to amino acids 803-811 of the amino acid sequence designated "Consensus" in FIGS. 16A-16L, or a corresponding HCV p7 amino acid sequence of any HCV genotype; and the HCV p7 T-cell epitope can have a length of from 9 amino acids (aa) to 15 amino acids (e.g., 9 aa, 10 aa, 11 aa, 12 aa, 13 aa, 14 aa, or 15 aa).

Polytopes Including HCV T-Cell Epitopes from More than One HCV Polypeptide Other than E1 and E2

As noted above, a heterologous polypeptide can include T-cell epitopes from more than one HCV polypeptide other than E1 and E2.

As one example, a heterologous polypeptide can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence:

QASLLKVPYFVRVQGLLRICALARKMAGGHYVQ-MAIIKLGALTGTYVYNALTP LRDWAHNGLRD-LAVAVEPVVFSQMETKLITWGADTAACGDI-INGLPVSARRGR EILLGPADGMVSKGWR-LLAPITAYAQQTRGLLGCIITSLTGRDKNQVEG-EVQIVS TAAQTFLATCINGVCWTVYHGAGTR-TIASPKGPVIQMYTNVDQDLVGWPAPQG ARSLTPCTCGSSDLYLVTRHADVIPVRRRG-DSRGSLLSPRPISYLKGSAGGPLLCP AGHAVGI-FRAAVCTRGVAKAVDFIPVENLETTMR-SPVFTDNSSPPAVPQSFQVA HLHAPTGSGK-STKVPAAYAAQGYKVLVLNPSVAATLGFGAYM-SKAHGIDPNIR TGVRTITTGSPITYSTYGKFLAD-GGCSGGAYDIIICDECHSTDATSILGIGTVLDQA ETAGARLVVLATATPPGSVTVPHPNIEEVALSTT-GEIPFYGKAIPLEVIKGGRHLIF CHSKKKCDE-LAAKLVALGINAVAYYRGLDVSVIPTSGDVVV-VATDALMTGFTG DFDSVIDCN (SEQ ID NO:12); and has a length of from 550 amino acids (aa) to 560 aa (e.g., 550 aa, 551 aa, 552 aa, 553 aa, 554 aa, 555 aa, 556 aa, 557 aa, 558 aa, 559 aa, or 560 aa). In some cases, the heterologous polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence:

QASLLKVPYFVRVQGLLRICALARKMAGGHYVQ-MAIIKLGALTGTYVYNALTP LRDWAHNGLRD-LAVAVEPVVFSQMETKLITWGADTAACGDI-INGLPVSARRGR EILLGPADGMVSKGWRL-LAPITAYAQQTRGLLGCIITSLTGRDKNQVEG-EVQIVS TAAQTFLATCINGVCWTVYHGAGTR-TIASPKGPVIQMYTNVDQDLVGWPAPQG ARSLTPCTCGSSDLYLVTRHADVIPVRRRG-DSRGSLLSPRPISYLKGSAGGPLLCP AGHAVGI-FRAAVCTRGVAKAVDFIPVENLETTMRSPVFT-DNSSPPAVPQSFQVA HLHAPTGSGKSTKVPAA-YAAQGYKVLVLNPSVAATLGFGAYMSKA-HGIDPNIR TGVRTITTGSPITYSTYGKFLADGGC-SGGAYDIIICDECHSTDATSILGIGTVLDQA ETAGARLVVLATATPPGSVTVPHPNIEEVALSTT-GEIPFYGKAIPLEVIKGGRHLIF CHSKKKCDE-LAAKLVALGINAVAYYRGLDVSVIPTSGDVVV-VATDALMTGFTG DFDSVIDCN (SEQ ID NO:12); and has a length of 553 amino acids. Such a polytope can include T-cell epitopes designated NS2-1, NS2-2, NS2-3, NS2-4, NS2-5, NS2-6, NS2-7, NS2-8, NS3-1, NS3-2, NS3-3, NS3-4, NS3-5, NS3-6, NS3-7, NS3-9, NS3-10, NS3-11, NS3-12, and NS3-13 in FIGS. 13A-

13B and FIGS. 15A-15N. This polytope is also referred to as "TP553" (FIGS. 14A-14D). In order to prevent self cleavage of the TP553 polytope (amino acids 917-1469) (FIGS. 15E-G) at the NS2-NS3 junction that is mediated by the catalytic domain of the NS2 protease (amino acids 917-1040), the histidine at position 966 (H966), a critical residue for NS2 protease activity, is mutated to alanine (H966A) (FIG. 15E).

As another example, the heterologous polypeptide can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to a contiguous stretch of from 25 amino acids (aa) to 778 aa (e.g., from 25 aa to 50 aa, from 50 aa to 75 aa, from 75 aa to 100 aa, from 100 an to 150 aa, from 150 aa to 200 aa, from 200 aa to 250 aa, from 250 aa to 300 aa, from 300 an to 350 aa, from 350 aa to 400 aa, from 400 aa to 450 aa, from 450 aa to 500 aa, from 500 an to 550 aa, from 550 aa to 600 aa, from 600 an to 650 aa, from 650 an to 700 aa, from 700 aa to 750 aa, or from 750 an to 778 aa) the following amino acid sequence:

LHAPTGSGKSTKVPAAYAAQGYKVLVLNPSVA-ATLGFGAYMSKAHGIDPNIRTGVRTIT TGSPI-TYSTYGKFLADGGCSGGAYDIIICDECHSTDAT-SILGIGTVLDQAETAGARLVVLA TATPPGSVTV-PHPNIEEVALSTTGEIPFYGKAIPLEVIKG-GRHLIFCHSKKKCDELAAKLV ALGINAVAYYR-GLDVSVIPTSGDVVVVATDALMTGFTGDFDS-VIDCNTCVTQTVDFSLD FTFTIETITLPQDAVSR-TQRRGRTGRGKPGIYRFVAPGERPSGMFDSSVL-CECYDAGCA WYELTPAETTVRLRAYMNTPGLP-VCQDHLEFWEGVFTGLTHIDAHFLSQTKQS-GENLP YLVAYQATVCARAQAPPPSWDQMWKC-LIRLKPTLHGPTPLLYRLGAVQNEVTLTHPIT KYIMTCMSADLEVVTSTWVLVGGVLAALAAY-CLSTGCVVIVGRIVLSGKPAIIPDREVL YREFDE-MEECSQHLPYIEQGMMLAEQFKQKALGLLQ-TASRQAEVIAPAVQTNWQKLEA FWAKHMW-NFISGIQYLAGLSTLPGNPAIASLMAFTAAVT-SPLTTSQTLLFNILGGWVAA QLAAPGAATAFVG-AGLAGAAIGSVGLGKVLVDILAGYGAGVAGAL-VAFKIMSGEVPST EDLVNLLPAILSPGALVVGVV-CAAILRRHVGPGEGAVQWMNRLIAFASRGNHV-SPTHY VPESDAAARVTAILSSLTVTQLLRRLHQ-WISSECTTPCSGSWLRDIWDWICEVLSDFKTW LKAKLMPQLPG (SEQ ID NO:64). In some cases, the heterologous polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to a contiguous stretch of from 25 amino acids (aa) to 778 an (e.g., from 25 an to 50 aa, from 50 aa to 75 aa, from 75 aa to 100 aa, from 100 aa to 150 aa, from 150 aa to 200 aa, from 200 aa to 250 aa, from 250 aa to 300 aa, from 300 aa to 350 aa, from 350 aa to 400 aa, from 400 aa to 450 aa, from 450 aa to 500 aa, from 500 aa to 550 aa, from 550 aa to 600 aa, from 600 aa to 650 aa, from 650 aa to 700 aa, from 700 aa to 750 aa, or from 750 an to 778 aa) of the following amino acid sequence:

LHAPTGSGKSTKVPAAYAAQGYKVLVLNPSVA-ATLGFGAYMSKAHGIDPNIRTGVRTIT TGSPI-TYSTYGKFLADGGCSGGAYDIIICDECHSTDAT-SILGIGTVLDQAETAGARLVVLA TATPPGSV-TVPHPNIEEVALSTTGEIPFYGKAIPLEVIKG-GRHLIFCHSKKKCDELAAKLV ALGINAVAYYR-GLDVSVIPTSGDVVVVATDALMTGFTGDFDSV-IDCNTCVTQTVDFSLD PTFTIETITLPQDAVSRT-QRRGRTGRGKPGIYRFVAPGERPSGMFDSSVL-CECYDAGCA WYELTPAETTVRLRAYMNTPGL-PVCQDHLEFWEGVFTGLTHIDAHFLSQTKQS-GENLP YLVAYQATVCARAQAPPPSWDQMWKC-LIRLKPTLHGPTPLLYRLGAVQNEVTLTHPIT KYIMTCMSADLEVVTSTWVLVGGVLAALAAY-CLSTGCVVIVGRIVLSGKPAIIPDREVL YREFDE-MEECSQHLPYIEQGMMLAEQFKQKALGLLQ-TASRQAEVIAPAVQTNWQKLEA FWAKHM-WNFISGIQYLAGLSTLPGNPAIASLMAFTAAVT-SPLTTSQTLLFNILGGWVAA QLAAPGAATAF-VGAGLAGAAIGSVGLGKVLVDILAGYGAGV-AGALVAFKIMSGEVPST EDLVNLLPAILSP-GALVVGVVCAAILRRHVGPGEGAVQWMNRLIA-FASRGNHVSPTHY VPESDAAARVTAILSSLT-VTQLLRRLHQWISSECTTPCSGSWLRDIWD-WICEVLSDFKTW LKAKLMPQLPG (SEQ ID NO:64); and has a length of from 25 amino acids (aa) to 50 aa, from 50 aa to 100 aa, from 100 an to 200 aa, from 200 an to 300 aa, from 300 aa to 400 aa, from 400 an to 500 aa, from 500 an to 600 aa, from 600 an to 700 aa, or from 700 an to 778 aa. In some cases, the heterologous polypeptide comprises an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence:

LHAPTGSGKSTKVPAAYAAQGYKVLVLNPSVAA-TLGFGAYMSKAHGIDPNIRTGVRTIT TGSPI-TYSTYGKFLADGGCSGGAYDIIICDECHSTDAT-SILGIGTVLDQAETAGARLVVLA TATPPGS-VTVPHPNIEEVALSTTGEIPFYGKAIPLEVIKG-GRHLIFCHSKKKCDELAAKLV ALGINAVAYYR-GLDVSVIPTSGDVVVVATDALMTGFTGDFDSV-IDCNTCVTQTVDFSLD PTFTIETITLPQDAVSR-TQRRGRTGRGKPGIYRFVAPGERPSGMFDSSVL-CECYDAGCA WYELTPAETTVRLRAYMNTPGLP-VCQDHLEFWEGVFTGLTHIDAHFLSQTKQS-GENLP YLVAYQATVCARAQAPPPSWDQMWKC-LIRLKPTLHGPTPLLYRLGAVQNEVTLTHPIT KYIMTCMSADLEVVTSTWVLVGGVLAALAAY-CLSTGCVVIVGRIVLSGKPAIIPDREVL YREFDE-MEECSQHLPYIEQGMMLAEQFKQKALGLLQ-TASRQAEVIAPAVQTNWQKLEA FWAKHMWN-FISGIQYLAGLSTLPGNPAIASLMAFTAAVT-SPLTTSQTLLFNILGGWVAA QLAAPGAATAFV-GAGLAGAAIGSVGLGKVLVDILAGYGAGVAG-ALVAFKIMSGEVPST EDLVNLLPAILSPGALVV-GVVCAAILRRHVGPGEGAVQWMNRLIAFAS-RGNHVSPTHY VPESDAAARVTAILSSLTVTQL-LRRLHQWISSECTTPCSGSWLRDIWDWICE-VLSDFKTW LKAKLMPQLPG (SEQ ID NO:64); and has a length of 778 amino acids. Such a polytope can include T-cell epitopes designated NS3-1, NS3-2, NS3-3, NS3-4, NS3-5, NS3-6, NS3-7, NS3-8, NS3-9, NS3-10, NS3-11, NS3-12, NS3-13, NS2-14, NS4a-1, NS4b-1, NS4b-2, NS4b-3, NS4b-4, NS4b-5, NS4b-6, NS4b-7, NS4b-8, NS4b-9, and NS4b-10 in FIG. 13B and FIGS. 15A-15N.

As another example, the heterologous polypeptide can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to a contiguous stretch of from 25 amino acids (aa) to 1985 aa (e.g., from 25 an to 50 aa, from 50 an to 75 an, from 75 an to 100 aa, from 100 an to 150 an, from 150 an to 200 aa, from 200 aa to 250 aa, from 250 aa to 500 aa, from 500 an to 750 an, from 750 an to 1000 aa, from 1000 aa to 1500 aa or from 1500 an to 1985 aa) of the following amino acid sequence:

(SEQ ID NO: 13)

APITAYAQQTRGLLGCIITSLTGRDKNQVEGEVQIVSTAAQTFLATCING

VCWTVYHGAGTRTIASPKGPVIQMYTNVDQDLVGWPAPQGARSLTPCTCG

SSDLYLVTRHADVIPVRRRGDSRGSLLSPRPISYLKGSAGGPLLCPAGHA

VGIFRAAVCTRGVAKAVDFIPVENLETTMRSPVFTDNSSPPAVPQSFQVA

HLHAPTGSGKSTKVPAAYAAQGYKVLVLNPSVAATLGFGAYMSKAHGIDP

NIRTGVRTITTGSPITYSTYGKFLADGGCSGGAYDIIICDECHSTDATSI

LGIGTVLDQAETAGARLVVLATATPPGSVTVPHPNIEEVALSTTGEIPFY

GKAIPLEVIKGGRHLIFCHSKKKCDELAAKLVALGINAVAYYRGLDVSVI

PTSGDVVVVATDALMTGFTGDFDSVIDCNTCVTQTVDFSLDPTFTIETTT

LPQDAVSRTQRRGRTGRGKPGIYRFVAPGERPSGMFDSSVLCECYDAGCA

WYELTPAETTVRLRAYMNTPGLPVCQDHLEFWEGVFTGLTHIDAHFLSQT

KQSGENLPYLVAYQATVCARAQAPPPSWDQMWKCLIRLKPTLHGPTPLLY

RLGAVQNEVTLTHPITKYIMTCMSADLEVVTSTWVLVGGVLAALAAYCLS

TGCVVIVGRIVLSGKPAIIPDREVLYREFDEMEECSQHLPYIEQGMMLAE

QFKQKALGLLQTASRQAEVIAPAVQTNWQKLEAFWAKHMWNFISGIQYLA

GLSTLPGNPAIASLMAFTAAVTSPLTTSQTLLFNILGGWVAAQLAAPGAA

TAFVGAGLAGAAIGSVGLGKVLVDILAGYGAGVAGALVAFKIMSGEVPST

EDLVNLLPAILSPGALVVGVVCAAILRRHVGPGEGAVQWMNRLIAFASRG

NHVSPTHYVPESDAAARVTAILSSLTVTQLLRRLHQWISSECTTPCSGSW

LRDIWDWICEVLSDFKTWLKAKLMPQLPGIPFVSCQRGYRGVWRGDGIMH

TRCHCGAEITGHVKNGTMRIVGPRTCRNMWSGTFPINAYTTGPCTPLPAP

NYTFALWRVSAEEYVEIRQVGDFHYVTGMTTDNLKCPCQVPSPEFFTELD

GVRLHRFAPPCKPLLREEVSFRVGLHEYPVGSQLPCEPEPDVAVLTSMLT

DPSHITAEAAGRRLARGSPPSVASSSASQLSAPSLKATCTANHDSPDAEL

IEANLLWRQEMGGNITRVESENKVVILDSFDPLVAEEDEREISVPAEILR

KSRRFAPALPIWARPDYNPPLLETWKKPDYEPPVVHGCPLPPPQSPPVPP

PRKKRTVVLTESTVSTALAELATKSFGSSSTSGITGDNTTTSSEPAPSGC

PPDSDAESYSSMPPLEGEPGDPDLSDGSWSTVSSEADTEDVVCCSMSYSW

-continued

TGALVTPCAAEEQKLPINALSNSLLRHHNLVYSTTSRSACQRQKKVTFDR

LQVLDSHYQDVLKEVKAAASKVKANLLSVEEACSLTPPHSAKSKFGYGAK

DVRCHARKAVNHINSVWKDLLEDSVTPIDTTIMAKNEVFCVQPEKGGRKP

ARLIVFPDLGVRVCEKMALYDVVSKLPLAVMGSSYGFQYSPGQRVEFLVQ

AWKSKKTPMGFSYDTRCFDSTVTESDIRTEEAIYQCCDLDPQARVAIKSL

TERLYVGGPLTNSRGENCGYRRCRASGVLTTSCGNTLTCYIKARAACRAA

GLQDCTMLVCGNNLVVICESAGVQEDAASLRAFTEAMTRYSAPPGDPPQP

EYDLELITSCSSNVSVAHDGAGKRVYYLTRDPTTPLARAAWETARHTPVN

SWLGNIIMFAPTLWARMILMTHFFSVLIARDQLEQALDCEIYGACYSIEP

LDLPPIIQRLHGLSAFSLHSYSPGEINRVAACLRKLGVPPLRAWRHRARS

VRARLLSRGGRAAICGKYLFNWAVRTKLKLTPIAAAGQLDLSGWFTAGYS

GGDIYHSVSHARPRWFWFCLLLLAAGVGIYLLPNR.

In some cases, the heterologous polypeptide can comprise an amino acid sequence having at least about 20%, at least about 25%, at least about 30%, at least about 35%, at least about 40%, at least about 45%, at least about 50%, at least about 60%, at least about 70%, at least about 75%, at least about 80%, at least about 85%, at least about 90%, at least about 95%, at least about 98%, at least about 99%, or 100%, amino acid sequence identity to the following amino acid sequence:

(SEQ ID NO: 13)

APITAYAQQTRGLLGCIITSLTGRDKNQVEGEVQIVSTAAQTFLATCING

VCWTVYHGAGTRTIASPKGPVIQMYTNVDQDLVGWPAPQGARSLTPCTCG

SSDLYLVTRHADVIPVRRRGDSRGSLLSPRPISYLKGSAGGPLLCPAGHA

VGIFRAAVCTRGVAKAVDFIPVENLETTMRSPVFTDNSSPPAVPQSFQVA

HLHAPTGSGKSTKVPAAYAAQGYKVLVLNPSVAATLGFGAYMSKAHGIDP

NIRTGVRTITTGSPITYSTYGKFLADGGCSGGAYDIIICDECHSTDATSI

LGIGTVLDQAETAGARLVVLATATPPGSVTVPHPNIEEVALSTTGEIPFY

GKAIPLEVIKGGRHLIFCHSKKKCDELAAKLVALGINAVAYYRGLDVSVI

PTSGDVVVVATDALMTGFTGDFDSVIDCNTCVTQTVDFSLDPTFTIETTT

LPQDAVSRTQRRGRTGRGKPGIYRFVAPGERPSGMFDSSVLCECYDAGCA

WYELTPAETTVRLRAYMNTPGLPVCQDHLEFWEGVFTGLTHIDAHFLSQT

KQSGENLPYLVAYQATVCARAQAPPPSWDQMWKCLIRLKPTLHGPTPLLY

RLGAVQNEVTLTHPITKYIMTCMSADLEVVTSTWVLVGGVLAALAAYCLS

TGCVVIVGRIVLSGKPAIIPDREVLYREFDEMEECSQHLPYIEQGMMLAE

QFKQKALGLLQTASRQAEVIAPAVQTNWQKLEAFWAKHMWNFISGIQYLA

GLSTLPGNPAIASLMAFTAAVTSPLTTSQTLLFNILGGWVAAQLAAPGAA

TAFVGAGLAGAAIGSVGLGKVLVDILAGYGAGVAGALVAFKIMSGEVPST

EDLVNLLPAILSPGALVVGVVCAAILRRHVGPGEGAVQWMNRLIAFASRG

NHVSPTHYVPESDAAARVTAILSSLTVTQLLRRLHQWISSECTTPCSGSW

LRDIWDWICEVLSDFKTWLKAKLMPQLPGIPFVSCQRGYRGVWRGDGIMH

TRCHCGAEITGHVKNGTMRIVGPRTCRNMWSGTFPINAYTTGPCTPLPAP

-continued

```
NYTFALWRVSAEEYVEIRQVGDFHYVTGMTTDNLKCPCQVPSPEFFTELD

GVRLHRFAPPCKPLLREEVSFRVGLHEYPVGSQLPCEPEPDVAVLTSMLT

DPSHITAEAAGRRLARGSPPSVASSSASQLSAPSLKATCTANHDSPDAEL

IEANLLWRQEMGGNITRVESENKVVILDSFDPLVAEEDEREISVPAEILR

KSRRFAPALPIWARPDYNPPLLETWKKPDYEPPVVHGCPLPPPQSPPVPP

PRKKRTVVLTESTVSTALAELATKSFGSSSTSGITGDNTTTSSEPAPSGC

PPDSDAESYSSMPPLEGEPGDPDLSDGSWSTVSSEADTEDVVCCSMSYSW

TGALVTPCAAEEQKLPINALSNSLLRHHNLVYSTTSRSACQRQKKVTFDR

LQVLDSHYQDVLKEVKAAASKVKANLLSVEEACSLTPPHSAKSKFGYGAK

DVRCHARKAVNHINSVWKDLLEDSVTPIDTTIMAKNEVFCVQPEKGGRKP

ARLIVFPDLGVRVCEKMALYDVVSKLPLAVMGSSYGFQYSPGQRVEFLVQ

AWKSKKTPMGFSYDTRCFDSTVTESDIRTEEAIYQCCDLDPQARVAIKSL

TERLYVGGPLTNSRGENCGYRRCRASGVLTTSCGNTLTCYIKARAACRAA

GLQDCTMLVCGNNLVVICESAGVQEDAASLRAFTEAMTRYSAPPGDPPQP

EYDLELITSCSSNVSVAHDGAGKRVYYLTRDPTTPLARAAWETARHTPVN

SWLGNIIMFAPTLWARMILMTHFFSVLIARDQLEQALDCEIYGACYSIEP

LDLPPIIQRLHGLSAFSLHSYSPGEINRVAACLRKLGVPPLRAWRHRARS

VRARLLSRGGRAAICGKYLFNWAVRTKLKLTPIAAAGQLDLSGWFTAGYS

GGDIYHSVSHARPRWFWFCLLLLAAGVGIYLLPNR;
```

and has a length of 1985 amino acids. Such a polytope can include T-cell epitopes designated NS3-1, NS3-2, NS3-3, NS3-4, NS3-5, NS3-6, NS3-7, NS3-8, NS3-9, NS3-10, NS3-11, NS3-12, NS3-13, NS3-14, NS4a-1, NS4b-1, NS4b-2, NS4b-3, NS4b-4, NS4b-5, NS4b-6, NS4b-7, NS4b-8, NS4b-9, NS4b-10, NS5a-1, NS5a-2, NS5b-1, NS5b-2 in FIGS. 13A-13B and FIGS. 15A-15N.

Additional T-Cell Epitopes

As discussed above, the one or more T-cell epitopes present in a heterologous polypeptide can include one or more T-cell epitopes present in: a) an HCV NS3 polypeptide; b) an HCV NS2 polypeptide; c) an HCV NS4A polypeptide; d) an HCV NS4B polypeptide; e) an HCV NS5A polypeptide; f) an HCV NS5B polypeptide; g) an HCV core polypeptide; or h) an HCV p7 polypeptide. In some cases, the one or more T-cell epitopes are T-cell epitopes present in an HCV NS3 polypeptide. In some cases, the heterologous polypeptide comprises one or more T cell epitopes present in: a) cholera toxin; and/or b) tetanus toxin; and/or c) diphtheria toxin; and/or d) a meningococcal outer membrane protein.

Thus, in some cases, a variant HCV polypeptide of includes: a) an HCV E1 polypeptide; and b) a heterologous polypeptide that comprises one or more T-cell epitopes, where the one or more T-cell epitopes are T-cell epitopes present in: i) one or more of an HCV NS3 polypeptide, an HCV NS2 polypeptide, an HCV NS4A polypeptide, an HCV NS4B polypeptide, an HCV NS5A polypeptide, an HCV NS5B polypeptide, an HCV core polypeptide, and an HCV p7 polypeptide; and ii) one or more of cholera toxin or toxoid, tetanus toxin or toxoid, diphtheria toxin or toxoid, and a meningococcal outer membrane protein.

A T helper tetanus toxin epitope or other bacterial T-cell epitope could be fused (e.g., by recombinant expression) or chemically conjugated to the HCV polytope/E2 fusion protein and/or to the HCV polytope E1 fusion protein of an E1/E2 heterodimer of the present disclosure to further enhance both T and B cell responses to both the HCV polytope and E1/E2 moieties. Alternatively, the whole or part of the detoxified toxin ("toxoid") could be fused (e.g., by recombinant expression) or chemically conjugated to the HCV polytope/E1E2 protein, wherein specific amino acids of the toxins are mutated to render the toxins inactive, thereby generating toxoids. Methods of generating toxoids are well known in the art. Examples of bacterial epitopes include the use of diphtheria toxoid, meningococcal outer membrane protein, or mutant diphtheria protein CRM197 (see, e.g.: http://www(dot)medscape(dot)com/viewarticle/431127)

In some cases, a suitable tetanus toxoid polypeptide comprises the amino acid sequence QYIKANSKFIGIFE (SEQ ID NO:14). In some cases, a suitable tetanus toxoid polypeptide comprises the amino acid sequence QYIKANSKFIGITE (SEQ ID NO:65).

In some cases, a heterologous polypeptide can comprise cholera toxin (or toxoid) epitope. In some cases, a suitable heterologous polypeptide comprising a cholera toxoid epitope comprises a fragment of cholera toxin-B subunit (CT-B), e.g., a fragment of from 5 amino acids to 25 amino acids, or from 25 amino acids to 50 amino acids, of the following amino acid sequence: MIKLKFGVFF TVLLSSAYAH GTPQNITDLC AEYHNTQIHT LNDKIFSYTE SLAGKREMAI ITFKNGATFQ VEVPGSQHID SQKKAIERMK DTLRIAYLTE AKVEKLCVWN NKTPHAIAAI SMAN (SEQ ID NO:15). In some cases, a suitable heterologous polypeptide comprising a cholera toxoid epitope comprises the following amino acid sequence: SLAGKREMAIITFKNGATFQVEVPG (SEQ ID NO:29).

In some cases, a heterologous polypeptide can comprise a tetanus toxin (or toxoid) T-cell epitope. In some cases, a suitable heterologous polypeptide comprising a tetanus toxin T-cell epitope comprises the amino acid sequence: ILMQYIKANSKFIGI (SEQ ID NO:16); and has a length of from 15 amino acids to 20 amino acids. In some cases, a suitable heterologous polypeptide comprising a tetanus toxin T-cell epitope comprises the amino acid sequence: VNNESSE (SEQ ID NO:17). In some cases, a suitable heterologous polypeptide comprising a tetanus toxin T-cell epitope comprises the amino acid sequence: PGINGKAIHLVNNESSE (SEQ ID NO:18). In some cases, a suitable heterologous polypeptide comprising a tetanus toxin T-cell epitope comprises the amino acid sequence: PNRDIL (SEQ ID NO:19). In some cases, a suitable heterologous polypeptide comprising a tetanus toxin T-cell epitope comprises the amino acid sequence: FIGITEL (SEQ ID NO:20). In some cases, a suitable tetanus toxin T-cell epitope comprises the amino acid sequence: SYFPSV (SEQ ID NO:21). In some cases, a suitable heterologous polypeptide comprising a tetanus toxin T-cell epitope comprises the amino acid sequence: NSVDDALINSTKIYSYFPSV (SEQ ID NO:22). In some cases, a suitable heterologous polypeptide comprising a tetanus toxin T-cell epitope comprises the amino acid sequence: IDKISDVSTIVPYIGPALNI (SEQ ID NO:23).

In some cases, a heterologous polypeptide can comprise a diphtheria toxin T-cell epitope In some cases, a suitable heterologous polypeptide comprising a diphtheria toxin T-cell epitope comprises the amino acid sequence: QSIALSSLMVAQAIP (SEQ ID NO:24); and has a length of from 15 amino acids to 20 amino acids. In some cases, a suitable heterologous polypeptide comprising a diphtheria toxin T-cell epitope comprises the amino acid sequence:

PVFAGANYAAWAVNVAQVI (SEQ ID NO:25). In some cases, a suitable heterologous polypeptide comprising a diphtheria toxin T-cell epitope comprises the amino acid sequence:

VHHNTEEIVAQSIALSSLMV (SEQ ID NO:26). In some cases, a suitable heterologous polypeptide comprising a diphtheria toxin T-cell epitope comprises the amino acid sequence:

QSIALSSLMVAQAIPLVGEL (SEQ ID NO:66). In some cases, a suitable heterologous polypeptide comprising a diphtheria toxin T-cell epitope comprises the amino acid sequence:

VDIGFAAYNFVESIINLFQV (SEQ ID NO:67). In some cases, a suitable heterologous polypeptide comprising a diphtheria toxin T-cell epitope comprises the amino acid sequence:

QGESGHDIKITAENTPLPIA (SEQ ID NO:68). In some cases, a suitable heterologous polypeptide comprising a diphtheria toxin T-cell epitope comprises the amino acid sequence:

GVLLPTIPGKLDVNKSKTHI (SEQ ID NO:69). In some cases, a suitable heterologous polypeptide comprising a diphtheria toxin T-cell epitope comprises the amino acid sequence of CRM197 (see, e.g., Giannini et al. (1984) Nucl. Acids. Res. 12:4063). The amino acid sequence of CRM197 is provided above.

In some cases, a heterologous polypeptide can comprise a tetanus toxin T-cell epitope and a diphtheria toxin T-cell epitope. In some of these cases, the heterologous polypeptide can comprise the amino acid sequence: IMQYIKANSKFIGIQSIALSSLMVAQ (SEQ ID NO:28); and can have a length of from 26 amino acids to 30 amino acids.

Additional Polypeptides

In any of the above-described embodiments, the variant E1 polypeptide can include one or more additional polypeptides. For example, in some cases, the variant E1 polypeptide includes an Ig Fc polypeptide at the C-terminus of variant E1 polypeptide. As another example, the variant E1 polypeptide includes an Ig Fc polypeptide at the N-terminus of variant E1 polypeptide. Ig Fc polypeptides are known in the art, and are described elsewhere herein.

IV. Nucleic Acids Encoding a Variant HCV E1 Polypeptide, a Variant HCV E2 Polypeptide, or an E1/E2 Heterodimer The present disclosure provides a nucleic acid comprising a nucleotide sequence encoding a variant HCV E2 polypeptide of the present disclosure. The present disclosure provides a nucleic acid comprising a nucleotide sequence encoding a variant HCV E1 polypeptide of the present disclosure. The present disclosure provides a nucleic acid comprising a nucleotide sequence an E1/E2 heterodimer of the present disclosure.

As described below, a variant HCV E1 polypeptide, a variant HCV E2 polypeptide, or a heterodimer comprising: i) a variant HCV E2 polypeptide and an HCV E1 polypeptide; ii) a variant HCV E1 polypeptide and an HCV E2 polypeptide; or iii) a variant HCV E1 polypeptide and a variant HCV E2 polypeptide, can be encoded by a nucleotide sequence of a nucleic acid of the present disclosure. Where an Ig Fc region is at the C-terminus of the encoded heterodimer, a proteolytically cleavable linker can be positioned between the Fc region and the polypeptide at the N-terminus of the Ig Fc region.

IV(A). Variant E2 and E1/E2 Heterodimers Comprising a Variant E2 Polypeptide

The present disclosure provides a nucleic acid comprising a nucleotide sequence encoding a variant HCV E2 polypeptide of the present disclosure, where the variant HCV E2 polypeptide comprises: i) an HCV E2 polypeptide; and ii) a heterologous polypeptide that comprises one or more T-cell epitopes (e.g., one or more T cell epitopes present in an HCV polypeptide other than an HCV E1 polypeptide or an HCV E2 polypeptide). The present disclosure provides a nucleic acid comprising a nucleotide sequence encoding a polyprotein comprising a variant E2 polypeptide of the present disclosure. In some cases, the nucleic acid is present in an expression vector. Thus, the present disclosure provides a recombinant expression vector comprising a nucleotide sequence encoding a variant E2 polypeptide of the present disclosure, where the variant HCV E2 polypeptide comprises: i) an HCV E2 polypeptide; and ii) a heterologous polypeptide that comprises one or more T-cell epitopes (e.g., one or more T cell epitopes present in an HCV polypeptide other than an HCV E1 polypeptide or an HCV E2 polypeptide).

In some cases, a nucleic acid of the present disclosure comprises a nucleotide sequence encoding a variant E2 polypeptide of the present disclosure, where the variant HCV E2 polypeptide comprises: i) an HCV E2 polypeptide; and ii) a heterologous polypeptide that comprises one or more T-cell epitopes (e.g., one or more T cell epitopes present in an HCV polypeptide other than an HCV E1 polypeptide or an HCV E2 polypeptide). In some cases, the nucleotide sequence encoding the variant E2 polypeptide is operably linked to a transcription control element, e.g., a promoter that is functional in a eukaryotic cell. Suitable promoters include, e.g., a cytomegalovirus (CMV) promoter, an SV40 promoter, and the like. In some cases, the nucleic acid is present in an expression vector (e.g., a lentivirus vector; an adenoassociated virus vector; an adenovirus vector; a retroviral vector; a non-viral vector; etc.). In some cases, the nucleic acid is present in an expression vector, where the expression vector is a non-viral vector.

In some cases, a nucleic acid of the present disclosure comprises a nucleotide sequence encoding a fusion protein comprising, in order from N-terminus to C-terminus: a) an immunoglobulin (Ig) Fc region; and b) a variant E2 polypeptide of the present disclosure, where the variant HCV E2 polypeptide comprises: i) an HCV E2 polypeptide; and ii) a heterologous polypeptide that comprises one or more T-cell epitopes (e.g., one or more T cell epitopes present in an HCV polypeptide other than an HCV E1 polypeptide or an HCV E2 polypeptide). In some cases, the variant HCV E2 polypeptide comprises, in order from N-terminus to C-terminus: i) the HCV E2 polypeptide; and ii) the heterologous polypeptide comprising the one or more T cell epitopes. In some cases, the variant HCV E2 polypeptide comprises, in order from N-terminus to C-terminus: i) the heterologous polypeptide comprising the one or more T cell epitopes; and ii) the HCV E2 polypeptide. In some cases, the nucleotide sequence encoding the fusion protein is operably linked to a transcription control element. e.g., a promoter that is functional in a eukaryotic cell. Suitable promoters include, e.g., a CMV promoter, an SV40 promoter, and the like. In some cases, the nucleic acid is present in an expression vector (e.g., a lentivirus vector; an adenoassociated virus vector; an adenovirus vector; a retroviral vector; a non-viral vector; etc.). In some cases, a nucleic acid of the present disclosure comprises a nucleotide sequence encoding a fusion protein comprising, in order from N-terminus to C-terminus: a) an Ig Fc region; b) a proteolytically cleavable linker; and c) a variant E2 polypeptide of the present disclosure, where the variant HCV E2 polypeptide comprises: i) an HCV E2 polypeptide; and ii) a heterologous polypeptide that comprises one or more T-cell epitopes (e.g., one or more T cell epitopes present in an HCV polypeptide other than an HCV E1 polypeptide or an HCV E2 polypeptide). In some cases, the variant HCV E2 polypeptide comprises, in order from N-terminus to C-terminus: i) the HCV E2 polypeptide; and ii) the heterologous polypeptide comprising the one or more T cell epitopes. In other cases, the variant HCV E2 polypeptide comprises, in order from N-terminus to C-terminus: i) the heterologous polypeptide comprising the one or more T cell epitopes; and ii) the HCV E2 polypeptide. In some cases, the nucleotide sequence encoding the fusion protein is operably linked to a transcription control element, e.g., a promoter that is functional in a eukaryotic cell. Suitable promoters include, e.g., a CMV promoter, an SV40 promoter, and the like. In some cases, the nucleic acid is present in an expression vector (e.g., a lentivirus vector; an adeno-associated virus vector; an adenovirus vector; a retroviral vector; a non-viral vector; etc.).

The proteolytically cleavable linker can include a protease recognition sequence recognized by a protease selected from the group consisting of alanine carboxypeptidase, *Armillaria mellea* astacin, bacterial leucyl aminopeptidase, cancer procoagulant, cathepsin B, clostripain, cytosol alanyl aminopeptidase, elastase, endoproteinase Arg-C, enterokinase, gastricsin, gelatinase, Gly-X carboxypeptidase, glycyl endopeptidase, human rhinovirus 3C protease, hypodermin C, IgA-specific serine endopeptidase, leucyl aminopeptidase, leucyl endopeptidase, lysC, lysosomal pro-X carboxypeptidase, lysyl aminopeptidase, methionyl aminopeptidase, myxobacter, nardilysin, pancreatic endopeptidase E, picornain 2A, picornain 3C, proendopeptidase, prolyl aminopeptidase, proprotein convertase I, proprotein convertase II, russellysin, saccharopepsin, semenogelase, T-plasminogen activator, thrombin, tissue kallikrein, tobacco etch virus (TEV), togavirin, tryptophanyl aminopeptidase, U-plasminogen activator, V8, venombin A, venombin AB, and Xaa-pro aminopeptidase.

For example, the proteolytically cleavable linker can comprise a matrix metalloproteinase cleavage site, e.g., a cleavage site for a MMP selected from collagenase-1, -2, and -3 (MMP-1, -8, and -13), gelatinase A and B (MMP-2 and -9), stromelysin 1, 2, and 3 (MMP-3, -10, and -11), matrilysin (MMP-7), and membrane metalloproteinases (MT1-MMP and MT2-MMP). For example, the cleavage sequence of MMP-9 is Pro-X-X-Hy (wherein, X represents an arbitrary residue; Hy, a hydrophobic residue; SEQ ID NO:70), e.g., Pro-X-X-Hy-(Ser/Thr) SEQ ID NO:71, e.g., Pro-Leu/Gln-Gly-Met-Thr-Ser (SEQ ID NO:72) or Pro-Leu/Gln-Gly-Met-Thr (SEQ ID NO:73). Another example of a protease cleavage site is a plasminogen activator cleavage site, e.g., a uPA or a tissue plasminogen activator (tPA) cleavage site. Another example of a suitable protease cleavage site is a prolactin cleavage site. Specific examples of cleavage sequences of uPA and tPA include sequences comprising Val-Gly-Arg. Another example of a protease cleavage site that can be included in a proteolytically cleavable linker is a tobacco etch virus (TEV) protease cleavage site, e.g., ENLYTQS (SEQ ID NO:6), where the protease cleaves between the glutamine and the serine. Another example of a protease cleavage site that can be included in a proteolytically cleavable linker is an enterokinase cleavage site, e.g., DDDDK (SEQ ID NO:7), where cleavage occurs after the lysine residue. Another example of a protease cleavage site that can be included in a proteolytically cleavable linker is a thrombin cleavage site, e.g., LVPR (SEQ ID NO:8). Additional suitable linkers comprising protease cleavage sites include linkers comprising one or more of the following amino acid sequences: LEVLFQGP (SEQ ID NO:5), cleaved by PreScission protease (a fusion protein comprising human rhinovirus 3C protease and glutathione-S-transferase; Walker et al. (1994) Biotechnol. 12:601); a thrombin cleavage site, e.g., CGLVPAGSGP (SEQ ID NO:30); SLLKSRMVPNFN (SEQ ID NO:31) or SLLIARRMPNFN (SEQ ID NO:32), cleaved by cathepsin B; SKLVQASASGVN (SEQ ID NO:33) or SSYLKASDAPDN (SEQ ID NO:34), cleaved by an Epstein-Barr virus protease; RPKPQQFFGLMN (SEQ ID NO:35) cleaved by MMP-3 (stromelysin); SLRPLALWRSFN (SEQ ID NO:36) cleaved by MMP-7 (matrilysin); SPQGIAGQRNFN (SEQ ID NO:37) cleaved by MMP-9; DVDERDVRGFASFL SEQ ID NO:38) cleaved by a thermolysin-like MMP; SLPLGLWAPNFN (SEQ ID NO:39) cleaved by matrix metalloproteinase 2(MMP-2); SLLIFRSWANFN (SEQ ID NO:40) cleaved by cathespin L; SGVVIATVIVIT (SEQ ID NO:41) cleaved by cathepsin D; SLGPQGIWGQFN (SEQ ID NO:42) cleaved by matrix metalloproteinase 1(MMP-1); KKSPGRVVGGSV (SEQ ID NO:43) cleaved by urokinase-type plasminogen activator; PQGLLGAPGILG (SEQ ID NO:44) cleaved by membrane type 1 matrixmetalloproteinase (MT-MMP); HGPEGLRVGFYESDVMGRGHARLVHVEEPHT (SEQ ID NO:45) cleaved by stromelysin 3 (or MMP-11), thermolysin, fibroblast collagenase and stromelysin-1; GPQGLAGQRGIV (SEQ ID NO:46) cleaved by matrix metalloproteinase 13 (collagenase-3); GGSGQRGRKALE (SEQ ID NO:47) cleaved by tissue-type plasminogen activator(tPA); SLSALLSSDIFN (SEQ ID NO:48) cleaved by human prostate-specific antigen; SLPRFKIIGGFN (SEQ ID NO:49) cleaved by kallikrein (hK3); SLLGIAVPGNFN (SEQ ID NO:50) cleaved by neutrophil elastase; and FFKNIVTPRTPP (SEQ ID NO:51) cleaved by calpain (calcium activated neutral protease).

The Fc region can be a human IgG1 Fc, a human IgG2 Fc, a human IgG3 Fc, a human IgG4 Fc, etc. In some cases, the Fc region comprises an amino acid sequence having at least about 70%, at least about 75%, at least about 80%, at least about 85%, at least about 90%, at least about 95%, at least about 98%, at least about 99%, or 100%, amino acid sequence identity to an amino acid sequence of an Fc region depicted in FIGS. 9A-9C. In some cases, the Fc region comprises an amino acid sequence having at least about 70%, at least about 75%, at least about 80%, at least about 85%, at least about 90%, at least about 95%, at least about 98%, at least about 99%, or 100%, amino acid sequence identity to the human IgG1 Fc polypeptide depicted in FIG. 9A. In some cases, the Fc region comprises an amino acid sequence having at least about 70%, at least about 75%, at least about 80%, at least about 85%, at least about 90%, at least about 95%, at least about 98%, at least about 99%, or 100%, amino acid sequence identity to the human IgG2 Fc polypeptide depicted in FIG. 9A; e.g., the Fc region comprises an amino acid sequence having at least about 70%, at least about 75%, at least about 80%, at least about 85%, at least about 90%, at least about 95%, at least about 98%, at least about 99%, or 100%, amino acid sequence identity to amino acids 99-325 of the human IgG2 Fc polypeptide depicted in FIG. 9A. In some cases, the Fc region comprises an amino acid sequence having at least about 70%, at least about 75%, at least about 80%, at least about 85%, at least about 90%, at least about 95%, at least about 98%, at least about 99%, or 100%, amino acid sequence identity to the human IgG3 Fc polypeptide depicted in FIG. 9A; e.g., the Fc region comprises an amino acid sequence having at least about 70%, at least about 75%, at least about 80%, at least about 85%, at least about 90%, at least about 95%, at least about 98%, at least about 99%, or 100%, amino acid sequence identity to amino acids 19-246 of the human IgG3 Fc polypeptide depicted in FIG. 9A.

In some cases, a nucleic acid of the present disclosure comprises a nucleotide sequence encoding a fusion protein comprising, in order from N-terminus to C-terminus: a) an Ig Fc region; b) a proteolytically cleavable linker comprising the amino acid sequence LEVLFQGP (SEQ ID NO:5) and having a length of from 8 amino acids to 15 amino acids; and c) a variant E2 polypeptide of the present disclosure, where the variant HCV E2 polypeptide comprises: i) an HCV E2 polypeptide; and ii) a heterologous polypeptide that comprises one or more T-cell epitopes (e.g., one or more T cell epitopes present in an HCV polypeptide other than an HCV E1 polypeptide or an HCV E2 polypeptide). In some cases, the variant HCV E2 polypeptide comprises, in order from N-terminus to C-terminus: i) the HCV E2 polypeptide; and ii) the heterologous polypeptide comprising the one or more T cell epitopes. In other cases, the variant HCV E2 polypeptide comprises, in order from N-terminus to C-terminus: i) the heterologous polypeptide comprising the one or more T cell epitopes; and ii) the HCV E2 polypeptide. In some cases, the nucleotide sequence encoding the fusion protein is operably linked to a transcription control element, e.g., a promoter that is functional in a eukaryotic cell. Suitable promoters include, e.g., a CMV promoter, an SV40 promoter, and the like. In some cases, the nucleic acid is present in an expression vector (e.g., a lentivirus vector; an adeno-associated virus vector; an adenovirus vector; a retroviral vector; a non-viral vector; etc.).

In some cases, a nucleic acid of the present disclosure comprises a nucleotide sequence encoding a fusion protein comprising, in order from N-terminus to C-terminus: a) an Ig Fc region; b) a proteolytically cleavable linker comprising the amino acid sequence ENLYTQS (SEQ ID NO:6) and having a length of from 7 amino acids to 12 amino acids; and c) a variant E2 polypeptide of the present disclosure, where the variant HCV E2 polypeptide comprises: i) an HCV E2 polypeptide; and ii) a heterologous polypeptide that comprises one or more T-cell epitopes (e.g., one or more T cell epitopes present in an HCV polypeptide other than an HCV E1 polypeptide or an HCV E2 polypeptide). In some cases, the variant HCV E2 polypeptide comprises, in order from N-terminus to C-terminus: i) the HCV E2 polypeptide; and ii) the heterologous polypeptide comprising the one or more T cell epitopes. In other cases, the variant HCV E2 polypeptide comprises, in order from N-terminus to C-terminus: i) the heterologous polypeptide comprising the one or more T cell epitopes; and ii) the HCV E2 polypeptide. In some cases, the nucleotide sequence encoding the fusion protein is operably linked to a transcription control element, e.g., a promoter that is functional in a eukaryotic cell. Suitable promoters include, e.g., a CMV promoter, an SV40 promoter, and the like. In some cases, the nucleic acid is present in an expression vector (e.g., a lentivirus vector; an adeno-associated virus vector; an adenovirus vector; a retroviral vector; a non-viral vector; etc.).

In some cases, a nucleic acid of the present disclosure comprises a nucleotide sequence encoding an E1/E2 polypeptide comprising, in order from N-terminus to C-terminus: a) an HCV E1 polypeptide; and b) a variant E2 polypeptide of the present disclosure, where the variant HCV E2 polypeptide comprises: i) an HCV E2 polypeptide; and ii) a heterologous polypeptide that comprises one or more T-cell epitopes (e.g., one or more T cell epitopes present in an HCV polypeptide other than an HCV E1 polypeptide or an HCV E2 polypeptide). In some cases, the variant HCV E2 polypeptide comprises, in order from N-terminus to C-terminus: i) the HCV E2 polypeptide; and ii) the heterologous polypeptide comprising the one or more T cell epitopes. In other cases, the variant HCV E2 polypeptide comprises, in order from N-terminus to C-terminus: i) the heterologous polypeptide comprising the one or more T cell epitopes; and ii) the HCV E2 polypeptide. In some cases, the nucleotide sequence encoding the E1/E2 polypeptide is operably linked to a transcription control element, e.g., a promoter that is functional in a eukaryotic cell. Suitable promoters include, e.g., a CMV promoter, an SV40 promoter, and the like. In some cases, the nucleic acid is present in an expression vector (e.g., a lentivirus vector; an adenoassociated virus vector; an adenovirus vector; a retroviral vector; a non-viral vector; etc.). In some cases, the E1/E2 polypeptide comprises a host-derived signal peptidase cleavage site between the HCV E1 polypeptide and the variant HCV E2 polypeptide. Thus, in some cases, a nucleic acid of the present disclosure comprises a nucleotide sequence encoding an E1/E2 polypeptide comprising, in order from N-terminus to C-terminus: a) an HCV E1 polypeptide; b) a host signal peptidase cleavage site; and c) a variant E2 polypeptide of the present disclosure, where the variant HCV E2 polypeptide comprises: i) an HCV E2 polypeptide; and ii) a heterologous polypeptide that comprises one or more T-cell epitopes (e.g., one or more T cell epitopes present in an HCV polypeptide other than an HCV E1 polypeptide or an HCV E2 polypeptide). In some cases, the variant HCV E2 polypeptide comprises, in order from N-terminus to C-terminus: i) the HCV E2 polypeptide; and ii) the heterologous polypeptide comprising the one or more T cell epitopes. In other cases, the variant HCV E2 polypeptide comprises, in order from N-terminus to C-terminus: i) the heterologous polypeptide comprising the one or more T cell epitopes; and ii) the HCV E2 polypeptide.

In some cases, a nucleic acid of the present disclosure comprises a nucleotide sequence encoding an E1/E2 polypeptide comprising, in order from N-terminus to C-terminus: a) an HCV E1 polypeptide; b) an Ig Fc region; and c) a variant E2 polypeptide of the present disclosure, where the variant HCV E2 polypeptide comprises: i) an HCV E2 polypeptide; and ii) a heterologous polypeptide that comprises one or more T-cell epitopes (e.g., one or more T cell epitopes present in an HCV polypeptide other than an HCV E1 polypeptide or an HCV E2 polypeptide). In some cases, the variant HCV E2 polypeptide comprises, in order from N-terminus to C-terminus: i) the HCV E2 polypeptide; and ii) the heterologous polypeptide comprising the one or more T cell epitopes. In other cases, the variant HCV E2 polypeptide comprises, in order from N-terminus to C-terminus: i) the heterologous polypeptide comprising the one or more T cell epitopes; and ii) the HCV E2 polypeptide. In some cases, the nucleotide sequence encoding the E1/E2 polypeptide is operably linked to a transcription control element, e.g., a promoter that is functional in a eukaryotic cell. Suitable promoters include, e.g., a CMV promoter, an SV40 promoter, and the like. In some cases, the nucleic acid is present in an expression vector (e.g., a lentivirus vector; an adenoassociated virus vector; an adenovirus vector; a retroviral vector; a non-viral vector; etc.). In some cases, the E1/E2 polypeptide comprises a host-derived signal peptidase cleavage site between the E1 polypeptide and the Ig Fc region. Thus, in some cases, a nucleic acid of the present disclosure comprises a nucleotide sequence encoding an E1/E2 polypeptide comprising, in order from N-terminus to C-terminus: a) an HCV E1 polypeptide; b) a host-derived signal peptidase cleavage site; c) an Ig Fc region; and d) a variant E2 polypeptide of the present disclosure, where the variant HCV E2 polypeptide comprises: i) an HCV E2 polypeptide; and ii) a heterologous polypeptide that comprises one or more T-cell epitopes (e.g., one or more T cell epitopes present in an HCV polypeptide other than an HCV E1 polypeptide or an HCV E2 polypeptide). In some cases, the variant HCV E2 polypeptide comprises, in order from N-terminus to C-terminus: i) the HCV E2 polypeptide; and ii) the heterologous polypeptide comprising the one or more T cell epitopes. In other cases, the variant HCV E2 polypeptide comprises, in order from N-terminus to C-terminus: i) the heterologous polypeptide comprising the one or more T cell epitopes; and ii) the HCV E2 polypeptide. In some cases, a nucleotide sequence encoding from 2 to 10 amino acids (e.g., 2 aa, 3 aa, 4 aa, 5 aa, 6 aa, 7 aa, 8 aa, 9 aa, or 10 aa) of the N-terminus of an E2 polypeptide is interposed between the E1-encoding nucleotide sequence and the Ig Fc-encoding nucleotide sequence. Examples are depicted in FIG. 5A. For example, in some cases, a nucleotide sequence encoding QT, ET, HT, GT, TT, RH, NT, AY, VI, or ST is interposed between the E1-encoding nucleotide sequence and the Ig Fc-encoding nucleotide sequence. In some cases, a nucleotide sequence encoding ET (Glu-Thr) is interposed between the E1-encoding nucleotide sequence and the Ig Fc-encoding nucleotide sequence. In some cases, a nucleotide sequence encoding QT (Gln-Thr) is interposed between the E1-encoding nucleotide sequence and the Ig Fc-encoding nucleotide sequence. In some cases, a nucleotide sequence encoding TT (Thr-Thr) is interposed between the E1-encoding nucleotide sequence and the Ig Fc-encoding nucleotide sequence. In some cases, a nucleotide sequence encoding GT (Gly-Thr) is interposed between the E1-encoding nucleotide sequence and the Ig Fc-encoding nucleotide sequence. In some cases, a nucleotide sequence encoding HT (His-Thr) is interposed between the E1-encoding nucleotide sequence and the Ig Fc-encoding nucleotide sequence. In some cases, a nucleotide sequence encoding NT (Asn-Thr) is interposed between the E1-encoding nucleotide sequence and the Ig Fc-encoding nucleotide sequence. In some cases, a nucleotide sequence encoding VT (Val-Thr) is interposed between the E1-encoding nucleotide sequence and the Ig Fc-encoding nucleotide sequence. In some cases, a nucleotide sequence encoding ST (Ser-Thr) is interposed between the E1-encoding nucleotide sequence and the Ig Fc-encoding nucleotide sequence.

In some Fc tagged E1E2 constructs (with or without TP insertion), the duplication of the first two amino acids of E2 is such that an amino acid is created at the N-terminus of E2 following processing by signal peptidase (SP) (FIG. 5A). Such amino acids at the amino terminus include asparagine (N), glutamine (Q) or cysteine (C). Such amino acids can target the protein for proteasome-mediated degradation via the N-end rule pathway (reviewed in: Tasaki T et al. 2012. *Annu Rev Biochem* 81261-289). For example in FIGS. 5A-5B: the insertion of QT in Avi1a129 (1A) creates an N-terminal glutamine (Q) residue following cleavage by signal peptidase. In this case, an alternative amino acid could be selected according to either the consensus sequence for the particular genotype or a particular genotype subclass (eg: genotype 1A in this case). The final purified E1E2 protein containing an N-terminal polytope addition (TPx) from Fc tagged E1E2 constructs contains an N-terminal glycine (G) residue and is not expected to be a substrate for the N-end rule pathway.

In some cases, a nucleic acid of the present disclosure comprises a nucleotide sequence encoding an E1/E2 polypeptide comprising, in order from N-terminus to C-terminus: a) an HCV E1 polypeptide; b) an Ig Fc region; c) a proteolytically cleavable linker; and d) a variant E2 polypeptide of the present disclosure, where the variant HCV E2 polypeptide comprises: i) an HCV E2 polypeptide; and ii) a heterologous polypeptide that comprises one or more T-cell epitopes (e.g., one or more T cell epitopes present in an HCV polypeptide other than an HCV E1 polypeptide or an HCV E2 polypeptide). In some cases, the variant HCV E2 polypeptide comprises, in order from N-terminus to C-terminus: i) the HCV E2 polypeptide; and ii) the heterologous polypeptide comprising the one or more T cell epitopes. In other cases, the variant HCV E2 polypeptide comprises, in order from N-terminus to C-terminus: i) the heterologous polypeptide comprising the one or more T cell epitopes; and ii) the HCV E2 polypeptide. In some cases, the nucleotide sequence encoding the fusion protein is operably linked to a transcription control element, e.g., a promoter that is functional in a eukaryotic cell. Suitable promoters include, e.g., a CMV promoter, an SV40 promoter, and the like. In some cases, the nucleic acid is present in an expression vector (e.g., a lentivirus vector; an adenoassociated virus vector; an adenovirus vector; a retroviral vector; a non-viral vector; etc.). In some cases, the E1/E2 polypeptide comprises a host-derived signal peptidase cleavage site between the E1 polypeptide and the Ig Fc region. Thus, in some cases, a nucleic acid of the present disclosure comprises a nucleotide sequence encoding an E1/E2 polypeptide comprising, in order from N-terminus to C-terminus: a) an HCV E1 polypeptide; b) a host-derived signal peptidase cleavage site; c) an Ig Fc region; d) a proteolytically cleavable linker; and e) a variant E2 polypeptide of the present disclosure, where the variant HCV E2 polypeptide comprises: i) an HCV E2 polypeptide; and ii) a heterologous polypeptide that comprises one or more T-cell epitopes (e.g., one or more T cell epitopes present in an HCV polypeptide other than an HCV E1 polypeptide or an HCV E2 polypeptide). In some cases, the variant HCV E2 polypeptide comprises, in order from N-terminus to C-terminus: i) the HCV E2 polypeptide; and ii) the heterologous polypeptide comprising the one or more T cell epitopes. In other cases, the variant HCV E2 polypeptide comprises, in order from N-terminus to C-terminus: i) the heterologous polypeptide comprising the one or more T cell epitopes; and ii) the HCV E2 polypeptide. In some cases, a nucleotide sequence encoding from 2 to 10 amino acids (e.g., 2 aa, 3 aa, 4 aa, 5 aa, 6 aa, 7 aa, 8 aa, 9 aa, or 10 aa) of the N-terminus of an E2 polypeptide is interposed between the E1-encoding nucleotide sequence and the Ig Fc-encoding nucleotide sequence. Examples are depicted in FIG. 5A. For example, in some cases, a nucleotide sequence encoding QT, ET, HT, GT, TT, RH, NT, AY, VI, or ST is interposed between the E1-encoding nucleotide sequence and the Ig Fc-encoding nucleotide sequence. In some cases, a nucleotide sequence encoding ET (Glu-Thr) is interposed between the E1-encoding nucleotide sequence and the Ig Fc-encoding nucleotide sequence. In some cases, a nucleotide sequence encoding QT (Gln-Thr) is interposed between the E1-encoding nucleotide sequence and the Ig Fc-encoding nucleotide sequence. In some cases, a nucleotide sequence encoding TT (Thr-Thr) is interposed between the E1-encoding nucleotide sequence and the Ig Fc-encoding nucleotide sequence. In some cases, a nucleotide sequence encoding GT (Gly-Thr) is interposed between the E1-encoding nucleotide sequence and the Ig Fc-encoding nucleotide sequence. In some cases, a nucleotide sequence encoding HT (His-Thr) is interposed between the E1-encoding nucleotide sequence and the Ig Fc-encoding nucleotide sequence. In some cases, a nucleotide sequence encoding NT (Asn-Thr) is interposed between the E1-encoding nucleotide sequence and the Ig Fc-encoding nucleotide sequence. In some cases, a nucleotide sequence encoding VT (Val-Thr) is interposed between the E1-encoding nucleotide sequence and the Ig Fc-encoding nucleotide sequence. In some cases, a nucleotide sequence encoding ST (Ser-Thr) is interposed between the E1-encoding nucleotide sequence and the Ig Fc-encoding nucleotide sequence.

In some cases, a nucleic acid of the present disclosure comprises a nucleotide sequence encoding an E1/E2 polypeptide comprising, in order from N-terminus to C-terminus: a) an HCV E1 polypeptide; b) an Ig Fc region; c) a proteolytically cleavable linker comprising the amino acid sequence LEVLFQGP (SEQ ID NO:5) and having a length of from 8 amino acids to 15 amino acids; and d) a variant E2 polypeptide of the present disclosure, where the variant HCV E2 polypeptide comprises: i) an HCV E2 polypeptide; and ii) a heterologous polypeptide that comprises one or more T-cell epitopes (e.g., one or more T cell epitopes present in an HCV polypeptide other than an HCV E1 polypeptide or an HCV E2 polypeptide). In some cases, the variant HCV E2 polypeptide comprises, in order from N-terminus to C-terminus: i) the HCV E2 polypeptide; and ii) the heterologous polypeptide comprising the one or more T cell epitopes. In other cases, the variant HCV E2 polypeptide comprises, in order from N-terminus to C-terminus: i) the heterologous polypeptide comprising the one or more T cell epitopes; and ii) the HCV E2 polypeptide. In some cases, the nucleotide sequence encoding the fusion protein is operably linked to a transcription control element, e.g., a promoter that is functional in a eukaryotic cell. Suitable promoters include, e.g., a CMV promoter, an SV40 promoter, and the like. In some cases, the nucleic acid is present in an expression vector (e.g., a lentivirus vector; an adeno-associated virus vector; an adenovirus vector; a retroviral vector; a non-viral vector; etc.). In some cases, the E1/E2 polypeptide comprises a host-derived signal peptidase cleavage site between the E1 polypeptide and the Ig Fc region. Thus, in some cases, a nucleic acid of the present disclosure comprises a nucleotide sequence encoding an E1/E2 polypeptide comprising, in order from N-terminus to C-terminus: a) an HCV E1 polypeptide; b) a host-derived signal peptidase cleavage site; c) an Ig Fc region; d) a proteolytically cleavable linker comprising the amino acid sequence LEVLFQGP (SEQ ID NO:5) and having a length of from 8 amino acids to 15 amino acids; and e) a variant E2 polypeptide of the present disclosure, where the variant HCV E2 polypeptide comprises: i) an HCV E2 polypeptide; and ii) a heterologous polypeptide that comprises one or more T-cell epitopes (e.g., one or more T cell epitopes present in an HCV polypeptide other than an HCV E1 polypeptide or an HCV E2 polypeptide). In some cases, the variant HCV E2 polypeptide comprises, in order from N-terminus to C-terminus: i) the HCV E2 polypeptide; and ii) the heterologous polypeptide comprising the one or more T cell epitopes. In other cases, the variant HCV E2 polypeptide comprises, in order from N-terminus to C-terminus: i) the heterologous polypeptide comprising the one or more T cell epitopes; and ii) the HCV E2 polypeptide. In some cases, a nucleotide sequence encoding from 2 to 10 amino acids (e.g., 2 aa, 3 aa, 4 aa, 5 aa, 6 aa, 7 aa, 8 aa, 9 aa, or 10 aa) of the N-terminus of an E2 polypeptide is interposed between the E1-encoding nucleotide sequence and the Ig Fc-encoding nucleotide sequence. Examples are depicted in FIG. 5A. For example, in some cases, a nucleotide sequence encoding QT, ET, HT, GT, TT, RH, NT, AY, VI, or ST is interposed between the E1-encoding nucleotide sequence and the Ig Fc-encoding nucleotide sequence. In some cases, a nucleotide sequence encoding ET (Glu-Thr) is interposed between the E1-encoding nucleotide sequence and the Ig Fc-encoding nucleotide sequence. In some cases, a nucleotide sequence encoding QT (Gln-Thr) is interposed between the E1-encoding nucleotide sequence and the Ig Fc-encoding nucleotide sequence. In some cases, a nucleotide sequence encoding TT (Thr-Thr) is interposed between the E1-encoding nucleotide sequence and the Ig Fc-encoding nucleotide sequence. In some cases, a nucleotide sequence encoding GT (Gly-Thr) is interposed between the E1-encoding nucleotide sequence and the Ig Fc-encoding nucleotide sequence. In some cases, a nucleotide sequence encoding HT (His-Thr) is interposed between the E1-encoding nucleotide sequence and the Ig Fc-encoding nucleotide sequence. In some cases, a nucleotide sequence encoding NT (Asn-Thr) is interposed between the E1-encoding nucleotide sequence and the Ig Fc-encoding nucleotide sequence. In some cases, a nucleotide sequence encoding VT (Val-Thr) is interposed between the E1-encoding nucleotide sequence and the Ig Fc-encoding nucleotide sequence. In some cases, a nucleotide sequence encoding ST (Ser-Thr) is interposed between the E1-encoding nucleotide sequence and the Ig Fc-encoding nucleotide sequence.

In some cases, a nucleic acid of the present disclosure comprises a nucleotide sequence encoding an E1/E2 polypeptide comprising, in order from N-terminus to C-terminus: a) an HCV E1 polypeptide; b) an Ig Fc region; c) a proteolytically cleavable linker comprising the amino acid sequence ENLYTQS (SEQ ID NO:6) and having a length of from 7 amino acids to 12 amino acids; and d) a variant E2 polypeptide of the present disclosure, where the variant HCV E2 polypeptide comprises: i) an HCV E2 polypeptide; and ii) a heterologous polypeptide that comprises one or more T-cell epitopes (e.g., one or more T cell epitopes present in an HCV polypeptide other than an HCV E1 polypeptide or an HCV E2 polypeptide). In some cases, the variant HCV E2 polypeptide comprises, in order from N-terminus to C-terminus: i) the HCV E2 polypeptide; and ii) the heterologous polypeptide comprising the one or more T cell epitopes. In other cases, the variant HCV E2 polypeptide comprises, in order from N-terminus to C-terminus: i) the heterologous polypeptide comprising the one or more T cell epitopes; and ii) the HCV E2 polypeptide. In some cases, the nucleotide sequence encoding the fusion protein is operably linked to a transcription control element, e.g., a promoter that is functional in a eukaryotic cell. Suitable promoters include, e.g., a CMV promoter, an SV40 promoter, and the like. In some cases, the nucleic acid is present in an expression vector (e.g., a lentivirus vector; an adeno-associated virus vector; an adenovirus vector; a retroviral vector; a non-viral vector; etc.). In some cases, the E1/E2 polypeptide comprises a host-derived signal peptidase cleavage site between the E1 polypeptide and the Ig Fc region. Thus, in some cases, a nucleic acid of the present disclosure comprises a nucleotide sequence encoding an E1/E2 polypeptide comprising, in order from N-terminus to C-terminus: a) an HCV E1 polypeptide; b) a host-derived signal peptidase cleavage site; c) an Ig Fc region; d) a proteolytically cleavable linker comprising the amino acid sequence ENLYTQS (SEQ ID NO:6) and having a length of from 7 amino acids to 12 amino acids; and e) a variant E2 polypeptide of the present disclosure, where the variant HCV E2 polypeptide comprises: i) an HCV E2 polypeptide; and ii) a heterologous polypeptide that comprises one or more T-cell epitopes (e.g., one or more T cell epitopes present in an HCV polypeptide other than an HCV E1 polypeptide or an HCV E2 polypeptide). In some cases, the variant HCV E2 polypeptide comprises, in order from N-terminus to C-terminus: i) the HCV E2 polypeptide; and ii) the heterologous polypeptide comprising the one or more T cell epitopes. In other cases, the variant HCV E2 polypeptide comprises, in order from N-terminus to C-terminus: i) the heterologous polypeptide comprising the one or more T cell epitopes; and ii) the HCV E2 polypeptide. In some cases, a nucleotide sequence encoding from 2 to 10 amino acids (e.g., 2 aa, 3 aa, 4 aa, 5 aa, 6 aa, 7 aa, 8 aa, 9 aa, or 10 aa) of the N-terminus of an E2 polypeptide is interposed between the E1-encoding nucleotide sequence and the Ig Fc-encoding nucleotide sequence. Examples are depicted in FIG. 5A. For example, in some cases, a nucleotide sequence encoding QT, ET, HT, GT, TT, RH, NT, AY, VI, or ST is interposed between the E1-encoding nucleotide sequence and the Ig Fc-encoding nucleotide sequence. In some cases, a nucleotide sequence encoding ET (Glu-Thr) is interposed between the E1-encoding nucleotide sequence and the Ig Fc-encoding nucleotide sequence. In some cases, a nucleotide sequence encoding QT (Gln-Thr) is interposed between the E1-encoding nucleotide sequence and the Ig Fc-encoding nucleotide sequence. In some cases, a nucleotide sequence encoding TT (Thr-Thr) is interposed between the E1-encoding nucleotide sequence and the Ig Fc-encoding nucleotide sequence. In some cases, a nucleotide sequence encoding GT (Gly-Thr) is interposed between the E1-encoding nucleotide sequence and the Ig Fc-encoding nucleotide sequence. In some cases, a nucleotide sequence encoding HT (His-Thr) is interposed between the E1-encoding nucleotide sequence and the Ig Fc-encoding nucleotide sequence. In some cases, a nucleotide sequence encoding NT (Asn-Thr) is interposed between the E1-encoding nucleotide sequence and the Ig Fc-encoding nucleotide sequence. In some cases, a nucleotide sequence encoding VT (Val-Thr) is interposed between the E1-encoding nucleotide sequence and the Ig Fc-encoding nucleotide sequence. In some cases, a nucleotide sequence encoding ST (Ser-Thr) is interposed between the E1-encoding nucleotide sequence and the Ig Fc-encoding nucleotide sequence.

In some cases, a nucleic acid of the present disclosure comprises a nucleotide sequence encoding an E1/E2 polypeptide comprising, in order from N-terminus to C-terminus: a) a signal peptide that directs the E1/E2 polypeptide to the endoplasmic reticulum (ER) following translation of the E1/E2 polypeptide; b) an HCV E1 polypeptide; c) an Ig Fc region; d) a proteolytically cleavable linker; and e) a variant E2 polypeptide of the present disclosure, where the variant HCV E2 polypeptide comprises: i) an HCV E2 polypeptide; and ii) a heterologous polypeptide that comprises one or more T-cell epitopes (e.g., one or more T cell epitopes present in an HCV polypeptide other than an HCV E1 polypeptide or an HCV E2 polypeptide). In some cases, the variant HCV E2 polypeptide comprises, in order from N-terminus to C-terminus: i) the HCV E2 polypeptide; and ii) the heterologous polypeptide comprising the one or more T cell epitopes. In other cases, the variant HCV E2 polypeptide comprises, in order from N-terminus to C-terminus: i) the heterologous polypeptide comprising the one or more T cell epitopes; and ii) the HCV E2 polypeptide. In some cases, the nucleotide sequence encoding the fusion protein is operably linked to a transcription control element, e.g., a promoter that is functional in a eukaryotic cell. Suitable promoters include, e.g., a CMV promoter, an SV40 promoter, and the like. In some cases, the nucleic acid is present in an expression vector (e.g., a lentivirus vector; an adeno-associated virus vector; an adenovirus vector; a retroviral vector; a non-viral vector; etc.). In some cases, the E1/E2 polypeptide comprises a host-derived signal peptidase cleavage site between the E1 polypeptide and the Ig Fc region, and comprises a host-derived signal peptidase cleavage site between the signal peptide and the HCV E1 polypeptide. Thus, in some cases, a nucleic acid of the present disclosure comprises a nucleotide sequence encoding an E1/E2 polypeptide comprising, in order from N-terminus to C-terminus: a) a signal peptide that directs the E1/E2 polypeptide to the ER following translation of the E1/E2 polypeptide; b) a host-derived signal peptidase cleavage site; c) an HCV E1 polypeptide; d) a host-derived signal peptidase cleavage site; e) an Ig Fc region; f) a proteolytically cleavable linker; and g) a variant E2 polypeptide of the present disclosure, where the variant HCV E2 polypeptide comprises: i) an HCV E2 polypeptide; and ii) a heterologous polypeptide that comprises one or more T-cell epitopes (e.g., one or more T cell epitopes present in an HCV polypeptide other than an HCV E1 polypeptide or an HCV E2 polypeptide). In some cases, the variant HCV E2 polypeptide comprises, in order from N-terminus to C-terminus: i) the HCV E2 polypeptide; and ii) the heterologous polypeptide comprising the one or more T cell epitopes. In other cases, the variant HCV E2 polypeptide comprises, in order from N-terminus to C-terminus: i) the heterologous polypeptide comprising the one or more T cell epitopes; and ii) the HCV E2 polypeptide. In some cases, a nucleotide sequence encoding from 2 to 10 amino acids (e.g., 2 aa, 3 aa, 4 aa, 5 aa, 6 aa, 7 aa, 8 aa, 9 aa, or 10 aa) of the N-terminus of an E2 polypeptide is interposed between the E1-encoding nucleotide sequence and the Ig Fc-encoding nucleotide sequence. Examples are depicted in FIG. 5A. For example, in some cases, a nucleotide sequence encoding QT, ET, HT, GT, TT, RH, NT, AY, VI, or ST is interposed between the E1-encoding nucleotide sequence and the Ig Fc-encoding nucleotide sequence. In some cases, a nucleotide sequence encoding ET (Glu-Thr) is interposed between the E1-encoding nucleotide sequence and the Ig Fc-encoding nucleotide sequence. In some cases, a nucleotide sequence encoding QT (Gln-Tbr) is interposed between the E1-encoding nucleotide sequence and the Ig Fc-encoding nucleotide sequence. In some cases, a nucleotide sequence encoding TT (Tbr-Thr) is interposed between the E1-encoding nucleotide sequence and the Ig Fc-encoding nucleotide sequence. In some cases, a nucleotide sequence encoding GT (Gly-Thr) is interposed between the E1-encoding nucleotide sequence and the Ig Fc-encoding nucleotide sequence. In some cases, a nucleotide sequence encoding HT (His-Thr) is interposed between the E1-encoding nucleotide sequence and the Ig Fc-encoding nucleotide sequence. In some cases, a nucleotide sequence encoding NT (Asn-Thr) is interposed between the E1-encoding nucleotide sequence and the Ig Fc-encoding nucleotide sequence. In some cases, a nucleotide sequence encoding VT (Val-Thr) is interposed between the E1-encoding nucleotide sequence and the Ig Fc-encoding nucleotide sequence. In some cases, a nucleotide sequence encoding ST (Ser-Thr) is interposed between the E1-encoding nucleotide sequence and the Ig Fc-encoding nucleotide sequence.

Suitable signal peptides include, e.g., a tissue plasminogen activator (tPA) signal peptide; an Ig kappa light chain precursor signal peptide; a serum albumin preproprotein signal peptide; an Immunoglobulin heavy chain signal peptide; an Immunoglobulin light chain signal peptide; an azuorcidin preproprotein signal peptide; a cystatin-S precursor signal peptide; a trypsinogen-2 precursor signal peptide; a chymotrypsinogen precursor signal peptide; and the like.

(Bendtsen et al. (2004) *J. Mol. Biol.* 340 783-795; Kober et al. (2012) *Biotechnology and Bioengineering* 110(4) 1164-1173).

In some cases, a nucleic acid of the present disclosure comprises a nucleotide sequence encoding an E1/E2 polypeptide comprising, in order from N-terminus to C-terminus: a) a signal peptide that directs the E1/E2 polypeptide to the endoplasmic reticulum (ER) following translation of the E1/E2 polypeptide; b) an HCV E1 polypeptide; c) an Ig Fc region; d) a proteolytically cleavable linker comprising the amino acid sequence LEVLFQGP (SEQ ID NO:5) and having a length of from 8 amino acids to 15 amino acids; and e) a variant E2 polypeptide of the present disclosure, where the variant HCV E2 polypeptide comprises: i) an HCV E2 polypeptide; and ii) a heterologous polypeptide that comprises one or more T-cell epitopes (e.g., one or more T cell epitopes present in an HCV polypeptide other than an HCV E1 polypeptide or an HCV E2 polypeptide). In some cases, the variant HCV E2 polypeptide comprises, in order from N-terminus to C-terminus: i) the HCV E2 polypeptide; and ii) the heterologous polypeptide comprising the one or more T cell epitopes. In other cases, the variant HCV E2 polypeptide comprises, in order from N-terminus to C-terminus: i) the heterologous polypeptide comprising the one or more T cell epitopes; and ii) the HCV E2 polypeptide. In some cases, the nucleotide sequence encoding the fusion protein is operably linked to a transcription control element, e.g., a promoter that is functional in a eukaryotic cell. Suitable promoters include, e.g., a CMV promoter, an SV40 promoter, and the like. In some cases, the nucleic acid is present in an expression vector (e.g., a lentivirus vector; an adeno-associated virus vector; an adenovirus vector; a retroviral vector; a non-viral vector; etc.). In some cases, the E1/E2 polypeptide comprises a host-derived signal peptidase cleavage site between the E1 polypeptide and the Ig Fc region, and comprises a host-derived signal peptidase cleavage site between the signal peptide and the HCV E1 polypeptide. Thus, in some cases, a nucleic acid of the present disclosure comprises a nucleotide sequence encoding an E1/E2 polypeptide comprising, in order from N-terminus to C-terminus: a) a signal peptide that directs the E1/E2 polypeptide to the endoplasmic reticulum (ER) following translation of the E1/E2 polypeptide; b) a host-derived signal peptidase cleavage site; c) an HCV E1 polypeptide; d) a host-derived signal peptidase cleavage site; e) an Ig Fc region; f) a proteolytically cleavable linker comprising the amino acid sequence LEVLFQGP (SEQ ID NO:5) and having a length of from 8 amino acids to 15 amino acids; and g) a variant E2 polypeptide of the present disclosure, where the variant HCV E2 polypeptide comprises: i) an HCV E2 polypeptide; and ii) a heterologous polypeptide that comprises one or more T-cell epitopes (e.g., one or more T cell epitopes present in an HCV polypeptide other than an HCV E1 polypeptide or an HCV E2 polypeptide). In some cases, the variant HCV E2 polypeptide comprises, in order from N-terminus to C-terminus: i) the HCV E2 polypeptide; and ii) the heterologous polypeptide comprising the one or more T cell epitopes. In other cases, the variant HCV E2 polypeptide comprises, in order from N-terminus to C-terminus: i) the heterologous polypeptide comprising the one or more T cell epitopes; and ii) the HCV E2 polypeptide. In some cases, a nucleotide sequence encoding from 2 to 10 amino acids (e.g., 2 aa, 3 aa, 4 aa, 5 aa, 6 aa, 7 aa, 8 aa, 9 aa, or 10 aa) of the N-terminus of an E2 polypeptide is interposed between the E1-encoding nucleotide sequence and the Ig Fc-encoding nucleotide sequence. Examples are depicted in FIG. 5A. For example, in some cases, a nucleotide sequence encoding QT, ET, HT, GT, TT, RH, NT, AY, VI, or ST is interposed between the E1-encoding nucleotide sequence and the Ig Fc-encoding nucleotide sequence. In some cases, a nucleotide sequence encoding ET (Glu-Thr) is interposed between the E1-encoding nucleotide sequence and the Ig Fc-encoding nucleotide sequence. In some cases, a nucleotide sequence encoding QT (Gln-Thr) is interposed between the E1-encoding nucleotide sequence and the Ig Fc-encoding nucleotide sequence. In some cases, a nucleotide sequence encoding TT (Thr-Thr) is interposed between the E1-encoding nucleotide sequence and the Ig Fc-encoding nucleotide sequence. In some cases, a nucleotide sequence encoding GT (Gly-Thr) is interposed between the E1-encoding nucleotide sequence and the Ig Fc-encoding nucleotide sequence. In some cases, a nucleotide sequence encoding HT (His-Thr) is interposed between the E1-encoding nucleotide sequence and the Ig Fc-encoding nucleotide sequence. In some cases, a nucleotide sequence encoding NT (Asn-Thr) is interposed between the E1-encoding nucleotide sequence and the Ig Fc-encoding nucleotide sequence. In some cases, a nucleotide sequence encoding VT (Val-Thr) is interposed between the E1-encoding nucleotide sequence and the Ig Fc-encoding nucleotide sequence. In some cases, a nucleotide sequence encoding ST (Ser-Thr) is interposed between the E1-encoding nucleotide sequence and the Ig Fc-encoding nucleotide sequence.

In some cases, a nucleic acid of the present disclosure comprises a nucleotide sequence encoding an E1/E2 polypeptide comprising, in order from N-terminus to C-terminus: a) a signal peptide that directs the E1/E2 polypeptide to the endoplasmic reticulum (ER) following translation of the E1/E2 polypeptide; b) an HCV E1 polypeptide; c) an Ig Fc region; d) a proteolytically cleavable linker comprising the amino acid sequence ENLYTQS (SEQ ID NO:6) and having a length of from 7 amino acids to 12 amino acids; and e) a variant E2 polypeptide of the present disclosure, where the variant HCV E2 polypeptide comprises: i) an HCV E2 polypeptide; and ii) a heterologous polypeptide that comprises one or more T-cell epitopes (e.g., one or more T cell epitopes present in an HCV polypeptide other than an HCV E1 polypeptide or an HCV E2 polypeptide). In some cases, the variant HCV E2 polypeptide comprises, in order from N-terminus to C-terminus: i) the HCV E2 polypeptide; and ii) the heterologous polypeptide comprising the one or more T cell epitopes. In other cases, the variant HCV E2 polypeptide comprises, in order from N-terminus to C-terminus: i) the heterologous polypeptide comprising the one or more T cell epitopes; and ii) the HCV E2 polypeptide. In some cases, the nucleotide sequence encoding the fusion protein is operably linked to a transcription control element, e.g., a promoter that is functional in a eukaryotic cell. Suitable promoters include, e.g., a CMV promoter, an SV40 promoter, and the like. In some cases, the nucleic acid is present in an expression vector (e.g., a lentivirus vector; an adeno-associated virus vector; an adenovirus vector; a retroviral vector; a non-viral vector; etc.). In some cases, the E1/E2 polypeptide comprises a host-derived signal peptidase cleavage site between the E1 polypeptide and the Ig Fc region, and comprises a host-derived signal peptidase cleavage site between the signal peptide and the HCV E1 polypeptide. Thus, in some cases, a nucleic acid of the present disclosure comprises a nucleotide sequence encoding an E1/E2 polypeptide comprising, in order from N-terminus to C-terminus: a) a signal peptide that directs the E1/E2 polypeptide to the ER following translation of the E1/E2 polypeptide; b) a host-derived signal peptidase cleavage site; c) an HCV E1 polypeptide; d) a host-derived signal peptidase cleavage site; e) an Ig Fc region; f) a proteolytically cleavable linker comprising the amino acid sequence ENLYTQS (SEQ ID NO:6) and having a length of from 7 amino acids to 12 amino acids; and g) a variant E2 polypeptide of the present disclosure, where the variant HCV E2 polypeptide comprises: i) an HCV E2 polypeptide; and ii) a heterologous polypeptide that comprises one or more T-cell epitopes (e.g., one or more T cell epitopes present in an HCV polypeptide other than an HCV E1 polypeptide or an HCV E2 polypeptide). In some cases, the variant HCV E2 polypeptide comprises, in order from N-terminus to C-terminus: i) the HCV E2 polypeptide; and ii) the heterologous polypeptide comprising the one or more T cell epitopes. In other cases, the variant HCV E2 polypeptide comprises, in order from N-terminus to C-terminus: i) the heterologous polypeptide comprising the one or more T cell epitopes; and ii) the HCV E2 polypeptide. In some cases, a nucleotide sequence encoding from 2 to 10 amino acids (e.g., 2 aa, 3 aa, 4 aa, 5 aa, 6 aa, 7 aa, 8 aa, 9 aa, or 10 aa) of the N-terminus of an E2 polypeptide is interposed between the E1-encoding nucleotide sequence and the Ig Fc-encoding nucleotide sequence. Examples are depicted in FIG. 5A. For example, in some cases, a nucleotide sequence encoding QT, ET, HT, GT, TT, RH, NT, AY, VI, or ST is interposed between the E1-encoding nucleotide sequence and the Ig Fc-encoding nucleotide sequence. In some cases, a nucleotide sequence encoding ET (Glu-Thr) is interposed between the E1-encoding nucleotide sequence and the Ig Fc-encoding nucleotide sequence. In some cases, a nucleotide sequence encoding QT (Gln-Thr) is interposed between the E1-encoding nucleotide sequence and the Ig Fc-encoding nucleotide sequence. In some cases, a nucleotide sequence encoding TT (Thr-Thr) is interposed between the E1-encoding nucleotide sequence and the Ig Fc-encoding nucleotide sequence. In some cases, a nucleotide sequence encoding GT (Gly-Thr) is interposed between the E1-encoding nucleotide sequence and the Ig Fc-encoding nucleotide sequence. In some cases, a nucleotide sequence encoding HT (His-Thr) is interposed between the E1-encoding nucleotide sequence and the Ig Fc-encoding nucleotide sequence. In some cases, a nucleotide sequence encoding NT (Asn-Thr) is interposed between the E1-encoding nucleotide sequence and the Ig Fc-encoding nucleotide sequence. In some cases, a nucleotide sequence encoding VT (Val-Thr) is interposed between the E1-encoding nucleotide sequence and the Ig Fc-encoding nucleotide sequence. In some cases, a nucleotide sequence encoding ST (Ser-Thr) is interposed between the E1-encoding nucleotide sequence and the Ig Fc-encoding nucleotide sequence.

As noted above, in some cases, a nucleic acid of the present disclosure is present in an expression vector. Thus, the present disclosure provides a recombinant expression vector comprising a nucleic acid comprising a nucleotide sequence encoding a variant E2 polypeptide of the present disclosure or comprising a nucleotide sequence encoding an E1/E2 heterodimer of the present disclosure. In some cases, the nucleotide sequence encoding the variant E2 polypeptide of the present disclosure or the nucleotide sequence encoding the E1/E2 heterodimer of the present disclosure is operably linked to a transcriptional control element, e.g., a promoter, such as a promoter functional in a eukaryotic cell.

Suitable expression vectors include, but are not limited to, baculovirus vectors, bacteriophage vectors, plasmids, phagemids, cosmids, fosmids, bacterial artificial chromosomes, viral vectors (e.g. viral vectors based on vaccinia virus, poliovirus, adenovirus, adeno-associated virus, SV40, herpes simplex virus, HIV-based lentivirus vectors, murine leukemia virus (MVL)-based gamma retrovirus vectors, and the like), P1-based artificial chromosomes, yeast plasmids, yeast artificial chromosomes, and any other vectors specific for specific hosts of interest (such as *E. coli*, mammalian cells, insect cells, or yeast cells).

IV(B). Variant E1 and E1/E2 Heterodimers Comprising a Variant E1 Polypeptide

The present disclosure provides a nucleic acid comprising a nucleotide sequence encoding a variant HCV E1 polypeptide of the present disclosure, where the variant HCV E1 polypeptide comprises: i) an HCV E1 polypeptide; and ii) a heterologous polypeptide that comprises one or more T-cell epitopes (e.g., one or more T cell epitopes present in an HCV polypeptide other than an HCV E1 polypeptide or an HCV E2 polypeptide). The present disclosure provides a nucleic acid comprising a nucleotide sequence encoding a polyprotein comprising a variant E1 polypeptide of the present disclosure. In some cases, the nucleic acid is present in an expression vector. Thus, the present disclosure provides a recombinant expression vector comprising a nucleotide sequence encoding a variant E1 polypeptide of the present disclosure, where the variant HCV E1 polypeptide comprises: i) an HCV E1 polypeptide; and ii) a heterologous polypeptide that comprises one or more T-cell epitopes (e.g., one or more T cell epitopes present in an HCV polypeptide other than an HCV E1 polypeptide or an HCV E2 polypeptide).

In some cases, a nucleic acid of the present disclosure comprises a nucleotide sequence encoding a variant E1 polypeptide of the present disclosure, where the variant HCV E1 polypeptide comprises: i) an HCV E1 polypeptide; and ii) a heterologous polypeptide that comprises one or more T-cell epitopes (e.g., one or more T cell epitopes present in an HCV polypeptide other than an HCV E1 polypeptide or an HCV E2 polypeptide). In some cases, the nucleotide sequence encoding the variant E2 polypeptide is operably linked to a transcription control element, e.g., a promoter that is functional in a eukaryotic cell. Suitable promoters include, e.g., a cytomegalovirus (CMV) promoter, an SV40 promoter, and the like. In some cases, the nucleic acid is present in an expression vector (e.g., a lentivirus vector; an adenoassociated virus vector; an adenovirus vector; a retroviral vector; a non-viral vector; etc.). In some cases, the nucleic acid is present in an expression vector, where the expression vector is a non-viral vector.

In some cases, a nucleic acid of the present disclosure comprises a nucleotide sequence encoding a fusion protein comprising, in order from N-terminus to C-terminus: a) an immunoglobulin (Ig) Fc region; and b) a variant E1 polypeptide of the present disclosure, where the variant HCV E1 polypeptide comprises: i) an HCV E1 polypeptide; and ii) a heterologous polypeptide that comprises one or more T-cell epitopes (e.g., one or more T cell epitopes present in an HCV polypeptide other than an HCV E1 polypeptide or an HCV E2 polypeptide). In some cases, the variant HCV E1 polypeptide comprises, in order from N-terminus to C-terminus: i) the HCV E1 polypeptide; and ii) the heterologous polypeptide comprising the one or more T cell epitopes. In some cases, the variant HCV E1 polypeptide comprises, in order from N-terminus to C-terminus: i) the heterologous polypeptide comprising the one or more T cell epitopes; and ii) the HCV E1 polypeptide. In some cases, the nucleotide sequence encoding the fusion protein is operably linked to a transcription control element. e.g., a promoter that is functional in a eukaryotic cell. Suitable promoters include, e.g., a CMV promoter, an SV40 promoter, and the like. In some cases, the nucleic acid is present in an expression vector (e.g., a lentivirus vector; an adenoassociated virus vector; an adenovirus vector; a retroviral vector; a non-viral vector; etc.).

In some cases, a nucleic acid of the present disclosure comprises a nucleotide sequence encoding a fusion protein comprising, in order from N-terminus to C-terminus: a) an Ig Fc region; b) a proteolytically cleavable linker; and c) a variant E1 polypeptide of the present disclosure, where the variant HCV E1 polypeptide comprises: i) an HCV E1 polypeptide; and ii) a heterologous polypeptide that comprises one or more T-cell epitopes (e.g., one or more T cell epitopes present in an HCV polypeptide other than an HCV E1 polypeptide or an HCV E2 polypeptide). In some cases, the variant HCV E1 polypeptide comprises, in order from N-terminus to C-terminus: i) the HCV E1 polypeptide; and ii) the heterologous polypeptide comprising the one or more T cell epitopes. In other cases, the variant HCV E1 polypeptide comprises, in order from N-terminus to C-terminus: i) the heterologous polypeptide comprising the one or more T cell epitopes; and ii) the HCV E1 polypeptide. In some cases, the nucleotide sequence encoding the fusion protein is operably linked to a transcription control element, e.g., a promoter that is functional in a eukaryotic cell. Suitable promoters include, e.g., a CMV promoter, an SV40 promoter, and the like. In some cases, the nucleic acid is present in an expression vector (e.g., a lentivirus vector; an adenoassociated virus vector; an adenovirus vector; a retroviral vector; a non-viral vector; etc.).

The proteolytically cleavable linker can include a protease recognition sequence recognized by a protease selected from the group consisting of alanine carboxypeptidase, *Armillaria mellea* astacin, bacterial leucyl aminopeptidase, cancer procoagulant, cathepsin B, clostripain, cytosol alanyl aminopeptidase, elastase, endoproteinase Arg-C, enterokinase, gastricsin, gelatinase, Gly-X carboxypeptidase, glycyl endopeptidase, human rhinovirus 3C protease, hypodermin C, IgA-specific serine endopeptidase, leucyl aminopeptidase, leucyl endopeptidase, lysC, lysosomal pro-X carboxypeptidase, lysyl aminopeptidase, methionyl aminopeptidase, myxobacter, nardilysin, pancreatic endopeptidase E, picornain 2A, picornain 3C, proendopeptidase, prolyl aminopeptidase, proprotein convertase I, proprotein convertase II, russellysin, saccharopepsin, semenogelase, T-plasminogen activator, thrombin, tissue kallikrein, tobacco etch virus (TEV), togavirin, tryptophanyl aminopeptidase, U-plasminogen activator, V8, venombin A, venombin AB, and Xaa-pro aminopeptidase.

For example, the proteolytically cleavable linker can comprise a matrix metalloproteinase cleavage site, e.g., a cleavage site for a MMP selected from collagenase-1, -2, and -3 (MMP-1, -8, and -13), gelatinase A and B (MMP-2 and -9), stromelysin 1, 2, and 3 (MMP-3, -10, and -11), matrilysin (MMP-7), and membrane metalloproteinases (MT1-MMP and MT2-MMP). For example, the cleavage sequence of MMP-9 is Pro-X-X-Hy (wherein, X represents an arbitrary residue; Hy, a hydrophobic residue; SEQ ID NO:70), e.g., Pro-X-X-Hy-(Ser/Thr) SEQ ID NO:71, e.g., Pro-Leu/Gln-Gly-Met-Thr-Ser (SEQ ID NO:72) or Pro-Leu/Gln-Gly-Met-Thr (SEQ ID NO:73). Another example of a protease cleavage site is a plasminogen activator cleavage site, e.g., a uPA or a tissue plasminogen activator (tPA) cleavage site. In some cases, the cleavage site is afurin cleavage site. Specific examples of cleavage sequences of uPA and tPA include sequences comprising Val-Gly-Arg. Another example of a protease cleavage site that can be included in a proteolytically cleavable linker is a tobacco etch virus (TEV) protease cleavage site, e.g., ENLYTQS (SEQ ID NO:6), where the protease cleaves between the glutamine and the serine. Another example of a protease cleavage site that can be included in a proteolytically cleavable linker is an enterokinase cleavage site, e.g., DDDDK (SEQ ID NO:7), where cleavage occurs after the lysine residue. Another example of a protease cleavage site that can be included in a proteolytically cleavable linker is a thrombin cleavage site, e.g., LVPR (SEQ ID NO:8). Additional suitable linkers comprising protease cleavage sites include linkers comprising one or more of the following amino acid sequences: LEVLFQGP (SEQ ID NO:5), cleaved by PreScission protease (a fusion protein comprising human rhinovirus 3C protease and glutathione-S-transferase; Walker et al. (1994) Biotechnol. 12:601); a thrombin cleavage site, e.g., CGLVPAGSGP (SEQ ID NO:30); SLLKSRMVPNFN (SEQ ID NO:31) or SLLIARRMPNFN (SEQ ID NO:32), cleaved by cathepsin B; SKLVQASASGVN (SEQ ID NO:33) or SSYLKASDAPDN (SEQ ID NO:34), cleaved by an Epstein-Barr virus protease; RPKPQQFFGLMN (SEQ ID NO:35) cleaved by MMP-3 (stromelysin); SLRPLALWRSFN (SEQ ID NO:36) cleaved by MMP-7 (matrilysin); SPQGIAGQRNFN (SEQ ID NO:37) cleaved by MMP-9; DVDERDVRGFASFL SEQ ID NO:38) cleaved by a thermolysin-like MMP; SLPLGLWAPNFN (SEQ ID NO:39) cleaved by matrix metalloproteinase 2(MMP-2); SLLIFRSWANFN (SEQ ID NO:40) cleaved by cathespin L; SGVVIATVIVIT (SEQ ID NO:41) cleaved by cathepsin D; SLGPQGIWGQFN (SEQ ID NO:42) cleaved by matrix metalloproteinase 1(MMP-1); KKSPGRVVGGSV (SEQ ID NO:43) cleaved by urokinase-type plasminogen activator; PQGLLGAPGILG (SEQ ID NO:44) cleaved by membrane type 1 matrixmetalloproteinase (MT-MMP); HGPEGLRVGFYESDVMGRGHARLVHVEEPHT (SEQ ID NO:45) cleaved by stromelysin 3 (or MMP-11), thermolysin, fibroblast collagenase and stromelysin-1; GPQGLAGQRGIV (SEQ ID NO:46) cleaved by matrix metalloproteinase 13 (collagenase-3); GGSGQRGRKALE (SEQ ID NO:47) cleaved by tissue-type plasminogen activator(tPA); SLSALLSSDIFN (SEQ ID NO:48) cleaved by human prostate-specific antigen; SLPRFKIIGGFN (SEQ ID NO:49) cleaved by kallikrein (hK3); SLLGIAVPGNFN (SEQ ID NO:50) cleaved by neutrophil elastase; and FFKNIVTPRTPP (SEQ ID NO:51) cleaved by calpain (calcium activated neutral protease).

The Fc region can be a human IgG1 Fc, a human IgG2 Fc, a human IgG3 Fc, a human IgG4 Fc, etc. In some cases, the Fc region comprises an amino acid sequence having at least about 70%, at least about 75%, at least about 80%, at least about 85%, at least about 90%, at least about 95%, at least about 98%, at least about 99%, or 100%, amino acid sequence identity to an amino acid sequence of an Fc region depicted in FIGS. 9A-9C. In some cases, the Fc region comprises an amino acid sequence having at least about 70%, at least about 75%, at least about 80%, at least about 85%, at least about 90%, at least about 95%, at least about 98%, at least about 99%, or 100%, amino acid sequence identity to the human IgG1 Fc polypeptide depicted in FIG. 9A. In some cases, the Fc region comprises an amino acid sequence having at least about 70%, at least about 75%, at least about 80%, at least about 85%, at least about 90%, at least about 95%, at least about 98%, at least about 99%, or 100%, amino acid sequence identity to the human IgG2 Fc polypeptide depicted in FIG. 9A; e.g., the Fc region comprises an amino acid sequence having at least about 70%, at least about 75%, at least about 80%, at least about 85%, at least about 90%, at least about 95%, at least about 98%, at least about 99%, or 100%, amino acid sequence identity to amino acids 99-325 of the human IgG2 Fc polypeptide depicted in FIG. 9A. In some cases, the Fc region comprises an amino acid sequence having at least about 70%, at least about 75%, at least about 80%, at least about 85%, at least about 90%, at least about 95%, at least about 98%, at least about 99%, or 100%, amino acid sequence identity to the human IgG3 Fc polypeptide depicted in FIG. 9A; e.g., the Fc region comprises an amino acid sequence having at least about 70%, at least about 75%, at least about 80%, at least about 85%, at least about 90%, at least about 95%, at least about 98%, at least about 99%, or 100%, amino acid sequence identity to amino acids 19-246 of the human IgG3 Fc polypeptide depicted in FIG. 9A.

In some cases, a nucleic acid of the present disclosure comprises a nucleotide sequence encoding a fusion protein comprising, in order from N-terminus to C-terminus: a) an Ig Fc region; b) a proteolytically cleavable linker comprising the amino acid sequence LEVLFQGP (SEQ ID NO:5) and having a length of from 8 amino acids to 15 amino acids; and c) a variant E1 polypeptide of the present disclosure, where the variant HCV E1 polypeptide comprises: i) an HCV E1 polypeptide; and ii) a heterologous polypeptide that comprises one or more T-cell epitopes (e.g., one or more T cell epitopes present in an HCV polypeptide other than an HCV E1 polypeptide or an HCV E2 polypeptide). In some cases, the variant HCV E1 polypeptide comprises, in order from N-terminus to C-terminus: i) the HCV E1 polypeptide; and ii) the heterologous polypeptide comprising the one or more T cell epitopes. In other cases, the variant HCV E1 polypeptide comprises, in order from N-terminus to C-terminus: i) the heterologous polypeptide comprising the one or more T cell epitopes; and ii) the HCV E1 polypeptide. In some cases, the nucleotide sequence encoding the fusion protein is operably linked to a transcription control element, e.g., a promoter that is functional in a eukaryotic cell. Suitable promoters include, e.g., a CMV promoter, an SV40 promoter, and the like. In some cases, the nucleic acid is present in an expression vector (e.g., a lentivirus vector; an adeno-associated virus vector; an adenovirus vector; a retroviral vector; a non-viral vector; etc.).

In some cases, a nucleic acid of the present disclosure comprises a nucleotide sequence encoding a fusion protein comprising, in order from N-terminus to C-terminus: a) an Ig Fc region; b) a proteolytically cleavable linker comprising the amino acid sequence ENLYTQS (SEQ ID NO:6) and having a length of from 7 amino acids to 12 amino acids; and c) a variant E1 polypeptide of the present disclosure, where the variant HCV E1 polypeptide comprises: i) an HCV E1 polypeptide; and ii) a heterologous polypeptide that comprises one or more T-cell epitopes (e.g., one or more T cell epitopes present in an HCV polypeptide other than an HCV E1 polypeptide or an HCV E2 polypeptide). In some cases, the variant HCV E1 polypeptide comprises, in order from N-terminus to C-terminus: i) the HCV E1 polypeptide; and ii) the heterologous polypeptide comprising the one or more T cell epitopes. In other cases, the variant HCV E1 polypeptide comprises, in order from N-terminus to C-terminus: i) the heterologous polypeptide comprising the one or more T cell epitopes; and ii) the HCV E1 polypeptide. In some cases, the nucleotide sequence encoding the fusion protein is operably linked to a transcription control element, e.g., a promoter that is functional in a eukaryotic cell. Suitable promoters include, e.g., a CMV promoter, an SV40 promoter, and the like. In some cases, the nucleic acid is present in an expression vector (e.g., a lentivirus vector; an adeno-associated virus vector; an adenovirus vector; a retroviral vector; a non-viral vector; etc.).

In some cases, a nucleic acid of the present disclosure comprises a nucleotide sequence encoding an E1/E2 polypeptide comprising, in order from N-terminus to C-terminus: a) an HCV E2 polypeptide; and b) a variant E1 polypeptide of the present disclosure, where the variant HCV E1 polypeptide comprises: i) an HCV E1 polypeptide; and ii) a heterologous polypeptide that comprises one or more T-cell epitopes (e.g., one or more T cell epitopes present in an HCV polypeptide other than an HCV E1 polypeptide or an HCV E2 polypeptide). In some cases, the variant HCV E1 polypeptide comprises, in order from N-terminus to C-terminus: i) the HCV E1 polypeptide; and ii) the heterologous polypeptide comprising the one or more T cell epitopes. In other cases, the variant HCV E1 polypeptide comprises, in order from N-terminus to C-terminus: i) the heterologous polypeptide comprising the one or more T cell epitopes; and ii) the HCV E1 polypeptide. In some cases, the nucleotide sequence encoding the E1/E2 polypeptide is operably linked to a transcription control element, e.g., a promoter that is functional in a eukaryotic cell. Suitable promoters include, e.g., a CMV promoter, an SV40 promoter, and the like. In some cases, the nucleic acid is present in an expression vector (e.g., a lentivirus vector; an adenoassociated virus vector; an adenovirus vector; a retroviral vector; a non-viral vector; etc.). In some cases, the E1/E2 polypeptide comprises a host-derived signal peptidase cleavage site between the HCV E2 polypeptide and the variant HCV E1 polypeptide. Thus, in some cases, a nucleic acid of the present disclosure comprises a nucleotide sequence encoding an E1/E2 polypeptide comprising, in order from N-terminus to C-terminus: a) an HCV E2 polypeptide; b) a host signal peptidase cleavage site; and c) a variant E1 polypeptide of the present disclosure, where the variant HCV E1 polypeptide comprises: i) an HCV E1 polypeptide; and ii) a heterologous polypeptide that comprises one or more T-cell epitopes (e.g., one or more T cell epitopes present in an HCV polypeptide other than an HCV E1 polypeptide or an HCV E2 polypeptide). In some cases, the variant HCV E1 polypeptide comprises, in order from N-terminus to C-terminus: i) the HCV E1 polypeptide; and ii) the heterologous polypeptide comprising the one or more T cell epitopes. In other cases, the variant HCV E1 polypeptide comprises, in order from N-terminus to C-terminus: i) the heterologous polypeptide comprising the one or more T cell epitopes; and ii) the HCV E1 polypeptide.

In some cases, a nucleic acid of the present disclosure comprises a nucleotide sequence encoding an E1/E2 polypeptide comprising, in order from N-terminus to C-terminus: a) an HCV E2 polypeptide; b) an Ig Fc region; and c) a variant E1 polypeptide of the present disclosure, where the variant HCV E1 polypeptide comprises: i) an HCV E1 polypeptide; and ii) a heterologous polypeptide that comprises one or more T-cell epitopes (e.g., one or more T cell epitopes present in an HCV polypeptide other than an HCV E1 polypeptide or an HCV E2 polypeptide). In some cases, the variant HCV E1 polypeptide comprises, in order from N-terminus to C-terminus: i) the HCV E1 polypeptide; and ii) the heterologous polypeptide comprising the one or more T cell epitopes. In other cases, the variant HCV E1 polypeptide comprises, in order from N-terminus to C-terminus: i) the heterologous polypeptide comprising the one or more T cell epitopes; and ii) the HCV E1 polypeptide. In some cases, the nucleotide sequence encoding the E1/E2 polypeptide is operably linked to a transcription control element, e.g., a promoter that is functional in a eukaryotic cell.

Suitable promoters include, e.g., a CMV promoter, an SV40 promoter, and the like. In some cases, the nucleic acid is present in an expression vector (e.g., a lentivirus vector; an adenoassociated virus vector; an adenovirus vector; a retroviral vector; a non-viral vector; etc.). In some cases, the E1/E2 polypeptide comprises a host-derived signal peptidase cleavage site between the E2 polypeptide and the Ig Fc region. Thus, in some cases, a nucleic acid of the present disclosure comprises a nucleotide sequence encoding an E1/E2 polypeptide comprising, in order from N-terminus to C-terminus: a) an HCV E2 polypeptide; b) a host-derived signal peptidase cleavage site; c) an Ig Fc region; and d) a variant E1 polypeptide of the present disclosure, where the variant HCV E1 polypeptide comprises: i) an HCV E1 polypeptide; and ii) a heterologous polypeptide that comprises one or more T-cell epitopes (e.g., one or more T cell epitopes present in an HCV polypeptide other than an HCV E1 polypeptide or an HCV E2 polypeptide). In some cases, the variant HCV E1 polypeptide comprises, in order from N-terminus to C-terminus: i) the HCV E1 polypeptide; and ii) the heterologous polypeptide comprising the one or more T cell epitopes. In other cases, the variant HCV E1 polypeptide comprises, in order from N-terminus to C-terminus: i) the heterologous polypeptide comprising the one or more T cell epitopes; and ii) the HCV E1 polypeptide.

In some cases, a nucleic acid of the present disclosure comprises a nucleotide sequence encoding an E1/E2 polypeptide comprising, in order from N-terminus to C-terminus: a) an HCV E2 polypeptide; b) an Ig Fc region; c) a proteolytically cleavable linker; and d) a variant E1 polypeptide of the present disclosure, where the variant HCV E1 polypeptide comprises: i) an HCV E1 polypeptide; and ii) a heterologous polypeptide that comprises one or more T-cell epitopes (e.g., one or more T cell epitopes present in an HCV polypeptide other than an HCV E1 polypeptide or an HCV E2 polypeptide). In some cases, the variant HCV E1 polypeptide comprises, in order from N-terminus to C-terminus: i) the HCV E1 polypeptide; and ii) the heterologous polypeptide comprising the one or more T cell epitopes. In other cases, the variant HCV E1 polypeptide comprises, in order from N-terminus to C-terminus: i) the heterologous polypeptide comprising the one or more T cell epitopes; and ii) the HCV E1 polypeptide. In some cases, the nucleotide sequence encoding the fusion protein is operably linked to a transcription control element, e.g., a promoter that is functional in a eukaryotic cell. Suitable promoters include, e.g., a CMV promoter, an SV40 promoter, and the like. In some cases, the nucleic acid is present in an expression vector (e.g., a lentivirus vector; an adenoassociated virus vector; an adenovirus vector; a retroviral vector; a non-viral vector; etc.). In some cases, the E1/E2 polypeptide comprises a host-derived signal peptidase cleavage site between the E2 polypeptide and the Ig Fc region. Thus, in some cases, a nucleic acid of the present disclosure comprises a nucleotide sequence encoding an E1/E2 polypeptide comprising, in order from N-terminus to C-terminus: a) an HCV E2 polypeptide; b) a host-derived signal peptidase cleavage site; c) an Ig Fc region; d) a proteolytically cleavable linker; and e) a variant E1 polypeptide of the present disclosure, where the variant HCV E1 polypeptide comprises: i) an HCV E1 polypeptide; and ii) a heterologous polypeptide that comprises one or more T-cell epitopes (e.g., one or more T cell epitopes present in an HCV polypeptide other than an HCV E1 polypeptide or an HCV E2 polypeptide). In some cases, the variant HCV E1 polypeptide comprises, in order from N-terminus to C-terminus: i) the HCV E1 polypeptide; and ii) the heterologous polypeptide comprising the one or more T cell epitopes. In other cases, the variant HCV E1 polypeptide comprises, in order from N-terminus to C-terminus: i) the heterologous polypeptide comprising the one or more T cell epitopes; and ii) the HCV E1 polypeptide.

In some cases, a nucleic acid of the present disclosure comprises a nucleotide sequence encoding an E1/E2 polypeptide comprising, in order from N-terminus to C-terminus: a) an HCV E2 polypeptide; b) an Ig Fc region; c) a proteolytically cleavable linker comprising the amino acid sequence LEVLFQGP (SEQ ID NO:5) and having a length of from 8 amino acids to 15 amino acids; and d) a variant E1 polypeptide of the present disclosure, where the variant HCV E1 polypeptide comprises: i) an HCV E1 polypeptide; and ii) a heterologous polypeptide that comprises one or more T-cell epitopes (e.g., one or more T cell epitopes present in an HCV polypeptide other than an HCV E1 polypeptide or an HCV E2 polypeptide). In some cases, the variant HCV E1 polypeptide comprises, in order from N-terminus to C-terminus: i) the HCV E1 polypeptide; and ii) the heterologous polypeptide comprising the one or more T cell epitopes. In other cases, the variant HCV E1 polypeptide comprises, in order from N-terminus to C-terminus: i) the heterologous polypeptide comprising the one or more T cell epitopes; and ii) the HCV E1 polypeptide. In some cases, the nucleotide sequence encoding the fusion protein is operably linked to a transcription control element, e.g., a promoter that is functional in a eukaryotic cell. Suitable promoters include, e.g., a CMV promoter, an SV40 promoter, and the like. In some cases, the nucleic acid is present in an expression vector (e.g., a lentivirus vector; an adeno-associated virus vector; an adenovirus vector; a retroviral vector; a non-viral vector; etc.). In some cases, the E1/E2 polypeptide comprises a host-derived signal peptidase cleavage site between the E2 polypeptide and the Ig Fc region. Thus, in some cases, a nucleic acid of the present disclosure comprises a nucleotide sequence encoding an E1/E2 polypeptide comprising, in order from N-terminus to C-terminus: a) an HCV E2 polypeptide; b) a host-derived signal peptidase cleavage site; c) an Ig Fc region; d) a proteolytically cleavable linker comprising the amino acid sequence LEVLFQGP (SEQ ID NO:5) and having a length of from 8 amino acids to 15 amino acids; and e) a variant E1 polypeptide of the present disclosure, where the variant HCV E1 polypeptide comprises: i) an HCV E1 polypeptide; and ii) a heterologous polypeptide that comprises one or more T-cell epitopes (e.g., one or more T cell epitopes present in an HCV polypeptide other than an HCV E1 polypeptide or an HCV E2 polypeptide). In some cases, the variant HCV E1 polypeptide comprises, in order from N-terminus to C-terminus: i) the HCV E1 polypeptide; and ii) the heterologous polypeptide comprising the one or more T cell epitopes. In other cases, the variant HCV E1 polypeptide comprises, in order from N-terminus to C-terminus: i) the heterologous polypeptide comprising the one or more T cell epitopes; and ii) the HCV E1 polypeptide.

In some cases, a nucleic acid of the present disclosure comprises a nucleotide sequence encoding an E1/E2 polypeptide comprising, in order from N-terminus to C-terminus: a) an HCV E2 polypeptide; b) an Ig Fc region; c) a proteolytically cleavable linker comprising the amino acid sequence ENLYTQS (SEQ ID NO:6) and having a length of from 7 amino acids to 12 amino acids; and d) a variant E1 polypeptide of the present disclosure, where the variant HCV E1 polypeptide comprises: i) an HCV E1 polypeptide; and ii) a heterologous polypeptide that comprises one or more T-cell epitopes (e.g., one or more T cell epitopes present in an HCV polypeptide other than an HCV E1 polypeptide or an HCV E2 polypeptide). In some cases, the variant HCV E1 polypeptide comprises, in order from N-terminus to C-terminus: i) the HCV E1 polypeptide; and ii) the heterologous polypeptide comprising the one or more T cell epitopes. In other cases, the variant HCV E1 polypeptide comprises, in order from N-terminus to C-terminus: i) the heterologous polypeptide comprising the one or more T cell epitopes; and ii) the HCV E1 polypeptide. In some cases, the nucleotide sequence encoding the fusion protein is operably linked to a transcription control element, e.g., a promoter that is functional in a eukaryotic cell. Suitable promoters include, e.g., a CMV promoter, an SV40 promoter, and the like. In some cases, the nucleic acid is present in an expression vector (e.g., a lentivirus vector; an adeno-associated virus vector; an adenovirus vector; a retroviral vector; a non-viral vector; etc.). In some cases, the E1/E2 polypeptide comprises a host-derived signal peptidase cleavage site between the E1 polypeptide and the Ig Fc region. Thus, in some cases, a nucleic acid of the present disclosure comprises a nucleotide sequence encoding an E1/E2 polypeptide comprising, in order from N-terminus to C-terminus: a) an HCV E2 polypeptide; b) a host-derived signal peptidase cleavage site; c) an Ig Fc region; d) a proteolytically cleavable linker comprising the amino acid sequence ENLYTQS (SEQ ID NO:6) and having a length of from 7 amino acids to 12 amino acids; and e) a variant E1 polypeptide of the present disclosure, where the variant HCV E1 polypeptide comprises: i) an HCV E1 polypeptide; and ii) a heterologous polypeptide that comprises one or more T-cell epitopes (e.g., one or more T cell epitopes present in an HCV polypeptide other than an HCV E1 polypeptide or an HCV E2 polypeptide). In some cases, the variant HCV E1 polypeptide comprises, in order from N-terminus to C-terminus: i) the HCV E1 polypeptide; and ii) the heterologous polypeptide comprising the one or more T cell epitopes. In other cases, the variant HCV E1 polypeptide comprises, in order from N-terminus to C-terminus: i) the heterologous polypeptide comprising the one or more T cell epitopes; and ii) the HCV E1 polypeptide.

In some cases, a nucleic acid of the present disclosure comprises a nucleotide sequence encoding an E1/E2 polypeptide comprising, in order from N-terminus to C-terminus: a) a signal peptide that directs the E1/E2 polypeptide to the endoplasmic reticulum (ER) following translation of the E1/E2 polypeptide; b) an HCV E2 polypeptide; c) an Ig Fc region; d) a proteolytically cleavable linker; and e) a variant E1 polypeptide of the present disclosure, where the variant HCV E1 polypeptide comprises: i) an HCV E1 polypeptide; and ii) a heterologous polypeptide that comprises one or more T-cell epitopes (e.g., one or more T cell epitopes present in an HCV polypeptide other than an HCV E1 polypeptide or an HCV E2 polypeptide). In some cases, the variant HCV E1 polypeptide comprises, in order from N-terminus to C-terminus: i) the HCV E1 polypeptide; and ii) the heterologous polypeptide comprising the one or more T cell epitopes. In other cases, the variant HCV E1 polypeptide comprises, in order from N-terminus to C-terminus: i) the heterologous polypeptide comprising the one or more T cell epitopes; and ii) the HCV E1 polypeptide. In some cases, the nucleotide sequence encoding the fusion protein is operably linked to a transcription control element. e.g., a promoter that is functional in a eukaryotic cell. Suitable promoters include, e.g., a CMV promoter, an SV40 promoter, and the like. In some cases, the nucleic acid is present in an expression vector (e.g., a lentivirus vector; an adeno-associated virus vector; an adenovirus vector; a retroviral vector; a non-viral vector; etc.). In some cases, the E1/E2 polypeptide comprises a host-derived signal peptidase cleavage site between the E1 polypeptide and the Ig Fc region, and comprises a host-derived signal peptidase cleavage site between the signal peptide and the HCV E2 polypeptide. Thus, in some cases, a nucleic acid of the present disclosure comprises a nucleotide sequence encoding an E1/E2 polypeptide comprising, in order from N-terminus to C-terminus: a) a signal peptide that directs the E1/E2 polypeptide to the ER following translation of the E1/E2 polypeptide; b) a host-derived signal peptidase cleavage site; c) an HCV E2 polypeptide; d) a host-derived signal peptidase cleavage site; e) an Ig Fc region; f) a proteolytically cleavable linker; and g) a variant E1 polypeptide of the present disclosure, where the variant HCV E1 polypeptide comprises: i) an HCV E1 polypeptide; and ii) a heterologous polypeptide that comprises one or more T-cell epitopes (e.g., one or more T cell epitopes present in an HCV polypeptide other than an HCV E1 polypeptide or an HCV E2 polypeptide). In some cases, the variant HCV E1 polypeptide comprises, in order from N-terminus to C-terminus: i) the HCV E1 polypeptide; and ii) the heterologous polypeptide comprising the one or more T cell epitopes. In other cases, the variant HCV E1 polypeptide comprises, in order from N-terminus to C-terminus: i) the heterologous polypeptide comprising the one or more T cell epitopes; and ii) the HCV E1 polypeptide.

In some cases, a nucleic acid of the present disclosure comprises a nucleotide sequence encoding an E1/E2 polypeptide comprising, in order from N-terminus to C-terminus: a) a signal peptide that directs the E1/E2 polypeptide to the endoplasmic reticulum (ER) following translation of the E1/E2 polypeptide; b) an HCV E2 polypeptide; c) an Ig Fc region; d) a proteolytically cleavable linker comprising the amino acid sequence LEVLFQGP (SEQ ID NO:5) and having a length of from 8 amino acids to 15 amino acids; and e) a variant E1 polypeptide of the present disclosure, where the variant HCV E1 polypeptide comprises: i) an HCV E1 polypeptide; and ii) a heterologous polypeptide that comprises one or more T-cell epitopes (e.g., one or more T cell epitopes present in an HCV polypeptide other than an HCV E1 polypeptide or an HCV E2 polypeptide). In some cases, the variant HCV E1 polypeptide comprises, in order from N-terminus to C-terminus: i) the HCV E1 polypeptide; and ii) the heterologous polypeptide comprising the one or more T cell epitopes. In other cases, the variant HCV E1 polypeptide comprises, in order from N-terminus to C-terminus: i) the heterologous polypeptide comprising the one or more T cell epitopes; and ii) the HCV E1 polypeptide. In some cases, the nucleotide sequence encoding the fusion protein is operably linked to a transcription control element, e.g., a promoter that is functional in a eukaryotic cell. Suitable promoters include, e.g., a CMV promoter, an SV40 promoter, and the like. In some cases, the nucleic acid is present in an expression vector (e.g., a lentivirus vector; an adeno-associated virus vector; an adenovirus vector; a retroviral vector; a non-viral vector; etc.). In some cases, the E1/E2 polypeptide comprises a host-derived signal peptidase cleavage site between the E2 polypeptide and the Ig Fc region, and comprises a host-derived signal peptidase cleavage site between the signal peptide and the HCV E2 polypeptide. Thus, in some cases, a nucleic acid of the present disclosure comprises a nucleotide sequence encoding an E1/E2 polypeptide comprising, in order from N-terminus to C-terminus: a) a signal peptide that directs the E1/E2 polypeptide to the endoplasmic reticulum (ER) following translation of the E1/E2 polypeptide; b) a host-derived signal peptidase cleavage site; c) an HCV E2 polypeptide; d)

a host-derived signal peptidase cleavage site; e) an Ig Fc region; f) a proteolytically cleavable linker comprising the amino acid sequence LEVLFQGP (SEQ ID NO:5) and having a length of from 8 amino acids to 15 amino acids; and g) a variant E1 polypeptide of the present disclosure, where the variant HCV E1 polypeptide comprises: i) an HCV E1 polypeptide; and ii) a heterologous polypeptide that comprises one or more T-cell epitopes (e.g., one or more T cell epitopes present in an HCV polypeptide other than an HCV E1 polypeptide or an HCV E2 polypeptide). In some cases, the variant HCV E1 polypeptide comprises, in order from N-terminus to C-terminus: i) the HCV E1 polypeptide; and ii) the heterologous polypeptide comprising the one or more T cell epitopes. In other cases, the variant HCV E1 polypeptide comprises, in order from N-terminus to C-terminus: i) the heterologous polypeptide comprising the one or more T cell epitopes; and ii) the HCV E1 polypeptide.

In some cases, a nucleic acid of the present disclosure comprises a nucleotide sequence encoding an E1/E2 polypeptide comprising, in order from N-terminus to C-terminus: a) a signal peptide that directs the E1/E2 polypeptide to the endoplasmic reticulum (ER) following translation of the E1/E2 polypeptide; b) an HCV E2 polypeptide; c) an Ig Fc region; d) a proteolytically cleavable linker comprising the amino acid sequence ENLYTQS (SEQ ID NO:6) and having a length of from 7 amino acids to 12 amino acids; and e) a variant E1 polypeptide of the present disclosure, where the variant HCV E1 polypeptide comprises: i) an HCV E1 polypeptide; and ii) a heterologous polypeptide that comprises one or more T-cell epitopes (e.g., one or more T cell epitopes present in an HCV polypeptide other than an HCV E1 polypeptide or an HCV E2 polypeptide). In some cases, the variant HCV E1 polypeptide comprises, in order from N-terminus to C-terminus: i) the HCV E1 polypeptide; and ii) the heterologous polypeptide comprising the one or more T cell epitopes. In other cases, the variant HCV E1 polypeptide comprises, in order from N-terminus to C-terminus: i) the heterologous polypeptide comprising the one or more T cell epitopes; and ii) the HCV E1 polypeptide. In some cases, the nucleotide sequence encoding the fusion protein is operably linked to a transcription control element, e.g., a promoter that is functional in a eukaryotic cell. Suitable promoters include, e.g., a CMV promoter, an SV40 promoter, and the like. In some cases, the nucleic acid is present in an expression vector (e.g., a lentivirus vector; an adeno-associated virus vector; an adenovirus vector; a retroviral vector; a non-viral vector; etc.). In some cases, the E1/E2 polypeptide comprises a host-derived signal peptidase cleavage site between the E2 polypeptide and the Ig Fc region, and comprises a host-derived signal peptidase cleavage site between the signal peptide and the HCV E2 polypeptide. Thus, in some cases, a nucleic acid of the present disclosure comprises a nucleotide sequence encoding an E1/E2 polypeptide comprising, in order from N-terminus to C-terminus: a) a signal peptide that directs the E1/E2 polypeptide to the ER following translation of the E1/E2 polypeptide; b) a host-derived signal peptidase cleavage site; c) an HCV E2 polypeptide; d) a host-derived signal peptidase cleavage site; e) an Ig Fc region; f) a proteolytically cleavable linker comprising the amino acid sequence ENLYTQS (SEQ ID NO:6) and having a length of from 7 amino acids to 12 amino acids; and g) a variant E1 polypeptide of the present disclosure, where the variant HCV E1 polypeptide comprises: i) an HCV E1 polypeptide; and ii) a heterologous polypeptide that comprises one or more T-cell epitopes (e.g., one or more T cell epitopes present in an HCV polypeptide other than an HCV E1 polypeptide or an HCV E2 polypeptide). In some cases, the variant HCV E1 polypeptide comprises, in order from N-terminus to C-terminus: i) the HCV E1 polypeptide; and ii) the heterologous polypeptide comprising the one or more T cell epitopes. In other cases, the variant HCV E1 polypeptide comprises, in order from N-terminus to C-terminus: i) the heterologous polypeptide comprising the one or more T cell epitopes; and ii) the HCV E1 polypeptide.

As noted above, in some cases, a nucleic acid of the present disclosure is present in an expression vector. Thus, the present disclosure provides a recombinant expression vector comprising a nucleic acid comprising a nucleotide sequence encoding a variant E1 polypeptide of the present disclosure or comprising a nucleotide sequence encoding an E1/E2 heterodimer of the present disclosure. In some cases, the nucleotide sequence encoding the variant E1 polypeptide of the present disclosure or the nucleotide sequence encoding the E1/E2 heterodimer of the present disclosure is operably linked to a transcriptional control element, e.g., a promoter, such as a promoter functional in a eukaryotic cell.

Suitable expression vectors include, but are not limited to, baculovirus vectors, bacteriophage vectors, plasmids, phagemids, cosmids, fosmids, bacterial artificial chromosomes, viral vectors (e.g. viral vectors based on vaccinia virus, poliovirus, adenovirus, adeno-associated virus, SV40, herpes simplex virus, HIV-based lentivirus vectors, murine leukemia virus (MVL)-based gamma retrovirus vectors, and the like), P1-based artificial chromosomes, yeast plasmids, yeast artificial chromosomes, and any other vectors specific for specific hosts of interest (such as *E. coli*, mammalian cells, insect cells, or yeast cells).

Additional Embodiments

In some cases, a nucleic acid of the present disclosure comprises a first nucleotide sequence encoding a variant E2 polypeptide of the present disclosure, where the nucleotide sequence encodes a polypeptide comprising, from N-terminus to C-terminus: a) a variant HCV E2 polypeptide comprising, in order from N-terminus to C-terminus: i) an HCV E2 polypeptide; and ii) one or more T-cell epitopes from an HCV polypeptide other than E1 or E2; b) a proteolytically cleavable linker; and c) an Ig Fc polypeptide. In some cases, the nucleic acid further includes a second nucleotide sequence 5' of the first nucleotide sequence, where the second nucleotide sequence encodes an HCV E1 polypeptide. In some cases, the nucleic acid further includes a second nucleotide sequence 5' of the first nucleotide sequence, where the second nucleotide sequence encodes a varian HCV E1 polypeptide, the variant HCV E1 polypeptide comprising, in order from N-terminus to C-terminus: i) an HCV E1 polypeptide; and ii) one or more T-cell epitopes from an HCV polypeptide other than E1 or E2.

In some cases, a nucleic acid of the present disclosure comprises a nucleotide sequence encoding a variant E1 polypeptide of the present disclosure, where the nucleotide sequence encodes a polypeptide comprising, from N-terminus to C-terminus: a) a variant HCV E1 polypeptide comprising, in order from N-terminus to C-terminus: i) an HCV E1 polypeptide; and ii) one or more T-cell epitopes from an HCV polypeptide other than E1 or E2; b) a proteolytically cleavable linker; and c) an Ig Fc polypeptide. In some cases, the nucleic acid further includes a second nucleotide sequence 5' of the first nucleotide sequence, where the second nucleotide sequence encodes an HCV E2 polypeptide. In some cases, the nucleic acid further includes a second nucleotide sequence 5' of the first nucleotide sequence, where the second nucleotide sequence encodes a varian HCV E2 polypeptide, the variant HCV E2 polypeptide comprising, in order from N-terminus to C-terminus: i) an HCV E2 polypeptide; and ii) one or more T-cell epitopes from an HCV polypeptide other than E1 or E2.

In some cases, a nucleic acid of the present disclosure comprises a nucleotide sequence encoding a polypeptide comprising, from N-terminus to C-terminus: a) an Ig Fc polypeptide; b) a proteolytically cleavable linker; c) an HCV E1 polypeptide; d) two amino acids from the N-terminus of E2; and e) an HCV E2 polypeptide. In some cases, a nucleic acid of the present disclosure comprises a nucleotide sequence encoding a polypeptide comprising, from N-terminus to C-terminus: a) an Ig Fc polypeptide; b) a proteolytically cleavable linker; c) a variant HCV E1 polypeptide comprising, in order from N-terminus to C-terminus: i) an HCV E1 polypeptide; and ii) one or more T-cell epitopes from an HCV polypeptide other than E1 or E2; d) two amino acids from the N-terminus of E2; and e) an HCV E2 polypeptide. In some cases, a nucleic acid of the present disclosure comprises a nucleotide sequence encoding a polypeptide comprising, from N-terminus to C-terminus: a) an Ig Fc polypeptide; b) a proteolytically cleavable linker; c) a variant HCV E1 polypeptide comprising, in order from N-terminus to C-terminus: i) one or more T-cell epitopes from an HCV polypeptide other than E1 or E2; and ii) an HCV E1 polypeptide; d) two amino acids from the N-terminus of E2; and e) an HCV E2 polypeptide. In some cases, a nucleic acid of the present disclosure comprises a nucleotide sequence encoding a polypeptide comprising, from N-terminus to C-terminus: a) an Ig Fc polypeptide; b) a proteolytically cleavable linker; c) an HCV E1 polypeptide; d) two amino acids from the N-terminus of E2; and e) a variant HCV E2 polypeptide comprising, in order from N-terminus to C-terminus: i) an HCV E2 polypeptide; and ii) one or more T-cell epitopes from an HCV polypeptide other than E1 or E2. In some cases, a nucleic acid of the present disclosure comprises a nucleotide sequence encoding a polypeptide comprising, from N-terminus to C-terminus: a) an Ig Fc polypeptide; b) a proteolytically cleavable linker; c) an HCV E1 polypeptide; d) two amino acids from the N-terminus of E2; and e) a variant HCV E2 polypeptide comprising, in order from N-terminus to C-terminus: i) one or more T-cell epitopes from an HCV polypeptide other than E1 or E2; and ii) an HCV E2 polypeptide.

In any of the above-described embodiments, the nucleic acid can be included in a recombinant expression vector, as described above. Suitable proteolytically cleavable linkers are described above.

V. Host Cells

The present disclosure provides genetically modified host cells, where the genetically modified host cells are genetically modified with a nucleic acid or recombinant expression vector of the present disclosure.

Suitable host cells include eukaryotic cells, such as yeast cells, insect cells, and mammalian cells. In some cases, the host cell is a cell of a mammalian cell line. Suitable mammalian cell lines include human cell lines, non-human primate cell lines, rodent (e.g., mouse, rat) cell lines, and the like. Suitable mammalian cell lines include, but are not limited to, HeLa cells (e.g., American Type Culture Collection (ATCC) No. CCL-2), CHO cells (e.g., ATCC Nos. CRL9618, CCL61, CRL9096), 293 cells (e.g., ATCC No. CRL-1573), Vero cells, NIH 3T3 cells (e.g., ATCC No. CRL-1658), Huh-7 cells, BHK cells (e.g., ATCC No. CCL10), PC12 cells (ATCC No. CRL1721), COS cells, COS-7 cells (ATCC No. CRL1651), RAT1 cells, mouse L cells (ATCC No. CCLI.3), human embryonic kidney (HEK) cells (ATCC No. CRL1573), HLHepG2 cells, MRC4 fibroblast cells, and the like.

Methods for introduction of nucleic acids into host cells include, for example, transformation, electroporation, conjugation, calcium phosphate methods and the like. The method for transfer can be selected so as to provide for stable expression of the introduced polypeptide-encoding nucleic acid. The polypeptide-encoding nucleic acid can be provided as an inheritable episomal element (e.g., a plasmid) or can be genomically-integrated.

Methods of Producing a Variant E2 Polypeptide, a Variant E1 Polypeptide, or an E1/E2 Heterodimer E1, E2, variant E2, variant E1, and E1/E2 polypeptides can be produced using any suitable method, including recombinant and non-recombinant methods (e.g., chemical synthesis).

Where a polypeptide is chemically synthesized, the synthesis may proceed via liquid phase or solid-phase. Solid-phase peptide synthesis (SPPS) allows the incorporation of unnatural amino acids and/or peptide/protein backbone modification. Various forms of SPPS, such as Fmoc and Boc, are available for synthesizing polypeptides. Details of the chemical synthesis are known in the art (e.g., Ganesan A. 2006 Mini Rev. Med Chem. 6:3-10 and Camarero J A et al. 2005 Protein Pept Lett. 12:723-8).

Where a polypeptide is produced using recombinant techniques, the polypeptide may be produced as an intracellular protein or as an secreted protein, using any suitable construct and any suitable host cell, which can be a prokaryotic or eukaryotic cell, such as a bacterial (e.g., *Escherichia coli*) cell or a yeast host cell, respectively. Other examples of eukaryotic cells that may be used as host cells include insect cells, mammalian cells, filamentous fungi, and plant cells. Suitable yeast cells include, e.g., *Saccharomyces cerevisiae* and *Pichia* (e.g., *Pichia pastoris*).

Suitable mammalian cells include human cell lines, non-human primate cell lines, rodent (e.g., mouse, rat) cell lines, and the like. Suitable mammalian cell lines include, but are not limited to, HeLa cells (e.g., American Type Culture Collection (ATCC) No. CCL-2), CHO cells (e.g., ATCC Nos. CRL9618, CCL61, CRL9096), 293 cells (e.g., ATCC No. CRL-1573), Vero cells, NIH 3T3 cells (e.g., ATCC No. CRL-1658), Huh-7 cells, BHK cells (e.g., ATCC No. CCL10), PC12 cells (ATCC No. CRL1721), COS cells, COS-7 cells (ATCC No. CRL1651), RAT1 cells, mouse L cells (ATCC No. CCLI.3), human embryonic kidney (HEK) cells (ATCC No. CRL1573), HLHepG2 cells, MRC5 cells (ATCC No. CCL-171), and the like. Where mammalian host cells are used, such host cells may include human cells (e.g., HeLa, 293, H9 and Jurkat cells); mouse cells (e.g., NIH3T3, L cells, and C127 cells); primate cells (e.g., Cos 1, Cos 7 and CV1); MRC4 cells; and hamster cells (e.g., Chinese hamster ovary (CHO) cells).

A variety of host-vector systems suitable for the expression of a polypeptide may be employed according to standard procedures known in the art. See, e.g., Sambrook et al., 1989 Current Protocols in Molecular Biology Cold Spring Harbor Press, New York; Ausubel et al. 1995 Current Protocols in Molecular Biology, Eds. Wiley and Sons; "Protein Expression: A Practical Approach" (1999) S. J. Higgins and B. D. James, eds., Oxford University Press; "Protein Expression in Mammalian Cells: Methods and Protocols (Methods in Molecular Biology)" (2012) James L. Hartley, ed., Humana Press; and "Production of Recombinant Proteins" (2005) Gerd Gellisen, ed., Wiley-VCH. Methods for introduction of nucleic acids into host cells include, for example, transformation, electroporation, conjugation, calcium phosphate methods and the like. The method for transfer can be selected so as to provide for stable expression of the introduced polypeptide-encoding nucleic acid. The polypeptide-encoding nucleic acid can be provided as an inheritable episomal element (e.g., a plasmid) or can be genomically-integrated. A variety of appropriate vectors for use in production of a peptide of interest are available commercially.

Suitable expression vectors include, but are not limited to, baculovirus vectors, bacteriophage vectors, plasmids, phagemids, cosmids, fosmids, bacterial artificial chromosomes, viral vectors (e.g. viral vectors based on vaccinia virus, poliovirus, adenovirus, adeno-associated virus, SV40, herpes simplex virus, HIV-based lentivirus vectors, murine leukemia virus (MVL)-based gamma retrovirus vectors, and the like), P1-based artificial chromosomes, yeast plasmids, yeast artificial chromosomes, and any other vectors specific for specific hosts of interest (such as *E. coli*, mammalian cells, insect cells, or yeast cells).

An E1 polypeptide, an E2 polypeptide, a variant E2 polypeptide, a variant E1 polypeptide, or an E1/E2 heterodimer can be produced by introducing a recombinant expression vector comprising a nucleotide sequence encoding the E1 polypeptide, E2 polypeptide, variant E2 polypeptide, variant E1 polypeptide, or E1/E2 heterodimer into an appropriate host cell, where the host cell produces the encoded E1 polypeptide, E2 polypeptide, variant E2 polypeptide, variant E1 polypeptide, or E1/E2 heterodimer. In the expression vector, a polynucleotide comprising a nucleotide sequence(s) encoding the E1 polypeptide, E2 polypeptide, variant E2 polypeptide, variant E1 polypeptide, or E1/E2 heterodimer is linked to a regulatory sequence as appropriate to obtain the desired expression properties. These regulatory sequences can include promoters, enhancers, terminators, operators, repressors, and inducers. The promoters can be regulated or constitutive. Expression vectors generally have convenient restriction sites located near the promoter sequence to provide for the insertion of nucleic acid sequences encoding a protein of interest. A selectable marker operative in the expression host cell may be present.

In some cases, the E1 polypeptide, E2 polypeptide, variant E2 polypeptide, variant E1 polypeptide, or E1/E2 heterodimer is encoded in a recombinant expression vector suitable for expression in a eukaryotic host cell (e.g., an insect cell; a yeast cell; a mammalian host cell, such as CHO cells, HeLa cells, 293 cells, MRC5 cells, etc.). In some cases, a recombinant expression vector comprises a nucleotide sequence encoding E1 and E2 polypeptides (which may be wild-type or variant) as a single polypeptide chain; the recombinant expression vector is introduced into a eukaryotic host cell to generate a genetically modified host cell. In some cases, E1 and variant E2 polypeptides are initially produced as a single polypeptide chain, which is cleaved in the endoplasmic reticulum (ER) of the genetically modified host cell to produce separate E1 and variant E2 polypeptides. The separate E1 and variant E2 polypeptides can form a heterodimer (e.g., a non-covalently linked heterodimer) in the ER. In some cases, variant E1 and E2 polypeptides are initially produced as a single polypeptide chain, which is cleaved in the ER of the genetically modified host cell to produce separate variant E1 and E2 polypeptides. The separate variant E1 and E2 polypeptides can form a heterodimer (e.g., a non-covalently linked heterodimer) in the ER The E1/E2 heterodimer can be isolated from the genetically modified host cell by, e.g., lysis using a non-ionic detergent, or using a freeze-thaw method. See, e.g., Frey et al. (2010) Vaccine 28:6367. The E1/E2 heterodimer can be purified from a cell lysate and/or cell culture medium using any of a variety of methods, including size exclusion chromatography, affinity chromatography, and the like, or combinations of such methods. In some cases, the E1/E2 heterodimer is purified from cell lysate and/or cell culture medium using *Galanthus nivalis* (GNA) lectin affinity chromatography. In some cases, the E1/E2 heterodimer is purified from a cell lysate. In some cases, the E1/E2 heterodimer is secreted from a cell and is purified from the cell culture medium. Suitable methods that can be used for purifying an E1/E2 heterodimer are described in, e.g., U.S. Pat. Nos. 6,121,020; 6,274,148; and Mazzocca et al. (2005) J. Biol. Chem. 280:11329. For example, in some cases, an E1/E2 heterodimer can be prepared in a method comprising cell disruption and debris removal by microfiltration, followed by purification using three subsequent chromatographic steps: lectin affinity chromatography, hydroxyapatite chromatography, and ion exchange chromatography.

Alternatively, the E1 and variant E2 polypeptides, or variant E1 and E2 polypeptides, can be encoded on separate recombinant expression vectors; and produced in a cell (e.g., the same host cell or separate host cells) as separate polypeptides.

If full-length E1 and variant E2 polypeptides are expressed in a eukaryotic host cell, the E1 and variant E2 polypeptides remain bound to the endoplasmic reticulum (ER) membrane as asialoglycoproteins. If the E1 and variant E2 polypeptides have C-terminal truncations, such that the C-terminal transmembrane regions are removed, the truncated polypeptides are secreted and can acquire complex glycans such as sialic acid. Removal of approximately amino acids 660-746 of E2, or amino acids 715-746 of E2, and removal of approximately amino acids 330-383 of E1, results in secretion of E2 and E1 from a eukaryotic host cell. If E1 and variant E2 are co-expressed in the same eukaryotic host cell as full-length polypeptides, they remain in the lumen of the ER as a heterodimer.

In some cases, an E2 polypeptide suitable for use in a variant E2 polypeptide, or suitable for use in an E1/E2 heterodimer together with a variant E1 polypeptide, lacks a transmembrane region. For example, in some cases, an E2 polypeptide suitable for use in a variant E2 polypeptide, or suitable for use in an E1/E2 heterodimer together with a variant E1 polypeptide, comprises amino acids 384-659, and lacks amino acids 660-746 of a naturally-occurring E2 polypeptide; and may be referred to as "E2 ectodomain polypeptide." For example, in some cases, an E2 polypeptide suitable for use in a variant E2 polypeptide, or suitable for use in an E1/E2 heterodimer together with a variant E1 polypeptide, comprises amino acids 384-659, lacks amino acids 660-746 of a naturally-occurring E2 polypeptide, and has a length of 276 amino acids.

In some cases, an E1 polypeptide suitable for use in a variant E1 polypeptide, or suitable for use in an E1/E2 heterodimer together with a variant E2 polypeptide, lacks a transmembrane region. For example, in some cases, an E1 polypeptide suitable for use in a variant E1 polypeptide, or suitable for use in an E1/E2 heterodimer together with a variant E2 polypeptide, comprises amino acids 191-329, and lacks amino acids 330-383 of a naturally-occurring E1 polypeptide; and may be referred to as an "E1 ectodomain polypeptide." For example, in some cases, an E1 polypeptide suitable for use in a variant E1 polypeptide, or suitable for use in an E1/E2 heterodimer together with a variant E2 polypeptide, comprises amino acids 191-329, lacks amino acids 330-383 of a naturally-occurring E1 polypeptide, and has a length of 139 amino acids.

After production in a host cell, an E1 polypeptide, an E2 polypeptide, a variant E2 polypeptide, a variant E1 polypeptide, or an E1/E2 heterodimer (e.g., as separate polypeptides or as a heterodimer) can be purified from the host cell. Methods of purification of recombinantly produced polypeptides from a host cell are known in the art and include, e.g., detergent lysis (e.g., with a non-ionic detergent) or freeze-thaw lysis, followed by one or more of size exclusion column chromatography, high performance liquid chromatography, affinity chromatography, and the like.

In some cases, an E1/E2 heterodimer of the present disclosure is produced using a method comprising: A) culturing a genetically modified eukaryotic host cell that is genetically modified with a nucleic acid (e.g., recombinant expression vector) comprising a nucleotide sequence encoding an E1/E2 polypeptide that comprises, in order from N-terminus to C-terminus: a) a signal peptide that directs the E1/E2 polypeptide to the ER following translation of the E1/E2 polypeptide; b) an HCV E1 polypeptide; c) an Ig Fc region; d) a proteolytically cleavable linker; and e) a variant E2 polypeptide of the present disclosure, where the variant HCV E2 polypeptide comprises: i) an HCV E2 polypeptide; and ii) a heterologous polypeptide that comprises one or more T-cell epitopes (e.g., one or more T cell epitopes present in an HCV polypeptide other than an HCV E1 polypeptide or an HCV E2 polypeptide); B) contacting a lysate of the cultured genetically modified eukaryotic host cell with a solid support comprising an Ig Fc binding moiety, generating an immobilized heterodimer comprising the HCV E1 polypeptide and a fusion polypeptide comprising: a) the Ig Fc; b) the proteolytically cleavable linker; and c) the variant E2 polypeptide; C) contacting the immobilized heterodimer with an enzyme that cleaves the proteolytically cleavable linker, thereby releasing the heterodimer; and D) collecting the released heterodimer.

In some cases, an E1/E2 heterodimer of the present disclosure is produced using a method comprising: A) culturing a genetically modified eukaryotic host cell that is genetically modified with a nucleic acid (e.g., recombinant expression vector) comprising a nucleotide sequence encoding an E1/E2 polypeptide that comprises, in order from N-terminus to C-terminus: a) a signal peptide that directs the E1/E2 polypeptide to the ER following translation of the E1/E2 polypeptide; b) an HCV E1 polypeptide; c) an Ig Fc region; d) a proteolytically cleavable linker; and e) a variant E2 polypeptide of the present disclosure, where the variant HCV E2 polypeptide comprises: i) an HCV E2 polypeptide; and ii) a heterologous polypeptide that comprises one or more T-cell epitopes present in an HCV NS3 polypeptide; B) contacting a lysate of the cultured genetically modified eukaryotic host cell with a solid support comprising an Ig Fc binding moiety, generating an immobilized heterodimer comprising the HCV E1 polypeptide and a fusion polypeptide comprising: a) the Ig Fc; b) the proteolytically cleavable linker; and c) the variant E2 polypeptide; C) contacting the immobilized heterodimer with an enzyme that cleaves the proteolytically cleavable linker, thereby releasing the heterodimer; and D) collecting the released heterodimer.

In some cases, an E1/E2 heterodimer of the present disclosure is produced using a method comprising: A) culturing a genetically modified eukaryotic host cell that is genetically modified with a nucleic acid (e.g., recombinant expression vector) comprising a nucleotide sequence encoding an E1/E2 polypeptide that comprises, in order from N-terminus to C-terminus: a) a signal peptide that directs the E1/E2 polypeptide to the ER following translation of the E1/E2 polypeptide; b) an HCV E1 polypeptide; c) an Ig Fc region; d) a proteolytically cleavable linker comprising the amino acid sequence LEVLFQGP (SEQ ID NO:5), and having a length of from 8 amino acids to 15 amino acids; and e) a variant E2 polypeptide of the present disclosure, where the variant HCV E2 polypeptide comprises: i) an HCV E2 polypeptide; and ii) a heterologous polypeptide that comprises one or more T-cell epitopes (e.g., one or more T cell epitopes present in an HCV polypeptide other than an HCV E1 polypeptide or an HCV E2 polypeptide); B) contacting a lysate of the cultured genetically modified eukaryotic host cell with a solid support comprising an Ig Fc binding moiety, generating an immobilized heterodimer comprising the HCV E1 polypeptide and a fusion polypeptide comprising: a) the Ig Fc; b) the proteolytically cleavable linker; and c) the variant E2 polypeptide; C) contacting the immobilized heterodimer with an enzyme (e.g., a rhinovirus 3C protease) that cleaves the proteolytically cleavable linker, thereby releasing the heterodimer; and D) collecting the released heterodimer.

In some cases, an E1/E2 heterodimer of the present disclosure is produced using a method comprising: A) culturing a genetically modified eukaryotic host cell that is genetically modified with a nucleic acid (e.g., recombinant expression vector) comprising a nucleotide sequence encoding an E1/E2 polypeptide that comprises, in order from N-terminus to C-terminus: a) a signal peptide that directs the E1/E2 polypeptide to the ER following translation of the E1/E2 polypeptide; b) an HCV E1 polypeptide; c) an Ig Fc region; d) a proteolytically cleavable linker comprising the amino acid sequence LEVLFQGP (SEQ ID NO:5), and having a length of from 8 amino acids to 15 amino acids; and e) a variant E2 polypeptide of the present disclosure, where the variant HCV E2 polypeptide comprises: i) an HCV E2 polypeptide; and ii) a heterologous polypeptide that comprises one or more T-cell epitopes (e.g., one or more T cell epitopes present in an HCV polypeptide other than an HCV E1 polypeptide or an HCV E2 polypeptide); B) contacting a lysate of the cultured genetically modified eukaryotic host cell with a solid support comprising an Ig Fc binding moiety, generating an immobilized heterodimer comprising the HCV E1 polypeptide and a fusion polypeptide comprising: a) the Ig Fc; b) the proteolytically cleavable linker; and c) the variant E2 polypeptide; C) contacting the immobilized heterodimer with an enzyme (e.g., a fusion polypeptide comprising a glutathione-S-transferase and a human rhinovirus 3C protease (GST-HRV3C protease)) that cleaves the proteolytically cleavable linker, thereby releasing the E1E2 heterodimer; and D) collecting the released E1E2 heterodimer. In some cases, a solution comprising the released E1E2 heterodimer is applied to glutathione immobilized on a solid support, to remove the GST-HRV3C protease. For example, a solution comprising the released heterodimer can be applied to a glutathione-Sepharose 4B column, where the GST-HRV3C binds to the glutathione-Sepharose 4B; the flow-through (unbound material) comprises the released E1E2 heterodimer. In some cases, the released E1E2 heterodimer is further subjected to hydroxyapatite chromatography. Hydroxyapatite chromatography can be carried out as described in, e.g., Mazzocca et al. (2005) *J. Biol. Chem.* 280:11329.

Suitable Ig Fc binding moieties include, but are not limited to, Protein A (Graille et al. (2000) Proc. Natl. Acad. Sci. USA 97:5399); Protein G (Sjöbring et al. (1991) *J. Biol. Chem.* 266:399); and a Protein A/G fusion polypeptide (Eliasson et al. (1988) *J. Biol. Chem.* 263:4323).

The Ig Fc binding moiety can be immobilized onto a solid support, where the solid support can be of any of a variety of forms, e.g., a bead, a magnetic bead, a plate, and the like. The solid support can be made of any of a variety of materials, including, but not limited to, polystyrene, agarose, polyesters, polyethylene, and the like.

Figure 8A:
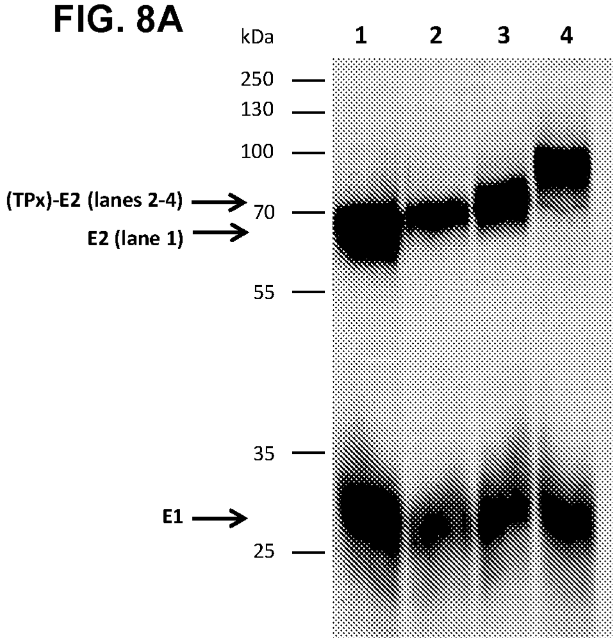
FIGS. 8A-8B depict purification of an E1E2 heterodimer from CHO cell extracts expressing Fc-tagged E1E2.
Figure 8B:
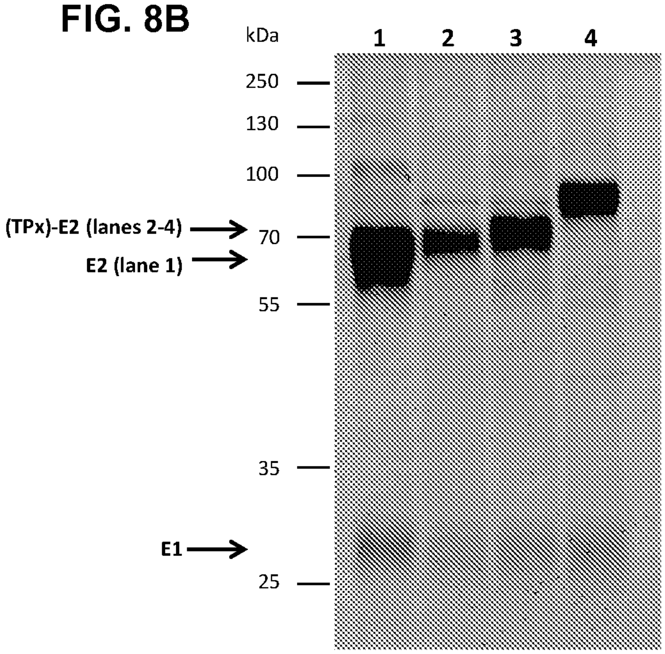

FIG. 5A and FIGS. 8A-8B demonstrate a purification scheme and purified proteins, respectively, for Fc-tagged E1E2 constructs. As an alternative to Fc, an affinity tag such as, e.g., polyhistidine (e.g., $(His)_6$), glutathione-S-transferase (GST), calmodulin-binding peptide (CBP), Streptavidin-binding peptide (SBP), Strep-tag II, FLAG (e.g., DYKDDDDK (SEQ ID NO:52), hemagglutinin (HA) (e.g., YPYDVPDYA (SEQ ID NO:53), c-myc T7 ((e.g., EQKLISEEDL; SEQ ID NO:54), Glu-Glu, and the like, can be used. (Wood D. 2014. *Current Opinion in Structural Biology* 26 54-61; Kimple M E et al. 2013. *Current Protocols in Protein Science* 9.9.1-9.9.23). Other suitable affinity tags include, e.g., starch-binding domain (SBD); and Flag-Acidic-Target Tag (FATT). See, e.g., Wood D. 2014. *Current Opinion in Structural Biology* 26 54-61).

One or more additional purification steps can be carried out. For example, a solution comprising the released heterodimer, produced as described above, can be subjected to size exclusion chromatography, hydroxyapatite chromatography, and the like. Hydroxyapatite chromatography can be carried out as described in, e.g., Mazzocca et al. (2005) *J. Biol. Chem.* 280:11329.

An E1/E2 heterodimer of the present disclosure can be purified such that the E1/E2 heterodimer is at least 60% pure, at least 65% pure, at least 70% pure, at least 75% pure, at least 80% pure, at least 85% pure, at least 90% pure, at least 95% pure, at least 98% pure, at least 99% pure, or greater than 99% pure.

Immunogenic Compositions

The present disclosure provides an immunogenic composition comprising an E1/E2 heterodimer of the present disclosure. The present disclosure also provides an immunogenic composition comprising a variant HCV E2 polypeptide of the present disclosure. The present disclosure also provides an immunogenic composition comprising a variant HCV E1 polypeptide of the present disclosure.

E1/E2 Heterodimers Comprising an HCV E1 Polypeptide and a Variant E2 Polypeptide In some cases, an immunogenic composition of the present disclosure includes an E1/E2 heterodimer of the present disclosure, the E1/E2 heterodimer comprising an HCV E1 polypeptide and a variant E2 polypeptide of the present disclosure. The E1 polypeptide and variant E2 polypeptide present in a subject immunogenic composition may be present in the composition as a covalently or non-covalently linked heterodimer. The E1 and variant E2 polypeptides can be present in the composition as a single polypeptide chain, or can be present as two separate polypeptide chains (which may or may not be covalently linked via a disulfide bond).

The E1 and variant E2 polypeptides are isolated, and can be purified. In some cases, a subject immunogenic composition comprises E1 and variant E2 polypeptides, where the polypeptides (or mixtures of E1 and variant E2 polypeptides) are at least 60% pure, at least 65% pure, at least 70% pure, at least 75% pure, at least 80% pure, at least 85% pure, at least 90% pure, at least 95% pure, at least 98% pure, at least 99% pure, or greater than 99% pure. In some embodiments, a subject immunogenic composition does not include any other polypeptides (e.g. no other HCV polypeptides) other than HCV E1 and variant HCV E2 polypeptides.

In some cases, where an immunogenic composition of the present disclosure includes an HCV E1 polypeptide and a variant E2 polypeptide of the present disclosure, the ratio of variant E2 polypeptide to HCV E1 polypeptide is in a range of from about 2:1 to 1:1, e.g., from about 2:1 to 1.5:1, or from 1.5:1 to 1:1. In some cases, where an immunogenic composition of the present disclosure includes an HCV E1 polypeptide and a variant E2 polypeptide of the present disclosure, the molar ratio of variant E2 polypeptide to HCV E1 polypeptide is in a range of from about 1:1 to 1.5:1, from 1.5:1 to 2:1, from 2:1 to 3:1, from 3:1 to 4:1, from 4:1 to 6:1, or from 6:1 to 8:1.

An immunogenic composition of the present disclosure can comprise:

1) an E1/E2 heterodimer comprising: a) a variant E2 polypeptide of the present disclosure, where the variant HCV E2 polypeptide comprises: i) an HCV genotype 1 E2 polypeptide; and ii) a heterologous polypeptide that comprises one or more T-cell epitopes (e.g., one or more T cell epitopes present in an HCV polypeptide other than an HCV E1 polypeptide or an HCV E2 polypeptide; e.g., one or more T-cell epitopes present in an HCV NS3 polypeptide), as described above; and b) an HCV genotype 1 E1 polypeptide;
2) an E1/E2 heterodimer comprising: a) a variant E2 polypeptide of the present disclosure, where the variant HCV E2 polypeptide comprises: i) an HCV genotype 1 E2 polypeptide; and ii) a heterologous polypeptide that comprises one or more T-cell epitopes (e.g., one or more T cell epitopes present in an HCV polypeptide other than an HCV E1 polypeptide or an HCV E2 polypeptide; e.g., one or more T-cell epitopes present in an HCV NS3 polypeptide), as described above; and b) an HCV genotype 2 E1 polypeptide;
3) an E1/E2 heterodimer comprising: a) a variant E2 polypeptide of the present disclosure, where the variant HCV E2 polypeptide comprises: i) an HCV genotype 1 E2 polypeptide; and ii) a heterologous polypeptide that comprises one or more T-cell epitopes (e.g., one or more T cell epitopes present in an HCV polypeptide other than an HCV E1 polypeptide or an HCV E2 polypeptide; e.g., one or more T-cell epitopes present in an HCV NS3 polypeptide), as described above; and b) an HCV genotype 3 E1 polypeptide;
4) an E1/E2 heterodimer comprising: a) a variant E2 polypeptide of the present disclosure, where the variant HCV E2 polypeptide comprises: i) an HCV genotype 2 E2 polypeptide; and ii) a heterologous polypeptide that comprises one or more T-cell epitopes (e.g., one or more T cell epitopes present in an HCV polypeptide other than an HCV E1 polypeptide or an HCV E2 polypeptide; e.g., one or more T-cell epitopes present in an HCV NS3 polypeptide), as described above; and b) an HCV genotype 1 E1 polypeptide;
5) an E1/E2 heterodimer comprising: a) a variant E2 polypeptide of the present disclosure, where the variant HCV E2 polypeptide comprises: i) an HCV genotype 2 E2 polypeptide; and ii) a heterologous polypeptide that comprises one or more T-cell epitopes (e.g., one or more T cell epitopes present in an HCV polypeptide other than an HCV E1 polypeptide or an HCV E2 polypeptide; e.g., one or more T-cell epitopes present in an HCV NS3 polypeptide), as described above; and b) an HCV genotype 2 E1 polypeptide;
6) an E1/E2 heterodimer comprising: a) a variant E2 polypeptide of the present disclosure, where the variant HCV E2 polypeptide comprises: i) an HCV genotype 2

E2 polypeptide; and ii) a heterologous polypeptide that comprises one or more T-cell epitopes (e.g., one or more T cell epitopes present in an HCV polypeptide other than an HCV E1 polypeptide or an HCV E2 polypeptide; e.g., one or more T-cell epitopes present in an HCV NS3 polypeptide), as described above; and b) an HCV genotype 3 E1 polypeptide;

7) an E1/E2 heterodimer comprising: a) a variant E2 polypeptide of the present disclosure, where the variant HCV E2 polypeptide comprises: i) an HCV genotype 3 E2 polypeptide; and ii) a heterologous polypeptide that comprises one or more T-cell epitopes (e.g., one or more T cell epitopes present in an HCV polypeptide other than an HCV E1 polypeptide or an HCV E2 polypeptide; e.g., one or more T-cell epitopes present in an HCV NS3 polypeptide), as described above; and b) an HCV genotype 1 E1 polypeptide;

8) an E1/E2 heterodimer comprising: a) a variant E2 polypeptide of the present disclosure, where the variant HCV E2 polypeptide comprises: i) an HCV genotype 3 E2 polypeptide; and ii) a heterologous polypeptide that comprises one or more T-cell epitopes (e.g., one or more T cell epitopes present in an HCV polypeptide other than an HCV E1 polypeptide or an HCV E2 polypeptide; e.g., one or more T-cell epitopes present in an HCV NS3 polypeptide), as described above; and b) an HCV genotype 2 E1 polypeptide; or 9) an E1/E2 heterodimer comprising: a) a variant E2 polypeptide of the present disclosure, where the variant HCV E2 polypeptide comprises: i) an HCV genotype 3 E2 polypeptide; and ii) a heterologous polypeptide that comprises one or more T-cell epitopes (e.g., one or more T cell epitopes present in an HCV polypeptide other than an HCV E1 polypeptide or an HCV E2 polypeptide; e.g., one or more T-cell epitopes present in an HCV NS3 polypeptide), as described above; and b) an HCV genotype 3 E1 polypeptide.

An immunogenic composition of the present disclosure can comprise:

1) a first E1/E2 heterodimer and a second E1/E2 heterodimer, where: A) the first E1/E2 heterodimer comprises: a) a variant E2 polypeptide of the present disclosure, where the variant HCV E2 polypeptide comprises: i) an HCV genotype 1A E2 polypeptide; and ii) a heterologous polypeptide that comprises one or more T-cell epitopes (e.g., one or more T cell epitopes present in an HCV polypeptide other than an HCV E1 polypeptide or an HCV E2 polypeptide; e.g., one or more T-cell epitopes present in an HCV NS3 polypeptide), as described above; and b) an HCV genotype 1A E1 polypeptide; and B) the second E1/E2 heterodimer comprises: a) a variant E2 polypeptide of the present disclosure, where the variant HCV E2 polypeptide comprises: i) an HCV genotype 2A E2 polypeptide; and ii) a heterologous polypeptide that comprises one or more T-cell epitopes (e.g., one or more T cell epitopes present in an HCV polypeptide other than an HCV E1 polypeptide or an HCV E2 polypeptide; e.g., one or more T-cell epitopes present in an HCV NS3 polypeptide), as described above; and b) an HCV genotype 2A E1 polypeptide;

2) a first E1/E2 heterodimer and a second E1/E2 heterodimer, where: A) the first E1/E2 heterodimer comprises: a) a variant E2 polypeptide of the present disclosure, where the variant HCV E2 polypeptide comprises: i) an HCV genotype 1A E2 polypeptide; and ii) a heterologous polypeptide that comprises one or more T-cell epitopes (e.g., one or more T cell epitopes present in an HCV polypeptide other than an HCV E1 polypeptide or an HCV E2 polypeptide; e.g., one or more T-cell epitopes present in an HCV NS3 polypeptide), as described above; and b) an HCV genotype 1A E1 polypeptide; and B) the second E1/E2 heterodimer comprises: a) a variant E2 polypeptide of the present disclosure, where the variant HCV E2 polypeptide comprises: i) an HCV genotype 3A E2 polypeptide; and ii) a heterologous polypeptide that comprises one or more T-cell epitopes (e.g., one or more T cell epitopes present in an HCV polypeptide other than an HCV E1 polypeptide or an HCV E2 polypeptide; e.g., one or more T-cell epitopes present in an HCV NS3 polypeptide), as described above; and b) an HCV genotype 3A E1 polypeptide; or 3) a first E1/E2 heterodimer and a second E1/E2 heterodimer, where: A) the first E1/E2 heterodimer comprises: a) a variant E2 polypeptide of the present disclosure, where the variant HCV E2 polypeptide comprises: i) an HCV genotype 2A E2 polypeptide; and ii) a heterologous polypeptide that comprises one or more T-cell epitopes (e.g., one or more T cell epitopes present in an HCV polypeptide other than an HCV E1 polypeptide or an HCV E2 polypeptide; e.g., one or more T-cell epitopes present in an HCV NS3 polypeptide), as described above; and b) an HCV genotype 2A E1 polypeptide; and B) the second E1/E2 heterodimer comprises: a) a variant E2 polypeptide of the present disclosure, where the variant HCV E2 polypeptide comprises: i) an HCV genotype 3A E2 polypeptide; and ii) a heterologous polypeptide that comprises one or more T-cell epitopes (e.g., one or more T cell epitopes present in an HCV polypeptide other than an HCV E1 polypeptide or an HCV E2 polypeptide; e.g., one or more T-cell epitopes present in an HCV NS3 polypeptide), as described above; and b) an HCV genotype 3A E1 polypeptide.

An immunogenic composition of the present disclosure can comprise:

1) a first E1/E2 heterodimer, a second E1/E2 heterodimer, and a third E1/E2 heterodimer where: A) the first E1/E2 heterodimer comprises: a) a variant E2 polypeptide of the present disclosure, where the variant HCV E2 polypeptide comprises: i) an HCV genotype 1A E2 polypeptide; and ii) a heterologous polypeptide that comprises one or more T-cell epitopes (e.g., one or more T cell epitopes present in an HCV polypeptide other than an HCV E1 polypeptide or an HCV E2 polypeptide; e.g., one or more T-cell epitopes present in an HCV NS3 polypeptide), as described above; and b) an HCV genotype 1A E1 polypeptide; B) the second E1/E2 heterodimer comprises: a) a variant E2 polypeptide of the present disclosure, where the variant HCV E2 polypeptide comprises: i) an HCV genotype 2A E2 polypeptide; and ii) a heterologous polypeptide that comprises one or more T-cell epitopes (e.g., one or more T cell epitopes present in an HCV polypeptide other than an HCV E1 polypeptide or an HCV E2 polypeptide; e.g., one or more T-cell epitopes present in an HCV NS3 polypeptide), as described above; and b) an HCV genotype 2A E1 polypeptide; and C) the third E1/E2 heterodimer comprises: a) a variant E2 polypeptide of the present disclosure, where the variant HCV E2 polypeptide comprises: i) an HCV genotype 3A E2 polypeptide; and ii) a heterologous polypeptide that comprises one or more T-cell epitopes (e.g., one or more T cell epitopes present in an HCV polypeptide other than an HCV E1 polypeptide or an HCV E2 polypeptide; e.g., one or more T-cell epitopes present in an HCV NS3 polypeptide), as described above; and b) an HCV genotype 3A E1 polypeptide;

2) a first E1/E2 heterodimer, a second E1/E2 heterodimer, and a third E1/E2 heterodimer where: A) the first E1/E2 heterodimer comprises: a) a variant E2 polypeptide of the present disclosure, where the variant HCV E2 polypeptide comprises: i) an HCV genotype 1A E2 polypeptide; and ii) a heterologous polypeptide that comprises one or more T-cell epitopes (e.g., one or more T cell epitopes present in an HCV polypeptide other than an HCV E1 polypeptide or an HCV E2 polypeptide; e.g., one or more T-cell epitopes present in an HCV NS3 polypeptide), as described above; and b) an HCV genotype 1A E1 polypeptide; B) the second E1/E2 heterodimer comprises: a) a variant E2 polypeptide of the present disclosure, where the variant HCV E2 polypeptide comprises: i) an HCV genotype 2A E2 polypeptide; and ii) a heterologous polypeptide that comprises one or more T-cell epitopes (e.g., one or more T cell epitopes present in an HCV polypeptide other than an HCV E1 polypeptide or an HCV E2 polypeptide; e.g., one or more T-cell epitopes present in an HCV NS3 polypeptide), as described above; and b) an HCV genotype 2A E1 polypeptide; and C) the third E1/E2 heterodimer comprises: a) a variant E2 polypeptide of the present disclosure, where the variant HCV E2 polypeptide comprises: i) an HCV genotype 7A E2 polypeptide; and ii) a heterologous polypeptide that comprises one or more T-cell epitopes (e.g., one or more T cell epitopes present in an HCV polypeptide other than an HCV E1 polypeptide or an HCV E2 polypeptide; e.g., one or more T-cell epitopes present in an HCV NS3 polypeptide), as described above; and b) an HCV genotype 7A E1 polypeptide; or 3) a first E1/E2 heterodimer, a second E1/E2 heterodimer, and a third E1/E2 heterodimer where: A) the first E1/E2 heterodimer comprises: a) a variant E2 polypeptide of the present disclosure, where the variant HCV E2 polypeptide comprises: i) an HCV genotype 1A E2 polypeptide; and ii) a heterologous polypeptide that comprises one or more T-cell epitopes (e.g., one or more T cell epitopes present in an HCV polypeptide other than an HCV E1 polypeptide or an HCV E2 polypeptide; e.g., one or more T-cell epitopes present in an HCV NS3 polypeptide), as described above; and b) an HCV genotype 1A E1 polypeptide; B) the second E1/E2 heterodimer comprises: a) a variant E2 polypeptide of the present disclosure, where the variant HCV E2 polypeptide comprises: i) an HCV genotype 3A E2 polypeptide; and ii) a heterologous polypeptide that comprises one or more T-cell epitopes (e.g., one or more T cell epitopes present in an HCV polypeptide other than an HCV E1 polypeptide or an HCV E2 polypeptide; e.g., one or more T-cell epitopes present in an HCV NS3 polypeptide), as described above; and b) an HCV genotype 3A E1 polypeptide; and C) the third E1/E2 heterodimer comprises: a) a variant E2 polypeptide of the present disclosure, where the variant HCV E2 polypeptide comprises: i) an HCV genotype 7A E2 polypeptide; and ii) a heterologous polypeptide that comprises one or more T-cell epitopes (e.g., one or more T cell epitopes present in an HCV polypeptide other than an HCV E1 polypeptide or an HCV E2 polypeptide; e.g., one or more T-cell epitopes present in an HCV NS3 polypeptide), as described above; and b) an HCV genotype 7A E1 polypeptide.

Other combinations of E1/E2 heterodimers are also possible.

E1/E2 Heterodimers Comprising an HCV E2 Polypeptide and a Variant E1 Polypeptide In some cases, an immunogenic composition of the present disclosure includes an E1/E2 heterodimer of the present disclosure, the E1/E2 heterodimer comprising an HCV E2 polypeptide and a variant E1 polypeptide of the present disclosure. The E2 polypeptide and the variant E1 polypeptide present in a subject immunogenic composition may be present in the composition as a covalently or non-covalently linked heterodimer. The E2 and variant E1 polypeptides can be present in the composition as a single polypeptide chain, or can be present as two separate polypeptide chains (which may or may not be covalently linked via a disulfide bond).

The variant E1 polypeptides and the E2 polypeptides are isolated, and can be purified. In some cases, a subject immunogenic composition comprises variant E1 polypeptides and E2 polypeptides, where the polypeptides (or mixtures of variant E1 polypeptides and E2 polypeptides) are at least 60% pure, at least 65% pure, at least 70% pure, at least 75% pure, at least 80% pure, at least 85% pure, at least 90% pure, at least 95% pure, at least 98% pure, at least 99% pure, or greater than 99% pure. In some embodiments, a subject immunogenic composition does not include any other polypeptides (e.g. no other HCV polypeptides) other than HCV E1 and variant HCV E2 polypeptides.

In some cases, where an immunogenic composition of the present disclosure includes an HCV E2 polypeptide and a variant E1 polypeptide of the present disclosure, the ratio of variant HCV E2 polypeptide to variant E1 polypeptide is in a range of from about 2:1 to 1:1, e.g., from about 2:1 to 1.5:1, or from 1.5:1 to 1:1. In some cases, where an immunogenic composition of the present disclosure includes an HCV E2 polypeptide and a variant E1 of the present disclosure, the molar ratio of variant HCV E2 polypeptide to variant E1 polypeptide is in a range of from about 1:1 to 1.5:1, from 1.5:1 to 2:1, from 2:1 to 3:1, from 3:1 to 4:1, from 4:1 to 6:1, or from 6:1 to 8:1.

An immunogenic composition of the present disclosure can comprise:

1) an E1/E2 heterodimer comprising: a) a variant E1 polypeptide of the present disclosure, where the variant HCV E1 polypeptide comprises: i) an HCV genotype 1 E1 polypeptide; and ii) a heterologous polypeptide that comprises one or more T-cell epitopes (e.g., one or more T cell epitopes present in an HCV polypeptide other than an HCV E1 polypeptide or an HCV E2 polypeptide; e.g., one or more T-cell epitopes present in an HCV NS3 polypeptide), as described above; and b) an HCV genotype 1 E2 polypeptide;

2) an E1/E2 heterodimer comprising: a) a variant E1 polypeptide of the present disclosure, where the variant HCV E1 polypeptide comprises: i) an HCV genotype 1 E1 polypeptide; and ii) a heterologous polypeptide that comprises one or more T-cell epitopes (e.g., one or more T cell epitopes present in an HCV polypeptide other than an HCV E1 polypeptide or an HCV E2 polypeptide; e.g., one or more T-cell epitopes present in an HCV NS3 polypeptide), as described above; and b) an HCV genotype 2 E2 polypeptide;

3) an E1/E2 heterodimer comprising: a) a variant E1 polypeptide of the present disclosure, where the variant HCV E1 polypeptide comprises: i) an HCV genotype 1 E1 polypeptide; and ii) a heterologous polypeptide that comprises one or more T-cell epitopes (e.g., one or more T cell epitopes present in an HCV polypeptide other than an HCV E1 polypeptide or an HCV E2 polypeptide; e.g., one or more T-cell epitopes present in an HCV NS3 polypeptide), as described above; and b) an HCV genotype 3 E2 polypeptide;

4) an E1/E2 heterodimer comprising: a) a variant E1 polypeptide of the present disclosure, where the variant HCV E1 polypeptide comprises: i) an HCV genotype 2 E1 polypeptide; and ii) a heterologous polypeptide that comprises one or more T-cell epitopes (e.g., one or more T cell epitopes present in an HCV polypeptide other than an HCV E1 polypeptide or an HCV E2 polypeptide; e.g., one or more T-cell epitopes present in an HCV NS3 polypeptide), as described above; and b) an HCV genotype 1 E2 polypeptide;

5) an E1/E2 heterodimer comprising: a) a variant E1 polypeptide of the present disclosure, where the variant HCV E1 polypeptide comprises: i) an HCV genotype 2 E1 polypeptide; and ii) a heterologous polypeptide that comprises one or more T-cell epitopes (e.g., one or more T cell epitopes present in an HCV polypeptide other than an HCV E1 polypeptide or an HCV E2 polypeptide; e.g., one or more T-cell epitopes present in an HCV NS3 polypeptide), as described above; and b) an HCV genotype 2 E2 polypeptide;

6) an E1/E2 heterodimer comprising: a) a variant E1 polypeptide of the present disclosure, where the variant HCV E1 polypeptide comprises: i) an HCV genotype 2 E1 polypeptide; and ii) a heterologous polypeptide that comprises one or more T-cell epitopes (e.g., one or more T cell epitopes present in an HCV polypeptide other than an HCV E1 polypeptide or an HCV E2 polypeptide; e.g., one or more T-cell epitopes present in an HCV NS3 polypeptide), as described above; and b) an HCV genotype 3 E2 polypeptide;

7) an E1/E2 heterodimer comprising: a) a variant E1 polypeptide of the present disclosure, where the variant HCV E1 polypeptide comprises: i) an HCV genotype 3 E1 polypeptide; and ii) a heterologous polypeptide that comprises one or more T-cell epitopes (e.g., one or more T cell epitopes present in an HCV polypeptide other than an HCV E1 polypeptide or an HCV E2 polypeptide; e.g., one or more T-cell epitopes present in an HCV NS3 polypeptide), as described above; and b) an HCV genotype 1 E2 polypeptide;

8) an E1/E2 heterodimer comprising: a) a variant E1 polypeptide of the present disclosure, where the variant HCV E1 polypeptide comprises: i) an HCV genotype 3 E1 polypeptide; and ii) a heterologous polypeptide that comprises one or more T-cell epitopes (e.g., one or more T cell epitopes present in an HCV polypeptide other than an HCV E1 polypeptide or an HCV E2 polypeptide; e.g., one or more T-cell epitopes present in an HCV NS3 polypeptide), as described above; and b) an HCV genotype 2 E2 polypeptide; or 9) an E1/E2 heterodimer comprising: a) a variant E1 polypeptide of the present disclosure, where the variant HCV E1 polypeptide comprises: i) an HCV genotype 3 E1 polypeptide; and ii) a heterologous polypeptide that comprises one or more T-cell epitopes (e.g., one or more T cell epitopes present in an HCV polypeptide other than an HCV E1 polypeptide or an HCV E2 polypeptide; e.g., one or more T-cell epitopes present in an HCV NS3 polypeptide), as described above; and b) an HCV genotype 3 E2 polypeptide.

An immunogenic composition of the present disclosure can comprise:

1) a first E1/E2 heterodimer and a second E1/E2 heterodimer, where: A) the first E1/E2 heterodimer comprises: a) a variant E1 polypeptide of the present disclosure, where the variant HCV E1 polypeptide comprises: i) an HCV genotype 1A E1 polypeptide; and ii) a heterologous polypeptide that comprises one or more T-cell epitopes (e.g., one or more T cell epitopes present in an HCV polypeptide other than an HCV E1 polypeptide or an HCV E2 polypeptide; e.g., one or more T-cell epitopes present in an HCV NS3 polypeptide), as described above; and b) an HCV genotype 1A E2 polypeptide; and B) the second E1/E2 heterodimer comprises: a) a variant E1 polypeptide of the present disclosure, where the variant HCV E1 polypeptide comprises: i) an HCV genotype 2A E1 polypeptide; and ii) a heterologous polypeptide that comprises one or more T-cell epitopes (e.g., one or more T cell epitopes present in an HCV polypeptide other than an HCV E1 polypeptide or an HCV E2 polypeptide; e.g., one or more T-cell epitopes present in an HCV NS3 polypeptide), as described above; and b) an HCV genotype 2A E2 polypeptide;

2) a first E1/E2 heterodimer and a second E1/E2 heterodimer, where: A) the first E1/E2 heterodimer comprises: a) a variant E1 polypeptide of the present disclosure, where the variant HCV E1 polypeptide comprises: i) an HCV genotype 1A E1 polypeptide; and ii) a heterologous polypeptide that comprises one or more T-cell epitopes (e.g., one or more T cell epitopes present in an HCV polypeptide other than an HCV E1 polypeptide or an HCV E2 polypeptide; e.g., one or more T-cell epitopes present in an HCV NS3 polypeptide), as described above; and b) an HCV genotype 1A E2 polypeptide; and B) the second E1/E2 heterodimer comprises: a) a variant E1 polypeptide of the present disclosure, where the variant HCV E1 polypeptide comprises: i) an HCV genotype 3A E1 polypeptide; and ii) a heterologous polypeptide that comprises one or more T-cell epitopes (e.g., one or more T cell epitopes present in an HCV polypeptide other than an HCV E1 polypeptide or an HCV E2 polypeptide; e.g., one or more T-cell epitopes present in an HCV NS3 polypeptide), as described above; and b) an HCV genotype 3A E2 polypeptide; or 3) a first E1/E2 heterodimer and a second E1/E2 heterodimer, where: A) the first E1/E2 heterodimer comprises: a) a variant E1 polypeptide of the present disclosure, where the variant HCV E1 polypeptide comprises: i) an HCV genotype 2A E1 polypeptide; and ii) a heterologous polypeptide that comprises one or more T-cell epitopes (e.g., one or more T cell epitopes present in an HCV polypeptide other than an HCV E1 polypeptide or an HCV E2 polypeptide; e.g., one or more T-cell epitopes present in an HCV NS3 polypeptide), as described above; and b) an HCV genotype 2A E2 polypeptide; and B) the second E1/E2 heterodimer comprises: a) a variant E1 polypeptide of the present disclosure, where the variant HCV E1 polypeptide comprises: i) an HCV genotype 3A E1 polypeptide; and ii) a heterologous polypeptide that comprises one or more T-cell epitopes (e.g., one or more T cell epitopes present in an HCV polypeptide other than an HCV E1 polypeptide or an HCV E2 polypeptide; e.g., one or more T-cell epitopes present in an HCV NS3 polypeptide), as described above; and b) an HCV genotype 3A E2 polypeptide.

An immunogenic composition of the present disclosure can comprise:

1) a first E1/E2 heterodimer, a second E1/E2 heterodimer, and a third E1/E2 heterodimer where: A) the first E1/E2 heterodimer comprises: a) a variant E1 polypeptide of the present disclosure, where the variant HCV E1 polypeptide comprises: i) an HCV genotype 1A E1 polypeptide; and ii) a heterologous polypeptide that comprises one or more T-cell epitopes (e.g., one or more T cell epitopes present in an HCV polypeptide other than an HCV E1 polypeptide or an HCV E2 polypeptide; e.g., one or more T-cell epitopes present in an HCV NS3 polypeptide), as described above; and b) an HCV genotype 1A E2 polypeptide; B) the second E1/E2 heterodimer comprises: a) a variant E1 polypeptide of the present disclosure, where the variant HCV E1 polypeptide comprises: i) an HCV genotype 2A E1 polypeptide; and ii) a heterologous polypeptide that comprises one or more T-cell epitopes (e.g., one or more T cell epitopes present in an HCV polypeptide other than an HCV E1 polypeptide or an HCV E2 polypeptide; e.g., one or more T-cell epitopes present in an HCV NS3 polypeptide), as described above; and b) an HCV genotype 2A E2 polypeptide; and C) the third E1/E2 heterodimer comprises: a) a variant E1 polypeptide of the present disclosure, where the variant HCV E1 polypeptide comprises: i) an HCV genotype 3A E1 polypeptide; and ii) a heterologous polypeptide that comprises one or more T-cell epitopes (e.g., one or more T cell epitopes present in an HCV polypeptide other than an HCV E1 polypeptide or an HCV E2 polypeptide; e.g., one or more T-cell epitopes present in an HCV NS3 polypeptide), as described above; and b) an HCV genotype 3A E2 polypeptide;
2) a first E1/E2 heterodimer, a second E1/E2 heterodimer, and a third E1/E2 heterodimer where: A) the first E1/E2 heterodimer comprises: a) a variant E1 polypeptide of the present disclosure, where the variant HCV E1 polypeptide comprises: i) an HCV genotype 1A E1 polypeptide; and ii) a heterologous polypeptide that comprises one or more T-cell epitopes (e.g., one or more T cell epitopes present in an HCV polypeptide other than an HCV E1 polypeptide or an HCV E2 polypeptide; e.g., one or more T-cell epitopes present in an HCV NS3 polypeptide), as described above; and b) an HCV genotype 1A E2 polypeptide; B) the second E1/E2 heterodimer comprises: a) a variant E1 polypeptide of the present disclosure, where the variant HCV E1 polypeptide comprises: i) an HCV genotype 2A E1 polypeptide; and ii) a heterologous polypeptide that comprises one or more T-cell epitopes (e.g., one or more T cell epitopes present in an HCV polypeptide other than an HCV E1 polypeptide or an HCV E2 polypeptide; e.g., one or more T-cell epitopes present in an HCV NS3 polypeptide), as described above; and b) an HCV genotype 2A E2 polypeptide; and C) the third E1/E2 heterodimer comprises: a) a variant E1 polypeptide of the present disclosure, where the variant HCV E1 polypeptide comprises: i) an HCV genotype 7A E1 polypeptide; and ii) a heterologous polypeptide that comprises one or more T-cell epitopes (e.g., one or more T cell epitopes present in an HCV polypeptide other than an HCV E1 polypeptide or an HCV E2 polypeptide; e.g., one or more T-cell epitopes present in an HCV NS3 polypeptide), as described above; and b) an HCV genotype 7A E2 polypeptide; or
3) a first E1/E2 heterodimer, a second E1/E2 heterodimer, and a third E1/E2 heterodimer where: A) the first E1/E2 heterodimer comprises: a) a variant E1 polypeptide of the present disclosure, where the variant HCV E1 polypeptide comprises: i) an HCV genotype 1A E1 polypeptide; and ii) a heterologous polypeptide that comprises one or more T-cell epitopes (e.g., one or more T cell epitopes present in an HCV polypeptide other than an HCV E1 polypeptide or an HCV E2 polypeptide; e.g., one or more T-cell epitopes present in an HCV NS3 polypeptide), as described above; and b) an HCV genotype 1A E2 polypeptide; B) the second E1/E2 heterodimer comprises: a) a variant E1 polypeptide of the present disclosure, where the variant HCV E1 polypeptide comprises: i) an HCV genotype 3A E1 polypeptide; and ii) a heterologous polypeptide that comprises one or more T-cell epitopes (e.g., one or more T cell epitopes present in an HCV polypeptide other than an HCV E1 polypeptide or an HCV E2 polypeptide; e.g., one or more T-cell epitopes present in an HCV NS3 polypeptide), as described above; and b) an HCV genotype 3A E2 polypeptide; and C) the third E1/E2 heterodimer comprises: a) a variant E1 polypeptide of the present disclosure, where the variant HCV E1 polypeptide comprises: i) an HCV genotype 7A E1 polypeptide; and ii) a heterologous polypeptide that comprises one or more T-cell epitopes (e.g., one or more T cell epitopes present in an HCV polypeptide other than an HCV E1 polypeptide or an HCV E2 polypeptide; e.g., one or more T-cell epitopes present in an HCV NS3 polypeptide), as described above; and b) an HCV genotype 7A E2 polypeptide.

Other combinations of E1/E2 heterodimers are also possible.

Formulations

HCV E1 polypeptides, HCV E2 polypeptides, variant E2 polypeptides, variant E1 polypeptides, and E1/E2 heterodimers can be formulated with a pharmaceutically acceptable excipient(s) to generate a subject immunogenic composition. A wide variety of pharmaceutically acceptable excipients is known in the art and need not be discussed in detail herein. Pharmaceutically acceptable excipients have been amply described in a variety of publications, including, for example, A. Gennaro (2000) "Remington: The Science and Practice of Pharmacy", 20th edition, Lippincott, Williams, & Wilkins; Pharmaceutical Dosage Forms and Drug Delivery Systems (1999) H. C. Ansel et al., eds 7th ed., Lippincott, Williams, & Wilkins; and Handbook of Pharmaceutical Excipients (2000) A. H. Kibbe et al., eds., 3rd ed. Amer. Pharmaceutical Assoc.

In some embodiments, the E1 polypeptides, E2 polypeptides, variant E2 polypeptides, variant E1 polypeptides, or E1/E2 heterodimers are formulated in an aqueous buffer. Suitable aqueous buffers include, but are not limited to, acetate, succinate, citrate, and phosphate buffers varying in strengths from about 5 mM to about 100 mM. In some embodiments, the aqueous buffer includes reagents that provide for an isotonic solution. Such reagents include, but are not limited to, sodium chloride; and sugars e.g., mannitol, dextrose, sucrose, and the like. In some embodiments, the aqueous buffer further includes a non-ionic surfactant such as polysorbate 20 (TWEEN®20) or polysorbate 80 (TWEEN®80). For example, a formulation of E1 and variant E2 polypeptides in an aqueous buffer can include, e.g., from about 0.01% to about 0.05% polysorbate-20

(TWEEN®20) non-ionic detergent. Optionally the formulations may further include a preservative. Suitable preservatives include, but are not limited to, a benzyl alcohol, phenol, chlorobutanol, benzalkonium chloride, and the like. In many cases, the formulation is stored at about 4° C. Formulations may also be lyophilized, in which case they generally include cryoprotectants such as sucrose, trehalose, lactose, maltose, mannitol, and the like. Lyophilized formulations can be stored over extended periods of time, even at ambient temperatures. In some cases, the aqueous buffer further includes a non-ionic surfactant. In some cases, the aqueous buffer includes the non-ionic surfactant Triton™ X-100, e.g., 0.1% Triton™ X-100.

E1 polypeptides, E2 polypeptides, variant E2 polypeptides, variant E1 polypeptides, and E1/E2 heterodimers can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

An immunogenic composition of the present disclosure can include, e.g., pharmaceutical grades of mannitol, lactose, starch, magnesium stearate, sodium saccharin, talcum, cellulose, glucose, sucrose, magnesium, carbonate, and the like. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like.

The concentration of E1 polypeptides, E2 polypeptides, variant E2 polypeptides, variant E1 polypeptides, or E1/E2 heterodimers in a formulation can vary widely (e.g., from less than about 0.1% to at least about 2%, to as much as 20% to 50% or more by weight) and can be selected primarily based on fluid volumes, viscosities, and patient-based factors in accordance with the particular mode of administration selected and the patient's needs.

The HCV polypeptide-containing formulations of the present disclosure can be provided in the form of a solution, suspension, tablet, pill, capsule, powder, gel, cream, lotion, ointment, aerosol or the like. It is recognized that oral administration can require protection of the compositions from digestion. This is typically accomplished either by association of the composition with an agent that renders it resistant to acidic and enzymatic hydrolysis or by packaging the composition in an appropriately resistant carrier. Means of protecting from digestion are well known in the art.

The HCV polypeptide-containing formulations of the present disclosure can also be provided so as to enhance serum half-life of the heterodimer following administration. For example, where isolated E1 polypeptides, E2 polypeptides, variant E2 polypeptides, variant E1 polypeptides, or E1/E2 heterodimers are formulated for injection, the HCV polypeptide may be provided in a liposome formulation, prepared as a colloid, or other conventional techniques for extending serum half-life. A variety of methods are available for preparing liposomes, as described in, e.g., Szoka et al., Ann. Rev. Biophys. Bioeng. 9:467 (1980), U.S. Pat. Nos. 4,235,871, 4,501,728 and 4,837,028. The preparations may also be provided in controlled release or slow-release forms.

Adjuvant

An immunogenic composition of the present disclosure can include an adjuvant. Examples of known suitable adjuvants that can be used in humans include, but are not necessarily limited to, alum, aluminum phosphate, aluminum hydroxide, MF59 (4.3% w/v squalene, 0.5% w/v Tween 80™, 0.5% w/v Span 85), CpG-containing nucleic acid (where the cytosine is unmethylated), QS21, MPL, 3DMPL, extracts from Aquilla, ISCOMS, LT/CT mutants, poly(D,L-lactide-co-glycolide) (PLG) microparticles, Quil A, interleukins, and the like. For experimental animals, one can use Freund's, N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE), and RIBI, which contains three components extracted from bacteria, monophosphoryl lipid A, trehalose dimycolate and cell wall skeleton (MPL+TDM+CWS) in a 2% squalene/Tween 80 emulsion. The effectiveness of an adjuvant may be determined by one or more of measuring the amount of antibodies directed against the immunogenic antigen or antigenic epitope thereof, measuring a cytotoxic T lymphocyte response to the antigen, and measuring a helper T cell response to the antigen.

Further exemplary adjuvants to enhance effectiveness of the composition include, but are not limited to: (1) oil-in-water emulsion formulations (with or without other specific immunostimulating agents such as muramyl peptides (see below) or bacterial cell wall components), such as for example (a) MF59™ (see, e.g., WO 90/14837), containing 5% Squalene, 0.5% Tween 80, and 0.5% Span 85 (optionally containing MTP-PE) formulated into submicron particles using a microfluidizer, (b) SAF, containing 10% Squalane, 0.4% Tween 80, 5% pluronic-blocked polymer L121, and thr-MDP either microfluidized into a submicron emulsion or vortexed to generate a larger particle size emulsion, and (c) RIBI™ adjuvant system (RAS), (Ribi Immunochem, Hamilton, Mont.) containing 2% Squalene, 0.2% Tween 80, and one or more bacterial cell wall components such as monophosphorylipid A (MPL), trehalose dimycolate (TDM), and cell wall skeleton (CWS), e.g., MPL+CWS (Detox™); (2) saponin adjuvants, such as QS21 or Stimulon™ (Cambridge Bioscience, Worcester, Mass.) may be used or particles generated therefrom such as ISCOMs (immunostimulating complexes), which ISCOMS may be devoid of additional detergent e.g. WO 00/07621; (3) Complete Freund's Adjuvant (CFA) and Incomplete Freund's Adjuvant (IFA); (4) cytokines, such as interleukins (e.g. IL-1, IL-2, IL-4, IL-5, IL-6, IL-7, IL-12 (WO99/44636), etc.), interferons (e.g. gamma interferon), macrophage colony stimulating factor (M-CSF), tumor necrosis factor (TNF), etc.; (5) monophosphoryl lipid A (MPL) or 3-O-deacylated MPL (3dMPL) e.g. GB-2220221, EP-A-0689454, optionally in the substantial absence of alum when used with pneumococcal saccharides e.g. WO 00/56358; (6) combinations of 3dMPL with, for example, QS21 and/or oil-in-water emulsions (see, e.g. EP-A-0835318, EP-A-0735898, EP-A-0761231); (7) oligonucleotides comprising a CpG motif containing at least one CG dinucleotide, where the cytosine is unmethylated (see, e.g., WO 96/02555, WO 98/16247, WO 98/18810, WO 98/40100, WO 98/55495, WO 98/37919 and WO 98/52581); (8) a polyoxyethylene ether or a polyoxyethylene ester (see, e.g. WO 99/52549); (9) a polyoxyethylene sorbitan ester surfactant in combination with an octoxynol (WO 01/21207) or a polyoxyethylene alkyl ether or ester surfactant in combination with at least one additional non-ionic surfactant such as an octoxynol (WO 01/21152); (10) a saponin and an immunostimulatory oligonucleotide (e.g. a CpG oligonucleotide) (WO 00/62800); (11) an immunostimulant and a particle of metal salt (see, e.g. WO 00/23105); (12) a saponin and an oil-in-water emulsion (see e.g. WO 99/11241); (13) a saponin (e.g. QS21)+3dMPL+IM2 (optionally including a sterol) (see, e.g. WO 98/57659); (14) other substances that act as immunostimulating agents to enhance the efficacy of the composition. Muramyl peptides include N-acetyl-muramyl-L-threonyl-D-isoglutamine (thr-MDP), N-25 acetyl-normuramyl-L-alanyl-D-isoglutamine (nor-MDP), N-acetylmuramyl-L-alanyl-D-isoglutarninyl-L-alanine-2-(1'-2'-dipalmitoyl-sn-glycero-3-hydroxyphosphoryloxy)-ethylamine MTP-PE), etc. Also suitable for use is Matrix-M™; Matrix-M™ is an adjuvant that comprises 40 nm nanoparticles comprising Quillaja saponins, cholesterol, and phospholipid. Adjuvants suitable for administration to a human are of particular interest. In some cases, the adjuvant is one that enhances a CD4+ T helper response to the immunogen.

In some instances, the adjuvant is MF59, with or without a CpG-containing oligonucleotide. In other instances, the adjuvant is alum, with or without a CpG-containing oligonucleotide. In other instances, the adjuvant is poly(D,L-lactide-co-glycolide), with or without a CpG-containing oligonucleotide. In other instances, the adjuvant is MPL, with or without a CpG-containing oligonucleotide. In some cases, the adjuvant is Matrix-M™, with or without a CpG-containing oligonucleotide. In some cases, the adjuvant is keyhole limpet hemocyanin.

Methods of Inducing an Immune Response to HCV

The present disclosure provides a method of inducing an immune response (e.g., a protective immune response) to at least one HCV genotype in a mammalian subject. In some cases, the methods comprise administering to an individual in need thereof an effective amount of a heterodimeric polypeptide of the present disclosure, or a composition (e.g., an immunogenic composition) comprising a heterodimeric polypeptide of the present disclosure. In other cases, the methods comprise administering to an individual in need thereof an effective amount of a nucleic acid(s) (e.g., a recombinant expression vector) comprising nucleotide sequences encoding a heterodimeric polypeptide of the present disclosure.

An HCV immunogenic composition of the present disclosure, or a nucleic acid(s) comprising nucleotide sequences encoding a heterodimeric polypeptide of the present disclosure, is generally administered to a human subject who has an HCV infection or who is at risk of acquiring an HCV infection (e.g., is at greater risk than the general population of acquiring an HCV infection) so as to prevent or at least partially arrest the development of disease and its complications. An amount adequate to accomplish this is defined as a "therapeutically effective dose" or a "therapeutically effective amount." "Prophylactic" use of a subject immunogenic composition generally refers to administration to an individual who has not been infected with HCV. "Therapeutic" use of a subject immunogenic composition can refer to "prophylactic" use (administration to an individual who has not been infected with HCV) and/or to administration to an individual who has an HCV infection. A "therapeutically effective amount" of an immunogenic composition of the present disclosure, can be an amount that, when administered in one or more doses to an individual who is not infected with HCV, is effective to induce an immune response in the individual to HCV. A "therapeutically effective amount" of an immunogenic composition of the present disclosure, can be an amount that, when administered in one or more doses to an individual who is infected with HCV, is effective to enhance an immune response in the individual to HCV.

Amounts effective for therapeutic use will depend on, e.g., the immunogenic composition or the nucleic acid(s) comprising nucleotide sequences encoding a heterodimeric polypeptide of the present disclosure, the manner of administration, the weight and general state of health of the patient, and the judgment of the prescribing physician. Single or multiple doses of a subject immunogenic composition, or a nucleic acid(s) comprising nucleotide sequences encoding a heterodimeric polypeptide of the present disclosure, can be administered depending on the dosage and frequency required and tolerated by the patient, and route of administration.

In some cases, an effective amount (e.g., a therapeutically effective amount) of an HCV E1/E2 immunogenic composition of the present disclosure, or a nucleic acid(s) comprising nucleotide sequences encoding a heterodimeric polypeptide of the present disclosure, is an amount that, when administered to an individual in one or more doses, is effective to induce an antibody response (e.g., a neutralizing antibody response) to HCV in the individual. For example, antibody to HCV (e.g., extracellular HCV), and/or to an HCV-infected cell, can be induced.

An effective amount of an HCV E1/E2 immunogenic composition of the present disclosure, or a nucleic acid(s) comprising nucleotide sequences encoding a heterodimeric polypeptide of the present disclosure, can be an amount that, when administered to an individual in one or more doses, is effective to induce a neutralizing antibody response to HCV of a variety of genotypes (e.g., genotype 1; genotype 3; etc.). A neutralizing antibody response reduces binding of HCV to one or more host receptors for HCV and inhibits entry of HCV into a cell.

In some cases, an effective amount (e.g., a therapeutically effective amount) of an HCV E1/E2 immunogenic composition of the present disclosure, or a nucleic acid(s) comprising nucleotide sequences encoding a heterodimeric polypeptide of the present disclosure, is an amount that, when administered to an individual in one or more doses, is effective to induce a cytotoxic T lymphocyte (CTL) response to HCV. For example, a CTL response to an HCV-infected cell can be induced.

In some cases, an effective amount (e.g., a therapeutically effective amount) of an HCV E1/E2 immunogenic composition of the present disclosure, or a nucleic acid(s) comprising nucleotide sequences encoding a heterodimeric polypeptide of the present disclosure, is an amount that, when administered to an individual in one or more doses, is effective to induce a helper T lymphocyte (e.g., $CD4^+$ T cell) to HCV in an individual.

In some cases, an effective amount (e.g., a therapeutically effective amount) of an HCV E1/E2 immunogenic composition of the present disclosure, or a nucleic acid(s) comprising nucleotide sequences encoding a heterodimeric polypeptide of the present disclosure, is an amount that, when administered to an individual in one or more doses, is effective to induce an antibody response (e.g., a neutralizing antibody response) and/or a CTL response and/or a helper T cell response to HCV genotype 1. In some cases, an effective amount (e.g., a therapeutically effective amount) of an HCV E1/E2 immunogenic composition of the present disclosure, or a nucleic acid(s) comprising nucleotide sequences encoding a heterodimeric polypeptide of the present disclosure, is an amount that, when administered to an individual in one or more doses, is effective to induce an antibody response (e.g., a neutralizing antibody response) and/or a CTL response and/or a helper T cell response to HCV genotype 3. In some cases, an effective amount (e.g., a therapeutically effective amount) of an HCV E1/E2 immunogenic composition of the present disclosure, or a nucleic acid(s) comprising nucleotide sequences encoding a heterodimeric polypeptide of the present disclosure, is an amount that, when administered to an individual in one or more doses, is effective to induce an antibody response (e.g., a neutralizing antibody response) and/or a CTL response and/or a helper T cell response to HCV genotype 1 and HCV genotype 3. In some cases, an effective amount (e.g., a therapeutically effective amount) of an HCV E1/E2 immunogenic composition of the present disclosure, or a nucleic acid(s) comprising nucleotide sequences encoding a heterodimeric polypeptide of the present disclosure, is an amount that, when administered to an individual in one or more doses, is effective to induce an antibody response (e.g., a neutralizing antibody response) and/or a CTL response and/or a helper T cell response to HCV of any genotype.

An HCV E1/E2 immunogenic composition of the present disclosure, or a nucleic acid(s) comprising nucleotide sequences encoding a heterodimeric polypeptide of the present disclosure, is generally administered in an amount effective to elicit an immune response, e.g., a humoral immune response (e.g., an antibody response) and/or a CTL response, in the mammalian subject. Effective amounts for immunization will vary, and can generally range from about 1 μg to 100 μg per 70 kg patient, e.g., from about 5 μg/70 kg to about 50 μg/70 kg. Substantially higher dosages (e.g. 10 mg to 100 mg or more) may be suitable in oral, nasal, or topical administration routes. The initial administration can be followed by booster immunization of the same HCV E1/E2 immunogenic composition or a different HCV E1/E2 immunogenic composition. In some instances, a subject method of inducing an immune response involves an initial administration of an HCV E1/E2 immunogenic composition of the present disclosure, followed by at least one booster, and in some instances involves two or more (e.g., three, four, or five) boosters. The interval between an initial administration and a booster, or between a give booster and a subsequent booster, can be from about 1 week to about 12 weeks, e.g., from about 1 week to about 2 weeks, from about 2 weeks to about 4 weeks, from about 4 weeks to about 6 weeks, from about 6 weeks to about 8 weeks, from about 8 weeks to about 10 weeks, or from about 10 weeks to about 12 weeks.

In general, immunization can be accomplished by administration of an HCV E1/E2 immunogenic composition of the present disclosure, or a nucleic acid(s) comprising nucleotide sequences encoding a heterodimeric polypeptide of the present disclosure, by any suitable route, including administration of the composition orally, nasally, nasopharyngeally, parenterally, enterically, gastrically, topically, transdermally, subcutaneously, intramuscularly, in tablet, solid, powdered, liquid, aerosol form, locally or systemically, with or without added excipients. Actual methods for preparing parenterally administrable compositions will be known or apparent to those skilled in the art and are described in more detail in such publications as Remington's Pharmaceutical Science, 15th ed., Mack Publishing Company, Easton, Pa. (1980). In some instances, immunization is accomplished by intramuscular injection of an HCV E1/E2 immunogenic composition of the present disclosure.

In some cases, a method of the present disclosure for inducing an immune response to HCV in an individual comprises administering to the individual an effective amount of a nucleic acid(s) comprising nucleotide sequences encoding a heterodimeric polypeptide of the present disclosure. In some cases, the nucleic acid is present in an expression vector. Suitable expression vectors include, but are not limited to, a replication-defective adenovirus vector; a replication-defective vaccinia virus vector; a lentivirus vector (e.g., a self-inactivating lentivirus vector); a retroviral vector (e.g., a self-inactivating retroviral vector); an adeno-associated virus vector; and the like. In some cases, the vector is a modified vaccinia Ankara (MVA) vector, or an MVA-based vector (see, e.g., Verheust et al. (2012) *Vaccine* 30:2623).

In some cases, a method of the present disclosure for inducing an immune response to HCV in an individual comprises administering to the individual an effective amount of a nucleic acid(s) comprising nucleotide sequences encoding a heterodimeric polypeptide of the present disclosure. In some cases, the nucleic acid is an RNA comprising nucleotide sequences encoding a heterodimeric polypeptide of the present disclosure. See, e.g., Weiner (2013) *Molec. Therapy* 21:506; and Ulmer et al. (2012) *Vaccine* 30:4414. In some cases, an RNA (e.g., a single mRNA molecule; or 2 mRNA molecules) comprising nucleotide sequences encoding a heterodimeric polypeptide of the present disclosure is formulated with a liposome. In some cases, an RNA (e.g., a single mRNA molecule; or 2 mRNA molecules) comprising nucleotide sequences encoding a heterodimeric polypeptide of the present disclosure is complexed with protamine. In some cases, an RNA (e.g., a single mRNA molecule; or 2 mRNA molecules) comprising nucleotide sequences encoding a heterodimeric polypeptide of the present disclosure is complexed with 1,2-dioleoyl-3-trimethylammonium-propane/1,2-dioleoyl-sn-glycero-3-phosphoethanolamine (DOTAP/DOPE).

Individuals Suitable for Administration

Individuals who are suitable for administration with an HCV composition of the present disclosure include immunologically naïve individuals (e.g., individuals who have not been infected with HCV and/or who have not been administered with an HCV vaccine).

Individuals who are suitable for administration with an HCV composition of the present disclosure include individuals who are at greater risk than the general population of becoming infected with HCV, where such individuals include, e.g., intravenous drug users; individuals who are the recipients, or the prospective recipients, of blood or blood products from another (donor) individual(s); individuals who are the recipients, or the prospective recipients, of non-autologous cells, tissues, or organs from another (donor) individual; health care workers; emergency medical and non-medical personnel (e.g., first responders; fire fighters; emergency medical team personnel; etc.) and the like.

Individuals who are suitable for administration with an HCV composition of the present disclosure include individuals who recently became exposed to HCV or who recently became infected with HCV. For example, a subject immunogenic composition can be administered to an individual within from about 24 hours to about 48 hours, from about 48 hours to about 1 week, or from about 1 week to about 4 weeks, following possible or suspected exposure to HCV or following infection with HCV.

Individuals who are suitable for administration with an HCV composition of the present disclosure include individuals who have been diagnosed as having an HCV infection, and include chronically infected individuals. In some cases, an individual who has been diagnosed as having an HCV infection is treated with an anti-viral agent and a subject HCV immunogenic composition. Suitable anti-viral agents for treating HCV infection include, e.g., ribavirin (1-β-D-ribofuranosyl-1H-1,2,4-triazole-3-carboxamide); interferon-alpha (IFN-α) (where "IFN-α" includes IFN-α2a; IFN-α2b; IFN-α that is conjugated with poly(ethylene glycol) ("pegylated IFN-α), where the pegylated IFN-α can be pegylated IFN-α2a or pegylated IFN-α 2b); an HCV NS3 protease inhibitor (e.g., boceprevir; telaprevir); and an HCV NS5 protease inhibitor. In some cases, an individual who has been diagnosed as having an HCV infection is treated with, e.g.: 1) IFN-α+ ribavirin; and a subject HCV immunogenic composition; or 2) IFN-α+ ribavirin+ an HCV protease inhibitor (e.g., boceprevir or telaprevir); and a subject HCV immunogenic composition. Suitable anti-viral agents for treating HCV infection include Sovaldi (Sofosbuvir; a nucleotide analog that functions as an NS5B polymerase inhibitor), alone or in combination with pegylated IFN-α and ribavirin.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Example 1: Identification of T-Cell Epitopes in HCV NS3

Consensus sequences for various HCV genotypes were built using Geneious software. This included consensus sequences for genotype HCV1a, 1b, 2a, 2b, 3, 4, 5, and 6 from 224, 357, 20, 27, 30, 18, 3, and 59 different isolates, respectively. For genotype HCV7, the only reported isolate was used in the alignment.

To identify CD4 T cell epitopes, all the reported CD4+ T cell epitopes through Jul. 12, 2013 were extracted from the Immune Epitope Database and Analysis Resource (IDEB). The sequence of each epitope was entered into an alignment, including sequences from HCV genotypes 1a, 1b, 2a, 2b, and 3, as these are common HCV genotypes around the world. More than 287 epitopes that were reported in 518 studies as MHC II-restricted CD4 T cells epitopes with positive response in humans for HCV were extracted. Of those, which were grouped in 159 clusters at 70% identity, 217 were located and annotated on the sequences of HCV genotypes of 1a, 1b, 2a, 2b, and 3. In the case of mismatch of 1-3 amino acids in the sequence of the epitope against the HCV sequences, the epitope was still included in the analysis. The excluded 70 epitopes consisted of those that were located on structural regions of HCV polyprotein (core, E1, E2, and P7), were repeats of other epitopes, or were not found on the sequence. After addition of all epitopes, it appeared that almost the whole non-structural region of HCV polyprotein from residue number 941 (based on the HCV1a sequence), in the middle of non-structural protein 2 (NS2), to the residue number 3000, close to the end of NS5b were heavily covered by epitopes with exception of the regions 1980-2081 (the beginning of NS5a) and 2710-2788 (in the middle of NS5b).

Two additional analyses were performed: first, a Conservancy Analysis for all 217 epitopes was performed using IDEB software. In one analysis, all epitopes were checked for conservation amongst all 9 HCV genotypes (HCV1a, 1b, 2a, 2b, 3, 4, 5, 6, and 7), which resulted in 6 conserved epitopes and in the second analysis, the same list of 217 epitopes were evaluated against genotypes 1a, 1b, and 3 that resulted in 16 conserved epitopes. The partially overlapped epitopes were combined and of the completely overlapped epitopes, the largest one was retained. This resulted in a total of 11 so called "Region" that were conserved among all 3 genotypes of HCV1a, 1b, and 3. Of these 11, 4 were conserved among 9 HCV genotypes (HCV1a, 1b, 2a, 2b, 3, 4, 5, 6, and 7) and the rest were conserved among 4 to 8 genotypes (Table 1; FIG. 10).

Similar to CD4 epitopes, all reported CD8 T cell epitopes through Jul. 12, 2013 were extracted from the Immune Epitope Database and Analysis Resource (IDEB). A total number of 413 epitopes in 216 clusters at 70% from 1226 studies were found; however, to narrow down the list, an alternative search performed based on the common HLA class-I Alleles in North America. According to the latest demographic statistics from 2013, the population of USA as the representative of the North America comprises of different ethnic groups including White (64%), Black (12%), Hispanic (16%), Asian or Pacific Islanders (5%), and others including Natives, Alaskans, and etc. (3%). The first 30 common MHC-I alleles (frequency>~6-7%) for each of the first four common populations in USA were used in a search for any HCV epitopes that were reported for any of these individual alleles, which comprised of A*01:01, A*02:03, A*02:06, A*02:07, A*03:01, A*11:01, A*23:01, A*24:02, A*25:01, A*26:01, A*29:02, A*30:01, A*30:02, A*31:01, A*32:01, A*33:03, A*34:02, A*68:01, A*68:02, A*74:01, B*07:02, B*08:01, B*14:02, B*15:01, B*15:02, B*15:03, B*18:01, B*35:01, B*38:02, B*40:01, B*40:02, B*42:01, B*44:01, B*44:03, B*45:01, B*46:01, B*49:01, B*51:01, B*52:01, B*53:01, B*54:01, B*55:02, B*57:01, B*58:01, C*01:02, C*02:02, C*03:03, C*03:04, C*04:01, C*05:01, C*06:02, C*07:01, C*07:02, C*08:01, C*08:02, C*14:02, and C*16:01.

Using IDEB database through Jul. 12, 2013, a total of 106 MHC-I CD8 T cell epitopes that were restricted to each of the afore-mentioned alleles were found as described in Table 2 (FIG. 11) with their specific anchor positions. The sequence of each epitope was searched and entered in an alignment including sequences from HCV genotypes 1a, 1b, and 3 as the genotypes of interest for a vaccine that will be potentially used in North America. Of 106 epitopes, 64 were located and annotated on the sequences of HCV genotypes of 1a, 1b, and 3. In the case of mismatch of 1-3 amino acids in the sequence of the epitope against the HCV sequences, the epitope was still included in the analysis. The excluded 42 epitopes consisted of those that were located on structural regions of HCV polyprotein (core, E1, E2, and P7), were repeats of other epitopes, or were not found on the sequence.

A Conservancy Analysis for all 106 epitopes was performed using IDEB software. In one analysis, all epitopes were checked for conservancy against nine HCV genotypes (1a, 1b, 2a, 2b, 3, 4, 5, 6, and 7) resulted in 2 conserved epitopes and in the second analysis the same list of epitopes were evaluated against genotypes 1a, 1b, and 3 that resulted in 6 conserved epitopes. The partially overlapped epitopes were combined and of the completely overlapped epitopes, the largest one was retained. This resulted in a total of 5 conserved epitopes or combination of epitopes (called Regions) with all to be conserved among 3 genotypes and 2 to be conserved among all 9 HCV genotypes. The list of these regions (CD8-R1 to CD8-R5) is described in Table 3 (FIG. 12).

In addition, a Conservancy Analysis for all 413 CD8 epitopes was done using IDEB software. When checked for conservancy against nine HCV genotypes (1a, 1b, 2a, 2b, 3, 4, 5, 6, and 7), 2 new conserved epitopes were found and in the second analysis the same list of epitopes were evaluated against genotypes 1a, 1b, and 3 that resulted in 7 new conserved epitopes. The partially overlapped epitopes were combined and of the completely overlapped epitopes, the largest one was retained. This resulted in a total of 5 new conserved epitopes or combination of epitopes (called Regions) with all to be conserved among 3 genotypes and 1 to be conserved among all 9 HCV genotypes. The list of these regions (CD8-R5 to CD8-R10) is described in Table 3 (FIG. 12).

According to the Immunodominancy Analysis (IDEB) and the relative location of conserved epitopes, as well to use a minimal sequence with which to extend the C-terminus of gpE2, 5 antigens were chosen based on CD4 epitopes and 4 antigens based on CD8 epitopes (Table 4; FIGS. 13A-13D) to be used for extension of gpE2. For each selected antigen (Ag), the number of CD4 and CD8 regions that are included is described (Table 4; FIGS. 13A-13D).

The CD8-based antigens were longer, so as to include more CD8 epitopes from different HLAs. The focus was on CD4-based antigens (CD4-Ag-1 to CD4-Ag-5) that also include CD8 epitopes; accordingly, 4 antigens Table 5; FIG. 14) were cloned to gpE1/gp/E2 sequence for expression and purification and animal studies.

Example 2: Expression of Fc-Tagged E1E2 with or without T-Cell Polytope (TPx) Extensions As shown in the schematic diagram (FIG. 5A) the nucleotide sequence for the full-length HCV E1E2 glycoprotein was inserted downstream of the cytomegalovirus promoter (PCMV) in a mammalian cell expression vector. The E1E2 sequence is preceded by the signal peptide sequence from tissue plasminogen activator (tPA) to direct the polypeptide to the endoplasmic reticulum (ER) following translation of the polypeptide. At the N terminus of E2, a duplication of amino acids 384-385 (ET) was inserted followed by the human IgG1 Fc tag and a PreScission Protease (PP) recognition sequence (LEVLFQGP; SEQ ID NO:5). Constructs containing a T-cell polytope (TPx; x=29, 52 or 100 amino acids) have this sequence inserted downstream of the PP recognition site. After translation of the E1E2 polypeptide and entry into the ER, host-derived signal peptidase (SP) cleaves the signal sequences in the tPA signal peptide as well as the C-terminus of E1, resulting in E1 and E2 polypeptides. For purification of E1E2 heterodimers, PreScission Protease (PP) can be added to the Fc-tagged E1E2 protein (immobilized on Protein A or Protein G affinity resins) to remove the Fc tag from the N terminus of the E2 polypeptide. This strategy can be applied to HCV E1E2 glycoproteins of different genotypes (FIGS. 6A-7B and 7A-8B).

As shown in the schematic diagram (FIG. 5A) the nucleotide sequence for the full-length HCV E1E2 glycoprotein was inserted downstream of the cytomegalovirus promoter (PCMV) in a mammalian cell expression vector. The E1E2 sequence is preceded by the signal peptide sequence from tissue plasminogen activator (tPA) to direct the polypeptide to the endoplasmic reticulum (ER) following translation of the polypeptide. At the N terminus of E2, a duplication of amino acids 384-385 relative to the particular genotype (e.g.: ET addition for H77; GenBank NP_671941) was inserted followed by the human IgG1 Fc tag and a PreScission Protease (PP) recognition sequence (LEVLFQGP; SEQ ID NO:5). Constructs containing a T-cell polytope (TPx; x=29, 52 or 100 amino acids; e.g., TP29, TP52, and TP100 as set forth in FIGS. 14A-14D) have this sequence inserted downstream of the PP recognition site. After translation of the E1E2 polypeptide and entry into the ER, host-derived signal peptidase (SP) cleaves the signal sequences in the tPA signal peptide as well as the C-terminus of E1, resulting in E1 and E2 polypeptides. For purification of E1E2 heterodimers, PreScission Protease (PP) can be added to the Fc-tagged E1E2 protein (immobilized on Protein A or Protein G affinity resins) to remove the Fc tag from the N terminus of the E2 polypeptide. This strategy can be applied to HCV E1E2 glycoproteins of different genotypes (FIGS. 6A-7B and 7A-8B).

Figure 5B:
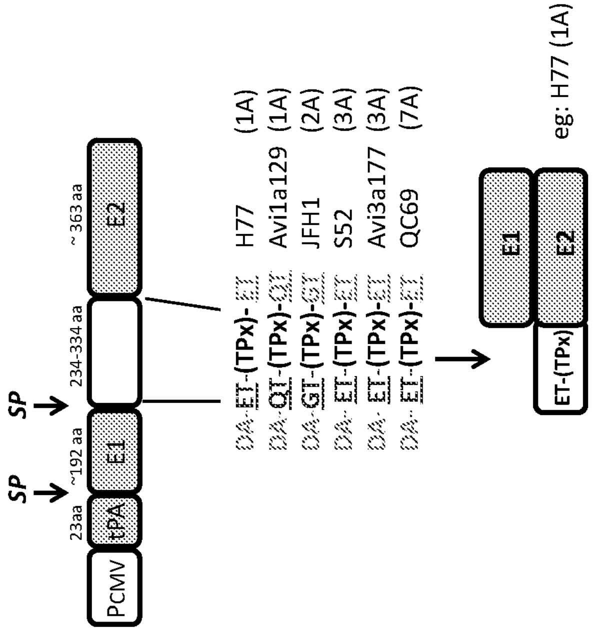
FIGS. 5A-5B present schematic representations of Fc-tagged and untagged E1E2 expression constructs and polypeptide processing.
Figure 5A:
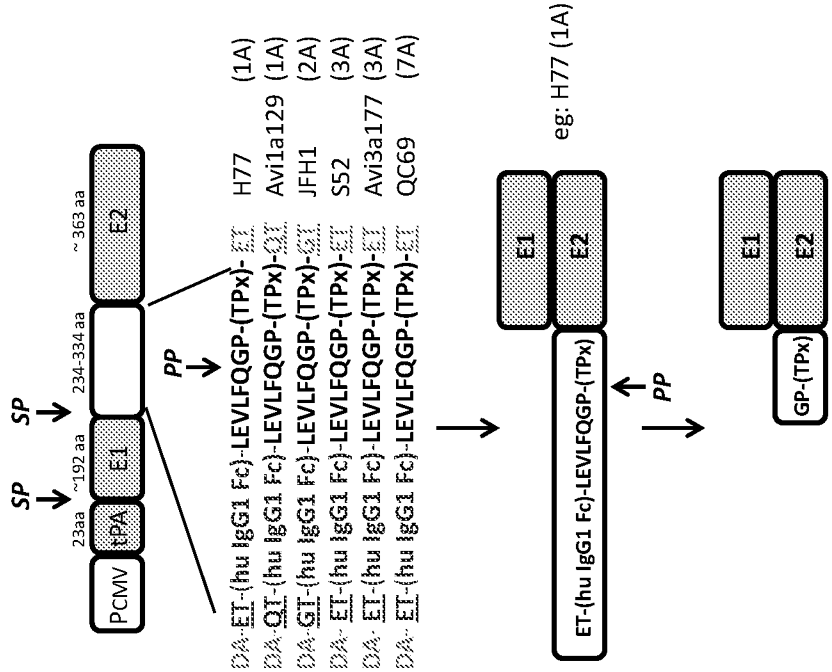

FIGS. 5A-5B. Schematic representation of Fc-tagged and untagged E1E2 expression constructs and polypeptide processing. The E1E2 polypeptide is expressed under the control of the CMV promoter ($P_{CMV}$) and includes the signal sequence from tissue plasminogen activator (tPA). Insertion sites are shown for representative HCV E1E2 sequences: H77 (GenBank NP_671941) and Alberta isolate Avi1a129 (genotype 1A), JFH1 (Genbank ABO47639; genotype 2A), S52 (Genbank ADF97232.1; genotype 3a), Alberta isolate Avi3a177 (genotype 3A), and isolate QC69 (Genbank: ABN05226.1; genotype 7A). Sizes of the polypeptide regions are shown at the top (aa=amino acids). (A) Fc tagged E1E2: At the N-terminus of E2, a duplication of the E2 N-terminal amino acids respective to the particular genotype (eg: ET addition for H77; GenBank NP_671941) is inserted followed by the human IgG1 Fc tag (hu IgG1 Fc) and a PreScission Protease (PP) recognition sequence (LEVLFQGP; SEQ ID NO:5). Constructs containing a T-cell polytope (TPx; where x is, e.g., 25, 52, or 100 amino acids) have this polytope sequence inserted C-terminal of the PP recognition site. Following expression of the polypeptide, signal peptidase (SP) cleavages result in the downstream E1 and E2 polypeptides shown. The E1 and E2 polypeptides interact to form a heterodimer. For purification purposes, the Fc tagged E1E2 is immobilized on Protein A or Protein G resin and digested with PreScission Protease (PP) (cleavage between Q and G in the LEVLFQGP (SEQ ID NO:5) sequence) to release the untagged E1E2 heterodimer. (B) Untagged E1E2: At the N-terminus of E2, a duplication of the E2 N-terminal amino acids respective to the particular genotype (eg: ET addition for H77; GenBank NP_671941) is inserted followed by a T-cell polytope (TPx; where x is, e.g., 25, 52, or 100 amino acids). Following expression of the polypeptide, signal peptidase (SP) cleavages result in the downstream E1 and E2 polypeptides shown. The E1 and E2 polypeptides interact to form a heterodimer. The untagged E1E2 is purified using *Galanthus nivalis* lectin agarose (GNA) chromatography. The duplicated E2 N-terminal residues (shown: ET addition for H77; GenBank NP_671941) and TPx are retained in the purified E1E2.

FIGS. 6A-6B. Alignment of the Fc-tagged E1-E2 polypeptide (with or without TPx extension) for H77 and Alberta isolate Avi1a129 (genotype 1A). The amino acid sequence for the coding region of the tPa-E1-Fc-PP-TPx-E2 construct (as diagrammed in FIGS. 5A-5B) for the Alberta isolate (Avi1a129) and H77 (GenBank NP_671941) was aligned using Geneious software v5.6.4. (*) denotes the insertion of the duplicated N-terminal E2 residues that precede the Fc-PP-TPx tag (Avi1a129: QT and H77: ET).

FIGS. 7A-7B. Alignment of the Fc-tagged E1-E2 polypeptide (with or without TPx extension) for S52 (Genbank ADF97232.1) and Alberta isolate Avi3a177 (genotype 3A). The amino acid sequence for the coding region of the tPA-E1-Fc-PP-TPx-E2 construct (as diagrammed in FIGS. 5A-5B) for the Alberta isolate (Avi3a177) and S52 was aligned using Geneious software v5.6.4. (*) denotes the insertion of the duplicated N-terminal E2 residues that precede the Fc-PP-TPx tag (ET for both Avi3a177 and S52).

In FIGS. 6A-6B and FIGS. 7A-7B, TP29 has the sequence AIPLEVIKGGRHLIFCHSKKKCDELAAKL (SEQ ID NO:1); TP52 has the sequence AIPLEVIKGGRHLIFCHSKKKCDELAAKLVALGINAVAYYRGLDVSVIPTSG (SEQ ID NO:2); and TP100 has the sequence

```
                                        (SEQ ID NO: 4)
VALSTTGEIPFYGKAIPLEVIKGGRHLIFCHSKKKCDELAAKLVALGINA

VAYYRGLDVSVIPTSGDVVVVATDALMTGFTGDFDSVIDCNTCVTQTVDF.
```

Methods for purification of Fc-tagged E1E2 with or without T-cell polytope (TPx) extensions from CHO cell extracts.

As shown in FIGS. 8A-8B, the following purification strategy results in capture of the Fc-tagged E1E2 glycoproteins (wild type or T cell polytope (TPx) extensions) by Protein G Sepharose chromatography medium, tag removal by PreScission Protease and the isolation of E1E2 heterodimers.

CHO cells stably expressing the Fc-tagged E1E2 expression vectors were pelleted, washed twice in sterile phosphate buffered saline (PBS) and frozen at −80° C. Frozen cell pellets were homogenized in lysis buffer (20 mM TRIS, 100 mM NaCl, 1 mM EDTA, 2% TX-100 pH 7.5) containing protease inhibitor cocktail (Calbiochem; 539134) by pipetting and incubated on ice for 30 minutes. Cell debris was removed by centrifugation for 15 min at 12000 g 4C using a JA25.5 rotor and Avanti J-26 XPI centrifuge (Beckman Coulter). Soluble cell extract (supernatant fraction) was filtered using a Stericup vacuum-driven filtration unit (Millipore SCGPU01RE).

Filtered cell extracts were bound to Protein G Sepharose 4 Fast Flow (GE; 17-0618-02) in batch mode (1 ml Protein G Sepharose: 1 g CHO cell extract in 40-50 ml volume) for 2 hours at 4° C. with gentle rotation. The Protein G Sepharose resin was sedimented by centrifugation at 200 g for 5 min in an Allegra X-15R swinging bucket centrifuge (Beckman Coulter). Unbound cell extract was removed and the Protein G Sepharose was washed in 15 ml final volume with wash buffer (20 mM TRIS, 150 mM NaCl, 0.5% TX-100 pH 7.5) for 10 minutes at 4C with gentle rotation. The Protein G Sepharose was sedimented by centrifugation at 200 g for 5 min and the wash step repeated two more times. The resin was resuspended to a final volume of 5 ml in digestion buffer (20 mM HEPES, 250 mM NaCl, 5% glycerol pH 7.5) containing GST-tagged PreScission Protease (GST-PP) (50 μg) and incubated overnight (16-20 hours) with gentle rotation at 4° C.

Following incubation with GST-PP, the Protein G Sepharose was transferred to a Poly-Prep chromatography column (Biorad; 731-1550) and the unbound material and 2 column volume (CV) (2×1 ml) washes with digestion buffer collected. The collected flow through was then added to a 0.5 ml Glutathione Sepharose 4B (GE; 17-0756-01) column (pre-equilibrated with 10 CV of digestion buffer) for GST-PP removal. The Glutathione Sepharose 4B flow-through and 2 CV (2×0.5 ml) washes with digestion buffer was collected. The collected flow through was concentrated using a centrifugal filter unit (50,000 MWCO) (Amicon; UFC805024) (final volume 200-300 l) and then diluted 10-fold in HAP buffer.

The diluted sample was applied to a hydroxyapatite type I (HAP) column; and the HAP flow through was collected. The final sample was concentrated using a centrifugal filter unit (50,000 molecular weight cutoff (MWCO)) (Amicon; UFC805024) to a final volume of 200-300 μl. Aliquots of the final antigen (10-20 μl) were stored at −80° C.

FIGS. 8A-8B. Purification of E1E2 heterodimer from CHO cell extracts expressing Fc-tagged E1E2. Fc-PP tagged wildtype or TP extension E1E2 (E1E2 heterodimer, where E2 includes a T-cell polytope) proteins from CHO cell extracts were immobilized on Protein-G Sepharose 4 Fast Flow, and digested with GST-PreScission protease (GST-PP) to remove the Fc tag. Following the digestion with GST-PP and release of untagged E1E2, GST-PP was removed by Glutathione Sepharose 4B. The untagged E1E2 protein concentrate was then applied to a HAP column. The HAP flow through containing the final E1E2 heterodimer was collected and samples loaded onto a sodium dodecyl sulfate-polyacrylamide gel electrophoresis (SDS-PAGE) gel. After electrophoresis, the gel was stained, or blotted then probed with antibodies. (A) Western blot with anti-E1 (A4) and anti-E2 (H52) monoclonal antibodies (mAbs) (0.5 μg loaded per lane). (B) Colloidal Coomassie Brilliant Blue G250 stained gel (2 μg loaded per lane). Lanes: (1) wild-type E1E2 (no TP extension); (2) E1-TP29-E2; (3) E1-TP52-E2; and (4) E1-TP100-E2. E1-TP29-E2: E1-E2 heterodimer, where E2 includes a 29-amino acid T-cell polytope ("TP29") as set forth in FIGS. 14A-D; E1-TP52-E2: E1-E2 heterodimer, where E2 includes a 52-amino acid T-cell polytope ("TP52") as set forth in FIGS. 14A-D; and E1-TP100-E2: E1-E2 heterodimer, where E2 includes a 100-amino acid T-cell polytope ("TP100") as set forth in FIGS. 14A-D.

Example 3: Analysis of E1/E2 Heterodimers

Immunization of Mice with Recombinant gpE1/gpE2 Antigens

CB6F1 mice were injected intramuscular (IM) with recombinant gpE1/gpE1 antigens at day 0, 14 and 28 days. Pre-vaccination serum was collected at day 0 at the time of the first injection and test bleeds obtained by jugular puncture at 28 days. Terminal bleeds are performed at day 42. In some cases, an extended protocol for immunizations may be applied with a fourth injection administered at day 56 and terminal bleed collected on day 70. Blood samples were centrifuged at 5000 g and serum collected and heat inactivated by incubation at 56° C. for 30 minutes. Serum samples were stored in aliquots at −80° C. until use.

Determination of Neutralizing Antibodies (nAb) Response to HCV from Immunized Mice HCVcc Assay Methods for detecting nAb responses from the sera of immunized animals by HCV cell culture-derived virus (HCVcc) are similar to those described previously (Law, J. et al. 2013. *Plos One* 8(3) e59776). Human hepatoma cells (Huh7.5) were plated on poly-lysine coated 96 well plates, 1 day prior to infection. For infection, 100 TCID50 HCV cell culture-derived virions (HCVcc) were premixed with heat inactivated sera diluted at 1 in 50 (by volume), for 1 hour at 37° C. followed by adding to cells. 12 hour post-infection, the antibody-virus inoculum was replaced with fresh culture media. Cells were fixed 48 hours post-infection with methanol using previously described methods. Infection was determined by quantitation of NS5A-positive foci using mouse monoclonal NS5A antibody (9E10). Foci were detected and counted using a CTL S6 immunospot analyzer. The percentage of neutralization was calculated in comparison to pre-vaccination serum. The neutralization activity was calculated using the following formula: % neutralization=(pre-post)/pre×100% where pre/post represent the number of NS5A-positive foci done after incubating with either the pre- or post-vaccination sera.

HCVpp Assay

Pseudotyped viruses enclosed by HCV glycoproteins (HCVpp) were generated by co-transfecting plasmids encoding HIV provirus expressing Luciferase and the HCV envelope glycoproteins (gpE1/gpE2) as previously described (Hsu et al. (2003) *Proc. Natl. Acad. Sci. USA* 100(12) 7271-7276). On the day prior to transfection $8\times10^5$ 293T cells were seeded in a 35 mm well. The following day a total of 1.5 μg DNA was transfected using Fugene 6 or other transfection reagent and media replaced after 6 h post-transfection. Supernatants containing HCVpp were harvested at 48 h and 72 h after transfection, pooled and filtered. Neutralization assays with immunized animal sera were performed as described for the HCVcc neutralization assay. Human hepatoma cells (Huh7.5) were plated on poly-lysine coated 96-well plates. 1 day prior to infection. HCVpp were diluted 1/10 and premixed with heat inactivated sera diluted at 1 in 50 (by volume) for 1 hour at 37° C. followed by adding to cells. 12 hour post-infection, the antibody-virus inoculum was replaced with fresh culture media. Cells were processed 48 hours post-infection using Bright-glo luciferase assay system (Promega). Luminescence was measured using an Enspire plate reader (Perkin Elmer). The neutralization activity was calculated using the following formula: % neutralization=(pre-post)/pre×100% where pre/post represent the luciferase activity done after incubating with either the pre- or post-vaccination sera.

Determination of Anti-gpE2 Specific Antibodies from Immunized Mice

Detection of anti-gpE2 antibodies from immunized mice were determined using recombinant gpE2 enzyme-linked immunosorbent assay (ELISA). Briefly, recombinant gpE2 (amino acids 384-661) was coated to 96-well microtiter plates in carbonate buffer (15 mM sodium carbonate, 35 mM sodium bicarbonate, pH 9.6) overnight at 4° C. Wells were then blocked for one hour at room temperature with 200 μl of phosphate buffered saline+0.2% non-ionic detergent TWEEN-20™ (PBST) containing 5% bovine serum albumin (BSA). Wells were washed three times with 250 μl PBST and 50 μl of heat inactivated sera from immunized animals added per well in triplicate in PBST for one hour at room temperature. Immunized sera were examined in serial dilution (eg: 1000, 2000, 4000, etc fold dilutions) and compared to either (i) pre-vaccinated sera from the same animal or (ii) a pooled pre-vaccinated serum sample from several animals. Wells were washed three times with 250 μl PBST and incubated for one hour with horseradish peroxidase (HRP) conjugated goat anti-mouse antibody at room temperature. HRP-activity was detected using peroxidase substrate and absorbance read at 450 nm−570 nm using an Enspire plate reader (Perkin Elmer).

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A heterodimeric polypeptide comprising:

a) a variant hepatitis C virus (HCV) E2 polypeptide comprising:

i) an HCV E2 polypeptide; and ii) a heterologous polypeptide comprising a T-cell epitope present in an HCV protein other than E1 and E2, wherein the heterologous polypeptide:

i) comprises an amino acid sequence having at least 20% amino acid sequence identity to the TP29 amino acid sequence set forth in SEQ ID NO:1, wherein the heterologous polypeptide has a length of from 29 amino acids to 32 amino acids;

ii) comprises an amino acid sequence having at least 20% amino acid sequence identity to the TP50 amino acid sequence set forth in SEQ ID NO:11, wherein the heterologous polypeptide has a length of from 50 amino acids to 55 amino acids;

iii) comprises an amino acid sequence having at least 20% amino acid sequence identity to the TP52 amino acid sequence set forth in SEQ ID NO:2, wherein the heterologous polypeptide has a length of from 52 amino acids to 55 amino acids;

iv) comprises an amino acid sequence having at least 20% amino acid sequence identity to the TP70 amino acid sequence set forth in SEQ ID NO:3, wherein the heterologous polypeptide has a length of from 70 amino acids to 75 amino acids;

v) comprises an amino acid sequence having at least 20% amino acid sequence identity to the TP100 amino acid sequence set forth in SEQ ID NO:4, wherein the heterologous polypeptide has a length of from 100 amino acids to 105 amino acids;

vi) comprises an amino acid sequence having at least 20% amino acid sequence identity to the TP171 amino acid sequence set forth in SEQ ID NO:63, wherein the heterologous polypeptide has a length of from 171 amino acids to 175 amino acids;

vii) comprises an amino acid sequence having at least 20% amino acid sequence identity to the TP228 amino acid sequence set forth in SEQ ID NO:10, wherein the heterologous polypeptide has a length of from 228 amino acids to 232 amino acids;

viii) comprises an amino acid sequence having at least 20% amino acid sequence identity to the TP553 amino acid sequence set forth in SEQ ID NO:12, wherein the heterologous polypeptide has a length of from 553 amino acids to 560 amino acids;

ix) comprises an amino acid sequence having at least 20% amino acid sequence identity to the TP778 amino acid sequence set forth in SEQ ID NO:64, wherein the heterologous polypeptide has a length of about 778 amino acids; or x) comprises an amino acid sequence having at least 20% amino acid sequence identity to the TP1985 amino acid sequence set forth in SEQ ID NO:13, wherein the heterologous polypeptide has a length of about 1985 amino acids; and b) an HCV E1 polypeptide.

2. The heterodimeric polypeptide of claim 1, wherein:

a) the HCV E2 polypeptide is derived from an HCV of genotype 1, 2, 3, or 7; and b) the HCV E1 polypeptide is derived from an HCV of genotype 1, 2, 3, or 7.

3. The heterodimeric polypeptide of claim 1, wherein the HCV E2 polypeptide comprises an amino acid sequence having at least 20% amino acid sequence identity to an E2 polypeptide depicted in one of FIGS. 1A-1C, FIGS. 2A-2C, FIGS. 3A-3C, and FIGS. 4A-4B.

4. The heterodimeric polypeptide of claim 1, wherein the HCV E2 polypeptide comprises an amino acid sequence having at least 50% amino acid sequence identity to an E2 polypeptide depicted in one of FIGS. 1A-1C, FIGS. 2A-2C, FIGS. 3A-3C, and FIGS. 4A-4B.

5. The heterodimeric polypeptide of claim 1, wherein the HCV E1 polypeptide comprises an amino acid sequence having at least 20% amino acid sequence identity to an E1 polypeptide depicted in FIGS. 1A-1C, FIGS. 2A-2C, FIGS. 3A-3C, and FIGS. 4A-4B.

6. The heterodimeric polypeptide of claim 1, wherein the HCV E1 polypeptide comprises an amino acid sequence having at least 50% amino acid sequence identity to an E1 polypeptide depicted in FIGS. 1A-1C, FIGS. 2A-2C, FIGS. 3A-3C, and FIGS. 4A-4B.

7. The heterodimeric polypeptide of claim 1, wherein the modified HCV E2 polypeptide and the HCV E1 polypeptide are derived from an HCV of the same genotype.

8. The heterodimeric polypeptide of claim 1, wherein the modified HCV E2 polypeptide and the HCV E1 polypeptide are derived from an HCV of different genotypes.

9. A heterodimeric polypeptide comprising:

a) a variant hepatitis C virus (HCV) E1 polypeptide comprising:

i) an HCV E1 polypeptide; and ii) a heterologous polypeptide comprising a T-cell epitope present in an HCV protein other than E1 and E2, wherein the heterologous polypeptide:

i) comprises an amino acid sequence having at least 20% amino acid sequence identity to the TP29 amino acid sequence set forth in SEQ ID NO:1, wherein the heterologous polypeptide has a length of from 29 amino acids to 32 amino acids;

ii) comprises an amino acid sequence having at least 20% amino acid sequence identity to the TP50 amino acid sequence set forth in SEQ ID NO:11, wherein the heterologous polypeptide has a length of from 50 amino acids to 55 amino acids;

iii) comprises an amino acid sequence having at least 20% amino acid sequence identity to the TP52 amino acid sequence set forth in SEQ ID NO:2, wherein the heterologous polypeptide has a length of from 52 amino acids to 55 amino acids;

iv) comprises an amino acid sequence having at least 20% amino acid sequence identity to the TP70 amino acid sequence set forth in SEQ ID NO:3, wherein the heterologous polypeptide has a length of from 70 amino acids to 75 amino acids;

v) comprises an amino acid sequence having at least 20% amino acid sequence identity to the TP100 amino acid sequence set forth in SEQ ID NO:4, wherein the heterologous polypeptide has a length of from 100 amino acids to 105 amino acids;

vi) comprises an amino acid sequence having at least 20% amino acid sequence identity to the TP171 amino acid sequence set forth in SEQ ID NO:63, wherein the heterologous polypeptide has a length of from 171 amino acids to 175 amino acids;

vii) comprises an amino acid sequence having at least 20% amino acid sequence identity to the TP228 amino acid sequence set forth in SEQ ID NO:10, wherein the heterologous polypeptide has a length of from 228 amino acids to 232 amino acids;

viii) comprises an amino acid sequence having at least 20% amino acid sequence identity to the TP553 amino acid sequence set forth in SEQ ID NO:12, wherein the heterologous polypeptide has a length of from 553 amino acids to 560 amino acids;

ix) comprises an amino acid sequence having at least 20% amino acid sequence identity to the TP778 amino acid sequence set forth in SEQ ID NO:64, wherein the heterologous polypeptide has a length of about 778 amino acids; or x) comprises an amino acid sequence having at least 20% amino acid sequence identity to the TP1985 amino acid sequence set forth in SEQ ID NO:13, wherein the heterologous polypeptide has a length of about 1985 amino acids; and b) an HCV E2 polypeptide.

10. The heterodimeric polypeptide of claim 9, wherein:

a) the HCV E2 polypeptide is derived from an HCV of genotype 1, 2, 3, or 7; and b) the HCV E1 polypeptide is derived from an HCV of genotype 1, 2, 3, or 7.

11. The heterodimeric polypeptide of claim 9, wherein the HCV E2 polypeptide comprises an amino acid sequence having at least 20% amino acid sequence identity to an E2 polypeptide depicted in one of FIGS. 1A-1C, FIGS. 2A-2C, FIGS. 3A-3C, and FIGS. 4A-4B.

12. The heterodimeric polypeptide of claim 9, wherein the HCV E2 polypeptide comprises an amino acid sequence having at least 50% amino acid sequence identity to an E2 polypeptide depicted in one of FIGS. 1A-1C, FIGS. 2A-2C, FIGS. 3A-3C, and FIGS. 4A-4B.

13. The heterodimeric polypeptide of claim 9, wherein the HCV E1 polypeptide comprises an amino acid sequence having at least 20% amino acid sequence identity to an E1 polypeptide depicted in FIGS. 1A-1C, FIGS. 2A-2C, FIGS. 3A-3C, and FIGS. 4A-4B.

14. The heterodimeric polypeptide of claim 9, wherein the HCV E1 polypeptide comprises an amino acid sequence having at least 50% amino acid sequence identity to an E1 polypeptide depicted in FIGS. 1A-1C, FIGS. 2A-2C, FIGS. 3A-3C, and FIGS. 4A-4B.

15. The heterodimeric polypeptide of claim 9, wherein the variant HCV E1 polypeptide and the HCV E2 polypeptide are derived from an HCV of the same genotype.

16. The heterodimeric polypeptide of claim 9, wherein the variant HCV E1 polypeptide and the HCV E2 polypeptide are derived from an HCV of different genotypes.

17. A heterodimeric polypeptide comprising:

a) a variant hepatitis C virus (HCV) E1 polypeptide comprising:

i) an HCV E1 polypeptide; and ii) a heterologous polypeptide comprising a T-cell epitope present in an HCV protein other than E1 and E2, wherein the heterologous polypeptide:

i) comprises an amino acid sequence having at least 20% amino acid sequence identity to the TP29 amino acid sequence set forth in SEQ ID NO:1, wherein the heterologous polypeptide has a length of from 29 amino acids to 32 amino acids;

ii) comprises an amino acid sequence having at least 20% amino acid sequence identity to the TP50 amino acid sequence set forth in SEQ ID NO:11, wherein the heterologous polypeptide has a length of from 50 amino acids to 55 amino acids;

iii) comprises an amino acid sequence having at least 20% amino acid sequence identity to the TP52 amino acid sequence set forth in SEQ ID NO:2, wherein the heterologous polypeptide has a length of from 52 amino acids to 55 amino acids;

iv) comprises an amino acid sequence having at least 20% amino acid sequence identity to the TP70 amino acid sequence set forth in SEQ ID NO:3, wherein the heterologous polypeptide has a length of from 70 amino acids to 75 amino acids;

v) comprises an amino acid sequence having at least 20% amino acid sequence identity to the TP100 amino acid sequence set forth in SEQ ID NO:4, wherein the heterologous polypeptide has a length of from 100 amino acids to 105 amino acids;

vi) comprises an amino acid sequence having at least 20% amino acid sequence identity to the TP171 amino acid sequence set forth in SEQ ID NO:63, wherein the heterologous polypeptide has a length of from 171 amino acids to 175 amino acids;

vii) comprises an amino acid sequence having at least 20% amino acid sequence identity to the TP228 amino acid sequence set forth in SEQ ID NO:10, wherein the heterologous polypeptide has a length of from 228 amino acids to 232 amino acids;

viii) comprises an amino acid sequence having at least 20% amino acid sequence identity to the TP553 amino acid sequence set forth in SEQ ID NO:12, wherein the heterologous polypeptide has a length of from 553 amino acids to 560 amino acids;

ix) comprises an amino acid sequence having at least 20% amino acid sequence identity to the TP778 amino acid sequence set forth in SEQ ID NO:64, wherein the heterologous polypeptide has a length of about 778 amino acids; or x) comprises an amino acid sequence having at least 20% amino acid sequence identity to the TP1985 amino acid sequence set forth in SEQ ID NO:13, wherein the heterologous polypeptide has a length of about 1985 amino acids; and b) a variant HCV E2 polypeptide comprising:

i) an HCV E2 polypeptide; and ii) a heterologous polypeptide comprising a T-cell epitope present in an HCV protein other than E1 and E2, wherein the heterologous polypeptide:

i) comprises an amino acid sequence having at least 20% amino acid sequence identity to the TP29 amino acid sequence set forth in SEQ ID NO:1, wherein the heterologous polypeptide has a length of from 29 amino acids to 32 amino acids;

ii) comprises an amino acid sequence having at least 20% amino acid sequence identity to the TP50 amino acid sequence set forth in SEQ ID NO:11, wherein the heterologous polypeptide has a length of from 50 amino acids to 55 amino acids;

iii) comprises an amino acid sequence having at least 20% amino acid sequence identity to the TP52 amino acid sequence set forth in SEQ ID NO:2, wherein the heterologous polypeptide has a length of from 52 amino acids to 55 amino acids;

iv) comprises an amino acid sequence having at least 20% amino acid sequence identity to the TP70 amino acid sequence set forth in SEQ ID NO:3, wherein the heterologous polypeptide has a length of from 70 amino acids to 75 amino acids;

v) comprises an amino acid sequence having at least 20% amino acid sequence identity to the TP100 amino acid sequence set forth in SEQ ID NO:4, wherein the heterologous polypeptide has a length of from 100 amino acids to 105 amino acids;

vi) comprises an amino acid sequence having at least 20% amino acid sequence identity to the TP171 amino acid sequence set forth in SEQ ID NO:63, wherein the heterologous polypeptide has a length of from 171 amino acids to 175 amino acids;

vii) comprises an amino acid sequence having at least 20% amino acid sequence identity to the TP228 amino acid sequence set forth in SEQ ID NO:10, wherein the heterologous polypeptide has a length of from 228 amino acids to 232 amino acids;

viii) comprises an amino acid sequence having at least 20% amino acid sequence identity to the TP553 amino acid sequence set forth in SEQ ID NO:12, wherein the heterologous polypeptide has a length of from 553 amino acids to 560 amino acids;

ix) comprises an amino acid sequence having at least 20% amino acid sequence identity to the TP778 amino acid sequence set forth in SEQ ID NO:64, wherein the heterologous polypeptide has a length of about 778 amino acids; or x) comprises an amino acid sequence having at least 20% amino acid sequence identity to the TP1985 amino acid sequence set forth in SEQ ID NO:13, wherein the heterologous polypeptide has a length of about 1985 amino acids.

18. The heterodimeric polypeptide of claim 17, wherein:

a) the HCV E2 polypeptide is derived from an HCV of genotype 1, 2, 3, or 7; and b) the HCV E1 polypeptide is derived from an HCV of genotype 1, 2, 3, or 7.

19. The heterodimeric polypeptide of claim 17, wherein the HCV E2 polypeptide comprises an amino acid sequence having at least 20% amino acid sequence identity to an E2 polypeptide depicted in one of FIGS. 1A-1C, FIGS. 2A-2C, FIGS. 3A-3C, and FIGS. 4A-4B.

20. The heterodimeric polypeptide of claim 17, wherein the HCV E2 polypeptide comprises an amino acid sequence having at least 50% amino acid sequence identity to an E2 polypeptide depicted in one of FIGS. 1A-1C, FIGS. 2A-2C, FIGS. 3A-3C, and FIGS. 4A-4B.

21. The heterodimeric polypeptide of claim 17, wherein the HCV E1 polypeptide comprises an amino acid sequence having at least 20% amino acid sequence identity to an E1 polypeptide depicted in FIGS. 1A-1C, FIGS. 2A-2C, FIGS. 3A-3C, and FIGS. 4A-4B.

22. The heterodimeric polypeptide of claim 17, wherein the HCV E1 polypeptide comprises an amino acid sequence having at least 50% amino acid sequence identity to an E1 polypeptide depicted in FIGS. 1A-1C, FIGS. 2A-2C, FIGS. 3A-3C, and FIGS. 4A-4B.

23. The heterodimeric polypeptide of claim 17, wherein the modified HCV E2 polypeptide and the variant HCV E1 polypeptide are derived from an HCV of the same genotype.

24. The heterodimeric polypeptide of claim 17, wherein the modified HCV E2 polypeptide and the variant HCV E1 polypeptide are derived from an HCV of different genotypes.

* * * * *

SEQUENCE LISTING

```
Sequence total quantity: 197
SEQ ID NO: 1          moltype = AA  length = 29
FEATURE               Location/Qualifiers
REGION                1..29
                      note = Synthetic amino acid sequence
source                1..29
                      mol_type = protein
                      organism = synthetic construct
SEQUENCE: 1
AIPLEVIKGG RHLIFCHSKK KCDELAAKL                                  29

SEQ ID NO: 2          moltype = AA  length = 52
FEATURE               Location/Qualifiers
REGION                1..52
                      note = Synthetic amino acid sequence
source                1..52
                      mol_type = protein
                      organism = synthetic construct
SEQUENCE: 2
AIPLEVIKGG RHLIFCHSKK KCDELAAKLV ALGINAVAYY RGLDVSVIPT SG        52

SEQ ID NO: 3          moltype = AA  length = 70
FEATURE               Location/Qualifiers
REGION                1..70
                      note = Synthetic amino acid sequence
source                1..70
                      mol_type = protein
                      organism = synthetic construct
SEQUENCE: 3
KGGRHLIFCH SKKKCDELAA KLVALGINAV AYYRGLDVSV IPTSGDVVVV ATDALMTGFT 60
```

```
GDFDSVIDCN                                                  70

SEQ ID NO: 4           moltype = AA  length = 100
FEATURE                Location/Qualifiers
REGION                 1..100
                       note = Synthetic amino acid sequence
source                 1..100
                       mol_type = protein
                       organism = synthetic construct
SEQUENCE: 4
VALSTTGEIP FYGKAIPLEV IKGGRHLIFC HSKKKCDELA AKLVALGINA VAYYRGLDVS  60
VIPTSGDVVV VATDALMTGF TGDFDSVIDC NTCVTQTVDF                     100

SEQ ID NO: 5           moltype = AA  length = 8
FEATURE                Location/Qualifiers
REGION                 1..8
                       note = Synthetic amino acid sequence
source                 1..8
                       mol_type = protein
                       organism = synthetic construct
SEQUENCE: 5
LEVLFQGP                                                    8

SEQ ID NO: 6           moltype = AA  length = 7
FEATURE                Location/Qualifiers
REGION                 1..7
                       note = Synthetic amino acid sequence
source                 1..7
                       mol_type = protein
                       organism = synthetic construct
SEQUENCE: 6
ENLYTQS                                                     7

SEQ ID NO: 7           moltype = AA  length = 5
FEATURE                Location/Qualifiers
REGION                 1..5
                       note = Synthetic amino acid sequence
source                 1..5
                       mol_type = protein
                       organism = synthetic construct
SEQUENCE: 7
DDDDK                                                       5

SEQ ID NO: 8           moltype = AA  length = 4
FEATURE                Location/Qualifiers
REGION                 1..4
                       note = Synthetic amino acid sequence
source                 1..4
                       mol_type = protein
                       organism = synthetic construct
SEQUENCE: 8
LVPR                                                        4

SEQ ID NO: 9           moltype = AA  length = 191
FEATURE                Location/Qualifiers
REGION                 1..191
                       note = Synthetic amino acid sequence
source                 1..191
                       mol_type = protein
                       organism = synthetic construct
SEQUENCE: 9
MSTNPKPQRK TKRNTNRRPQ DVKFPGGGQI VGGVYLLPRR GPRLGVRATR KTSERSQPRG  60
RRQPIPKARR PEGRTWAQPG YPWPLYGNEG CGWAGWLLSP RGSRPSWGPT DPRRRSRNLG  120
KVIDTLTCGF ADLMGYIPLV GAPLGGAARA LAHGVRVLED GVNYATGNLP GCSFSIFLLA  180
LLSCLTVPAS A                                                191

SEQ ID NO: 10          moltype = AA  length = 228
FEATURE                Location/Qualifiers
REGION                 1..228
                       note = Synthetic amino acid sequence
source                 1..228
                       mol_type = protein
                       organism = synthetic construct
SEQUENCE: 10
LHAPTGSGKS TKVPAAYAAQ GYKVLVLNPS VAATLGFGAY MSKAHGIDPN IRTGVRTITT  60
GSPITYSTYG KFLADGGCSG GAYDIIICDE CHSTDATSIL GIGTVLDQAE TAGARLVVLA  120
TATPPGSVTV PHPNIEEVAL STTGEIPFYG KAIPLEVIKG GRHLIFCHSK KKCDELAAKL  180
VALGINAVAY YRGLDVSVIP TSGDVVVVAT DALMTGFTGD FDSVIDCN          228
```

-continued

```
SEQ ID NO: 11          moltype = AA  length = 50
FEATURE                Location/Qualifiers
REGION                 1..50
                       note = Synthetic amino acid sequence
source                 1..50
                       mol_type = protein
                       organism = synthetic construct
SEQUENCE: 11
LGALTGTYVY NHLTPLRDWA HNGLRDLAVA VEPVVFSQME TKLITWGADT            50

SEQ ID NO: 12          moltype = AA  length = 553
FEATURE                Location/Qualifiers
REGION                 1..553
                       note = Synthetic amino acid sequence
source                 1..553
                       mol_type = protein
                       organism = synthetic construct
SEQUENCE: 12
QASLLKVPYF VRVQGLLRIC ALARKMAGGH YVQMAIIKLG ALTGTYVYNA LTPLRDWAHN  60
GLRDLAVAVE PVVFSQMETK LITWGADTAA CGDIINGLPV SARRGREILL GPADGMVSKG  120
WRLLAPITAY AQQTRGLLGC IITSLTGRDK NQVEGEVQIV STAAQTFLAT CINGVCWTVY  180
HGAGTRTIAS PKGPVIQMYT NVDQDLVGWP APQGARSLTP CTCGSSDLYL VTRHADVIPV  240
RRRGDSRGSL LSPRPISYLK GSAGGPLLCP AGHAVGIFRA AVCTRGVAKA VDFIPVENLE  300
TTMRSPVFTD NSSPPAVPQS FQVAHLHAPT GSGKSTKVPA AYAAQGYKVL VLNPSVAATL  360
GFGAYMSKAH GIDPNIRTGV RTITTGSPIT YSTYGKFLAD GGCSGGAYDI IICDECHSTD  420
ATSILGIGTV LDQAETAGAR LVVLATATPP GSVTVPHPNI EEVALSTTGE IPFYGKAIPL  480
EVIKGGRHLI FCHSKKKCDE LAAKLVALGI NAVAYYRGLD VSVIPTSGDV VVVATDALMT  540
GFTGDFDSVI DCN                                                     553

SEQ ID NO: 13          moltype = AA  length = 1985
FEATURE                Location/Qualifiers
REGION                 1..1985
                       note = Synthetic amino acid sequence
source                 1..1985
                       mol_type = protein
                       organism = synthetic construct
SEQUENCE: 13
APITAYAQQT RGLLGCIITS LTGRDKNQVE GEVQIVSTAA QTFLATCING VCWTVYHGAG  60
TRTIASPKGP VIQMYTNVDQ DLVGWPAPQG ARSLTPCTCG SSDLYLVTRH ADVIPVRRRG  120
DSRGSLLSPR PISYLKGSAG GPLLCPAGHA VGIFRAAVCT RGVAKAVDFI PVENLETTMR  180
SPVFTDNSSP PAVPQSFQVA HLHAPTGSGK STKVPAAYAA QGYKVLVLNP SVAATLGFGA  240
YMSKAHGIDP NIRTGVRTIT TGSPITYSTY GKFLADGGCS GGAYDIIICD ECHSTDATSI  300
LGIGTVLDQA ETAGARLVVL ATATPPGSVT VPHPNIEEVA LSTTGEIPFY GKAIPLEVIK  360
GGRHLIFCHS KKKCDELAAK LVALGINAVA YYRGLDVSVI PTSGDVVVVA TDALMTGFTG  420
DFDSVIDCNT CVTQTVDFSL DPTFTIETTT LPQDAVSRTQ RRGRTGRGKP GIYRFVAPGE  480
RPSGMFDSSV LCECYDAGCA WYELTPAETT VRLRAYMNTP GLPVCQDHLE FWEGVFTGLT  540
HIDAHFLSQT KQSGENLPYL VAYQATVCAR AQAPPPSWDQ MWKCLIRLKP TLHGPTPLLY  600
RLGAVQNEVT LTHPITKYIM TCMSADLEVV TSTWVLVGGV LAALAAYCLS TGCVVIVGRI  660
VLSGKPAIIP DREVLYREFD EMEECSQHLP YIEQGMMLAE QFKQKALGLL QTASRQAEVI  720
APAVQTNWQK LEAFWAKHMW NFISGIQYLA GLSTLPGNPA IASLMAFTAA VTSPLTTSQT  780
LLFNILGGWV AAQLAAPGAA TAFVGAGLAG AAIGSVGLGK VLVDILAGYG AGVAGALVAF  840
KIMSGEVPST EDLVNLLPAI LSPGALVVGV VCAAILRRHV GPGEGAVQWM NRLIAFASRG  900
NHVSPTHYVP ESDAAARVTA ILSSLTVTQL LRRLHQWISS ECTTPCSGSW LRDIWDWICE  960
VLSDFKTWLK AKLMPQLPGI PFVSCQRGYR GVWRGDGIMH TRCHCGAEIT GHVKNGTMRI  1020
VGPRTCRNMW SGTFPINAYT TGPCTPLPAP NYTFALWRVS AEEYVEIRQV GDFHYVTGMT  1080
TDNLKCPCQV PSPEFFTELD GVRLHRFAPP CKPLLREEVS FRVGLHEYPV GSQLPCEPEP  1140
DVAVLTSMLT DPSHITAEAA GRRLARGSPP SVASSSASQL SAPSLKATCT ANHDSPDAEL  1200
IEANLLWRQE MGGNITRVES ENKVVILDSF DPLVAEEDER EISVPAEILR KSRRFAPALP  1260
IWARPDYNPP LLETWKKPDY EPPVVHGCPL PPPQSPPVPP PRKKRTVVLT ESTVSTALAE  1320
LATKSFGSSS TSGITGDNTT TSSEPAPSGC PPDSDAESYS SMPPLEGEPG DPDLSDGSWS  1380
TVSSEADTED VVCCSMSYSW TGALVTPCAA EEQKLPINAL SNSLLRHHNL VYSTTSRSAC  1440
QRQKKVTFDR LQVLDSHYQD VLKEVKAAAS KVKANLLSVE EACSLTPPHS AKSKFGYGAK  1500
DVRCHARKAV NHINSVWKDL LEDSVTPIDT TIMAKNEVFC VQPEKGGRKP ARLIVFPDLG  1560
VRVCEKMALY DVVSKLPLAV MGSSYGFQYS PGQRVEFLVQ AWKSKKTPMG FSYDTRCFDS  1620
TVTESDIRTE EAIYQCCDLD PQARVAIKSL TERLYVGGPL TNSRGENCGY RRCRASGVLT  1680
TSCGNTLTCY IKARAACRAA GLQDCTMLVC GNNLVVICES AGVQEDAASL RAFTEAMTRY  1740
SAPPGDPPQP EYDLELITSC SSNVSVAHDG AGKRVYYLTR DPTTPLARAA WETARHTPVN  1800
SWLGNIIMFA PTLWARMILM THFFSVLIAR DQLEQALDCE IYGACYSIEP LDLPPIIQRL  1860
HGLSAFSLHS YSPGEINRVA ACLRKLGVPP LRAWRHRARS VRARLLSRGG RAAICGKYLF  1920
NWAVRTKLKL TPIAAAGQLD LSGWFTAGYS GGDIYHSVSH ARPRWFWFCL LLLAAGVGIY  1980
LLPNR                                                              1985

SEQ ID NO: 14          moltype = AA  length = 14
FEATURE                Location/Qualifiers
REGION                 1..14
                       note = Synthetic amino acid sequence
source                 1..14
                       mol_type = protein
                       organism = synthetic construct
```

```
SEQUENCE: 14
QYIKANSKFI GIFE                                                    14

SEQ ID NO: 15           moltype = AA  length = 124
FEATURE                 Location/Qualifiers
REGION                  1..124
                        note = Synthetic amino acid sequence
source                  1..124
                        mol_type = protein
                        organism = synthetic construct
SEQUENCE: 15
MIKLKFGVFF TVLLSSAYAH GTPQNITDLC AEYHNTQIHT LNDKIFSYTE SLAGKREMAI  60
ITFKNGATFQ VEVPGSQHID SQKKAIERMK DTLRIAYLTE AKVEKLCVWN NKTPHAIAAI  120
SMAN                                                               124

SEQ ID NO: 16           moltype = AA  length = 15
FEATURE                 Location/Qualifiers
REGION                  1..15
                        note = Synthetic amino acid sequence
source                  1..15
                        mol_type = protein
                        organism = synthetic construct
SEQUENCE: 16
ILMQYIKANS KFIGI                                                   15

SEQ ID NO: 17           moltype = AA  length = 7
FEATURE                 Location/Qualifiers
REGION                  1..7
                        note = Synthetic amino acid sequence
source                  1..7
                        mol_type = protein
                        organism = synthetic construct
SEQUENCE: 17
VNNESSE                                                            7

SEQ ID NO: 18           moltype = AA  length = 17
FEATURE                 Location/Qualifiers
REGION                  1..17
                        note = Synthetic amino acid sequence
source                  1..17
                        mol_type = protein
                        organism = synthetic construct
SEQUENCE: 18
PGINGKAIHL VNNESSE                                                 17

SEQ ID NO: 19           moltype = AA  length = 6
FEATURE                 Location/Qualifiers
REGION                  1..6
                        note = Synthetic amino acid sequence
source                  1..6
                        mol_type = protein
                        organism = synthetic construct
SEQUENCE: 19
PNRDIL                                                             6

SEQ ID NO: 20           moltype = AA  length = 7
FEATURE                 Location/Qualifiers
REGION                  1..7
                        note = Synthetic amino acid sequence
source                  1..7
                        mol_type = protein
                        organism = synthetic construct
SEQUENCE: 20
FIGITEL                                                            7

SEQ ID NO: 21           moltype = AA  length = 6
FEATURE                 Location/Qualifiers
REGION                  1..6
                        note = Synthetic amino acid sequence
source                  1..6
                        mol_type = protein
                        organism = synthetic construct
SEQUENCE: 21
SYFPSV                                                             6

SEQ ID NO: 22           moltype = AA  length = 20
FEATURE                 Location/Qualifiers
REGION                  1..20
                        note = Synthetic amino acid sequence
```

```
source                  1..20
                        mol_type = protein
                        organism = synthetic construct
SEQUENCE: 22
NSVDDALINS TKIYSYFPSV                                                20

SEQ ID NO: 23           moltype = AA  length = 20
FEATURE                 Location/Qualifiers
REGION                  1..20
                        note = Synthetic amino acid sequence
source                  1..20
                        mol_type = protein
                        organism = synthetic construct
SEQUENCE: 23
IDKISDVSTI VPYIGPALNI                                                20

SEQ ID NO: 24           moltype = AA  length = 15
FEATURE                 Location/Qualifiers
REGION                  1..15
                        note = Synthetic amino acid sequence
source                  1..15
                        mol_type = protein
                        organism = synthetic construct
SEQUENCE: 24
QSIALSSLMV AQAIP                                                     15

SEQ ID NO: 25           moltype = AA  length = 19
FEATURE                 Location/Qualifiers
REGION                  1..19
                        note = Synthetic amino acid sequence
source                  1..19
                        mol_type = protein
                        organism = synthetic construct
SEQUENCE: 25
PVFAGANYAA WAVNVAQVI                                                 19

SEQ ID NO: 26           moltype = AA  length = 20
FEATURE                 Location/Qualifiers
REGION                  1..20
                        note = Synthetic amino acid sequence
source                  1..20
                        mol_type = protein
                        organism = synthetic construct
SEQUENCE: 26
VHHNTEEIVA QSIALSSLMV                                                20

SEQ ID NO: 27           moltype = AA  length = 534
FEATURE                 Location/Qualifiers
source                  1..534
                        mol_type = protein
                        organism = Homo sapiens
SEQUENCE: 27
ADDVVDSSKS FVMENFSSYH GTKPGYVDSI QKGIQKPKSG TQGNYDDDWK EFYSTDNKYD  60
AAGYSVDNEN PLSGKAGGVV KVTYPGLTKV LALKVDNAET IKKELGLSLT EPLMEQVGTE  120
EFIKRFGDGA SRVVLSLPFA EGSSSVEYIN NWEQAKALSV ELEINFETRG KRGQDAMYEY  180
MAQACAGNRV RRSVGSSLSC INLDWDVIRD KTKTKIESLK EHGPIKNKMS ESPNKTVSEE  240
KAKQYLEEFH QTALEHPELS ELKTVTGTNP VFAGANYAAW AVNVAQVIDS ETADNLEKTT  300
AALSILPGIG SVMGIADGAV HHNTEEIVAQ SIALSSLMVA QAIPLVGELV DIGFAAYNFV  360
ESIINLFQVV HNSYNRPAYS PGHKTQPFLH DGYAVSWNTV EDSIIRTGFQ GESGHDIKIT  420
AENTPLPIAG VLLPTIPGKL DVNKSKTHIS VNGRKIRMRC RAIDGDVTFC RPKSPVYVGN  480
GVHANLHVAF HRSSSEKIHS NEISSDSIGV LGYQKTVDHT KVNSKLSLFF EIKS        534

SEQ ID NO: 28           moltype = AA  length = 26
FEATURE                 Location/Qualifiers
REGION                  1..26
                        note = Synthetic amino acid sequence
source                  1..26
                        mol_type = protein
                        organism = synthetic construct
SEQUENCE: 28
IMQYIKANSK FIGIQSIALS SLMVAQ                                         26

SEQ ID NO: 29           moltype = AA  length = 25
FEATURE                 Location/Qualifiers
REGION                  1..25
                        note = Synthetic amino acid sequence
source                  1..25
                        mol_type = protein
                        organism = synthetic construct
```

```
SEQUENCE: 29
SLAGKREMAI ITFKNGATFQ VEVPG                                            25

SEQ ID NO: 30           moltype = AA  length = 10
FEATURE                 Location/Qualifiers
REGION                  1..10
                        note = Synthetic amino acid sequence
source                  1..10
                        mol_type = protein
                        organism = synthetic construct
SEQUENCE: 30
CGLVPAGSGP                                                             10

SEQ ID NO: 31           moltype = AA  length = 12
FEATURE                 Location/Qualifiers
REGION                  1..12
                        note = Synthetic amino acid sequence
source                  1..12
                        mol_type = protein
                        organism = synthetic construct
SEQUENCE: 31
SLLKSRMVPN FN                                                          12

SEQ ID NO: 32           moltype = AA  length = 12
FEATURE                 Location/Qualifiers
REGION                  1..12
                        note = Synthetic amino acid sequence
source                  1..12
                        mol_type = protein
                        organism = synthetic construct
SEQUENCE: 32
SLLIARRMPN FN                                                          12

SEQ ID NO: 33           moltype = AA  length = 12
FEATURE                 Location/Qualifiers
REGION                  1..12
                        note = Synthetic amino acid sequence
source                  1..12
                        mol_type = protein
                        organism = synthetic construct
SEQUENCE: 33
SKLVQASASG VN                                                          12

SEQ ID NO: 34           moltype = AA  length = 12
FEATURE                 Location/Qualifiers
REGION                  1..12
                        note = Synthetic amino acid sequence
source                  1..12
                        mol_type = protein
                        organism = synthetic construct
SEQUENCE: 34
SSYLKASDAP DN                                                          12

SEQ ID NO: 35           moltype = AA  length = 12
FEATURE                 Location/Qualifiers
REGION                  1..12
                        note = Synthetic amino acid sequence
source                  1..12
                        mol_type = protein
                        organism = synthetic construct
SEQUENCE: 35
RPKPQQFFGL MN                                                          12

SEQ ID NO: 36           moltype = AA  length = 12
FEATURE                 Location/Qualifiers
REGION                  1..12
                        note = Synthetic amino acid sequence
source                  1..12
                        mol_type = protein
                        organism = synthetic construct
SEQUENCE: 36
SLRPLALWRS FN                                                          12

SEQ ID NO: 37           moltype = AA  length = 12
FEATURE                 Location/Qualifiers
REGION                  1..12
                        note = Synthetic amino acid sequence
source                  1..12
                        mol_type = protein
```

```
                        organism = synthetic construct
SEQUENCE: 37
SPQGIAGQRN FN                                                        12

SEQ ID NO: 38           moltype = AA  length = 14
FEATURE                 Location/Qualifiers
REGION                  1..14
                        note = Synthetic amino acid sequence
source                  1..14
                        mol_type = protein
                        organism = synthetic construct
SEQUENCE: 38
DVDERDVRGF ASFL                                                      14

SEQ ID NO: 39           moltype = AA  length = 12
FEATURE                 Location/Qualifiers
REGION                  1..12
                        note = Synthetic amino acid sequence
source                  1..12
                        mol_type = protein
                        organism = synthetic construct
SEQUENCE: 39
SLPLGLWAPN FN                                                        12

SEQ ID NO: 40           moltype = AA  length = 12
FEATURE                 Location/Qualifiers
REGION                  1..12
                        note = Synthetic amino acid sequence
source                  1..12
                        mol_type = protein
                        organism = synthetic construct
SEQUENCE: 40
SLLIFRSWAN FN                                                        12

SEQ ID NO: 41           moltype = AA  length = 12
FEATURE                 Location/Qualifiers
REGION                  1..12
                        note = Synthetic amino acid sequence
source                  1..12
                        mol_type = protein
                        organism = synthetic construct
SEQUENCE: 41
SGVVIATVIV IT                                                        12

SEQ ID NO: 42           moltype = AA  length = 12
FEATURE                 Location/Qualifiers
REGION                  1..12
                        note = Synthetic amino acid sequence
source                  1..12
                        mol_type = protein
                        organism = synthetic construct
SEQUENCE: 42
SLGPQGIWGQ FN                                                        12

SEQ ID NO: 43           moltype = AA  length = 12
FEATURE                 Location/Qualifiers
REGION                  1..12
                        note = Synthetic amino acid sequence
source                  1..12
                        mol_type = protein
                        organism = synthetic construct
SEQUENCE: 43
KKSPGRVVGG SV                                                        12

SEQ ID NO: 44           moltype = AA  length = 12
FEATURE                 Location/Qualifiers
REGION                  1..12
                        note = Synthetic amino acid sequence
source                  1..12
                        mol_type = protein
                        organism = synthetic construct
SEQUENCE: 44
PQGLLGAPGI LG                                                        12

SEQ ID NO: 45           moltype = AA  length = 31
FEATURE                 Location/Qualifiers
REGION                  1..31
                        note = Synthetic amino acid sequence
source                  1..31
```

-continued

```
                        mol_type = protein
                        organism = synthetic construct
SEQUENCE: 45
HGPEGLRVGF YESDVMGRGH ARLVHVEEPH T                             31

SEQ ID NO: 46           moltype = AA  length = 12
FEATURE                 Location/Qualifiers
REGION                  1..12
                        note = Synthetic amino acid sequence
source                  1..12
                        mol_type = protein
                        organism = synthetic construct
SEQUENCE: 46
GPQGLAGQRG IV                                                  12

SEQ ID NO: 47           moltype = AA  length = 12
FEATURE                 Location/Qualifiers
REGION                  1..12
                        note = Synthetic amino acid sequence
source                  1..12
                        mol_type = protein
                        organism = synthetic construct
SEQUENCE: 47
GGSGQRGRKA LE                                                  12

SEQ ID NO: 48           moltype = AA  length = 12
FEATURE                 Location/Qualifiers
REGION                  1..12
                        note = Synthetic amino acid sequence
source                  1..12
                        mol_type = protein
                        organism = synthetic construct
SEQUENCE: 48
SLSALLSSDI FN                                                  12

SEQ ID NO: 49           moltype = AA  length = 12
FEATURE                 Location/Qualifiers
REGION                  1..12
                        note = Synthetic amino acid sequence
source                  1..12
                        mol_type = protein
                        organism = synthetic construct
SEQUENCE: 49
SLPRFKIIGG FN                                                  12

SEQ ID NO: 50           moltype = AA  length = 12
FEATURE                 Location/Qualifiers
REGION                  1..12
                        note = Synthetic amino acid sequence
source                  1..12
                        mol_type = protein
                        organism = synthetic construct
SEQUENCE: 50
SLLGIAVPGN FN                                                  12

SEQ ID NO: 51           moltype = AA  length = 12
FEATURE                 Location/Qualifiers
REGION                  1..12
                        note = Synthetic amino acid sequence
source                  1..12
                        mol_type = protein
                        organism = synthetic construct
SEQUENCE: 51
FFKNIVTPRT PP                                                  12

SEQ ID NO: 52           moltype = AA  length = 8
FEATURE                 Location/Qualifiers
REGION                  1..8
                        note = Synthetic amino acid sequence
source                  1..8
                        mol_type = protein
                        organism = synthetic construct
SEQUENCE: 52
DYKDDDDK                                                       8

SEQ ID NO: 53           moltype = AA  length = 9
FEATURE                 Location/Qualifiers
REGION                  1..9
                        note = Synthetic amino acid sequence
```

```
source                  1..9
                        mol_type = protein
                        organism = synthetic construct
SEQUENCE: 53
YPYDVPDYA                                                                  9

SEQ ID NO: 54           moltype = AA  length = 10
FEATURE                 Location/Qualifiers
REGION                  1..10
                        note = Synthetic amino acid sequence
source                  1..10
                        mol_type = protein
                        organism = synthetic construct
SEQUENCE: 54
EQKLISEEDL                                                                 10

SEQ ID NO: 55           moltype = AA  length = 5
FEATURE                 Location/Qualifiers
REGION                  1..5
                        note = synthetic peptide sequence
source                  1..5
                        mol_type = protein
                        organism = synthetic construct
SEQUENCE: 55
GSGGS                                                                      5

SEQ ID NO: 56           moltype = AA  length = 4
FEATURE                 Location/Qualifiers
REGION                  1..4
                        note = synthetic peptide sequence
source                  1..4
                        mol_type = protein
                        organism = synthetic construct
SEQUENCE: 56
GGGS                                                                       4

SEQ ID NO: 57           moltype = AA  length = 4
FEATURE                 Location/Qualifiers
REGION                  1..4
                        note = synthetic peptide sequence
source                  1..4
                        mol_type = protein
                        organism = synthetic construct
SEQUENCE: 57
GGSG                                                                       4

SEQ ID NO: 58           moltype = AA  length = 5
FEATURE                 Location/Qualifiers
REGION                  1..5
                        note = synthetic peptide sequence
source                  1..5
                        mol_type = protein
                        organism = synthetic construct
SEQUENCE: 58
GGSGG                                                                      5

SEQ ID NO: 59           moltype = AA  length = 5
FEATURE                 Location/Qualifiers
REGION                  1..5
                        note = synthetic peptide sequence
source                  1..5
                        mol_type = protein
                        organism = synthetic construct
SEQUENCE: 59
GSGSG                                                                      5

SEQ ID NO: 60           moltype = AA  length = 5
FEATURE                 Location/Qualifiers
REGION                  1..5
                        note = synthetic peptide sequence
source                  1..5
                        mol_type = protein
                        organism = synthetic construct
SEQUENCE: 60
GSGGG                                                                      5

SEQ ID NO: 61           moltype = AA  length = 5
FEATURE                 Location/Qualifiers
REGION                  1..5
```

```
                         note = synthetic peptide sequence
source                   1..5
                         mol_type = protein
                         organism = synthetic construct
SEQUENCE: 61
GGGSG                                                                    5

SEQ ID NO: 62            moltype = AA  length = 5
FEATURE                  Location/Qualifiers
REGION                   1..5
                         note = synthetic peptide sequence
source                   1..5
                         mol_type = protein
                         organism = synthetic construct
SEQUENCE: 62
GSSSG                                                                    5

SEQ ID NO: 63            moltype = AA  length = 171
FEATURE                  Location/Qualifiers
REGION                   1..171
                         note = sythetic amino acid sequence
source                   1..171
                         mol_type = protein
                         organism = synthetic construct
SEQUENCE: 63
MSTNPKPQRK TKRNTNRRPQ DVKFPGGGQI VGGVYLLPRR GPRLGVRATR KTSERSQPRG  60
RRQPIPKARR PEGRTWAQPG YPWPLYGNEG CGWAGWLLSP RGSRPSWGPT DPRRRSRNLG  120
KVIDTLTCGF ADLMGYIPLV GAPLGGAARA LAHGVRVLED GVNYATGNLP G            171

SEQ ID NO: 64            moltype = AA  length = 778
FEATURE                  Location/Qualifiers
REGION                   1..778
                         note = sythetic amino acid sequence
source                   1..778
                         mol_type = protein
                         organism = synthetic construct
SEQUENCE: 64
LHAPTGSGKS TKVPAAYAAQ GYKVLVLNPS VAATLGFGAY MSKAHGIDPN IRTGVRTITT  60
GSPITYSTYG KFLADGGCSG GAYDIIICDE CHSTDATSIL GIGTVLDQAE TAGARLVVLA  120
TATPPGSVTV PHPNIEEVAL STTGEIPFYG KAIPLEVIKG GRHLIFCHSK KKCDELAAKL  180
VALGINAVAY YRGLDVSVIP TSGDVVVVAT DALMTGFTGD FDSVIDCNTC VTQTVDFSLD  240
PTFTIETTTL PQDAVSRTQR RGRTGRGKPG IYRFVAPGER PSGMFDSSVL CECYDAGCAW  300
YELTPAETTV RLRAYMNTPG LPVCQDHLEF WEGVFTGLTH IDAHFLSQTK QSGENLPYLV  360
AYQATVCARA QAPPPSWDQM WKCLIRLKPT LHGPTPLLYR LGAVQNEVTL THPITKYIMT  420
CMSADLEVVT STWVLVGGVL AALAAYCLST GCVVIVGRIV LSGKPAIIPD REVLYREFDE  480
MEECSQHLPY IEQGMMLAEQ FKQKALGLLQ TASRQAEVIA PAVQTNWQKL EAFWAKHMWN  540
FISGIQYLAG LSTLPGNPAI ASLMAFTAAV TSPLTTSQTL LFNILGGWVA AQLAAPGAAT  600
AFVGAGLAGA AIGSVGLGKV LVDILAGYGA GVAGALVAFK IMSGEVPSTE DLVNLLPAIL  660
SPGALVVGVV CAAILRRHVG PGEGAVQWMN RLIAFASRGN HVSPTHYVPE SDAAARVTAI  720
LSSLTVTQLL RRLHQWISSE CTTPCSGSWL RDIWDWICEV LSDFKTWLKA KLMPQLPG    778

SEQ ID NO: 65            moltype = AA  length = 14
FEATURE                  Location/Qualifiers
REGION                   1..14
                         note = synthetic peptide sequence
source                   1..14
                         mol_type = protein
                         organism = synthetic construct
SEQUENCE: 65
QYIKANSKFI GITE                                                          14

SEQ ID NO: 66            moltype = AA  length = 20
FEATURE                  Location/Qualifiers
REGION                   1..20
                         note = synthetic peptide sequence
source                   1..20
                         mol_type = protein
                         organism = synthetic construct
SEQUENCE: 66
QSIALSSLMV AQAIPLVGEL                                                    20

SEQ ID NO: 67            moltype = AA  length = 20
FEATURE                  Location/Qualifiers
REGION                   1..20
                         note = synthetic peptide sequence
source                   1..20
                         mol_type = protein
                         organism = synthetic construct
SEQUENCE: 67
```

```
VDIGFAAYNF VESIINLFQV                                        20

SEQ ID NO: 68          moltype = AA  length = 20
FEATURE                Location/Qualifiers
REGION                 1..20
                       note = synthetic peptide sequence
source                 1..20
                       mol_type = protein
                       organism = synthetic construct
SEQUENCE: 68
QGESGHDIKI TAENTPLPIA                                        20

SEQ ID NO: 69          moltype = AA  length = 20
FEATURE                Location/Qualifiers
REGION                 1..20
                       note = synthetic peptide sequence
source                 1..20
                       mol_type = protein
                       organism = synthetic construct
SEQUENCE: 69
GVLLPTIPGK LDVNKSKTHI                                        20

SEQ ID NO: 70          moltype =   length =
SEQUENCE: 70
000

SEQ ID NO: 71          moltype =   length =
SEQUENCE: 71
000

SEQ ID NO: 72          moltype = AA  length = 6
FEATURE                Location/Qualifiers
VARIANT                2
                       note = X can be Leu or Gln
source                 1..6
                       mol_type = protein
                       organism = synthetic construct
SEQUENCE: 72
PXGMTS                                                       6

SEQ ID NO: 73          moltype = AA  length = 5
FEATURE                Location/Qualifiers
VARIANT                2
                       note = X can be Leu or Gln
source                 1..5
                       mol_type = protein
                       organism = synthetic construct
SEQUENCE: 73
PXGMT                                                        5

SEQ ID NO: 74          moltype = AA  length = 746
FEATURE                Location/Qualifiers
VARIANT                248
                       note = X can be any naturally occurring amino acid
VARIANT                262
                       note = X can be any naturally occurring amino acid
VARIANT                270
                       note = X can be any naturally occurring amino acid
VARIANT                275
                       note = X can be any naturally occurring amino acid
VARIANT                399
                       note = X can be any naturally occurring amino acid
VARIANT                408
                       note = X can be any naturally occurring amino acid
VARIANT                524
                       note = X can be any naturally occurring amino acid
VARIANT                580
                       note = X can be any naturally occurring amino acid
VARIANT                641
                       note = X can be any naturally occurring amino acid
VARIANT                709
                       note = X can be any naturally occurring amino acid
VARIANT                733
                       note = X can be any naturally occurring amino acid
source                 1..746
                       mol_type = protein
                       organism = synthetic construct
SEQUENCE: 74
MSTNPKPQRK TKRNTNRRPQ DVKFPGGGQI VGGVYLLPRR GPRLGVRATR KTSERSQPRG  60
```

```
RRQPIPKARR PEGRTWAQPG YPWPLYGNEG CGWAGWLLSP RGSRPSWGPT DPRRRSRNLG  120
KVIDTLTCGF ADLMGYIPLV GAPLGGAARA LAHGVRVLED GVNYATGNLP GCSFSIFLLA  180
LLSCLTVPAS AYQVRNSSGL YHVTNDCPNS SIVYETADTI LHSPGCVPCV REGNASRCWV  240
ALTPTVAXRD GSLPTTQLRR HXDLLVGSAX LCSAXYVGDL CGSVFLVGQL FTFSPRRHWT  300
TQDCNCSIYP GHITGHRMAW DMMMNWSPTT ALVVAQLLRI PQAILDMIAG AHWGVLAGIA  360
YFSMVGNWAK VLVVLLLFAG VDAETHVTGG SAARATSGXA SLFSPGAXQN IQLINTNGSW  420
HINRTALNCN DSLDTGWVAG LFYYHKFNSS GCPERMASCR PLADFDQGWG PISYANGSGP  480
DQRPYCWHYP PKPCGIVPAQ QVCGPVYCFT PSPVVVGTTD RLGXPTYNWG ENETDVLVLN  540
NTRPPLGNWF GCTWMNSTGF TKVCGAPPCN IGGVGNNTLX CPTDCFRKHP EATYSRCGSG  600
PWLTPRCLVD YPYRLWHYPC TVNYTIFKVR MYVGGVEHRL XAACNWTRGE RCDLDDRDRS  660
ELSPLLLSTT QWQVLPCSFT TLPALSTGLI HLHQNIVDVQ YLYGVGSSXV SWAIKWEYVI  720
LLFLLLADAR ICXCLWMMLL ISQAEA                                       746

SEQ ID NO: 75          moltype = AA  length = 746
FEATURE                Location/Qualifiers
source                 1..746
                       mol_type = protein
                       organism = Hepatitis C virus
SEQUENCE: 75
MSTNPKPQRK TKRNTNRRPQ DVKFPGGGQI VGGVYLLPRR GPRLGVRATR KTSERSQPRG  60
RRQPIPKARR PEGRTWAQPG YPWPLYGNEG CGWAGWLLSP RGSRPSWGPT DPRRRSRNLG  120
KVIDTLTCGF ADLMGYIPLV GAPLGGAARA LAHGVRVLED GVNYATGNLP GCSFSIFLLA  180
LLSCLTVPAS AYQVRNSTGL YHVTNDCPNS SIVYEAADAI LHTPGCVPCV REGNTSRCWV  240
AMTPTVATRD GKLPTTQLRR HIDLLVGSAT LCSALYVGDL CGSIFLVGQM FTFSPRRHWT  300
TQDCNCSLYP GHITGHRMAW DMMMNWSPTA ALITAQLLRI PQAILDMIAG AHWGVLAGIA  360
YFSMVGNWAK VLVVLLLFAG VDAQTHVTGG RAAHITAGLT SLFSPGPSQK LQLVNTNGSW  420
HINSTALNCN DSLKTGWIAG LLYSYKFNSS GCPERLASCR RLTDFAQGWG PISHANGSGP  480
DERPYCWHYP PRPCGIVPAK SVCGPVYCFT PSPVVVGTTD KSGAPTYNWG ENDTDVFVLN  540
NTRPPLGNWF GCTWMNSTGF TKVCGAPPCV IGGAGNNTLR CPTDCFRKHP DATYSRCGSG  600
PWITPRCLVD YPYRLWHYPC TVNYSIFKIR MYLGGVEHRL EAACNWTRGE RCDLEDRDRS  660
ELSPLLLSTT QWQVLPCSFT TLPALSTGLI HLHQNIVDVQ YLYGVGSSVA SWAIKWDYVV  720
LLFLLLADAR ICSCLWMMLL ISQAEA                                       746

SEQ ID NO: 76          moltype = AA  length = 746
FEATURE                Location/Qualifiers
source                 1..746
                       mol_type = protein
                       organism = Hepatitis C virus
SEQUENCE: 76
MSTNPKPQRK TKRNTNRRPQ DVKFPGGGQI VGGVYLLPRR GPRLGVRATR KTSERSQPRG  60
RRQPIPKARR PEGRTWAQPG YPWPLYGNEG CGWAGWLLSP RGSRPSWGPT DPRRRSRNLG  120
KVIDTLTCGF ADLMGYIPLV GAPLGGAARA LAHGVRVLED GVNYATGNLP GCSFSIFLLA  180
LLSCLTVPAS AYQVRNSSGL YHVTNDCPNS SIVYEAADAI LHTPGCVPCV REGNASRCWV  240
AVTPTVATRD GKLPTTQLRR HIDLLVGSAT LCSALYVGDL CGSVFLVGQL FTFSPRRHWT  300
TQDCNCSIYP GHITGHRMAW DMMMNWSPTA ALVVAQLLRI PQAIMDMIAG AHWGVLAGIA  360
YFSMVGNWAK VLVVLLLFAG VDAETHVTGG SAGRTTAGLV GLLTPGAKQN IQLINTNGSW  420
HINSTALNCN ESLNTGWLAG LFYQHKFNSS GCPERLASCR RLTDFAQGWG PISYANGSGL  480
DERPYCWHYP PRPCGIVPAK SVCGPVYCFT PSPVVVGTTD RSGAPTYSWG ANDTDVFVLN  540
NTRPPLGNWF GCTWMNSTGF TKVCGAPPCV IGGVGNNTLL CPTDCFRKHP EATYSRCGSG  600
PWITPRCMVD YPYRLWHYPC TINYTIFKVR MYVGGVEHRL EAACNWTRGE RCDLEDRDRS  660
ELSPLLLSTT QWQVLPCSFT TLPALSTGLI HLHQNIVDVQ YLYGVGSSIA SWAIKWEYVV  720
LLFLLLADAR VCSCLWMMLL ISQAEA                                       746

SEQ ID NO: 77          moltype = AA  length = 746
FEATURE                Location/Qualifiers
source                 1..746
                       mol_type = protein
                       organism = Hepatitis C virus
SEQUENCE: 77
MSTNPKPQRK TKRNTNRRPQ DVKFPGGGQI VGGVYLLPRR GPRLGVRAVR KTSERSQPRG  60
RRQPIPKARR PEGRTWAQPG YPWPLYGNEG CGWAGWLLSP RGSRPSWGPT DPRRRSRNLG  120
KVIDTLTCGF ADLMGYIPLV GAPLGGAARA LAHGVRVLED GVNYATGNLP GCSFSIFLLA  180
LLSCLTVPAS AYQVRNSSGI YHVTNDCPNS SIVYETADTI LHSPGCVPCV REGNASKCWV  240
ALAPTVATRD GKLPTTQLRR HIDLLVGSAT LCSALYVGDL CGSVFLVGQL FTFSPRRHWT  300
TQDCNCSIYP GHITGHRMAW DMMMNWSPTT ALVVAQLLRV PQAILDMIAG AHWGVLAGIA  360
YFSMVGNWAK VLVVLLLFAG VDAETYTTGG SVAQAAFGLT SLFRPGPKQD IQLINTNGSW  420
HINRTALNCN ASLDTGWVAG LFYYHKFNSS GCPERMASCR SLADFDQGWG PISYANGSGP  480
EHRPYCWHYP PKPCGIVPAQ NVCGPVYCFT PSPVVVGTTN KLGVPTYSWG SNETDVLVLN  540
NTRPPLGNWF GCTWMNSSGF TKVCGAPPCV IGGAGNRTLH CPTDCFRKHP EATYSRCGSG  600
PWITPRCLVH YPYRLWHYPC TVNYTMFKVR MYVGGVEHRL EVACNWTRGE RCDLDDRDRS  660
ELSPLLLSTT QWQVLPCSFT TLPALTTGLI HLHQNIVDVQ YLYGVGSSIV SWAIKWEYVI  720
LLFLLLADAR ICSCLWMMLL ISQAEA                                       746

SEQ ID NO: 78          moltype = AA  length = 746
FEATURE                Location/Qualifiers
source                 1..746
                       mol_type = protein
                       organism = Hepatitis C virus
SEQUENCE: 78
```

-continued

```
MSTNPKPQRK TKRNTNRRPQ DVKFPGGGQI VGGVYLLPRR GPRLGVRATR KTSERSQPRG  60
RRQPIPKARR PEGRSWAQPG YPWPLYGNEG CGWAGWLLSP RGSRPSWGPT DPRRRSRNLG  120
KVIDTLTCGF ADLMGYIPLV GAPLGGAARA LAHGVRVLED GVNYATGNLP GCSFSIFLLA  180
LLSCLTVPAS AFQVRNSSGL YHVTNDCPNS SIVYETADTI LHSPGCVPCV REDNTSRCWV  240
AVAPTVATRD GRLPTTQLRR HIDLLVGSAT LCSALYVGDL CGSVFLVGQL FTFSPRRHWT  300
TQDCNCSIYP GHITGHRMAW DMMMNWSPTT ALVVAQLLRV PQAILDMIAG AHWGVLAGIA  360
YFSMVGNWAK VLVVLLLFAS VDAETYTSGG SVARATAGFA GIFNPGAKQD IQLINTNGSW  420
HINRTALNCN ASLDTGWVAG LFYYHKFNSS GCPERMASCK PLAHFAQGWG PISYANGSGP  480
DHRPYCWHYP PKPCGIVPAQ NVCGPVYCFT PSPVVVGTTN KLGAPTYNWG SNDTDVFILN  540
NTRPPGGNWF GCTWMNSSGF TKVCGAPPCT IGGVGNNTLL CPTDCFRKHP EATYSRCGSG  600
PWVTPRFLVH YPYRLWHYPC TVNYTLFKVR MYVGGVEHRL EVACNWTRGE RCDLDDRDRS  660
ELSPLLLSTT QWQVLPCSFT TLPALTTGLI HLHQNIVDVQ YLYGVGSSLV SWAIKWEYVI  720
LLFLLLADAR ICSCLWMMLL ISQAEA                                     746

SEQ ID NO: 79          moltype = AA  length = 746
FEATURE                Location/Qualifiers
source                 1..746
                       mol_type = protein
                       organism = Hepatitis C virus
SEQUENCE: 79
MSTNPKPQRK TKRNTNRRPQ DVKFPGGGQI VGGVYLLPRR GPRLGVRATR KTSERSQPRG  60
RRQPIPKARR PEGRTWAQPG YPWPLYGNEG CGWAGWLLSP RGSRPSWGPT DPRRRSRNLG  120
KVIDTLTCGF ADLMGYIPLV GAPLGGAARA LAHGVRVLED GVNYATGNLP GCSFSIFLLA  180
LLSCLTVPAS AYQVRNSSGL YHVTNDCPNS SIVYETADTI LHSPGCVPCV REGNTSKCWV  240
AVAPTVATRD GKLPTTQLRR HIDLLVGSAT LCSALYVGDL CGSVFLVGQL FTFSPRRHWT  300
TQDCNCSIYP GHITGHRMAW DMMMNWSPTA ALVTAQLLRV PQAILDMIAG AHWGVLAGIA  360
YFSMAGNWAK VLLVLLLFAG VDAETYTTGG SVARTTRGLA SLLQVGPKQD IRLIHTNGSW  420
HINRTALNCN ASLDTGWLAG LLYYHKFNSS GCPERMASCR PLADFDQGWG PISYANGSGP  480
EHRPYCWHYP PKPCGIVPAQ TVCGPVYCFT PSPVVVGTTN KLGVPTYTWG SNDTDVFVLN  540
NTRPPLGNWF GCTWMNSTGF TKVCGAPPCV IGGVGNNTLH CPTDCFRKHP EATYSRCGSG  600
PWITPRCLVD YPYRLWHYPC TVNYTLFKVR MYVGGVEHRL QAACNWTRGE RCDLDDRDRS  660
ELSPLLLSTT QWQVLPCSFT TLPALTTGLI HLHQNIVDVQ YLYGVGSSIV SWAIKWEYVI  720
LLFLLLADAR ICSCLWMMLL ISQAEA                                     746

SEQ ID NO: 80          moltype = AA  length = 746
FEATURE                Location/Qualifiers
source                 1..746
                       mol_type = protein
                       organism = Hepatitis C virus
SEQUENCE: 80
MSTNPKPQRK TKRNTNRRPQ DVKFPGGGQI VGGVYLLPRR GPRLGVRATR KTSERSQPRG  60
RRQPIPKARR PEGRTWAQPG YPWPLYGNEG CGWAGWLLSP RGSRPSWGPT DPRRRSRNLG  120
KVIDTLTCGF ADLMGYIPLV GAPLGGAARA LAHGVRVLED GVNYATGNLP GCSFSIFLLA  180
LLSCLTVPAS AYQVRNSSGL YHVTNDCPNS SIVYETADTI LHSPGCVPCV REDNASRCWV  240
PVAPTVATRD GKLPTTQLRR HIDLLVGSAT LCSALYVGDL CGSVFLVSQL FTFSPRRHWT  300
TQDCNCSIYP GHITGHRMAW DMMMNWSPTV ALVMAQLLRV PQAILDMIAG AHWGVLAGIA  360
YFSMVGNWAK VLVVLLLFAG VDAQTYVTGG SAARGASGLA NLFTPGAKQD IQLINTNGSW  420
HINRTALNCN ASLDTGWVAG LFYYHKFNSS GCPERMASCK PLADFDQGWG PIRHANGSGP  480
EHRPYCWHYP PKPCGIVSAQ TVCGPVYCFT PSPVVVGTTN RLGVPTYSWG TNDTDVFVLN  540
NTRPPLGNWF GCTWMNSSGF TKVCGAPPCV IGGVGNNTLH CPTDCFRKHP EATYSRCGSG  600
PWITPRCLVH YPYRLWHYPC TVNYTLFKVR MYVGGVEHRL EVACNWTRGE RCDLDDRDRS  660
ELSPLLLSTT QWQVLPCSFT TLPALTTGLI HLHQNIVDVQ YLYGVGSSIV SWAIKWEYVI  720
LLFLLLADAR ICSCLWMMLL ISQAEA                                     746

SEQ ID NO: 81          moltype = AA  length = 746
FEATURE                Location/Qualifiers
source                 1..746
                       mol_type = protein
                       organism = Hepatitis C virus
SEQUENCE: 81
MSTNPKPQRK TKRNTNRRPQ DVKFPGGGQI VGGVYLLPRR GPRLGVRTTR KTSERSEPRG  60
RRQPIPKARR PEGRTWAQPG YPWPLYGNEG CGWAGWLLSP RGSRPSWGPT DPRRRSRNLG  120
KVIDTLTCGF ADLMGYIPLV GAPLGGAARA LAHGVRVLED GVNYATGNLP GCSFSIFLLA  180
LLSCLTVPAS AYQVRNSSGL YHVTNDCPNS SIVYETKDTI LHSPGCVPCV REGNVSKCWV  240
PVALTVATRD GNLPTTQLRR HIDLLVGSAT LCSALYVGDL CGSVFLVGQL FTFSPRRHWT  300
TQDCNCSMYP GHITGHRMAW DMMMNWSPTS ALVVAQLLRV PQAILDMIAG AHWGVLAGLA  360
YFSMVGNWAK VLVVLLLFAS VDAGTHVTGG SAAHDVSALA GFFRRGAKQN IQLINTNGSW  420
HVNRTALNCN ASLDTGWVAG LLYYHRFNSS GCPERMASCR PLADFDQGWG PITNVDGGGS  480
EYRPYCWHYP PKPCGIEPAQ NVCGPVYCFT PSPVVVGTTD KVGVPTYNWG ENDTDVFVLN  540
NTRPPLGNWF GCTWMNSSGF VKVCGAPPCI IGGAGNKTLH CPTDCFRKHP DATYSRCGSG  600
PWLTPRCLVD YPYRLWHYPC TVNYTLFKIR MYVGGVEHRL VAACNWTYGE RCNLDDRDRS  660
ELSPLLLSTT QWQVLPCSFT TLPALTTGLI HLHQNIVDVQ YLYGVGSSIV SWAIKWEYVI  720
LLFLLLADAR ICSCLWMMLL ISQAEA                                     746

SEQ ID NO: 82          moltype = AA  length = 746
FEATURE                Location/Qualifiers
source                 1..746
                       mol_type = protein
                       organism = Hepatitis C virus
```

-continued

```
SEQUENCE: 82
MSTNPKPQRK TKRNTNRRPQ DVKFPGGGQI VGGVYLLPRR GPRLGVRATR KTSERSQPRG  60
RRQPIPKARR PEGRTWAQPG YPWPLYGNEG CGWAGWLLSP RGSRPSWGPT DPRRRSRNLG  120
KVIDTLTCGF ADLMGYIPLV GAPLGGAARA LAHGVRVLED GVNYATGNLP GCSFSIFLLA  180
LLSCLTVPAS AYQVRNSSGL YHVTNDCPNS SIVYETADTI LHSPGCVPCV REGNASKCWV  240
AVAPTVATRD GTLPTTQLRR HIDLLVGGAT LCSALYVGDL CGSVFLVGQL FTFSPRRHWT  300
TQDCNCSIYP GHITGHRMAW DMMMNWSPTT ALIVAQLLRV PQAILDMIAG AHWGVLAGIA  360
YFSMVGNWAK VLVVLLLFAG VDAETHVTGG SAAQVTSRVA GFFNPGPKQN VQLINTNGSW  420
HINRTALNCN ASLDTGWVAG LFYHYNFNSS GCPERMASCR PLADFDQGWG PISYANGSGP  480
EHRPYCWHYP PKPCGIVPAQ NVCGPVYCFT PSPVVVGTTN RLGVPTYNWG SNDTDVFVLN  540
NTRPPLGNWF GCTWMNSSGF TKVCGAPPCV IGGVGNNTLH CPTDCFRKHP EATYSRCGSG  600
PWITPRCLVH YPYRLWHYPC TVNYTLFKVR MYVGGVEHRL EAACNWTRGE RCDLDDRDRS  660
ELSPLLLSTT QWQVLPCSFT TLPALTTGLI HLHQNIVDVQ YLYGVGSSIV SWAIKWEYVI  720
LLFLLLADAR ICSCLWMMLL ISQAEA                                      746

SEQ ID NO: 83           moltype = AA  length = 746
FEATURE                 Location/Qualifiers
source                  1..746
                        mol_type = protein
                        organism = Hepatitis C virus
SEQUENCE: 83
MSTNPKPQRK TKRNTNRRPQ DVKFPGGGQI VGGVYLLPRR GPRLGVRATR KTSERSQPRG  60
RRQPIPKARR PEGRSWAQPG YPWPLYGNEG CGWAGWLLSP RGSRPSWGPT DPRRRSRNLG  120
KVIDTLTCGF ADLMGYIPLV GAPLGGAARA LAHGVRVLED GVNYATGNLP GCSFSIFLLA  180
LLSCLTVPAS AYQVRNSSGI YHVTNDCPNS SIVYETADTI LHSPGCVPCV REGNASKCWV  240
ALAPTVATRD GRLPTTQLRR HIDLLVGSAT LCSALYVGDL CGSVFLVGQL FTFSPRRHWT  300
TQDCNCSIYP GHITGHRMAW DMMMNWSPTT ALVVAQLLRI PQAILDMIAG AHWGVLAGIA  360
YFSMVGNWAK VLVVLLLFAG VDAHTRVTGG SAARATARLT TLFSPGAKQD IQLINTNGSW  420
HINRTALNCN ASLDTGWVAG LFYYHKFNSS GCPERMASCR PLADFDQGWG PISYANGSGP  480
EHRPYCWHYP PKPCGIIPAK TVCGPVYCFT PSPVVVGTTD RSGAPTFNWG DNDTDVLVLN  540
NTRPPLGNWF GCTWMNSSGY TKVCGAPPCI IGGVGNNTLH CPTDCFRKHP EATYSRCGSG  600
PWITPRCLVH YPYRLWHYPC TVNYTLFKVR MYVGGVEHRL EAACNWTRGE RCNLDDRDRS  660
ELSPLLLSTT QWQVLPCSFT TLPALTTGLI HLHQNIVDVQ YLYGVGSSIV SWAIKWEYVI  720
LLFLLLADAR VCSCLWMMLL ISQVEA                                      746

SEQ ID NO: 84           moltype = AA  length = 746
FEATURE                 Location/Qualifiers
source                  1..746
                        mol_type = protein
                        organism = Hepatitis C virus
SEQUENCE: 84
MSTNPKPQRK TKRNTNRRPQ DVKFPGGGQI VGGVYLLPRR GPRLGVRATR KTSERSQPRG  60
RRQPIPKARR PEGRTWAQPG YPWPLYGNEG CGWAGWLLSP RGSRPSWGPT DPRRRSRNLG  120
KVIDTLTCGF ADLMGYIPLV GAPLGGAARA LAHGVRVLED GVNYATGNLP GCSFSIFLLA  180
LLSCLTVPAS AYQVRNSSGL YHVTNDCPNS SIVYETADTI LHSPGCVPCV REGNASKCWV  240
AVTPTVATRD GRLPATQLRR HIDLLVGSAT LCSALYVGDL CGSIFLVGQL FTFSPRRHWT  300
TQDCNCSIYP GHITGHRMAW DMMMNWSPTT ALVVAQLLRV PQAILDMIAG AHWGVLAGIA  360
YFSMVGNWAK VLVVLLLFAG VDAGTHVTGG SAAKDTSGFT SLFRIGARQN IQLINSNGSW  420
HINRTALNCN ESLDTGWVAG LLYYHKFNSS GCPERMASCR SLADFDQGWG PISYANGSGP  480
EHRPYCWHYP PKPCGIVPAQ SVCGPVYCFT PSPVVVGTTD KSGAPTYNWG CNETDVFVLN  540
NTRPPLGNWF GCTWMNSSGF TKVCGAPPCV IGGVGNNTLH CPTDCFRKHP EATYSRCGSG  600
PWITPRCLVH YAYRLWHYPC TVNYTLFKVR MYVGGVEHRL DVACNWTRGE RCNLDDRDRS  660
ELSPLLLSTT QWQVLPCSFT TLPALSTGLI HLHQNIVDVQ YLYGVGSSIV SWAIKWEYVI  720
LLFLLLADAR ICSCLWMMLL ISQAEA                                      746

SEQ ID NO: 85           moltype = AA  length = 746
FEATURE                 Location/Qualifiers
source                  1..746
                        mol_type = protein
                        organism = Hepatitis C virus
SEQUENCE: 85
MSTNPKPQRK TKRNTNRRPQ DVKFPGGGQI VGGVYLLPRR GPRLGVRATR KTSERSQPRG  60
RRQPIPKARR PEGRTWAQPG YPWPLYGNEG CGWAGWLLSP RGSRPSWGPT DPRRRSRNLG  120
KVIDTLTCGF ADLMGYIPLV GAPLGGAARA LAHGVRVLED GVNYATGNLP GCSFSIFLLA  180
LLSCLTVPAS AYQVRNSSGL YHVTNDCPNS SIVYETADTI LHSPGCVPCV REGNASKCWV  240
AVTPTVATRD GRLPATQLRR HIDLLVGSAT LCSALYVGDL CGSIFLVGQL FTFSPRRHWT  300
TQDCNCSIYP GHITGHRMAW DMMMNWSPTT ALVVAQLLRV PQAILDMIAG AHWGVLAGIA  360
YFSMVGNWAK VLVVLLLFAG VDAGTHVTGG SAAKDTSGFT SLFRIGARQN IQLINSNGSW  420
HINRTALNCN ESLDTGWVAG LLYYHKFNSS GCPERMASCR SLADFDQGWG PISYANGSGP  480
EHRPYCWHYP PKPCGIVPAQ SVCGPVYCFT PSPVVVGTTD KSGAPTYNWG CNETDVFVLN  540
NTRPPLGNWF GCTWMNSSGF TKVCGAPPCV IGGVGNNTLH CPTDCFRKHP EATYSRCGSG  600
PWITPRCLVH YAYRLWHYPC TVNYTLFKVR MYVGGVEHRL DVACNWTRGE RCNLDDRDRS  660
ELSPLLLSTT QWQVLPCSFT TLPALSTGLI HLHQNIVDVQ YLYGVGSSIV SWAIKWEYVI  720
LLFLLLADAR ICSCLWMMLL ISQAEA                                      746

SEQ ID NO: 86           moltype = AA  length = 746
FEATURE                 Location/Qualifiers
source                  1..746
                        mol_type = protein
```

```
                         organism = Hepatitis C virus
SEQUENCE: 86
MSTNPKPQRK TKRNTNRRPQ DVKFPGGGQI VGGVYLLPRR GPRLGVRATR KTSERSQPRG  60
RRQPIPKARR PEGRTWAQPG YPWPLYGNEG CGWAGWLLSP RGSRPSWGPT DPRRRSRNLG  120
KVIDTLTCGF ADLMGYIPLV GAPLGGAARA LAHGVRVLED GVNYATGNLP GCSFSIFLLA  180
LLSCLTVPAS AYQVRNSSGL YHVTNDCPNS SIVYETADTI LHSPGCVPCV REGNASKCWV  240
AVTPTVATRD GRLPATQLRR HIDLLVGSAT LCSALYVGDL CGSIFLVGQL FTFSPRRHWT  300
TQDCNCSIYP GHITGHRMAW DMMMNWSPTT ALVVAQLLRV PQAILDMIAG AHWGVLAGIA  360
YFSMVGNWAK VLVVLLLFAG VDAGTHVTGG SAAKDTSGFT SLFRIGARQN IQLINSNGSW  420
HINRTALNCN ESLDTGWVAG LLYYHKFNSS GCPERMASCR SLADFDQGWG PISYANGSGP  480
EHRPYCWHYP PKPCGIVPAQ SVCGPVYCFT PSPVVVGTTD KSGAPTYNWG CNETDVFVLN  540
NTRPPLGNWF GCTWMNSSGF TKVCGAPPCV IGGVGNNTLH CPTDCFRKHP EATYSRCGSG  600
PWITPRCLVH YAYRLWHYPC TVNYTLFKVR MYVGGVEHRL DVACNWTRGE RCNLDDRDRS  660
ELSPLLLSTT QWQVLPCSFT TLPALSTGLI HLHQNIVDVQ YLYGVGSSIV SWAIKWEYVI  720
LLFLLLADAR ICSCLWMMLL ISQAEA                                     746

SEQ ID NO: 87            moltype = AA  length = 746
FEATURE                  Location/Qualifiers
source                   1..746
                         mol_type = protein
                         organism = Hepatitis C virus
SEQUENCE: 87
MSTNPKPQRK TKRNTNRRPQ DVKFPGGGQI VGGVYLLPRR GPRLGVRATR KTSERSQPRG  60
RRQPIPKARR PEGRTWAQPG YPWPLYGNEG CGWAGWLLSP RGSRPSWGPT DPRRRSRNLG  120
KVIDTLTCGF ADLMGYIPLV GAPLGGAARA LAHGVRVLED GVNYATGNLP GCSFSIFLLA  180
LLSCLTVPAS AYQVRNSSGL YHVTNDCPNS SIVYETADSI LHSPGCVPCV REGNASKCWV  240
AVAPTVATRD GKLPATQLRR HIDLLVGSAT LCSALYVGDL CGSVFLVSQL FTFSPRRHWT  300
TQDCNCSIYP GHITGHRMAW DMMMNWSPTT ALVVSQLLRV PQAILDMIAG AHWGVLAGIA  360
YFSMVGNWAK VLVVLLLFAG VDAETHTTGG SAAYATSGFV GLFRQGAKQN IQLINTNGSW  420
HVNRTALNCN ASLDTGWVAG LFYYHKFNSS GCPERLASCK PLANFDQGWG SISYTNGSGP  480
EHRPYCWHYP PKPCGIVPAQ NVCGPVYCFT PSPVVVGTTD RLGAPTFNWG ENESDVFVLN  540
NTRPPSGNWF GCTWMNSSGF TKVCGAPPCN IGGVGNNTLH CPTDCFRKHP EATYSRCGSG  600
PWVTPRCLVH YPYRLWHYPC TLNYSLFKVR MYVGGIEHRL EVACNWTRGE RCNLDDRDRS  660
ELSPLLLTTT QWQVLPCSFT TLPALTTGLI HLHQNVVDVQ YLYGVGSSIV SWAIKWEYVI  720
LLFLLLADAR ICSCLWMMLL ISQAEA                                     746

SEQ ID NO: 88            moltype = AA  length = 746
FEATURE                  Location/Qualifiers
source                   1..746
                         mol_type = protein
                         organism = Hepatitis C virus
SEQUENCE: 88
MSTNPKPQRK TKRNTNRRPQ DVKFPGGGQI VGGVYLLPRR GPRLGVRATR KTSERSQPRG  60
RRQPIPKARR PEGRTWAQPG YPWPLYGNEG CGWAGWLLSP RGSRPSWGPT DPRRRSRNLG  120
KVIDTLTCGF ADLMGYIPLV GAPLGGAARA LAHGVRVLED GVNYATGNLP GCSFSIFLLA  180
LLSCLTVPAS AYQVRNSSGL YHVTNDCPNS SIVYETADTI LHSPGCVPCV REGNASKCWV  240
AVAPTVATRD GRLPTTQLRR HIDLLVGSAT LCSALYVGDL CGSVFLVGQL FTFSPRHHWT  300
TQDCNCSIYP GHITGHRMAW DMMMNWSPTT ALVVAQLLRV PQAILDMIAG AHWGVLAGIA  360
YFSMVGNWAK VLVVLLLFAG VDATTHTTGG AVAHNTRMFT SIFSLGPRQE IQLVNTNGSW  420
HINRTALNCN ASLETGWIAG LLYANRFNSS GCPERMASCK PLADFDQGWG PISYANGSGP  480
EHRPYCWHYP PKPCGIVPAQ NVCGPVYCFT PSPVVVGTTD RLGTPTYDWG SNDTDVFVLN  540
NTRPPAGNWF GCTWMNSSGY TKVCGAPPCV IGGVSNNTLH CPTDCFRKHP EATYSRCGSG  600
PWITPRCLVH YAYRLWHYPC TVNYTLFKVR MYVGGVEHRL EVACNWTRGE RCNLDDRDRS  660
ELSPLLLSTT QWQVLPCSFT TLPALTTGLI HLHQNIVDVQ YLYGVGSSIV SWAVKWEYVI  720
LLFLLLADAR ICSCLWMMLL ISQAEA                                     746

SEQ ID NO: 89            moltype = AA  length = 746
FEATURE                  Location/Qualifiers
source                   1..746
                         mol_type = protein
                         organism = Hepatitis C virus
SEQUENCE: 89
MSTNPKPQRK TKRNTNRRPQ DVKFPGGGQI VGGVYLLPRR GPRLGVRATR KTSERSQPRG  60
RRQPIPKARQ PEGRAWAQPG YPWPLYGNEG LGWAGWLLSP RGSRPSWGPT DPRRRSRNLG  120
KVIDTLTCGF ADLMGYIPLV GAPLGGAARA LAHGVRVLED GVNYATGNLP GCSFSIFLLA  180
LLSCLTIPAS AYEVRNVSGV YHVTNDCSNA SIVYEAADMI MHTPGCVPCV RENNSSRCWV  240
ALTPTLAARN ASVPTTTIRR HVDLLVGAAA LCSAMYVGDL CGSVFLVAQL FTFSPRRHET  300
VQDCNCSIYP GHVTGHRMAW DMMMNWSPTA ALVVSQLLRI PQAVVDMVAG AHWGVLAGLA  360
YYSMVGNWAK VLIVMLLFAG VDGGTYVTGG TMAKNTLGIT SLFSPGSSQK IQLVNTNGSW  420
HINRTALNCN DSLNTGFLAA LFYVHKFNSS GCPERMASCS PIDAFAQGWG PITYNESHSS  480
DQRPYCWHYA PRPCGIVPAA QVCGPVYCFT PSPVVVGTTD RFGVPTYSWG ENETDVLLLN  540
NTRPPQGNWF GCTWMNSTGF TKTCGGPPCN IGGIGNKTLT CPTDCFRKHP EATYTKCGSG  600
PWLTPRCLVH YPYRLWHYPC TVNFTIFKVR MYVGGVEHRL EAACNWTRGE RCNLEDRDRS  660
ELSPLLLSTT EWQVLPCSFT TLPALSTGLI HLHQNVVDVQ YLYGIGSAVV SFAIKWEYVL  720
LLFLLLADAR VCACLWMMLL IAQAEA                                     746

SEQ ID NO: 90            moltype = AA  length = 746
FEATURE                  Location/Qualifiers
source                   1..746
```

```
                         mol_type = protein
                         organism = Hepatitis C virus
SEQUENCE: 90
MSTNPKPQRK TKRNTNRRPQ DVKFPGGGQI VGGVYLLPRR GPRLGVRATR KTSERSQPRG  60
RRQPIPKARQ PEGRAWAQPG YPWPLYGNEG MGWAGWLLSP RGSRPSWGPT DPRRRSRNLG  120
KVIDTLTCGF ADLMGYIPLV GAPLGGVARA LAHGVRVVED GVNYATGNLP GCSFSIFLLA  180
LLSCLTIPAS AYEVRNVSGI YHVTNDCSNS SIVYEAADMI MHTPGCVPCV REGNSSRCWV  240
ALTPTLAARN ASVPTTAIRR HVDLLVGAAA FCSAMYVGDL CGSVFLVSQL FTFSPRRHET  300
IQDCNCSIYP GHVSGHRMAW DMMMNWSPTT ALVVSQLLRI PQAIVDMVAG AHWGVLAGLA  360
YYSMVGNWAK VLIVMLLFAG VDGETRVTGG QIARNAYSLT TLFSSGSAQN IQLINTNGSW  420
HINRTALNCN DSLNTGFLAA LFYTHKFNAS GCPERLASCR PIDKFDQGWG PITYAEQGGQ  480
DQRPYCWHYA PKPCGIVSAS KVCGPVYCFT PSPVVVGTTD RFGVPTYSWG ENETDVLLLN  540
NTRPPQGNWF GCTWMNGTGF TKTCGGPPCN IGGGGNNTLT CPTDCFRKHP AATYTKCGSG  600
PWLTPRCLVD YPYRLWHYPC TANFTIFKVR MYVGGVEHRL DAACNWTRGE RCNLEDRDRL  660
ELSPLLLSTT EWQVLPCSFT TLPALSTGLI HLHQNIVDVQ YLYGIGSAVV SFAIKWDYIV  720
ILFLLLADAR VCACLWMMLL IAQAEA                                        746

SEQ ID NO: 91            moltype = AA  length = 747
FEATURE                  Location/Qualifiers
source                   1..747
                         mol_type = protein
                         organism = Hepatitis C virus
SEQUENCE: 91
MSTNPKPQRK TKRNTNRRPQ DVKFPGGGQI VGGVYLLPRR GPRLGVRAIR KTSERSQPRG  60
RRQPIPKARR PEGRAWAQPG YPWPLYGNEG MGWAGWLLSP RGSRPSWGPT DPRRRSRNLG  120
KVIDTLTCGL ADLMGYIPLV GGPLGGAARA LAHGVRVLED GVNYATGNLP GCSFSIFLLA  180
LLSCLTVPAS AHEVRNASGV YHVTNDCSNS SIVFEAADLI MHTPGCVPCV REGNSSRCWV  240
ALTPTLAARN ATIPTTTIRH HVDLLVGAAA LCSAMYVGDL CGSVFLVSQL FTFSPRRHAT  300
LQDCNCSIYP GHASGHRMAW DMMMNWSPTT ALVVSQLLRI PQAVIDMVAG AHWGVLAGLA  360
YYSMAGNWAK VLIVMLLFAG VDGHTLTTGG HAARLTSGFA GLFTPGPSQR IQLINTNGSW  420
HINRTALNCN DSLQTGFLAA LFYAHRFNSS GCPERMASCR SIDKFDQGWG PITYAEPTKD  480
PDQRPYCWHY PPQQCGIVPA SQVCGPVYCF TPSPVVVGTT DRLGNPTYSW GENDTDVLLL  540
NNTRPPQGNW FGCTWMNSTG FTKTCGAPPC NIGGVGNNTL TCPTDCFRKH PEATYSKCGS  600
GPWLTPRCMV DYPYRLWHYP CTVNFSIFKV RMYVGGVEHR LNAACNWTRG ERCNLDDRDR  660
SELSPLLLST TEWQVLPCSF TTLPALSTGL IHLHQNIVDV QYLYGIGSAV VSFAIKWEYV  720
VLLFLLLADA RVCACLWMML LIAQAEA                                       747

SEQ ID NO: 92            moltype = AA  length = 746
FEATURE                  Location/Qualifiers
source                   1..746
                         mol_type = protein
                         organism = Hepatitis C virus
SEQUENCE: 92
MSTNPKPQRK TKRNTNRRPQ DVKFPGGGQI VGGVYLLPRR GPRLGVRATR KTSERSQPRG  60
RRQPIPKARH PEGRTWAQPG YPWPLYGNEG LGWAGWLLSP RGSRPSWGPT DPRRRSRNLG  120
KVIDTLTCGF ADLMGYIPLV GAPLGGVARA LAHGVRVLED GVNYATGNLP GCSFSIFLLA  180
LLSCLTIPAS AYEVRNVSGV YHVTNDCSNS SIVYEAADVI MHTPGCVPCV QDGNTSRCWV  240
ALTPTLAARN ASVPVTAIRR HVDLLVGTAA FCSAMYVGDL CGSVFPVSQL FTFSPRRHQT  300
VQDCNCSIYP GHISGHRMAW DMMMNWSPTA ALVVSQLLRI PQAIVDMVAG AHWGVLAGLA  360
YYSMVGNWAK VMIVLLLFAG VDGTTHTTGG AAARATQGFT SFFSLGPSQK IQLINTNGSW  420
HINRTALNCN DSLQTGFLAA LFYTYRFNAS GCPERMASCR PIDKFDQGWG PITYAEPDSS  480
DQRPYCWHYA PRPCGIVPAS QVCGPVYCFT PSPVVVGTTD RFGVPTYTWG ENETDVLLLN  540
NTRPPLGNWF GCTWMNSTGF TKTCGGPPCN IGGAGNTTLT CPTDCFRKHP EATYTKCGSG  600
PWLTPRCLVD YPYRLWHYPC AVNFTIFKVR MYVGGVEHRL NAACNWTRGE RCDLEDRDRS  660
ELSPLLLSTT EWQVLPCSFT TLPALSTGLI HLHQNIVDVQ YLYGIGSAVI PFAIKWEYVL  720
LLFLLLADAR VCACLWMMLL IAQAEA                                        746

SEQ ID NO: 93            moltype = AA  length = 746
FEATURE                  Location/Qualifiers
source                   1..746
                         mol_type = protein
                         organism = Hepatitis C virus
SEQUENCE: 93
MSTNPKPQRK TKRNTNRRPQ DVKFPGGGQI VGGVYLLPRR GPRLGVRATR KTSERSQPRG  60
RRQPIPKARR PEGRTWAQPG YPWPLYGNEG MGWAGWLLSP RGSRPNWGPT DPRRRSRNLG  120
KVIDTLTCGF ADLMGYIPLV GAPLGGVARA LAHGVRVLED GVNYATGNLP GCSFSIFLLA  180
LLSCLTTPAS AYEVRNVSGI YHVTNDCSNS SIVYEAADII MHTPGCVPCV REKNISRCWV  240
ALTPTLAARN ISVPTATIRR HVDLLVGTAA FCSAMYVGDL CGSVFLVSQL FTFSPRWHET  300
VQDCNCSLYP GHVSGHRMAW DMMMNWSPTA ALVVSQLLRI PQAVVDMVAG AHWGVLAGLA  360
YYSMIGNWAK VLIVMLLFAG ADGTTHVTGG VQAHGAYGLA SLFNVGPHQK IQLVNTNGSW  420
HINRTALNCN DTLQTGFLAA LFYKHRFNAS GCPERMASCR PIDKFAQGWG PITYAEPDRL  480
DQRPYCWHYP PRPCGIVPAL EVCGPVYCFT PSPVVVGTTD RFGVPTYSWG ENETDVLLLN  540
NTRPPQGNWF GCTWMNSTGY TKTCGGPPCN IGGVGNNTLT CPTDCFRKHP EATYTKCGSG  600
PWLTPRCLVH YPYRLWHYPC TVNFTIFKVR MYVGGIEHRL DAACNWTRGE RCDLEDRDRS  660
ELSPLLLSTT EWQILPCSFT TLPALSTGLI HLHRNIVDVQ YLYGIGSAVV SFAIKWEYVL  720
LLFLLLADAR VCACLWMMLL IAQAEA                                        746

SEQ ID NO: 94            moltype = AA  length = 746
FEATURE                  Location/Qualifiers
```

-continued

```
source                  1..746
                        mol_type = protein
                        organism = Hepatitis C virus
SEQUENCE: 94
MSTNPKPQRK TKRNTNRRPQ DVKFPGGGQI VGGVYLLPRR GPRLGVRATR KTSERSQPRG  60
RRQPIPKARR PEGRTWAQPG YPWPLYGNEG LGWAGWLLSP RGSRPSWGPN DPRRRSRNLG  120
KVIDTLTCGF ADLMGYIPLV GAPLGGAARA LAHGVRVLED GVNYATGNLP GCSFSIFLLA  180
LLSCLTIPAS AYEVRNVSGI YHVTNDCSNS SIVYEAADVI MHAPGCVPCV RENNSSRCWV  240
ALTPTLAARN ASVPTTTLRR HVDLLVGTAA FCSAMYVGDL CGSVFLISQL FTFSPRRHET  300
VQDCNCSIYP GHVSGHRMAW DMMMNWSPTA ALVVSQLLRI PQAVMDMVAG AHWGVLAGLA  360
YYSMVGNWAK VLIVMLLFAG VDGHTRVTGG VQGHVTSTLT SLFRPGASQK IQLVNTNGSW  420
HINRTALNCN DSLKTGFLAA LFYTHKFNAS GCPERMASCR SIDKFDQGWG PITYAQPDNS  480
DQRPYCWHYA PRQCGIVPAS QVCGPVYCFT PSPVVVGTTD RFGAPTYNWG DNETDVLLLN  540
NTRPPHGNWF GCTWMNSTGF TKTCGGPPCN IRGVGNNTLT CPTDCFRKHP DATYTKCGSG  600
PWLTPRCLVD YPYRLWHYPC TVNFTIFKVR MYVGGVEHRL DAACNWTRGE RCDLEDRDRA  660
ELSPLLLSTT EWQILPCSYT TLPALSTGLI HLHQNIVDIQ YLYGIGSAVV SIAIKWEYVV  720
LLFLLLADAR VCACLWMMLL IAQAEA                                       746

SEQ ID NO: 95           moltype = AA  length = 746
FEATURE                 Location/Qualifiers
source                  1..746
                        mol_type = protein
                        organism = Hepatitis C virus
SEQUENCE: 95
MSTNPKPQRK TKRNTNRRPQ DVKFPGGGQI VGGVYLLPRR GPRLGVRATR KTSERSQPRG  60
RRQPIPKARR PEGRTWAQPG YPWPLYGDEG MGWAGWLLSP RGSRPNWGPT DPRRRSRNLG  120
KVIDTLTCGF ADLMGYIPLV GAPLGGVARA LAHGVRVLED GVNYATGNLP GCSFSIFLLA  180
LLSCLTTPAS AYEVRNVSGI YHVTNDCSNS SIVYEAADII MHTPGCVPCV REKNTSRCWV  240
ALTPTLAARN ISVPTTTIRR HVDLLVGTAA FCSAMYVGDL CGSVFLVSQL FTFSPRRHET  300
VQDCNCSLYP GHVSGHRMAW DMMMNWSPTA ALVVSQLLRI PQAIVDMVAG AHWGVLAGLA  360
YYSMVGNWAK VLIVMLLFAG ADGTTHVTGG VQAHGAYGLA SLFNVGPHQK IQLVNTNGSW  420
HINRTALNCN DTLQTGFLAA LFYKHRFNAS GCPERMASCR PIDKFAQGWG PITYAEPDRL  480
DQRPYCWHYP PRPCGIVPAL EVCGPVYCFT PSPVVVGTTD RFGVPTYSWG ENETDVLLLN  540
NTRPPQGNWF GCTWMNNTGF TKTCGGPPCN IGGVGNNTLT CPTDCFRKHP EATYTKCGSG  600
PWLTPRCLVD YPYRLWHYPC TVNFTVFKVR MYVGGIEHRL DAACNWTRGE RCDLEDRDRS  660
ELSPLLLSTT EWQILPCSFT TLPALSTGLI HLHRNIVDVQ YLYGIGSAVV SFAIKWEYIL  720
LLFLLLADAR VCACLWMMLL IAQAEA                                       746

SEQ ID NO: 96           moltype = AA  length = 746
FEATURE                 Location/Qualifiers
source                  1..746
                        mol_type = protein
                        organism = Hepatitis C virus
SEQUENCE: 96
MSTNPKPQRK TKRNTNRRPQ DVKFPGGGQI VGGVYLLPRR GPRLGVRATR KTSERSQPRG  60
RRQPIPKARQ PEGRAWAQPG YPWPLYGNEG LGWAGWLLSP RGSRPSWGPT DPRRRSRNLG  120
KVIDTLTCGF ADLMGYIPLV GAPLGGAARA LAHGVRVLED GVNYATGNLP GCSFSIFLLA  180
LLSCLTIPAS AYEVRNVSGV YHVTNDCSNS SIVYEAADMI MHTPGCVPCV REDNSSRCWV  240
ALTPTLAARN SSVPTTTIRR HVDLLVGAAA FCSAMYVGDL CGSVFLISQL FTFSPRRYET  300
VQDCNCSLYP GHVSGHRMAW DMMMNWSPTT ALVVSQLLRI PQAVVDMVAG AHWGVLAGLA  360
YYSMVGNWAK VLIVMLLFAG VDGNTRVSGG EAAKNTMGFA SLFVSGPSQK IQLINTNGSW  420
HINRTALNCD DSLHTGFLAA LFYAHKFNSS GCSGRMASCR PIDEFAQGWG PITHGVPDNL  480
DQRPYCWHYA PRPCGIVPAS QVCGPVYCFT PSPVVVGTTD RFGAPTYSWG ENETDVLLLN  540
NTRPPQGNWF GCTWMNSTGF TKTCGGPPCN IGGVGNNTLT CPTDCFRKHP EATYTKCGSG  600
PWLTPRCMVD YPYRLWHYPC TVNFTIFKVR MYVGGVEHRL DAACNWTRGE RCNVEDRDRS  660
ELSPLLLSTT EWQILPCSFT TLPALSTGLI HLHQNIVDVQ YLYGVGSVVV SVVIRWEYVV  720
LLFLLLADAR VCACLWMMLL IAQAEA                                       746

SEQ ID NO: 97           moltype = AA  length = 746
FEATURE                 Location/Qualifiers
source                  1..746
                        mol_type = protein
                        organism = Hepatitis C virus
SEQUENCE: 97
MSTNPKPQRK TKRNTNRRPQ DVKFPGGGQI VGGVYLLPRR GPRLGVRATR KTSERSQPRG  60
RRQPIPKARQ PEGRAWAQPG YPWPLYGNEG MGWAGWLLSP RGSRPSWGPT DPRRRSRNLG  120
KVIDTLTCGF ADLMGYIPLV GAPLGGAARA LAHGVRVLED GVNYATGNLP GCSFSIFLLA  180
LLSCLTIPAS AYEVRNVSGM YHVTNDCSNS SIVYEAADMI LHAPGCVPCV RENNSSRCWV  240
ALTPTLAARN ASVPTTAIRR HVDLLVGAAA FCSAMYVGDL CGSVLLVSQI FTFSPRRHET  300
MQDCNCSIYP GHITGHRMAW DMMMNWSPTT ALVVSQLLRI PQAIVDMVAG AHWGVLAGLA  360
YYSMVGNWAK VLIVMLLFAG VDGGTYVTGG EAGRRTSGFA SIFTPGASQN IQLINTNGSW  420
HINRTALNCN DSLHTGFIAA LFYHHKFNAS GCPERMASCR PIGEFAQGWG PISYTEPPSS  480
DQRPYCWHYP PRPCGIVPAS QVCGPVYCFT PSPVVVGTTD RLGAPTYNWG DNDTDVLLLN  540
NTRPPQGNWF GCTWMNGTGF TKTCGGPPCN IGGVGNNTLT CPTDCFRKHP EATYTKCGSG  600
PWLTPRCIVD YPYRLWHYPC TVNFTITKIR MYVGGVEHRL TAACNWTRGE RCDLEDRDRS  660
ELSPLLLSTT EWQIMPCSFT TLPALSTGLI HLHQNIVDIQ YLYGIGSAAV SFAIRWEYVL  720
LLFLLLADAR VCACLWMMLL IAQAEA                                       746

SEQ ID NO: 98           moltype = AA  length = 746
```

-continued

```
FEATURE                Location/Qualifiers
source                 1..746
                       mol_type = protein
                       organism = Hepatitis C virus
SEQUENCE: 98
MSTNPKPQRK TKRNTNRRPQ DVKFPGGGQI VGGVYLLPRR GPRLGVRATR KTSERSQPRG  60
RRQPIPKARQ PEGRAWAQPG YPWPLYGNEG MGWAGWLLSP RGSRPSWGPT DPRRRSRNLG  120
KVIDTLTCGF ADLMGYIPLV GAPLGGAARA LAHGVRVLED GVNYATGNLP GCSFSIFLLA  180
LLSCLTIPAS AYEVRNVSGM YHVTNDCSNS SIVYEAADMI LHAPGCVPCV RENNSSRCWV  240
ALTPTLAARN ASVPTTAIRR HVDLLVGAAA FCSAMYVGDL CGSVLLVSQI FTFSPRRHET  300
MQDCNCSIYP GHITGHRMAW DMMMNWSPTT ALVVSQLLRI PQAIVDMVAG AHWGVLAGLA  360
YYSMVGNWAK VLIVMLLFAG VDGGTYVTGG EAGRRTSGFA SIFTPGASQN IQLINTNGSW  420
HINRTALNCN DSLHTGFIAA LFYHHKFNAS GCPERMASCR PIGEFAQGWG PISYTEPPSS  480
DQRPYCWHYP PRPCGIVPAS QVCGPVYCFT PSPVVVGTTD RLGAPTYNWG DNDTDVLLLN  540
NTRPPQGNWF GCTWMNGTGF TKTCGGPPCN IGGVGNNTLT CPTDCFRKHP EATYTKCGSG  600
PWLTPRCIVD YPYRLWHYPC TVNFTITKIR MYVGGVEHRL TAACNWTRGE RCDLEDRDRS  660
ELSPLLLSTT EWQIMPCSFT TLPALSTGLI HLHQNIVDIQ YLYGIGSAAV SFAIRWEYVL  720
LLFLLLADAR VCACLWMMLL IAQAEA                                      746

SEQ ID NO: 99          moltype = AA  length = 746
FEATURE                Location/Qualifiers
source                 1..746
                       mol_type = protein
                       organism = Hepatitis C virus
SEQUENCE: 99
MSTNPKPQRK TKRNTNRRPQ DVKFPGGGQI VGGVYLLPRR GPRLGVRATR KTSERSQPRG  60
RRQPIPKARR PEGRAWAQPG YPWPLYGNEG LGWAGWLLSP RGSRPSWGPT DPRRRSRNLG  120
KVIDTLTCGF ADLMGYIPLV GAPLGGTARA LAHGVRVLED GVNYATGNLP GCSFSIFLLA  180
LLSCLTIPAS AYEVRNVSGV YHVTNDCSNS SIVYETADMI MHTPGCVPCV REDNFTRCWV  240
ALTPTLAARN GSVPTTAIRR HVDLLVGAAA FCSAMYVGDL CGSVFLVSQL FTFSPRWHET  300
VQECNCSIYP GHVTGHRMAW DMMMNWSPTT ALVVSQLLRI PQAVVDMVAG AHWGVLAGLA  360
YYSMVGNWAK VLIVTLLFAG VDGNTHTIGG KQAQATGGFV AWLARGPSQE IQLINTNGSW  420
HINRTALNCN DSLKTGFIAA LFYAHRFNSS GCPERMASCR PIDKFAQGWG PITYAKPDSL  480
DQRPYCWHYA PQPCGIVPAS EVCGPVYCFT PSPVVVGTTD RSGVPTYRWG ENETDVLLLN  540
NTRPPQGNWF GCTWMNATGF TKTCGGPPCK IGGLGNNTLT CPTDCFRKHP EATYTKCGSG  600
PWLTPRCIVD YPYRLWHYPC TVNFTIFKVR MYVGGIEHRL SAACNWTRGE RCDLEDRDRS  660
ELSPLLLSTT EWQILPCSFT TLPALSTGLI HLHQNTVDVQ YLYGVGSVLV SFAIKWEYIL  720
LFFLLLADAR VCACLWMMLL IAQAEA                                      746

SEQ ID NO: 100         moltype = AA  length = 746
FEATURE                Location/Qualifiers
source                 1..746
                       mol_type = protein
                       organism = Hepatitis C virus
SEQUENCE: 100
MSTNPKPQRK TKRNTNRRPQ NVKFPGGGQI VGGVCLLPRR GPRVGVRATR KTSERSQPRG  60
RRQPIPKARR PEGRSWAQPG YPWPLYGNEG CGWAGWLLSP RGSRPSRGPS DPRRRSRNLG  120
KVIDTLTCGF ADLMGYIPLV GAPLGGAARA LAHGVRVLED GVNYATGNLP GCSFSIFLLA  180
LLSCLTVPAS AVEVRNSSGI YHVTNDCPNA SVVYETDSLI IHLPGCVPCV REGNASRCWV  240
SLSPTVAAKD PGVPVNEIRR HVDLIVGAAA FCSAMYVGDL CGSIFLVGQL FTLSPRRHWT  300
TQDCNCSIYP GHVTGHRMAW DMMMNWSPTG ALVVAQLLRI PQAVLDMIAG AHWGVLAGPA  360
YYSMVGNWAK VLVVLLLFAG VDATTQVTGG TAGRNAYRLA SLFSTGPSQN IQLINSNGSW  420
HINRTALNCN DSLHTGWVAA LFYSHKFNSS GRPERMASCR PLTAFDQGWG PITYGGKASN  480
DQRPYCWHYA PRPCGIVPAK EVCGPVYCFT PSPVVVGTTD KYGVPTYTWG ENETDVLLLN  540
NSRPPIGNWF GCTWMNSTGF TKTCGAPACN VGGSETNTLS CPTDCFRRHP DATYAKCGSG  600
PWLNPRCMVD YPYRLWHYPC TVNYTIFKIR MFVGGIEHRL TAACNWTRGE RCDLDDRDRA  660
ELSPLLLSTT QWQVLPCSFT TLPALSTGLI HLHQNIVDVQ YLYGLSSVVT SWAIRWEYVV  720
LLFLLLADAR ICACLWMMLL ISQVEA                                      746

SEQ ID NO: 101         moltype = AA  length = 746
FEATURE                Location/Qualifiers
source                 1..746
                       mol_type = protein
                       organism = Hepatitis C virus
SEQUENCE: 101
MSTNPKPQRK TKRNTNRRPQ DVKFPGGGQI VGGVYLLPRR GPRLGVRATR KTSERSQPRG  60
RRQPIPKARR PEGRTWAQPG YPWPLYGNEG CGWAGWLLSP RGSRPSWGPT DPRRRSRNLG  120
KVIDTLTYGF ADLMGYIPLV GAPLGGAARA LAHGVRVLED GVNYATGNLP GCSFSIFLLA  180
LLSCLTVPAS AVGVRNSSGV YHVTNDCPNA SVVYETDSLI IHLPGCVPCV REGNGSRCWV  240
SLSPTVAAKD PGVPVNEIRR HVDLIAGAAA FCSAMYVGHL CGSIFLVGQL FTLSPRRHWT  300
TQDCNCSIYP GHVTGHRMAW DMMMNWSPTT ALVVAQLLRI PQAILDMIAG AHWGVLAGIA  360
YFSMVGNWTK VLVVLLLFAG VDATTIVSGG SAGRSTAGLV GLFSPGARQN IQLINTNGSW  420
HINRTALNCN DTLQTGWVAG LFYTNKFNSS GCPERLASCR PLADFDQGWG PISYTNGSGP  480
DQRPYCWHYP PKPCGIVPAE SVCGPVYCFT PSPVVVGTTD RSGAPTYNWG ENETDVFVLN  540
NTRPRLGNWF GGTWMNSTGF TKVCGAPPCA IGGVGNNTLY CPTDCFRKHP EATYSRCGSG  600
PWITPRCLIH YPYRLWHYPC TINYTIFKIR MFVGGVEHRL DAACNWTRGE RCDLDDRDRA  660
ELSPLLLSTT QWQVLPCSFT TLPALSTGLI HLHQNIVDVQ YLYGLSSAVT SWVIKWEYVV  720
LLFLLLADAR ICACLWMMLL ISQVEA                                      746
```

-continued

```
SEQ ID NO: 102          moltype = AA  length = 746
FEATURE                 Location/Qualifiers
source                  1..746
                        mol_type = protein
                        organism = Hepatitis C virus
SEQUENCE: 102
MSTNPKPQRK TKRNTNRRPQ DVKFPGGGQI VGGVYLLPRR GPRVGVRATR KTSERSQPRG  60
RRQPIPKARR PEGRSWAQPG YPWPLYGNEG CGWAGWLLSP RGSRPSWGPS DPRRRSRNLG  120
KVIDTLTCGF ADLMGYIPLV GAPLGGAARA LAHGVRVLED GVNYATGNLP GCSFSIFLLA  180
LLSCLTVPAS AVGVRNSSGV YHVTNDCPNA SVVYETENLI MHLPGCVPYV REGNASRCWV  240
SLSPTVAARD SRVPVSEVRR RVDSIVGAAA FCSAMYVGDL CGSIFLVGQI FTFSPRHHWT  300
TQDCNCSIYP GHVTGHRMAW DMMMNWSPTG ALVVAQLLRI PQAIVDMIAG AHWGVLAGLA  360
YYSMVGNWAK VVVVLLLFAG VDAETRVTGG AAGHTAFGFA SFLAPGAKQK IQLINTNGSW  420
HINRTALNCN ESLDTGWLAG LLYYHKFNSS GCPERMASCQ PLTAFDQGWG PITHEGNASD  480
DQRPYCWHYA LRPCGIVPAK KVCGPVYCFT PSPVVVGTTD RAGVPTYRWG ANETDVLLLN  540
NSRPPMGNWF GCTWMNSSGF TKTCGAPACN IGGSGNNTLL CPTDCFRKHP DATYSRCGSG  600
PWLTPRCLVD YPYRLWHYPC TVNYTIFKIR MFVGGVEHRL DAACNWTRGE RCDLDDRDRA  660
ELSPLLLSTT QWQVLPCSFT TLPALSTGLI HLHQNIVDVQ YLYGLSSAVT SWVIKWEYVV  720
LLFLLLADAR ICACLWMMLL ISQVEA                                      746

SEQ ID NO: 103          moltype = AA  length = 750
FEATURE                 Location/Qualifiers
VARIANT                 233
                        note = X can be any naturally occurring amino acid
VARIANT                 249..250
                        note = X can be any naturally occurring amino acid
VARIANT                 290
                        note = X can be any naturally occurring amino acid
VARIANT                 378
                        note = X can be any naturally occurring amino acid
VARIANT                 392
                        note = X can be any naturally occurring amino acid
VARIANT                 399
                        note = X can be any naturally occurring amino acid
VARIANT                 445
                        note = X can be any naturally occurring amino acid
VARIANT                 495
                        note = X can be any naturally occurring amino acid
VARIANT                 599
                        note = X is a I or L
VARIANT                 628
                        note = X can be any naturally occurring amino acid
VARIANT                 664
                        note = X can be any naturally occurring amino acid
VARIANT                 683
                        note = X can be any naturally occurring amino acid
source                  1..750
                        mol_type = protein
                        organism = synthetic construct
SEQUENCE: 103
MSTNPKPQRK TKRNTNRRPQ DVKFPGGGQI VGGVYLLPRR GPRLGVRATR KTSERSQPRG  60
RRQPIPKDRR STGKSWGKPG YPWPLYGNEG LGWAGWLLSP RGSRPSWGPT DPRHRSRNVG  120
KVIDTLTCGF ADLMGYIPVV GAPLGGVARA LAHGVRVLED GVNYATGNLP GCSFSIFLLA  180
LLSCITVPVS AVEVKNISTS YMVTNDCSND SITWQLQAAV LHVPGCVPCE NDXNTSRCWI  240
PVSPNVAVXX PGALTQGLRT HIDMVVMSAT LCSALYVGDL CGGVMLAAQX FIVSPQRHWF  300
VQECNCSIYP GTITGHRMAW DMMMNWSPTA TMILAYAMRV PEVIIDIIFG AHWGVMFGLA  360
YFSMQGAWAK VIVILLLXAG VDARTHTVGG SXGRTTSGXA GLFSSGPKQN IQLINTNGSW  420
HINRTALNCN DSLQTGFIAS LFYTXNFNSS GCPERLSACR GIEAFRIGWG TLQYEDNVTN  480
PEDMRPYCWH YPPKXCGIVP ARSVCGPVYC FTPSPVVVGT TDRLGVPTYT WGENETDVFL  540
LNSTRPPRGS WFGCTWMNST GFTKTCGAPP CRIRADFNAS TDLLCPTDCF RKHPDATYXK  600
CGSGPWLTPR CLVDYPYRLW HYPCTVNXTI FKIRMYVGGV EHRLTAACNF TRGDRCNLED  660
RDRXQLSPLL HSTTEWAILP CSXSDLPALS TGLLHLHQNI VDVQYMYGLS PALTKYIVRW  720
EWVVLLFLLL ADARVCACLW MLILLGQAEA                                  750

SEQ ID NO: 104          moltype = AA  length = 750
FEATURE                 Location/Qualifiers
source                  1..750
                        mol_type = protein
                        organism = Hepatitis C virus
SEQUENCE: 104
MSTNPKPQRK TKRNTNRRPE DVKFPGGGQI VGGVYLLPRR GPRLGVRTTR KTSERSQPRG  60
RRQPIPKDRR STGKAWGKPG RPWPLYGNEG LGWAGWLLSP RGSRPSWGPT DPRHRSRNVG  120
KVIDTLTCGF ADLMGYIPVV GAPLSGAARA VAHGVRVLED GVNYATGNLP GFPFSIFLLA  180
LLSCITVPVS AAQVKNTSSS YMVTNDCSND SITWQLEAAV LHVPGCVPCE RVGNTSRCWV  240
PVSPNMAVRQ PGALTQGLRT HIDMVVMSAT FCSALYVGDL CGGVMLAAQV FIVSPQYHWF  300
VQECNCSIYP GTITGHRMAW DMMMNWSPTA TMILAYVMRV PEVIIDIVSG AHWGVMFGLA  360
YFSMQGAWAK VIVILLLAAG VDAGTTTVGG AVARSTNVIA GVFSHGPQQN IQLINTNGSW  420
HINRTALNCN DSLNTGFLAA LFYTNRFNSS GCPGRLSACR NIEAFRIGWG TLQYEDNVTN  480
PEDMRPYCWH YPPKPCGVVP ARSVCGPVYC FTPSPVVVGT TDRRGVPTYT WGENETDVFL  540
```

```
LNSTRPPQGS WFGCTWMNST GFTKTCGAPP CRTRADFNAS TDLLCPTDCF RKHPDATYIK  600
CGSGPWLTPK CLVHYPYRLW HYPCTVNFTI FKIRMYVGGV EHRLTAACNF TRGDRCDLED  660
RDRSQLSPLL HSTTEWAILP CTYSDLPALS TGLLHLHQNI VDVQYMYGLS PAITKYVVRW  720
EWVVLLFLLL ADARVCACLW MLILLGQAEA                                   750

SEQ ID NO: 105          moltype = AA  length = 749
FEATURE                 Location/Qualifiers
source                  1..749
                        mol_type = protein
                        organism = Hepatitis C virus
SEQUENCE: 105
MSTNPKPQRK TKRNTNRRPQ DVKFPGGGQI VGGVYLLPRR GPRLGVRATR KTSERSQPRG  60
RRQPIPKDRR STGKSWGKPG YPWPLYGNEG LGWAGWLLSP RGSRPSWGPT DPRHRSRNVG  120
KVIDTLTCGF ADLMGYIPVV GAPLGGVARA LAHGVRVLED GVNYATGNLP GCSFSIFLLA  180
LLSCITTPVS AAQVKNTSDI YMVTNDCSND SITWQLQAAA LHVPGCVPCE RVGNTSRCWI  240
PVSPNVAVRQ PGALTQGLRT HIDMVVMSAT LCSALYVGDL CGGVMLAAQM FIISPQHHWF  300
VQECNCSIYP GTITGHRMAW DMMMNWSPTT TMILAYVMRV PEVIIDIIGG AHWGVMFGLA  360
YFSMQGAWAK VVVILLLAAG VDAHTRTGSS VGYATSGIVG LFTSGPKQNI QLINTNGSWH  420
INRTALNCND SLNTGFIVSL FYARNFNSTG CPERLSACRG IEGFRIGWGT LQYEDNVTNP  480
EDMRPYCWHY PPKQCGIVPA GSVCGPVYCF TPSPVVVGTT DRLGVPTYTW GENETDVFLL  540
NSTRPPVGSW FGCTWMNSTG FTKTCGAPPC RIRADFNAST DLLCPTDCFR KHPEATYIKC  600
GSGPWLTPRC LVDYPYRLWH YPCTVNYSIF KIRMYVGGVE HRLTAACNFT RGDRCNLEDR  660
DRSQLTPLLH STTEWAILPC TYSDLPALST GLLHLHQNIV DVQYMYGLSP ALTKYVVRWE  720
WVVLLFLLLA DARVCACVWM LILLGQAEA                                    749

SEQ ID NO: 106          moltype = AA  length = 750
FEATURE                 Location/Qualifiers
VARIANT                 458
                        note = X can be any naturally occurring amino acid
source                  1..750
                        mol_type = protein
                        organism = Hepatitis C virus
SEQUENCE: 106
MSTNPKPQRK TKRNTNRRPQ DVKFPGGGQI VGGVYLLPRR GPRLGVRATR KTSERSQPRG  60
RRQPIPKDRR STGKSWGKPG YPWPLYGNEG LGWAGWLLSP RGSRPSWGPT DPRHRSRNVG  120
KVIDTLTCGF ADLMGYIPVV GAPLGGVARA LAHGVRVLED GVNYATGNLP GCSFSIFLLA  180
LLSCVTVPVS AVQVKNTSET YMVTNDCSND SITWQLQAAV LHVPGCVPCE RTGNTSRCWI  240
PVSPNVAVQQ PGALTQGLRT HIDMVVMSAT LCSALYVGDL CGGVVLAAQL FIVSPRRHWF  300
VQECNCSIYP GAITGHRMAW DMMMNWSPTT TMVLAYAMRV PEVIIDIISG AHWGVMFGLA  360
YFSMQGAWAK VAVILLLTAG VEARTHTTGS VAGRTTSGFA GIFTSGPKQN IQLINTNGSW  420
HINRTALNCN DSLNTGFMAA LFYTKNFNSS GCPERLSXCR NIEAFRIGWG TLQYEDDVTN  480
PEDMRPYCWH YPPKQCGIFP AGSVCGPVYC FTPSPVVVGT TNKLGVPTYT WGENETDVFI  540
LNSTRPPRGS WFGCTWMNST GFTKTCGAPP CRIRADFNAS TDLLCPTDCF RKHPEATYIK  600
CGSGPWLTPR CLVDYPYRLW HYPCTVNYSI FKIRMYVGGV EHRLTAACNF SRGDRCNLED  660
RDRSQLTPLL HSTTEWAILP CSYSDLPALS TGLLHLHQNI VDVQYMYGLT PALTKYVVRW  720
EWVVLLFLLL ADARVCACLW MLILLGQAEA                                   750

SEQ ID NO: 107          moltype = AA  length = 750
FEATURE                 Location/Qualifiers
source                  1..750
                        mol_type = protein
                        organism = Hepatitis C virus
SEQUENCE: 107
MSTNPKPQRK TKRNTSRRPQ DVKFPGGGQI VGGVYLLPRR GPRLGVRATR KTSERSQPRG  60
RRQPIPKDRR STGKSWGKPG YPWPLYGNEG LGWAGWLLSP RGSRPSWGPT DPRHRSRNVG  120
KVIDTLTCGF ADLMGYIPVV GAPLGGVARA LAHGVRVLED GVNYATGNLP GCSFSIFLLA  180
LLSCITVPVS AVQVKNISDS YMVTNDCSND SITWQLQAAV LHVPGCVPCE KMGNISRCWI  240
PVSPNVAVQR PGALTQGLRA HIDMVVMSAT LCSALYVGDL CGGVMLAAQM FIVSPQHHHF  300
VQECNCSIYP GAITGHRMAW DMMMNWSPTA TMILAYAMRV PEVIIDIISG AHWGVMFGLA  360
YFSMQGAWAK VVVILLLTAG VDAHTRSIAG SVAHATSGLA GLFTSGAKQN IQLINTNGSW  420
HINRTALNCN DSLNTGFIAS LFYTYRFNSS GCPERLSACR GIQAFRIGWG TLRYEDNVTN  480
PEDMRPYCWH YPPKQCGIVS ARSVCGPVYC FTPSPVVVGT TDRLGVPTYT WGENETDVFI  540
LNSTRPPGGS WFGCTWMNST GFTKTCGAPP CRIRADFNAS MDLLCPTDCF RKHPDATYIK  600
CGSGPWLTPR CLVDYPYRLW HYPCTINYTI FKIRMYVGGV EHRLTAACNF TRGDPCNLED  660
RDRSQLSPLL HSTTEWAILP CSYSDLPALS TGLLHLHQNI VDVQYMYGLS PALTKYIVRW  720
EWVVLLFLLL ADARVCACLW MLILLGQAEA                                   750

SEQ ID NO: 108          moltype = AA  length = 751
FEATURE                 Location/Qualifiers
source                  1..751
                        mol_type = protein
                        organism = Hepatitis C virus
SEQUENCE: 108
MSTNPKPQRK TQRNTNRRPQ DVKFPGGGQI VGGVYLLPRR GPRLGVRTAR KTSERSQPRG  60
RRQPIPKDRR STGKSWGRPG YPWPLYGNEG LGWAGWLLSP RGSRPSWGPT DPRHRSRNVG  120
KVIDTLTCGF ADLMGYIPVV GAPLGGVARA LAHGVRVLED GVNYATGNLP GCSFSIFLLA  180
LLSCITIPAS AVEVKNTSTG YMVTNDCANS SITWQLHAAV LHVPGCVPCE RVDNNTSRCW  240
IPVSPNIAVQ RPGALTQGLR SHIDIVVMSA TLCSALYVGD LCGGVMLAAQ MFVVSPEHHW  300
FVQECNCSIY PGTITGHRMA WDMMMNWSPT ATMILAYAMR VPEVIIDIIG GAHWGVMFGL  360
```

```
AYFSMQGAWA KVVVILLLAA GVDAYTHTVG GAAASTANSI AGLLSRGPRQ NLQLINSNGS  420
WHINRTALNC HDSLQTGFIT ALFYARHFNS SGCPERLAAC RNIEAFRVGW GALQYEDNVT  480
NPEDMRPYCW HYPPKQCGIV PARSVCGPVY CFTPSPVVVG TTDKLGVPTY TWGENETDVF  540
LLNSTRPPQG PWFGCTWMNS TGFTKTCGAP PCRTRADFNA STDLLCPTDC FRKHPDATYN  600
KCGSGPWLTP RCLIDYPYRL WHYPCTVNYT TFKIRMYVGG VEHRLMAACN FTRGDSCDLS  660
QRDRGQLSPL LHSTTEWAIL PCSFSDLPAL STGLLHLHQN IVDVQYMYGL SPALTKYIVR  720
WEWVVLLFLL LADARVCACI WMLILLGQAE A                                 751

SEQ ID NO: 109          moltype = AA  length = 750
FEATURE                 Location/Qualifiers
source                  1..750
                        mol_type = protein
                        organism = Hepatitis C virus
SEQUENCE: 109
MSTNPKPQRK TKRNTNRRPQ DVKFPGGGQI VGGVYLLPRR GPRLGVRATR KTSERSQPRG  60
RRQPIPKDRR STGKSWGKPG YPWPLYGNEG LGWAGWLLSP RGSRPSWGPN DPRHRSRNVG  120
KVIDTLTCGF ADLMGYIPVV GAPLGGVARA LAHGVRVLED GVNFATGNLP GCSFSIFLLA  180
LLSCITTPVS AAEVKNISTG YMVTNDCTND SITWQLQAAV LHVPGCVPCE KVGNTSRCWI  240
PVSPNVAVQQ PGALTQGLRT HIDMVVMSAT LCSALYVGDL CGGVMLAAQM FIVSPQHHWF  300
VQDCNCSIYP GTITGHRMAW DMMMNWSPTA TMILAYAMRV PEVIIDIIGG AHWGVMFGLA  360
YFSMQGAWAK VVVILLLAAG VDAQTHTVGG STAHNARTLT GMFSLGARQK IQLINTNGSW  420
HINRTALNCN DSLHTGFLAS LFYTHSFNSS GCPERMSACR SIEAFRVGWG ALQYEDNVTN  480
PEDMRPYCWH YPPRQCGVVS ASSVCGPVYC FTPSPVVVGT TDRLGAPTYT WGENETDVFL  540
LNSTRPPQGS WFGCTWMNST GYTKTCGAPP CRIRADFNAS MDLLCPTDCF RKHPDTTYIK  600
CGSGPWLTPR CLIDYPYRLW HYPCTVNYTI FKIRMYVGGV EHRLTAACNF TRGDRCNLED  660
RDRSQLSPLL HSTTEWAILP CTYSDLPALS TGLLHLHQNI VDVQFMYGLS PALTKYIVRW  720
EWVVLLFLLL ADARVCACLW MLILLGQAEA                                   750

SEQ ID NO: 110          moltype = AA  length = 750
FEATURE                 Location/Qualifiers
source                  1..750
                        mol_type = protein
                        organism = Hepatitis C virus
SEQUENCE: 110
MSTNPKPQRK TKRNTNRRPQ DVKFPGGGQI VGGVYLLPRR GPRLGVRATR KTSERSQPRG  60
RRQPIPKDRR STGKSWGKPG YPWPLYGNEG LGWAGWLLSP RGSRPSWGPN DPRHRSRNVG  120
KVIDTLTCGF ADLMGYIPVV GAPLGGVARA LAHGVRVLED GVNFATGNLP GCSFSIFLLA  180
LLSCITTPVS AAEVKNISTG YMVTNDCTND SITWQLQAAV LHVPGCVPCE KVGNASQCWI  240
PVSPNVAVQR PGALTQGLRT HIDMVVMSAT LCSALYVGDL CGGVMLAAQM FIVSPQHHWF  300
VQDCNCSIYP GTITGHRMAW DMMMNWSPTA TMILAYAMRV PEVIIDIISG AHWGVMFGLA  360
YFSMQGAWAK VVVILLLAAG VDARTHTVGG SAAQTTGRLT SLFDMGPRQK IQLVNTNGSW  420
HINRTALNCN DSLHTGFIAS LFYTHSFNSS GCPERMSACR SIEAFRVGWG ALQYEDNVTN  480
PEDMRPYCWH YPPRQCGVVS AKTVCGPVYC FTPSPVVVGT TDRLGAPTYT WGENETDVFL  540
LNSTRPPLGS WFGCTWMNSS GYTKTCGAPP CRTRADFNAS TDLLCPTDCF RKHPDTTYLK  600
CGSGPWLTPR CLIDYPYRLW HYPCTVNYTI FKIRMYVGGV EHRLTAACNF TRGDRCNLED  660
RDRSQLSPLL HSTTEWAILP CSYSDLPALS TGLLHLHQNI VDVQFMYGLS PALTKYIVRW  720
EWVILLFLLL ADARVCACLW MLILLGQAEA                                   750

SEQ ID NO: 111          moltype = AA  length = 750
FEATURE                 Location/Qualifiers
source                  1..750
                        mol_type = protein
                        organism = Hepatitis C virus
SEQUENCE: 111
MSTNPKPQRK TKRNTNRRPQ DVKFPGGGQI VGGVYLLPRR GPRLGVRATR KTSERSQPRG  60
RRQPIPKDRR STGKSWGKPG YPWPLYGNEG CGWAGWLLSP RGSRPTWGPT DPRHRSRNLG  120
RVIDTITCGF ADLMGYIPVV GAPVGGVARA LAHGVRVLED GINYATGNLP GCSFSIFLLA  180
LLSCVTVPVS AVEVRNISSS YYATNDCSNN SITWQLTDAV LHLPGCVPCE NDNGTLHCWI  240
QVTPNVAVKH RGALTRSLRT HVDMIVMAAT ACSALYVGDV CGAVMILSQA FMVSPQRHNF  300
TQECNCSIYQ GHITGHRMAW DMMLSWSPTL TMILAYAARV PELVLEIIFG GHWGVVFGLA  360
YFSMQGAWAK VIAILLLVAG VDATTYSSGQ EAGRTVAGFA GLFTTGAKQN LYLINTNGSW  420
HINRTALNCN DSLQTGFLAS LFYTHKFNSS GCPERLSSCR GLDDFRIGWG TLEYETNVTN  480
DGDMRPYCWH YPPRPCGIVP ARTVCGPVYC FTPSPVVVGT TDKQGVPTYT WGENETDVFL  540
LNSTRPPRGA WFGCTWMNGT GFTKTCGAPP CRIRKDYNST IDLLCPTDCF RKHPDATYLK  600
CGAGPWLTPR CLVDYPYRLW HYPCTVNFTI FKARMYVGGV EHRFSAACNF TRGDRCRLED  660
RDRGQQSPLL HSTTEWAVLP CSFSDLPALS TGLLHLHQNI VDVQYLYGLS PALTRYIVKW  720
EWVILLFLLL ADARICACLW MLIILGQAEA                                   750

SEQ ID NO: 112          moltype = AA  length = 750
FEATURE                 Location/Qualifiers
source                  1..750
                        mol_type = protein
                        organism = Hepatitis C virus
SEQUENCE: 112
MSTNPKPQRK TKRNTNRRPQ DVKFPGGGQI VGGVYLLPRR GPRLGVRATR KTSERSQPRG  60
RRQPIPKDRR STGKSWGKPG YPWPLYGNEG CGWAGWLLSP RGSRPHWGPT DPRHRSRNLG  120
KVIDTITCGF ADLMGYIPVI GAPVGGVARA LAHGVRVLED GVNYATGNLP GCSFSIFLLA  180
LLSCVTVPVS AVEVRNISSS YYATNDCSNN SITWQLENAV LHLPGCVPCE NDNGTLRCWT  240
QVTPNVAVKH RGALTQNLRT HVDVIVVAAT VCSALYVGDV CGAVMIASQA LIVSPARHNF  300
```

-continued

```
TQECNCSIYQ GRITGHHMAW DMMLNWSPTI TMILAYAARI PELVLEVIFG GHWGVMFGLA  360
YFSMQGAWAK VIVILLLVAG VDARHHTTGL QAGKTLARVT SLFSIGAKQN IQLINTNGSW  420
HINRTALNCN DSLQTGFIAS LFYVNNINSS GCPERMSSCR ELDDFRIGWG TLEYETNVTN  480
DEDMRPYCWH YPPKPCGIVP ARTVCGPVYC FTPSPIVVGT TDKQGVPTYS WGENETDVFL  540
LNSTRPPRGS WFGCTWMNGT GFTKTCGAPP CRIRRDYNST LDLLCPTDCF RKHPDTTYLK  600
CGSGPWLTPK CLVEYPYRLW HYPCTVNFTI FKVRMYVGAV EHRFSAACNF TRGDRCRLED  660
RDRGQQSPLL HSTTEWAVLP CSFSDLPALS TGLLHLHQNI VDVQYLYGLS PAITRYIVKW  720
EWVVLLFLLL ADARVCACLW MLIILGQAEA                                  750

SEQ ID NO: 113          moltype = AA  length = 750
FEATURE                 Location/Qualifiers
source                  1..750
                        mol_type = protein
                        organism = Hepatitis C virus
SEQUENCE: 113
MSTNPKPQRK TKRNTNRRPQ DVKFPGGGQI VGGVYLLPRR GPRLGVRATR KTSERSQPRG  60
RRQPIPKDRR STGKSWGKPG YPWPLYGNEG CGWAGWLLSP RGSRPTWGPT DPRHRSRNLG  120
RVIDTITCGF ADLMGYIPVV GAPVGGVARA LAHGVRVLED GINYATGNLP GCSFSIFLLA  180
LLSCCTVPVS AVEVRNISTS YYATNDCSNT SITWQLTNAV LHLPGCVPCE NDNGTLRCWI  240
QVTPNVAVKH RGALTHNLRT HVDVIVMAAT VCSALYVGDI CGAVMIVSQA FIISPERHNF  300
TQECNCSMYQ GHITGHRMAW DMMLNWSPTL TMILAYAARV PELVLEVIFG GHWGVVFGLA  360
YFSMQGAWAK VIAILLLVAG VDANTYSSGV TVGHTTSTFA NIFSVGPSQK INLINTNGSW  420
HINRTALNCN DSLQTGFLAS LFYVRNFNSS GCRERLSSCR RLDDFRIGWG TLEYETNVTN  480
DEDMRPYCWH YPPKPCGIVS ARTVCGPVYC FTPSPVVVGT TDRQGVPTYS WGENETDVFL  540
LNSTRPPRGA WFGCTWMNGT GFTKTCGAPP CRIRRDYNST LDLLCPTDCF RKHPDTTYLK  600
CGAGPWLTPK CLVDYPYRLW HYPCTVNFTI FKVRMYVGGV EHRLSAACNF TRGDRCGLED  660
RDRGQQSPLL HSTTEWAVLP CSFSDLPALS TGLLHLHQNI VDVQYLYGLS PAITRYIVKW  720
EWVVLLFLLL ADARVCACLW MLIILGQAEA                                  750

SEQ ID NO: 114          moltype = AA  length = 750
FEATURE                 Location/Qualifiers
source                  1..750
                        mol_type = protein
                        organism = Hepatitis C virus
SEQUENCE: 114
MSTNPKPQRK TKRNTNRRPQ DVKFPGGGQI VGGVYLLPRR GPRLGVRATR KTSERSQPRG  60
RRQPIPKDRR STGKSWGKPG YPWPLYGNEG CGWAGWLLSP RGSRPTWGPS DPRHRSRNLG  120
RVIDTITCGF ADLMGYIPVV GAPVGGVARA LAHGVRVLED GINYATRNLP GCSFSIFLLA  180
LLSCVTVPVS SVEIRNISTS YYATNDCSNN SITWQLTNAV LHLPGCVPCE NDNGTLRCWI  240
QVTPNVAVKH RGALTHNLRA HVDVIVMAAT VCSALYVGDV CGAVMIVSQA LIVSPERHNF  300
TQECNCSIYQ GHITGQRMAW DMMLNWSPTL TMILAYAARV PELVLEIVFG GHWGVVFGLA  360
YFSMQGAWAK VIAILLLVAG VDATTYSTGA TVGRTVGSFA GLFKLGAQQN VQLINTNGSW  420
HINRTALNCN DSLHTGFMAA LFYANKFNSS GCPERLSSCR GLDDFRIGWG TLEYETNVTN  480
VEDMRPYCWH YPPKPCGIVP AQSVCGPVYC FTPSPVVVGT TDRQGVPTYN WGDNETDVFL  540
LNSTRPPRGA WFGCTWMNGT GFTKTCGAPP CRIRKDFNST LDLLCPTDCF RKHPDATYVK  600
CGAGPWLTPR CLIDYPYRLW HYPCTVNFTI FKVRMYVGGV EHRFSAACNF TRGDRCRLED  660
RDRGQQSPLL HSTTEWAVLP CSFSDLPALS TGLLHLHQNI VDVQYLYGLS PAVTKYIVKW  720
EWVVLLFLLL ADARICACLW MLIILGQAEA                                  750

SEQ ID NO: 115          moltype = AA  length = 750
FEATURE                 Location/Qualifiers
VARIANT                 203
                        note = X can be any naturally occurring amino acid
VARIANT                 295
                        note = X can be any naturally occurring amino acid
VARIANT                 343
                        note = X can be any naturally occurring amino acid
VARIANT                 401
                        note = X can be any naturally occurring amino acid
VARIANT                 426
                        note = X can be any naturally occurring amino acid
VARIANT                 626
                        note = X can be any naturally occurring amino acid
source                  1..750
                        mol_type = protein
                        organism = Hepatitis C virus
SEQUENCE: 115
MSTDPKPQRK TKRNTNRRPQ DVKFPGGGQI VGGVYLLPRR GPRLGVRAAR KTSERSQPRG  60
RRQPIPKDRR SPGKSWGKPG YPWPLYGNEG CGWAGWLLSP RGSRPTWGPT DPRHRSRNLG  120
KVIDTITCGF ADLMGYIPVV GAPVGGVARA LAHGVRVLED GINYATGNLP GCSFSIFLLA  180
LLSCLTVPAS AVEVRNISSG YYXTNDCSNS SITWQLTNAV LHLPGCVPCE NDNGTLRCWI  240
QVTPNVAVKY RGALTHNLRT HVDMIVMAAT VCSALYVGDV CGAVMIVSQA FIMSXERHNF  300
TQECNCSIYQ GHITGHRMAW DMMLGWSPTL TMILAYAARV PEXVLEVVFG GHWGVVFGLA  360
YFSMQGAWAK VIAILLLVAG VDAGTYSSGA TIGQGTRGLV XLFSAGPSQK ISLINTNGSW  420
HINRTXLNCN DSLQTGFIAS LFYAKSFNSS GCPERLSSCR GLDDFRIGWG TLEYENNVTN  480
DEDMRPYCWH YPPKPCGIVP ARTVCGPVYC FTPSPVVVGT TDKQGVPTYS WGENETDVFL  540
LNSTRPPQGA WFGCTWMNGT GFTKTCGAPP CRIRRDHTST LDLLCPTDCF RKHPDTTYLK  600
CGAGPWLTPK CLVDYPYRLW HYPCTXNFTI FKVRMYVGGV EHRFSAACNF TRGDRCRLED  660
RDRGQQSPLL HSTTEWAVLP CSFSDLPALS TGLLHLHQNI VDVQYLYGLS PAITKYIVKW  720
```

```
EWVILLFLLL ADARVCACLW MLIILGQAEA                               750

SEQ ID NO: 116          moltype = AA  length = 752
FEATURE                 Location/Qualifiers
VARIANT                 431
                        note = X can be any naturally occurring amino acid
VARIANT                 466
                        note = X can be any naturally occurring amino acid
source                  1..752
                        mol_type = protein
                        organism = hepatitis C virus
SEQUENCE: 116
MSTLPKPQRK TKRNTIRRPQ DVKFPGGGQI VGGVYVLPRR GPRLGVRATR KTSERSQPRG  60
RRQPIPKARR SEGRSWAQPG YPWPLYGNEG CGWAGWLLSP RGSRPSWGPN DPRRRSRNLG  120
KVIDTLTCGF ADLMGYIPLV GAPVGGVARA LAHGVRALED GINFATGNLP GCSFSIFLLA  180
LFSCLIHPAA SLEWRNTSGL YVLTNDCSNS SIVYEADDVI LHTPGCVPCV QDGNTSTCWT  240
PVTPTVAVRY VGATTASIRS HVDLLVGAAT MCSALYVGDM CGAVFLVGQA FTFRPRRHQT  300
VQTCNCSLYP GHLSGHRMAW DMMMNWSPAV GMVVAHVLRL PQTLFDIIAG AHWGILAGLA  360
YYSMQGNWAK VAIIMVMFSG VDATTYTTGG SAARGARGLT SLFSVGAKQK LQLVNTNGSW  420
HINSTALNCN XSINTGFIAG LFYYHKFNST GCPQRLSSCK PITFFXQGWG PLTDANITGP  480
SDDKPYCWHY APRPCDVVPA SSVCGPVYCF TPSPVVVGTT DAKGVPTYTW GENETDVFLL  540
ESLRPPSGRW FGCTWMNSTG FVKTCGAPPC NIYGGGGNPH NESDLFCPTD CFRKHPEATY  600
SRCGAGPWLT PRCMVDYPYR LWHYPCTVNF TLFKVRMFVG GFEHRFTAAC NWTRGERCDI  660
EDRDRSEQHP LLHSTTELAI LPCSFTPMPA LSTGLIHLHQ NIVDVQYLYG VGSGMVGWAL  720
KWEFVILVFL LLADARVCVA LWLMLMISQA EA                             752

SEQ ID NO: 117          moltype = AA  length = 752
FEATURE                 Location/Qualifiers
source                  1..752
                        mol_type = protein
                        organism = hepatitis C virus
SEQUENCE: 117
MSTLPKPQRK TKRNTIRRPQ DVKFPGGGQI VGGVYVLPRR GPRLGVRATR KTSERSQPRE  60
RRQPIPKARR SDGRSWAQPG YPWPLYGNEG CGWAGWLLSP RGSRPSWGPN DPRRRSRNLG  120
KVIDTLTCGF ADLMGYIPIV GAPVGGVARA LAHGVRALED GINFATGNLP GCSFSIFLLA  180
LLSCLIHPAA SLEWRNTSGL YILTNDCPNS SIVYEADDVI LHTPGCIPCV QDGNTSTCWT  240
SVSPTVAVRY VGATTASIRS HVDLLVGAAT LCSALYVGDM CGAVFLVGQA FTFRPRRHQT  300
VQTCNCSLYP GHLTGHRMAW DMMMNWSPAV GMVVAHVLRM PQTVFDIIAG AHWGILAGLA  360
YYSMQGNWAK VAIIMVMFSG VDAETHTTGG TAARNAFTLT GLFTQGARQK LELINTNGSW  420
HINRTALNCN ESLNTGFIAG LFYLHKFNST GCPERLSSCK PITFFRQGWG SLTDANITGP  480
SDDKPYCWHY APRPCEVVPA LNVCGPVYCF TPSPVVVGTT DRQGVPTYTW GENETDVFLL  540
RSLRPPSGQW FGCTWMNSTG FVKTCGAPPC DIYGGGGNRC NESDLFCPTD CFRKHPEATY  600
SRCGAGPWLT PRCLVDYPYR LWHYPCTVNF TLFKVRMFVG GFEHRFTAAC NWTRGERCNI  660
EDRDRSEQHP LLHSTTELAI LPCSFTPMPA LSTGLIHLHQ NIVDVQYLYG VGSGVVGWAL  720
RWEFVVLVFL LLADARVCVA LWLMLMISQA EA                             752

SEQ ID NO: 118          moltype = AA  length = 752
FEATURE                 Location/Qualifiers
source                  1..752
                        mol_type = protein
                        organism = hepatitis C virus
SEQUENCE: 118
MSTLPKPQRK TKRNTIRRPQ DVKFPGGGQI VGGVYVLPRR GPRLGVRATR KTSERSQPRG  60
RRQPIPKARR SEGRSWAQPG YPWPLYGNEG CGWAGWLLSP RGSRPSWGPN DPRRRSRNLG  120
KVIDTLTCGF ADLMGYIPLV GAPVGGVARA LAHGVRALED GINFATGNLP GCSFSIFLLA  180
LFSCLVHPAA SLEWRNTSGL YVLTNDCSNS SIVYEADDVI LHTPGCVPCV QDDNTSTCWT  240
PVTPTVAVRY VGATTASIRS HVDLLVGAAT LCSALYVGDM CGAVFLVGQA FTFRPRRHQT  300
VQTCNCSLYP GHVSGHRMAW DMMMNWSPAV GMVVAHILRL PQTLFDILAG AHWGILAGLA  360
YYSMQGNWAK VAIVMIMFSG VDAETYVTGG SVAHSARGLT SLFSMGAKQK LQLVNTNGSW  420
HINSTALNCN ESINTGFIAG LFYYHKFNST GCPQRLSSCK PIISFRQGWG PLTDANITGP  480
SDDRPYCWHY APRPCSVVPA SSVCGPVYCF TPSPVVVGTT DIKGKPTYNW GENETDVFLL  540
ESLRPPSGRW FGCAWMNSTG FLKTCGAPPC NIYGGEGDPE NETDLFCPTD CFRKHPEATY  600
SRCGAGPWLT PRCMVDYPYR LWHYPCTVNF TLFKVRMFVG GFEHRFTAAC NWTRGERCNI  660
EDRDRSEQHP LLHSTTELAI LPCSFTPMPA LSTGLIHLHQ NIVDVQYLYG VGSDMVGWAL  720
KWEFVILVFL LLADARVCVA LWLMLMVSQA EA                             752

SEQ ID NO: 119          moltype = AA  length = 752
FEATURE                 Location/Qualifiers
source                  1..752
                        mol_type = protein
                        organism = hepatitis C virus
SEQUENCE: 119
MSTLPKPQRK TKRNTIRRPQ DVKFPGGGQI VGGVYVLPRR GPRLGVRATR KTSERSQPRG  60
RRQPIPKARR SEGRSWAQPG YPWPLYGNEG CGWAGWLLSP RGSRPSWGPN DPRRRSRNLG  120
KVIDTLTCGF ADLMGYIPLV GAPVGGVARA LAHGVRALED GINFATGNLP GCSFSIFLLA  180
LFSCLIHPAA SLEWRNTSGL YVLTNDCSNS SIVYEADDVI LHTPGCVPCV QDGNTSTCWT  240
PVTPTVAVRY VGATTASIRS HVDLLVGAAT MCSALYVGDM CGAVFLVGQA FTFRPRRHQT  300
VQTCNCSLYP GHLSGHRMAW DMMMNWSPAV GMVVAHVLRL PQTLFDIMAG AHWGILAGLA  360
YYSMQGNWAK VAIIMVMFSG VDAHTYTTGG TASRHTQAFA GLFDIGPQQK LQLVNTNGSW  420
```

-continued

```
HINSTALNCN ESINTGFIAG LFYYHKFNST GCPQRLSSCK PITFFRQGWG PLTDANITGP  480
SDDRPYCWHY APRPCDIVPA SSVCGPVYCF TPSPVVVGTT DARGVPTYTW GENEKDVFLL  540
KSQRPPSGRW FGCSWMNSTG FLKTCGAPPC NIYGGEGNPH NESDLFCPTD CFRKHPETTY  600
SRCGAGPWLT PRCMVDYPYR LWHYPCTVDF RLFKVRMFVG GFEHRFTAAC NWTRGERCDI  660
EDRDRSEQHP LLHSTTELAI LPCSFTPMPA LSTGLIHLHQ NIVDVQYLYG VGSGMVGWAL  720
KWEFVILVFL LLADARVCVA LWLMLMISQT EA                                752

SEQ ID NO: 120          moltype = AA  length = 752
FEATURE                 Location/Qualifiers
source                  1..752
                        mol_type = protein
                        organism = hepatitis C virus
SEQUENCE: 120
MSTLPKPQRK TKRNTIRRPQ DVKFPGGGQI VGGVYVLPRR GPRLGVRATR KTSERSQPRG  60
RRQPIPKARR SEGRSWAQPG YPWPLYGNEG CGWAGWLLSP RGSRPSWGQN DPRRRSRNLG  120
KVIDTLTCGF ADLMGYIPLV GAPVGGVARA LAHGVRALED GINFATGNLP GCSFSIFLLA  180
LFSCLIHPAA SLEWRNTSGL YVLTNDCSNS SIVYEADDVI LHTPGCVPCV QDGNTSTCWT  240
PVTPTVAVRY VGATTASIRS HVDLLVGAAT MCSALYVGDM CGAVFLVGQA FTFRPRRHQT  300
VQTCNCSLYP GHLSGHRMAW DMMMNWSPAV GMVVSHVLRL PQTLFDIIAG AHWGILAGLA  360
YYSMQGNWAK VAVIMVMFSG VDAETYITGG SAAHGVSTLT SLFSSGPQQK LQLVKTNGSW  420
HINSTALNCN ESINTGFIAG LFYYHKFNST GCPQRLSSCK PITFFRQGWG SLTDANVTGA  480
SADKPYCWHY APRPCDVVPA LNVCGPVYCF TPSPVVVGTT DRKGVPTYNW GENESDVFLL  540
ESLRPPSGRW FGCAWMNSTG FLKTCGAPPC NIYGGGGNPN NESHLFCPTD CFRKHPDATY  600
SRCGAGPWLT PRCMVDYPYR LWHYPCTVNF TLFKVRMFVG GFEHRFTAAC NWTRGERCNI  660
EDRDRSEQHP LLHSTTELAI LPCSFTPMPA LSTGLIHLHQ NIVDVQYLYG VGSGMVGWAL  720
KWEFVILIFL LLADARVCVA LWLMLMISQA EA                                752

SEQ ID NO: 121          moltype = AA  length = 752
FEATURE                 Location/Qualifiers
source                  1..752
                        mol_type = protein
                        organism = hepatitis C virus
SEQUENCE: 121
MSTLPKPQRK TKRNTIRRPQ DVKFPGGGQI VGGVYVLPRR GPRLGVCATR KTSERSQPRR  60
RRQPIPKARQ SGGRSWAQPG YPWPLYGNEG CGWAGWLLSP RGSRPSWGPN DPRRRSRNLG  120
KVIDTLTCGF ADLMGYIPLV GAPVGGVARA LAHGVRALED GINFATGNLP GCSFSIFLLA  180
LFSCLIHPAA SLEWRNTSGL YVLTNDCSNS SIVYEADDVI LHTPGCVPCV QNDNISTCWT  240
PVTPTVAVRY VGATTASIRS HVDLLVGAAT MCSALYVGDM CGAVFLVGQA FTFRPRRHQT  300
VQTCNCSLYP GHLSGHRMAW DMMMNWFPAL GMAVAHVLRV PQTLFDIIAG AHWGILAGLA  360
YYSMQGNWAK VAIIMVMFSG VDAVTYTTGG SAAHATRGLT SLFSVGAQQK LQLVNTNGSW  420
HINSTALNCN ESINTGFIAG LFYYHRFNST GCPQRLSSCK PITFFKQGWG PLTDANISGP  480
SDDKPYCWHY APRPCKVVPA SGVCGPVYCF TPSPVVVGTT DAKGVPTYTW GANDTDVFLL  540
ESLRPPGGRW FGCTWMNSTG FVKTCGASPC DIYGGGGNSG NESDLFCPTD CFRKHPEATY  600
SRCGAGPWLT PRCMVDYPYR LWHYPCTVNF TLFKVRMFVG GFEHRFTAAC NWTRGERCDI  660
EDRDRSEQHP LLHSTTELAI LPCSFTPMPA LSTGLIHLHQ NIVDVQYLYG VGSGMVGWAL  720
KWEFVILIFL LLADRRVCVA LWLMLMITQA EA                                752

SEQ ID NO: 122          moltype = AA  length = 752
FEATURE                 Location/Qualifiers
source                  1..752
                        mol_type = protein
                        organism = hepatitis C virus
SEQUENCE: 122
MSTLPKPQRK TKRNTVCRPQ DVKFPGGGQI VGGVYVLPRR GPRLGVRATR KTSERSQPRG  60
RRQPIPKARR SEGRSWAQPG YPWPLYGNEG CGWAGWLLSP RGSRPSWGPN DPRRRSRNLG  120
KVIDTLTCGF ADLMGYIPLV GAPVGGVARA LAHGVRALED GINFATGNLP GCSFSIFLLA  180
LFSCLIHPAA SLEWRNVSGL YILTNDCPNS SIVYEADDVI LHTPGCIPCV QDGNTSTCWT  240
ALTPTVAVRY VGATTASIRS HVDLLVGAAT MCSALYVGDM CGAVFLVGQA FTFRPRRHQT  300
VQTCNCSLYP GHLTGHRMAW DMMMNWSPAV GMVVAHVLRL PQTLFDIIAG AHWGILAGLA  360
YYSMQGNWAK VIIIMVMFSG VDATTHVTGG TAGLTAFRLT GLFTVGPQQK LQLVNTNGSW  420
HINRTALNCN DSLNTGFIAG LFRFHKFNST GCPEMLSSCK PITSFKQGWG PLTDANITIP  480
SDDRPYCWHY PPRSCEVVPA LSVCGPVYCF TPSPVVVGTT DAKGVPTYTW GENETDVFLL  540
KSLRPPGGRW FGCTWMNSTG FVQTCGAPPC NIYGGGDLK NESDLFCPTD CFRKHPEATY  600
SRCGAGPWLT PRCMVDYPYR LWHYPCTVNF TLFKVRMFVG GFEHRFTAAC NWTRGERCDI  660
EDRDRSELHP LLHSTTELAI LPCSFTPMPA LSTGLIHLHQ NIVDVQYLYG VGSGMVGWAV  720
KWEFVILVFL LLADARVCVA LWLMLMISQA EA                                752

SEQ ID NO: 123          moltype = AA  length = 752
FEATURE                 Location/Qualifiers
source                  1..752
                        mol_type = protein
                        organism = hepatitis C virus
SEQUENCE: 123
MSTLPKPQRK TKRNTIRRPQ DVKFPGGGQI VGGVYVLPRR GPRLGVRATR KTSERSQPRG  60
RRQPIPKARR SEGRSWAQPG YPWPLYGNEG CGWAGWLLSP RGSRPSWGPN DPRRRSRNLG  120
KVIDTLTCGF ADLMGYIPLV GAPVGGVARA LAHGVRALED GINFATGNLP GCSFSIFLLA  180
LFSCLIHPAA SLQWRNTSGL YVLTNDCSNS SIVYEADDVI LHTPGCVPCV QDGNTSTCWT  240
PVTPTVAVRY VGATTASIRS HVDLLVGAAT MCSALYVGDM CGAVFLVGQA FTFRPRRHQT  300
VQTCNCSLYP GHLSGHRMAW DMMMNWSPAA GMVVAHILRL PQTLFDIIAG AHWGILAGLA  360
```

```
YYSMQGNWAK VAIIMVMFSG VDATTYTSGG SVAQQARGLA DLFSVGAKQN LQLVNTNGSW  420
HINSTALNCD DSINTGFIAG LFYYHKFNST GCPQRLSDCK PITFFKQGWG PLTDANITGP  480
SDDKPYCWHY APRRCGVVPA SSVCGPVYCF TPSPVVVGTT DAKGVPTYTW GANETDVFLL  540
ESLRPPSGRW FGCAWMNSTG FLKTCGAPPC NIYGGGGNPH NESDLFCPTD CFRKHPEATY  600
SRCGAGPWLT PRCMVDYPYR LWHYPCTVNF TLFKMRTFVG GFEHRFTAAC NWTRGERCDI  660
EDRDRSEQHP LLHSTTELAI LPCSFTPMPA LSTGLIHLHQ NIVDVQYLYG VGSGMVGWAL  720
KWEFVILVFL LLADARVCVA LWLMLMISQA EA                                752

SEQ ID NO: 124          moltype = AA  length = 752
FEATURE                 Location/Qualifiers
source                  1..752
                        mol_type = protein
                        organism = hepatitis C virus
SEQUENCE: 124
MSTLPKPQRK TKRNTIRRPQ DVKFPGGGQI VGGVYVLPRR GPRLGVRATR KTSERSQPRG  60
RRQPIPKARR SEGRSWAQPG YPWPLYGNEG CGWAGWLLSP RGSRPSWGPN DPRRRSRNLG  120
KVIDTLTCGF ADLMGYIPLV GAPVGGVARA LAHGVRALED GINFATGNLP GCSFSIFLLA  180
LFSCLIHPAA SLQWRNTSGL YVLTNDCSNS SIVYEADDVI LHTPGCVPCV QDGNTSTCWT  240
PVTPTVAVRY VGATTASIRS HVDLLVGAAT MCSALYVGDM CGAVFLVGQA FTFRPRRHQT  300
VQTCNCSLYP GHLSGHRMAW DMMMNWSPAA GMVVAHILRL PQTLFDIIAG AHWGILAGLA  360
YYSMQGNWAK VAIIMVMFSG VDATTYTSGG SVAQQARGLA DLFSVGAKQN LQLVNTNGSW  420
HINSTALNCD DSINTGFIAG LFYYHKFNST GCPQRLSDCK PITFFKQGWG PLTDANITGP  480
SDDKPYCWHY APRRCGVVPA SSVCGPVYCF TPSPVVVGTT DAKGVPTYTW GANETDVFLL  540
ESLRPPSGRW FGCAWMNSTG FLKTCGAPPC NIYGGGGNPH NESDLFCPTD CFRKHPEATY  600
SRCGAGPWLT PRCMVDYPYR LWHYPCTVNF TLFKMRTFVG GFEHRFTAAC NWTRGERCDI  660
EDRDRSEQHP LLHSTTELAI LPCSFTPMPA LSTGLIHLHQ NIVDVQYLYG VGSGMVGWAL  720
KWEFVILVFL LLADARVCVA LWLMLMISQA EA                                752

SEQ ID NO: 125          moltype = AA  length = 752
FEATURE                 Location/Qualifiers
source                  1..752
                        mol_type = protein
                        organism = hepatitis C virus
SEQUENCE: 125
MSTLPKPQRK TKRNTIRRPQ DVKFPGGGQI VGGVYVLPRR GPRLGVCATR KTSERSQPRG  60
RRQPIPKARR SEGRSWAQPG YPWPLYGNEG CGWAGWLLSP RGSRPSWGPN DPRRRSRNLG  120
KVIDTLTCGF ADLMGYIPLV GAPVGGVARA LAHGVRALED GINFATGNLP GCSFSIFLLA  180
LFSCLVHPAA SLEWRNTSGL YVLTNDCPNS SIVYEADDVI LHTPGCIPCV QDGNKSTCWT  240
SVTPTVAVKY VGATTASIRS HVDLLVGAAT MCSALYVGDM CGAVFLVGQA FTFRPRRHQT  300
VQTCNCSLYP GHLSGHRMAW DMMMNWSPAV GMVVAHVLRL PQTLFDIIAG AHWGILAGLA  360
YYSMQGNWAK VAIIMVMFSG VDATTYTTGG NAARGASGIV SLFTPGAKQN LQLVNTNGSW  420
HINRTALNCN DSINTGFIAG LIYYHKFNST GCPQRLSSCK PITFFRQGWG SLTDANITGP  480
SDDKPYCWHY PPRPCDTIRA SSVCGPVYCF TPSPVVVGTT DAKGAPTYNW GANETDMFLL  540
QSLRPPSGRW FGCTWMNSTG FTKTCGAPPC NIYGGGGNLN NESDLFCPTD CFRKHPEATY  600
SRCGAGPWLT PRCLVDYPYR LWHYPCTVNF TLFRMRTFVG GFEHRFTAAC NWTRGERCNI  660
EDRDRSEQHP LLHSTTELAI LPCSFTPMPA LSTGLIHLHQ NIVDVQYLYG IGSGVVGWAL  720
KWEFVILVFL LLADARVCVA LWLMLMISQA EA                                752

SEQ ID NO: 126          moltype = AA  length = 752
FEATURE                 Location/Qualifiers
source                  1..752
                        mol_type = protein
                        organism = hepatitis C virus
SEQUENCE: 126
MSTLPKPQRK TKRNTIRRPQ DVKFPGGGVI YVGVYVLPRR GPRLGVRATR KTSERSQPRG  60
RRKPIPKARR SEGRSWAQPG YPWPLYGNEG CGWAGWLLSP RGSRPNWAPN DPRRRSRNLG  120
KVIDTLTCGF ADLMGYIPLV GAPLGGAARA LAHGVRALED GINFATGNLP GCSFSIFLLA  180
LFSCLIHPAA SLEWRNTSGL YVLTNDCSNS SIVYEADDVI LHTPGCIPCV QDGNTSTCWT  240
PVTPTVAVRY VGATTASIRS HVDLLVGAGT MCSALYVGDM CGPVFLVGQA FTFRPRRHRT  300
VQTCNCSLYP GHLSGQRMAW DMMMNWSPAV GMVVAHILRL PQTLFDVVAG AHWGIIAGLA  360
YYSMQGNWAK VAIIMVMFSG VDASTHVTAG QAARNAYGIT SLFSVGAKQN LQLINTNGSW  420
HINRTALNCN ESINTGFIAG LFYYHKFNST GCPQRLSSCK PITFFKQGWG PLTDANITGP  480
SDDKPYCWHY APRPCGIVPA LNVCGPVYCF TPSPVVVGTT DAKGAPTYTW GANKTDVFLL  540
ESLRPPSGRW FGCTWMNSTG FVKTCGAPPC NIYGDGRDAQ NESDLFCPTD CFRKHPEATY  600
SRCGAGPWLT PRCLVDYPYR LWHYPCTVNF TLFKVRMFVG GFEHRFTAAC NWTRGERCDI  660
EDRDRSEQHP LLHSTTELAI LPCSFTPMPA LSTGLIHLHQ NIVDVQYLYG IGSGMVGWAL  720
KWEFVILIFL LLADARVCVA LWLILTISQA EA                                752

SEQ ID NO: 127          moltype = AA  length = 754
FEATURE                 Location/Qualifiers
source                  1..754
                        mol_type = protein
                        organism = hepatitis C virus
SEQUENCE: 127
MSTLPKPKRQ TKRNTLRRPK NVKFPAGGQI VGEVYVLPRR GPQLGVREVR KTSERSQPRG  60
RRQPTPKARP REGRSWAQPG YPWPLYGNEG CGWAGWLLPP RGSRPSWGQN DPRRRSRNLG  120
KVIDTLTCGF ADLMGYIPLI GAPVGGVARA LAHGVRALED GVNYATGNLP GCSFSIFLLA  180
LFSCLTCPAS SLEYRNASGL YLLTNDCSNR SIVYEADDVI LHLPGCVPCV ETDNNNTSCW  240
TPISPTVAVK HPGVTTASIR NHVNMLVAPP TLCSALYVED AFGAVSLVGQ AFTFRPRQHK  300
```

-continued

```
TVQTCNCSIY PGHVSGHRMA WDMMMNWSPA IGLVISHLMR LPQTFFDLVV GAHWGVMAGL  360
AYFSMQGNWA KVVIVLIMFS GVDATTHTTG GSAAQATAGF TSFFTRGPSQ NLQLVNSNGS  420
WHINSTALNC NDSLNTGFIA GLFYYHKFNS SGCPERMSSC KPITYFNQGW GPLTDANING  480
PSEDRPYCWH YPPRPCNITK PLNVCGPVYC FTPSPVVVGT TDIKGLPTYR FGVNESDVFL  540
LTSLRPPQGR WFGCVWMNST GFVKTCGAPP CNIYGGMKDI EANQTHLKCP TDCFRKHHDA  600
TFTRCGSGPW LTPRCLVDYP YRLWHYPCTV NFSIFKVRMF VGGHEHRFSA ACNWTRGERC  660
DLEDRDRSEQ QPLLHSTTDS LILPCSFTPM RRLSTGLIHL HQNIVDVQYL YGVGSAVVGW  720
ALKWEFVVLV FLLLADARVC VALWMMLLIS QAEA                              754

SEQ ID NO: 128         moltype = AA  length = 751
FEATURE                Location/Qualifiers
source                 1..751
                       mol_type = protein
                       organism = hepatitis C virus
SEQUENCE: 128
MSTLPKPQRI TKRNINRRPQ DVKFPGGGQI VGGVYVLPRR GPKLGVRAVR KTSERSQPRS  60
RRQPIPRARR TEGRSWAQPG YPWPLYGNEG CGWAGWLLSP RGSRPSWGPN DPRRRSRNLG  120
KVIDTLTCGF ADLMGYIPLV GAPVGGVARA LAHGVRALED GINFATGNLP GCSFSIFLLA  180
LLSCLLTPTA GLEYRNASGL YTVTNDCSNG SIVYEAGDVI LHLPGCIPCV RLNNASKCWT  240
PVSPTVAVSR PGAATASLRT HVDMMVGAAT LCSALYVGDL CGALFLVGQG FSWRHRQHWT  300
VQDCNCSIYP GHLTGHRMAW DMMMNWSPAM TLIVSQVLRL PQTMFDLVIG AHWGVMAGVA  360
YYSMQGNWAK VFLVLCLFSG VDASTTITGG VAASGAFTIT SLFSTGAKQP LHLVNTNGSW  420
HINRTALNCN DSLNTGFIAG LLYYHKFNSS GCVERMSACS PLDRFAQGWG PLGPANISGP  480
SSEKPYCWHY APRPCDTVPA QSVCGPVYCF TPSPVVVGAT DKRGAPTYTW GENESDVFLL  540
ESARPPTEPW FGCTWMNGSG YVKTCGAPPC HIYGGREGKS NNSLVCPTDC FRKHPDATYN  600
RCGAGPWLTP RCLVDYPYRL WHYPCTVNYT IFKVRMFVGG LEHRFNAACN WTRGERCNLE  660
DRDRSEMYPL LHSTTEQAIL PCSFVPIPAL STGLIHLHQN IVDVQYLYGI SSGLVGWAIK  720
WEFVILIFLL LADARVCVVL WMMMLISQAE A                                 751

SEQ ID NO: 129         moltype = AA  length = 750
FEATURE                Location/Qualifiers
source                 1..750
                       mol_type = protein
                       organism = hepatitis C virus
SEQUENCE: 129
MSTNPKPQRL TKRNTVRRPQ NVKFPGGGQI VGGVYLLPRR GPRLGVRGTR KSSERSQPRG  60
RRQRIPKAAS SQGKAWGKPG YPWPLYGNEG CGWAGWLLSP RGSRPTWGPT DPRHRSRNLG  120
KVIDTMTCGF ADLMGYIPVL GAPLGGVARA LAHGVRVLED GVNYATGNLP GCSFSIFLLA  180
LLSCLTVPAS AYEVRNSSGV YHLTNDCPNA SIVYETDNAI LHEPGCVPCV REGNTSRCWE  240
PVAPTLAVRY RGALTDDLRT HIDLVVASAT LCSALYVGDI CGAIFIASQA VLWKPGGGRI  300
VQDCNCSIYP GHVTGHRMAW DMMQNWAPAL SMVAAYAVRV PGVIITTVAG GHWGVLFGLA  360
YFGMAGNWAK VILIMLLMSG VDAETMAVGA RAAHTTGALV SLLNPGPSQR LQLINTNGSW  420
HINRTALNCN DSLQTGFIAA LFYTHRFNSS GCPERMASCK PLSDFDQGWG PLWYNSTERP  480
SDQRPYCWHY APSPCGIVPA KDVCGPVYCF TPSPVVVGTT DRRGVPTYTW GENESDVFLL  540
NSTRPPQGSW FGCSWMNTTG FTKTCGGPPC KIRPQGAQSN TSLTCPTDCF RKHPRATYSA  600
CGSGPWLTPR CMVHYPYRLW HYPCTVNFTI HKVRLYIGGV EHRLDAACNW TRGERCDLED  660
RDRVDMSPLL HSTTELAILP CSFVPLPALS TGLIHLHQNI VDAQYLYGLS PAIISWAIRW  720
EWVVLVFLLL ADARICACLW MMMLMAQAEA                                   750

SEQ ID NO: 130         moltype = AA  length = 659
FEATURE                Location/Qualifiers
source                 1..659
                       mol_type = protein
                       organism = hepatitis C virus
SEQUENCE: 130
MDAMKRGLCC VLLLCGAVFV SPSYQVRNST GLYHVTNDCP NSSIVYEAAD AILHTPGCVP  60
CVREGNTSRC WVAMTPTVAT RDGKLPTTQL RRHIDLLVGS ATLCSALYVG DLCGSIFLVG  120
QMFTFSPRRH WTTQDCNCSL YPGHITGHRM AWDMMMNWSP TAALITAQLL RIPQAILDMI  180
AGAHWGVLAG IAYFSMVGNW AKVLVVLLLF AGVDAQTDKT HTCPPCPAPE AEGAPSVFLF  240
PPKPKDTLMI SRTPEVTCVV VDVSHEDPEV KFNWYVDGVE VHNAKTKPRE EQYNSTYRVV  300
SVLTVLHQDW LNGKEYKCKV SNKALPAPIE KTISKAKGQP REPQVYTLPP SREEMTKNQV  360
SLTCLVKGFY PSDIAVEWES NGQPENNYKT TPPVLDSDGS FFLYSKLTVD KSRWQQGNVF  420
SCSVMHEALH NHYTQKSLSL SPGKLEVLFQ GPQTHVTGGR AAHITAGLTS LFSPGPSQKL  480
QLVNTNGSWH INSTALNCND SLKTGWIAGL LYSYKFNSSG CPERLASCRR LTDFAQGWGP  540
ISHANGSGPD ERPYCWHYPP RPCGIVPAKS VCGPVYCFTP SPVVVGTTDK SGAPTYNWGE  600
NDWDVFVLNN TRPPLGNWFG CTWMNSTGFT KVCGAPPCVI GGAGNNTLRC PTDCFRKHP   659

SEQ ID NO: 131         moltype = AA  length = 688
FEATURE                Location/Qualifiers
source                 1..688
                       mol_type = protein
                       organism = hepatitis C virus
SEQUENCE: 131
MDAMKRGLCC VLLLCGAVFV SPSYQVRNST GLYHVTNDCP NSSIVYEAAD AILHTPGCVP  60
CVREGNTSRC WVAMTPTVAT RDGKLPTTQL RRHIDLLVGS ATLCSALYVG DLCGSIFLVG  120
QMFTFSPRRH WTTQDCNCSL YPGHITGHRM AWDMMMNWSP TAALITAQLL RIPQAILDMI  180
AGAHWGVLAG IAYFSMVGNW AKVLVVLLLF AGVDAQTDKT HTCPPCPAPE AEGAPSVFLF  240
PPKPKDTLMI SRTPEVTCVV VDVSHEDPEV KFNWYVDGVE VHNAKTKPRE EQYNSTYRVV  300
SVLTVLHQDW LNGKEYKCKV SNKALPAPIE KTISKAKGQP REPQVYTLPP SREEMTKNQV  360
```

```
SLTCLVKGFY PSDIAVEWES NGQPENNYKT TPPVLDSDGS FFLYSKLTVD KSRWQQGNVF  420
SCSVMHEALH NHYTQKSLSL SPGKLEVLFQ GPAIPLEVIK GGRHLIFCHS KKKCDELAAK  480
LQTHVTGGRA AHITAGLTSL FSPGPSQKLQ LVNTNGSWHI NSTALNCNDS LKTGWIAGLL  540
YSYKFNSSGC PERLASCRRL TDFAQGWGPI SHANGSGPDE RPYCWHYPPR PCGIVPAKSV  600
CGPVYCFTPS PVVVGTTDKS GAPTYNWGEN DWDVFVLNNT RPPLGNWFGC TWMNSTGFTK  660
VCGAPPCVIG GAGNNTLRCP TDCFRKHP                                    688

SEQ ID NO: 132          moltype = AA  length = 866
FEATURE                 Location/Qualifiers
source                  1..866
                        mol_type = protein
                        organism = hepatitis C virus
SEQUENCE: 132
MDAMKRGLCC VLLLCGAVFV SPSYQVRNST GLYHVTNDCP NSSIVYEAAD AILHTPGCVP  60
CVREGNTSRC WVAMTPTVAT RDGKLPTTQL RRHIDLLVGS ATLCSALYVG DLCGSIFLVG  120
QMFTFSPRRH WTTQDCNCSL YPGHITGHRM AWDMMMNWSP TAALITAQLL RIPQAILDMI  180
AGAHWGVLAG IAYFSMVGNW AKVLVVLLLF AGVDAQTDKT HTCPPCPAPE AEGAPSVFLF  240
PPKPKDTLMI SRTPEVTCVV VDVSHEDPEV KFNWYVDGVE VHNAKTKPRE EQYNSTYRVV  300
SVLTVLHQDW LNGKEYKCKV SNKALPAPIE KTISKAKGQP REPQVYTLPP SREEMTKNQV  360
SLTCLVKGFY PSDIAVEWES NGQPENNYKT TPPVLDSDGS FFLYSKLTVD KSRWQQGNVF  420
SCSVMHEALH NHYTQKSLSL SPGKLEVLFQ GPAIPLEVIK GGRHLIFCHS KKKCDELAAK  480
LVALGINAVA YYRGLDVSVI PTSQTHVTGG RAAHITAGLT SLFSPGPSQK LQLVNTNGSW  540
HINSTALNCN DSLKTGWIAG LLYSYKFNSS GCPERLASCR RLTDFAQGWG PISHANGSGP  600
DERPYCWHYP PRPCGIVPAK SVCGPVYCFT PSPVVVGTTD KSGAPTYNWG ENDWDVFVLN  660
NTRPPLGNWF GCTWMNSTGF TKVCGAPPCV IGGAGNNTLR CPTDCFRKHP DATYSRCGSG  720
PWITPRCLVD YPYRLWHYPC TVNYSIFKIR MYLGGVEHRL EAACNWTRGE RCDLEDRDRS  780
ELSPLLLSTT QWQVLPCSFT TLPALSTGLI HLHQNIVDVQ YLYGVGSSVA SWAIKWDYVV  840
LLFLLLADAR ICSCLWMMLL ISQAEA                                      866

SEQ ID NO: 133          moltype = AA  length = 915
FEATURE                 Location/Qualifiers
source                  1..915
                        mol_type = protein
                        organism = hepatitis C virus
SEQUENCE: 133
MDAMKRGLCC VLLLCGAVFV SPSYQVRNST GLYHVTNDCP NSSIVYEAAD AILHTPGCVP  60
CVREGNTSRC WVAMTPTVAT RDGKLPTTQL RRHIDLLVGS ATLCSALYVG DLCGSIFLVG  120
QMFTFSPRRH WTTQDCNCSL YPGHITGHRM AWDMMMNWSP TAALITAQLL RIPQAILDMI  180
AGAHWGVLAG IAYFSMVGNW AKVLVVLLLF AGVDAQTDKT HTCPPCPAPE AEGAPSVFLF  240
PPKPKDTLMI SRTPEVTCVV VDVSHEDPEV KFNWYVDGVE VHNAKTKPRE EQYNSTYRVV  300
SVLTVLHQDW LNGKEYKCKV SNKALPAPIE KTISKAKGQP REPQVYTLPP SREEMTKNQV  360
SLTCLVKGFY PSDIAVEWES NGQPENNYKT TPPVLDSDGS FFLYSKLTVD KSRWQQGNVF  420
SCSVMHEALH NHYTQKSLSL SPGKLEVLFQ GPVALSTTGE IPFYGKAIPL EVIKGGRHLI  480
FCHSKKKCDE LAAKLVALGI NAVAYYRGLD VSVIPTSGDV VVVATDALMT GFTGDFDSVI  540
DCNTCVTQTV DFQTHVTGGR AAHITAGLTS LFSPGPSQKL QLVNTNGSWH INSTALNCND  600
SLKTGWIAGL LYSYKFNSSG CPERLASCRR LTDFAQGWGP ISHANGSGPD ERPYCWHYPP  660
RPCGIVPAKS VCGPVYCFTP SPVVVGTTDK SGAPTYNWGE NDWDVFVLNN TRPPLGNWFG  720
CTWMNSTGFT KVCGAPPCVI GGAGNNTLRC PTDCFRKHPD ATYSRCGSGP WITPRCLVDY  780
PYRLWHYPCT VNYSIFKIRM YLGGVEHRLE AACNWTRGER CDLEDRDRSE LSPLLLSTTQ  840
WQVLPCSFTT LPALSTGLIH LHQNIVDVQY LYGVGSSVAS WAIKWDYVVL LFLLLADARI  900
CSCLWMMLLI SQAEA                                                  915

SEQ ID NO: 134          moltype = AA  length = 659
FEATURE                 Location/Qualifiers
source                  1..659
                        mol_type = protein
                        organism = hepatitis C virus
SEQUENCE: 134
MDAMKRGLCC VLLLCGAVFV SPSYQVRNSS GLYHVTNDCP NSSIVYEAAD AILHTPGCVP  60
CVREGNASRC WVAVTPTVAT RDGKLPTTQL RRHIDLLVGS ATLCSALYVG DLCGSVFLVG  120
QLFTFSPRRH WTTQDCNCSI YPGHITGHRM AWDMMMNWSP TAALVVAQLL RIPQAIMDMI  180
AGAHWGVLAG IAYFSMVGNW AKVLVVLLLF AGVDAETDKT HTCPPCPAPE AEGAPSVFLF  240
PPKPKDTLMI SRTPEVTCVV VDVSHEDPEV KFNWYVDGVE VHNAKTKPRE EQYNSTYRVV  300
SVLTVLHQDW LNGKEYKCKV SNKALPAPIE KTISKAKGQP REPQVYTLPP SREEMTKNQV  360
SLTCLVKGFY PSDIAVEWES NGQPENNYKT TPPVLDSDGS FFLYSKLTVD KSRWQQGNVF  420
SCSVMHEALH NHYTQKSLSL SPGKLEVLFQ GPETHVTGGS AGRTTAGLVG LLTPGAKQNI  480
QLINTNGSWH INSTALNCNE SLNTGWLAGL FYQHKFNSSG CPERLASCRR LTDFAQGWGP  540
ISYANGSGLD ERPYCWHYPP RPCGIVPAKS VCGPVYCFTP SPVVVGTTDR SGAPTYSWGA  600
NDTDVFVLNN TRPPLGNWFG CTWMNSTGFT KVCGAPPCVI GGVGNNTLLC PTDCFRKHP   659

SEQ ID NO: 135          moltype = AA  length = 688
FEATURE                 Location/Qualifiers
source                  1..688
                        mol_type = protein
                        organism = hepatitis C virus
SEQUENCE: 135
MDAMKRGLCC VLLLCGAVFV SPSYQVRNSS GLYHVTNDCP NSSIVYEAAD AILHTPGCVP  60
CVREGNASRC WVAVTPTVAT RDGKLPTTQL RRHIDLLVGS ATLCSALYVG DLCGSVFLVG  120
QLFTFSPRRH WTTQDCNCSI YPGHITGHRM AWDMMMNWSP TAALVVAQLL RIPQAIMDMI  180
```

-continued

```
AGAHWGVLAG IAYFSMVGNW AKVLVVLLLF AGVDAETDKT HTCPPCPAPE AEGAPSVFLF  240
PPKPKDTLMI SRTPEVTCVV VDVSHEDPEV KFNWYVDGVE VHNAKTKPRE EQYNSTYRVV  300
SVLTVLHQDW LNGKEYKCKV SNKALPAPIE KTISKAKGQP REPQVYTLPP SREEMTKNQV  360
SLTCLVKGFY PSDIAVEWES NGQPENNYKT TPPVLDSDGS FFLYSKLTVD KSRWQQGNVF  420
SCSVMHEALH NHYTQKSLSL SPGKLEVLFQ GPAIPLEVIK GGRHLIFCHS KKKCDELAAK  480
LETHVTGGSA GRTTAGLVGL LTPGAKQNIQ LINTNGSWHI NSTALNCNES LNTGWLAGLF  540
YQHKFNSSGC PERLASCRRL TDFAQGWGPI SYANGSGLDE RPYCWHYPPR PCGIVPAKSV  600
CGPVYCFTPS PVVVGTTDRS GAPTYSWGAN DTDVFVLNNT RPPLGNWFGC TWMNSTGFTK  660
VCGAPPCVIG GVGNNTLLCP TDCFRKHP                                     688

SEQ ID NO: 136          moltype = AA  length = 866
FEATURE                 Location/Qualifiers
source                  1..866
                        mol_type = protein
                        organism = hepatitis C virus
SEQUENCE: 136
MDAMKRGLCC VLLLCGAVFV SPSYQVRNSS GLYHVTNDCP NSSIVYEAAD AILHTPGCVP  60
CVREGNASRC WVAVTPTVAT RDGKLPTTQL RRHIDLLVGS ATLCSALYVG DLCGSVFLVG  120
QLFTFSPRRH WTTQDCNCSI YPGHITGHRM AWDMMMNWSP TAALVVAQLL RIPQAIMDMI  180
AGAHWGVLAG IAYFSMVGNW AKVLVVLLLF AGVDAETDKT HTCPPCPAPE AEGAPSVFLF  240
PPKPKDTLMI SRTPEVTCVV VDVSHEDPEV KFNWYVDGVE VHNAKTKPRE EQYNSTYRVV  300
SVLTVLHQDW LNGKEYKCKV SNKALPAPIE KTISKAKGQP REPQVYTLPP SREEMTKNQV  360
SLTCLVKGFY PSDIAVEWES NGQPENNYKT TPPVLDSDGS FFLYSKLTVD KSRWQQGNVF  420
SCSVMHEALH NHYTQKSLSL SPGKLEVLFQ GPAIPLEVIK GGRHLIFCHS KKKCDELAAK  480
LVALGINAVA YYRGLDVSVI PTSETHVTGG SAGRTTAGLV GLLTPGAKQN IQLINTNGSW  540
HINSTALNCN ESLNTGWLAG LFYQHKFNSS GCPERLASCR RLTDFAQGWG PISYANGSGL  600
DERPYCWHYP PRPCGIVPAK SVCGPVYCFT PSPVVVGTTD RSGAPTYSWG ANDTDVFVLN  660
NTRPPLGNWF GCTWMNSTGF TKVCGAPPCV IGGVGNNTLL CPTDCFRKHP EATYSRCGSG  720
PWITPRCMVD YPYRLWHYPC TINYTIFKVR MYVGGVEHRL EAACNWTRGE RCDLEDRDRS  780
ELSPLLLSTT QWQVLPCSFT TLPALSTGLI HLHQNIVDVQ YLYGVGSSIA SWAIKWEYVV  840
LLFLLLADAR VCSCLWMMLL ISQAEA                                       866

SEQ ID NO: 137          moltype = AA  length = 915
FEATURE                 Location/Qualifiers
source                  1..915
                        mol_type = protein
                        organism = hepatitis C virus
SEQUENCE: 137
MDAMKRGLCC VLLLCGAVFV SPSYQVRNSS GLYHVTNDCP NSSIVYEAAD AILHTPGCVP  60
CVREGNASRC WVAVTPTVAT RDGKLPTTQL RRHIDLLVGS ATLCSALYVG DLCGSVFLVG  120
QLFTFSPRRH WTTQDCNCSI YPGHITGHRM AWDMMMNWSP TAALVVAQLL RIPQAIMDMI  180
AGAHWGVLAG IAYFSMVGNW AKVLVVLLLF AGVDAETDKT HTCPPCPAPE AEGAPSVFLF  240
PPKPKDTLMI SRTPEVTCVV VDVSHEDPEV KFNWYVDGVE VHNAKTKPRE EQYNSTYRVV  300
SVLTVLHQDW LNGKEYKCKV SNKALPAPIE KTISKAKGQP REPQVYTLPP SREEMTKNQV  360
SLTCLVKGFY PSDIAVEWES NGQPENNYKT TPPVLDSDGS FFLYSKLTVD KSRWQQGNVF  420
SCSVMHEALH NHYTQKSLSL SPGKLEVLFQ GPVALSTTGE IPFYGKAIPL EVIKGGRHLI  480
FCHSKKKCDE LAAKLVALGI NAVAYYRGLD VSVIPTSGDV VVVATDALMT GFTGDFDSVI  540
DCNTCVTQTV DFETHVTGGS AGRTTAGLVG LLTPGAKQNI QLINTNGSWH INSTALNCNE  600
SLNTGWLAGL FYQHKFNSSG CPERLASCRR LTDFAQGWGP ISYANGSGLD ERPYCWHYPP  660
RPCGIVPAKS VCGPVYCFTP SPVVVGTTDR SGAPTYSWGA NDTDVFVLNN TRPPLGNWFG  720
CTWMNSTGFT KVCGAPPCVI GGVGNNTLLC PTDCFRKHPE ATYSRCGSGP WITPRCMVDY  780
PYRLWHYPCT INYTIFKVRM YVGGVEHRLE AACNWTRGER CDLEDRDRSE LSPLLLSTTQ  840
WQVLPCSFTT LPALSTGLIH LHQNIVDVQY LYGVGSSIAS WAIKWEYVVL LFLLLADARV  900
CSCLWMMLLI SQAEA                                                   915

SEQ ID NO: 138          moltype = AA  length = 653
FEATURE                 Location/Qualifiers
source                  1..653
                        mol_type = protein
                        organism = hepatitis C virus
SEQUENCE: 138
MDAMKRGLCC VLLLCGAVFV SPSLEWRNTS GLYVLTNDCS NSSIVYEADD VILHTPGCVP  60
CVQDDNTSTC WTPVTPTVAV RYVGATTASI RSHVDLLVGA ATLCSALYVG DMCGAVFLVG  120
QAFTFRPRRH QTVQTCNCSL YPGHVSGHRM AWDMMMNWSP AVGMVVAHIL RLPQTLFDIL  180
AGAHWGILAG LAYYSMQGNW AKVAIVMIMF SGVDAETDKT HTCPPCPAPE AEGAPSVFLF  240
PPKPKDTLMI SRTPEVTCVV VDVSHEDPEV KFNWYVDGVE VHNAKTKPRE EQYNSTYRVV  300
SVLTVLHQDW LNGKEYKCKV SNKALPAPIE KTISKAKGQP REPQVYTLPP SREEMTKNQV  360
SLTCLVKGFY PSDIAVEWES NGQPENNYKT TPPVLDSDGS FFLYSKLTVD KSRWQQGNVF  420
SCSVMHEALH NHYTQKSLSL SPGKLEVLFQ GPETYVTGGS VAHSARGLTS LFSMGAKQKL  480
QLVNTNGSWH INSTALNCNE SINTGFIAGL FYYHKFNSTG CPQRLSSCKP IISFRQGWGP  540
LTDANITGPS DDRPYCWHYA PRPCSVVPAS SVCGPVYCFT PSPVVVGTTD IKGKPTYNWG  600
ENETDVFLLE SLRPPSGRWF GCAWMNSTGF LKTCGAPPCN IYGGEGDPEN ETD         653

SEQ ID NO: 139          moltype = AA  length = 682
FEATURE                 Location/Qualifiers
source                  1..682
                        mol_type = protein
                        organism = hepatitis C virus
SEQUENCE: 139
```

-continued

```
MDAMKRGLCC VLLLCGAVFV SPSLEWRNTS GLYVLTNDCS NSSIVYEADD VILHTPGCVP  60
CVQDDNTSTC WTPVTPTVAV RYVGATTASI RSHVDLLVGA ATLCSALYVG DMCGAVFLVG  120
QAFTFRPRRH QTVQTCNCSL YPGHVSGHRM AWDMMMNWSP AVGMVVAHIL RLPQTLFDIL  180
AGAHWGILAG LAYYSMQGNW AKVAIVMIMF SGVDAETDKT HTCPPCPAPE AEGAPSVFLF  240
PPKPKDTLMI SRTPEVTCVV VDVSHEDPEV KFNWYVDGVE VHNAKTKPRE EQYNSTYRVV  300
SVLTVLHQDW LNGKEYKCKV SNKALPAPIE KTISKAKGQP REPQVYTLPP SREEMTKNQV  360
SLTCLVKGFY PSDIAVEWES NGQPENNYKT TPPVLDSDGS FFLYSKLTVD KSRWQQGNVF  420
SCSVMHEALH NHYTQKSLSL SPGKLEVLFQ GPAIPLEVIK GGRHLIFCHS KKKCDELAAK  480
LETYVTGGSV AHSARGLTSL FSMGAKQKLQ LVNTNGSWHI NSTALNCNES INTGFIAGLF  540
YYHKFNSTGC PQRLSSCKPI ISFRQGWGPL TDANITGPSD DRPYCWHYAP RPCSVVPASS  600
VCGPVYCFTP SPVVVGTTDI KGKPTYNWGE NETDVFLLES LRPPSGRWFG CAWMNSTGFL  660
KTCGAPPCNI YGGEGDPENE TD                                          682

SEQ ID NO: 140         moltype = AA  length = 872
FEATURE                Location/Qualifiers
source                 1..872
                       mol_type = protein
                       organism = hepatitis C virus
SEQUENCE: 140
MDAMKRGLCC VLLLCGAVFV SPSLEWRNTS GLYVLTNDCS NSSIVYEADD VILHTPGCVP  60
CVQDDNTSTC WTPVTPTVAV RYVGATTASI RSHVDLLVGA ATLCSALYVG DMCGAVFLVG  120
QAFTFRPRRH QTVQTCNCSL YPGHVSGHRM AWDMMMNWSP AVGMVVAHIL RLPQTLFDIL  180
AGAHWGILAG LAYYSMQGNW AKVAIVMIMF SGVDAETDKT HTCPPCPAPE AEGAPSVFLF  240
PPKPKDTLMI SRTPEVTCVV VDVSHEDPEV KFNWYVDGVE VHNAKTKPRE EQYNSTYRVV  300
SVLTVLHQDW LNGKEYKCKV SNKALPAPIE KTISKAKGQP REPQVYTLPP SREEMTKNQV  360
SLTCLVKGFY PSDIAVEWES NGQPENNYKT TPPVLDSDGS FFLYSKLTVD KSRWQQGNVF  420
SCSVMHEALH NHYTQKSLSL SPGKLEVLFQ GPAIPLEVIK GGRHLIFCHS KKKCDELAAK  480
LVALGINAVA YYRGLDVSVI PTSETYVTGG SVAHSARGLT SLFSMGAKQK LQLVNTNGSW  540
HINSTALNCN ESINTGFIAG LFYYHKFNST GCPQRLSSCK PIISFRQGWG PLTDANITGP  600
SDDRPYCWHY APRPCSVVPA SSVCGPVYCF TPSPVVVGTT DIKGKPTYNW GENETDVFLL  660
ESLRPPSGRW FGCAWMNSTG FLKTCGAPPC NIYGGEGDPE NETDLFCPTD CFRKHPEATY  720
SRCGAGPWLT PRCMVDYPYR LWHYPCTVNF TLFKVRMFVG GFEHRFTAAC NWTRGERCNI  780
EDRDRSEQHP LLHSTTELAI LPCSFTPMPA LSTGLIHLHQ NIVDVQYLYG VGSDMVGWAL  840
KWEFVILVFL LLADARVCVA LWLMLMVSQA EA                                872

SEQ ID NO: 141         moltype = AA  length = 921
FEATURE                Location/Qualifiers
source                 1..921
                       mol_type = protein
                       organism = hepatitis C virus
SEQUENCE: 141
MDAMKRGLCC VLLLCGAVFV SPSLEWRNTS GLYVLTNDCS NSSIVYEADD VILHTPGCVP  60
CVQDDNTSTC WTPVTPTVAV RYVGATTASI RSHVDLLVGA ATLCSALYVG DMCGAVFLVG  120
QAFTFRPRRH QTVQTCNCSL YPGHVSGHRM AWDMMMNWSP AVGMVVAHIL RLPQTLFDIL  180
AGAHWGILAG LAYYSMQGNW AKVAIVMIMF SGVDAETDKT HTCPPCPAPE AEGAPSVFLF  240
PPKPKDTLMI SRTPEVTCVV VDVSHEDPEV KFNWYVDGVE VHNAKTKPRE EQYNSTYRVV  300
SVLTVLHQDW LNGKEYKCKV SNKALPAPIE KTISKAKGQP REPQVYTLPP SREEMTKNQV  360
SLTCLVKGFY PSDIAVEWES NGQPENNYKT TPPVLDSDGS FFLYSKLTVD KSRWQQGNVF  420
SCSVMHEALH NHYTQKSLSL SPGKLEVLFQ GPVALSTTGE IPFYGKAIPL EVIKGGRHLI  480
FCHSKKKCDE LAAKLVALGI NAVAYYRGLD VSVIPTSGDV VVVATDALMT GFTGDFDSVI  540
DCNTCVTQTV DFETYVTGGS VAHSARGLTS LFSMGAKQKL QLVNTNGSWH INSTALNCNE  600
SINTGFIAGL FYYHKFNSTG CPQRLSSCKP IISFRQGWGP LTDANITGPS DDRPYCWHYA  660
PRPCSVVPAS SVCGPVYCFT PSPVVVGTTD IKGKPTYNWG ENETDVFLLE SLRPPSGRWF  720
GCAWMNSTGF LKTCGAPPCN IYGGEGDPEN ETDLFCPTDC FRKHPEATYS RCGAGPWLTP  780
RCMVDYPYRL WHYPCTVNFT LFKVRMFVGG FEHRFTAACN WTRGERCNIE DRDRSEQHPL  840
LHSTTELAIL PCSFTPMPAL STGLIHLHQN IVDVQYLYGV GSDMVGWALK WEFVILVFLL  900
LADARVCVAL WLMLMVSQAE A                                           921

SEQ ID NO: 142         moltype = AA  length = 653
FEATURE                Location/Qualifiers
source                 1..653
                       mol_type = protein
                       organism = hepatitis C virus
SEQUENCE: 142
MDAMKRGLCC VLLLCGAVFV SPSLEWRNTS GLYILTNDCP NSSIVYEADD VILHTPGCIP  60
CVQDGNTSTC WTSVSPTVAV RYVGATTASI RSHVDLLVGA ATLCSALYVG DMCGAVFLVG  120
QAFTFRPRRH QTVQTCNCSL YPGHLTGHRM AWDMMMNWSP AVGMVVAHVL RMPQTVFDII  180
AGAHWGILAG LAYYSMQGNW AKVAIIMVMF SGVDAETDKT HTCPPCPAPE AEGAPSVFLF  240
PPKPKDTLMI SRTPEVTCVV VDVSHEDPEV KFNWYVDGVE VHNAKTKPRE EQYNSTYRVV  300
SVLTVLHQDW LNGKEYKCKV SNKALPAPIE KTISKAKGQP REPQVYTLPP SREEMTKNQV  360
SLTCLVKGFY PSDIAVEWES NGQPENNYKT TPPVLDSDGS FFLYSKLTVD KSRWQQGNVF  420
SCSVMHEALH NHYTQKSLSL SPGKLEVLFQ GPETHTTGGT AARNAFTLTG LFTQGARQKL  480
ELINTNGSWH INRTALNCNE SLNTGFIAGL FYLHKFNSTG CPERLSSCKP ITFFRQGWGS  540
LTDANITGPS DDKPYCWHYA PRPCEVVPAL NVCGPVYCFT PSPVVVGTTD RQGVPTYTWG  600
ENETDVFLLR SLRPPSGQWF GCTWMNSTGF VKTCGAPPCD IYGGGGNRCN ESD         653

SEQ ID NO: 143         moltype = AA  length = 682
FEATURE                Location/Qualifiers
source                 1..682
```

```
                        mol_type = protein
                        organism = hepatitis C virus
SEQUENCE: 143
MDAMKRGLCC VLLLCGAVFV SPSLEWRNTS GLYILTNDCP NSSIVYEADD VILHTPGCIP  60
CVQDGNTSTC WTSVSPTVAV RYVGATTASI RSHVDLLVGA ATLCSALYVG DMCGAVFLVG  120
QAFTFRPRRH QTVQTCNCSL YPGHLTGHRM AWDMMMNWSP AVGMVVAHVL RMPQTVFDII  180
AGAHWGILAG LAYYSMQGNW AKVAIIMVMF SGVDAETDKT HTCPPCPAPE AEGAPSVFLF  240
PPKPKDTLMI SRTPEVTCVV VDVSHEDPEV KFNWYVDGVE VHNAKTKPRE EQYNSTYRVV  300
SVLTVLHQDW LNGKEYKCKV SNKALPAPIE KTISKAKGQP REPQVYTLPP SREEMTKNQV  360
SLTCLVKGFY PSDIAVEWES NGQPENNYKT TPPVLDSDGS FFLYSKLTVD KSRWQQGNVF  420
SCSVMHEALH NHYTQKSLSL SPGKLEVLFQ GPAIPLEVIK GGRHLIFCHS KKKCDELAAK  480
LETHTTGGTA ARNAFTLTGL FTQGARQKLE LINTNGSWHI NRTALNCNES LNTGFIAGLF  540
YLHKFNSTGC PERLSSCKPI TFFRQGWGSL TDANITGPSD DKPYCWHYAP RPCEVVPALN  600
VCGPVYCFTP SPVVVGTTDR QGVPTYTWGE NETDVFLLRS LRPPSGQWFG CTWMNSTGFV  660
KTCGAPPCDI YGGGGNRCNE SD                                          682

SEQ ID NO: 144          moltype = AA  length = 873
FEATURE                 Location/Qualifiers
source                  1..873
                        mol_type = protein
                        organism = hepatitis C virus
SEQUENCE: 144
MDAMKRGLCC VLLLCGAVFV SPSLEWRNTS GLYILTNDCP NSSIVYEADD VILHTPGCIP  60
CVQDGNTSTC WTSVSPTVAV RYVGATTASI RSHVDLLVGA ATLCSALYVG DMCGAVFLVG  120
QAFTFRPRRH QTVQTCNCSL YPGHLTGHRM AWDMMMNWSP AVGMVVAHVL RMPQTVFDII  180
AGAHWGILAG LAYYSMQGNW AKVAIIMVMF SGVDAETDKT HTCPPCPAPE AEGAPSVFLF  240
PPKPKDTLMI SRTPEVTCVV VDVSHEDPEV KFNWYVDGVE VHNAKTKPRE EQYNSTYRVV  300
SVLTVLHQDW LNGKEYKCKV SNKALPAPIE KTISKAKGQP REPQVYTLPP SREEMTKNQV  360
SLTCLVKGFY PSDIAVEWES NGQPENNYKT TPPVLDSDGS FFLYSKLTVD KSRWQQGNVF  420
SCSVMHEALH NHYTQKSLSL SPGKLEVLFQ GPAIPLEVIK GGRHLIFCHS KKKCDELAAK  480
LVALGINAVA YYRGLDVSVI PTSGETHTTG GTAARNAFTL TGLFTQGARQ KLELINTNGS  540
WHINRTALNC NESLNTGFIA GLFYLHKFNS TGCPERLSSC KPITFFRQGW GSLTDANITG  600
PSDDKPYCWH YAPRPCEVVP ALNVCGPVYC FTPSPVVVGT TDRQGVPTYT WGENETDVFL  660
LRSLRPPSGQ WFGCTWMNST GFVKTCGAPP CDIYGGGGNR CNESDLFCPT DCFRKHPEAT  720
YSRCGAGPWL TPRCLVDYPY RLWHYPCTVN FTLFKVRMFV GGFEHRFTAA CNWTRGERCN  780
IEDRDRSEQH PLLHSTTELA ILPCSFTPMP ALSTGLIHLH QNIVDVQYLY GVGSGVVGWA  840
LRWEFVVLVF LLLADARVCV ALWLMLMISQ AEA                               873

SEQ ID NO: 145          moltype = AA  length = 921
FEATURE                 Location/Qualifiers
source                  1..921
                        mol_type = protein
                        organism = hepatitis C virus
SEQUENCE: 145
MDAMKRGLCC VLLLCGAVFV SPSLEWRNTS GLYILTNDCP NSSIVYEADD VILHTPGCIP  60
CVQDGNTSTC WTSVSPTVAV RYVGATTASI RSHVDLLVGA ATLCSALYVG DMCGAVFLVG  120
QAFTFRPRRH QTVQTCNCSL YPGHLTGHRM AWDMMMNWSP AVGMVVAHVL RMPQTVFDII  180
AGAHWGILAG LAYYSMQGNW AKVAIIMVMF SGVDAETDKT HTCPPCPAPE AEGAPSVFLF  240
PPKPKDTLMI SRTPEVTCVV VDVSHEDPEV KFNWYVDGVE VHNAKTKPRE EQYNSTYRVV  300
SVLTVLHQDW LNGKEYKCKV SNKALPAPIE KTISKAKGQP REPQVYTLPP SREEMTKNQV  360
SLTCLVKGFY PSDIAVEWES NGQPENNYKT TPPVLDSDGS FFLYSKLTVD KSRWQQGNVF  420
SCSVMHEALH NHYTQKSLSL SPGKLEVLFQ GPVALSTTGE IPFYGKAIPL EVIKGGRHLI  480
FCHSKKKCDE LAAKLVALGI NAVAYYRGLD VSVIPTSGDV VVVATDALMT GFTGDFDSVI  540
DCNTCVTQTV DFETHTTGGT AARNAFTLTG LFTQGARQKL ELINTNGSWH INRTALNCNE  600
SLNTGFIAGL FYLHKFNSTG CPERLSSCKP ITFFRQGWGS LTDANITGPS DDKPYCWHYA  660
PRPCEVVPAL NVCGPVYCFT PSPVVVGTTD RQGVPTYTWG ENETDVFLLR SLRPPSGQWF  720
GCTWMNSTGF VKTCGAPPCD IYGGGGNRCN ESDLFCPTDC FRKHPEATYS RCGAGPWLTP  780
RCLVDYPYRL WHYPCTVNFT LFKVRMFVGG FEHRFTAACN WTRGERCNIE DRDRSEQHPL  840
LHSTTELAIL PCSFTPMPAL STGLIHLHQN IVDVQYLYGV GSGVVGWALR WEFVVLVFLL  900
LADARVCVAL WLMLMISQAE A                                            921

SEQ ID NO: 146          moltype = AA  length = 227
FEATURE                 Location/Qualifiers
source                  1..227
                        mol_type = protein
                        organism = Homo sapiens
SEQUENCE: 146
DKTHTCPPCP APELLGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALPA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVMHE ALHNHYTQKS LSLSPGK                227

SEQ ID NO: 147          moltype = AA  length = 325
FEATURE                 Location/Qualifiers
source                  1..325
                        mol_type = protein
                        organism = Homo sapiens
SEQUENCE: 147
STKGPSVFPL APCSRSTSES TAALGCLVKD YFPEPVTVSW NSGALTSGVH TFPAVLQSSG  60
```

-continued

```
LYSLSSVVTV PSSNFGTQTY TCNVDHKPSN TKVDKTVERK CCVECPPCPA PPVAGPSVFL  120
FPPKPKDTLM ISRTPEVTCV VVDVSHEDPE VQFNWYVDGV EVHNAKTKPR EEQFNSTFRV  180
VSVLTVVHQD WLNGKEYKCK VSNKGLPAPI EKTISKTKGQ PREPQVYTLP PSREEMTKNQ  240
VSLTCLVKGF YPSDIAVEWE SNGQPENNYK TTPPMLDSDG SFFLYSKLTV DKSRWQQGNV  300
FSCSVMHEAL HNHYTQKSLS LSPGK                                       325

SEQ ID NO: 148         moltype = AA  length = 246
FEATURE                Location/Qualifiers
source                 1..246
                       mol_type = protein
                       organism = Homo sapiens
SEQUENCE: 148
HKPSNTKVDK RVELKTPLGD TTHTCPPCPA PELLGGPSVF LFPPKPKDTL MISRTPEVTC  60
VVVDVSHEDP EVKFNWYVDG VEVHNAKTKP REEQYNSTYR VVSVLTVLHQ DWLNGKEYKC  120
KVSNKALPAP IEKTISKAKG QPREPQVYTL PPSRDELTKN QVSLTCLVKG FYPSDIAVEW  180
ESNGQPENNY KTTPPVLDSD GSFFLYSKLT VDKSRWQQGN VFSCSVMHEA LHNHYTQKSL  240
SLSPGK                                                            246

SEQ ID NO: 149         moltype = AA  length = 383
FEATURE                Location/Qualifiers
source                 1..383
                       mol_type = protein
                       organism = Homo sapiens
SEQUENCE: 149
PTKAPDVFPI ISGCRHPKDN SPVVLACLIT GYHPTSVTVT WYMGTQSQPQ RTFPEIQRRD  60
SYYMTSSQLS TPLQQWRQGE YKCVVQHTAS KSKKEIFRWP ESPKAQASSV PTAQPQAEGS  120
LAKATTAPAT TRNTGRGGEE KKKEKEKEEQ EERETKTPEC PSHTQPLGVY LLTPAVQDLW  180
LRDKATFTCF VVGSDLKDAH LTWEVAGKVP TGGVEEGLLE RHSNGSQSQH SRLTLPRSLW  240
NAGTSVTCTL NHPSLPPQRL MALREPAAQA PVKLSLNLLA SSDPPEAASW LLCEVSGFSP  300
PNILLMWLED QREVNTSGFA PARPPPQPRS TTFWAWSVLR VPAPPSPQPA TYTCVVSHED  360
SRTLLNASRS LEVSYVTDHG PMK                                         383

SEQ ID NO: 150         moltype = AA  length = 276
FEATURE                Location/Qualifiers
source                 1..276
                       mol_type = protein
                       organism = Homo sapiens
SEQUENCE: 150
VTSTLTIKZS DWLGESMFTC RVDHRGLTFQ QNASSMCVPD QDTAIRVFAI PPSFASIFLT  60
KSTKLTCLVT DLTTYBSVTI SWTREENGAV KTHTNISESH PNATFSAVGE ASICEDBDWS  120
GERFTCTVTH TDLPSPLKQT ISRPKGVALH RPBVYLLPPA RZZLNLRESA TITCLVTGFS  180
PADVFVEWMQ RGEPLSPQKY VTSAPMPEPQ APGRYFAHSI LTVSEEEWNT GGTYTCVVAH  240
EALPNRVTER TVDKSTGKPT LYNVSLVMSD TAGTCY                           276

SEQ ID NO: 151         moltype = AA  length = 353
FEATURE                Location/Qualifiers
source                 1..353
                       mol_type = protein
                       organism = Homo sapiens
SEQUENCE: 151
ASPTSPKVFP LSLCSTQPDG NVVIACLVQG FFPQEPLSVT WSESGQGVTA RNFPPSQDAS  60
GDLYTTSSQL TLPATQCLAG KSVTCHVKHY TNPSQDVTVP CPVPSTPPTP SPSTPPTPSP  120
SCCHPRLSLH RPALEDLLLG SEANLTCTLT GLRDASGVTF TWTPSSGKSA VQGPPERDLC  180
GCYSVSSVLP GCAEPWNHGK TFTCTAAYPE SKTPLTATLS KSGNTFRPEV HLLPPPSEEL  240
ALNELVTLTC LARGFSPKDV LVRWLQGSQE LPREKYLTWA SRQEPSQGTT TFAVTSILRV  300
AAEDWKKGDT FSCMVGHEAL PLAFTQKTID RLAGKPTHVN VSVVMAEVDG TCY        353

SEQ ID NO: 152         moltype = AA  length = 222
FEATURE                Location/Qualifiers
source                 1..222
                       mol_type = protein
                       organism = Homo sapiens
SEQUENCE: 152
ADPCDSNPRG VSAYLSRPSP FDLFIRKSPT ITCLVVDLAP SKGTVNLTWS RASGKPVNHS  60
TRKEEKQRNG TLTVTSTLPV GTRDWIEGET YQCRVTHPHL PRALMRSTTK TSGPRAAPEV  120
YAFATPEWPG SRDKRTLACL IQNFMPEDIS VQWLHNEVQL PDARHSTTQP RKTKGSGFFV  180
FSRLEVTRAE WEQKDEFICR AVHEAASPSQ TVQRAVSVNP GK                    222

SEQ ID NO: 153         moltype = AA  length = 327
FEATURE                Location/Qualifiers
source                 1..327
                       mol_type = protein
                       organism = Homo sapiens
SEQUENCE: 153
ASTKGPSVFP LAPCSRSTSE STAALGCLVK DYFPEPVTVS WNSGALTSGV HTFPAVLQSS  60
GLYSLSSVVT VPSSSLGTKT YTCNVDHKPS NTKVDKRVES KYGPPCPSCP APEFLGGPSV  120
FLFPPKPKDT LMISRTPEVT CVVVDVSQED PEVQFNWYVD GVEVHNAKTK PREEQFNSTY  180
RVVSVLTVLH QDWLNGKEYK CKVSNKGLPS SIEKTISKAK GQPREPQVYT LPPSQEEMTK  240
NQVSLTCLVK GFYPSDIAVE WESNGQPENN YKTTPPVLDS DGSFFLYSRL TVDKSRWQEG  300
```

-continued

```
NVFSCSVMHE ALHNHYTQKS LSLSLGK                                327

SEQ ID NO: 154          moltype = AA  length = 15
FEATURE                 Location/Qualifiers
REGION                  1..15
                        note = synthetic amino acid sequence
source                  1..15
                        mol_type = protein
                        organism = synthetic construct
SEQUENCE: 154
VLVLNPSVAA TLGFG                                             15

SEQ ID NO: 155          moltype = AA  length = 15
FEATURE                 Location/Qualifiers
REGION                  1..15
                        note = synthetic amino acid sequence
source                  1..15
                        mol_type = protein
                        organism = synthetic construct
SEQUENCE: 155
TYGKFLADGG CSGGA                                             15

SEQ ID NO: 156          moltype = AA  length = 15
FEATURE                 Location/Qualifiers
REGION                  1..15
                        note = synthetic amino acid sequence
source                  1..15
                        mol_type = protein
                        organism = synthetic construct
SEQUENCE: 156
GGRHLIFCHS KKKCD                                             15

SEQ ID NO: 157          moltype = AA  length = 11
FEATURE                 Location/Qualifiers
REGION                  1..11
                        note = synthetic amino acid sequence
source                  1..11
                        mol_type = protein
                        organism = synthetic construct
SEQUENCE: 157
VAYYRGLDVS V                                                 11

SEQ ID NO: 158          moltype = AA  length = 18
FEATURE                 Location/Qualifiers
REGION                  1..18
                        note = synthetic amino acid sequence
source                  1..18
                        mol_type = protein
                        organism = synthetic construct
SEQUENCE: 158
ATDALMTGFT GDFDSVID                                          18

SEQ ID NO: 159          moltype = AA  length = 15
FEATURE                 Location/Qualifiers
REGION                  1..15
                        note = synthetic amino acid sequence
source                  1..15
                        mol_type = protein
                        organism = synthetic construct
SEQUENCE: 159
TGLTHIDAHF LSQTK                                             15

SEQ ID NO: 160          moltype = AA  length = 13
FEATURE                 Location/Qualifiers
REGION                  1..13
                        note = synthetic amino acid sequence
source                  1..13
                        mol_type = protein
                        organism = synthetic construct
SEQUENCE: 160
QYLAGLSTLP GNP                                               13

SEQ ID NO: 161          moltype = AA  length = 8
FEATURE                 Location/Qualifiers
REGION                  1..8
                        note = synthetic amino acid sequence
source                  1..8
                        mol_type = protein
                        organism = synthetic construct
```

```
SEQUENCE: 161
NLLPAILS                                                          8

SEQ ID NO: 162          moltype = AA  length = 27
FEATURE                 Location/Qualifiers
REGION                  1..27
                        note = synthetic amino acid sequence
source                  1..27
                        mol_type = protein
                        organism = synthetic construct
SEQUENCE: 162
RHVGPGEGAV QWMNRLIAFA SRGNHVS                                     27

SEQ ID NO: 163          moltype = AA  length = 15
FEATURE                 Location/Qualifiers
REGION                  1..15
                        note = synthetic amino acid sequence
source                  1..15
                        mol_type = protein
                        organism = synthetic construct
SEQUENCE: 163
SSASQLSAPS LKATC                                                  15

SEQ ID NO: 164          moltype = AA  length = 5
FEATURE                 Location/Qualifiers
REGION                  1..5
                        note = synthetic amino acid sequence
source                  1..5
                        mol_type = protein
                        organism = synthetic construct
SEQUENCE: 164
SNVSV                                                             5

SEQ ID NO: 165          moltype = AA  length = 9
FEATURE                 Location/Qualifiers
REGION                  1..9
                        note = synthetic amino acid sequence
source                  1..9
                        mol_type = protein
                        organism = synthetic construct
SEQUENCE: 165
TYSTYGKFL                                                         9

SEQ ID NO: 166          moltype = AA  length = 9
FEATURE                 Location/Qualifiers
REGION                  1..9
                        note = synthetic amino acid sequence
source                  1..9
                        mol_type = protein
                        organism = synthetic construct
SEQUENCE: 166
LIFCHSKKK                                                         9

SEQ ID NO: 167          moltype = AA  length = 16
FEATURE                 Location/Qualifiers
REGION                  1..16
                        note = synthetic amino acid sequence
source                  1..16
                        mol_type = protein
                        organism = synthetic construct
SEQUENCE: 167
ATDALMTGFT GDFDSV                                                 16

SEQ ID NO: 168          moltype = AA  length = 10
FEATURE                 Location/Qualifiers
REGION                  1..10
                        note = synthetic amino acid sequence
source                  1..10
                        mol_type = protein
                        organism = synthetic construct
SEQUENCE: 168
VLAALAAYCL                                                        10

SEQ ID NO: 169          moltype = AA  length = 9
FEATURE                 Location/Qualifiers
REGION                  1..9
                        note = synthetic amino acid sequence
source                  1..9
                        mol_type = protein
```

```
                        organism = synthetic construct
SEQUENCE: 169
ILAGYGAGV                                                         9

SEQ ID NO: 170          moltype = AA  length = 8
FEATURE                 Location/Qualifiers
REGION                  1..8
                        note = synthetic amino acid sequence
source                  1..8
                        mol_type = protein
                        organism = synthetic construct
SEQUENCE: 170
IPFYGKAI                                                          8

SEQ ID NO: 171          moltype = AA  length = 9
FEATURE                 Location/Qualifiers
REGION                  1..9
                        note = synthetic amino acid sequence
source                  1..9
                        mol_type = protein
                        organism = synthetic construct
SEQUENCE: 171
RAQAPPPSW                                                         9

SEQ ID NO: 172          moltype = AA  length = 36
FEATURE                 Location/Qualifiers
REGION                  1..36
                        note = synthetic amino acid sequence
source                  1..36
                        mol_type = protein
                        organism = synthetic construct
SEQUENCE: 172
EGAVQWMNRL IAFASRGNHV SPTHYVPESD AAARVT                           36

SEQ ID NO: 173          moltype = AA  length = 9
FEATURE                 Location/Qualifiers
REGION                  1..9
                        note = synthetic amino acid sequence
source                  1..9
                        mol_type = protein
                        organism = synthetic construct
SEQUENCE: 173
RPDYNPPLL                                                         9

SEQ ID NO: 174          moltype = AA  length = 9
FEATURE                 Location/Qualifiers
REGION                  1..9
                        note = synthetic amino acid sequence
source                  1..9
                        mol_type = protein
                        organism = synthetic construct
SEQUENCE: 174
TIMAKNEVF                                                         9

SEQ ID NO: 175          moltype = AA  length = 29
FEATURE                 Location/Qualifiers
REGION                  1..29
                        note = synthetic amino acid sequence
source                  1..29
                        mol_type = protein
                        organism = synthetic construct
SEQUENCE: 175
AIPLEVIKGG RHLIFCHSKK KCDELAAKL                                   29

SEQ ID NO: 176          moltype = AA  length = 50
FEATURE                 Location/Qualifiers
REGION                  1..50
                        note = synthetic amino acid sequence
source                  1..50
                        mol_type = protein
                        organism = synthetic construct
SEQUENCE: 176
LGALTGTYVY NHLTPLRDWA HNGLRDLAVA VEPVVFSQME TKLITWGADT            50

SEQ ID NO: 177          moltype = AA  length = 52
FEATURE                 Location/Qualifiers
REGION                  1..52
                        note = synthetic amino acid sequence
source                  1..52
```

```
                        mol_type = protein
                        organism = synthetic construct
SEQUENCE: 177
AIPLEVIKGG RHLIFCHSKK KCDELAAKLV ALGINAVAYY RGLDVSVIPT SG          52

SEQ ID NO: 178          moltype = AA  length = 70
FEATURE                 Location/Qualifiers
REGION                  1..70
                        note = synthetic amino acid sequence
source                  1..70
                        mol_type = protein
                        organism = synthetic construct
SEQUENCE: 178
KGGRHLIFCH SKKKCDELAA KLVALGINAV AYYRGLDVSV IPTSGDVVVV ATDALMTGFT  60
GDFDSVIDCN                                                         70

SEQ ID NO: 179          moltype = AA  length = 100
FEATURE                 Location/Qualifiers
REGION                  1..100
                        note = synthetic amino acid sequence
source                  1..100
                        mol_type = protein
                        organism = synthetic construct
SEQUENCE: 179
VALSTTGEIP FYGKAIPLEV IKGGRHLIFC HSKKKCDELA AKLVALGINA VAYYRGLDVS  60
VIPTSGDVVV VATDALMTGF TGDFDSVIDC NTCVTQTVDF                        100

SEQ ID NO: 180          moltype = AA  length = 171
FEATURE                 Location/Qualifiers
REGION                  1..171
                        note = synthetic amino acid sequence
source                  1..171
                        mol_type = protein
                        organism = synthetic construct
SEQUENCE: 180
MSTNPKPQRK TKRNTNRRPQ DVKFPGGGQI VGGVYLLPRR GPRLGVRATR KTSERSQPRG  60
RRQPIPKARR PEGRTWAQPG YPWPLYGNEG CGWAGWLLSP RGSRPSWGPT DPRRRSRNLG  120
KVIDTLTCGF ADLMGYIPLV GAPLGGAARA LAHGVRVLED GVNYATGNLP G          171

SEQ ID NO: 181          moltype = AA  length = 228
FEATURE                 Location/Qualifiers
REGION                  1..228
                        note = synthetic amino acid sequence
source                  1..228
                        mol_type = protein
                        organism = synthetic construct
SEQUENCE: 181
LHAPTGSGKS TKVPAAYAAQ GYKVLVLNPS VAATLGFGAY MSKAHGIDPN IRTGVRTITT  60
GSPITYSTYG KFLADGGCSG GAYDIIICDE CHSTDATSIL GIGTVLDQAE TAGARLVVLA  120
TATPPGSVTV PHPNIEEVAL STTGEIPFYG KAIPLEVIKG GRHLIFCHSK KKCDELAAKL  180
VALGINAVAY YRGLDVSVIP TSGDVVVVAT DALMTGFTGD FDSVIDCN               228

SEQ ID NO: 182          moltype = AA  length = 553
FEATURE                 Location/Qualifiers
REGION                  1..553
                        note = synthetic amino acid sequence
source                  1..553
                        mol_type = protein
                        organism = synthetic construct
SEQUENCE: 182
QASLLKVPYF VRVQGLLRIC ALARKMAGGH YVQMAIIKLG ALTGTYVYNH LTPLRDWAHN  60
GLRDLAVAVE PVVFSQMETK LITWGADTAA CGDIINGLPV SARRGREILL GPADGMVSKG  120
WRLLAPITAY AQQTRGLLGC IITSLTGRDK NQVEGEVQIV STAAQTFLAT CINGVCWTVY  180
HGAGTRTIAS PKGPVIQMYT NVDQDLVGWP APQGARSLTP CTCGSSDLYL VTRHADVIPV  240
RRRGDSRGSL LSPRPISYLK GSAGGPLLCP AGHAVGIFRA AVCTRGVAKA VDFIPVENLE  300
TTMRSPVFTD NSSPPAVPQS FQVAHLHAPT GSGKSTKVPA AYAAQGYKVL VLNPSVAATL  360
GFGAYMSKAH GIDPNIRTGV RTITTGSPIT YSTYGKFLAD GGCSGGAYDI IICDECHSTD  420
ATSILGIGTV LDQAETAGAR LVVLATATPP GSVTVPHPNI EEVALSTTGE IPFYGKAIPL  480
EVIKGGRHLI FCHSKKKCDE LAAKLVALGI NAVAYYRGLD VSVIPTSGDV VVVATDALMT  540
GFTGDFDSVI DCN                                                     553

SEQ ID NO: 183          moltype = AA  length = 778
FEATURE                 Location/Qualifiers
REGION                  1..778
                        note = synthetic amino acid sequence
source                  1..778
                        mol_type = protein
                        organism = synthetic construct
SEQUENCE: 183
```

-continued

```
LHAPTGSGKS TKVPAAYAAQ GYKVLVLNPS VAATLGFGAY MSKAHGIDPN IRTGVRTITT  60
GSPITYSTYG KFLADGGCSG GAYDIIICDE CHSTDATSIL GIGTVLDQAE TAGARLVVLA  120
TATPPGSVTV PHPNIEEVAL STTGEIPFYG KAIPLEVIKG GRHLIFCHSK KKCDELAAKL  180
VALGINAVAY YRGLDVSVIP TSGDVVVVAT DALMTGFTGD FDSVIDCNTC VTQTVDFSLD  240
PTFTIETTTL PQDAVSRTQR RGRTGRGKPG IYRFVAPGER PSGMFDSSVL CECYDAGCAW  300
YELTPAETTV RLRAYMNTPG LPVCQDHLEF WEGVFTGLTH IDAHFLSQTK QSGENLPYLV  360
AYQATVCARA QAPPPSWDQM WKCLIRLKPT LHGPTPLLYR LGAVQNEVTL THPITKYIMT  420
CMSADLEVVT STWVLVGGVL AALAAYCLST GCVVIVGRIV LSGKPAIIPD REVLYREFDE  480
MEECSQHLPY IEQGMMLAEQ FKQKALGLLQ TASRQAEVIA PAVQTNWQKL EAFWAKHMWN  540
FISGIQYLAG LSTLPGNPAI ASLMAFTAAV TSPLTTSQTL LFNILGGWVA AQLAAPGAAT  600
AFVGAGLAGA AIGSVGLGKV LVDILAGYGA GVAGALVAFK IMSGEVPSTE DLVNLLPAIL  660
SPGALVVGVV CAAILRRHVG PGEGAVQWMN RLIAFASRGN HVSPTHYVPE SDAAARVTAI  720
LSSLTVTQLL RRLHQWISSE CTTPCSGSWL RDIWDWICEV LSDFKTWLKA KLMPQLPG    778

SEQ ID NO: 184          moltype = AA  length = 1985
FEATURE                 Location/Qualifiers
REGION                  1..1985
                        note = synthetic amino acid sequence
source                  1..1985
                        mol_type = protein
                        organism = synthetic construct
SEQUENCE: 184
APITAYAQQT RGLLGCIITS LTGRDKNQVE GEVQIVSTAA QTFLATCING VCWTVYHGAG  60
TRTIASPKGP VIQMYTNVDQ DLVGWPAPQG ARSLTPCTCG SSDLYLVTRH ADVIPVRRRG  120
DSRGSLLSPR PISYLKGSAG GPLLCPAGHA VGIFRAAVCT RGVAKAVDFI PVENLETTMR  180
SPVFTDNSSP PAVPQSFQVA HLHAPTGSGK STKVPAAYAA QGYKVLVLNP SVAATLGFGA  240
YMSKAHGIDP NIRTGVRTIT TGSPITYSTY GKFLADGGCS GGAYDIIICD ECHSTDATSI  300
LGIGTVLDQA ETAGARLVVL ATATPPGSVT VPHPNIEEVA LSTTGEIPFY GKAIPLEVIK  360
GGRHLIFCHS KKKCDELAAK LVALGINAVA YYRGLDVSVI PTSGDVVVVA TDALMTGFTG  420
DFDSVIDCNT CVTQTVDFSL DPTFTIETTT LPQDAVSRTQ RRGRTGRGKP GIYRFVAPGE  480
RPSGMFDSSV LCECYDAGCA WYELTPAETT VRLRAYMNTP GLPVCQDHLE FWEGVFTGLT  540
HIDAHFLSQT KQSGENLPYL VAYQATVCAR AQAPPPSWDQ MWKCLIRLKP TLHGPTPLLY  600
RLGAVQNEVT LTHPITKYIM TCMSADLEVV TSTWVLVGGV LAALAAYCLS TGCVVIVGRI  660
VLSGKPAIIP DREVLYREFD EMEECSQHLP YIEQGMMLAE QFKQKALGLL QTASRQAEVI  720
APAVQTNWQK LEAFWAKHMW NFISGIQYLA GLSTLPGNPA IASLMAFTAA VTSPLTTSQT  780
LLFNILGGWV AAQLAAPGAA TAFVGAGLAG AAIGSVGLGK VLVDILAGYG AGVAGALVAF  840
KIMSGEVPST EDLVNLLPAI LSPGALVVGV VCAAILRRHV GPGEGAVQWM NRLIAFASRG  900
NHVSPTHYVP ESDAAARVTA ILSSLTVTQL LRRLHQWISS ECTTPCSGSW LRDIWDWICE  960
VLSDFKTWLK AKLMPQLPGI PFVSCQRGYR GVWRGDGIMH TRCHCGAEIT GHVKNGTMRI  1020
VGPRTCRNMW SGTFPINAYT TGPCTPLPAP NYTFALWRVS AEEYVEIRQV GDFHYVTGMT  1080
TDNLKCPCQV PSPEFFTELD GVRLHRFAPP CKPLLREEVS FRVGLHEYPV GSQLPCEPEP  1140
DVAVLTSMLT DPSHITAEAA GRRLARGSPP SVASSSASQL SAPSLKATCT ANHDSPDAEL  1200
IEANLLWRQE MGGNITRVES ENKVVILDSF DPLVAEEDER EISVPAEILR KSRRFAPALP  1260
IWARPDYNPP LLETWKKPDY EPPVVHGCPL PPPQSPPVPP PRKKRTVVLT ESTVSTALAE  1320
LATKSFGSSS TSGITGDNTT TSSEPAPSGC PPDSDAESYS SMPPLEGEPG DPDLSDGSWS  1380
TVSSEADTED VVCCSMSYSW TGALVTPCAA EEQKLPINAL SNSLLRHHNL VYSTTSRSAC  1440
QRQKKVTFDR LQVLDSHYQD VLKEVKAAAS KVKANLLSVE EACSLTPPHS AKSKFGYGAK  1500
DVRCHARKAV NHINSVWKDL LEDSVTPIDT TIMAKNEVFC VQPEKGGRKP ARLIVFPDLG  1560
VRVCEKMALY DVVSKLPLAV MGSSYGFQYS PGQRVEFLVQ AWKSKKTPMG FSYDTRCFDS  1620
TVTESDIRTE EAIYQCCDLD PQARVAIKSL TERLYVGGPL TNSRGENCGY RRCRASGVLT  1680
TSCGNTLTCY IKARAACRAA GLQDCTMLVC GNNLVVICES AGVQEDAASL RAFTEAMTRY  1740
SAPPGDPPQP EYDLELITSC SSNVSVAHDG AGKRVYYLTR DPTTPLARAA WETARHTPVN  1800
SWLGNIIMFA PTLWARMILM THFFSVLIAR DQLEQALDCE IYGACYSIEP LDLPPIIQRL  1860
HGLSAFSLHS YSPGEINRVA ACLRKLGVPP LRAWRHRARS VRARLLSRGG RAAICGKYLF  1920
NWAVRTKLKL TPIAAAGQLD LSGWFTAGYS GGDIYHSVSH ARPRWFWFCL LLLAAGVGIY  1980
LLPNR                                                             1985

SEQ ID NO: 185          moltype = AA  length = 3012
FEATURE                 Location/Qualifiers
VARIANT                 3012
                        note = X can be any naturally occurring amino acid
source                  1..3012
                        mol_type = protein
                        organism = synthetic construct
SEQUENCE: 185
MSTNPKPQRK TKRNTNRRPQ DVKFPGGGQI VGGVYLLPRR GPRLGVRATR KTSERSQPRG  60
RRQPIPKARR PEGRTWAQPG YPWPLYGNEG CGWAGWLLSP RGSRPSWGPT DPRRRSRNLG  120
KVIDTLTCGF ADLMGYIPLV GAPLGGAARA LAHGVRVLED GVNYATGNLP GCSFSIFLLA  180
LLSCLTVPAS AYQVRNSTGL YHVTNDCPNS SIVYEAADAI LHTPGCVPCV REGNASRCWV  240
AVTPTVATRD GKLPTTQLRR HIDLLVGSAT LCSALYVGDL CGSVFLVGQL FTFSPRRHWT  300
TQDCNCSIYP GHITGHRMAW DMMMNWSPTT ALVVAQLLRI PQAILDMIAG AHWGVLAGIA  360
YFSMVGNWAK VLVVLLLFAG VDAETHVTGG SAARTTSGLA SLFTPGAKQN IQLINTNGSW  420
HINRTALNCN DSLNTGWLAG LFYYHKFNSS GCPERLASCR PLTDFDQGWG PISYANGSGP  480
DQRPYCWHYP PKPCGIVPAK SVCGPVYCFT PSPVVVGTTD RSGAPTYNWG ENDTDVFVLN  540
NTRPPLGNWF GCTWMNSTGF TKVCGAPPCV IGGVGNNTLH CPTDCFRKHP EATYSRCGSG  600
PWITPRCLVD YPYRLWHYPC TINYTIFKVR MYVGGVEHRL EAACNWTRGE RCDLEDRDRS  660
ELSPLLLSTT QWQVLPCSFT TLPALSTGLI HLHQNIVDVQ YLYGVGSSIA SWAIKWEYVV  720
LLFLLLADAR VCSCLWMMLL ISQAEAALEN LVVLNAASLA GTHGLVSFLV FFCFAWYLKG  780
RWVPGAAYAL YGMWPLLLLL LALPQRAYAL DTEVAASCGG VVLVGLMALT LSPYYKRYIS  840
```

-continued

```
WCLWWLQYFL TRVEAQLHVW VPPLNVRGGR DAVILLMCVV HPTLVFDITK LLLAVFGPLW  900
ILQASLLKVP YFVRVQGLLR ICALARKMAG GHYVQMAIIK LGALTGTYVY NHLTPLRDWA  960
HNGLRDLAVA VEPVVFSQME TKLITWGADT AACGDIINGL PVSARRGREI LLGPADGMVS  1020
KGWRLLAPIT AYAQQTRGLL GCIITSLTGR DKNQVEGEVQ IVSTAAQTFL ATCINGVCWT  1080
VYHGAGTRTI ASPKGPVIQM YTNVDQDLVG WPAPQGARSL TPCTCGSSDL YLVTRHADVI  1140
PVRRRGDSRG SLLSPRPISY LKGSSGGPLL CPAGHAVGIF RAAVCTRGVA KAVDFIPVEN  1200
LETTMRSPVF TDNSSPPAVP QSFQVAHLHA PTGSGKSTKV PAAYAAQGYK VLVLNPSVAA  1260
TLGFGAYMSK AHGIDPNIRT GVRTITTGSP ITYSTYGKFL ADGGCSGGAY DIIICDECHS  1320
TDATSILGIG TVLDQAETAG ARLVVLATAT PPGSVTVPHP NIEEVALSTT GEIPFYGKAI  1380
PLEVIKGGRH LIFCHSKKKC DELAAKLVAL GINAVAYYRG LDVSVIPTSG DVVVVATDAL  1440
MTGFTGDFDS VIDCNTCVTQ TVDFSLDPTF TIETTTLPQD AVSRTQRRGR TGRGKPGIYR  1500
FVAPGERPSG MFDSSVLCEC YDAGCAWYEL TPAETTVRLR AYMNTPGLPV CQDHLEFWEG  1560
VFTGLTHIDA HFLSQTKQSG ENLPYLVAYQ ATVCARAQAP PPSWDQMWKC LIRLKPTLHG  1620
PTPLLYRLGA VQNEVTLTHP ITKYIMTCMS ADLEVVTSTW VLVGGVLAAL AAYCLSTGCV  1680
VIVGRIVLSG KPAIIPDREV LYREFDEMEE CSQHLPYIEQ GMMLAEQFKQ KALGLLQTAS  1740
RQAEVIAPAV QTNWQKLEAF WAKHMWNFIS GIQYLAGLST LPGNPAIASL MAFTAAVTSP  1800
LTTSQTLLFN ILGGWVAAQL AAPGAATAFV GAGLAGAAIG SVGLGKVLVD ILAGYGAGVA  1860
GALVAFKIMS GEVPSTEDLV NLLPAILSPG ALVVGVVCAA ILRRHVGPGE GAVQWMNRLI  1920
AFASRGNHVS PTHYVPESDA AARVTAILSS LTVTQLLRRL HQWISSECTT PCSGSWLRDI  1980
WDWICEVLSD FKTWLKAKLM PQLPGIPFVS CQRGYRGVWR GDGIMHTRCH CGAEITGHVK  2040
NGTMRIVGPR TCRNMWSGTF PINAYTTGPC TPLPAPNYTF ALWRVSAEEY VEIRQVGDFH  2100
YVTGMTTDNL KCPCQVPSPE FFTELDGVRL HRFAPPCKPL LREEVSFRVG LHEYPVGSQL  2160
PCEPEPDVAV LTSMLTDPSH ITAEAAGRRL ARGSPPSVAS SSASQLSAPS LKATCTANHD  2220
SPDAELIEAN LLWRQEMGGN ITRVESENKV VILDSFDPLV AEEDEREISV PAEILRKSRR  2280
FAPALPIWAR PDYNPPLLET WKKPDYEPPV VHGCPLPPPQ SPPVPPPRKK RTVVLTESTV  2340
STALAELATK SFGSSSTSGI TGDNTTTSSE PAPSGCPPDS DAESYSSMPP LEGEPGDPDL  2400
SDGSWSTVSS EADTEDVVCC SMSYSWTGAL VTPCAAEEQK LPINALSNSL LRHHNLVYST  2460
TSRSACQRQK KVTFDRLQVL DSHYQDVLKE VKAAASKVKA NLLSVEEACS LTPPHSAKSK  2520
FGYGAKDVRC HARKAVNHIN SVWKDLLEDS VTPIDTTIMA KNEVFCVQPE KGGRKPARLI  2580
VFPDLGVRVC EKMALYDVVS KLPLAVMGSS YGFQYSPGQR VEFLVQAWKS KKTPMGFSYD  2640
TRCFDSTVTE SDIRTEEAIY QCCDLDPQAR VAIKSLTERL YVGGPLTNSR GENCGYRRCR  2700
ASGVLTTSCG NTLTCYIKAR AACRAAGLQD CTMLVCGDDL VVICESAGVQ EDAASLRAFT  2760
EAMTRYSAPP GDPPQPEYDL ELITSCSSNV SVAHDGAGKR VYYLTRDPTT PLARAAWETA  2820
RHTPVNSWLG NIIMFAPTLW ARMILMTHFF SVLIARDQLE QALDCEIYGA CYSIEPLDLP  2880
PIIQRLHGLS AFSLHSYSPG EINRVAACLR KLGVPPLRAW RHRARSVRAR LLSRGGRAAI  2940
CGKYLFNWAV RTKLKLTPIA AAGQLDLSGW FTAGYSGGDI YHSVSHARPR WFWFCLLLLA  3000
AGVGIYLLPN RX                                                    3012

SEQ ID NO: 186          moltype = AA  length = 3014
FEATURE                 Location/Qualifiers
VARIANT                 197
                        note = X can be any naturally occurring amino acid
VARIANT                 241
                        note = X can be any naturally occurring amino acid
VARIANT                 251
                        note = X can be any naturally occurring amino acid
VARIANT                 290
                        note = X can be any naturally occurring amino acid
VARIANT                 331
                        note = X can be any naturally occurring amino acid
VARIANT                 334
                        note = X can be any naturally occurring amino acid
VARIANT                 343..344
                        note = X can be any naturally occurring amino acid
VARIANT                 372
                        note = X can be any naturally occurring amino acid
VARIANT                 390
                        note = X can be any naturally occurring amino acid
VARIANT                 407
                        note = X can be any naturally occurring amino acid
VARIANT                 433
                        note = X can be any naturally occurring amino acid
VARIANT                 476
                        note = X can be any naturally occurring amino acid
VARIANT                 523
                        note = X can be any naturally occurring amino acid
VARIANT                 597
                        note = X can be any naturally occurring amino acid
VARIANT                 715
                        note = X can be any naturally occurring amino acid
VARIANT                 767
                        note = X can be any naturally occurring amino acid
VARIANT                 786
                        note = X can be any naturally occurring amino acid
VARIANT                 792
                        note = X can be any naturally occurring amino acid
VARIANT                 821
                        note = X can be any naturally occurring amino acid
VARIANT                 826
```

-continued

| | |
|---|---|
| | note = X can be any naturally occurring amino acid |
| VARIANT | 843 |
| | note = X can be any naturally occurring amino acid |
| VARIANT | 857 |
| | note = X can be any naturally occurring amino acid |
| VARIANT | 873..874 |
| | note = X can be any naturally occurring amino acid |
| VARIANT | 884 |
| | note = X can be any naturally occurring amino acid |
| VARIANT | 922 |
| | note = X can be any naturally occurring amino acid |
| VARIANT | 928 |
| | note = X can be any naturally occurring amino acid |
| VARIANT | 955 |
| | note = X can be any naturally occurring amino acid |
| VARIANT | 1020 |
| | note = X can be any naturally occurring amino acid |
| VARIANT | 1099 |
| | note = X can be any naturally occurring amino acid |
| VARIANT | 1143 |
| | note = X can be any naturally occurring amino acid |
| VARIANT | 1161 |
| | note = X can be any naturally occurring amino acid |
| VARIANT | 1210 |
| | note = X can be any naturally occurring amino acid |
| VARIANT | 1223 |
| | note = X can be any naturally occurring amino acid |
| VARIANT | 1371 |
| | note = X can be any naturally occurring amino acid |
| VARIANT | 1385 |
| | note = X can be any naturally occurring amino acid |
| VARIANT | 1409 |
| | note = X can be any naturally occurring amino acid |
| VARIANT | 1599 |
| | note = X can be any naturally occurring amino acid |
| VARIANT | 1607 |
| | note = X can be any naturally occurring amino acid |
| VARIANT | 1695 |
| | note = X can be any naturally occurring amino acid |
| VARIANT | 1753 |
| | note = X can be any naturally occurring amino acid |
| VARIANT | 1874 |
| | note = X can be any naturally occurring amino acid |
| VARIANT | 2071..2072 |
| | note = X can be any naturally occurring amino acid |
| VARIANT | 2074 |
| | note = X can be any naturally occurring amino acid |
| VARIANT | 2087 |
| | note = X can be any naturally occurring amino acid |
| VARIANT | 2106 |
| | note = X can be any naturally occurring amino acid |
| VARIANT | 2134 |
| | note = X can be any naturally occurring amino acid |
| VARIANT | 2279 |
| | note = X can be any naturally occurring amino acid |
| VARIANT | 2321 |
| | note = X can be any naturally occurring amino acid |
| VARIANT | 2335 |
| | note = X can be any naturally occurring amino acid |
| VARIANT | 2358 |
| | note = X can be any naturally occurring amino acid |
| VARIANT | 2361..2362 |
| | note = X can be any naturally occurring amino acid |
| VARIANT | 2364 |
| | note = X can be any naturally occurring amino acid |
| VARIANT | 2367 |
| | note = X can be any naturally occurring amino acid |
| VARIANT | 2373..2374 |
| | note = X can be any naturally occurring amino acid |
| VARIANT | 2376 |
| | note = X can be any naturally occurring amino acid |
| VARIANT | 2383 |
| | note = X can be any naturally occurring amino acid |
| VARIANT | 2487 |
| | note = X can be any naturally occurring amino acid |
| VARIANT | 2496 |
| | note = X can be any naturally occurring amino acid |
| VARIANT | 2542 |
| | note = X can be any naturally occurring amino acid |

```
VARIANT                2546
                       note = X can be any naturally occurring amino acid
VARIANT                2572
                       note = X can be any naturally occurring amino acid
VARIANT                2601
                       note = X can be any naturally occurring amino acid
VARIANT                2653
                       note = X can be any naturally occurring amino acid
VARIANT                2660
                       note = X can be any naturally occurring amino acid
VARIANT                2676
                       note = X can be any naturally occurring amino acid
VARIANT                2689
                       note = X can be any naturally occurring amino acid
VARIANT                2695
                       note = X can be any naturally occurring amino acid
VARIANT                2722
                       note = X can be any naturally occurring amino acid
VARIANT                2757
                       note = X can be any naturally occurring amino acid
VARIANT                2798
                       note = X can be any naturally occurring amino acid
VARIANT                2857
                       note = X can be any naturally occurring amino acid
VARIANT                2863
                       note = X can be any naturally occurring amino acid
VARIANT                2966
                       note = X can be any naturally occurring amino acid
VARIANT                3002
                       note = X can be any naturally occurring amino acid
VARIANT                3014
                       note = X can be any naturally occurring amino acid
source                 1..3014
                       mol_type = protein
                       organism = synthetic construct
SEQUENCE: 186
MSTNPKPQRK TKRNTNRRPQ DVKFPGGGQI VGGVYLLPRR GPRLGVRATR KTSERSQPRG  60
RRQPIPKARR SEGRSWAQPG YPWPLYGNEG CGWAGWLLSP RGSRPSWGPT DPRRRSRNLG  120
KVIDTLTCGF ADLMGYIPLV GAPLGGVARA LAHGVRVLED GINYATGNLP GCSFSIFLLA  180
LLSCLTVPAS AYEVRNXSGL YHVTNDCPNS SIVYEADDAI LHTPGCVPCV REGNTSRCWV  240
XVTPTVAVRY XGAPTTSLRR HVDLLVGAAT LCSALYVGDL CGAVFLVGQX FTFSPRRHWT  300
VQDCNCSIYP GHITGHRMAW DMMMNWSPTT XLVXAQLLRI PQXXLDIIAG AHWGVLAGLA  360
YFSMQGNWAK VXVLLLFAGV DAETHTTGGX AARTTSGLTS LFSPGPXQNL QLINTNGSWH  420
INRTALNCND SLXTGFIAGL FYTHKFNSSG CPERLASCRP LTDFDQGWGP LTYANXISGP  480
SDDRPYCWHY PPRPCGIVPA RSVCGPVYCF TPSPVVVGTT DRXGVPTYTW GENETDVFLL  540
NSTRPPQGNW FGCTWMNSTG FTKTCGAPPC NIGGGGNNDL LCPTDCFRKH PEATYSXCGS  600
GPWLTPRCLV DYPYRLWHYP CTVNFTIFKV RMYVGGVEHR LEAACNWTRG ERCDLEDRDR  660
SELSPLLHST TEWAILPCSF TTLPALSTGL IHLHQNIVDV QYLYGVGSAV VSWAXKWEYV  720
VLLFLLLADA RVCACLWMML LISQAEAALE NLVVLNAASA AGTHGIXWFL VFFCAAWYLK  780
GRLVPXATYA LXGLWPLLLL LLALPQRAYA LDREVAASLG XAVLVXLTIF TLSPHYKHLL  840
SRXLWWLQYF ITRAEAXLQV WVPPLNVRGG RDXXILLTCL LHPXLVFDIT KLLLAVLGPL  900
YLLQASLLRV PYFVRAHALL RXCMLVRXLA GGKYVQMALL KLGRWTGTYI YDHLXPLSDW  960
AAAGLRDLAV AVEPVIFSPM EKKVITWGAD TAACGDILCG LPVSARLGRE ILLGPADDYX  1020
SKGWRLLAPI TAYAQQTRGL LGTIVTSLTG RDKNEVEGEV QVLSTATQTF LGTCINGVMW  1080
TVYHGAGSKT LAGPKGPVXQ MYTNVDQDLV GWPAPPGAKS LTPCTCGSSD LYLVTRHADV  1140
IPXRRRGDSR GSLLSPRPIS XLKGSSGGPV LCPSGHAVGI FRAAVCTRGV AKAVDFIPVE  1200
SLETTMRSPX FTDNSTPPAV PQXYQVGYLH APTGSGKSTK VPAAYAAQGY KVLVLNPSVA  1260
ATLGFGAYMS KAHGIDPNIR TGVRTVTTGA PITYSTYGKF LADGGCSGGA YDIIICDECH  1320
STDATTILGI GTVLDQAETA GVRLVVLATA TPPGSVTVPH PNIEEVALGT XGEIPFYGKA  1380
IPLEXIKGGR HLIFCHSKKK CDELAAKLXG LGLNAVAYYR GLDVSVIPTS GDVVVVATDA  1440
LMTGFTGDFD SVIDCNVAVT QTVDFSLDPT FTIETTTVPQ DAVSRSQRRG RTGRGRLGIY  1500
RYVSPGERPS GMFDSVVLCE CYDAGCAWYE LTPAETTVRL RAYLNTPGLP VCQDHLEFWE  1560
GVFTGLTHID AHFLSQTKQS GENFPYLVAY QATVCARAXA PPPSWDXMWK CLIRLKPTLH  1620
GPTPLLYRLG AVQNEVTLTH PITKYIMTCM SADLEVVTST WVLVGGVLAA LAAYCLSTGC  1680
VVIVGRIVLS GKPAXIPDRE VLYQQFDEME ECSQHLPYIE QGQQIAEQFK QKALGLLQTA  1740
TKQAEVIAPA VQXNWQKLEQ FWAKHMWNFI SGIQYLAGLS TLPGNPAVAS LMAFTAAVTS  1800
PLTTSQTLLF NILGGWVASQ LAPPTAATAF VVSGLAGAAV GSIGLGKVLV DILAGYGAGV  1860
AGALVAFKIM SGEXPSTEDL VNLLPAILSP GALVVGVVCA AILRRHVGPG EGAVQWMNRL  1920
IAFASRGNHV SPTHYVPESD AAARVTQILS SLTVTSLLRR LHQWINEDCS TPCSGSWLRD  1980
IWDWVCTVLS DFKTWLKAKL LPQLPGIPFL SCQRGYKGVW RGDGVMHTRC PCGAEITGHV  2040
KNGSMRIVGP KTCSNTWHGT FPINAYTTGP XXPXPAPNYK RALWRVXAEE YVEVRRVGDF  2100
HYVTGXTTDN LKCPCQVPAP EFFTEVDGVR LHRXAPPCKP LLRDEVTFSV GLNSYVVGSQ  2160
LPCEPEPDVA VLTSMLTDPS HITAETAARR LARGSPPSLA SSSASQLSAP SLKATCTTHH  2220
DHPDAELIEA NLLWRQEMGG NITRVESENK VVILDSFDPL VAEEDDREIS VPAECLRKXR  2280
KFPPALPIWA RPDYNPPLLE TWKRPDYEPP TVHGCALPPP XAPPVPPPRR KRTVXLTEST  2340
VSTALAELAE KSFGSSEXSG XXSXSGXDTT SSXXSXPPDC DAXSDAESYS SMPPLEGEPG  2400
DPDLSDGSWS TVSDEEDSVV CCSMSYSWTG ALITPCAAEE EKLPINPLSN SLLRHHNLVY  2460
STTSRSASQR QKKVTFDRLQ VLDDHYXDVL KEVKAXASKV KARLLSVEEA CALTPPHSAR  2520
SKFGYGAKDV RSLSRKAVNH IXSVWXDLLE DSTTPIPTTI MAKNEVFCVD PXKGGRKPAR  2580
```

-continued

```
LIVYPDLGVR VCEKRALYDV XQKLPKAVMG SSYGFQYSPA QRVEFLLKAW KSKKTPMGFS  2640
YDTRCFDSTV TEXDIRTEEX IYQCCDLDPE ARKAIXSLTE RLYVGGPMXN SKGQXCGYRR  2700
CRASGVLTTS MGNTLTCYIK AXAACRAAGL RDCTMLVCGD DLVVICESAG VZEDAAXLRA  2760
FTEAMTRYSA PPGDPPQPEY DLELITSCSS NVSVAHDXSG KRVYYLTRDP TTPLARAAWE  2820
TARHTPVNSW LGNIIMYAPT IWVRMVLMTH FFSILQXQEQ LEXALDFEMY GATYSVTPLD  2880
LPAIIQRLHG LSAFSLHSYS PGELNRVAAC LRKLGVPPLR AWRHRARAVR AKLIAQGGRA  2940
AICGKYLFNW AVRTKLKLTP LPAAGXLDLS SWFTVGAGGG DIYHSVSRAR PRWLLLCLLL  3000
LXVGVGIFLL PARX                                                    3014

SEQ ID NO: 187          moltype = AA  length = 3012
FEATURE                 Location/Qualifiers
VARIANT                 3012
                        note = X can be any naturally occurring amino acid
source                  1..3012
                        mol_type = protein
                        organism = synthetic construct
SEQUENCE: 187
MSTNPKPQRK TKRNTNRRPQ DVKFPGGGQI VGGVYLLPRR GPRLGVRATR KTSERSQPRG  60
RRQPIPKARR PEGRTWAQPG YPWPLYGNEG CGWAGWLLSP RGSRPSWGPT DPRRRSRNLG  120
KVIDTLTCGF ADLMGYIPLV GAPLGGAARA LAHGVRVLED GVNYATGNLP GCSFSIFLLA  180
LLSCLTVPAS AYQVRNSTGL YHVTNDCPNS SIVYEAADAI LHTPGCVPCV REGNASRCWV  240
AVTPTVATRD GKLPTTQLRR HIDLLVGSAT LCSALYVGDL CGSVFLVGQL FTFSPRRHWT  300
TQDCNCSIYP GHITGHRMAW DMMMNWSPTT ALVVAQLLRI PQAILDMIAG AHWGVLAGIA  360
YFSMVGNWAK VLVVLLLFAG VDAETHVTGG SAARTTSGLA SLFTPGAKQN IQLINTNGSW  420
HINRTALNCN DSLNTGWLAG LFYYHKFNSS GCPERLASCR PLTDFDQGWG PISYANGSGP  480
DQRPYCWHYP PKPCGIVPAK SVCGPVYCFT PSPVVVGTTD RSGAPTYNWG ENDTDVFVLN  540
NTRPPLGNWF GCTWMNSTGF TKVCGAPPCV IGGVGNNTLH CPTDCFRKHP EATYSRCGSG  600
PWITPRCLVD YPYRLWHYPC TINYTIFKVR MYVGGVEHRL EAACNWTRGE RCDLEDRDRS  660
ELSPLLLSTT QWQVLPCSFT TLPALSTGLI HLHQNIVDVQ YLYGVGSSIA SWAIKWEYVV  720
LLFLLLADAR VCSCLWMMLL ISQAEAALEN LVVLNAASLA GTHGLVSFLV FFCFAWYLKG  780
RWVPGAAYAL YGMWPLLLLL LALPQRAYAL DTEVAASCGG VVLVGLMALT LSPYYKRYIS  840
WCLWWLQYFL TRVEAQLHVW VPPLNVRGGR DAVILLMCVV HPTLVFDITK LLLAVFGPLW  900
ILQASLLKVP YFVRVQGLLR ICALARKMAG GHYVQMAIIK LGALTGTYVY NHLTPLRDWA  960
HNGLRDLAVA VEPVVFSQME TKLITWGADT AACGDIINGL PVSARRGREI LLGPADGMVS  1020
KGWRLLAPIT AYAQQTRGLL GCIITSLTGR DKNQVEGEVQ IVSTAAQTFL ATCINGVCWT  1080
VYHGAGTRTI ASPKGPVIQM YTNVDQDLVG WPAPQGARSL TPCTCGSSDL YLVTRHADVI  1140
PVRRRGDSRG SLLSPRPISY LKGSSGGPLL CPAGHAVGIF RAAVCTRGVA KAVDFIPVEN  1200
LETTMRSPVF TDNSSPPAVP QSFQVAHLHA PTGSGKSTKV PAAYAAQGYK VLVLNPSVAA  1260
TLGFGAYMSK AHGIDPNIRT GVRTITTGSP ITYSTYGKFL ADGGCSGGAY DIIICDECHS  1320
TDATSILGIG TVLDQAETAG ARLVVLATAT PPGSVTVPHP NIEEVALSTT GEIPFYGKAI  1380
PLEVIKGGRH LIFCHSKKKC DELAAKLVAL GINAVAYYRG LDVSVIPTSG DVVVVATDAL  1440
MTGFTGDFDS VIDCNTCVTQ TVDFSLDPTF TIETTTLPQD AVSRTQRRGR TGRGKPGIYR  1500
FVAPGERPSG MFDSSVLCEC YDAGCAWYEL TPAETTVRLR AYMNTPGLPV CQDHLEFWEG  1560
VFTGLTHIDA HFLSQTKQSG ENLPYLVAYQ ATVCARAQAP PPSWDQMWKC LIRLKPTLHG  1620
PTPLLYRLGA VQNEVTLTHP ITKYIMTCMS ADLEVVTSTW VLVGGVLAAL AAYCLSTGCV  1680
VIVGRIVLSG KPAIIPDREV LYREFDEMEE CSQHLPYIEQ GMMLAEQFKQ KALGLLQTAS  1740
RQAEVIAPAV QTNWQKLEAF WAKHMWNFIS GIQYLAGLST LPGNPAIASL MAFTAAVTSP  1800
LTTSQTLLFN ILGGWVAAQL AAPGAATAFV GAGLAGAAIG SVGLGKVLVD ILAGYGAGVA  1860
GALVAFKIMS GEVPSTEDLV NLLPAILSPG ALVVGVVCAA ILRRHVGPGE GAVQWMNRLI  1920
AFASRGNHVS PTHYVPESDA AARVTAILSS LTVTQLLRRL HQWISSECTT PCSGSWLRDI  1980
WDWICEVLSD FKTWLKAKLM PQLPGIPFVS CQRGYRGVWR GDGIMHTRCH CGAEITGHVK  2040
NGTMRIVGPR TCRNMWSGTF PINAYTTGPC TPLPAPNYTF ALWRVSAEEY VEIRQVGDFH  2100
YVTGMTTDNL KCPCQVPSPE FFTELDGVRL HRFAPPCKPL LREEVSFRVG LHEYPVGSQL  2160
PCEPEPDVAV LTSMLTDPSH ITAEAAGRRL ARGSPPSVAS SSASQLSAPS LKATCTANHD  2220
SPDAELIEAN LLWRQEMGGN ITRVESENKV VILDSFDPLV AEEDEREISV PAEILRKSRR  2280
FAPALPIWAR PDYNPPLLET WKKPDYEPPV VHGCPLPPPQ SPPVPPPRKK RTVVLTESTV  2340
STALAELATK SFGSSSTSGI TGDNTTTSSE PAPSGCPPDS DAESYSSMPP LEGEPGDPDL  2400
SDGSWSTVSS EADTEDVVCC SMSYSWTGAL VTPCAAEEQK LPINALSNSL LRHHNLVYST  2460
TSRSACQRQK KVTFDRLQVL DSHYQDVLKE VKAAASKVKA NLLSVEEACS LTPPHSAKSK  2520
FGYGAKDVRC HARKAVNHIN SVWKDLLEDS VTPIDTTIMA KNEVFCVQPE KGGRKPARLI  2580
VFPDLGVRVC EKMALYDVVS KLPLAVMGSS YGFQYSPGQR VEFLVQAWKS KKTPMGFSYD  2640
TRCFDSTVTE SDIRTEEAIY QCCDLDPQAR VAIKSLTERL YVGGPLTNSR GENCGYRRCR  2700
ASGVLTTSCG NTLTCYIKAR AACRAAGLQD CTMLVCGDDL VVICESAGVQ EDAASLRAFT  2760
EAMTRYSAPP GDPPQPEYDL ELITSCSSNV SVAHDGAGKR VYYLTRDPTT PLARAAWETA  2820
RHTPVNSWLG NIIMFAPTLW ARMILMTHFF SVLIARDQLE QALDCEIYGA CYSIEPLDLP  2880
PIIQRLHGLS AFSLHSYSPG EINRVAACLR KLGVPPLRAW RHRARSVRAR LLSRGGRAAI  2940
CGKYLFNWAV RTKLKLTPIA AAGQLDLSGW FTAGYSGGDI YHSVSHARPR WFWFCLLLLA  3000
AGVGIYLLPN RX                                                      3012

SEQ ID NO: 188          moltype = AA  length = 3008
FEATURE                 Location/Qualifiers
VARIANT                 3008
                        note = X can be any naturally occurring amino acid
source                  1..3008
                        mol_type = protein
                        organism = synthetic construct
SEQUENCE: 188
MSTNPKPQRK TKRNTNRRPQ DVKFPGGGQI VGGVYLLPRR GPRLGVRATR KTSERSQPRG  60
RRQPIPKARR PEGRAWAQPG YPWPLYGNEG MGWAGWLLSP RGSRPSWGPT DPRRRSRNLG  120
```

```
KVIDTLTCGF ADLMGYIPLV GAPLGGAARA LAHGVRVLED GVNYATGNLP GCSFSIFLLA  180
LLSCLTIPAS AYEVRNVSGV YHVTNDCSNS SIVYEAADMI MHTPGCVPCV RENNSSRCWV  240
ALTPTLAARN ASVPTTTIRR HVDLLVGAAA FCSAMYVGDL CGSVFLVSQL FTFSPRRHET  300
VQDCNCSIYP GHVSGHRMAW DMMMNWSPTT ALVVSQLLRI PQAVVDMVAG AHWGVLAGLA  360
YYSMVGNWAK VLIVMLLFAG VDGTHVTGGA AARTTSGFTS LFSPGPSQKI QLINTNGSWH  420
INRTALNCND SLQTGFLAAL FYTHKFNSSG CPERMASCRP IDKFAQGWGP ITYAEPSSDQ  480
RPYCWHYAPR PCGIVPASQV CGPVYCFTPS PVVVGTTDRF GVPTYSWGEN ETDVLLLNNT  540
RPPQGNWFGC TWMNSTGFTK TCGGPPCNIG GVGNNTLTCP TDCFRKHPEA TYTKCGSGPW  600
LTPRCLVDYP YRLWHYPCTV NFTIFKVRMY VGGVEHRLNA ACNWTRGERC DLEDRDRSEL  660
SPLLLSTTEW QILPCSFTTL PALSTGLIHL HQNIVDVQYL YGIGSAVVSF AIKWEYVLLL  720
FLLLADARVC ACLWMMLLIA QAEAALENLV VLNAASVAGA HGILSFLVFF CAAWYIKGRL  780
VPGAAYAFYG VWPLLLLLLA LPPRAYAMDR EMAASCGGAV FVGLALLTLS PHYKVFLARL  840
IWWLQYFITR AEAHLQVWIP PLNVRGGRDA IILLTCAVHP ELIFDITKLL LAILGPLMVL  900
QAGITRVPYF VRAQGLIRAC MLVRKVAGGH YVQMAFMKLA ALTGTYVYDH LTPLRDWAHA  960
GLRDLAVAVE PVVFSDMETK IITWGADTAA CGDIILGLPV SARRGREILL GPADSLEGQG  1020
WRLLAPITAY SQQTRGLLGC IITSLTGRDK NQVEGEVQVV STATQSFLAT CVNGVCWTVY  1080
HGAGSKTLAG PKGPITQMYT NVDQDLVGWQ APPGARSLTP CTCGSSDLYL VTRHADVIPV  1140
RRRGDSRGSL LSPRPVSYLK GSSGGPLLCP SGHAVGIFRA AVCTRGVAKA VDFVPVESME  1200
TTMRSPVFTD NSSPPAVPQT FQVAHLHAPT GSGKSTKVPA AYAAQGYKVL VLNPSVAATL  1260
GFGAYMSKAH GVDPNIRTGV RTITTGAPIT YSTYGKFLAD GGCSGGAYDI IICDECHSTD  1320
STTILGIGTV LDQAETAGAR LVVLATATPP GSVTVPHPNI EEVALSNTGE IPFYGKAIPI  1380
ETIKGGRHLI FCHSKKKCDE LAAKLSGLGL NAVAYYRGLD VSVIPTSGDV VVVATDALMT  1440
GFTGDFDSVI DCNTCVTQTV DFSLDPTFTI ETTTVPQDAV SRSQRRGRTG RGRRGIYRFV  1500
TPGERPSGMF DSSVLCECYD AGCAWYELTP AETSVRLRAY LNTPGLPVCQ DHLEFWESVF  1560
TGLTHIDAHF LSQTKQAGDN FPYLVAYQAT VCARAQAPPP SWDQMWKCLI RLKPTLHGPT  1620
PLLYRLGAVQ NEVTLTHPIT KYIMACMSAD LEVVTSTWVL VGGVLAALAA YCLTTGSVVI  1680
VGRIILSGKP AIIPDREVLY QEFDEMEECA SHLPYIEQGM QLAEQFKQKA LGLLQTATKQ  1740
AEAAAPVVES KWRALEFWAK HMWNFISGIQ YLAGLSTLPG NPAIASLMAF TASITSPLTT  1800
QHTLLFNILG GWVAAQLAPP SAASAFVGAG IAGAAVGSIG LGKVLVDILA GYGAGVAGAL  1860
VAFKVMSGEM PSTEDLVNLL PAILSPGALV VGVVCAAILR RHVGPGEGAV QWMNRLIAFA  1920
SRGNHVSPTH YVPESDAAAR VTQILSSLTI TQLLKRLHQW INEDCSTPCS GSWLRDVWDW  1980
ICTVLTDFKT WLQSKLLPRL PGVPFLSCQR GYKGVWRGDG IMQTTCPCGA QITGHVKNGS  2040
MRIVGPKTCS NTWHGTFPIN AYTTGPCTPS PAPNYSRALW RVAAEEYVEV TRVGDFHYVT  2100
GMTTDNVKCP CQVPAPEFFT EVDGVRLHRY APACKPLLRE EVTFQVGLNQ YLVGSQLPCE  2160
PEPDVAVLTS MLTDPSHITA ETAKRRLARG SPPSLASSSA SQLSAPSLKA TCTTRHDSPD  2220
ADLIEANLLW RQEMGGNITR VESENKVVIL DSFDPLRAEE DEREVSVPAE ILRKSRKFPP  2280
AMPIWARPDY NPPLLESWKD PDYVPPVVHG CPLPPTKAPP IPPPRRKRTV VLTESTVSSA  2340
LAELATKTFG SSESSAVDSG TATAPPDQPS DDGDAGSDVE SYSSMPPLEG EPGDPDLSDG  2400
SWSTVSEEAS EDVVCCSMSY TWTGALITPC AAEESKLPIN ALSNSLLRHH NMVYATTSRS  2460
ASQRQKKVTF DRLQVLDDHY RDVLKEMKAK ASTVKAKLLS VEEACKLTPP HSARSKFGYG  2520
AKDVRNLSSK AVNHIRSVWK DLLEDTETPI DTTIMAKNEV FCVQPEKGGR KPARLIVFPD  2580
LGVRVCEKMA LYDVVSTLPQ AVMGSSYGFQ YSPGQRVEFL VNAWKSKKCP MGFAYDTRCF  2640
DSTVTESDIR VEESIYQCCD LAPEARQAIR SLTERLYIGG PLTNSKGQNC GYRRCRASGV  2700
LTTSCGNTLT CYLKASAACR AAKLQDCTML VCGDDLVVIC ESAGTQEDAA SLRVFTEAMT  2760
RYSAPPGDPP QPEYDLELIT SCSSNVSVAH DASGKRVYYL TRDPTTPLAR AAWETARHTP  2820
VNSWLGNIIM YAPTLWARMI LMTHFFSILL AQEQLEKALD CQIYGACYSI EPLDLPQIIQ  2880
RLHGLSAFSL HSYSPGEINR VASCLRKLGV PPLRVWRHRA RSVRAKLLSQ GGRAATCGKY  2940
LFNWAVRTKL KLTPIPAASQ LDLSGWFVAG YSGGDIYHSL SRARPRWFMW CLLLLSVGVG  3000
IYLLPNRX                                                        3008

SEQ ID NO: 189          moltype = AA  length = 3034
FEATURE                 Location/Qualifiers
VARIANT                 250
                        note = X can be any naturally occurring amino acid
VARIANT                 406
                        note = X can be any naturally occurring amino acid
VARIANT                 408..409
                        note = X can be any naturally occurring amino acid
VARIANT                 3023
                        note = X can be any naturally occurring amino acid
source                  1..3034
                        mol_type = protein
                        organism = synthetic construct
SEQUENCE: 189
MSTNPKPQRK TKRNTNRRPQ DVKFPGGGQI VGGVYLLPRR GPRLGVRATR KTSERSQPRG  60
RRQPIPKDRR STGKSWGKPG YPWPLYGNEG LGWAGWLLSP RGSRPSWGPT DPRHRSRNVG  120
KVIDTLTCGF ADLMGYIPVV GAPLGGVARA LAHGVRVLED GVNYATGNLP GCSFSIFLLA  180
LLSCITVPVS AAQVKNTSSS YMVTNDCSND SITWQLQAAV LHVPGCVPCE KVGNNTSRCW  240
IPVSPNVAVX QPGALTQGLR THIDMVVMSA TLCSALYVGD LCGGVMLAAQ MFIVSPQHHW  300
FVQECNCSIY PGTITGHRMA WDMMMNWSPT ATMILAYAMR VPEVIIDIIS GAHWGVMFGL  360
AYFSMQGAWA KVVVILLLAA GVDAGTHTVG GSAAHTTSGL AGLFSXGXXQ NIQLINTNGS  420
WHINRTALNC NDSLNTGFLA SLFYTHRFNS SGCPERLSAC RNIEAFRIGW GTLQYEDNVT  480
NPEDMRPYCW HYPPKQCGIV PARSVCGPVY CFTPSPVVVG TTDRLGVPTY TWGENETDVF  540
LLNSTRPPQG SWFGCTWMNS TGFTKTCGAP PCRIRADFNA STDLLCPTDC FRKHPEATYI  600
KCGSGPWLTP RCLVDYPYRL WHYPCTVNYT IFKIRMYVGG VEHRLTAACN FTRGDRCNLE  660
DRDRSQLSPL LHSTTEWAIL PCSYSDLPAL STGLLHLHQN IVDVQYMYGL SPALTKYVVR  720
WEWVVLLFLL LADARVCACL WMLILLGQAE AALEKLVVLH AASAASCNGF LYFVIFFVAA  780
WYIKGRAVPL AAYSLTGLWP FCLLLLALPQ QAYAYDASVH GQIGAALLIL ITLFTLTPGY  840
KTLLSRCLWW LCYLLTLGEA MVQEWAPPMQ ARGGRDGIIW AATIFCPGVV FDITKWLLAV  900
```

-continued

```
LGPAYLLRDA LTRVPYFVRA HALLRMCTMV RHLAGGRYVQ MALLALGRWT GTYIYDHLTP  960
MSDWAASGLR DLAVAVEPII FSPMEKKVIV WGAETAACGD ILHGLPVSAR LGREILLGPA  1020
DGYTSKGWRL LAPITAYAQQ TRGLLGAIVV SMTGRDKTEQ AGEIQVLSTV TQSFLGTSIS  1080
GVLWTVYHGA GNKTLAGSRG PVTQMYSSAE GDLVGWPSPP GTKSLEPCTC GAVDLYLVTR  1140
NADVIPARRR GDKRGALLSP RPLSTLKGSS GGPVLCPRGH AVGIFRAAVC SRGVAKSIDF  1200
IPVETLDIVT RSPTFSDNST PPAVPQTYQV GYLHAPTGSG KSTKVPVAYA AQGYKVLVLN  1260
PSVAATLGFG AYLSKAHGIN PNIRTGVRTV TTGEAITYST YGKFLADGGC AGGAYDIIIC  1320
DECHAVDATT ILGIGTVLDQ AETAGVRLTV LATATPPGSV TTPHPNIEEV ALGQEGEIPF  1380
YGRAIPLSYI KGGRHLIFCH SKKKCDELAA ALRGMGLNAV AYYRGLDVSI IPTQGDVVVV  1440
ATDALMTGYT GDFDSVIDCN VAVTQVVDFS LDPTFTITTQ TVPQDAVSRS QRRGRTGRGR  1500
LGIYRYVSTG ERASGMFDSV VLCECYDAGA AWYELTPAET TVRLRAYFNT PGLPVCQDHL  1560
EFWEAVFTGL THIDAHFLSQ TKQSGENFAY LVAYQATVCA RAKAPPPSWD VMWKCLTRLK  1620
PTLVGPTPLL YRLGSVTNEV TLTHPVTKYI ATCMQADLEV MTSTWVLAGG VLAAVAAYCL  1680
ATGCVSIIGR LHINQRAVVA PDKEVLYEAF DEMEECASRA ALIEEGQRIA EMLKSKIQGL  1740
LQQASKQAQD IQPAVQASWP KVEQFWAKHM WNFISGIQYL AGLSTLPGNP AVASMMAFSA  1800
ALTSPLSTST TILLNILGGW LASQIAPPAG ATGFVVSGLV GAAVGSIGLG KVLVDILAGY  1860
GAGISGALVA FKIMSGEKPS MEDVVNLLPG ILSPGALVVG VICAAILRRH VGPGEGAVQW  1920
MNRLIAFASR GNHVAPTHYV TESDASQRVT QLLGSLTITS LLRRLHNWIT EDCPIPCAGS  1980
WLRDVWDWVC TILTDFKNWL TSKLFPKMPG LPFISCQKGY KGVWAGTGIM TTRCPCGANI  2040
SGNVRLGSMR ITGPKTCMNT WQGTFPINCY TEGQCVPKPA PNFKTAIWRV AASEYAEVTQ  2100
HGSYSYITGL TTDNLKVPCQ LPSPEFFSWV DGVQIHRFAP TPKPFFRDEV SFCVGLNSFV  2160
VGSQLPCDPE PDTDVLMSML TDPSHITAEA AARRLARGSP PSEASSSASQ LSAPSLRATC  2220
TTHGKTYDVD MVDANLFMGG DVTRIESESK VVVLDSLDPM AEERSDLEPS IPSEYMLPRN  2280
RFPPALPAWA RPDYNPPLVE SWKRPDYQPP TVAGCALPPP KKTPTPPPRR RRTVGLSEST  2340
IGDALQQLAI KTFGQPPPSG DSGLSTGADA ADSGGRTPPD ELALSETGSI SSMPPLEGEP  2400
GDPDLEPEQV ELQPPPQGGE VAPGSDSGSW STCSEEDDSV VCCSMSYSWT GALITPCSPE  2460
EEKLPINPLS NSLLRYHNKV YCTTSKSASL RAKKVTFDRM QVLDAHYDSV LKDIKLAASK  2520
VSARLLTLEE ACQLTPPHSA RSKYGFGAKE VRSLSGRAVN HIKSVWKDLL EDSQTPIPTT  2580
IMAKNEVFCV DPTKGGKKAA RLIVYPDLGV RVCEKMALYD VTQKLPQAVM GASYGFQYSP  2640
AQRVEFLLKA WAEKKDPMGF SYDTRCFDST VTERDIRTEE SIYQACSLPE EARTAIHSLT  2700
ERLYVGGPMF NSKGQTCGYR RCRASGVLTT SMGNTITCYV KALAACKAAG IVAPTMLVCG  2760
DDLVVISESQ GTEEDERNLR AFTEAMTRYS APPGDPPRPE YDLELITSCS SNVSVALGPQ  2820
GRRRYYLTRD PTTPIARAAW ETVRHSPVNS WLGNIIQYAP TIWVRMVLMT HFFSILMAQD  2880
TLDQNLNFEM YGSVYSVSPL DLPAIIERLH GLDAFSLHTY TPHELTRVAS ALRKLGAPPL  2940
RAWKSRARAV RASLISRGGR AAVCGRYLFN WAVKTKLKLT PLPEARLLDL SSWFTVGAGG  3000
GDIYHSVSRA RPRLLLLSLL LLXVGVGLFL LPAR                              3034

SEQ ID NO: 190          moltype = AA  length = 3033
FEATURE                 Location/Qualifiers
REGION                  1..3033
                        note = synthetic amino acid sequence
source                  1..3033
                        mol_type = protein
                        organism = synthetic construct
SEQUENCE: 190
MSTNPKPQRK TKRNTNRRPQ DVKFPGGGQI VGGVYLLPRR GPRLGVRATR KTSERSQPRG  60
RRQPIPKDRR STGKSWGKPG YPWPLYGNEG CGWAGWLLSP RGSRPTWGPT DPRHRSRNLG  120
KVIDTITCGF ADLMGYIPVV GAPVGGVARA LAHGVRVLED GINYATGNLP GCSFSIFLLA  180
LLSCVTVPVS AVEVRNISSS YYATNDCSNN SITWQLTNAV LHLPGCVPCE NDNGTLRCWI  240
QVTPNVAVKH RGALTHNLRT HVDMIVMAAT VCSALYVGDV CGAVMIVSQA LIVSPERHNF  300
TQECNCSIYQ GHITGHRMAW DMMLNWSPTL TMILAYAARV PELVLEVVFG GHWGVVFGLA  360
YFSMQGAWAK VIAILLLVAG VDATTYSSGA QAGRTTSGFA GLFSPGPKQN IQLINTNGSW  420
HINRTALNCN DSLQTGFIAS LFYTNNFNSS GCPERLSSCR GLDDFRIGWG TLEYETNVTN  480
DEDMRPYCWH YPPKPCGIVS ARTVCGPVYC FTPSPVVVGT TDRQGVPTYS WGENETDVFL  540
LNSTRPPQGA WFGCTWMNGT GFTKTCGAPP CRIRRDYNST LDLLCPTDCF RKHPDATYLK  600
CGAGPWLTPR CLVDYPYRLW HYPCTVNFTI FKVRMYVGGV EHRLSAACNF TRGDRCRLED  660
RDRGQQSPLL HSTTEWAVLP CSFSDLPALS TGLLHLHQNI VDVQYLYGLS PAITRYIVKW  720
EWVVLLFLLL ADARVCACLW MLIILGQAEA ALEKLIILHS ASAASANGPL WFFIFFTAAW  780
YLKGRVVPVA TYSVLGLWSF LLLVLALPQQ AYALDAAEQG ELGLVILVII SIFTLTPAYK  840
ILLSRSVWWL SYMLVLAEAQ IQQWVPPLEA RGGRDGIIWV AVILHPRLVF EVTKWLLAIL  900
GPAYLLKASL LRVPYFVRAH ALLRVCTLVR HLAGARYIQM LLITIGRWTG TYIYDHLSPL  960
STWAAQGLRD LAVAVEPVVF SPMEKKVIVW GAETVACGDI LHGLPVSARL GREVLLGPAD  1020
SYTSKGWKLL APITAYTQQT RGLLGAIVVS LTGRDKNEQA GQVQVLSSVT QSFLGTSISG  1080
VLWTVYHGAG NKTLAGPKGP VTQMYTSAEG DLVGWPSPPG TKSLDPCTCG AVDLYLVTRN  1140
ADVIPVRRKD DRRGALLSPR PLSTLKGSSG GPVLCPRGHA VGLFRAAVCA RGVAKSIDFI  1200
PVESLDIATR TPSFSDNSTP PAVPQSYQVG YLHAPTGSGK STKVPAAYAS QGYKVLVLNP  1260
SVAATLGFGA YMSKAHGINP NIRTGVRTVT TGDPITYSTY GKFLADGGCS AGAYDVIICD  1320
ECHSVDATTI LGIGTVLDQA ETAGARLVVL ATATPPGTVT TPHSNIEEVA LGHEGEIPFY  1380
GKAIPLAFIK GGRHLIFCHS KKKCDELAAA LRGMGVNAVA YYRGLDVSVI PTQGDVVVVA  1440
TDALMTGYTG DFDSVIDCNV AVTQIVDFSL DPTFTITTQT VPQDAVSRSQ RRGRTGRGRL  1500
GIYRYVSSGE RPSGMFDSVV LCECYDAGAA WYELTPAETT VRLRAYFNTP GLPVCQDHLE  1560
FWEAVFTGLT HIDAHFLSQT KQGGDNFAYL TAYQATVCAR AKAPPPSWDV MWKCLTRLKP  1620
TLTGPTPLLY RLGAVTNEVT LTHPVTKYIA TCMQADLEIM TSTWVLAGGV LAAVAAYCLA  1680
TGCISIIGRL HLNDQVVVAP DKEILYEAFD EMEECASKAA LIEEGQRMAE MLKSKIQGLL  1740
QQATRQAQDI QPAIQSSWPK LEQFWAKHMW NFISGIQYLA GLSTLPGNPA VASMMAFSAA  1800
LTSPLPTSTT ILLNIMGGWL ASQIAPPAGA TGFVVSGLVG AAVGSIGLGK ILVDVLAGYG  1860
AGISGALVAF KIMSGEKPSV EDVVNLLPAI LSPGALVVGV ICAAILRRHV GQGEGAVQWM  1920
NRLIAFASRG NHVAPTHYVA ESDASQRVTQ VLSSLTITSL LRRLHAWITE DCPVPCSGSW  1980
LRDIWDWVCS ILTDFKNWLS SKLLPKMPGL PFISCQKGYR GVWAGTGVMT TRCPCGANIS  2040
```

-continued

```
GHVRMGTMKI TGPKTCLNLW QGTFPINCYT EGPCVPKPPP NYKTAIWRVA ASEYVEVTQH  2100
GSFSYVTGLT SDNLKVPCQV PAPEFFSWVD GVQIHRFAPT PGPFFRDEVT FTVGLNSFVV  2160
GSQLPCDPEP DTEVLASMLT DPSHITAEAA ARRLARGSPP SQASSSASQL SAPSLKATCT  2220
THKMAYDCDM VDANLFMGGD VTRIESDSKV IVLDSLDSMT EVEDDREPSV PSEYLIRRRK  2280
FPPALPPWAR PDYNPPVIET WKRPGYEPPT VLGCALPPTP QAPVPPPRRR RAKVLTQDNV  2340
EGVLREMADK VLSPLQDHND SGHSTGADTG GDSVQQPSDE TAASEAGSLS SMPPLEGEPG  2400
DPDLEFEPAG SAPPSEGECE VIDSDSKSWS TVSDQEDSVI CCSMSYSWTG ALITPCGPEE  2460
EKLPINPLSN SLMRFHNKVY STTSRSASLR AKKVTFDRVQ VLDAHYDSVL QDVKRAASKV  2520
SARLLSVEEA CALTPPHSAK SRYGFGAKEV RSLSRRAVNH IRSVWEDLLE DQHTPIDTTI  2580
MAKNEVFCVD PTKGGKKPAR LIVYPDLGVR VCEKMALYDI AQKLPKAIMG PSYGFQYSPA  2640
ERVDFLLKAW GSKKDPMGFS YDTRCFDSTV TERDIRTEES IYQACSLPQE ARTVIHSLTE  2700
RLYVGGPMTN SKGQSCGYRR CRASGVFTTS MGNTMTCYIK ALAACKAAGI VDPIMLVCGD  2760
DLVVISESQG NEEDERNLRA FTEAMTRYSA PPGDLPRPEY DLELITSCSS NVSVALDSRG  2820
RRRYFLTRDP TTPITRAAWE TVRHSPVNSW LGNIIQYAPT IWVRMVIMTH FFSILLAQDT  2880
LNQNLNFEMY GAVYSVNPLD LPAIIERLHG LDAFSLHTYS PHELSRVAAT LRKLGAPPLR  2940
AWKSRARAVR ASLIAQGGRA AICGRYLFNW AVKTKLKLTP LPEASRLDLS GWFTVGAGGG  3000
DIFHSVSHAR PRLLLLCLLL LSVGVGIFLL PAR                              3033

SEQ ID NO: 191          moltype = AA  length = 3068
FEATURE                 Location/Qualifiers
VARIANT                 385
                        note = X can be any naturally occurring amino acid
VARIANT                 409
                        note = X can be any naturally occurring amino acid
VARIANT                 585
                        note = X can be any naturally occurring amino acid
VARIANT                 3048
                        note = X can be any naturally occurring amino acid
source                  1..3068
                        mol_type = protein
                        organism = synthetic construct
SEQUENCE: 191
MSTLPKPQRK TKRNTIRRPQ DVKFPGGGQI VGGVYVLPRR GPRLGVRATR KTSERSQPRG  60
RRQPIPKARR SEGRSWAQPG YPWPLYGNEG CGWAGWLLSP RGSRPSWGPN DPRRRSRNLG  120
KVIDTLTCGF ADLMGYIPLV GAPVGGVARA LAHGVRALED GINFATGNLP GCSFSIFLLA  180
LFSCLIHPAA SLEWRNTSGL YVLTNDCSNS SIVYEADDVI LHTPGCIPCV QTDGNTSTCW  240
TPVTPTVAVK YVGATTASIR SHVDLLVGAA TMCSALYVGD MCGAVFLVGQ AFTFRPRRHQ  300
TVQTCNCSLY PGHLSGHRMA WDMMMNWSPA VGMVVAHVLR LPQTLFDIIA GAHWGILAGL  360
AYYSMQGNWA KVAIIMVMFS GVDAXTHTTG GSAARGARGL TSLFSVGPXQ NLQLVNTNGS  420
WHINRTALNC NDSINTGFIA GLFYYHKFNS TGCPQRLSSC KPITFFRQGW GPLTDANNIT  480
GPSDDKPYCW HYAPRPCDVV PASSVCGPVY CFTPHHSPVV VGTTDAKGVP TYTWGENETD  540
VFLLESLRPP SGRWFGCTWM NSTRGFVKTC GAPPCNIYGG GGNPXNNESD LFCPTDCFRK  600
HPEATYSRCG AGPWLTPRCM VDYPYRLWHY PCTVNFTLFK VRMFVGGFEH RFTAACNWTR  660
GERCDIEDRD RSEQHPLLHS TTELAILPCS FTPMPALSTG LIHLHQNIVD VQYLYGVGSG  720
MVGWALKWEF VILVFLLLAD ARVCVALWLM LMISQAEAAL ENLVTLNAVA AAGTHGIGWY  780
LVAFCAAWHV RRAGKLVPLV TYSLTGLWSL ALLVLLLPQR AYAWSGEDSA TLGAGILVLF  840
GFFTLSPWYK HWIGRLMWWN QYTICRCEAA LQVWVPPLLA RGSRDGVILL TSLLYPSLIF  900
DITKLLIAVL GPLYLIQAAI TTTPYFVRAH VLVRLCMLVR SVMGGKYFQM IILSIGRWFN  960
TYLYDHLAPM QHWAAAGLKD LAVATEPVIF SPMEIKVITW GADTAACGDI LCGLPVSARL  1020
GREVLLGPAD DYREMGWRLL APITAYAQQT RGLLGTIVTS LTGRDKNVVT GEVQVLSTAT  1080
QTFLGTTVGG VMWTVYHGAG SRTLAGAKHP ALQMYTNVDQ DLVGWPAPPG AKSLEPCACG  1140
SADLYLVTRD ADVIPARRRG DSTASLLSPR PLACLKGSSG GPVMCPSGHV AGIFRAAVCT  1200
RGVAKALQFI PVETLSTQAR SPSFSDNSTP PAVPQSYQVG YLHAPTGSGK STKVPAAYVA  1260
QGYNVLVLNP SVAATLGFGS FMSRAYGIDP NIRTGNRTVT TGAKLTYSTY GKFLADGGCS  1320
GGAYDVIICD ECHAQDATSI LGIGTVLDQA ETAGVRLTVL ATATPPGSIT VPHSNIEEVA  1380
LGSEGEIPFY GKAIPIAQLK GGRHLIFCHS KKKCDEIASK LRGMGLNAVA YYRGLDVSVI  1440
PTTGDVVVCA TDALMTGFTG DFDSVIDCNV AVEQYVDFSL DPTFSIETRT APQDAVSRSQ  1500
RRGRTGRGRL GTYRYVTPGE RPSGMFDSVV LCECYDAGCS WYDLQPAETT VRLRAYLSTP  1560
GLPVCQDHLD FWESVFTGLT HIDAHFLSQT KQQGLNFSYL TAYQATVCAR AQAPPPSWDE  1620
TWKCLVRLKP TLHGPTPLLY RLGPVQNEIC LTHPITKYIM ACMSADLEVT TSTWSTWVLL  1680
GGVLAALAAY CLSVGCVVIV GHIELGGKPA LVPDKEVLYQ QYDEMEECSQ AAPYIEQAQV  1740
IAHQFKEKVL GLLQRATQQQ AVIEPIVATN WQKLEAFWHK HMWNFVSGIQ YLAGLSTLPG  1800
NPAVASLMAF TASVTSPLTT NQTMFFNILG GWVATHLAGP QSSSAFVVSG LAGAAIGGIG  1860
LGRVLLDILA GYGAGVSGAL VAFKIMGGEL PTAEDMVNLL PAILSPGALV VGVICAAILR  1920
RHVGPGEGAV QWMNRLIAFA SRGNHVSPTH YVPESDAAAR VTALLSSLTV TSLLRRLHQW  1980
INEDYPSPCS GDWLRTIWDW VCTVLSDFKT WLSAKIMPAL PGLPFISCQK GYKGVWRGDG  2040
VMSTRCPCGA SITGHVKNGS MRLAGPRTCA NMWHGTFPIN EYTTGPSTPC PSPNYTRALW  2100
RVAANSYVEV RRVGDFHYIT GATEDELKCP CQVPAAEFFT EVDGVRLHRY APPCKPLLRD  2160
EITFMVGLNS YAIGSQLPCE PEPDVSVLTS MLRDPSHITA ETAARRLARG SPPSEASSSA  2220
SQLSAPSLKA TCQTHRPHPD AELVDANLLW RQEMGSNITR VESETKVVIL DSFEPLRAET  2280
DDAELSVAAE CFKKPPKYPP ALPIWARPDY NPPLLDRWKA PDYVPPTVHG CALPPRGAPP  2340
VPPPRRKRTI QLDGSNVSAA LAALAEKSFP SSKPQEENSS SSGVDTQSST TSKVPPSPGG  2400
ESDSESCSSM PPLEGEPGDP DLSCDQVELQ PPPQGGGVAP GSGSGSWSTV SDSEEQSVVC  2460
CSMSYSWTGA LITPCSAEEE KLPISPLSNS LLRHHNLVYS TSSRSASQRQ KKVTFDRLQV  2520
LDDHYKTALK EVKERASRVK ARMLTIEEAC ALVPPHSARS KFGYSAKDVR SLSSKAINQI  2580
RSVWEDLLED TTTPIPTTIM AKNEVFCVDP AKGGRKPARL IVYPDLGVRV CEKRALYDVI  2640
QKLSIETMGS AYGFQYSPQQ RVERLLKMWT SKKTPLGVLF SYDTRCFDST VTGEQDIRVE  2700
EEIYQCCNLE PEARKVISSL TERLYCGGPM FNSKGAQCGY RRCRASGVLP TSFGNTITCY  2760
IKATAAARAA GLRNPDFLVC GDDLVVVAES DGVDEDRAAL RAFTEAMTRL WTRYYSAPPG  2820
```

```
DAPHRPTLQP TYDLELITSC SSNVSVARDN KGKRYYYLTR DATTPLARAA WETARHTPGW  2880
GVNSWLGNII MYAPTIWVRM VMMTHFFSIL QSQEILDRPL DFEMYGATYS VTPLDLPAII  2940
ERLHGLSAFT LHSYSPVELN RVAGTLRKLG CPPLRAWRHR ARAVRAKLIA QGGKAKICGL  3000
YLFNWAVRTK TKLTPLPAAG QLDLSSWFTV GVGGNDIYHS VSRARTRXLL LCLLLLTVGV  3060
GIFLLPAR                                                           3068

SEQ ID NO: 192          moltype = AA  length = 3035
FEATURE                 Location/Qualifiers
VARIANT                 232
                        note = X can be any naturally occurring amino acid
VARIANT                 397
                        note = X can be any naturally occurring amino acid
VARIANT                 407
                        note = X can be any naturally occurring amino acid
VARIANT                 678
                        note = X can be any naturally occurring amino acid
VARIANT                 1002
                        note = X can be any naturally occurring amino acid
source                  1..3035
                        mol_type = protein
                        organism = synthetic construct
SEQUENCE: 192
MSTNPKPQRK TKRNTNRRPM DVKFPGGGQI VGGVYLLPRR GPRLGVRATR KTSERSQPRG  60
RRQPIPKARR SEGRSWAQPG YPWPLYGNEG CGWAGWLLSP RGSRPSWGPN DPRRRSRNLG  120
KVIDTLTCGF ADLMGYIPLV GAPVGGVARA LAHGVRAVED GINYATGNLP GCSFSIFLLA  180
LLSCLTVPAS AINYRNTSGI YHVTNDCPNS SIVYEADHHI LHLPGCVPCV RXGNQSRCWV  240
ALTPTVAAPY IGAPLESLRS HVDLMVGAAT VCSALYIGDL CGGLFLVGQM FSFRPRRHWT  300
TQDCNCSIYT GHITGHRMAW DMMMNWSPTT TLVLAQVMRI PSTLVDLLAG GHWGVLVGVA  360
YFSMQANWAK VILVLFLFAG VDAETHVSGG AAGRTTXGLT SLFSPGXQQN LQLINSNGSW  420
HINRTALNCN DSLNTGFLAS LFYTHKFNSS GCPERLASCK SLDSFDQGWG PLGVANNISG  480
PSDDRPYCWH YPPRPCGIVP ASSVCGPVYC FTPSPVVVGT TDRLGVPTYT WGENESDVFL  540
LNSTRPPQGA WFGCVWMNST GFTKACGAPP CEVRTNNGTS TDWPCPTDCF RKHPETTYAK  600
CGSGPWITPR CLIHYPYRLW HYPCTVNFTV FKIRTFIGGI EHRMEAACNW TRGEVCGLEH  660
RDRAELSPLL LSTTTWQXLP CSFTTLPALS TGLIHLHQNI VDVQYLYGVG SAVVSWALKW  720
EYVVLAFLLL ADARVSACLW MMFMVSQVEA ALSNLININA ASAAGTHGFW YAIFFICIAW  780
HVKGRLPAAA TYAACGMWPL LLLLLMLPER AYAYDREVAG SLGGAVVVAL TILTLSPHYK  840
SWLARGLWWI QYFIARAEAL LHVYVPSFDV RGPRDSLIIL AVLACPHLVF DITKYLLAIL  900
GPLYILQASL LRVPYFVRAH ALVKICSLLR GVVYGKYCQM AVLKVGALTG TYIYDHLTPL  960
SDWAAEGLRD LAVALEPVVF TPMEKKVIVW GADTAACGDI IXGLPVSARL GNEILLGPAD  1020
SETSKGWRLL APITAYAQQT RGLFSTIITS LTGRDTNENC GEVQVLSTAT QSFLGTAVNG  1080
VMWTVYHGAG SKTISGPKGP VNQMYTNVDQ DLVGWPAPPG VKSLAPCTCG ASDLYLVTRH  1140
ADVVPVRRRG DTRGALLSPR PISTLKGSSG GPLLCPMGHA AGIFRAAVCT RGVAKAVDFV  1200
PVESLETTMR SPVFTDNSTP PAVPQTYQVA HLHAPTGSGK STKVPAAYAA QGYKVLVLNP  1260
SVAATLGFGA YMSKAYGIDP NIRSGVRTIT TGAPITYSTY GKFLADGGCS GGAYDIIICD  1320
ECHSTDSTTI LGIGTVLDQA ETAGVRLVVL ATATPPGSVT TPHSNIEEVA LPTTGEIPFY  1380
GKAIPLELIK GGRHLIFCHS KKKCDELAKQ LTSLGLNAVA YYRGLDVSVI PTSGDVVVCA  1440
TDALMTGFTG DFDSVIDCNT SVIQTVDFSL DPTFSIETTT VPQDAVSRSQ RRGRTGRGRL  1500
GIYRYVTPGE RPSGIFDTSV LCECYDAGCA WYELTPAETT TRLRAYFNTP GLPVCQDHLE  1560
FWESVFTGLT QIDGHFLSQT KQSGENFPYL VAYQATVCAR ALAPPPSWDT MWKCLIRLKP  1620
TLHGPTPLLY RLGSVQNEVT LTHPITKYIM ACMSADLEVV TSTWVLVGGV LAALAAYCLS  1680
VGSVVIVGRV VLSGQPAVIP DREVLYQQFD EMEECSKHLP LVEHGLQLAE QFKQKAVGLL  1740
NFAGKQAQEA TPVIQSNFAK LEQFWAKHMW NFISGIQYLA GLSTLPGNPA IASLMSFTAA  1800
VTSPLTTQQT LLFNILGGWV ASQIATPTAS TAFVVSGLAG AAVGSVGLGK ILVDILAGYG  1860
AGVAGAVVTF KIMSGEMPST EDLVNLLPAI LSPGALVVGV VCAAILRRHV GPGEGAVQWM  1920
NRLIAFASRG NHVSPTHYVP ESDAAARVTQ ILSSLTVTSL LRRLHKWINE DCSTPCAESW  1980
LWEVWDWVCT VLSDFKTWLK AKLLPLMPGI PFLSCQRGYK GEWRGDGVMH TTCPCGAELA  2040
GHIKNGSMRI TGPKTCSNTW HGTFPINAYT TGPGVPIPAP NYKFALWRVS AEEYVEVRRV  2100
GDFHYVTGVT QDNIKCPCQV PAPEFFTEVD GIRLHRHAPK CKPLLRDEVS FSVGLNSFVV  2160
GSQLPCEPEP DVAVLTSMLT DPSHITAETA SRRLARGSPP SLASSSASQL SAPSLKATCT  2220
ARHDSPGTDL LEANLLWGST ATRVETDEKV IILDSFEPCV AEPDDDREVS VAAEILRPTK  2280
KFPPALPIWA RPDYNPPLTE TWKQQDYKPP TVHGCALPPS KQPPVPPPRR KRTVQLTESV  2340
VSTALAELAA KTFGQSELGS DSGADLTTGP TETTDSGPIL VDDASDDGSY SSMPPLEGEP  2400
GDPDLTSDQV ELQPPPQGGG VAPGSGSGSW STVSGSEDTV VCCSMSYSWT GALVTPCAAE  2460
ESKLPISPLS NSLLRHHNMV YATTTRSAVT RQKKVTFDRL QVVDNHYNET LKEIKARASR  2520
VKARLLTTEE ACDLTPPHSA KSKFGYGAKD VRSHSRKAIN HINSVWEDLL EDNNTPIPTT  2580
IMAKNEVFAV NPAKGGRKPA RLIVYPDLGG VRVCEKRALH DVINQLPKAV MGAAYGFQYS  2640
PAQRVEFLLT SWKSKKTPMG FSYDTRCFDS TVTEKDIRTE EEVYQCCDLE PEARKVITAL  2700
TERLYVGGPM HNSKGDLCGY RRCRASGVYT TSFGNTLTCY LKATAAIKAA GLRDCTMLVC  2760
GDDLVVIAES DGVEEDNRAL RAFTEAMTRY SAPPGDAPQP AYDLELITSC SSNVSVAHDA  2820
TGKKVYYLTR DPETPLARAA WETVRHTPVN SWLGNIIVYA PTIWVRMVLM THFFSILQSQ  2880
EALEKALDFD MYGVTYSITP LDLPAIIQRL HGLSAFTLHG YSPHELNRVA GSLRKLGVPP  2940
LRAWRHRARA VRAKLIAQGG KAKICGIYLF NWAVKTKLKL TPLPAAANLD LSSWFTVGAG  3000
GGDIYHSVSR ARPRYLLLCL LLLSVGVGIF LLPAR                             3035

SEQ ID NO: 193          moltype = AA  length = 3013
FEATURE                 Location/Qualifiers
VARIANT                 178
                        note = X can be any naturally occurring amino acid
VARIANT                 189
```

```
                         note = X can be any naturally occurring amino acid
VARIANT                  232
                         note = X can be any naturally occurring amino acid
VARIANT                  251
                         note = X can be any naturally occurring amino acid
VARIANT                  257
                         note = X can be any naturally occurring amino acid
VARIANT                  285
                         note = X can be any naturally occurring amino acid
VARIANT                  297
                         note = X can be any naturally occurring amino acid
VARIANT                  300
                         note = X can be any naturally occurring amino acid
VARIANT                  333
                         note = X can be any naturally occurring amino acid
VARIANT                  365
                         note = X can be any naturally occurring amino acid
VARIANT                  384
                         note = X can be any naturally occurring amino acid
VARIANT                  386
                         note = X can be any naturally occurring amino acid
VARIANT                  391
                         note = X can be any naturally occurring amino acid
VARIANT                  396..398
                         note = X can be any naturally occurring amino acid
VARIANT                  404
                         note = X can be any naturally occurring amino acid
VARIANT                  442
                         note = X can be any naturally occurring amino acid
VARIANT                  444
                         note = X can be any naturally occurring amino acid
VARIANT                  476
                         note = X can be any naturally occurring amino acid
VARIANT                  502
                         note = X can be any naturally occurring amino acid
VARIANT                  523
                         note = X can be any naturally occurring amino acid
VARIANT                  525
                         note = X can be any naturally occurring amino acid
VARIANT                  529
                         note = X can be any naturally occurring amino acid
VARIANT                  532
                         note = X can be any naturally occurring amino acid
VARIANT                  547
                         note = X can be any naturally occurring amino acid
VARIANT                  723
                         note = X can be any naturally occurring amino acid
VARIANT                  742
                         note = X can be any naturally occurring amino acid
VARIANT                  763
                         note = X can be any naturally occurring amino acid
VARIANT                  773
                         note = X can be any naturally occurring amino acid
VARIANT                  775
                         note = X can be any naturally occurring amino acid
VARIANT                  779
                         note = X can be any naturally occurring amino acid
VARIANT                  794
                         note = X can be any naturally occurring amino acid
VARIANT                  825
                         note = X can be any naturally occurring amino acid
VARIANT                  839
                         note = X can be any naturally occurring amino acid
VARIANT                  844
                         note = X can be any naturally occurring amino acid
VARIANT                  857
                         note = X can be any naturally occurring amino acid
VARIANT                  905
                         note = X can be any naturally occurring amino acid
VARIANT                  908
                         note = X can be any naturally occurring amino acid
VARIANT                  914
                         note = X can be any naturally occurring amino acid
VARIANT                  931
                         note = X can be any naturally occurring amino acid
VARIANT                  1020..1021
                         note = X can be any naturally occurring amino acid
VARIANT                  1088
                         note = X can be any naturally occurring amino acid
```

```
VARIANT                 1114
                        note = X can be any naturally occurring amino acid
VARIANT                 1118
                        note = X can be any naturally occurring amino acid
VARIANT                 1384
                        note = X can be any naturally occurring amino acid
VARIANT                 1613
                        note = X can be any naturally occurring amino acid
VARIANT                 1756
                        note = X can be any naturally occurring amino acid
VARIANT                 2262
                        note = X can be any naturally occurring amino acid
VARIANT                 2356
                        note = X can be any naturally occurring amino acid
VARIANT                 2374
                        note = X can be any naturally occurring amino acid
VARIANT                 2385
                        note = X can be any naturally occurring amino acid
VARIANT                 2540
                        note = X can be any naturally occurring amino acid
VARIANT                 2601
                        note = X can be any naturally occurring amino acid
VARIANT                 2636
                        note = X can be any naturally occurring amino acid
VARIANT                 2674
                        note = X can be any naturally occurring amino acid
VARIANT                 2994
                        note = X can be any naturally occurring amino acid
VARIANT                 3002
                        note = X can be any naturally occurring amino acid
source                  1..3013
                        mol_type = protein
                        organism = synthetic construct
SEQUENCE: 193
MSTNPKPQRK TKRNTNRRPQ DVKFPGGGQI VGGVYLLPRR GPRLGVRATR KTSERSQPRG  60
RRQPIPKARR PTGRSWGQPG YPWPLYANEG LGWAGWLLSP RGSRPNWGPN DPRRKSRNLG  120
KVIDTLTCGF ADLMGYIPLV GGPVGGVARA LAHGVRVLED GINYATGNLP GCSFSIFXLA  180
LLSCLTVPXS AVPYRNASGV YHVTNDCPNS SIVYEAENLI LHAPGCVPCV RXGNVSRCWV  240
QITPTLSAPS XGAVTAXLRR AVDYLAGGAA LCSALYVGDA CGAVXLVGQM FTYSPRXHTX  300
VQDCNCSIYS GHITGHRMAW DMMMNWSPTT ALXMAQLLRI PQVVIDIIAG AHWGVLFAAA  360
YFASXANWAK VILVLFLFAG VDAXTXTVGG XAGQGXXXLT SFFXPGPQQN LQLINTNGSW  420
HINRTALNCN DSLQTGFIAG LXYXHKFNSS GCPQRMASCR PLAAFDQGWG TISYAXVSGP  480
SDDKPYCWHY PPRPCGVVPA RXVCGPVYCF TPSPVVVGTT DRXGXPTYXW GXNETDIFLL  540
NNTRPPXGNW FGCTWMNSTG FVKTCGAPPC NLGPTGNNSL KCPTDCFRKH PDATYTKCGS  600
GPWLTPRCLV HYPYRLWHYP CTVNYTIFKV RMFIGGLEHR LEAACNWTRG ERCDLEDRDR  660
AELSPLLHTT TQWAILPCSF TPTPALSTGL IHLHQNIVDT QYLYGLSSSI VSWAVKWEYI  720
VLXFLLLADA RICTCLWILL LXCQAEAALE NVIVLNAAAA AGXHGFFWGL LVXCXAWHXK  780
GRLVPGATYL CLGXWPLLLL LLLLPQRALA LDSSDGGTVG CLVLXILTIF TLTPGYKKXV  840
VLVXWWLQYF IARVEAXIHV WVPPLQVRGG RDAIIMLTCL FHPALGFEVT KILLGILGPL  900
YLLQXSLXKV PYFXRARALL RACLLAKHLV XGKYVQAALL HLGRLTGTYI YDHLAPMKDW  960
AASGLRDLAV ATEPIIFSPM ETKVITWGAD TAACGDILAG LPVSARRGRE IFLGPADDIX  1020
XAGWRLLAPI TAYAQQTRGV LGAIVVSLTG RDKNEAEGEV QVLSTATQTF LGTCINGVMW  1080
TVFHGAGXKT LAGPKGPVVQ MYTNVDKDLV GWPXPPGXRS LTPCTCGSAD LYLVTRHADV  1140
IPARRRGDTR ASLLSPRPIS YLKGSSGGPI MCPSGHVVGV FRAAVCTRGV AKALDFIPVE  1200
NLETTMRSPV FTDNSTPPAV PHEFQVGHLH APTGSGKSTK VPAAYAAQGY KVLVLNPSVA  1260
ATLGFGAYMS RAYGVDPNIR TGVRTVTTGA AITYSTYGKF LADGGCSGGA YDVIICDECH  1320
SQDATTILGI GTVLDQAETA GARLVVLATA TPPGSVTTPH PNIEEVALPS EGEIPFYGRA  1380
IPLXLIKGGR HLIFCHSKKK CDELAKQLTS LGVNAVAYYR GLDVAVIPAT GDVVVCSTDA  1440
LMTGFTGDFD SVIDCNTAVT QTVDFSLDPT FTIETTTVPQ DAVSRSQRRG RTGRGRHGIY  1500
RYVSSGERPS GIFDSVVLCE CYDAGCAWYD LTPAETTVRL RAYLNTPGLP VCQDHLEFWE  1560
GVFTGLTNID AHMLSQTKQG GENFPYLVAY QATVCVRAKA PPPSWDTMWK CMXRLKPTLT  1620
GPTPLLYRLG AVQNEITLTH PITKYIMACM SADLEVITST WVLVGGVVAA LAAYCLTVGS  1680
VAIVGRIILS GRPAIIPDRE VLYQQFDEME ECSASLPYMD EARAIAEQFK EKVLGLIGTA  1740
GQKAETLKPA ATSMWXKAEQ FWAKHMWNFV SGIQYLAGLS TLPGNPAVAT LMSFTAAVTS  1800
PLTTQQTLLF NILGGWVASQ IAPPTAATAF VVSGMAGAAV GSIGLGRVLI DILAGYGAGV  1860
AGALVAFKIM CGERPTAEDL VNLLPSILCP GALVVGVICA AVLRRHIGPG EGAVQWMNRL  1920
IAFASRGNHV SPTHYVPETD ASAKVTQLLS SLTVTSLLKR LHTWIGEDYS TPCDGTWLRA  1980
IWDWVCTALT DFKAWLQAKL LPQLPGVPFL SCQRGYKGVW RGDGVNSTKC PCGATISGHV  2040
KNGTMRIVGP KLCSNTWHGT FPINATTGP SVPAPAPNYK FALWRVGAAD YAEVRRVGDY  2100
HYITGVTQDN LKCPCQVPSP EFFTELDGVR IHRYAPPCNP LLREEVCFSV GLHSYVVGSQ  2160
LPCEPEPDVT VLTSMLSDPA HITAETAKRR LDRGSPPSLA SSSASQLSAP SLKATCTTQG  2220
HHPDADLIEA NLLWRQCMGG NITRVEAENK VVILDSFEPL KXEEDDREIS VSADCFRRGP  2280
AFPPALPIWA RPGYDPPLLE TWKRPDYDPP QVSGCPLPPA GLPPVPPPRR KRKPVELSDS  2340
TVSQVLADLA DARFKXDTPS IEGQDSAVGT SSQXDSGPEE KRDDXSDAAS YSSMPPLEGE  2400
PGDPDLSSGS WSTVSDEDSV VCCSMSYSWT GALITPCSAE EEKLPINPLS NTLLRHHNLV  2460
YSTSSRSAGL RQKKVTFDRL QVLDDHYREV VDEMKRLASK VKARLLPLEE ACGLTPPHSA  2520
RSKYGYGAKE VRSLDKKALX HIEGVWQDLL DDSDTPLPTT IMAKNEVFAV EPSKGGKKPA  2580
RLIVYPDLGV RVCEKRALYD XAQKLPTALM GPSYGFQYSP AQRVEFLLKT WKSKKXPMAF  2640
SYDTRCFDST VTEHDIMTEE SIYQSCDLQP EARXAIRSLT QRLYCGGPMY NSKGQQCGYR  2700
```

```
RCRASGVFTT SMGNTMTCYI KALASCRAAK LRDCTLLVCG DDLVAICESQ GTHEDEASLR  2760
AFTEAMTRYS APPGDPPVPA YDLELVTSCS SNVSVARDAS GNRVYYLTRD PQVPLARAAW  2820
ETAKHSPVNS WLGNIIMYAP TLWARIVLMT HFFSVLQSQE QLEKALAFEM YGSVYSVTPL  2880
DLPAIIQRLH GLSAFSLHSY SPSEINRVAS CLRKLGVPPL RAWRHRARAV RAKLIAQGGK  2940
AAICGIYLFN WAVKTKRKLT PLADADRLDL SSWFTVGAGG GDIYHSMSRA RPRXLLCLLL  3000
LXVGVGIFLL PAR                                                     3013

SEQ ID NO: 194          moltype = AA  length = 3014
FEATURE                 Location/Qualifiers
VARIANT                 195
                        note = X can be any naturally occurring amino acid
VARIANT                 237
                        note = X can be any naturally occurring amino acid
VARIANT                 389
                        note = X can be any naturally occurring amino acid
VARIANT                 400
                        note = X can be any naturally occurring amino acid
VARIANT                 403
                        note = X can be any naturally occurring amino acid
VARIANT                 572
                        note = X can be any naturally occurring amino acid
VARIANT                 1877
                        note = X can be any naturally occurring amino acid
VARIANT                 1944
                        note = X can be any naturally occurring amino acid
VARIANT                 1967
                        note = X can be any naturally occurring amino acid
source                  1..3014
                        mol_type = protein
                        organism = synthetic construct
SEQUENCE: 194
MSTLPKPQRK TKRNTNRRPM DVKFPGGGQI VGGVYLLPRR GPRLGVRATR KTSERSQPRG  60
RRQPIPKARQ PTGRHWAQPG YPWPLYGNEG CGWAGWLLSP RGSRPHWGPN DPRRRSRNLG  120
KVIDTLTCGF ADLMGYIPVV GAPLGGVAAA LAHGVRAIED GINYATGNLP GCSFSIFLLA  180
LLSCLTTPAS AVHYXNSSGI YHLTNDCPNS SIVYEADAMI LHLPGCVPCV RVGNQSXCWV  240
PVSPTLAVPN ASTPATGFRR HVDLLVGAAA FCSALYIGDL CGGVFLVGQL FTFRPRRHQT  300
VQDCNCSIYT GHVTGHRMAW DMMMNWSPTA TLVLSSILRV PQLLLDIFLG GHWGVLGAVL  360
YYSMVANWAK VLAVLLLFAG VDATTTTGXA AGRTTSGLTX LFXPGAKQNL QLINTNGSWH  420
INRTALNCND SLQTGFIAGL FYTHKFNSSG CPERMSSCKP LTDFDQGWGP ITYANISGPS  480
EDRPYCWHYA PRPCDVVPAR TVCGPVYCFT PSPVVVGTTD RRGLPTYTWG ENETDVFLLE  540
SLRPPTGGWF GCTWMNSTGF VKTCGAPPCN IXPNSSNNSL LCPTDCFRKH PEATYARCGS  600
GPWLTPRCLV DYPYRLWHYP CTVNFTIHKV RMFVGGVEHR FDAACNWTRG ERCELDDRDR  660
IEMSPLLFST TELAILPCSF TTMPALSTGL IHLHQNIVDV QYLYGVSSSV VSWAVKWEYV  720
VLAFLVLADA RICACLWLML LIGQAEAALE NLIVLNAASA ASTQGWWWGL LFLCCAWYVK  780
GRLVPACTYA LLQLWPLLLL VLALPRRAYA YDNEQAASLG ALVLLVITIF TLTPAYKQLL  840
VSFLWWNQYF IARAEAMLHV WVPSLRVRGG RDAVILLTCL LHPQLGFEVT KILLALLGPL  900
YLLQYSLLKV PYFVRAHILL RACLLVRRLA GGKYVQACLL RLGAWTGTYI YDHLAPLSDW  960
ASDGLRDLAV AVEPVIFSPM EKKVITWGAD TAACGDILAG LPVSARRGNL VLLGPADDMK  1020
RGGWRLLAPI TAYAQQTRGL LGTIVTSLTG RDKNEVEGEV QVVSTATQSF LATSINGVLW  1080
TVYHGAGSKT LAGPKGPVCQ MYTNVDQDLV GWPAPPGARS LTPCTCGSSD LYLVTRNADV  1140
IPARRRGDTR AALLSPRPIS TLKGSSGGPI LCPSGHVVGL FRAAVCTRGV AKSLDFVPVE  1200
NMETTMRSPS FTDNSTPPAV PQTYQVGYLH APTGSGKSTK VPAAYASQGY KVLVLNPSVA  1260
ATLGFGSYMS KAHGIDPNIR TGVRTITTGG AITYSTYGKF LADGGCSGGA YDIIICDECH  1320
STDPTTVLGI GTVLDQAETA GVRLTVLATA TPPGSVTVPH PNITETALPT TGEIPFYGKA  1380
IPLEYIKGGR HLIFCHSKKK CDELAKQLTS LGLNAVAFYR GVDVSVIPTS GDVVVCATDA  1440
LMTGYTGDFD SVIDCNVAVT QVVDFSLDPT FSIETTTVPQ DAVSRSQRRG RTGRGKPGVY  1500
RYVSQGERPS GMFDTVVLCE AYDTGCAWYE LTPSETTVRL RAYLNTPGLP VCQDHLEFWE  1560
GVFTGLTHID AHFLSQTKQG GENFAYLVAY QATVCARAKA PPPSWDTMWK CLIRLKPMLT  1620
GPTPLLYRLG AVQNEITTTH PITKYIMTCM SADLEVITST WVLVGGVLAA LAAYCLSVGC  1680
VVICGRITTT GKPAVIPDRE VLYQQFDEME ECSRHIPYLA EGQQIAEQFK QKVLGLLQTT  1740
AKQAEELKPA VHSAWPKLEQ FWQKHLWNFV SGIQYLAGLS TLPGNPAVAS LMSFSASLTS  1800
PLSTSTTLLL NILGGWVASQ LAPPTASTAF VVSGLAGAAV GSIGLGRVLV DILAGYGAGV  1860
SGALVAFKIM SGETPAXEDM VNLLPALLSP GALVVGVVCA AILRRHVGPA EGATQWMNRL  1920
IAFASRGNHV SPTHYVPETD ASRXVTTILS SLTITSLLRR LHEWINXDWS TPCATSWLRD  1980
IWDWVCTVLS DFKTWLKAKL VPSLPGIPFL SCQRGFRGVW RGDGVCHTTC TCGAVIAGHV  2040
KNGTMKISGP RTCSNTWHGT FPINATTGP SVPIPEPNYK RALWRVSAED YVEVVRVGDC  2100
HYVVGATADN LKCPCQVPAP EFFTEVDGVR LHRYAPPCKP LLRDEVTFSV GLSSYAIGSQ  2160
LPCEPEPDVT VVTSMLTDPS HITAETAARR LARGSPPSLA SSSASQLSAP SLKATCTTHG  2220
DHPDAELIEA NLLWRQEMGG NITRVESENK VIVLDSFDPL VAEYDDREIS VSAECHRPPR  2280
PKFPPALPIW ARPDYNPPLL ETWKAPDYEP PVVSGCALPP PGPPPIPPPR RKKVVHLDES  2340
TVSHALAQLA EKSFPESSSD STSSDSGLSI TSSGSPEPTT DDDACSEAGS YSSMPPLEGE  2400
PGDPDLSSGS WSTVSEEDSV VCCSMSYSWT GALITPCAAE EEKLPINPLS NSLIRHHNLV  2460
YSTTSRSASL RQKKVTFDRV QVLDQHYQDV LKEIKLRASQ VQARLLSTEE ACDLTPPHSA  2520
RSKFGYGAKD VRSHASKAIN HINSVWEDLL EDNQTPIPTT IMAKNEVFCV DPSKGGRKPA  2580
RLIVYPDLGV RVCEKRALYD ITRKLPVAVM GDAYGFQYSP KQRVDYLLKM WRSKKTPMGF  2640
SYDTRCFDST VTERDIRTEH DIYQSCQLDP EARKAITSLT ERLYVGGPMY NSKGQSCGYR  2700
RCRASGVLPT SLGNTLTCYL KAQAACRAAG LKDFDMLVCG DDLVVISESA GVQEDAAALR  2760
AFTEAMTRYS APPGDEPQPT YDLELITSCS SNVSVAHDGT GQRYYYLTRD PTTPLARAAW  2820
ETARHTPVNS WLGNIIMYAP TIWVRMVLMT HFFQILQSQE QLHKALDFDI YGVTYSITPL  2880
```

-continued

```
DLPAIIQRLH GMAAFSLHGY SPGELNRVAA CLRKLGAPPL RAWRHRARAV RAKLIAQGGK  2940
AAICGKYLFN WAVKTKLKLT PLRGASKLDL SGWFVAGYSG GDIYHSVSRA RPRMLLLCLL  3000
LLTVGVGIFL LPAR                                                    3014

SEQ ID NO: 195         moltype = AA  length = 3013
FEATURE                Location/Qualifiers
source                 1..3013
                       mol_type = protein
                       organism = hepatitis C virus
SEQUENCE: 195
MSTNPKPQRL TKRNTVRRPQ NVKFPGGGQI VGGVYLLPRR GPRLGVRGTR KSSERSQPRG  60
RRQRIPKAAS SQGKAWGKPG YPWPLYGNEG CGWAGWLLSP RGSRPTWGPT DPRHRSRNLG  120
KVIDTMTCGF ADLMGYIPVL GAPLGGVARA LAHGVRVLED GVNYATGNLP GCSFSIFLLA  180
LLSCLTVPAS AYEVRNSSGV YHLTNDCPNA SIVYETDNAI LHEPGCVPCV REGNTSRCWE  240
PVAPTLAVRY RGALTDDLRT HIDLVVASAT LCSALYVGDI CGAIFIASQA VLWKPGGGRI  300
VQDCNCSIYP GHVTGHRMAW DMMQNWAPAL SMVAAYAVRV PGVIITTVAG GHWGVLFGLA  360
YFGMAGNWAK VILIMLLMSG VDAETMAVGA RAAHTTGALV SLLNPGPSQR LQLINTNGSW  420
HINRTALNCN DSLQTGFIAA LFYTHRFNSS GCPERMASCK PLSDFDQGWG PLWYNSTERP  480
SDQRPYCWHY APSPCGIVPA KDVCGPVYCF TPSPVVVGTT DRRGVPTYTW GENESDVFLL  540
NSTRPPQGSW FGCSWMNTTG FTKTCGGPPC KIRPQGAQSN TSLTCPTDCF RKHPRATYSA  600
CGSGPWLTPR CMVHYPYRLW HYPCTVNFTI HKVRLYIGGV EHRLDAACNW TRGERCDLED  660
RDRVDMSPLL HSTTELAILP CSFVPLPALS TGLIHLHQNI VDAQYLYGLS PAIISWAIRW  720
EWVVLVFLLL ADARICACLW MMMLMAQAEA ALENLIHLNA ASLAGTHGIW WLLLVFCASW  780
HLRGRVVPLV TYGICGMWPF FLMLLSLPPR AYALDREVSA ALGTGMLAII LLVTLGPHYK  840
RLLALILWWV TYFLTRCEAA LQTWVPPLNP RGGRDGFILC VLLCYPGLVF DITKWLLVMM  900
CPLYLLQLCL VRTPYFVRAQ ALIRVCSLFK TLAGGRYVQA ALLTIGRWTG TYIYNHLAPL  960
ETWAAGGLRD LAVAVEPVIF SPMEKKIIVW GAETTACGDI LCGLPVSARL GREVLLGPAD  1020
DYRSMGWQLL APISAYAQQT RGLISTLVVS LTGRDKNETA GEVQVLSTST QTFLGTNVGG  1080
VMWGPYHGAG TRTVAGRGGP VLQMYTSVSD DLVGWPAPPG SKSLEPCSCG SADLYLVTRN  1140
ADVLPLRRKG DGTASLLSPR PVSSLKGSSG GPVLCPQSHC VGIFRAAVCT RGVAKAVQFV  1200
PIEKMQVAQR SPSFSDNSTP PAVPSTYQVG YLHAPTGSGK STKVPAAYAS QGYKVLVLNP  1260
SVAATLGFGA YMSKAYGIDP SVRTGARTVT TGAPITYSTY GKFLADGGCS GGAYDIIICD  1320
ECHAIDATTV VGIGTVLDQA ETSGVRLVVL ATATPPGSVT VPHPNIEEVA LGNDGEIPFY  1380
GKAIPLQHIK GGRHLIFCHS KKKCDELAGK LTSLGLTAVA YYRGLDVSVI PTSGDVVVVA  1440
TDALMTGFTG DFDSVIDCNV AVTQTVDFSL DPTFTIETTT VPQDSVSRSQ RRGRTGRGRL  1500
GIYRYVSSGE RPSGMFDTSV LCECYDLGCS WYELTPSETT TRLRAYLNCP GLPVCQDHLE  1560
FWEGVFTGLT HIDAHFLSQT KQEGQNYAYL TAYQATVCAR AKAPPPSWDV QWKCLQRLKP  1620
LLVGPTPLLY RLGSVTNEVT FTHPITKYIA TCMAADLEVT TSTWVIVGGV LAAVAAYCMS  1680
TGSVVVVGRV VLGSNVVTAP DREVLYQHFD EMEECSKAPE LLKHAQTIGG MFKDKALAVL  1740
DTLKPAAQAA VPIVETNFQK VEKLWNQHMW NFISGIQYLA GLSTLPGNPT VASLMAFTAS  1800
VTSPLATSTT LLVNILGGWF ASQLAPPSAA TTFVVSGLAG AAVGSVGLGK VLVDVLAGYG  1860
AGIAGALVAF KIMSGEVPST EDLANLLPAI LSPGALVVGV VCAAIIKRHT GTSEGVTQWM  1920
NRLIAFASRG NHVSPTHYIQ DDDASKRVMG ILSSLTITSL IKRVLAWAQT DYSAPCAGSW  1980
LREVWDWVCM VLSDFASWLK AKVLPSLPGI PFLSCQKGYK GEWRNDGIMN TKCPCGALIA  2040
GHVKNGSMRI VGPKTCRNTW WGTFPINSHT TGPSSPVPSH CYQRALWRVS ATEYVEILRH  2100
NDQHYVVGVT AEDLKCPCQV PSPEFFSFVD GVRIHRFAPE PKPMIREEAA FVVGLHSYVV  2160
GSQLPCEPEP DVQTVSQLLT DPSHITAETA ARRLRRGSPP SNASSSASQL SAPSLKATHT  2220
TLPQHPDAEL IEANLMWEHK VGAIRRMETD TKVIILDSFD SASSVEDDME PSTAAECLRT  2280
RKVFPPAMPI WARPDYNPPV VENWKDPEYA PPQVSGCALP PAQTPPVPPP RRKRAVIQLT  2340
ESAVSTALAE LAERSFPKEE APPSDSAISL DSPAANDPPS DCDQGSEISF SSMPPLEGEP  2400
GDPDLSDGSW STVSTRSDVI CCSMSYSWTG ALVTPSGPEE ERLPINALSN TMLRHYNMVY  2460
STTSRSASQR AKKVTFDRLQ VLDDHYKRAL ADVKADASTV KAQLLSVEEA AALTPAHSAR  2520
SKFGYGAKEV RSLAPKAMSH IKEVWKDLLQ DMTTPIPTTI MAKNEVFCVN PAKGGKKPAR  2580
LIVYPDLGVR VCEKRALYDI AQKLPKAIMG QAYGFQYSPS QRVEYLVKTW KSKRTPMGFS  2640
YDTRCFDSTV TEQDIRTESE IYQCCNLDPE ARTIINALTE RLYVGGPMFN SKGQRVGYRR  2700
CRASGVFPTS MGNTMTCYIK AKAAAAAAGL ESTDFLVCGD DLVVICESKG VERDRADLQA  2760
FAAAMTRYSA PPGDMPQPAY DLEHIDSCSS NVSVARDNSG KRVYYLTRDP TNPLSRAAWE  2820
TARHSPVNSW VGNIIMFAPT IWVRMVLMTH FFALLLNEER LNDPVSFEMY GATYTVCPTD  2880
LPDIIQRLHG LRAFELHTYS PAELTRVAAT LRKLGVPPLR TWRQRARKVR AGLIGQGGRA  2940
RICGLYLFNW AVRTKIKLTP LAGAGRLDLS SWFSVCAGEA DVDHSTPRAH PRPLLLCLLL  3000
LAVGVGIFLL PAR                                                     3013

SEQ ID NO: 196         moltype = AA  length = 3008
FEATURE                Location/Qualifiers
VARIANT                1871
                       note = X can be any naturally occurring amino acid
source                 1..3008
                       mol_type = protein
                       organism = hepatitis C virus
SEQUENCE: 196
MSTNPKPQRK TKRNTNRRPQ DVKFPGGGQI VGGVYLLPRR GPRLGVRATR KTSERSQPRG  60
RRQPIPKARR PEGRTWAQPG YPWPLYGNEG CGWAGWLLSP RGSRPSWGPT DPRRRSRNLG  120
KVIDTLTCGF ADLMGYIPLV GAPLGGAARA LAHGVRVLED GVNYATGNLP GCSFSIFLLA  180
LLSCLTVPAS AYQVRNSTGL YHVTNDCPNS SIVYEAADAI LHTPGCVPCV REGNTSRCWV  240
AMTPTVATRD GKLPTTQLRR HIDLLVGSAT LCSALYVGDL CGSVFLVGQM FTFSPRRHWT  300
TQDCNCSLYP GHITGHRMAW DMMMNWSPTA ALITAQLLRI PQAILDMIAG AHWGVLAGIA  360
YFSMVGNWAK VLVVLLLFAG VDAQTHVTGG RAAHITAGLT SLFSPGPSQK LQLVNTNGSW  420
HINSTALNCN DSLKTGWIAG LLYSYKFNSS GCPERLASCR RLTDFAQGWG PISHANGSGP  480
DERPYCWHYP PRPCGIVPAK SVCGPVYCFT PSPVVVGTTD KSGAPTYNWG ENDWDVFVLN  540
```

-continued

```
NTRPPLGNWF GCTWMNSTGF TKVCGAPPCV IGGAGNNTLR CPTDCFRKHP DATYSRCGSG  600
PWITPRCLVD YPYRLWHYPC TVNYSIFKIR MYLGGVEHRL EAACNWTRGE RCDLEDRDRS  660
ELSPLLLSTT QWQVLPCSFT TLPALSTGLI HLHQNIVDVQ YLYGVGSSVA SWAIKWDYVV  720
LLFLLLADAR ICSCLWMMLL ISQAEAALEN LVVLNAASLA GTHGLAPFLV FFCLAWYLKG  780
KWAPGAVYAV YGMWPLLLLL LALPQRAYAL DTEVAASCGG AVLVGLMVLT LSPHYKHYIS  840
WCLWWLQYFL TRAEAQLHVW VPPLNVRGGR DAVILLMCVV HPTLVFDITK LLLAVGPLWI  900
LQTSLLKVPY FVRVQGLLRI CALARKIAGG HYVQMAIIKL GALTGTYIYD HLTPLRDWAH  960
NGLRDLAVAV EPVVFSRMET KLITWGADTA ACGDIINGLP VSARRGQEIL LGPADGMVSK  1020
GWRLLAPITA YAQQTRGLLG CIITSLTGRD KNQVEGEVQI VSTAAQTFLA TCINGVCWTV  1080
YHGAGTRTIA SPKGPVIQMY TNVDKDLVGW PAPPGSRSLT PCTCGSSDLY LVTRHADVIP  1140
VRRRGDSRGS LLSPRPISYL KGSSGGPLLC PAGHAVGIFR AAVCTRGVAK AVDFIPVESL  1200
ETTMRSPVFT DNSSPPVVPQ SFQVAHLHAP TGSGKSTKVP AAYAAQGYKV LVLNPSVAAT  1260
LFGAYMSKAH GVDPNIRTGV RTITTGSPIT YSTYGKFLAD GGCSGGAYDI IICDECHSTD  1320
ATSILGIGTV LDQAETAGAR LVVLATATPP GSVTVPHPNI EEVALSTTGE IPFYGKAIPL  1380
EVIKGGRHLI FCHSKKKCDE LAAKLVALGI NAVAYYRGLD VSVIPTSGDV VVVATDALMT  1440
GYTGDFDSVI DCNTCVTQTV DFSLDPTFTI ETTTLPQDAV SRTQRRGRTG RGKPGIYRFV  1500
APGERPSGMF DSSVLCECYD AGCAWYELTP AETTVRLRAY MNTPGLPVCQ DHLEFWEGVF  1560
TGLTHIDAHF LSQTKQSGEN FPYLVAYQAT VCARAQAPPP SWDQMWKCLI RLKPTLHGPT  1620
PLLYRLGAVQ NEVVLTHPIT KYIMTCMSAD LEVVTSTWVL VGGVLAALAA YCLSTGCVVI  1680
VGRVVLSGKP AIIPDREVLY QEFDEMEECS QHLPYIEQGM MLAEQFKQKA LGLLQTASRQ  1740
AEVIAPAVQT NWQKLEAFWA KHMWNFISGI QYLAGLSTLP GTPAIASLMA FTAAVTSPLT  1800
TSQTLLFNIL GGWVAAQLAA PGAATAFVGA GLAGAAIGSV GLGKVLVDIL AGYGAGVAGA  1860
LVAFKIMSGE XPSTEDLVNL LPAILSPGAL VVGVVCAAIL RRHVGPGEGA VQWMNRLIAF  1920
ASRGNHVSPT HYVPESDAAA RVTAILSSLT VTQLLRRLHQ WISSECTTPC SGSWLRDIWD  1980
WICEVLSDFK TWLKAKLMPQ LPGIPFVSCQ RGYRGVWRGD GIMHTRCHCG AEITGHVKNG  2040
TMRIVGPRTC RNMWSGTFPI NAYTTGPCTP LPAPNYKFAL WRVSAEEYVE IRQVGDFHYV  2100
TGMTTDDLKC PCQVPSPEFF TELDGVRLHR FAPPCKPLLR EEVSFRVGLH AYPVGSQLPC  2160
EPEPDVAVLT SMLTDPSHIT AETARRLARG SPPSVASSSA SQLSAPSLKA TCTANHDSPD  2220
AELIEANLLW RQEMGGNITR VESENKVVIL DSFDPLVAEE DEREISVPAE ILRKSRRFTQ  2280
ALPVWARPDY NPPLVEAWKK PDYEPPVVHG CPLPPPKSPP VPPPRKKRTV VLTESTLSTA  2340
LAELATKSFG SSSTSGITGD NTTTSSEPAP PGCSPDSDAE SCSSMPPLEG EPGDPDLSDG  2400
SWSTVSSEAD TEDVVCCSMS YTWTGALITP CAAEEQKLPI NALSNSLLRH HNLVYSTTSR  2460
SACQRQKKVT FDRLQVLDNH YQDVLKEVKA AASKVKANLL SVEEACSLTP PHSAKSKFGY  2520
GAKDVRCHAR KAVNHINSVW KDLLEDSVTP IDTTIMAKNE VFCVQPEKGG RKPARLIVFP  2580
DLGVRVCEKM ALYDVVSKLP LAVMGDSYGF QYSPGQRVEF LVQAWKSKKT PMGFSYDTRC  2640
FDSTVTESDI RTEEAIYQCC DLDPQARVAI KSLTERLYVG GPLTNSRGEN CGYRRCRASG  2700
VLTTSCGNTL TCYIKAKAAC RAAGLQNCTM LVCGDDLVVI CESAGVQEDA ASLRAFTEAM  2760
TRYSAPPGDP PQPEYDLELI TSCSSNVSVA HDGAGKRVYY LTRDPTTPLA RAAWETARHT  2820
PVNSWLGNII MFAPTLWARM VLMTHFFSVL IARDQLEQAL DCEIYGACYS IEPLDLPPII  2880
QRLHGLSAFS LHSYSPGEIN RVAACLRKLG VPPLRTWRHR ARSVRAKLLS RGGRAAICGK  2940
YLFNWAVRTK LKLTPIAAAG RLDLSGWFTA GYSGGDIYHS VSHARPRWFW FCLLLLAAGV  3000
GIYLLPNR                                                           3008

SEQ ID NO: 197          moltype = AA  length = 3021
FEATURE                 Location/Qualifiers
source                  1..3021
                        mol_type = protein
                        organism = hepatitis C virus
SEQUENCE: 197
MSTLPKPQRK TKRNTIRRPQ DVKFPGGGQI VGGVYVLPRR GPRLGVRATR KTSERSQPRE  60
RRQPIPKARR SDGRSWAQPG YPWPLYGNEG CGWAGWLLSP RGSRPSWGPN DPRRRSRNLG  120
KVIDTLTCGF ADLMGYIPIV GAPVGGVARA LAHGVRALED GINFATGNLP GCSFSIFLLA  180
LLSCLIHPAA SLEWRNTSGL YILTNDCPNS SIVYEADDVI LHTPGCIPCV QDGNTSTCWT  240
SVSPTVAVRY VGATTASIRS HVDLLVGAAT LCSALYVGDM CGAVFLVGQA FTFRPRRHQT  300
VQTCNCSLYP GHLTGHRMAW DMMMNWSPAV GMVVAHVLRM PQTVFDIIAG AHWGILAGLA  360
YYSMQGNWAK VAIIMVMFSG VDAETHTTGG TAARNAFTLT GLFTQGARQK LQLINTNGSW  420
HINRTALNCN ESLNTGFIAG LFYLHKFNST GCPERLSSCK PITFFRQGWG SLTDANITGP  480
SDDKPYCWHY APRPCEVVPA LNVCGPVYCF TPSPVVVGTT DRQGVPTYTW GENETDVFLL  540
RSLRPPSGQW FGCTWMNSTG FVKTCGAPPC DIYGGGGNRC NESDLFCPTD CFRKHPEATY  600
SRCGAGPWLT PRCLVDYPYR LWHYPCTVNF TLFKVRMFVG GFEHRFTAAC NWTRGERCNI  660
EDRDRSEQHP LLHSTTELAI LPCSFTPMPA LSTGLIHLHQ NIVDVQYLYG VGSGVVGWAL  720
RWEFVVLVFL LLADARVCVA LWLMLMISQA EAALENLVTL NAVAAAGTHG IGWYLVAFCA  780
AWHLRGKLVP LVTYSLTGLW SLAVLVLLLP QRAYAWSGED SATLGAGILV LFGFFTLSPW  840
YKHWIGRLMW WNQYTICRCE AALQVWVPPL LARGSRDGAI LLTSLLYPSL IFDITKLLIA  900
VLGPLYLIQA AITTTPYFVR AHVLVRLCML VRSVMGGKYF QMIILSIGRW FNTYLYDHLA  960
PMQHWAAAGL KDLAVATEPV IFSPMEIKVI TWGADTAACG DILCGLPVSA RLGHEVLLGP  1020
ADDYREMGWR LLAPITAYAQ QTRGLLGTIV TSLTGRDKNV VTGEVQVLST ATQTFLGTTI  1080
GGVMWTVYHG AGSRTLAGVK HPALQMYTNV DQDLVGWPAP PGAKSLEPCS CGSTDLYLVT  1140
READVIPARR RGDSTASLLS PRPLACLKGS SGGPVMCPSG HVAGIFRAAV CTRGVAKALQ  1200
FIPVETLSAQ ARSPSFSDNS TPPIVPQSYQ VGYLHAPTGS GKSTKVPAAY VAQGYNVLVL  1260
NPSVAATLGF GSFMSRAYGI DPNIRTGNRT VTTGAKLTYS TYGKFLADGG CSGGAYDVII  1320
CDECHAQDAT SILGIGTVLD QAETAGVRLT VLATATPPGS ITVPHSNIEE VALGSEGEIP  1380
FYGKAIPLAQ LKGGRHLIFC HSKKKCDEMA SKLRGMGLNA VAYYRGLDVS VIPTAGDVVV  1440
CATDALMTGF TGDFDSVIDC NVTVEQYVDF SLDPTFSIET RTAPQDAVSR SQRRGRTGRG  1500
RLGTYRYVAP GERPSGMFDS VVLCECYDAG CSWYDLQPAE TTVRLRAYLS TPGLPVCQDH  1560
LDFWESVFTG LTHIDAHFLS QTKQQGLNFS YLTAYQATVC ARAQAPPPSW DEMWKCLLRL  1620
KPTLHGPTPL LYRLGPVQNE TCLTHPVTKY IMACMSADLE VTTSTWVLLG GVLAALAAYC  1680
LSVGCVVIVG HIELGGKPAL IPDKEVLYQQ YDEMEECSQA APYVEQAQAI AHQFKEKLLG  1740
LLQRATQQQA VIEPIVATNW QKLEAFWHKH MWNFVSGIQY LAGLSTLPGN PAVASLMAFT  1800
```

-continued

```
ASVTSPLTTN QTMFFNILGG WVATHLAGPQ SSSAFVVSGL AGAAIGGIGL GRVLLDILAG  1860
YGAGVSGALV AFKIMGGEIP TAEDMVNLLP AILSPGALVV GVICAAILRR HVGPGEGAVQ  1920
WMNRLIAFAS RGNHVSPTHY VPESDAAARV TALLSSLTVT SLLRRLHHWI NEDYPSPCSG  1980
DWLRTIWDWV CMVLSDFRTW LSAKIMPALP GLPFLSCQKG YKGVWRGDGV VSTRCPCGAS  2040
ITGHVKNGSM RLAGPRTCAN MWHGTFPINE YTTGPSTPCP SPNYTRALWR VAANSYVEVR  2100
QVGDFHYITG ATEDGLKCPC QVPAAEFFTE VDGVRLHRYA PPCKPLLRDE ITFMVGLNSY  2160
AIGSQLPCEP EPDVSVLTSM LRDPSHITAE TAARRLARGS PPSEASSSAS QLSAPSLKAT  2220
CQTHRPHPDA ELVDANLLWR QEMGSNITRV ESETKVVILD SFEPLRAEAD DAELSVAAEC  2280
FKKPPKYPPA LPIWARPDYN PPLLDRWKTP DYVPPTVHGC ALPPRGAPPV PPPRRKRTVQ  2340
LDGSNVSAAL AALAEKSFPS LEPQGENSSS SGIDIQSSTA SEVPPSPEGE SDSESCTSMP  2400
PLEGEPGDPD LSCDSWSTVS DSEEQSVVCC SMSYSWTGAL ITPCSAEEEK LPISPLSNSL  2460
LRHHNLVYST SSRSASQRQK KVTFDRLQVL DDHYKAVLKE VKERASRVKA RMLTIEEACA  2520
LVPPHSARSK FGYSAKDVRS LSGRAVNQIR SVWEDLLEDT TTPIPTTIMA KNEVFCVDPS  2580
KGGRKPARLI VYPDLGVRVC EKRALYDVIQ KLSIATMGSA YGFQYSPQQR VERLLEMWTS  2640
KKTPMGFSYD TRCFDSTVTE QDIRVEEEIY QCCNLEPEAR KVISSLTERL YCGGPMFNSK  2700
GAQCGYRRCR ASGVLPTSFG NTITCYIKAT AAARAAGLRN PDFLVCGDDL VLVAESDGVD  2760
EDRAALRAFT EAMTRYSAPP GDAPQPTYDL ELITSCSSNV SVARDNKGKR YYYLTRDATT  2820
PLARAAWETA RHTPVNSWLG NIIMYAPTIW VRMVMMTHFF SILQSQEILD RPLDFEMYGA  2880
TYSVTPLDLP AIIERLHGLS AFTLHSYSPV ELNRVAGTLR KLGCPPLRAW RHRARAVRAK  2940
LIAQGGKAKI CGLYLFNWAV RTKTNLTPLP AAGQLDLSSW FTVGVGGNDI YHSVSRARTR  3000
HLLLCLLLLT VGVGIFLLPA R                                            3021
```